US011878970B2

(12) United States Patent
Anderson et al.

(10) Patent No.: US 11,878,970 B2
(45) Date of Patent: Jan. 23, 2024

(54) ALLOSTERIC CHROMENONE INHIBITORS OF PHOSPHOINOSITIDE 3-KINASE (PI3K) FOR THE TREATMENT OF DISEASE

(71) Applicant: Petra Pharma Corporation, New York, NY (US)

(72) Inventors: Erin Danielle Anderson, Arvada, CO (US); Sean Douglas Aronow, Boulder, CO (US); Nicholas A. Boyles, Hillsboro, OR (US); Xiaohong Chen, Broomfield, CO (US); Surendra Dawadi, Longmont, CO (US); Eugene R. Hickey, Danbury, CT (US); Thomas Combs Irvin, Erie, CO (US); Edward A. Kesicki, New York, NY (US); Gabrielle R. Kolakowski, Durango, CO (US); Jennifer Lynn Knight, Jersey City, NJ (US); Manoj Kumar, Broomfield, CO (US); Katelyn Frances Long, Lafayette, CO (US); Christopher Glenn Mayne, Boulder, CO (US); Johnathan Alexander McLean, Boulder, CO (US); Gerit Maria Pototschnig, San Diego, CA (US); Hua-Yu Wang, Chula Vista, CA (US); Michael Brian Welch, Westminster, CO (US); Tien Widjaja, Lafayette, CO (US)

(73) Assignee: PETRA PHARMA CORPORATION, New York, NY (US)

( * ) Notice: Subject to any disclaimer, the term of this patent is extended or adjusted under 35 U.S.C. 154(b) by 0 days.

(21) Appl. No.: 17/825,680

(22) Filed: May 26, 2022

(65) Prior Publication Data

US 2023/0096175 A1 Mar. 30, 2023

Related U.S. Application Data

(60) Provisional application No. 63/253,352, filed on Oct. 7, 2021, provisional application No. 63/250,592, filed (Continued)

(51) Int. Cl.

| | |
|---|---|
| ***C07D 405/04*** | (2006.01) |
| ***C07D 405/14*** | (2006.01) |
| ***C07D 407/04*** | (2006.01) |
| ***C07D 413/04*** | (2006.01) |
| ***C07D 417/04*** | (2006.01) |
| ***C07D 417/14*** | (2006.01) |
| ***C07D 471/04*** | (2006.01) |
| ***C07D 487/04*** | (2006.01) |
| ***C07D 491/048*** | (2006.01) |

(Continued)

(52) U.S. Cl.

CPC ......... *C07D 405/04* (2013.01); *C07D 405/14* (2013.01); *C07D 407/04* (2013.01); *C07D 413/04* (2013.01); *C07D 417/04* (2013.01); *C07D 417/14* (2013.01); *C07D 471/04* (2013.01); *C07D 487/04* (2013.01); *C07D 491/048* (2013.01); *C07D 491/052* (2013.01); *C07D 495/04* (2013.01); *C07D 498/04* (2013.01); *C07D 513/04* (2013.01)

(58) Field of Classification Search

CPC .. C07D 405/04; C07D 405/14; C07D 407/04; C07D 487/04; C07D 417/04; C07D 417/14

USPC ...................................................... 514/252.1

See application file for complete search history.

(56) References Cited

U.S. PATENT DOCUMENTS 7,598,377 B2 10/2009 Jackson et al.
7,872,011 B2 1/2011 Jackson et al.

(Continued)

FOREIGN PATENT DOCUMENTS

CN 108299365 A 7/2018
EP 0223744 A2 5/1987

(Continued)

OTHER PUBLICATIONS

Barlaam et al., Journal of Medical Chemistry, vol. 58, No. 2, Jan. 22, 2015, pp. 943-962.

Barlaam et al., Biorganic & Medicinal Chemistry Letters, vol. 26, No. 9, Mar. 11, 2016, pp. 2318-2323.

Fitzgerald et al., Annals of Oncology, v30, Supplement 5, Oct. 1, 2019, p. v110.

(Continued)

*Primary Examiner* — Kahsay Habte
(74) *Attorney, Agent, or Firm* — Joseph M Pletcher

(57) ABSTRACT

The disclosure relates to compounds of Formula (I) as allosteric chromenone inhibitors of phosphoinositide 3-kinase (PI3K) useful in the treatment of diseases or disorders associated with PI3K modulation, Formula (I):

(I)

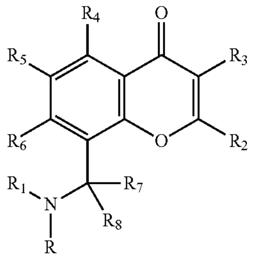

or pharmaceutically acceptable salts thereof wherein R, $R_1$, $R_2$, $R_3$, $R_4$, $R_5$, $R_6$, $R_7$, and $R_8$, are as defined herein. The disclosure also relates to methods of making and using compounds of Formula (I) or pharmaceutically acceptable salts thereof.

65 Claims, No Drawings

Related U.S. Application Data on Sep. 30, 2021, provisional application No. 63/227,493, filed on Jul. 30, 2021, provisional application No. 63/193,917, filed on May 27, 2021.

(51) Int. Cl.

| | |
|---|---|
| ***C07D 491/052*** | (2006.01) |
| ***C07D 495/04*** | (2006.01) |
| ***C07D 498/04*** | (2006.01) |
| ***C07D 513/04*** | (2006.01) |

(56) References Cited

U.S. PATENT DOCUMENTS

| | | | |
|---|---|---|---|
| 8,399,460 | B2 | 3/2013 | Barlaam et al. |
| 8,513,221 | B2 | 8/2013 | Liang et al. |
| 2007/0015802 | A1 | 1/2007 | Lal et al. |
| 2011/0098271 | A1 | 4/2011 | Barlaam et al. |

FOREIGN PATENT DOCUMENTS

| | | | |
|---|---|---|---|
| EP | 0341104 | A2 | 11/1989 |
| WO | 90/06921 | A1 | 6/1990 |
| WO | 01/53266 | A1 | 7/2001 |
| WO | 2004/004632 | A2 | 1/2004 |
| WO | 2004/016607 | A1 | 2/2004 |
| WO | 2009/093972 | A1 | 7/2009 |
| WO | 2010/037127 | A1 | 4/2010 |
| WO | 2010/037129 | A1 | 4/2010 |
| WO | 2011/051704 | A1 | 5/2011 |
| WO | 2017/156520 | A1 | 9/2017 |
| WO | 2021/202964 | A1 | 10/2021 |
| WO | 2021/226677 | A1 | 11/2021 |
| WO | 2022/164812 | A1 | 8/2022 |
| WO | 2022/235574 | A1 | 11/2022 |
| WO | 2022/235575 | A1 | 11/2022 |
| WO | 2023/056407 | A1 | 4/2023 |
| WO | 2023/060262 | A1 | 4/2023 |
| WO | 2023/078401 | A1 | 5/2023 |
| WO | 2023/081209 | A1 | 5/2023 |
| WO | 2023/104111 | A1 | 6/2023 |

OTHER PUBLICATIONS

Gaestel et al., Current Medicinal Chemistry, vol. 14, No. 21, Sep. 1, 2007, pp. 2214-2234.
Giordanetto et al., Bioorganic & Medicinal Chemistry Letters vol. 24, Issue 16, Aug. 15, 2014, pp. 3936-3943.
Golub et al., Science (Oct. 15, 1999), Vo. 286, 531-537.
Hon et al., Oncogene (2012) 31, 3655-3666, published online Nov. 28, 2011.
Klippel, A. et al. Preclinical characterization of LOXO-783 (LOX-22783), a highly potent, mutant selective and brain-penetrant allosteric PI3Kα H1047R inhibitor. Presented at: 2021 AACR-NCI-EORTC Virtual International Conference on Molecular Targets and Cancer Therapeutics, On: Oct. 7, 2021.
Lala et al., Cancer and Metastasis Reviews (Mar. 1998), 17(1), 91-106.
Li et al., Am J Clin Exp Urol 2014; 2(3):188-198; Epub Oct. 2, 2014.
Written Opinion for PCT/US2022/031112 (dated Aug. 1, 2022).
International Search Report for PCT/US2022/031112 (dated Aug. 1, 2022).
Copending U.S. Appl. No. 17/936,973.
Copending U.S. Appl. No. 17/221,209.
Copending U.S. Appl. No. 17/734,705.
Copending U.S. Appl. No. 17/734,745.
Acute Leukemia, Merck Manual (Online Edition) 6 pages, pp. 1-6 (2013).
Fry, Review: Phosphoinositide 3-kinase signaling in breast cancer:how big a role might it play?, Breast Cancer Res 2001, 3:304-312.
Gura, Systems for identifying New Drugs Are Often Faulty, Cancer Models, Science, vol. 278, No. 5340, pp. 1041-1042, Nov. 1997.
Johnson et al., Relationships between drug activity in NCI preclinical in vitro and in vivo models and early clinical trials, British Journal of Cancer (2001) 64(10): 1424-1431 .
Miller et al. Identification of allosteric binding sites for PI3Kα oncogenic mutant specific inhibitor design. Bioorg Med Chem. Feb. 15, 2017; 25(4):1481-1486 .
Pearce et al., Failure modes in anticancer drug discovery and development, Cancer Drug Design and Discovery Edited by Stephen Neidle, Chapter 18, pp. 424-435 (2008).
Simone, Oncology: Introduction, Cecil Textbook of Medicine, 20th Edition, vol. 1, pp. 1004-1101 O, 1996.
Copending U.S. Appl. No. 18/309,226.

ALLOSTERIC CHROMENONE INHIBITORS OF PHOSPHOINOSITIDE 3-KINASE (PI3K) FOR THE TREATMENT OF DISEASE

FIELD

The present invention is directed to allosteric chromenone inhibitors of phosphoinositide 3-kinase (PI3K) useful in the treatment of diseases, or disorders associated with PI3K modulation. The invention is directed toward compounds, and compositions which inhibit PI3K, methods of (or uses for) treating a disease, or disorder associated with PI3K (e.g., CLOVES syndrome (congenital lipomatous overgrowth, vascular malformations, epidermal naevi, scoliosis/skeletal and spinal syndrome), PIK3CA-related overgrowth syndrome (PROS), breast cancer, brain cancer, prostate cancer, endometrial cancer, gastric cancer, leukemia, lymphoma, sarcoma, colorectal cancer, lung cancer, ovarian cancer, skin cancer, or head and neck cancer), and using, or methods of using, PI3K inhibitors in combination with one or more additional cancer therapies.

BACKGROUND

The activity of cells can be regulated by external signals that stimulate, or inhibit intracellular events. The process by which stimulatory, or inhibitory signals are transmitted into, and within a cell to elicit an intracellular response is referred to as signal transduction. Over the past decades, cascades of signal transduction events have been elucidated, and found to play a central role in a variety of biological responses. Defects in various components of signal transduction pathways have been found to account for a vast number of diseases, including numerous forms of cancer, inflammatory disorders, metabolic disorders, vascular, and neuronal diseases (Gaestel et al. *Current Medicinal Chemistry* (2007) 14:2214-2234).

Kinases represent a class of important signaling molecules. Kinases can generally be classified into protein kinases, lipid kinases, and certain kinases exhibiting dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids within cells. These enzymes, and the resulting phosphorylated lipids, and lipid-derived biologically active organic molecules, play a role in many different physiological processes, including cell proliferation, migration, adhesion, and differentiation. A particular group of lipid kinases comprises membrane lipid kinases, i.e., kinases that catalyze the phosphorylation of lipids contained in, or associated with cell membranes. Examples of such enzymes include phosphoinositide(s) kinases (such as PI3-kinases, PI4-Kinases), diacylglycerol kinases, and sphingosine kinases.

The phosphoinositide 3-kinases (PI3Ks) signaling pathway is one of the most highly mutated systems in human cancers. PI3K signaling is involved in many other disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique, and conserved family of intracellular lipid kinases that phosphorylate the 3'-OH group on phosphatidylinositols, or phosphoinositides. The PI3K family comprises 15 kinases with distinct substrate specificities, expression patterns, and modes of regulation (Katso et al., Annu Rev Cell Dev Biol. 2001; 17:615-75). The class I PI3Ks (p110α, p110β, p110δ, and p110γ) are typically activated by tyrosine kinases, or G-protein coupled receptors to generate PIP3, which engages downstream effectors such as those in the pathways of Akt/PDK1, mTOR, the Tec family kinases, and the Rho family GTPases. The class II, and III PI3Ks play a key role in intracellular trafficking through the synthesis of PI(3)P, and PI(3,4)$P_2$.

The PI3K isoforms have been implicated, for example, in a variety of human cancers, and disorders. Mutations in the gene coding for PI3K isoforms, or mutations which lead to upregulation of a PI3K isoform are believed to occur in many human cancers. Mutations in the gene coding for a PI3K isoform are point mutations clustered within several hotspots in helical, and kinase domains. Because of the high rate of PI3K mutations, targeting of this pathway may provide valuable therapeutic opportunities.

Genetic alterations in genes in PI3K signaling are believed to be involved in a range of cancers such as endometrial cancer, breast cancer, esophageal squamous-cell cancer, cervical squamous-cell carcinoma, cervical adenocarcinoma, colorectal adenocarcinoma, bladder urothelial carcinoma, glioblastoma, ovarian cancer, non-small-cell lung cancer, esophagogastric cancer, nerve-sheath tumor, head and neck squamous-cell carcinoma, melanoma, esophagogastric adenocarcinoma, soft-tissue sarcoma, prostate cancer, fibrolamellar carcinoma, hepatocellular carcinoma, diffuse glioma, colorectal cancer, pancreatic cancer, cholangiocarcinoma, B-cell lymphoma, mesothelioma, adrenocortical carcinoma, renal non-clear-cell carcinoma, renal clear-cell carcinoma, germ-cell carcinoma, thymic tumor, pheochromocytoma, miscellaneous neuroepithelial tumor, thyroid cancer, leukemia, and encapsulated glioma (Goncalves M D, Hopkins B D, Cantley L C. Phosphatidylinositoi 3-Kinase, Growth Disorders, and Cancer. N Engl. Jr Med. 2018 Nov. 22; 379(21):2052-2062).

The alpha (α) isoform of PI3K has been implicated, for example, in a variety of human cancers. Angiogenesis has been shown to selectively require the a isoform of PI3K in the control of endothelial cell migration. (Graupera et al, Nature 2008; 453; 662-6). Mutations in the gene coding for PI3Kα, or mutations which lead to upregulation of PI3Kα are believed to occur in many human cancers such as lung, stomach, endometrial, ovarian, bladder, breast, colon, brain, prostate, and skin cancers. Mutations in the gene coding for PI3Kα are point mutations clustered within several hotspots in helical, and kinase domains, such as E542K, E545K, and H1047R.

Many of these mutations have been shown to be oncogenic gain-of-function mutations. Because of the high rate of PI3Kα mutations, targeting of this pathway may provide valuable therapeutic opportunities. While other PI3K isoforms such as PI3Kδ, or PI3Kγ are expressed primarily in hematopoietic cells, PI3Kα, along with PI3Kβ, is expressed constitutively.

Mutated PI3Kα has been implicated in brain metastases in HR+/HER2− metastatic breast cancers. Development of brain-penetrant PI3Kα inhibitors may provide improved therapeutic benefit over current PI3Kα inhibitors. (Fitzgerald et al., Association between PIK3CA mutation status and development of brain metastases in HR+/HER2− metastatic breast cancer. Ann Oncol 30:v110, 2019 (suppl 5)).

Due to the central role of PI3Kα in regulating organismal glucose homeostasis, PI3K inhibition in patients often gives rise to hyperglycemia and/or hyperinsulinemia (Busaidy N L, et al, Management of metabolic effects associated with anticancer agents targeting the PI3K-Akt-mTOR pathway. J Clin Oncol 2012; 30:2919-28). High levels of circulating insulin could potentially be mitogenic and/or antiapoptotic for cancer cells, and thus negate the antiproliferative effects of PI3K inhibitors (Blouin M-J, et al, Abstract 4615: The hyperinsulinemia caused by PI3K inhibitors attenuates their antineoplastic efficacy, but can be minimized by co-administration of metformin. Cancer Res 2013; 73:4615).

In the setting of cancer with mutated PI3Kα, one way to overcome the problem of compensatory production of insulin and/or glucose upon systemic PI3Kα inhibition would be to develop inhibitors with enhanced selectivity for mutant PI3Kα over wild-type PI3Kα. This would create an increased window for drug dosing to selectively inhibit the pathologic signaling of mutant PI3Kα in the cancer cells without affecting the wild-type PI3Kα in the host tissues that control systemic metabolism (Okkenhaug K, Graupera M, Vanhaesebroeck B. Targeting PI3K in Cancer: Impact on Tumor Cells, Their Protective Stroma, Angiogenesis, and Immunotherapy. Cancer Discov. 2016 October; 6(10):1090-1105), thus limiting toxicities, and permitting higher doses, and more complete inhibition of the drug target (Ariella B. Hanker, et al, Challenges for the clinical development of PI3K inhibitors: Strategies to improve their impact in solid tumors. Cancer Discov. 2019 April; 9(4): 482-491).

Currently PI3Kα inhibitors are nearly equipotent to wild-type, and mutant PI3Kα. Mutant selective inhibitors have been elusive due to the PI3Kα mutations location far from the active site. As such, inhibitors which target a second, peripheral binding pocket near a known mutation (e.g., H1047R) may provide a route to selective PI3Kα inhibition. Thus, targeting a mutated, peripheral binding pocket of PI3Kα, provides a valuable therapeutic target for drug development.

As such, kinases, for example lipid kinases such as PI3Ks, are prime targets for drug development. The present invention provides a new class of kinase inhibitors.

SUMMARY

In one aspect, the present invention relates to compounds of Formula (I):

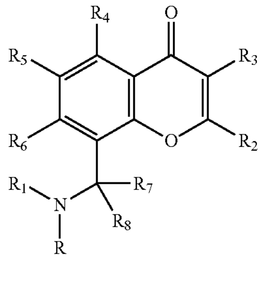

or pharmaceutically acceptable salts thereof, wherein:

R is —H or $C_1$-$C_3$ alkyl;

$R_1$ is a group of the formula:

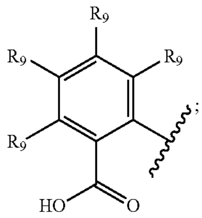
;
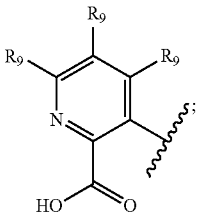
;
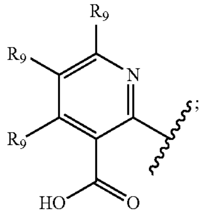
;
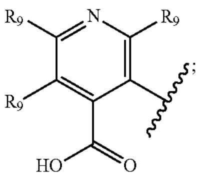
;
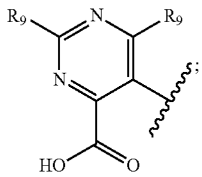
;
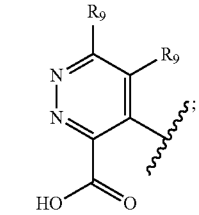
; or
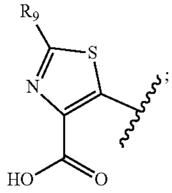
;

$R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine, or an optionally substituted bicyclic heteroaryl of 8 to 10 ring atoms containing 1, 2, 3, 4, or 5 ring heteroatoms independently selected from N, O, or S; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —C(O)$OC_1$-$C_3$ alkyl, —$CONR_{10}R_{10}$, —$NR_{10}R_{10}$, —$NR_{10}CO_2R_{10}$, —OH, an optionally substituted $C_1$-$C_6$ alkyl, an optionally substituted $C_2$-$C_6$ alkenyl, an optionally substituted $C_2$-$C_6$ alkynyl, an optionally substituted $C_3$-$C_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyridine, pyrimidine, pyridazine, pyrazine, pyrazole, isoxazole, isothiazole, imidazole, oxazole, or thiazole; wherein the optionally substituted $C_1$-$C_6$ alkyl, $C_2$-$C_6$ alkenyl, or $C_2$-$C_6$ alkynyl is each optionally substituted with a —CN, —OH, oxetanyl, $C_1$-$C_3$ alkoxy, —$CONR_{10}R_{10}$, or phenyl; the optionally substituted $C_3$-$C_5$ cycloalkyl, phenyl, 1,3-benzodioxole, 2,3-dihydro-1,4-benzodioxine, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$SO_2R_{10}$, —$NR_{10}R_{10}$, —OH or —CN;

$R_3$ is —H, halogen, —CN, —N(H)($C_1$-$C_3$ alkyl), —N($C_1$-$C_3$ alkyl)$_2$, —N(H)($CH_2CH_2CO_2H$), —C(O)$C_1$-$C_3$ alkyl, $C_1$-$C_6$ alkyl $C_1$-$C_6$ haloalkyl, $C_1$-$C_6$ hydroxyalkyl, $C_3$-$C_5$ cycloalkyl, an optionally substituted heterocycle of 3 to 5 ring atoms containing 1, 2, or 3 ring heteroatoms independently selected from N, O, or S, or an optionally substituted heteroaryl of 5 or 6 ring atoms containing 1, 2, or 3 ring heteroatoms independently selected from N, O, or S; wherein the optionally substituted heterocycle or heteroaryl is each optionally substituted with one to three substituents each independently selected from halogen, $C_1$-$C_3$ alkyl, or $C_1$-$C_3$ haloalkyl;

each of $R_4$, $R_5$ and $R_6$ is independently —H, halogen, $C_1$-$C_6$ alkyl or $C_1$-$C_6$ haloalkyl;

$R_7$ is —CN, $C_1$-$C_6$ alkyl or $C_1$-$C_6$ haloalkyl;

$R_8$ is —H or $C_1$-$C_6$ alkyl;

each $R_9$ is independently —H, halogen, —CN, $C_1$-$C_6$ alkyl, $C_1$-$C_6$ haloalkyl, $C_1$-$C_6$ alkoxy or $C_3$-$C_5$ cycloalkyl; and each $R_{10}$ is independently —H or $C_1$-$C_3$ alkyl.

In another aspect, the present invention provides a pharmaceutical composition comprising a compound of Formula (I), (II), or (III), or a pharmaceutically acceptable salt thereof, and a pharmaceutically acceptable diluent, or carrier.

In another aspect, the present invention provides a method of modulating PI3K (e.g., PI3Kα) activity (e.g., in vitro, or in vivo), comprising contacting a cell with a therapeutically effective amount of a compound of Formula (I), (II), or (III), or a pharmaceutically acceptable salt thereof.

In some aspects, the present invention provides a method of treating, or preventing a disease, or disorder disclosed herein in a subject in need thereof, comprising administering to the subject a therapeutically effective amount of a compound of Formula (I), (II), or (III), or a pharmaceutically acceptable salt thereof.

In some aspects, the present invention provides a method of treating, or preventing a disease, or disorder disclosed herein in a subject in need thereof, comprising administering to the subject a therapeutically effective amount of a pharmaceutical composition of a compound of Formula (I), (II), or (III), or a pharmaceutically acceptable salt thereof.

In some aspects, the present invention provides a method of treating a disease, or disorder disclosed herein in a subject in need thereof, comprising administering to the subject a therapeutically effective amount of a compound of Formula (I), (II), or (III), or a pharmaceutically acceptable salt thereof.

In some aspects, the present invention provides a method of treating a disease, or disorder disclosed herein in a subject in need thereof, comprising administering to the subject a therapeutically effective amount of a pharmaceutical composition of a compound of Formula (I), (II), or (III), or a pharmaceutically acceptable salt thereof.

In another aspect, the present invention provides a compound of Formula (I), (II), or (III), or a pharmaceutically acceptable salt thereof for use in therapy.

In another aspect, the present invention provides a compound of Formula (I), (II), or (III), or a pharmaceutically acceptable salt thereof for use in modulating PI3K (e.g., PI3Kα) activity (e.g., in vitro, or in vivo).

In another aspect, the present invention provides a compound of Formula (I), (II), or (III), or a pharmaceutically acceptable salt thereof, for use in selective inhibition for mutant PI3Kα over wild-type PI3Kα.

In another aspect, the present invention provides a compound of Formula (I), (II), or (III), or a pharmaceutically acceptable salt thereof, for use in treating, or preventing a disease, or disorder disclosed herein.

In another aspect, the present invention provides a compound of Formula (I), (II), or (III), or a pharmaceutically acceptable salt thereof, for use in treating a disease, or disorder disclosed herein.

In another aspect, the present invention provides use of a compound of Formula (I), (II), or (III), or a pharmaceutically acceptable salt thereof, in the manufacture of a medicament for modulating PI3K (e.g., PI3Kα) activity (e.g., in vitro, or in vivo).

In another aspect, the present invention provides use of a compound of Formula (I), (II), or (III), or a pharmaceutically acceptable salt thereof, in the manufacture of a medicament for treating, or preventing a disease, or disorder disclosed herein.

In another aspect, the present invention provides use of a compound of Formula (I), (II), or (III), or a pharmaceutically acceptable salt thereof, in the manufacture of a medicament for treating a disease, or disorder disclosed herein.

In another aspect, the present invention provides a method of preparing a compound of Formula (I), (II), or (III), or a pharmaceutically acceptable salt thereof.

In another aspect, the present invention provides a method of preparing a compound, comprising one, or more steps described herein.

In another aspect, the present invention provides a compound obtainable by, or obtained by, a method for preparing a compound as described herein (e.g., a method comprising one, or more steps described in the Schemes).

In another aspect, the present invention provides an intermediate as described herein, being suitable for use in a method for preparing a compound as described herein (e.g., the intermediate is selected from the intermediates described in the Examples).

Other features, and advantages of the invention will be apparent from the following detailed description, and claims.

DETAILED DESCRIPTION

The present invention provides methods of treating, preventing, or ameliorating a disease, or disorder, (or uses in the treatment, prevention, or amelioration of a disease, or disorder), in which PI3K plays a role by administering to a patient in need thereof a therapeutically effective amount of a PI3K inhibitor of the present invention. The methods (or uses) of the present invention can be used in the treatment of a variety of PI3K-dependent diseases, and disorders.

In some embodiments, the disease, or disorder is a cancer (e.g., breast cancer, brain cancers, prostate cancer, endometrial cancer, gastric cancer, leukemia, lymphoma, sarcoma, colorectal cancer, lung cancer, ovarian cancer, skin cancer, or head and neck cancer). In some embodiments, the disease, or disorder associated with PI3K includes, but is not limited to, CLOVES syndrome (congenital lipomatous overgrowth, vascular malformations, epidermal naevi, scoliosis/skeletal and spinal syndrome), PIK3CA-related overgrowth syndrome (PROS), endometrial cancer, breast cancer, esophageal squamous-cell cancer, cervical squamous-cell carcinoma, cervical adenocarcinoma, colorectal adenocarcinoma, bladder urothelial carcinoma, glioblastoma, ovarian cancer, non-small-cell lung cancer, esophagogastric cancer, nerve-sheath tumor, head and neck squamous-cell carcinoma, melanoma, esophagogastric adenocarcinoma, soft-tissue sarcoma, prostate cancer, fibrolamellar carcinoma, hepatocellular carcinoma, diffuse glioma, colorectal cancer, pancreatic cancer, cholangiocarcinoma, B-cell lymphoma, mesothelioma, adrenocortical carcinoma, renal non-clear-cell carcinoma, renal clear-cell carcinoma, germ-cell carcinoma, thymic tumor, pheochromocytoma, miscellaneous neuroepithelial tumor, thyroid cancer, leukemia, and encapsulated glioma.

The details of the invention are set forth in the accompanying description below. Although methods, and materials similar, or equivalent to those described herein can be used in the practice, or testing of the present disclosure, illustrative methods, and materials are now described. Other features, objects, and advantages of the invention will be apparent from the description, and from the claims. In the specification, and the appended claims, the singular forms also include the plural unless the context clearly dictates otherwise. Unless defined otherwise, all technical, and scientific terms used herein have the same meaning as commonly understood by one of ordinary skill in the art to which this invention belongs. All patents, and publications cited in this specification are incorporated herein by reference in their entireties.

Definitions

The articles "a", and "an" refer to one, or more than one (i.e., to at least one) of the grammatical object of the article. By way of example, "an element" means one element, or more than one element.

The term "and/or" means either "and", or "or" unless indicated otherwise.

The term "administer", "administering", or "administration" refers to either directly administering a disclosed compound, or pharmaceutically acceptable salt of the disclosed compound, or a composition to a subject.

The term "alkenyl" refers to a straight, or branched chain unsaturated hydrocarbon containing 2-12 carbon atoms. The "alkenyl" group contains at least one double bond in the chain. The double bond of an alkenyl group can be unconjugated, or conjugated to another unsaturated group. Examples of alkenyl groups include ethenyl, propenyl, n-butenyl, iso-butenyl, pentenyl, or hexenyl.

The term "alkoxy" refers to a straight, or branched chain saturated hydrocarbon containing 1-12 carbon atoms containing a terminal "0" in the chain, i.e., —O(alkyl). Examples of alkoxy groups include without limitation, methoxy, ethoxy, propoxy, butoxy, t-butoxy, or pentoxy groups.

The term "alkyl" refers to a straight, or branched chain saturated hydrocarbon containing 1-12 carbon atoms, preferably 1-6 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

The term "alkynyl" refers to a straight, or branched chain unsaturated hydrocarbon containing 2-12 carbon atoms. The "alkynyl" group contains at least one triple bond in the chain. Examples of alkynyl groups include ethynyl, propargyl, n-butynyl, iso-butynyl, pentynyl, or hexynyl.

The term "aromatic" means a planar ring having 4n+2 electrons in a conjugated system. As used herein, "conjugated system" means a system of connected p-orbitals with delocalized electrons, and the system may include lone electron pairs.

The term "aryl" unless otherwise specifically defined refers to cyclic, aromatic hydrocarbon groups that have 1 to 3 aromatic rings, including monocyclic, or bicyclic groups such as phenyl, biphenyl, or naphthyl. Where containing two aromatic rings (bicyclic, etc.), the aromatic rings of the aryl group may be joined at a single point (e.g., biphenyl), or fused (e.g., naphthyl). Furthermore, when containing two fused rings the aryl groups herein defined may have one, or more saturated, or partially unsaturated ring fused with a fully unsaturated aromatic ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, and tetrahydrob enzoannulenyl.

The term "carrier" encompasses carriers, excipients, and diluents, and means a material, composition, or vehicle, such as a liquid, or solid filler, diluent, excipient, solvent, or encapsulating material, involved in carrying, or transporting a pharmaceutical agent from one organ, or portion of the body, to another organ, or portion of the body of a subject.

The term "cyano" means a substituent having a carbon atom joined to a nitrogen atom by a triple bond, i.e., C≡N.

The term "cycloalkyl" means mono, or polycyclic saturated carbon rings containing 3-18 carbon atoms, preferably 3-10 carbon atoms. Examples of cycloalkyl groups include, without limitation, cyclopropyl, cyclobutyl, cyclopentyl, cyclohexyl, cycloheptanyl, cyclooctanyl, norbornyl, norborenyl, bicyclo[2.2.2]octanyl, and bicyclo[2.2.2]octenyl.

The term "disorder" means, and is used interchangeably with, the terms disease, condition, or illness, unless otherwise indicated.

The term "haloalkoxy" refers to an alkoxy group, as defined herein, which is substituted with one, or more halogen. Examples of haloalkoxy groups include, but are not limited to, trifluoromethoxy, difluoromethoxy, pentafluoroethoxy, and trichloromethoxy.

The term "haloalkyl" refers to an alkyl group, as defined herein, which is substituted with one, or more halogens. Examples of haloalkyl groups include, but are not limited to, trifluoromethyl, difluoromethyl, pentafluoroethyl, and trichloromethyl.

The term "halogen" or "halo" refers to fluorine, chlorine, bromine, or iodine.

The term "heteroaryl" unless otherwise specifically defined means a monovalent monocyclic, or a polycyclic aromatic radical of 5 to 24 ring atoms, preferably 5 to 10 ring atoms, containing one, or more ring heteroatoms selected from N, O, S, P, or B, preferably 1, 2, 3, or 4 ring heteroatoms selected from N, O, or S, the remaining ring atoms being C. A polycyclic aromatic radical includes two, or more fused rings, and may further include two, or more spiro-fused rings, e.g., bicyclic, tricyclic, tetracyclic, and the like. Unless otherwise specifically defined, "fused" means two rings sharing two ring atoms. Unless otherwise specifically defined, "spiro-fused" means two rings sharing one ring atom. Heteroaryl as herein defined also means a bicyclic heteroaromatic group wherein the heteroatom is selected from N, O, S, P, or B, preferably N, O, or S. Heteroaryl as herein defined also means a tricyclic heteroaromatic group containing one, or more ring heteroatoms selected from N, O, S, P, or B, preferably N, O, or S. Heteroaryl as herein defined also means a tetracyclic heteroaromatic group containing one, or more ring heteroatoms selected from N, O, S, P, or B, preferably N, O, or S. Examples of heteroaromatic groups include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolinyl, indolinonyl, dihydrobenzothiophenyl, dihydrobenzofuranyl, benzofuranyl, chromanyl, thiochromanyl, tetrahydroquinolinyl, dihydrobenzothiazinyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, and 3H-indolyl. Furthermore, when containing two, or more fused rings, the heteroaryl groups defined herein may have one, or more saturated, or partially unsaturated ring fused with one, or more fully unsaturated aromatic ring. In heteroaryl ring systems containing more than two fused rings, a saturated, or partially unsaturated ring may further be fused with a saturated, or partially unsaturated ring described herein. Furthermore, when containing three, or more fused rings, the heteroaryl groups defined herein may have one, or more saturated, or partially unsaturated ring spiro-fused. Any saturated, or partially unsaturated ring described herein is optionally substituted with one, or more oxo. Exemplary ring systems of these heteroaryl groups include, for example, indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuranyl, benzofuranonyl, oxindolyl, indolyl, 1,6-dihydro-7H-pyrazolo[3,4-c]pyridin-7-onyl, 7,8-dihydro-6H-pyrido[3,2-b]pyrrolizinyl, 8H-pyrido[3,2-b]pyrrolizinyl, 1,5,6,7-tetrahydrocyclopenta[b]pyrazolo[4,3-e]pyridinyl, 7,8-dihydro-6H-pyrido[3,2-b]pyrrolizinyl, pyrazolo[1,5-a]pyrimidin-7(4H)-onyl, 3,4-dihydropyrazino[1,2-a]indol-1(2H)-onyl, benzo[c][1,2]oxaborol-1(3H)-olyl, 6,6a,7,8-tetrahydro-9H-pyrido[2,3-b]pyrrolo[1,2-d][1,4]oxazin-9-onyl, and 6a',7'-dihydro-6'H,9'H-spiro[cyclopropane-1,8'-pyrido[2,3-b]pyrrolo[1,2-d][1,4]oxazin]-9'-onyl. Further exemplary bicyclic heteroaryl groups include, but are not limited to, indole, benzothiophene, benzofuran, isoindole, benzo[c]thiophene, isobenzofuran, indazole, benzimidazole, benzoxazole, benzothiazole, benzisoxazole, benzisothiazole, pyrrolopyridine, furopyridine, thienopyridine, pyrazolopyridine, isoxazolepyridine, isothiazolepyridine, imidazopyridine, oxazolepyridine, thiazolepyridine, pyrrolopyridazine, pyrrolopyrimidine, pyrrolopyrazine, furopyridazine, furopyrimidine, furopyrazine, thienopyridazine, thienopyrimidine, thienopyrazine, pyrazolopyrimidine, pyrazolopyridazine, pyrazolopyrazine, isoxazolepyridazine, isoxazolepyrimidine, isoxazolepyrazine, isothiazolepyridazine, isothiazolepyrimidine, isothiazolepyrazine, imidazopyridazine, imidazopyrimidine, imidazopyrazine, oxazolepyridazine, oxazolepyrimidine, oxazolepyrazine thiazolepyridazine, thiazolepyrimidine, thiazolepyrazine, quinazoline, quinoxaline, cinnoline, phthalazine, pyridopyridazine, pyridopyrimidine, pyridopyrazine, pyridazinopyridazine, pyrimidopyridazine, pyrazinopyridazine, pyrimidopyrimidine, pteridine, pyrazinopyrazine, pyridotriazine, pyridazinotriazine, pyrimidotriazine, and pyrazinotriazine.

The term "heterocyclyl", "heterocycle", or "heterocycloalkyl" means mono, or polycyclic rings containing 3-24 atoms, preferably 3-10 atoms, which include carbon, and one, or more heteroatoms selected from N, O, S, P, or B, preferably 1, 2, 3, or 4 heteroatoms selected from N, O, and S, and wherein the rings are not aromatic. Examples of heterocyclyl rings include, but are not limited to, oxetanyl, azetidinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl.

The term "hydroxyalkyl" refers to an alkyl group, as defined herein, which is substituted with a hydroxy group.

The term "isomers" refers to compounds that have the same molecular formula but differ in the nature or sequence of bonding of their atoms or the arrangement of their atoms in space. Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomers or as a mixture thereof. A mixture containing equal proportions of the enantiomers is called a "racemic mixture".

The term "modulate", "modulation", or "modulating" refers to a biological activity of a compound, or substrate that inhibits and/or activates PI3K.

The term "patient", or "subject" is a mammal, e.g., a human, mouse, rat, guinea pig, dog, cat, horse, cow, pig, or non-human primate, such as a monkey, chimpanzee, baboon, or rhesus. Preferably, the mammal is human.

The term "therapeutically effective amount" when used in connection with a compound refers to the amount or dose of the compound which upon single or multiple dose administration to the patient, provides the desired effect in the patient under diagnosis or treatment. An effective amount can be determined by one skilled in the art by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The term "treating" with regard to a subject, includes restraining, slowing, stopping, or reversing the progression or severity of an existing symptom or disorder.

Compounds of the Present Invention

In one aspect, the present invention provides compounds of Formula (I), or pharmaceutically acceptable salts thereof:

(I)

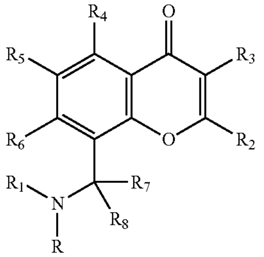

wherein R, $R_1$, $R_2$, $R_3$, $R_4$, $R_5$, $R_6$, $R_7$, and $R_8$, are as defined in the Summary for Formula (I).

In a further aspect, compounds of Formula (I) wherein $R_8$ is H have Formula (II), or pharmaceutically acceptable salts thereof:

(II)

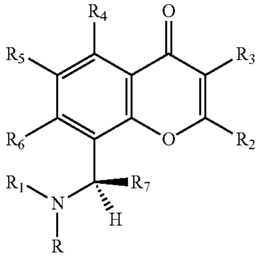

wherein R, $R_1$, $R_2$, $R_3$, $R_4$, $R_5$, $R_6$, and $R_7$, are as defined in the Summary for Formula (I).

In a compound of Formula (I), or pharmaceutically acceptable salts thereof,

R is —H or $C_1$-$C_3$ alkyl;

$R_1$ is a group of the formula:

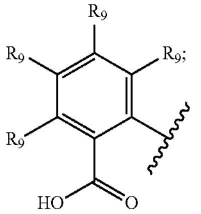

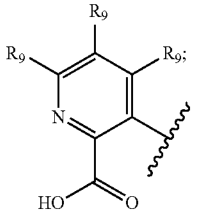

-continued

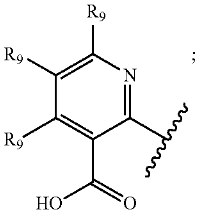

;

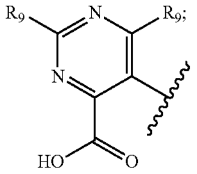

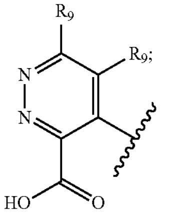

or

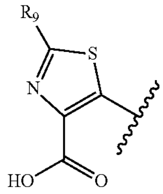

;

$R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine, or an optionally substituted bicyclic heteroaryl of 8 to 10 ring atoms containing 1, 2, 3, 4, or 5 ring heteroatoms independently selected from N, O, or S; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$CONR_{10}R_{10}$, —$NR_{10}R_{10}$, —$NR_{10}CO_2R_{10}$, an optionally substituted $C_1$-$C_6$ alkyl, an optionally substituted $C_2$-$C_6$ alkenyl, an optionally substituted $C_2$-$C_6$ alkynyl, an optionally substituted $C_3$-$C_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyridine, pyrimidine, pyridazine, pyrazine, pyrazole, isoxazole, isothiazole, imidazole, oxazole, or thiazole; wherein the optionally substituted $C_1$-$C_6$ alkyl, $C_2$-$C_6$ alkenyl, or $C_2$-$C_6$ alkynyl is each optionally substituted with a —CN, —OH, oxetanyl, or $C_1$-$C_3$ alkoxy; the optionally substituted $C_3$-$C_5$ cycloalkyl, phenyl, 1,3-benzodioxole, 2,3-dihydro-1,4-benzodioxine, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$SO_2R_{10}$, —$NR_{10}R_{10}$, —OH or —CN;

$R_3$ is —H, halogen, —CN, $C_1$-$C_6$ alkyl, $C_1$-$C_6$ haloalkyl, $C_3$-$C_5$ cycloalkyl, a heterocycle of 3 to 5 ring atoms containing 1, 2, or 3 ring heteroatoms independently selected from N, O, or S, or a heteroaryl of 5 ring atoms containing 1, 2, or 3 ring heteroatoms independently selected from N, O, or S;

each of $R_4$, $R_5$ and $R_6$ is independently —H, halogen, $C_1$-$C_6$ alkyl or $C_1$-$C_6$ haloalkyl;

$R_7$ is —CN, $C_1$-$C_6$ alkyl or $C_1$-$C_6$ haloalkyl;

$R_8$ is —H or $C_1$-$C_6$ alkyl;

each $R_9$ is independently —H, halogen, $C_1$-$C_6$ alkyl, $C_1$-$C_6$ haloalkyl, $C_1$-$C_6$ alkoxy or $C_3$-$C_5$ cycloalkyl; and each $R_{10}$ is independently —H or $C_1$-$C_3$ alkyl.

In a compound of Formula (I), or pharmaceutically acceptable salts thereof,

R is —H or $C_1$-$C_3$ alkyl;

$R_1$ is a group of the formula:

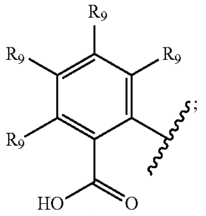

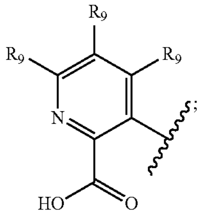

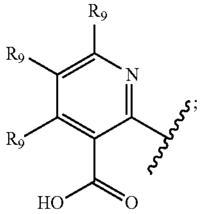

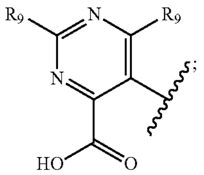

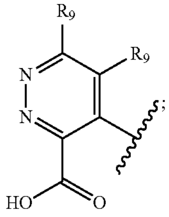

or

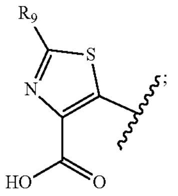

$R_2$ is an optionally substituted bicyclic ring selected from 1,3-benzodioxole, 2,3-dihydro-1,4-benzodioxine, isoindolin-1-one, indolin-2-one, or benzo[d]oxazol-2(3H)-one, or an optionally substituted bicyclic heteroaryl of 8 to 10 ring atoms containing 1, 2, 3, 4, or 5 ring heteroatoms independently selected from N, O, or S; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$CONR_{10}R_{10}$, —$NR_{10}R_{10}$, —$NR_{10}CO_2R_{10}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN;

$R_3$ is —H, —CN, $C_1$-$C_6$ alkyl or $C_1$-$C_6$ haloalkyl;

each of $R_4$, $R_5$ and $R_6$ is independently —H, halogen, $C_1$-$C_6$ alkyl or $C_1$-$C_6$ haloalkyl;

$R_7$ is —CN, $C_1$-$C_6$ alkyl or $C_1$-$C_6$ haloalkyl;

$R_8$ is —H or $C_1$-$C_6$ alkyl;

each $R_9$ is independently —H, halogen, $C_1$-$C_6$ alkyl, $C_1$-$C_6$ haloalkyl, $C_1$-$C_6$ alkoxy or $C_3$-$C_5$ cycloalkyl; and each $R_{10}$ is independently —H or $C_1$-$C_3$ alkyl In a compound of Formula (I), or pharmaceutically acceptable salts thereof, R is —H or $C_1$-$C_3$ alkyl;

$R_1$ is a group of the formula:

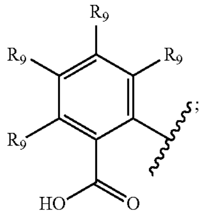

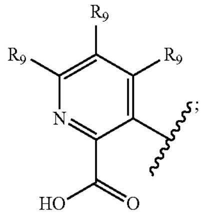

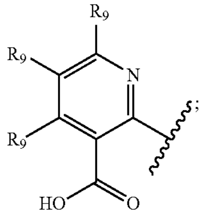

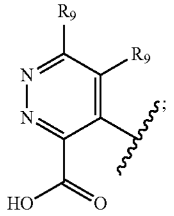

or

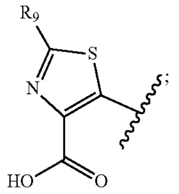

$R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$CONR_{10}R_{10}$, —$NR_{10}R_{10}$, —$NR_{10}CO_2R_{10}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN;

$R_3$ is —H, —CN, $C_1$-$C_6$ alkyl or $C_1$-$C_6$ haloalkyl;

each of $R_4$, $R_5$ and $R_6$ is independently —H, halogen, $C_1$-$C_6$ alkyl or $C_1$-$C_6$ haloalkyl;

$R_7$ is —CN, $C_1$-$C_6$ alkyl or $C_1$-$C_6$ haloalkyl;

$R_8$ is —H or $C_1$-$C_6$ alkyl;

each $R_9$ is independently —H, halogen, $C_1$-$C_6$ alkyl, $C_1$-$C_6$ haloalkyl, $C_1$-$C_6$ alkoxy or $C_3$-$C_5$ cycloalkyl; and each $R_{10}$ is independently —H or $C_1$-$C_3$ alkyl.

In a compound of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine, or an optionally substituted bicyclic heteroaryl of 8 to 10 ring atoms containing 1, 2, 3, 4, or 5 ring heteroatoms independently selected from N, O, or S; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$CONR_{10}R_{10}$, —$NR_{10}R_{10}$, —$NR_{10}CO_2R_{10}$, an optionally substituted $C_1$-$C_6$ alkyl, an optionally substituted $C_2$-$C_6$ alkenyl, an optionally substituted $C_2$-$C_6$ alkynyl, an optionally substituted $C_3$-$C_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyridine, pyrimidine, pyridazine, pyrazine, pyrazole, isoxazole, isothiazole, imidazole, oxazole, or thiazole; wherein the optionally substituted $C_1$-$C_6$ alkyl, $C_2$-$C_6$ alkenyl, or $C_2$-$C_6$ alkynyl is each optionally substituted with a —CN, —OH, oxetanyl, or $C_1$-$C_3$ alkoxy; the optionally substituted $C_3$-$C_5$ cycloalkyl, phenyl, 1,3-benzodioxole, 2,3-dihydro-1,4-benzodioxine, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$SO_2R_{10}$, —$NR_{10}R_{10}$, —OH or —CN.

In a compound of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, indolin-2-one, or benzo[d]oxazol-2(3H)-one, or an optionally substituted bicyclic heteroaryl of 8 to 10 ring atoms containing 1, 2, 3, 4, or 5 ring heteroatoms independently selected from N, O, or S; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$CONR_{10}R_{10}$, —$NR_{10}R_{10}$, —$NR_{10}CO_2R_{10}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In a compound of Formula (I), or (II), or pharmaceutically acceptable salts thereof, $R_2$ is an optionally substituted bicyclic heteroaryl and the optionally substituted bicyclic heteroaryl is a phenyl, pyridine, pyrazine, pyrimidine, or pyridazine ring fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$C(O)OC_1$-$C_3$ alkyl, —$CONR_{10}R_{10}$, —$NR_{10}R_{10}$, —$NR_{10}CO_2R_{10}$, —OH, an optionally substituted $C_1$-$C_6$ alkyl, an optionally substituted $C_2$-$C_6$ alkenyl, an optionally substituted $C_2$-$C_6$ alkynyl, an optionally substituted $C_3$-$C_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyridine, pyrimidine, pyridazine, pyrazine, pyrazole, isoxazole, isothiazole, imidazole, oxazole, or thiazole; wherein the optionally substituted $C_1$-$C_6$ alkyl, $C_2$-$C_6$ alkenyl, or $C_2$-$C_6$ alkynyl is each optionally substituted with a —CN, —OH, oxetanyl, $C_1$-$C_3$ alkoxy, —$CONR_{10}R_{10}$, or phenyl; the optionally substituted $C_3$-$C_5$ cycloalkyl, phenyl, 1,3-benzodioxole, 2,3-dihydro-1,4-benzodioxine, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$SO_2R_{10}$, —$NR_{10}R_{10}$, —OH or —CN In a compound of Formula (I), or (II), or pharmaceutically acceptable salts thereof, $R_2$ is an optionally substituted bicyclic heteroaryl and the optionally substituted bicyclic heteroaryl is a phenyl, pyridine, pyrazine, pyrimidine, or pyridazine ring fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$CONR_{10}R_{10}$, —$NR_{10}R_{10}$, —$NR_{10}CO_2R_{10}$, an optionally substituted $C_1$-$C_6$ alkyl, an optionally substituted $C_2$-$C_6$ alkenyl, an optionally substituted $C_2$-$C_6$ alkynyl, an optionally substituted $C_3$-$C_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyridine, pyrimidine, pyridazine, pyrazine, pyrazole, isoxazole, isothiazole, imidazole, oxazole, or thiazole; wherein the optionally substituted $C_1$-$C_6$ alkyl, $C_2$-$C_6$ alkenyl, or $C_2$-$C_6$ alkynyl is each optionally substituted with a —CN, —OH, oxetanyl, or $C_1$-$C_3$ alkoxy; the optionally substituted $C_3$-$C_5$ cycloalkyl, phenyl, 1,3-benzodioxole, 2,3-dihydro-1,4-benzodioxine, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$SO_2R_{10}$, —$NR_{10}R_{10}$, —OH or —CN; preferably the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$CONR_{10}R_{10}$, —$NR_{10}R_{10}$, —$NR_{10}CO_2R_{10}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In a compound of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, indolin-2-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$CONR_{10}R_{10}$, —$NR_{10}R_{10}$, —$NR_{10}CO_2R_{10}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In a compound of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$CONR_{10}R_{10}$, —$NR_{10}R_{10}$, —$NR_{10}CO_2R_{10}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In a compound of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, indolin-2-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In a compound of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In a compound of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine, or an optionally substituted bicyclic heteroaryl selected from indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, quinazoline, naphthyridine, quinoline, or oxazolopyridine; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —C(O)O$C_1$-$C_3$ alkyl, —$CONR_{10}R_{10}$, —$NR_{10}R_{10}$, —$NR_{10}CO_2R_{10}$, —OH, an optionally substituted $C_1$-$C_6$ alkyl, an optionally substituted $C_2$-$C_6$ alkenyl, an optionally substituted $C_2$-$C_6$ alkynyl, an optionally substituted $C_3$-$C_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyridine, pyrimidine, pyridazine, pyrazine, pyrazole, isoxazole, isothiazole, imidazole, oxazole, or thiazole; wherein the optionally substituted $C_1$-$C_6$ alkyl, $C_2$-$C_6$ alkenyl, or $C_2$-$C_6$ alkynyl is each optionally substituted with a —CN, —OH, oxetanyl, $C_1$-$C_3$ alkoxy, —$CONR_{10}R_{10}$, or phenyl; the optionally substituted $C_3$-$C_5$ cycloalkyl, phenyl, 1,3-benzodioxole, 2,3-dihydro-1,4-benzodioxine, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$SO_2R_{10}$, —$NR_{10}R_{10}$, —OH or —CN.

In a compound of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine, or an optionally substituted bicyclic heteroaryl selected from indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, quinazoline, or naphthyridine; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$CONR_{10}R_{10}$, —$NR_{10}R_{10}$, —$NR_{10}CO_2R_{10}$, an optionally substituted $C_1$-$C_6$ alkyl, an optionally substituted $C_2$-$C_6$ alkenyl, an optionally substituted $C_2$-$C_6$ alkynyl, an optionally substituted $C_3$-$C_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyridine, pyrimidine, pyridazine, pyrazine, pyrazole, isoxazole, isothiazole, imidazole, oxazole, or thiazole; wherein the optionally substituted $C_1$-$C_6$ alkyl, $C_2$-$C_6$ alkenyl, or $C_2$-$C_6$ alkynyl is each optionally substituted with a —CN, —OH, oxetanyl, or $C_1$-$C_3$ alkoxy; the optionally substituted $C_3$-$C_5$ cycloalkyl, phenyl, 1,3-benzodioxole, 2,3-dihydro-1,4-benzodioxine, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$SO_2R_{10}$, —$NR_{10}R_{10}$, —OH or —CN.

In yet a further compound of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine, or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, indolin-2-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine, or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, quinazoline, or naphthyridine (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$CONR_{10}R_{10}$, —$NR_{10}R_{10}$, —$NR_{10}CO_2R_{10}$, an optionally substituted $C_1$-$C_6$ alkyl, an optionally substituted $C_2$-$C_6$ alkenyl, an optionally substituted $C_2$-$C_6$ alkynyl, an optionally substituted $C_3$-$C_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyridine, pyrimidine, pyridazine, pyrazine, pyrazole, isoxazole, isothiazole, imidazole, oxazole, or thiazole; wherein the optionally substituted $C_1$-$C_6$ alkyl, $C_2$-$C_6$ alkenyl, or $C_2$-$C_6$ alkynyl is each optionally substituted with a —CN, —OH, oxetanyl, or $C_1$-$C_3$ alkoxy; the optionally substituted $C_3$-$C_5$ cycloalkyl, phenyl, 1,3-benzodioxole, 2,3-dihydro-1,4-benzodioxine, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$SO_2R_{10}$, —$NR_{10}R_{10}$, —OH or —CN; preferably the optionally substituted bicyclic ring is optionally substituted with one to three substituents each independently selected from halogen and $C_1$-$C_6$ alkyl; and the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ alkyl optionally substituted with —OH or oxetanyl, or a heteroaryl selected from a pyridine or oxazole.

In yet a further embodiment of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine, or an optionally substituted bicyclic heteroaryl selected from indole, indazole, pyrrolo[2,3-b]pyridine, pyrrolo[3,2-b]pyridine, furo[2,3-c]pyridine, furo[3,2-c]pyridine, pyrazolo[1,5-a]pyridine, pyrazolo[3,4-b]pyridine, pyrazolo[3,4-c]pyridine, pyrazolo[4,3-b]pyridine, imidazo[1,2-a]pyridine, imidazo[1,5-a]pyridine, pyrazolo[1,5-a]pyrimidine, imidazo[1,2-b]pyridazine, phthalazine, [1,2,4]triazolo[4,3-a]pyridine, triazolo[1,5-a]pyridine, benzimidazole, pyrrolo[2,3-d]pyrimidine, thiazolo[5,4-b]pyridine, benzotriazole, 1,3-benzoxazole, 1,3-benzothiazole, pyrrolo[1,2-a]pyrazine, quinazoline, 1,5-naphthyridine, 1,7-naphthyridine, quinoline, or oxazolo[5,4-b]pyridine; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$C(O)OC_1$-$C_3$ alkyl, —$CONR_{10}R_{10}$, —$NR_{10}R_{10}$, —$NR_{10}CO_2R_{10}$, —OH, an optionally substituted $C_1$-$C_6$ alkyl, an optionally substituted $C_2$-$C_6$ alkenyl, an optionally substituted $C_2$-$C_6$ alkynyl, an optionally substituted $C_3$-$C_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyridine, pyrimidine, pyridazine, pyrazine, pyrazole, isoxazole, isothiazole, imidazole, oxazole, or thiazole; wherein the optionally substituted $C_1$-$C_6$ alkyl, $C_2$-$C_6$ alkenyl, or $C_2$-$C_6$ alkynyl is each optionally substituted with a —CN, —OH, oxetanyl, $C_1$-$C_3$ alkoxy, —$CONR_{10}R_{10}$, or phenyl; the optionally substituted $C_3$-$C_5$ cycloalkyl, phenyl, 1,3-benzodioxole, 2,3-dihydro-1,4-benzodioxine, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$SO_2R_{10}$, —$NR_{10}R_{10}$, —OH or —CN.

In yet a further embodiment of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine, or an optionally substituted bicyclic heteroaryl selected from indole, indazole, pyrrolo[2,3-b]pyridine, pyrrolo[3,2-b]pyridine, furo[2,3-c]pyridine, furo[3,2-c]pyridine, pyrazolo[1,5-a]pyridine, pyrazolo[3,4-b]pyridine, pyrazolo[3,4-c]pyridine, pyrazolo[4,3-b]pyridine, imidazo[1,2-a]pyridine, imidazo[1,5-a]pyridine, pyrazolo[1,5-a]pyrimidine, imidazo[1,2-b]pyridazine, phthalazine, [1,2,4]triazolo[4,3-a]pyridine, triazolo[1,5-a]pyridine, benzimidazole, pyrrolo[2,3-d]pyrimidine, thiazolo[5,4-b] pyridine, benzotriazole, 1,3-benzoxazole, 1,3-benzothiazole, pyrrolo[1,2-a]pyrazine, quinazoline, or 1,7-naphthyridine; wherein the optionally substituted bicyclic ring is optionally substituted with one to three substituents each independently selected from halogen and $C_1$-$C_6$ alkyl; and the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$CONR_{10}R_{10}$, —$NR_{10}R_{10}$, —$NR_{10}CO_2R_{10}$, an optionally substituted $C_1$-$C_6$ alkyl, an optionally substituted $C_2$-$C_6$ alkenyl, an optionally substituted $C_2$-$C_6$ alkynyl, an optionally substituted $C_3$-$C_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyridine, pyrimidine, pyridazine, pyrazine, pyrazole, isoxazole, isothiazole, imidazole, oxazole, or thiazole; wherein the optionally substituted $C_1$-$C_6$ alkyl, $C_2$-$C_6$ alkenyl, or $C_2$-$C_6$ alkynyl is each optionally substituted with a —CN, —OH, oxetanyl, or $C_1$-$C_3$ alkoxy; the optionally substituted $C_3$-$C_5$ cycloalkyl, phenyl, 1,3-benzodioxole, 2,3-dihydro-1,4-benzodioxine, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$SO_2R_{10}$, —$NR_{10}R_{10}$, —OH or —CN; preferably the optionally substituted bicyclic ring is optionally substituted with one to three substituents each independently selected from halogen and $C_1$-$C_6$ alkyl; and the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ alkyl optionally substituted with —OH or oxetanyl, or a heteroaryl selected from a pyridine or oxazole.

In yet a further compound of Formula (I), or (II), or pharmaceutically acceptable salts thereof, $R_2$ is a group of the formula:

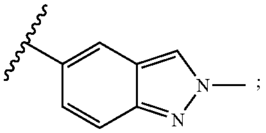

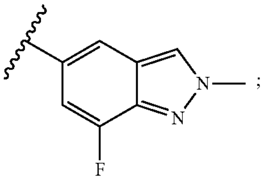

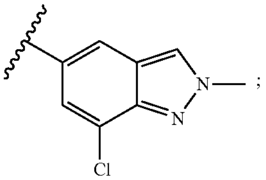

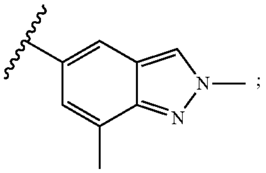

-continued

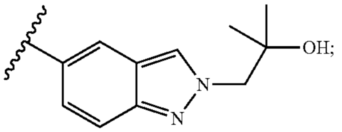

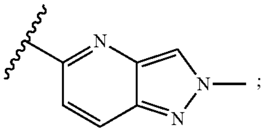

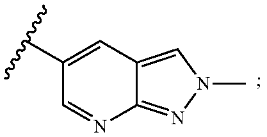

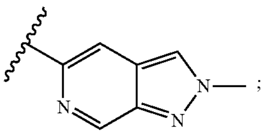

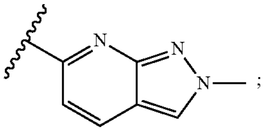

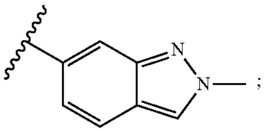

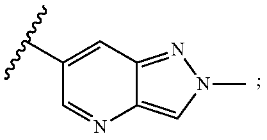

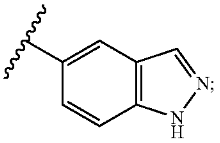

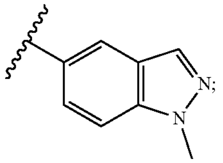

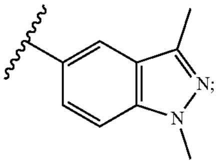

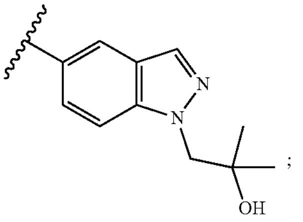

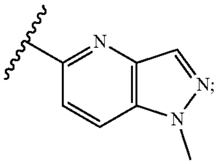

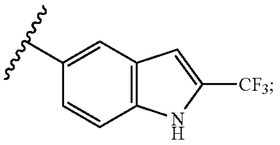

-continued
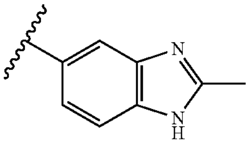;
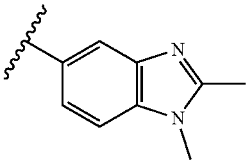;
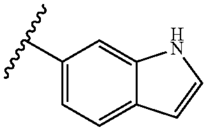; 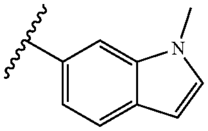;
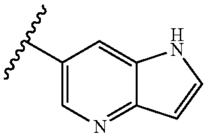; 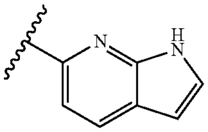;
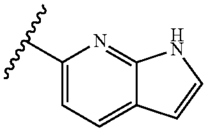; 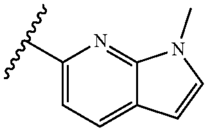;
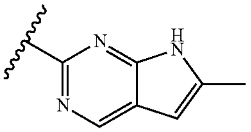; 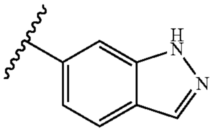;
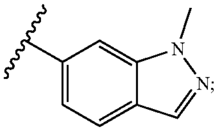; 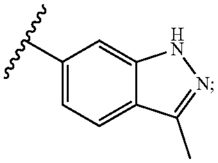;
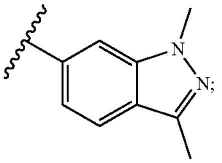; 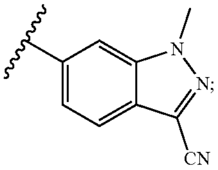;
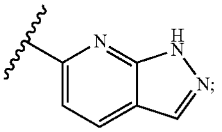; 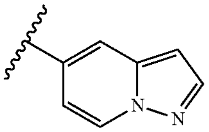;
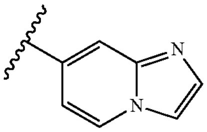; 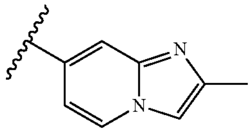;
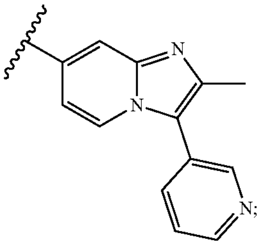;
-continued
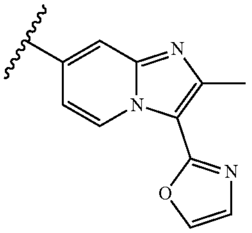; 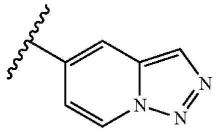;
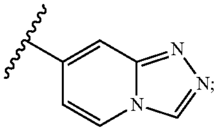; 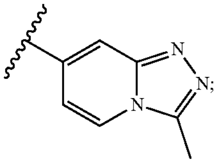;
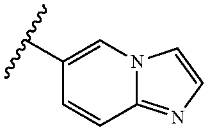; 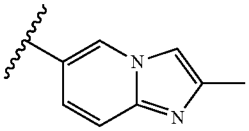;
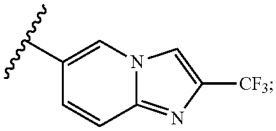; 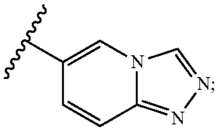;
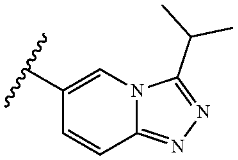; 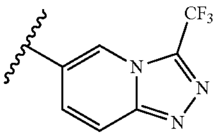;
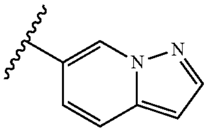; 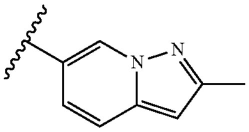;
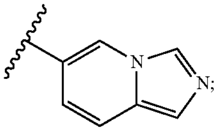; 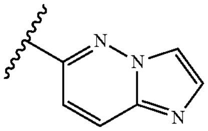;
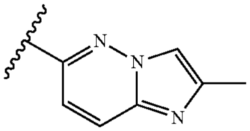; 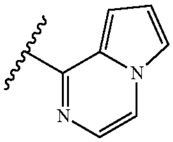;
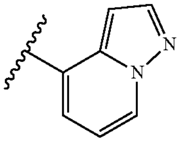; 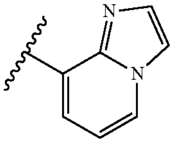;
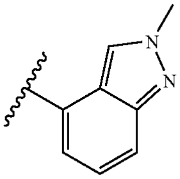; 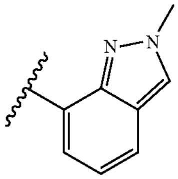;
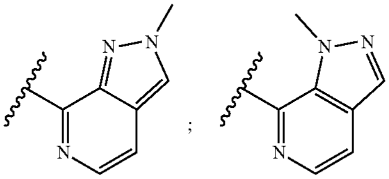;

-continued
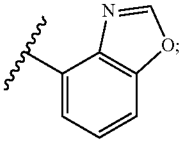
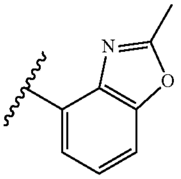 ;
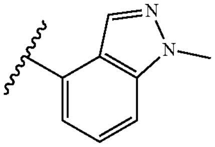 ;
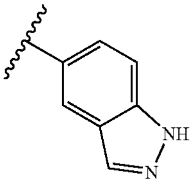 ;
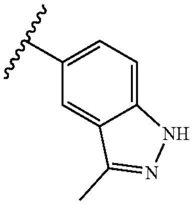 ;
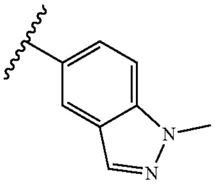 ;
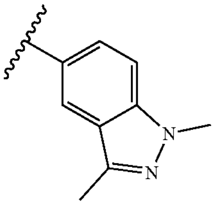 ;
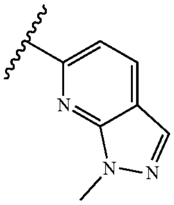 ;
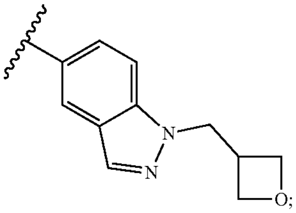
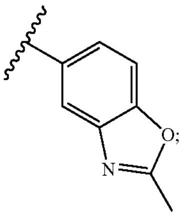
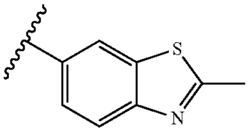 ;
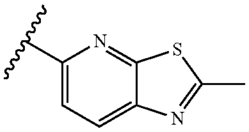 ;
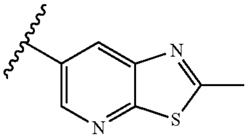 ;
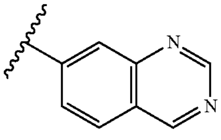 ;
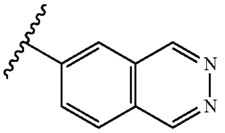 ;
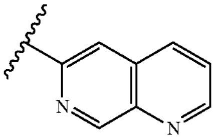 ;
-continued
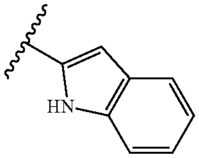 ;
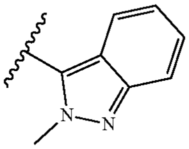 ;
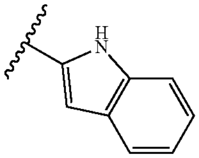 ;
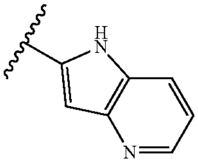 ;
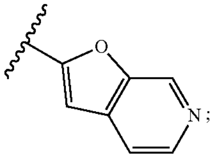
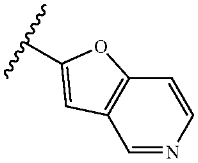 ;
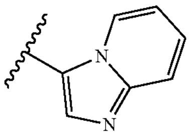 ;
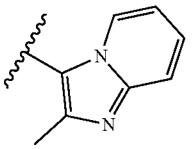 ;
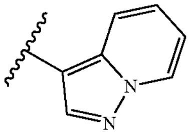 ;
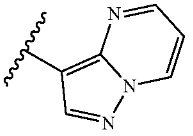 ;
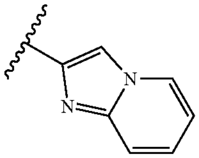 ;
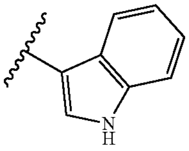 ;
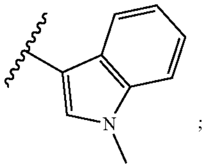 ;
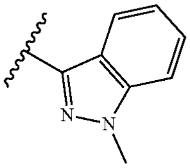 ;
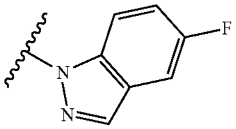 ;
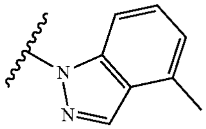 ;
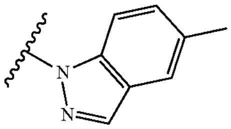 ;
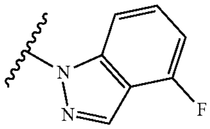 ;
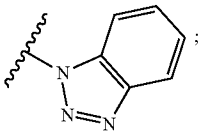 ;
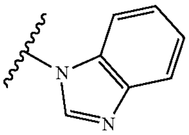 ;
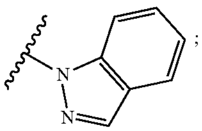 ;
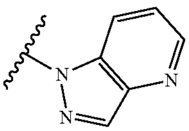 ;

-continued
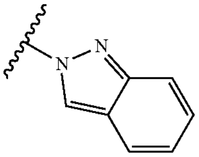 ; 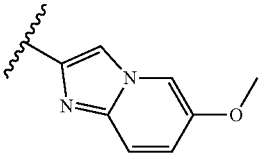 ;
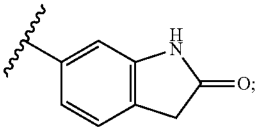
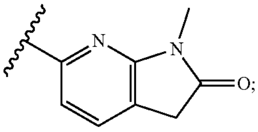
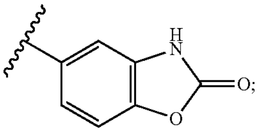
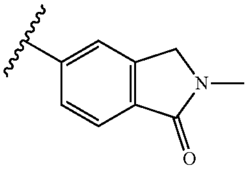 ;
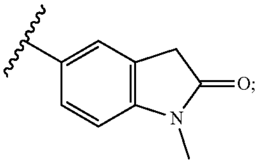
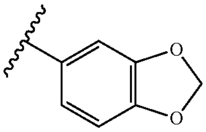 ; 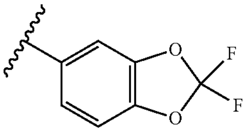 ;
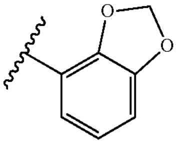 ; 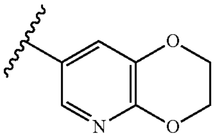 ;
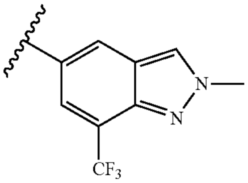 ; 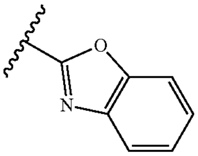 ;
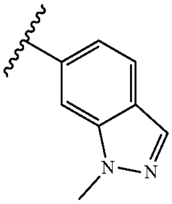 ; 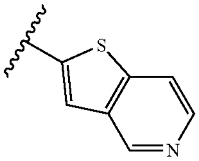 ;
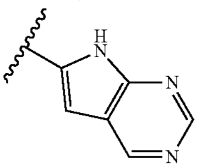 ; 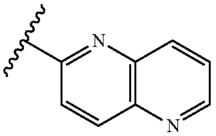 ;
-continued
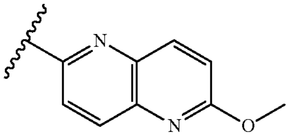 ;
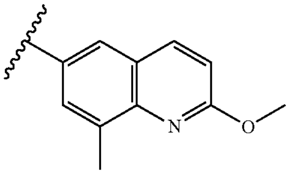 ;
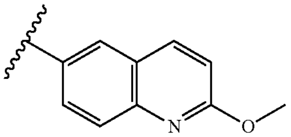 ;
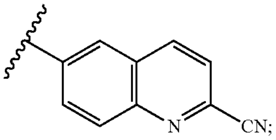
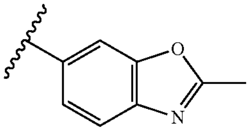 ;
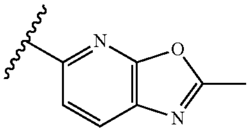 ;
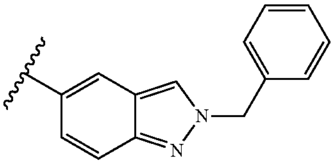 ; or
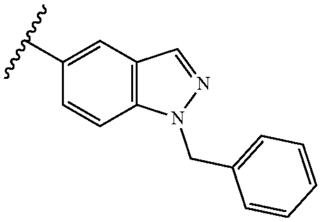 .
In yet a further compound of Formula (I), or (II), or pharmaceutically acceptable salts thereof, $R_2$ is a group of the formula:
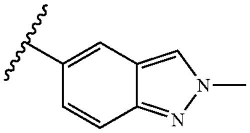 ;
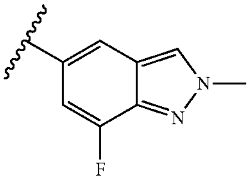 ;

-continued
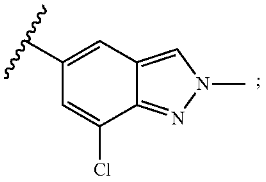
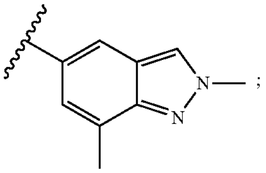
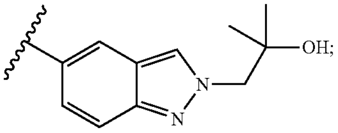
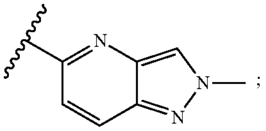
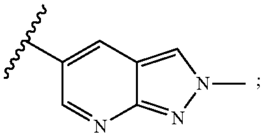
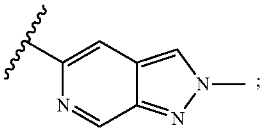
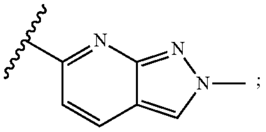
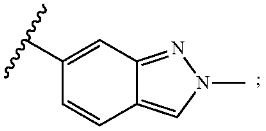
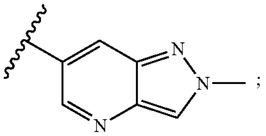
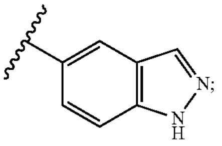
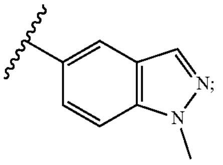
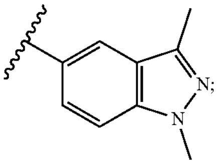
-continued
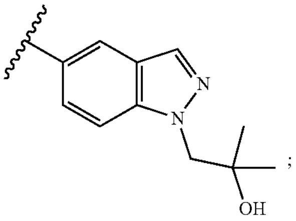
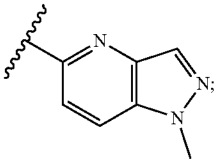
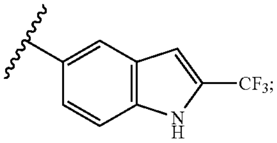
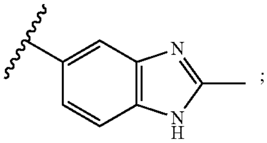
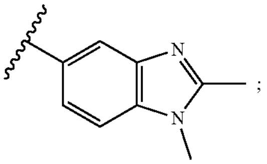
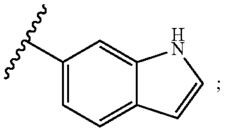
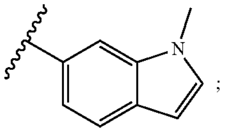
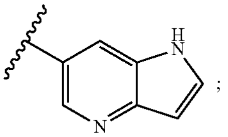
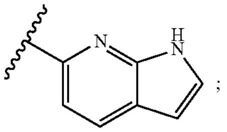
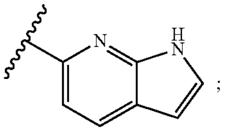
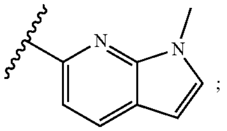
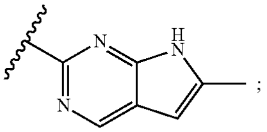
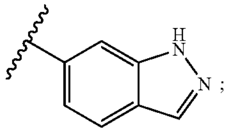
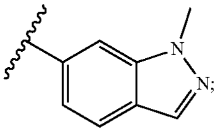
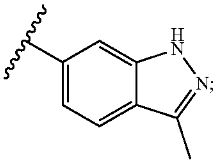
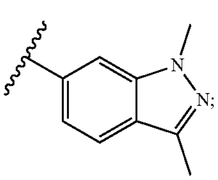
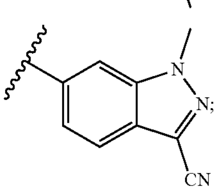
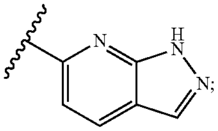
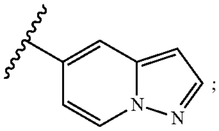

-continued
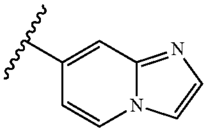 ; 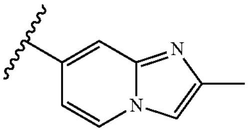 ;
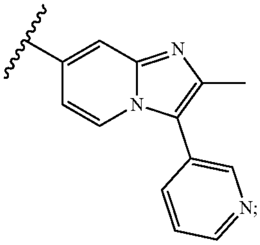 ;
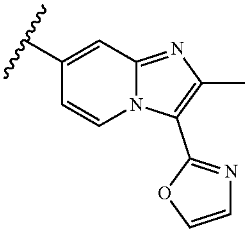 ; 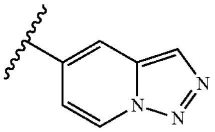 ;
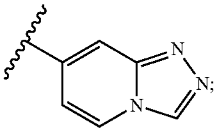 ; 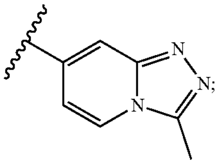 ;
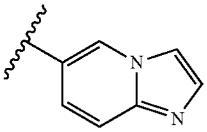 ; 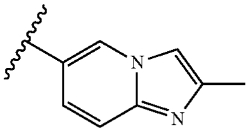 ;
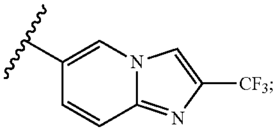 ; 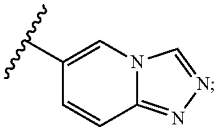 ;
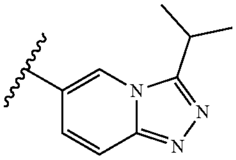 ; 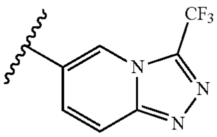 ;
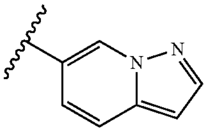 ; 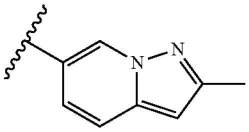 ;
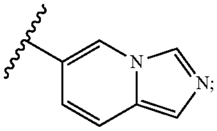 ; 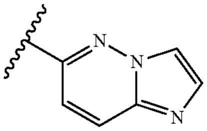 ;
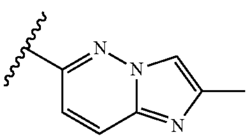 ; 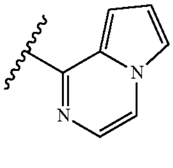 ;
-continued
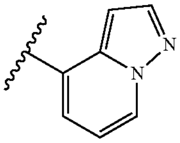 ; 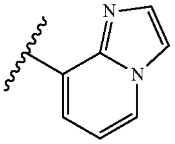 ;
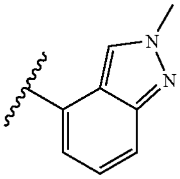 ; 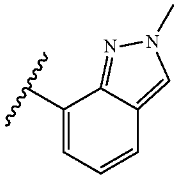 ;
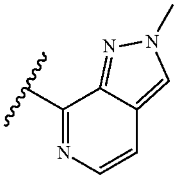 ; 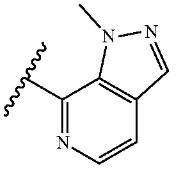 ;
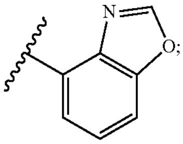 ; 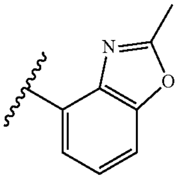 ;
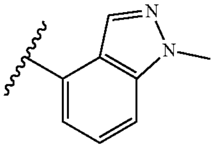 ; 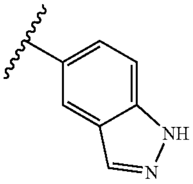 ;
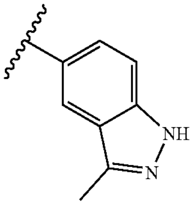 ; 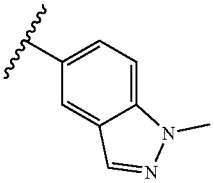 ;
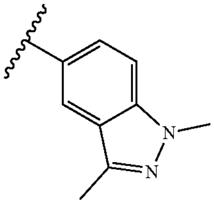 ; 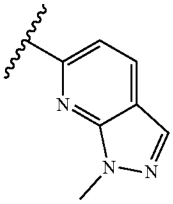 ;
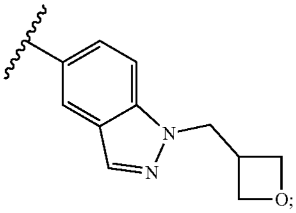 ;
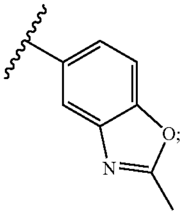 ; 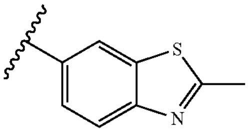 ;

-continued
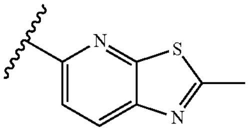
;
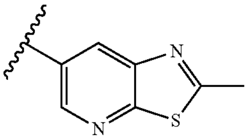
;
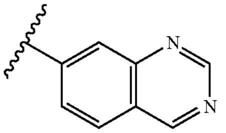
;
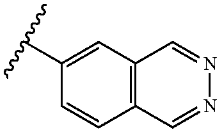
;
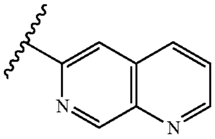
;
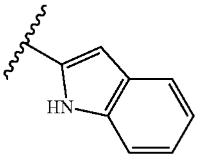
;
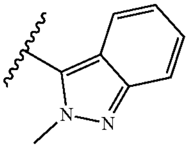
;
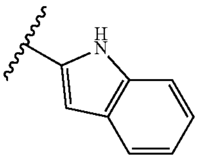
;
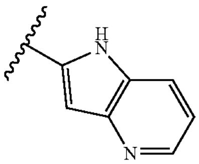
;
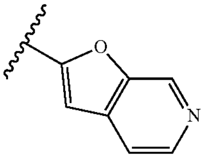
;
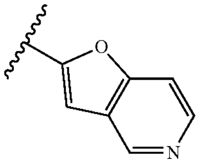
;
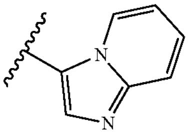
;
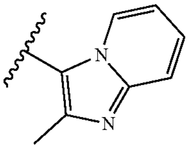
;
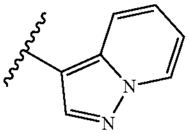
;
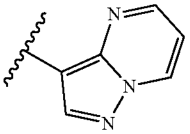
;
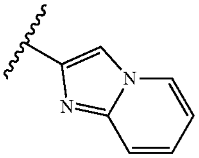
;
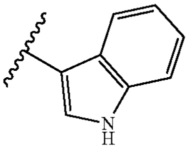
;
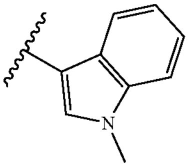
;
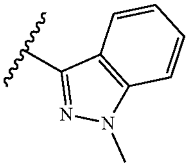
;
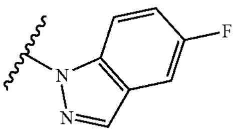
;
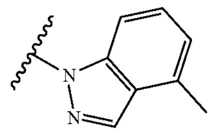
;
-continued
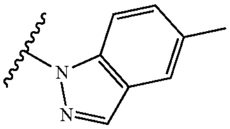
;
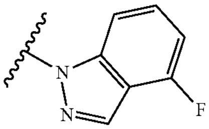
;
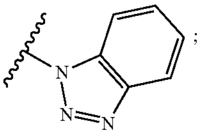
;
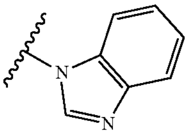
;
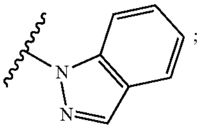
;
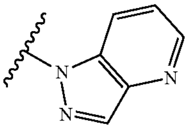
;
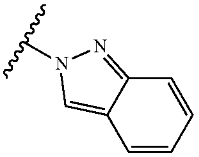
;
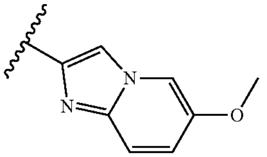
;
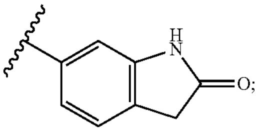
;
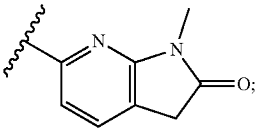
;
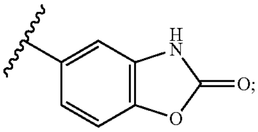
;
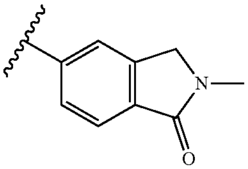
;
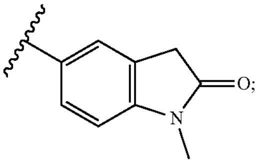
;
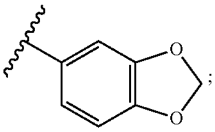
;
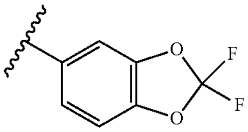
;
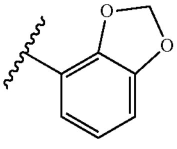
; or
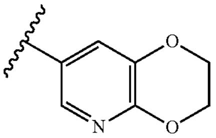
.
In yet a further compound of Formula (I), or (II), or pharmaceutically acceptable salts thereof, $R_3$ is —H, halogen, —CN, —N(H)($CH_2CH_2CO_2H$), —C(O)$C_1$-$C_3$ alkyl, $C_1$-$C_6$ alkyl, $C_1$-$C_6$ haloalkyl, oxetane, isoxazole, or pyridine (preferably 3-pyridine). In yet a further compound of Formula (I), or (II), or pharmaceutically acceptable salts thereof, $R_3$ is —H, halogen, —CN, $C_1$-$C_6$ alkyl, $C_1$-$C_6$ haloalkyl, $C_3$-$C_5$ cycloalkyl, a heterocycle of 3 to 5 ring atoms containing 1, 2, or 3 ring heteroatoms independently selected from N, O, or S, or a heteroaryl of 5 ring atoms containing 1, 2, or 3 ring heteroatoms independently selected from N, O, or S. In yet a further compound of Formula (I), or (II), or pharmaceutically acceptable salts thereof, $R_3$ is —H, halogen, —CN, $C_1$-$C_6$ alkyl, $C_1$-$C_6$ haloalkyl, oxetane, or isoxazole. In yet a further compound of Formula (I), or (II), or pharmaceutically acceptable salts thereof, $R_3$ is —H, —CN, $C_1$-$C_6$ alkyl or $C_1$-$C_6$ haloalkyl, preferably $R_3$ is —H, —CN, $C_1$-$C_3$ alkyl or $C_1$-$C_3$ haloalkyl; more preferably $R_3$ is —H, —CN, or $C_1$-$C_3$ alkyl; most preferably $R_3$ is —H, or methyl. Also preferably $R_3$ is —H, methyl, or trifluoromethyl.

In yet a further compound of Formula (I), or (II), or pharmaceutically acceptable salts thereof, $R_4$ is H or halogen, preferably $R_4$ is —H.

In yet a further compound of Formula (I), or (II), or pharmaceutically acceptable salts thereof, $R_8$ is —H, halogen, $C_1$-$C_3$ alkyl or $C_1$-$C_3$ haloalkyl; more preferably $R_8$ is —H, halogen, methyl, or trifluoromethyl.

In yet a further compound of Formula (I), or (II), or pharmaceutically acceptable salts thereof, $R_6$ is —H, or halogen.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, methyl or trifluoromethyl (preferably $R_3$ is —H, or methyl), and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one) or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, methyl or trifluoromethyl (preferably $R_3$ is —H, or methyl), and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_4$ is —H or halogen (preferably $R_4$ is —H), and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_4$ is —H or halogen (preferably $R_4$ is —H), and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_4$ is —H or halogen (preferably $R_4$ is —H), and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_4$ is —H or halogen (preferably $R_4$ is —H), and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_8$ is —H, halogen, $C_1$-$C_3$ alkyl or $C_1$-$C_3$ haloalkyl, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_5$ is —H, halogen, $C_1$-$C_3$ alkyl or $C_1$-$C_3$ haloalkyl, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_5$ is —H, halogen, methyl, or trifluoromethyl, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_5$ is —H, halogen, methyl, or trifluoromethyl, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_6$ is —H, or halogen, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_6$ is —H, or halogen, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_6$ is —H, or halogen, and $R_2$ is an optionally substituted bicyclic ring selected from 1,3-benzodioxole, 2,3-dihydro-1,4-benzodioxine, isoindolin-1-one, indoline-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_6$ is —H, or halogen, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, —CN, $C_1$-$C_3$ alkyl or $C_1$-$C_3$ haloalkyl, and $R_4$ is H or halogen; more preferably $R_3$ is —H, —CN, or $C_1$-$C_3$ alkyl, and $R_4$ is H; most preferably $R_3$ is —H, or methyl, and $R_4$ is —H.

In yet a further compound of Formula (I), or (II), or pharmaceutically acceptable salts thereof, $R_3$ is —H, —CN, $C_1$-$C_3$ alkyl or $C_1$-$C_3$ haloalkyl, (preferably $R_3$ is —H, —CN, or $C_1$-$C_3$ alkyl), and $R_5$ is —H, halogen, $C_1$-$C_3$ alkyl or $C_1$-$C_3$ haloalkyl; more preferably $R_3$ is —H, or methyl, and $R_5$ is —H, halogen, methyl, or trifluoromethyl.

In yet a further compound of Formula (I), or (II), or pharmaceutically acceptable salts thereof, $R_3$ is —H, —CN, $C_1$-$C_3$ alkyl or $C_1$-$C_3$ haloalkyl, (preferably $R_3$ is —H, —CN, or $C_1$-$C_3$ alkyl), and $R_6$ is —H, or halogen; more preferably $R_3$ is —H, or methyl, and $R_6$ is —H, or halogen.

In yet a further compound of Formula (I), or (II), or pharmaceutically acceptable salts thereof, $R_4$ is —H or halogen (preferably $R_4$ is —H), and $R_5$ is —H, halogen, $C_1$-$C_3$ alkyl or $C_1$-$C_3$ haloalkyl; preferably $R_5$ is —H, halogen, methyl, or trifluoromethyl.

In yet a further compound of Formula (I), or (II), or pharmaceutically acceptable salts thereof, $R_4$ is —H or halogen (preferably $R_4$ is —H) and $R_6$ is —H, or halogen.

In yet a further compound of Formula (I), or (II), or pharmaceutically acceptable salts thereof, $R_5$ is —H, halogen, $C_1$-$C_3$ alkyl or $C_1$-$C_3$ haloalkyl, and $R_6$ is —H, or halogen; preferably $R_5$ is —H, halogen, methyl, or trifluoromethyl, and $R_6$ is —H.

In yet a further compound of Formula (I), or (II), or pharmaceutically acceptable salts thereof, $R_3$ is —H, —CN, $C_1$-$C_3$ alkyl or $C_1$-$C_3$ haloalkyl, (preferably $R_3$ is —H, —CN, or $C_1$-$C_3$ alkyl), $R_4$ is —H or halogen (preferably $R_4$ is —H), and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_3$ is —H, or methyl, $R_4$ is —H, and $R_2$ is an optionally substituted bicyclic ring selected from 1,3-benzodioxole, 2,3-dihydro-1,4-benzodioxine, isoindolin-1-one, indoline-2-one, or benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, —CN, $C_1$-$C_3$ alkyl or $C_1$-$C_3$ haloalkyl, (preferably $R_3$ is —H, —CN, or $C_1$-$C_3$ alkyl), $R_4$ is —H or halogen (preferably $R_4$ is —H), and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_3$ is —H, or methyl, $R_4$ is —H, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, —CN, $C_1$-$C_3$ alkyl or $C_1$-$C_3$ haloalkyl, (preferably $R_3$ is —H, —CN, or $C_1$-$C_3$ alkyl), and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_3$ is —H, or methyl, $R_5$ is —H, halogen, methyl, or trifluoromethyl, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, —CN, $C_1$-$C_3$ alkyl or $C_1$-$C_3$ haloalkyl, (preferably $R_3$ is —H, —CN, or $C_1$-$C_3$ alkyl), and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_3$ is —H, or methyl, $R_5$ is —H, halogen, methyl, or trifluoromethyl, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, —CN, $C_1$-$C_3$ alkyl or $C_1$-$C_3$ haloalkyl, (preferably $R_3$ is —H, —CN, or $C_1$-$C_3$ alkyl), $R_6$ is —H, or halogen, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_3$ is —H, or methyl, $R_6$ is —H, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, —CN, $C_1$-$C_3$ alkyl or $C_1$-$C_3$ haloalkyl, (preferably $R_3$ is —H, —CN, or $C_1$-$C_3$ alkyl), $R_6$ is —H, or halogen, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_3$ is —H, or methyl, $R_6$ is —H, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_4$ is —H or halogen (preferably $R_4$ is —H), $R_5$ is —H, halogen, $C_1$-$C_3$ alkyl or $C_1$-$C_3$ haloalkyl, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_8$ is —H, halogen, methyl, or trifluoromethyl, and $R_2$ is an optionally substituted bicyclic ring selected from 1,3-benzodioxole, 2,3-dihydro-1,4-benzodioxine, isoindolin-1-one, indoline-2-one, benzo[d]oxazol-2(3H)-one, dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_4$ is —H or halogen (preferably $R_4$ is —H), $R_5$ is —H, halogen, $C_1$-$C_3$ alkyl or $C_1$-$C_3$ haloalkyl, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_5$ is —H, halogen, methyl, or trifluoromethyl, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_4$ is —H or halogen (preferably $R_4$ is —H), $R_6$ is —H, or halogen, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_4$ and $R_6$ are each —H, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_4$ is —H or halogen (preferably $R_4$ is —H), $R_6$ is —H, or halogen, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_4$ and $R_6$ are each —H, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_5$ is —H, halogen, $C_1$-$C_3$ alkyl or $C_1$-$C_3$ haloalkyl, $R_6$ is —H, or halogen, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_8$ is —H, halogen, methyl, or trifluoromethyl, $R_6$ is —H, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_5$ is —H, halogen, $C_1$-$C_3$ alkyl or $C_1$-$C_3$ haloalkyl, $R_6$ is —H, or halogen, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_5$ is —H, halogen, methyl, or trifluoromethyl, $R_6$ is —H, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), and $R_8$ is —H, halogen, $C_1$-$C_3$ alkyl or $C_1$-$C_3$ haloalkyl; more preferably $R_3$ is —H, or methyl, $R_4$ is —H, and $R_8$ is —H, halogen, methyl, or trifluoromethyl.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), and $R_6$ is —H, or halogen; more preferably $R_3$ is —H, or methyl, and $R_4$ and $R_6$ are each —H.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_5$ is —H, halogen, $C_1$-$C_3$ alkyl or $C_1$-$C_3$ haloalkyl, $R_6$ is —H, or halogen; more preferably $R_3$ is —H, or methyl, $R_5$ is —H, halogen, methyl, or trifluoromethyl, and $R_6$ is —H.

In yet a further compound of Formula (I), or (II), or pharmaceutically acceptable salts thereof, $R_3$ is —H, halogen, $C_1$-$C_3$ alkyl or $C_1$-$C_3$ haloalkyl, $R_4$ is —H or halogen (preferably $R_4$ is —H), and $R_6$ is —H, or halogen; preferably $R_5$ is —H, halogen, methyl, or trifluoromethyl, and $R_4$ and $R_6$ are each —H.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_3$ is —H, or methyl, $R_4$ is —H, $R_5$ is —H, halogen, methyl, or trifluoromethyl, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_3$ is —H, or methyl, $R_4$ is —H, $R_5$ is —H, halogen, methyl, or trifluoromethyl, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), $R_6$ is —H, or halogen, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_3$ is —H, or methyl, $R_4$ and $R_6$ are each —H, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), $R_6$ is —H, or halogen, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_3$ is —H, or methyl, $R_4$ and $R_6$ are each —H, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_6$ is —H, or halogen, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; more preferably $R_3$ is —H, or methyl, $R_5$ is —H, halogen, methyl, or trifluoromethyl, $R_6$ is —H, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_6$ is —H, or halogen, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; more preferably $R_3$ is —H, or methyl, $R_5$ is —H, halogen, methyl, or trifluoromethyl, $R_6$ is —H, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_5$ is —H, halogen, $C_1$-$C_3$ alkyl or $C_1$-$C_3$ haloalkyl, $R_4$ is —H or halogen (preferably $R_4$ is —H), $R_6$ is —H, or halogen, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2, 3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_8$ is —H, halogen, methyl, or trifluoromethyl, $R_4$ is —H, $R_6$ is —H, or halogen, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_5$ is —H, halogen, $C_1$-$C_3$ alkyl or $C_1$-$C_3$ haloalkyl, $R_4$ is —H or halogen (preferably $R_4$ is —H), $R_6$ is —H, or halogen, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_5$ is —H, halogen, methyl, or trifluoromethyl, $R_4$ is —H, $R_6$ is —H, or halogen, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), $R_6$ is —H, or halogen, and $R_8$ is —H, halogen, $C_1$-$C_3$ alkyl or $C_1$-$C_3$ haloalkyl; preferably $R_3$ is —H, or methyl, $R_4$ and $R_6$ are each —H, and $R_8$ is —H, halogen, methyl, or trifluoromethyl.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), $R_6$ is —H, or halogen, $R_5$ is —H, halogen, $C_1$-$C_3$ alkyl or $C_1$-$C_3$ haloalkyl, and $R_2$ is an optionally substituted bicyclic ring selected from 1,3-benzodioxole, 2,3-dihydro- 1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; more preferably $R_3$ is —H, or methyl, $R_4$ is —H, $R_6$ is —H, or halogen, $R_8$ is —H, halogen, methyl, or trifluoromethyl, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), $R_6$ is —H, or halogen, $R_5$ is —H, halogen, $C_1$-$C_3$ alkyl or $C_1$-$C_3$ haloalkyl, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; more preferably $R_3$ is —H, or methyl, $R_4$ is —H, $R_6$ is —H, or halogen, $R_5$ is —H, halogen, methyl, or trifluoromethyl, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, R is —H.

In yet a further compound of Formula (I), or (II), or pharmaceutically acceptable salts thereof, $R_7$ is —CN, $C_1$-$C_3$ alkyl or $C_1$-$C_3$ haloalkyl; more preferably $R_7$ is —CN, methyl or trifluoromethyl.

In yet a further compound of Formula (I), or (II), or pharmaceutically acceptable salts thereof, $R_8$ is —H.

In yet a further compound of Formula (I), or (II), or pharmaceutically acceptable salts thereof, $R_7$ is —CN, $C_1$-$C_3$ alkyl or $C_1$-$C_3$ haloalkyl, and R is —H. In yet a further compound of Formula (I), or (II), or pharmaceutically acceptable salts thereof, $R_7$ is $C_1$-$C_3$ alkyl (preferably methyl), and R is —H.

In yet a further compound of Formula (I), or (II), or pharmaceutically acceptable salts thereof, $R_8$ and R are each —H.

In yet a further compound of Formula (I), or (II), or pharmaceutically acceptable salts thereof, $R_7$ is —CN, $C_1$-$C_3$ alkyl or $C_1$-$C_3$ haloalkyl, and $R_8$ is —H. In yet a further compound of Formula (I), or (II), or pharmaceutically acceptable salts thereof, $R_7$ is $C_1$-$C_3$ alkyl (preferably methyl), and $R_8$ is —H.

In yet a further compound of Formula (I), or (II), or pharmaceutically acceptable salts thereof, $R_7$ is —CN, $C_1$-$C_3$ alkyl or $C_1$-$C_3$ haloalkyl, and $R_8$ and R are each —H. In yet a further compound of Formula (I), or (II), or pharmaceutically acceptable salts thereof, $R_7$ is $C_1$-$C_3$ alkyl (preferably methyl), and $R_8$ and R are each —H.

In yet a further compound of Formula (I), or (II), or pharmaceutically acceptable salts thereof, $R_7$ is —CN, $C_1$-$C_3$ alkyl or $C_1$-$C_3$ haloalkyl, $R_8$ is —H, R is —H, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_7$ is —CN, $C_1$-$C_3$ alkyl or $C_1$-$C_3$ haloalkyl, $R_8$ is —H, R is —H, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_7$ is $C_1$-$C_3$ alkyl (preferably methyl), $R_8$ is —H, R is —H, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_7$ is $C_1$-$C_3$ alkyl (preferably methyl), $R_8$ is —H, R is —H, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_7$ is —CN, $C_1$-$C_3$ alkyl or $C_1$-$C_3$ haloalkyl, and $R_8$ and R are each —H. In yet a further compound of Formula (I), or (II), or pharmaceutically acceptable salts thereof, $R_3$ is —H, or methyl, $R_7$ is $C_1$-$C_3$ alkyl (preferably methyl), and $R_8$ and R are each —H.

In yet a further compound of Formula (I), or (II), or pharmaceutically acceptable salts thereof, $R_7$ is —CN, $C_1$-$C_3$ alkyl or $C_1$-$C_3$ haloalkyl, and $R_4$, $R_8$ and R are each —H. In yet a further compound of Formula (I), or (II), or pharmaceutically acceptable salts thereof, $R_7$ is $C_1$-$C_3$ alkyl (preferably methyl), and $R_4$, $R_8$ and R are each —H.

In yet a further compound of Formula (I), or (II), or pharmaceutically acceptable salts thereof, $R_5$ is —H, halogen, $C_1$-$C_3$ alkyl or $C_1$-$C_3$ haloalkyl, $R_7$ is —CN, methyl or trifluoromethyl, and $R_8$ and R are each —H. In yet a further compound of Formula (I), or (II), or pharmaceutically acceptable salts thereof, $R_5$ is —H, halogen, methyl, or trifluoromethyl, $R_7$ is methyl, and $R_8$ and R are each —H.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), $R_6$ is —H, or halogen, $R_7$ is —CN, methyl or trifluoromethyl, $R_8$ is —H, R is —H, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_3$ is —H, or methyl, $R_4$ is —H, $R_6$ is —H, or halogen, $R_5$ is —H, halogen, methyl, or trifluoromethyl, $R_7$ is methyl, $R_8$ is —H, R is —H, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_4$ is —H or halogen (preferably $R_4$ is —H), $R_6$ is —H, or halogen, $R_7$ is —CN, methyl or trifluoromethyl, $R_8$ is —H, R is —H, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_3$ is —H, or methyl, $R_4$ is —H, $R_6$ is —H, or halogen, $R_5$ is —H, halogen, methyl, or trifluoromethyl, $R_7$ is methyl, $R_8$ is —H, R is —H, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, each $R_9$ is independently —H, halogen, $C_1$-$C_6$ alkyl, $C_1$-$C_6$ haloalkyl, $C_1$-$C_6$ alkoxy, or $C_3$-$C_5$ cycloalkyl. In yet a further compound of Formula (I), or (II), or pharmaceutically acceptable salts thereof, each $R_9$ is independently —H, halogen, $C_1$-$C_3$ alkyl or $C_1$-$C_3$ haloalkyl; preferably each $R_9$ is independently —H, halogen, methyl or trifluoromethyl.

In yet a further compound of Formula (I), or (II), or pharmaceutically acceptable salts thereof, $R_1$ is a group of the formula:

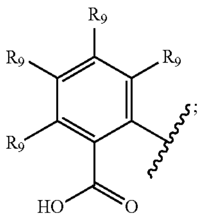
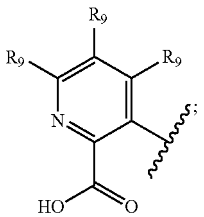
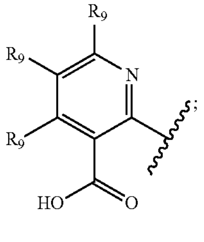
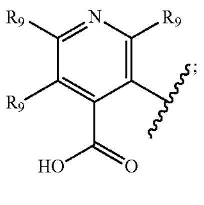

-continued

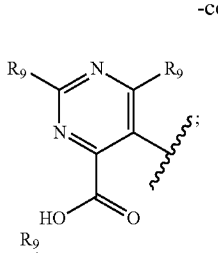
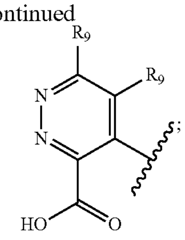
or
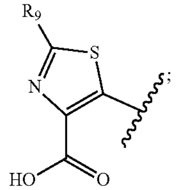

wherein each $R_9$ is independently —H, halogen, —CN, $C_1$-$C_3$ alkyl, $C_1$-$C_3$ haloalkyl, $C_1$-$C_3$ alkoxy, or $C_3$-$C_5$ cycloalkyl; preferably each $R_9$ is independently —H, halogen, —CN, methyl, trifluoromethyl, methoxy, or cyclopropyl.

In yet a further compound of Formula (I), or (II), or pharmaceutically acceptable salts thereof, $R_1$ is a group of the formula: $C_1$-$C_3$ alkoxy, or $C_3$-$C_5$ cycloalkyl; preferably each $R_9$ is independently —H, halogen, methyl, trifluoromethyl, methoxy, or cyclopropyl.

In yet a further compound of Formula (I), or (II), or pharmaceutically acceptable salts thereof, $R_1$ is a group of the formula:

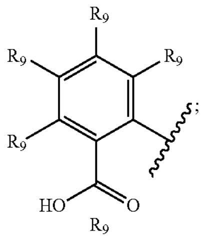
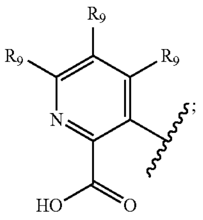
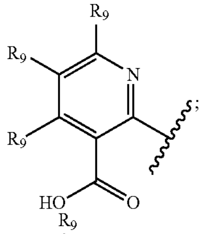
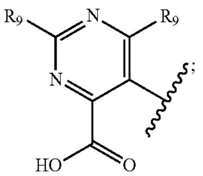
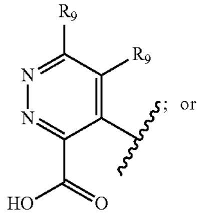
or
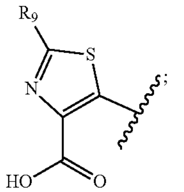

wherein each $R_9$ is independently —H, halogen, $C_1$-$C_3$ alkyl, $C_1$-$C_3$ haloalkyl, $C_1$-$C_3$ alkoxy, or $C_3$-$C_5$ cycloalkyl, preferably each $R_9$ is independently, —H, halogen, methyl, trifluoromethyl, methoxy, or cyclopropyl.

In yet a further compound of Formula (I), or (II), or pharmaceutically acceptable salts thereof, $R_1$ is a group of the formula:

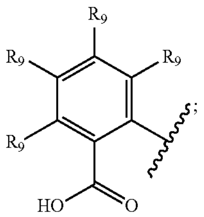
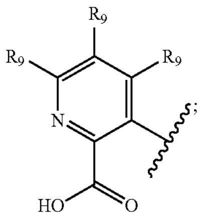
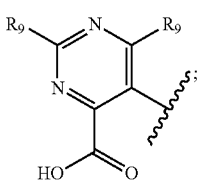
or
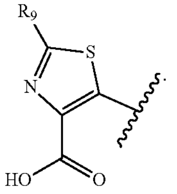

Preferably each $R_9$ is independently —H, halogen, $C_1$-$C_3$ alkyl, $C_1$-$C_3$ haloalkyl, or $C_3$-$C_5$ cycloalkyl. More preferably each $R_9$ is independently —H, halogen, methyl, trifluoromethyl, or cyclopropyl.

In yet a further compound of Formula (I), or (II), or pharmaceutically acceptable salts thereof, $R_1$ is a group of the formula:

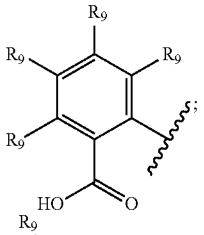
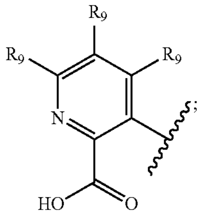
or
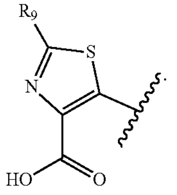

Preferably each $R_9$ is independently —H, halogen, $C_1$-$C_3$ alkyl or $C_1$-$C_3$ haloalkyl. More preferably each $R_9$ is independently —H, halogen, methyl or trifluoromethyl.

In yet a further compound of Formula (I), or (II), or pharmaceutically acceptable salts thereof, $R_1$ is a group of the formula

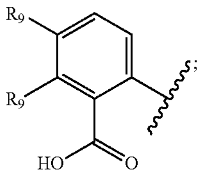
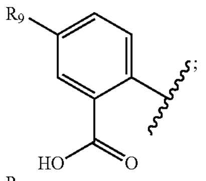
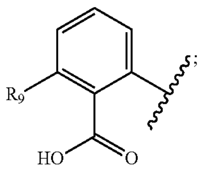
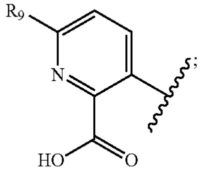

-continued

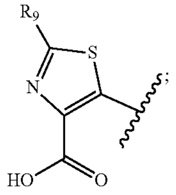
or
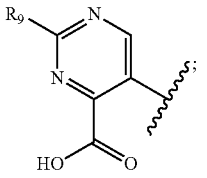

wherein each $R_9$ is independently —H, halogen, —CN, $C_1$-$C_6$ alkyl, $C_1$-$C_6$ haloalkyl, $C_1$-$C_6$ alkoxy, or $C_3$-$C_5$ cycloalkyl; preferably each $R_9$ is independently —H, halogen, —CN, $C_1$-$C_3$ alkyl, $C_1$-$C_3$ haloalkyl, $C_1$-$C_3$ alkoxy, or $C_3$-$C_5$ cycloalkyl; more preferably each $R_9$ is independently —H, halogen, —CN, methyl, trifluoromethyl, methoxy, or cyclopropyl.

In yet a further compound of Formula (I), or (II), or pharmaceutically acceptable salts thereof, $R_1$ is a group of the formula

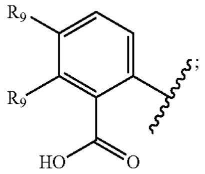
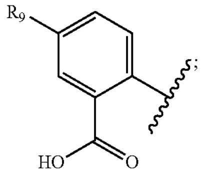
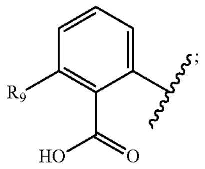
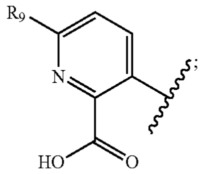
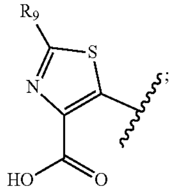
or
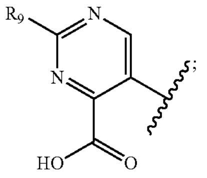

wherein each $R_9$ is independently —H, halogen, $C_1$-$C_6$ alkyl, $C_1$-$C_6$ haloalkyl, $C_1$-$C_6$ alkoxy, or $C_3$-$C_5$ cycloalkyl; preferably each $R_9$ is independently —H, halogen, $C_1$-$C_3$ alkyl, $C_1$-$C_3$ haloalkyl, $C_1$-$C_3$ alkoxy, or $C_3$-$C_5$ cycloalkyl; more preferably each $R_9$ is independently —H, halogen, methyl, trifluoromethyl, methoxy, or cyclopropyl.

In yet a further compound of Formula (I), or (II), or pharmaceutically acceptable salts thereof, $R_1$ is a group of the formula:

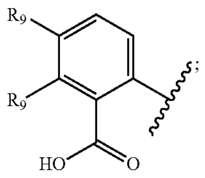

wherein each $R_9$ is independently —H, halogen, —CN, $C_1$-$C_3$ alkyl, $C_1$-$C_3$ haloalkyl or $C_1$-$C_3$ alkoxy. Preferably each $R_9$ is independently —H, halogen, $C_1$-$C_3$ alkyl or $C_1$-$C_3$ haloalkyl. More preferably each $R_9$ is independently —H, halogen, methyl or trifluoromethyl.

In yet a further compound of Formula (I), or (II), or pharmaceutically acceptable salts thereof, $R_1$ is a group of the formula:

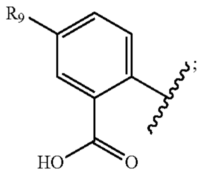

wherein $R_9$ is —H, halogen, —CN, $C_1$-$C_3$ haloalkyl, or $C_1$-$C_3$ alkoxy. Preferably $R_9$ is —H, halogen, or $C_1$-$C_3$ haloalkyl. More preferably $R_9$ is —H, or trifluoromethyl.

In yet a further compound of Formula (I), or (II), or pharmaceutically acceptable salts thereof, $R_1$ is a group of the formula:

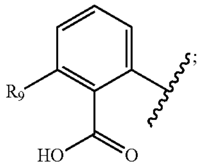

wherein $R_9$ is —H, halogen, —CN, $C_1$-$C_3$ haloalkyl, or $C_1$-$C_3$ alkoxy Preferably $R_9$ is —H, halogen, or $C_1$-$C_3$ haloalkyl. More preferably $R_9$ is —H, or halogen. Even more preferably, $R_9$ is —H, or fluoro.

In yet a further compound of Formula (I), or (II), or pharmaceutically acceptable salts thereof, $R_1$ is a group of the formula:

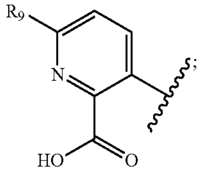

wherein $R_9$ is —H, halogen, —CN, $C_1$-$C_3$ alkyl, $C_1$-$C_3$ haloalkyl, $C_1$-$C_3$ alkoxy, or $C_3$-$C_5$ cycloalkyl. Preferably $R_9$ is —H, halogen, $C_1$-$C_3$ alkyl, $C_1$-$C_3$ haloalkyl, or $C_3$-$C_5$ cycloalkyl. More preferably $R_9$ is —H, halogen, methyl, trifluoromethyl, or cyclopropyl.

In yet a further compound of Formula (I), or (II), or pharmaceutically acceptable salts thereof, $R_1$ is a group of the formula:

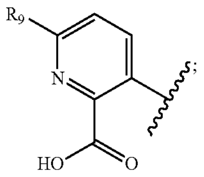

wherein $R_9$ is —H, halogen, or $C_1$-$C_3$ haloalkyl. Preferably $R_9$ is halogen or trifluoromethyl. More preferably $R_9$ is chloro or trifluoromethyl.

In yet a further compound of Formula (I), or (II), or pharmaceutically acceptable salts thereof, $R_1$ is a group of the formula:

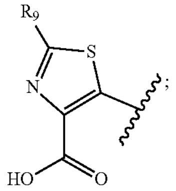

wherein $R_9$ is —H, halogen, —CN, $C_1$-$C_6$ alkyl, $C_1$-$C_6$ haloalkyl or $C_1$-$C_6$ alkoxy. Preferably $R_9$ is —H, halogen, $C_1$-$C_6$ alkyl or $C_1$-$C_6$ haloalkyl. More preferably $R_9$ is —H, halogen, $C_1$-$C_3$ alkyl or $C_1$-$C_3$ haloalkyl.

In yet a further compound of Formula (I), or (II), or pharmaceutically acceptable salts thereof, $R_1$ is a group of the formula:

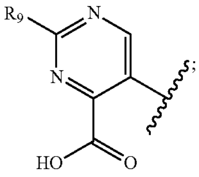

wherein $R_9$ is —H, halogen, —CN, $C_1$-$C_3$ alkyl, $C_1$-$C_3$ haloalkyl, $C_1$-$C_3$ alkoxy, or $C_3$-$C_5$ cycloalkyl. Preferably $R_9$ is —H, halogen, $C_1$-$C_3$ alkyl, $C_1$-$C_3$ haloalkyl, or $C_3$-$C_5$ cycloalkyl. More preferably $R_9$ is —H, halogen, methyl, trifluoromethyl, or cyclopropyl.

In yet a further compound of Formula (I), or (II), or pharmaceutically acceptable salts thereof, $R_1$ is a group of the formula:

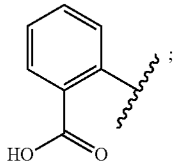 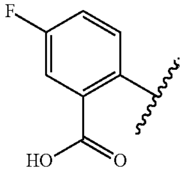

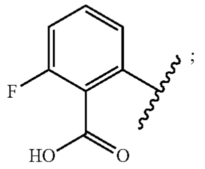 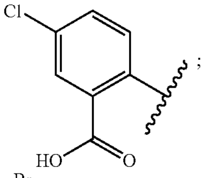

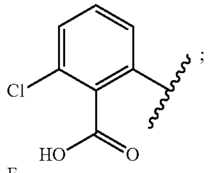 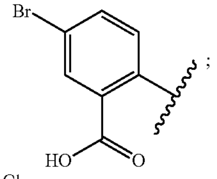

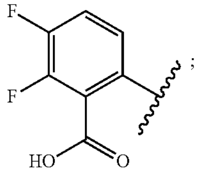 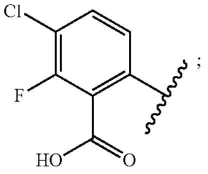

-continued
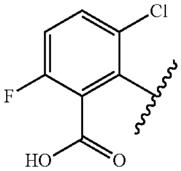 ; 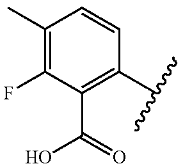 ;
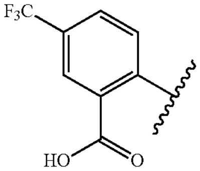 ; 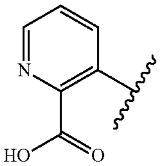 ;
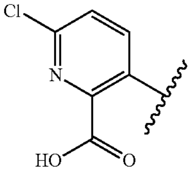 ; 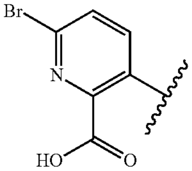 ;
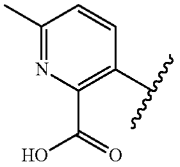 ; 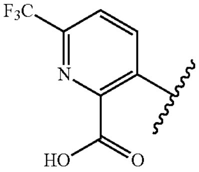 ;
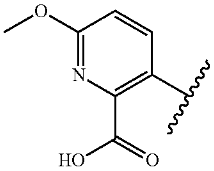 ; 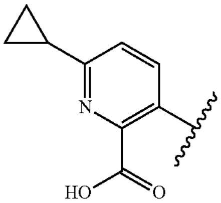 ;
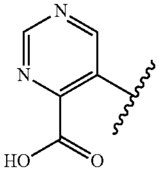 ; 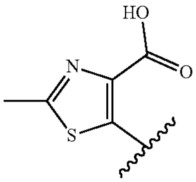 ;
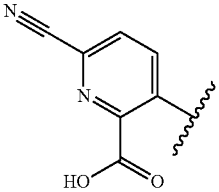 ; 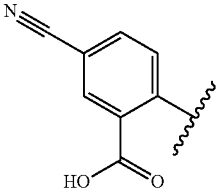 ;
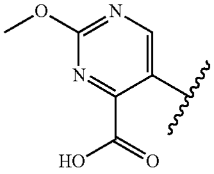 ; 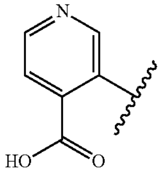 ; or
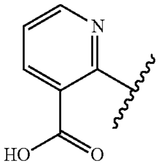 .
In yet a further compound of Formula (I), or (II), or pharmaceutically acceptable salts thereof, $R_1$ is a group of the formula:
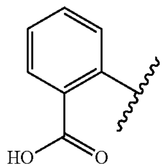 ; 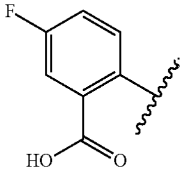 ;
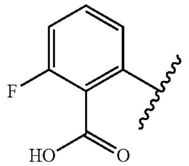 ; 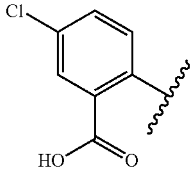 ;
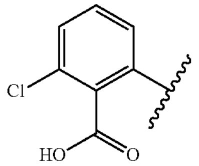 ; 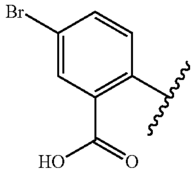 ;
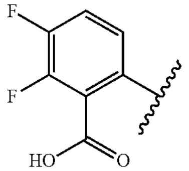 ; 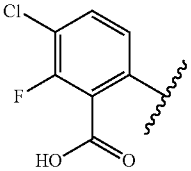 ;
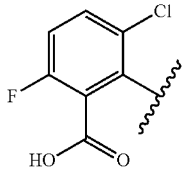 ; 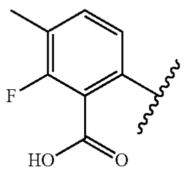 ;
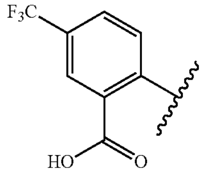 ; 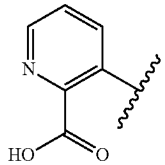 ;
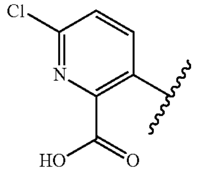 ; 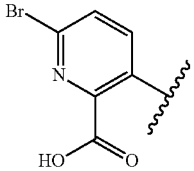 ;
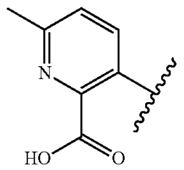 ; 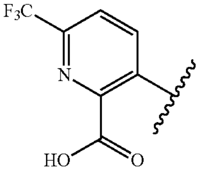 ;
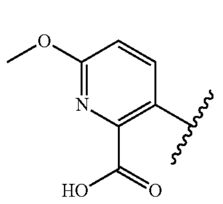 ; 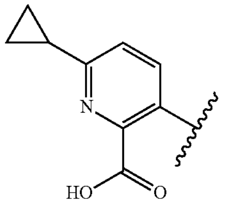 ;

-continued

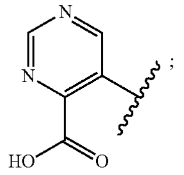

or

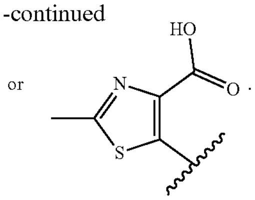

In yet a further compound of Formula (I), or (II), or pharmaceutically acceptable salts thereof, $R_1$ is a group of the formula:

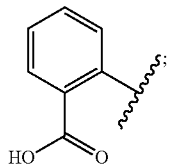

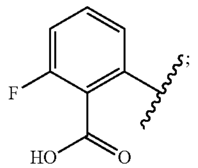

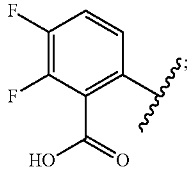

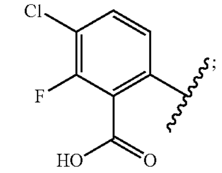

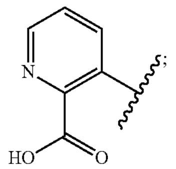

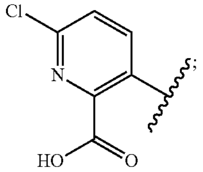

or

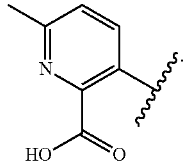

In yet a further compound of Formula (I), or (II), or pharmaceutically acceptable salts thereof, $R_3$ is —H, —CN, $C_1$-$C_3$ alkyl, or $C_1$-$C_3$ haloalkyl, $R_4$ is —H, or halogen, $R_6$ is —H, or halogen, $R_5$ is —H, halogen, $C_1$-$C_3$ alkyl or $C_1$-$C_3$ haloalkyl, and $R_1$ is a group of the formula:

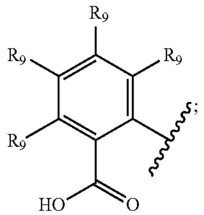

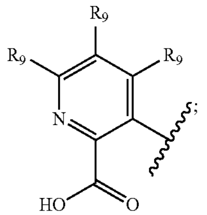

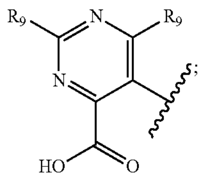

or

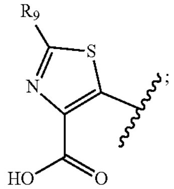

wherein each $R_9$ is independently —H, halogen, $C_1$-$C_3$ alkyl, $C_1$-$C_3$ haloalkyl, or $C_3$-$C_5$ cycloalkyl. Preferably $R_3$ is —H, methyl, or trifluoromethyl, $R_4$ is —H, or halogen, $R_6$ is —H, or halogen, $R_5$ is —H, halogen, methyl, or trifluoromethyl, and each $R_9$ is independently —H, halogen, methyl, trifluoromethyl, or cyclopropyl.

In yet a further compound of Formula (I), or (II), or pharmaceutically acceptable salts thereof, $R_3$ is —H, —CN, or $C_1$-$C_3$ alkyl, $R_4$ is —H, $R_6$ is —H, or halogen, $R_5$ is —H, halogen, $C_1$-$C_3$ alkyl or $C_1$-$C_3$ haloalkyl, and $R_1$ is a group of the formula:

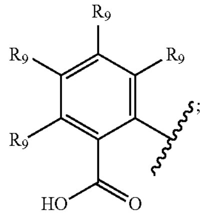

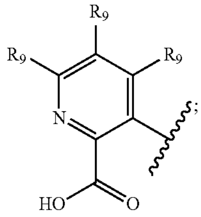

or

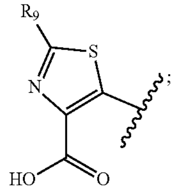

wherein each $R_9$ is independently —H, halogen, $C_1$-$C_3$ alkyl or $C_1$-$C_3$ haloalkyl. Preferably $R_3$ is —H, or methyl, $R_4$ is —H, $R_6$ is —H, or halogen, $R_5$ is —H, halogen, methyl, or trifluoromethyl, and each $R_9$ is independently —H, halogen, methyl, or trifluoromethyl.

In yet a further compound of Formula (I), or (II), or pharmaceutically acceptable salts thereof, $R_7$ is —CN, methyl or trifluoromethyl, $R_8$ and R are each —H, and $R_1$ is a group of the formula:

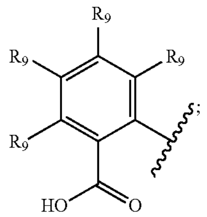

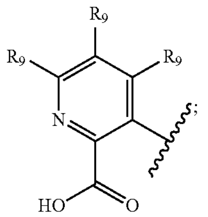

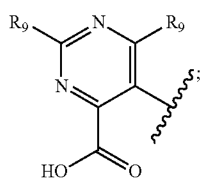

or

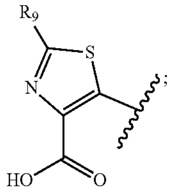

wherein each $R_9$ is independently —H, halogen, $C_1$-$C_3$ alkyl, $C_1$-$C_3$ haloalkyl, or $C_3$-$C_5$ cycloalkyl; more preferably $R_7$ is methyl, $R_8$ and R are each —H, and each $R_9$ is independently —H, halogen, methyl, trifluoromethyl, or cyclopropyl.

In yet a further compound of Formula (I), or (II), or pharmaceutically acceptable salts thereof, $R_7$ is —CN, methyl or trifluoromethyl, $R_8$ and R are each —H, and $R_1$ is a group of the formula:

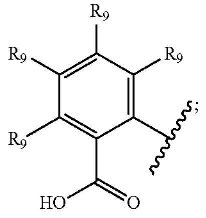
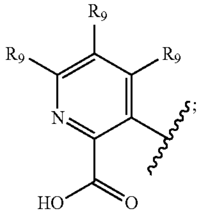
or
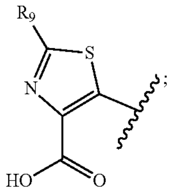

wherein each $R_9$ is independently —H, halogen, $C_1$-$C_3$ alkyl or $C_1$-$C_3$ haloalkyl; more preferably $R_7$ is methyl, $R_8$ and R are each —H, and each $R_9$ is independently —H, halogen, methyl, or trifluoromethyl.

In yet a further compound of Formula (I), or (II), or pharmaceutically acceptable salts thereof, $R_3$ is —H, —CN, $C_1$-$C_3$ alkyl, or $C_1$-$C_3$ haloalkyl, $R_4$ is —H, or halogen, $R_8$ and R are each —H, $R_5$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

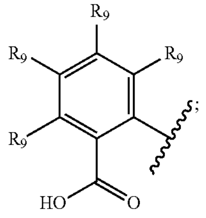
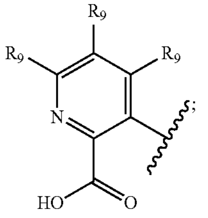
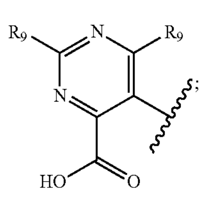
or
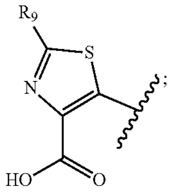

wherein each $R_9$ is independently —H, halogen, $C_1$-$C_3$ alkyl, $C_1$-$C_3$ haloalkyl, or $C_3$-$C_5$ cycloalkyl; more preferably $R_3$ is —H, methyl, or trifluoromethyl, $R_4$ is —H, or halogen, $R_6$ is —H, or halogen, $R_8$ and R are each —H, $R_5$ is —H, halogen, methyl, or trifluoromethyl, $R_7$ is methyl, and each $R_9$ is independently —H, halogen, methyl, trifluoromethyl, or cyclopropyl.

In yet a further compound of Formula (I), or (II), or pharmaceutically acceptable salts thereof, $R_3$ is —H, —CN, or $C_1$-$C_3$ alkyl, $R_4$, $R_8$ and R are each —H, $R_5$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

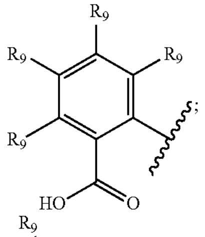
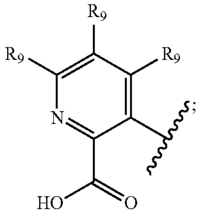
or
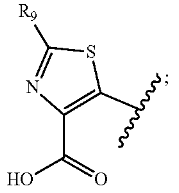

wherein each $R_9$ is independently —H, halogen, $C_1$-$C_3$ alkyl or $C_1$-$C_3$ haloalkyl; more preferably $R_3$ is —H, or methyl, $R_4$, $R_6$, $R_8$ and R are each —H, $R_5$ is —H, halogen, methyl, or trifluoromethyl, $R_7$ is methyl, and each $R_9$ is independently —H, halogen, methyl, or trifluoromethyl.

In yet a further compound of Formula (I), or (II), or pharmaceutically acceptable salts thereof, $R_3$ is —H, —CN, $C_1$-$C_3$ alkyl, or $C_1$-$C_3$ haloalkyl, $R_4$ is —H, or halogen, $R_8$ and R are each —H, $R_5$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

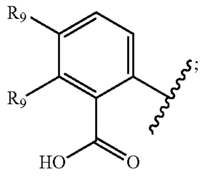

wherein each $R_9$ is independently —H, halogen, $C_1$-$C_3$ alkyl or $C_1$-$C_3$ haloalkyl; preferably $R_3$ is —H, methyl, or trifluoromethyl, $R_4$ is —H, or halogen, $R_6$ is —H, or halogen, $R_8$ and R are each —H, $R_5$ is —H, halogen, methyl, or trifluoromethyl, $R_7$ is methyl, and each $R_9$ is independently —H, halogen, methyl or trifluoromethyl.

In yet a further compound of Formula (I), or (II), or pharmaceutically acceptable salts thereof, $R_3$ is —H, —CN, or $C_1$-$C_3$ alkyl, $R_4$, $R_8$ and R are each —H, $R_5$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

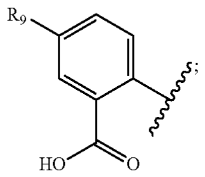

wherein $R_9$ is —H, halogen, or $C_1$-$C_3$ haloalkyl; preferably $R_3$ is —H, or methyl, $R_4$, $R_6$, $R_8$ and R are each —H, $R_5$ is —H, halogen, methyl, or trifluoromethyl, $R_7$ is methyl, and $R_9$ is —H, or trifluoromethyl.

In yet a further compound of Formula (I), or (II), or pharmaceutically acceptable salts thereof, $R_3$ is —H, —CN, or $C_1$-$C_3$ alkyl, $R_4$, $R_8$ and R are each —H, $R_5$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

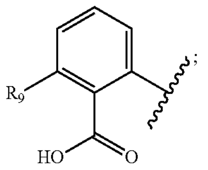

wherein $R_9$ is —H, halogen, or $C_1$-$C_3$ haloalkyl; preferably $R_3$ is —H, or methyl, $R_4$, $R_6$, $R_8$ and R are each —H, $R_5$ is —H, halogen, methyl, or trifluoromethyl, $R_7$ is methyl, and $R_9$ is —H, or halogen.

In yet a further compound of Formula (I), or (II), or pharmaceutically acceptable salts thereof, $R_3$ is —H, —CN, $C_1$-$C_3$ alkyl, or $C_1$-$C_3$ haloalkyl, $R_4$ is —H, or halogen, $R_8$ and R are each —H, $R_5$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

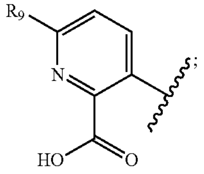

wherein $R_9$ is —H, halogen, $C_1$-$C_3$ alkyl, $C_1$-$C_3$ haloalkyl, or $C_3$-$C_5$ cycloalkyl; preferably $R_3$ is —H, methyl, or trifluoromethyl, $R_4$ is —H, or halogen, $R_6$ is —H, or halogen, $R_8$ and R are each —H, $R_5$ is —H, halogen, methyl, or trifluoromethyl, $R_7$ is methyl, and $R_9$ is —H, halogen, methyl, trifluoromethyl, or cyclopropyl.

In yet a further compound of Formula (I), or (II), or pharmaceutically acceptable salts thereof, $R_3$ is —H, —CN, or $C_1$-$C_3$ alkyl, $R_4$, $R_8$ and R are each —H, $R_5$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

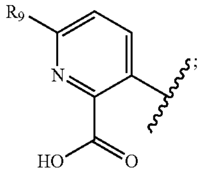

wherein $R_9$ is —H, halogen, or $C_1$-$C_3$ haloalkyl; preferably $R_3$ is —H, or methyl, $R_4$, $R_6$, $R_8$ and R are each —H, $R_5$ is —H, halogen, methyl, or trifluoromethyl, $R_7$ is methyl, and $R_9$ is independently halogen or trifluoromethyl.

In yet a further compound of Formula (I), or (II), or pharmaceutically acceptable salts thereof, $R_3$ is —H, —CN, or $C_1$-$C_3$ alkyl, $R_4$, $R_8$ and R are each —H, $R_5$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

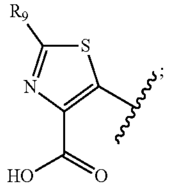

wherein $R_9$ is —H, halogen, $C_1$-$C_3$ alkyl or $C_1$-$C_3$ haloalkyl; preferably $R_3$ is —H, or methyl, $R_4$, $R_6$, $R_8$ and R are each —H, $R_5$ is —H, halogen, methyl, or trifluoromethyl, $R_7$ is methyl, and $R_9$ is —H, halogen, $C_1$-$C_3$ alkyl or $C_1$-$C_3$ haloalkyl.

In yet a further compound of Formula (I), or (II), or pharmaceutically acceptable salts thereof, $R_3$ is —H, —CN, $C_1$-$C_3$ alkyl, or $C_1$-$C_3$ haloalkyl, $R_4$ is —H, or halogen, $R_8$ and R are each —H, $R_5$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

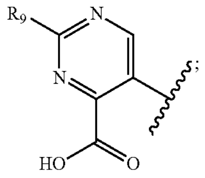

wherein $R_9$ is —H, halogen, $C_1$-$C_3$ alkyl, $C_1$-$C_3$ haloalkyl, or $C_3$-$C_5$ cycloalkyl; preferably $R_3$ is —H, methyl, or trifluoromethyl, $R_4$ is —H, or halogen, $R_6$ is —H, or halogen, $R_8$ and R are each —H, $R_5$ is —H, halogen, methyl, or trifluoromethyl, $R_7$ is methyl, and $R_9$ is —H, halogen, methyl, trifluoromethyl, or cyclopropyl.

In yet a further compound of Formula (I), or (II), or pharmaceutically acceptable salts thereof, $R_1$ is a group of the formula:

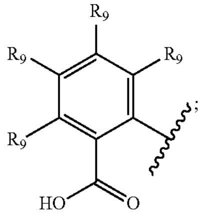

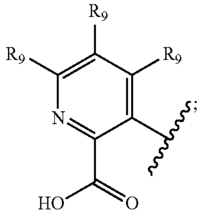

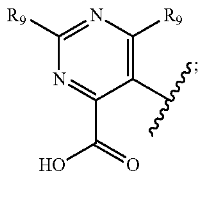

or

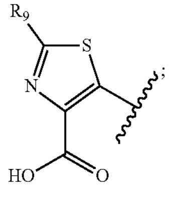

wherein each $R_9$ is independently —H, halogen, $C_1$-$C_3$ alkyl, $C_1$-$C_3$ haloalkyl, or $C_3$-$C_5$ cycloalkyl; and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN. Preferably each $R_9$ is independently —H, halogen, $C_1$-$C_3$ alkyl or $C_1$-$C_3$ haloalkyl. Most preferably each $R_9$ is independently —H, halogen, methyl, or trifluoromethyl.

In yet a further compound of Formula (I), or (II), or pharmaceutically acceptable salts thereof, $R_1$ is a group of the formula:

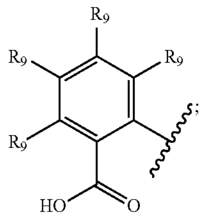

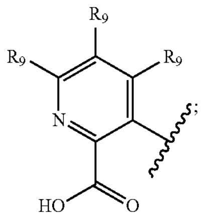

or

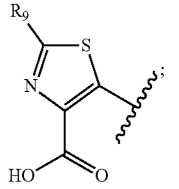

wherein $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN. Preferably each $R_9$ is independently —H, halogen, $C_1$-$C_3$ alkyl or $C_1$-$C_3$ haloalkyl. Most preferably each $R_9$ is independently —H, halogen, methyl, or trifluoromethyl.

In yet a further compound of Formula (I), or (II), or pharmaceutically acceptable salts thereof, $R_1$ is a group of the formula:

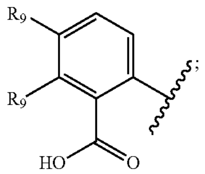

wherein each $R_9$ is independently —H, halogen, $C_1$-$C_3$ alkyl or $C_1$-$C_3$ haloalkyl, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN. Preferably $R_9$ is independently —H, halogen, methyl or trifluoromethyl.

In yet a further compound of Formula (I), or (II), or pharmaceutically acceptable salts thereof, $R_1$ is a group of the formula:

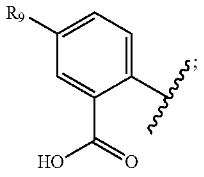

wherein $R_9$ is —H, halogen, or $C_1$-$C_3$ haloalkyl, and $R_2$ is an optionally substituted bicyclic ring selected from 1,3-benzodioxole, 2,3-dihydro-1,4-benzodioxine, isoindolin-1-one, indoline-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN. Preferably $R_9$ is —H, or trifluoromethyl.

In yet a further compound of Formula (I), or (II), or pharmaceutically acceptable salts thereof, $R_1$ is a group of the formula:

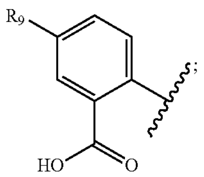

wherein $R_9$ is —H, halogen, or $C_1$-$C_3$ haloalkyl, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN. Preferably $R_9$ is —H, or trifluoromethyl.

In yet a further compound of Formula (I), or (II), or pharmaceutically acceptable salts thereof, $R_1$ is a group of the formula:

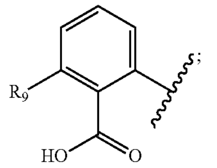

wherein $R_9$ is —H, halogen, or $C_1$-$C_3$ haloalkyl, and $R_2$ is an optionally substituted bicyclic ring selected from 1,3-benzodioxole, 2,3-dihydro-1,4-benzodioxine, isoindolin-1-one, indoline-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN. Preferably $R_9$ is —H, or halogen.

In yet a further compound of Formula (I), or (II), or pharmaceutically acceptable salts thereof, $R_1$ is a group of the formula:

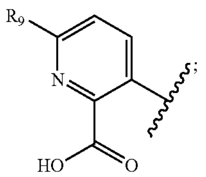

wherein $R_9$ is —H, halogen, $C_1$-$C_3$ alkyl, $C_1$-$C_3$ haloalkyl, or $C_3$-$C_5$ cycloalkyl, and $R_2$ is an optionally substituted bicyclic ring selected from 1,3-benzodioxole, 2,3-dihydro-1,4-benzodioxine, isoindolin-1-one, indoline-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, or triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_9$ is —H, halogen, methyl, trifluoromethyl, or cyclopropyl.

In yet a further compound of Formula (I), or (II), or pharmaceutically acceptable salts thereof, $R_1$ is a group of the formula:

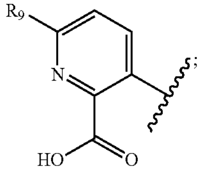

wherein $R_9$ is halogen, or $C_1$-$C_3$ haloalkyl, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_9$ is halogen or trifluoromethyl. More preferably $R_9$ is chloro or trifluoromethyl.

In yet a further compound of Formula (I), or (II), or pharmaceutically acceptable salts thereof, $R_1$ is a group of the formula:

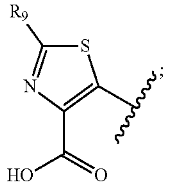

wherein $R_9$ is —H, halogen, $C_1$-$C_3$ alkyl or $C_1$-$C_3$ haloalkyl, and $R_2$ is an optionally substituted bicyclic ring selected from 1,3-benzodioxole, 2,3-dihydro-1,4-benzodioxine, isoindolin-1-one, indoline-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_1$ is a group of the formula:

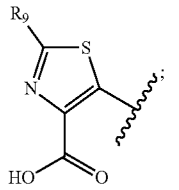

wherein $R_9$ is —H, halogen, $C_1$-$C_3$ alkyl or $C_1$-$C_3$ haloalkyl, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (I), or (II), or pharmaceutically acceptable salts thereof, $R_1$ is a group of the formula:

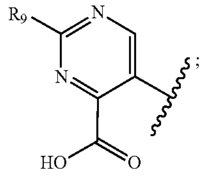

wherein $R_9$ is —H, halogen, $C_1$-$C_3$ alkyl, $C_1$-$C_3$ haloalkyl, or $C_3$-$C_5$ cycloalkyl, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_9$ is —H, halogen, methyl, trifluoromethyl, or cyclopropyl.

In yet a further compound of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, indoline-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, —CN, $C_1$-$C_3$ alkyl, or $C_1$-$C_3$ haloalkyl, $R_4$ is —H, or halogen, $R_6$ is —H, or halogen, $R_5$ is —H, halogen, $C_1$-$C_3$ alkyl or $C_1$-$C_3$ haloalkyl, and $R_1$ is a group of the formula:

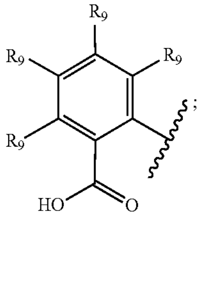
;
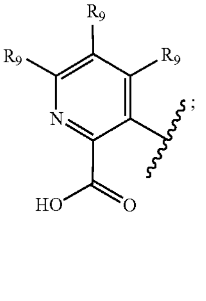
;

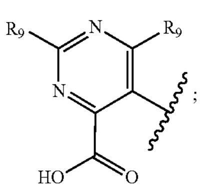
; or
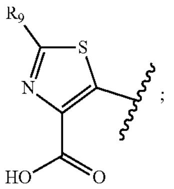
;

wherein each $R_9$ is independently —H, halogen, $C_1$-$C_3$ alkyl, $C_1$-$C_3$ haloalkyl, or $C_3$-$C_5$ cycloalkyl. Preferably $R_3$ is —H, methyl, or trifluoromethyl, $R_4$ is —H, or halogen, $R_6$ is —H, or halogen, $R_5$ is —H, halogen, methyl, or trifluoromethyl, and each $R_9$ is independently —H, halogen, methyl, trifluoromethyl, or cyclopropyl.

In yet a further compound of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, —CN, or $C_1$-$C_3$ alkyl, $R_4$ is —H, $R_6$ is —H, or halogen, $R_5$ is —H, halogen, $C_1$-$C_3$ alkyl or $C_1$-$C_3$ haloalkyl, and $R_1$ is a group of the formula:

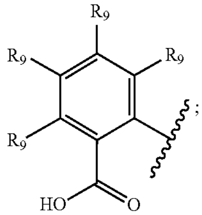
;
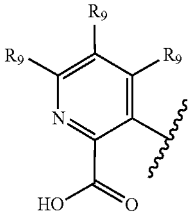
; or

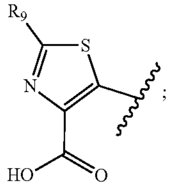
;

wherein each $R_9$ is independently —H, halogen, or $C_1$-$C_3$ haloalkyl. Preferably $R_3$ is —H, or methyl, $R_4$ and $R_6$ are each —H, $R_8$ is —H, halogen, methyl, or trifluoromethyl, and each $R_9$ is independently —H, halogen, methyl, or trifluoromethyl.

In yet a further compound of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, indoline-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_7$ is —CN, methyl or trifluoromethyl, $R_8$ and R are each —H, and $R_1$ is a group of the formula:

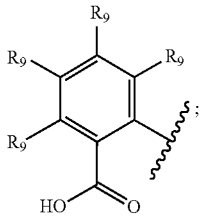
;
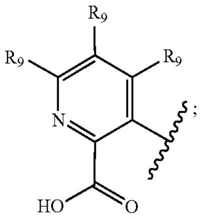
;

-continued

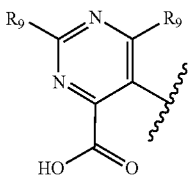
; or
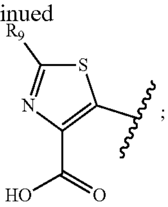
;

wherein each $R_9$ is independently —H, halogen, methyl, $C_1$-$C_3$ haloalkyl, or cyclopropyl.

In yet a further compound of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_7$ is —CN, methyl or trifluoromethyl, $R_8$ and R are each —H, and $R_1$ is a group of the formula:

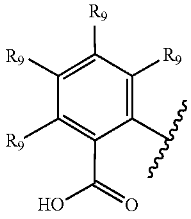
;
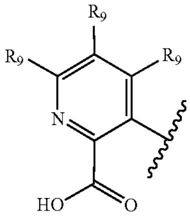
; or
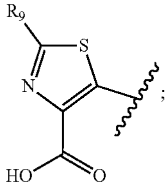
;

wherein each $R_9$ is independently —H, halogen, methyl, or $C_1$-$C_3$ haloalkyl.

In yet a further compound of Formula (I), or (II), or pharmaceutically acceptable salts thereof, $R_1$ is a group of the formula:

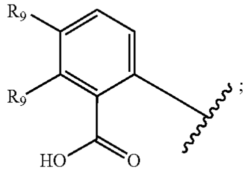
;

wherein each $R_9$ is independently —H, halogen, methyl or trifluoromethyl, $R_2$ is an optionally substituted bicyclic ring selected from 1,3-benzodioxole, 2,3-dihydro-1,4-benzodioxine, isoindolin-1-one, indoline-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_7$ is $C_1$-$C_3$ alkyl (preferably methyl), and $R_8$ and R are each —H.

In yet a further compound of Formula (I), or (II), or pharmaceutically acceptable salts thereof, $R_1$ is a group of the formula:

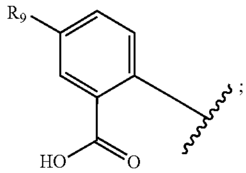
;

wherein $R_9$ is —H, halogen, or trifluoromethyl, (preferably $R_9$ is —H, or trifluoromethyl), $R_2$ is an optionally substituted bicyclic ring selected from 1,3-benzodioxole, 2,3-dihydro-1,4-benzodioxine, isoindolin-1-one, indoline-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_7$ is $C_1$-$C_3$ alkyl (preferably methyl), and $R_8$ and R are each —H.

In yet a further compound of Formula (I), or (II), or pharmaceutically acceptable salts thereof, $R_1$ is a group of the formula:

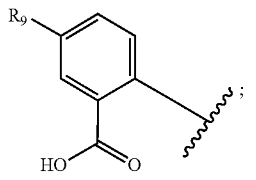

wherein $R_9$ is —H, halogen, or trifluoromethyl, (preferably $R_9$ is —H, or trifluoromethyl), $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_7$ is $C_1$-$C_3$ alkyl (preferably methyl), and $R_8$ and R are each —H.

In yet a further compound of Formula (I), or (II), or pharmaceutically acceptable salts thereof, $R_1$ is a group of the formula:

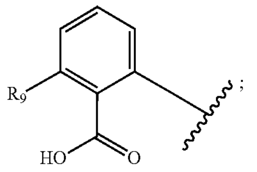

wherein $R_9$ is —H, halogen, or trifluoromethyl, (preferably $R_9$ is —H, or halogen), $R_2$ is an optionally substituted bicyclic ring selected from 1,3-benzodioxole, 2,3-dihydro-1,4-benzodioxine, isoindolin-1-one, indoline-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_7$ is $C_1$-$C_3$ alkyl (preferably methyl), and $R_8$ and R are each —H.

In yet a further compound of Formula (I), or (II), or pharmaceutically acceptable salts thereof, $R_1$ is a group of the formula:

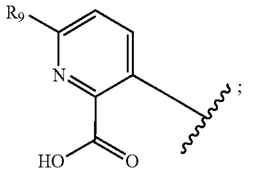

wherein $R_9$ is —H, halogen, methyl, trifluoromethyl, or cyclopropyl, $R_2$ is an optionally substituted bicyclic ring selected from 1,3-benzodioxole, 2,3-dihydro-1,4-benzodioxine, isoindolin-1-one, indoline-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_7$ is $C_1$-$C_3$ alkyl (preferably methyl), and $R_8$ and R are each —H.

In yet a further compound of Formula (I), or (II), or pharmaceutically acceptable salts thereof, $R_1$ is a group of the formula:

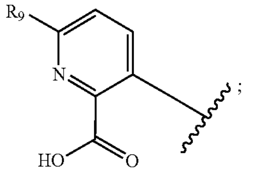

wherein $R_9$ is —H, halogen, or trifluoromethyl (preferably $R_9$ is halogen or trifluoromethyl), $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_7$ is $C_1$-$C_3$ alkyl (preferably methyl), and $R_8$ and R are each —H.

In yet a further compound of Formula (I), or (II), or pharmaceutically acceptable salts thereof, $R_1$ is a group of the formula:

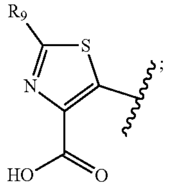

wherein $R_9$ is —H, halogen, $C_1$-$C_3$ alkyl or $C_1$-$C_3$ haloalkyl, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_7$ is $C_1$-$C_3$ alkyl (preferably methyl), and $R_8$ and R are each —H.

In yet a further compound of Formula (I), or (II), or pharmaceutically acceptable salts thereof, $R_1$ is a group of the formula:

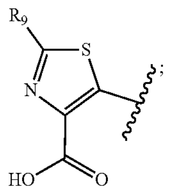

wherein $R_9$ is —H, halogen, $C_1$-$C_3$ alkyl or $C_1$-$C_3$ haloalkyl, $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_7$ is $C_1$-$C_3$ alkyl (preferably methyl), and $R_8$ and R are each —H.

In yet a further compound of Formula (I), or (II), or pharmaceutically acceptable salts thereof, $R_1$ is a group of the formula:

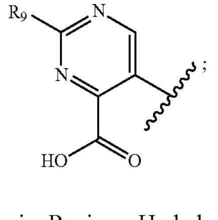

wherein $R_9$ is —H, halogen, methyl, trifluoromethyl, or cyclopropyl, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_7$ is $C_1$-$C_3$ alkyl (preferably methyl), and $R_8$ and R are each —H.

In yet a further compound of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, indoline-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, —CN, $C_1$-$C_3$ alkyl, or $C_1$-$C_3$ haloalkyl, $R_4$ is —H, or halogen, $R_8$ and R are each —H, $R_5$ is —H, halogen, $C_1$-$C_3$ alkyl or $C_1$-$C_3$ haloalkyl, $R_6$ is —H, or halogen, $R_7$ is —CN, methyl or trifluoromethyl, and $R_1$ is a group of the formula:

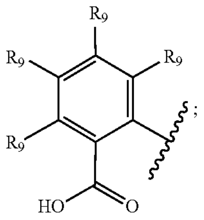
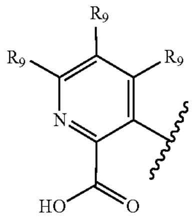

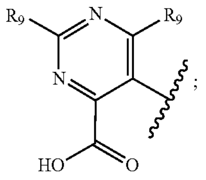 or 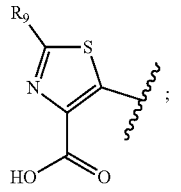

wherein each $R_9$ is independently —H, halogen, methyl, $C_1$-$C_3$ haloalkyl, or cyclopropyl.

In yet a further compound of Formula (I), or (II), or pharmaceutically acceptable salts thereof, $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, —CN, or $C_1$-$C_3$ alkyl, $R_4$, $R_8$ and R are each —H, $R_5$ is —H, halogen, $C_1$-$C_3$ alkyl or $C_1$-$C_3$ haloalkyl, $R_6$ is —H or halogen, $R_7$ is —CN, methyl or trifluoromethyl, and $R_1$ is a group of the formula:

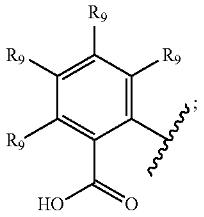 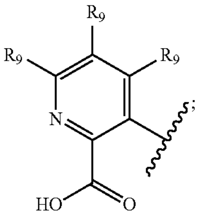 or

-continued

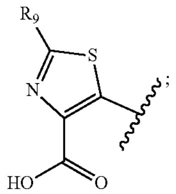

wherein each $R_9$ is independently —H, halogen, methyl, or $C_1$-$C_3$ haloalkyl.

In yet a further compound of Formula (I), or (II), or pharmaceutically acceptable salts thereof, $R_1$ is a group of the formula:

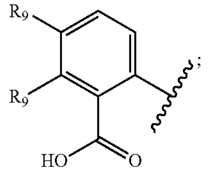

wherein each $R_9$ is independently —H, halogen, methyl or trifluoromethyl, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, or triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, methyl, or trifluoromethyl, $R_4$ is —H, or halogen, $R_8$ and R are each —H, $R_5$ is —H, halogen, methyl or trifluoromethyl, $R_6$ is —H, or halogen, and $R_7$ is $C_1$-$C_3$ alkyl (preferably methyl).

In yet a further compound of Formula (I), or (II), or pharmaceutically acceptable salts thereof, $R_1$ is a group of the formula:

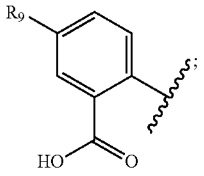

wherein $R_9$ is —H, halogen, or trifluoromethyl, (preferably $R_9$ is —H, or trifluoromethyl), $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, or methyl, $R_4$, $R_8$ and R are each —H, $R_5$ is —H, halogen, methyl, or trifluoromethyl, $R_6$ is —H or halogen, and $R_7$ is $C_1$-$C_3$ alkyl (preferably methyl).

In yet a further compound of Formula (I), or (II), or pharmaceutically acceptable salts thereof, $R_1$ is a group of the formula:

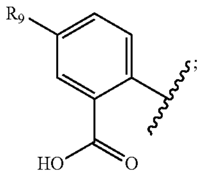

wherein $R_9$ is —H, halogen, or trifluoromethyl, (preferably $R_9$ is —H, or trifluoromethyl), $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, or methyl, $R_4$, $R_8$ and R are each —H, $R_5$ is —H, halogen, methyl, or trifluoromethyl, $R_6$ is —H or halogen, and $R_7$ is $C_1$-$C_3$ alkyl (preferably methyl).

In yet a further compound of Formula (I), or (II), or pharmaceutically acceptable salts thereof, $R_1$ is a group of the formula:

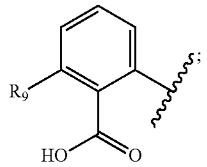

wherein $R_9$ is —H, halogen, or trifluoromethyl, (preferably $R_9$ is —H, or halogen), $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, or methyl, $R_4$, $R_8$ and R are each —H, $R_5$ is —H, halogen, methyl, or trifluoromethyl, $R_6$ is —H or halogen, and $R_7$ is $C_1$-$C_3$ alkyl (preferably methyl).

In yet a further compound of Formula (I), or (II), or pharmaceutically acceptable salts thereof, $R_1$ is a group of the formula:

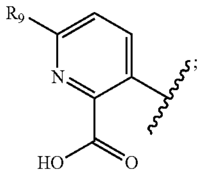

wherein $R_9$ is —H, halogen, methyl, trifluoromethyl, or cyclopropyl, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, methyl, or trifluoromethyl, $R_4$ is —H, or halogen, $R_8$ and R are each —H, $R_5$ is —H, halogen, methyl or trifluoromethyl, $R_6$ is —H, or halogen, and $R_7$ is $C_1$-$C_3$ alkyl (preferably methyl).

In yet a further compound of Formula (I), or (II), or pharmaceutically acceptable salts thereof, $R_1$ is a group of the formula:

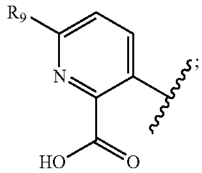

wherein $R_9$ is —H, halogen, or trifluoromethyl, (preferably $R_9$ is halogen or trifluoromethyl), $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, or methyl, $R_4$, $R_8$ and R are each —H, $R_5$ is —H, halogen, methyl, or trifluoromethyl, $R_6$ is —H or halogen, and $R_7$ is $C_1$-$C_3$ alkyl (preferably methyl).

In yet a further compound of Formula (I), or (II), or pharmaceutically acceptable salts thereof, $R_1$ is a group of the formula:

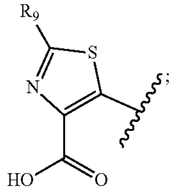

wherein $R_9$ is —H, halogen, $C_1$-$C_3$ alkyl or $C_1$-$C_3$ haloalkyl, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, or methyl, $R_4$, $R_8$ and R are each —H, $R_5$ is —H, halogen, methyl, or trifluoromethyl, $R_6$ is —H or halogen, and $R_7$ is $C_1$-$C_3$ alkyl (preferably methyl).

In yet a further compound of Formula (I), or (II), or pharmaceutically acceptable salts thereof, $R_1$ is a group of the formula:

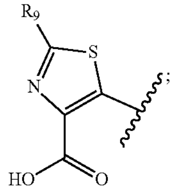

wherein $R_9$ is —H, halogen, $C_1$-$C_3$ alkyl or $C_1$-$C_3$ haloalkyl, $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, or methyl, $R_4$, $R_8$ and R are each —H, $R_5$ is —H, halogen, methyl, or trifluoromethyl, $R_6$ is —H or halogen, and $R_7$ is $C_1$-$C_3$ alkyl (preferably methyl).

In yet a further compound of Formula (I), or (II), or pharmaceutically acceptable salts thereof, $R_1$ is a group of the formula:

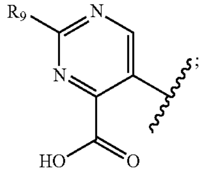

wherein $R_9$ is —H, halogen, methyl, trifluoromethyl, or cyclopropyl, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, methyl, or trifluoromethyl, $R_4$ is —H, or halogen, $R_8$ and R are each —H, $R_5$ is —H, halogen, methyl or trifluoromethyl, $R_6$ is —H, or halogen, and $R_7$ is $C_1$-$C_3$ alkyl (preferably methyl).

In a further aspect, compounds of Formula (I) or (II) have Formula (III), or pharmaceutically acceptable salts thereof:

(III)

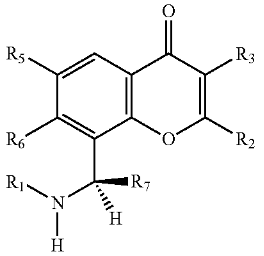

wherein $R_1$, $R_2$, $R_3$, $R_5$, $R_6$, and $R_7$ are as defined in the Summary for Formula (I) above.

In a compound of Formula (III), or pharmaceutically acceptable salts thereof, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In a compound of Formula (III), or pharmaceutically acceptable salts thereof, $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (III), or pharmaceutically acceptable salts thereof, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (III), or pharmaceutically acceptable salts thereof, $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (III), or pharmaceutically acceptable salts thereof, $R_3$ is —H, —CN, $C_1$-$C_3$ alkyl, $C_1$-$C_3$ haloalkyl; preferably $R_3$ is —H, —CN, or $C_1$-$C_3$ alkyl; most preferably $R_3$ is —H, or methyl.

In yet a further compound of Formula (III), or pharmaceutically acceptable salts thereof, $R_5$ is —H, halogen, $C_1$-$C_3$ alkyl or $C_1$-$C_3$ haloalkyl; more preferably $R_5$ is —H, halogen, methyl, or trifluoromethyl.

In yet a further compound of Formula (III), or pharmaceutically acceptable salts thereof, $R_6$ is —H or halogen; preferably $R_6$ is —H.

In yet a further compound of Formula (III), or pharmaceutically acceptable salts thereof, $R_7$ is —CN, $C_1$-$C_3$ alkyl or $C_1$-$C_3$ haloalkyl; more preferably $R_7$ is —CN, methyl or trifluoromethyl.

In yet a further compound of Formula (III), or pharmaceutically acceptable salts thereof, each $R_9$ is independently —H, halogen, $C_1$-$C_3$ alkyl or $C_1$-$C_3$ haloalkyl; preferably each $R_9$ is independently —H, halogen, methyl, or trifluoromethyl.

In yet a further compound of Formula (III), or pharmaceutically acceptable salts thereof, $R_1$ is a group of the formula:

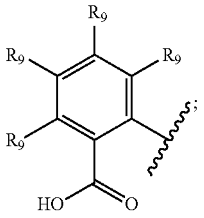
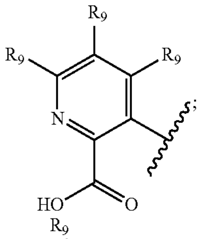
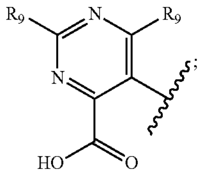
or
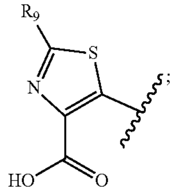

wherein each $R_9$ is independently —H, halogen, $C_1$-$C_6$ alkyl, $C_1$-$C_6$ haloalkyl, $C_1$-$C_6$ alkoxy, or $C_3$-$C_5$ cycloalkyl. Preferably each $R_9$ is independently —H, halogen, $C_1$-$C_3$ alkyl, $C_1$-$C_3$ haloalkyl, or $C_3$-$C_5$ cycloalkyl. More preferably each $R_9$ is independently —H, halogen, methyl, trifluoromethyl, or cyclopropyl.

In yet a further compound of Formula (III), or pharmaceutically acceptable salts thereof, $R_1$ is a group of the formula:

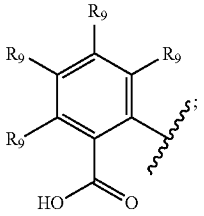
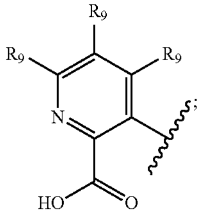
or

-continued

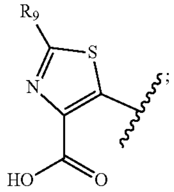

Preferably each $R_9$ is independently —H, halogen, $C_1$-$C_3$ alkyl or $C_1$-$C_3$ haloalkyl. More preferably each $R_9$ is independently —H, halogen, methyl, or trifluoromethyl.

In yet a further compound of Formula (III), or pharmaceutically acceptable salts thereof, $R_1$ is a group of the formula:

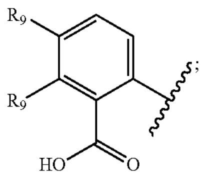

wherein each $R_9$ is independently —H, halogen, $C_1$-$C_3$ alkyl or $C_1$-$C_3$ haloalkyl. Preferably each $R_9$ is independently —H, halogen, methyl or trifluoromethyl.

In yet a further compound of Formula (III), or pharmaceutically acceptable salts thereof, $R_1$ is a group of the formula:

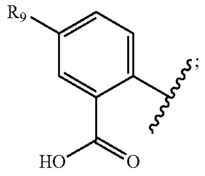

wherein $R_9$ is —H, halogen, or $C_1$-$C_3$ haloalkyl. Preferably $R_9$ is —H, or trifluoromethyl.

In yet a further compound of Formula (III), or pharmaceutically acceptable salts thereof, $R_1$ is a group of the formula:

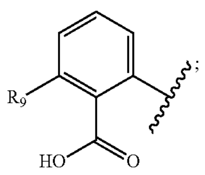

wherein $R_9$ is —H, halogen, or $C_1$-$C_3$ haloalkyl. Preferably $R_9$ is —H, or halogen.

In yet a further compound of Formula (III), or pharmaceutically acceptable salts thereof, $R_1$ is a group of the formula:

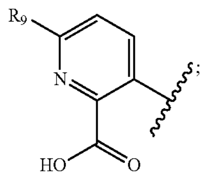

wherein $R_9$ is —H, halogen, $C_1$-$C_3$ alkyl, $C_1$-$C_3$ haloalkyl, or $C_3$-$C_5$ cycloalkyl. Preferably $R_9$ is independently —H, halogen, methyl, trifluoromethyl, or cyclopropyl.

In yet a further compound of Formula (III), or pharmaceutically acceptable salts thereof, $R_1$ is a group of the formula:

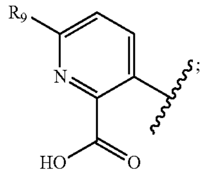

wherein $R_9$ is —H, halogen, or $C_1$-$C_3$ haloalkyl. Preferably $R_9$ is independently halogen or trifluoromethyl. More preferably $R_9$ is chloro or trifluoromethyl.

In yet a further compound of Formula (III), or pharmaceutically acceptable salts thereof, $R_1$ is a group of the formula:

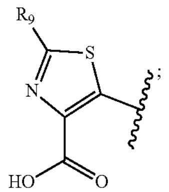

wherein $R_9$ is —H, halogen, $C_1$-$C_3$ alkyl or $C_1$-$C_3$ haloalkyl. Preferably $R_9$ is —H, methyl, or trifluoromethyl.

In yet a further compound of Formula (III), or pharmaceutically acceptable salts thereof, $R_1$ is a group of the formula:

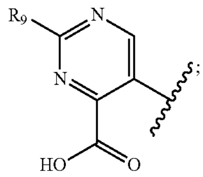

wherein $R_9$ is —H, halogen, $C_1$-$C_3$ alkyl, $C_1$-$C_3$ haloalkyl, or $C_3$-$C_5$ cycloalkyl. Preferably $R_9$ is —H, halogen, methyl, trifluoromethyl, or cyclopropyl.

In yet a further compound of Formula (III), or pharmaceutically acceptable salts thereof, $R_1$ is a group of the formula:

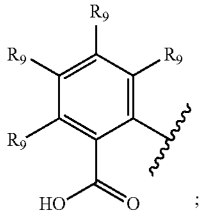 ; 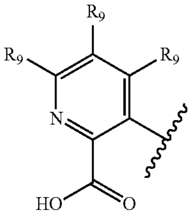 ;

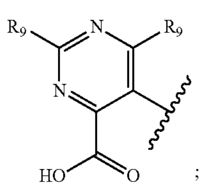 ; or 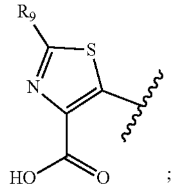 ;

wherein each $R_9$ is independently —H, halogen, $C_1$-$C_3$ alkyl, $C_1$-$C_3$ haloalkyl, or $C_3$-$C_5$ cycloalkyl; and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN. Preferably each $R_9$ is independently —H, halogen, $C_1$-$C_3$ alkyl or $C_1$-$C_3$ haloalkyl. Most preferably each $R_9$ is independently —H, halogen, methyl, or trifluoromethyl.

In yet a further compound of Formula (III), or pharmaceutically acceptable salts thereof, $R_1$ is a group of the formula:

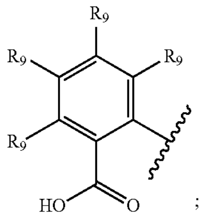 ; 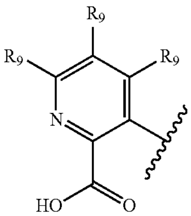 ; or

-continued

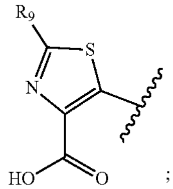

;

wherein $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN. Preferably each $R_9$ is independently —H, halogen, $C_1$-$C_3$ alkyl or $C_1$-$C_3$ haloalkyl. Most preferably each $R_9$ is independently —H, halogen, methyl, or trifluoromethyl.

In yet a further compound of Formula (III), or pharmaceutically acceptable salts thereof, $R_1$ is a group of the formula:

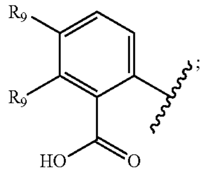

;

wherein each $R_9$ is independently —H, halogen, $C_1$-$C_3$ alkyl or $C_1$-$C_3$ haloalkyl, and $R_2$ is an optionally substituted bicyclic ring selected from 1,3-benzodioxole, 2,3-dihydro-1,4-benzodioxine, isoindolin-1-one, indoline-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN. Preferably $R_9$ is —H, halogen, methyl or trifluoromethyl.

In yet a further compound of Formula (III), or pharmaceutically acceptable salts thereof, $R_1$ is a group of the formula:

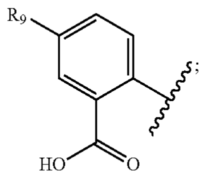

;

wherein $R_9$ is —H, halogen, or $C_1$-$C_3$ haloalkyl, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN. Preferably $R_9$ is —H, or trifluoromethyl.

In yet a further compound of Formula (III), or pharmaceutically acceptable salts thereof, $R_1$ is a group of the formula:

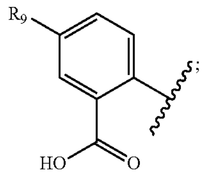

wherein $R_9$ is —H, halogen, or $C_1$-$C_3$ haloalkyl, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN. Preferably $R_9$ is —H, or trifluoromethyl.

In yet a further compound of Formula (III), or pharmaceutically acceptable salts thereof, $R_1$ is a group of the formula:

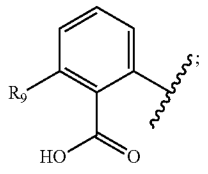

wherein $R_9$ is —H, halogen, or $C_1$-$C_3$ haloalkyl, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN. Preferably $R_9$ is —H, or halogen.

In yet a further compound of Formula (III), or pharmaceutically acceptable salts thereof, $R_1$ is a group of the formula:

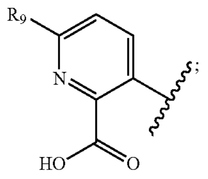

wherein $R_9$ is —H, halogen, $C_1$-$C_3$ alkyl, $C_1$-$C_3$ haloalkyl, or $C_3$-$C_5$ cycloalkyl, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_9$ is —H, halogen, methyl, trifluoromethyl, or cyclopropyl.

In yet a further compound of Formula (III), or pharmaceutically acceptable salts thereof, $R_1$ is a group of the formula:

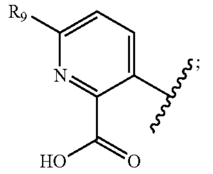

wherein $R_9$ is halogen, or $C_1$-$C_3$ haloalkyl, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_9$ is halogen or trifluoromethyl. More preferably $R_9$ is chloro or trifluoromethyl.

In yet a further compound of Formula (III), or pharmaceutically acceptable salts thereof, $R_1$ is a group of the formula:

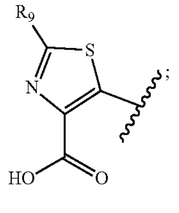

wherein $R_9$ is —H, halogen, $C_1$-$C_3$ alkyl or $C_1$-$C_3$ haloalkyl, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (III), or pharmaceutically acceptable salts thereof, $R_1$ is a group of the formula:

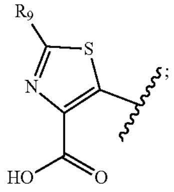

wherein $R_9$ is —H, halogen, $C_1$-$C_3$ alkyl or $C_1$-$C_3$ haloalkyl, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (III), or pharmaceutically acceptable salts thereof, $R_1$ is a group of the formula:

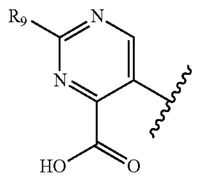

wherein $R_9$ is —H, halogen, $C_1$-$C_3$ alkyl, $C_1$-$C_3$ haloalkyl, or $C_3$-$C_5$ cycloalkyl, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; preferably $R_9$ is —H, halogen, methyl, trifluoromethyl, or cyclopropyl.

In yet a further compound of Formula (III), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_6$ is —H or halogen, $R_7$ is —CN, methyl or trifluoromethyl, and $R_2$ is an optionally substituted bicyclic ring selected from 1,3-benzodioxole, 2,3-dihydro-1,4-benzodioxine, isoindolin-1-one, indoline-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; more preferably $R_3$ is —H, or methyl, $R_5$ is —H, halogen, methyl, or trifluoromethyl, $R_6$ is —H, $R_7$ is methyl, and $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (III), or pharmaceutically acceptable salts thereof, $R_3$ is —H, —CN, $C_1$-$C_3$ alkyl, or $C_1$-$C_3$ haloalkyl (preferably $R_3$ is —H, —CN, or $C_1$-$C_3$ alkyl), $R_6$ is —H or halogen, $R_7$ is —CN, methyl or trifluoromethyl, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN; more preferably $R_3$ is —H, or methyl, $R_5$ is —H, halogen, methyl, or trifluoromethyl, $R_6$ is —H, $R_7$ is methyl, and $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

In yet a further compound of Formula (III), or pharmaceutically acceptable salts thereof, $R_2$ is an optionally substituted bicyclic ring selected from 1,3-benzodioxole, 2,3-dihydro-1,4-benzodioxine, isoindolin-1-one, indoline-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, —CN, $C_1$-$C_3$ alkyl, or $C_1$-$C_3$ haloalkyl, $R_5$ is —H, halogen, $C_1$-$C_3$ alkyl or $C_1$-$C_3$ haloalkyl, $R_6$ is —H or halogen, and $R_1$ is a group of the formula:

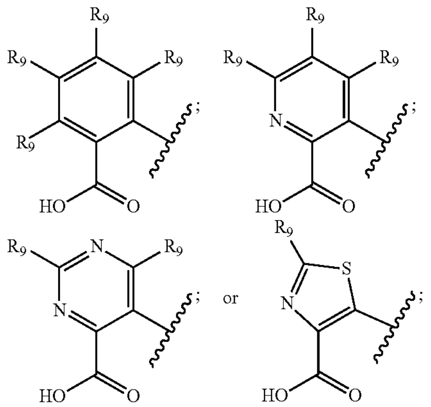

wherein each $R_9$ is independently —H, halogen, $C_1$-$C_3$ alkyl, $C_1$-$C_3$ haloalkyl, or $C_3$-$C_5$ cycloalkyl.

In yet a further compound of Formula (III), or pharmaceutically acceptable salts thereof, $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, —CN, or $C_1$-$C_3$ alkyl, $R_5$ is —H, halogen, $C_1$-$C_3$ alkyl or $C_1$-$C_3$ haloalkyl, $R_6$ is —H or halogen, and $R_1$ is a group of the formula:

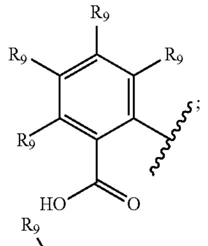
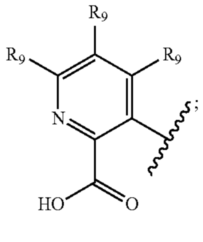
or
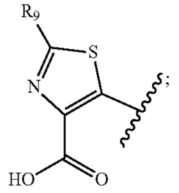

wherein each $R_9$ is independently —H, halogen, $C_1$-$C_3$ alkyl or $C_1$-$C_3$ haloalkyl. Preferably $R_3$ is —H, or methyl, $R_5$ is —H, halogen, methyl, or trifluoromethyl, $R_6$ is —H or halogen, and each $R_9$ is independently —H, halogen, methyl, or trifluoromethyl.

In yet a further compound of Formula (III), or pharmaceutically acceptable salts thereof, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, —CN, $C_1$-$C_3$ alkyl, or $C_1$-$C_3$ haloalkyl, $R_5$ is —H, halogen, $C_1$-$C_3$ alkyl or $C_1$-$C_3$ haloalkyl, $R_6$ is —H or halogen, $R_7$ is —CN, methyl or trifluoromethyl, and $R_1$ is a group of the formula:

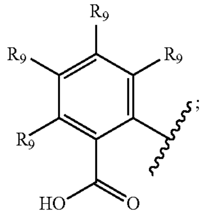
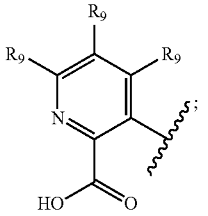
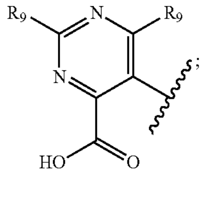
or
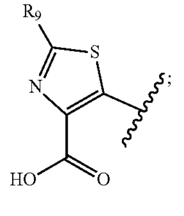

wherein each $R_9$ is independently —H, halogen, $C_1$-$C_3$ alkyl, $C_1$-$C_3$ haloalkyl, or $C_3$-$C_5$ cycloalkyl.

In yet a further compound of Formula (III), or pharmaceutically acceptable salts thereof, $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, —CN, or $C_1$-$C_3$ alkyl, $R_5$ is —H, halogen, $C_1$-$C_3$ alkyl or $C_1$-$C_3$ haloalkyl, $R_6$ is —H or halogen, $R_7$ is —CN, methyl or trifluoromethyl, and $R_1$ is a group of the formula:

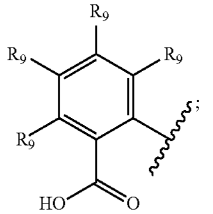
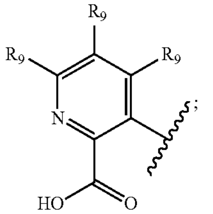
or

-continued

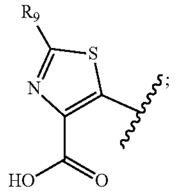

wherein each $R_9$ is independently —H, halogen, $C_1$-$C_3$ alkyl or $C_1$-$C_3$ haloalkyl.

In yet a further compound of Formula (III), or pharmaceutically acceptable salts thereof, $R_1$ is a group of the formula:

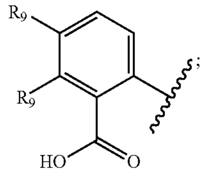

wherein each $R_9$ is independently —H, halogen, methyl or trifluoromethyl, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, methyl, or trifluoromethyl, $R_5$ is —H, halogen, methyl, or trifluoromethyl, $R_6$ is —H or halogen, and $R_7$ is $C_1$-$C_3$ alkyl (preferably methyl).

In yet a further compound of Formula (III), or pharmaceutically acceptable salts thereof, $R_1$ is a group of the formula:

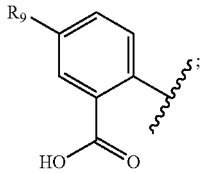

wherein $R_9$ is —H, halogen, or trifluoromethyl, (preferably $R_9$ is —H, or trifluoromethyl), $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, or methyl, $R_5$ is —H, halogen, methyl, or trifluoromethyl, $R_6$ is —H or halogen, and $R_7$ is $C_1$-$C_3$ alkyl (preferably methyl).

In yet a further compound of Formula (III), or pharmaceutically acceptable salts thereof, $R_1$ is a group of the formula:

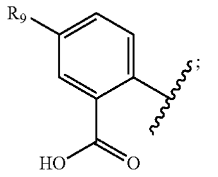

wherein $R_9$ is —H, halogen, or trifluoromethyl, (preferably $R_9$ is —H, or trifluoromethyl), $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, or methyl, $R_5$ is —H, halogen, methyl, or trifluoromethyl, $R_6$ is —H or halogen, and $R_7$ is $C_1$-$C_3$ alkyl (preferably methyl).

In yet a further compound of Formula (III), or pharmaceutically acceptable salts thereof, $R_1$ is a group of the formula:

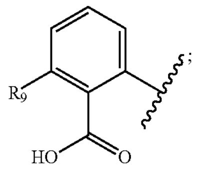

wherein $R_9$ is —H, halogen, or trifluoromethyl, (preferably $R_9$ is —H, or halogen), $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, or methyl, $R_5$ is —H, halogen, methyl, or trifluoromethyl, $R_6$ is —H or halogen, and $R_7$ is $C_1$-$C_3$ alkyl (preferably methyl).

In yet a further compound of Formula (III), or pharmaceutically acceptable salts thereof, $R_1$ is a group of the formula:

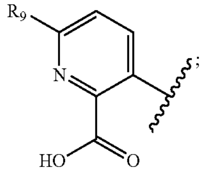

wherein $R_9$ is independently —H, halogen, methyl, trifluoromethyl, or cyclopropyl, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, methyl, or trifluoromethyl, $R_5$ is —H, halogen, methyl, or trifluoromethyl, $R_6$ is —H or halogen, and $R_7$ is $C_1$-$C_3$ alkyl (preferably methyl).

In yet a further compound of Formula (III), or pharmaceutically acceptable salts thereof, $R_1$ is a group of the formula:

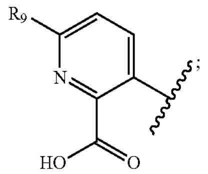

wherein $R_9$ is —H, halogen, or trifluoromethyl, (preferably $R_9$ is halogen or trifluoromethyl), $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, or methyl, $R_5$ is —H, halogen, methyl, or trifluoromethyl, $R_6$ is —H or halogen, and $R_7$ is $C_1$-$C_3$ alkyl (preferably methyl).

In yet a further compound of Formula (III), or pharmaceutically acceptable salts thereof, $R_1$ is a group of the formula:

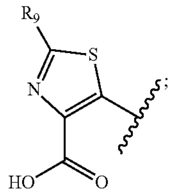

wherein $R_9$ is —H, halogen, $C_1$-$C_3$ alkyl or $C_1$-$C_3$ haloalkyl, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, or methyl, $R_5$ is —H, halogen, methyl, or trifluoromethyl, $R_6$ is —H or halogen, and $R_7$ is $C_1$-$C_3$ alkyl (preferably methyl).

In yet a further compound of Formula (III), or pharmaceutically acceptable salts thereof, $R_1$ is a group of the formula:

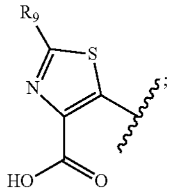

wherein $R_9$ is —H, halogen, $C_1$-$C_3$ alkyl or $C_1$-$C_3$ haloalkyl, $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN, $R_3$ is —H, or methyl, $R_5$ is —H, halogen, methyl, or trifluoromethyl, $R_6$ is —H or halogen, and $R_7$ is $C_1$-$C_3$ alkyl (preferably methyl).

In yet a further compound of Formula (III), or pharmaceutically acceptable salts thereof, $R_1$ is a group of the formula:

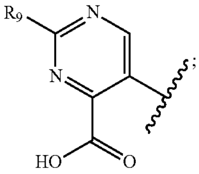
;

wherein $R_9$ is —H, halogen, methyl, trifluoromethyl, or cyclopropyl, $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine (preferably 1,3-benzodioxole, 2,3-dihydro-1,4-benzodioxine, isoindolin-1-one, indolin-2-one, or benzo[d]oxazol-2(3H)-one), or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline (preferably indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole); wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, $-NR_{10}R_{10}$, —OH or —CN, $R_3$ is —H, methyl, or trifluoromethyl, $R_5$ is —H, halogen, methyl, or trifluoromethyl, $R_6$ is —H or halogen, and $R_7$ is $C_1$-$C_3$ alkyl (preferably methyl).

In yet a further compound of Formula (I), the compound is selected from:

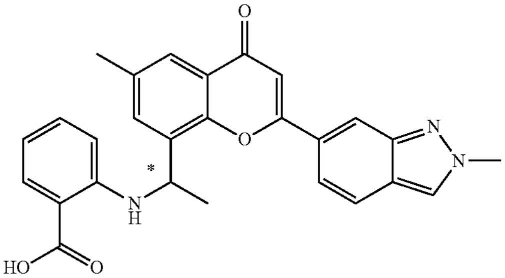
;

-continued

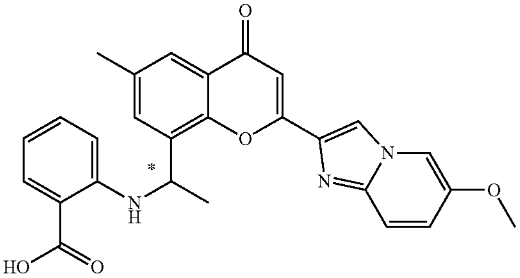
;

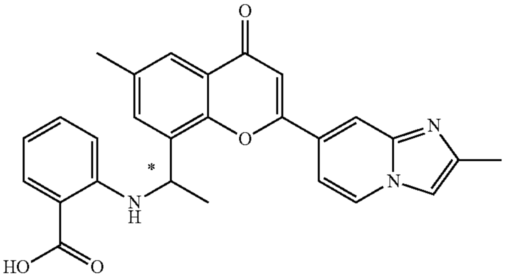
;

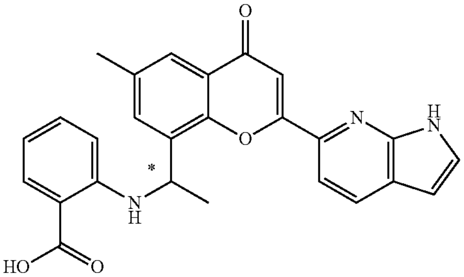
;

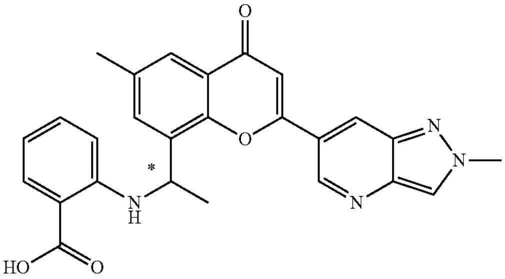
;

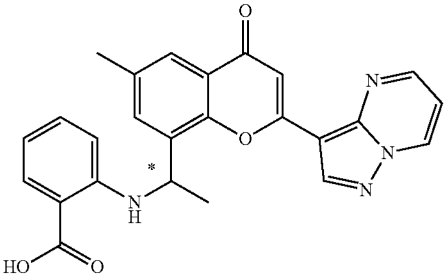
;

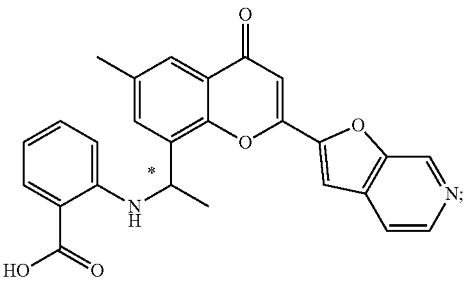
;

-continued
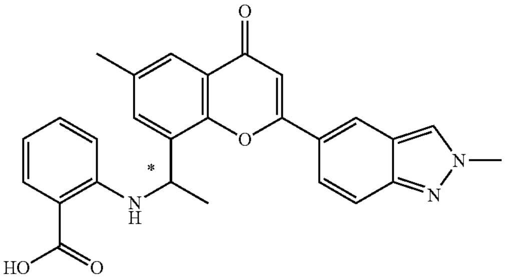
;
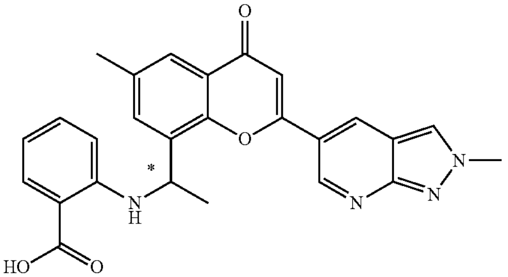
;
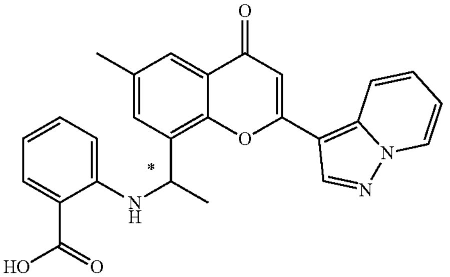
;
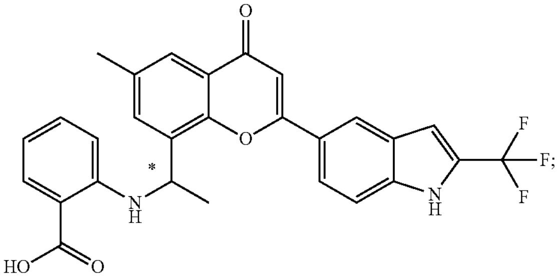
;
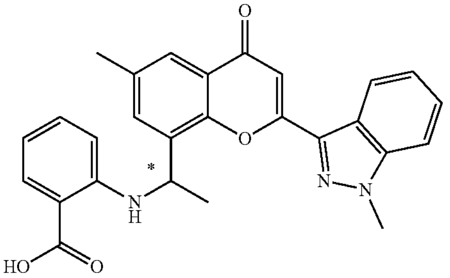
;
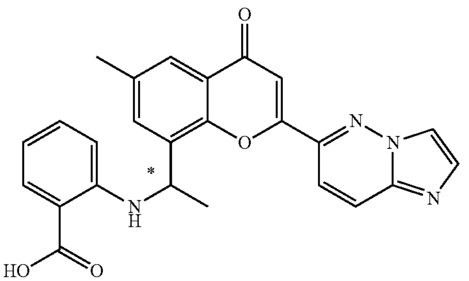
;
-continued
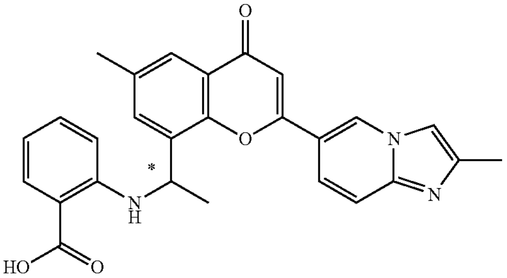
;
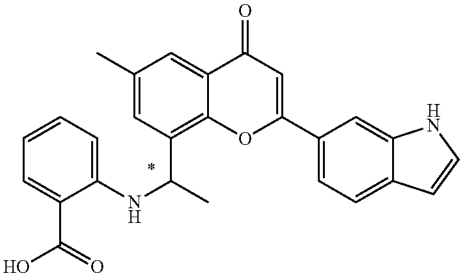
;
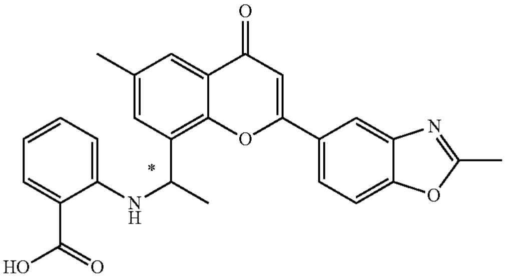
;
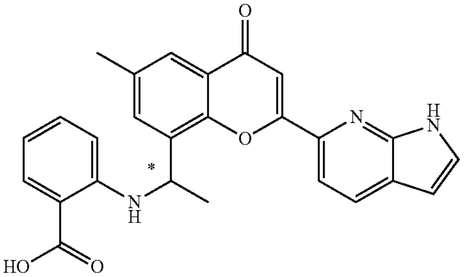
;
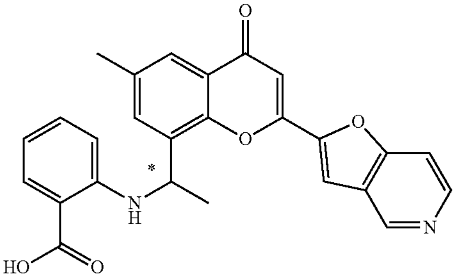
;
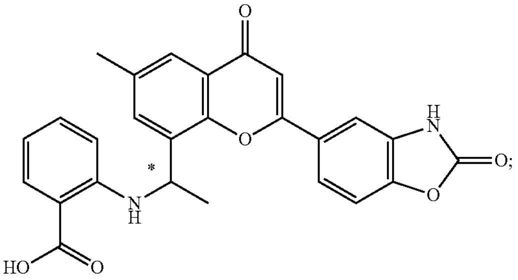
;

-continued
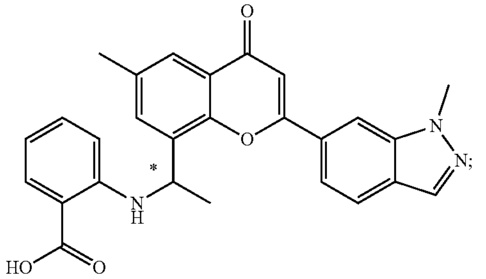
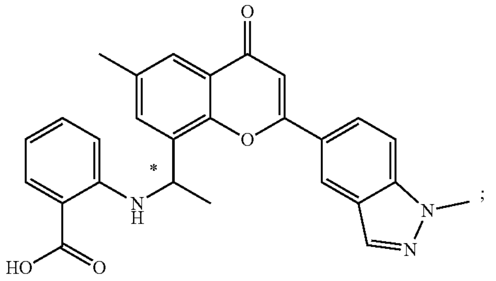
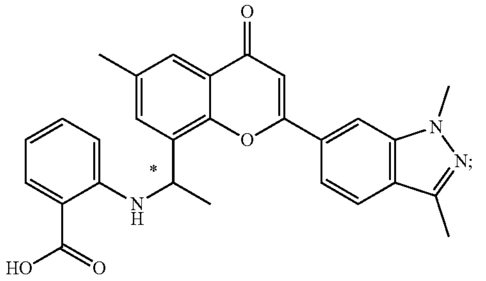
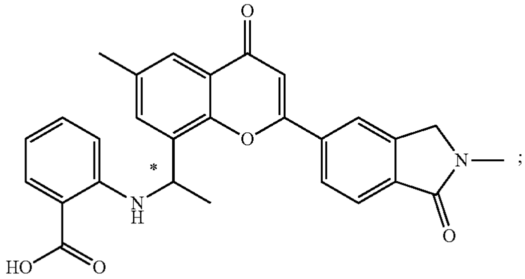
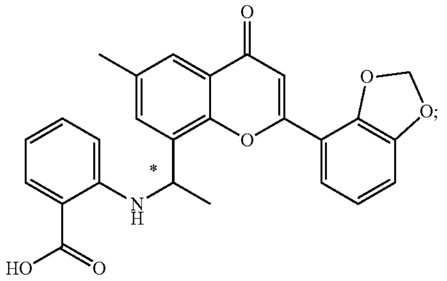
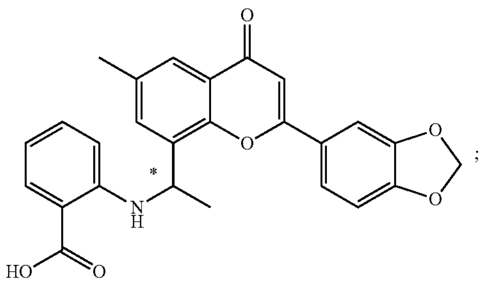
-continued
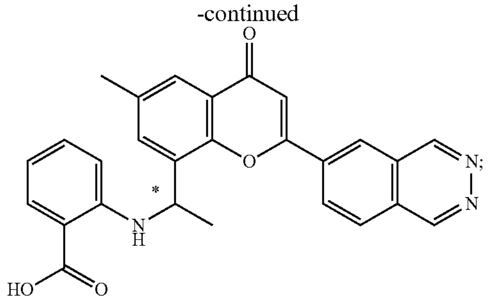
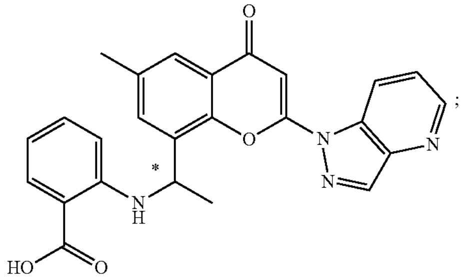
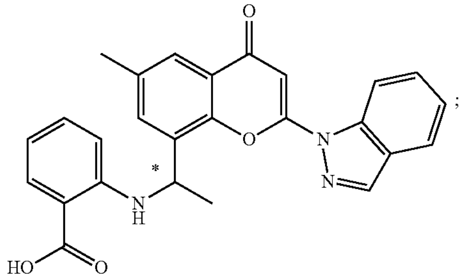
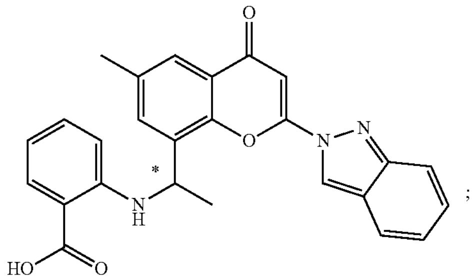
and
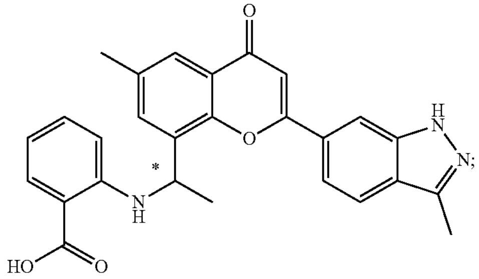
or a pharmaceutically acceptable salt of any of the foregoing;
wherein the bond at the * position is as represented
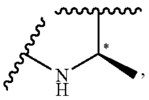
or
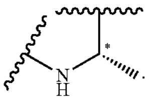
In yet a further compound of Formula (I), the compound is selected from:

-continued
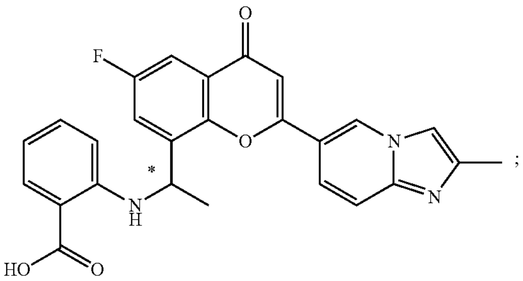
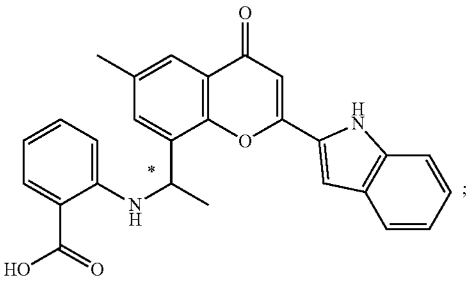
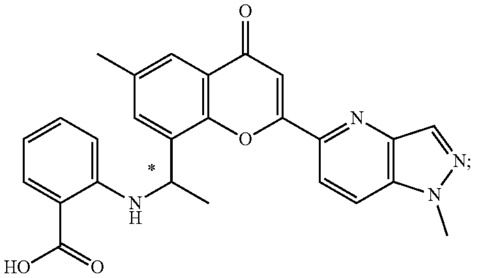
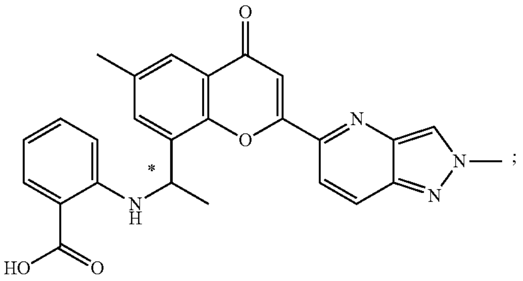
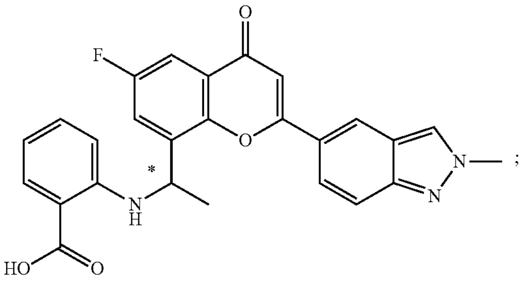
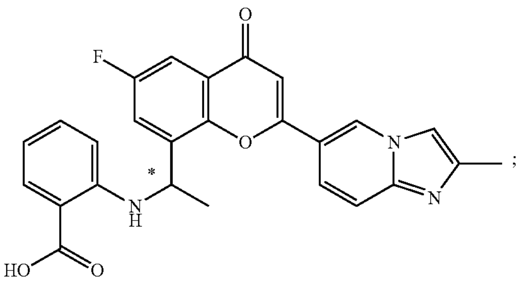
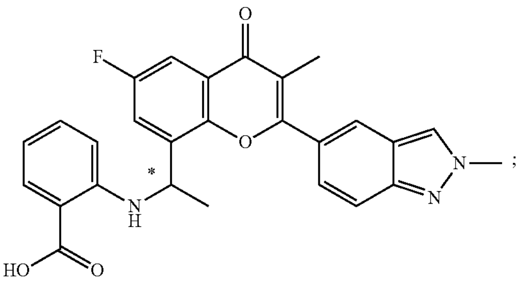
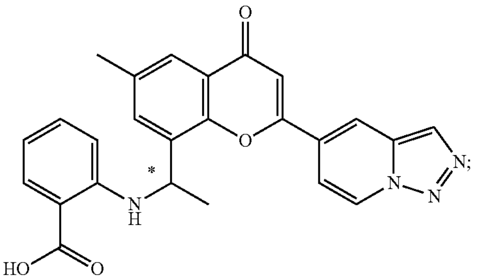
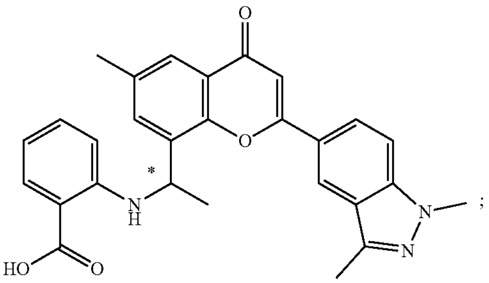
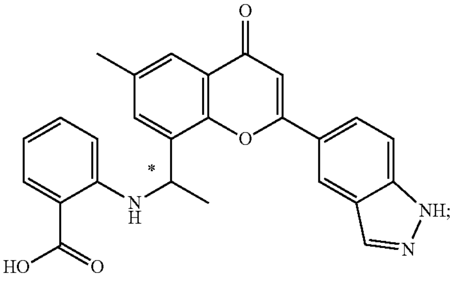
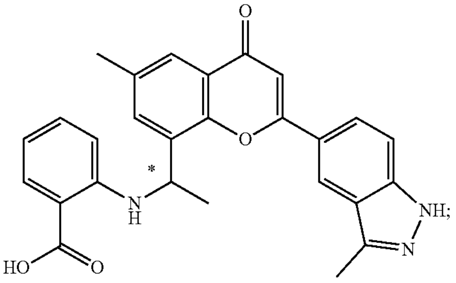
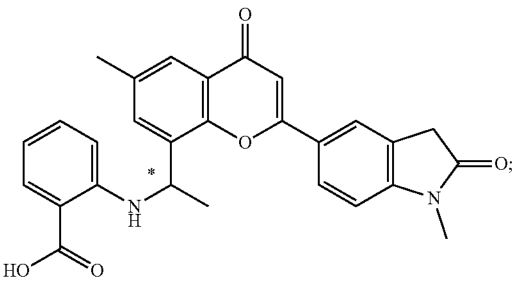

-continued
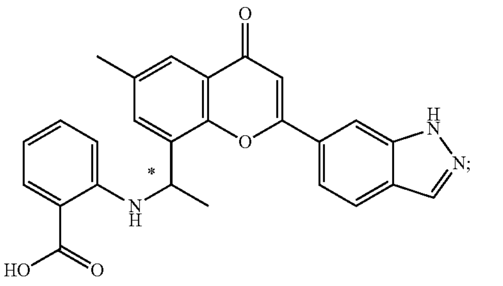
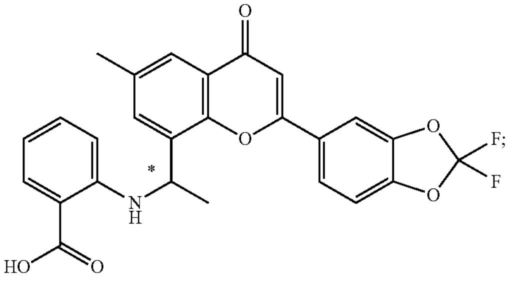
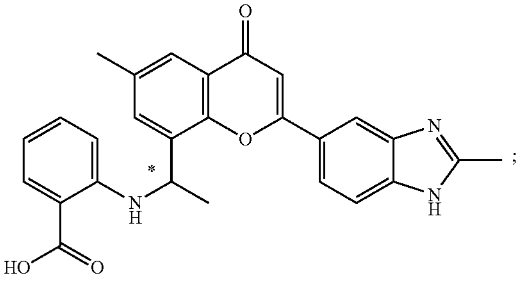
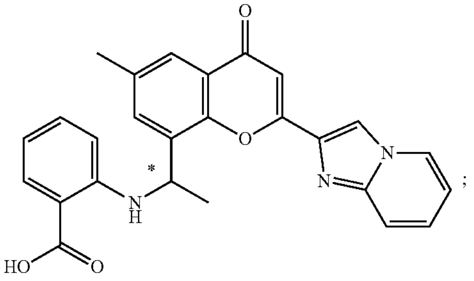
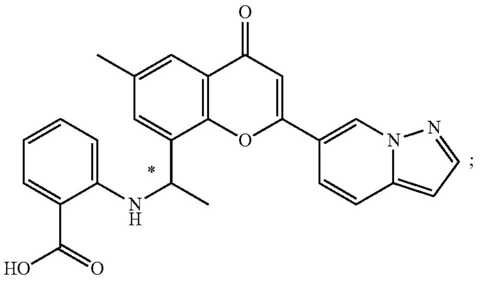
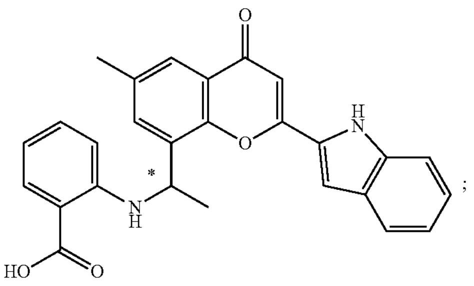
-continued
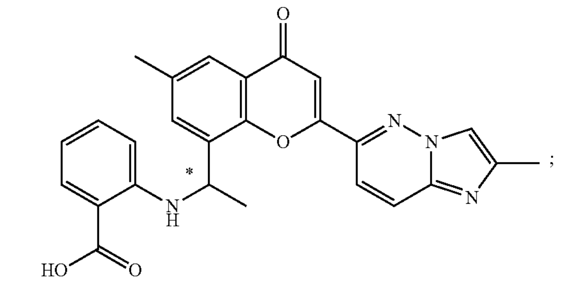
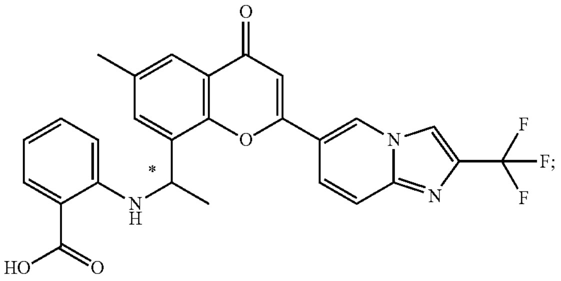
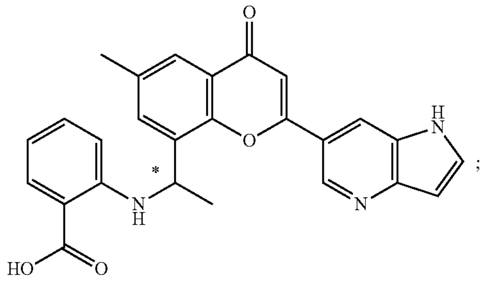
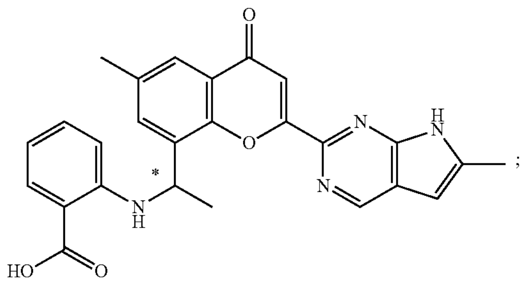
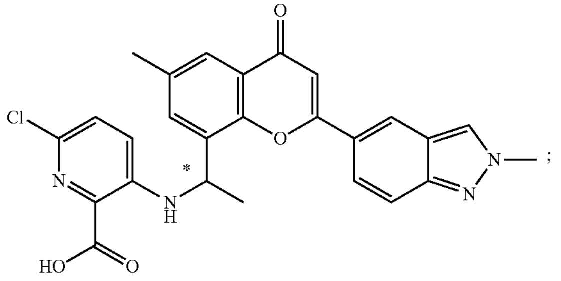
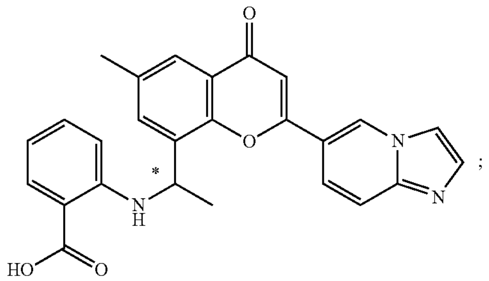

-continued
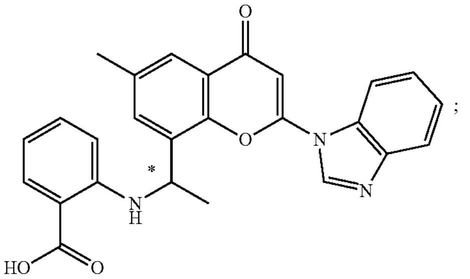
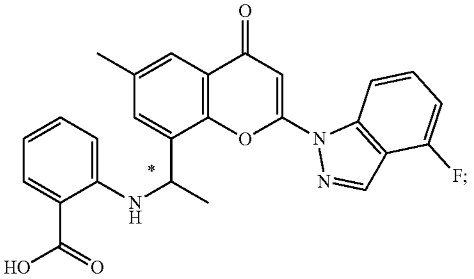
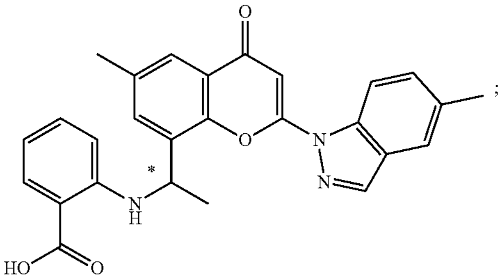
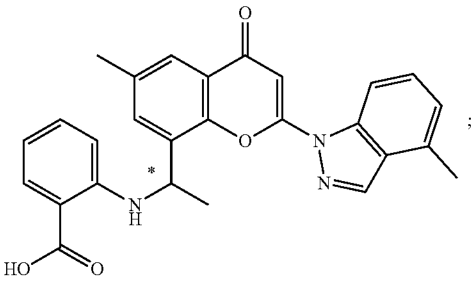
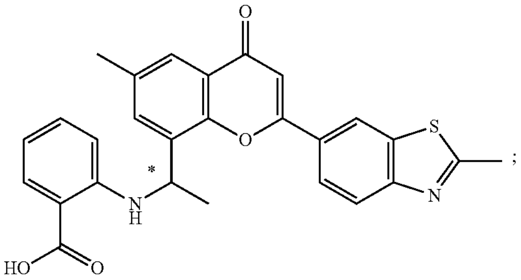
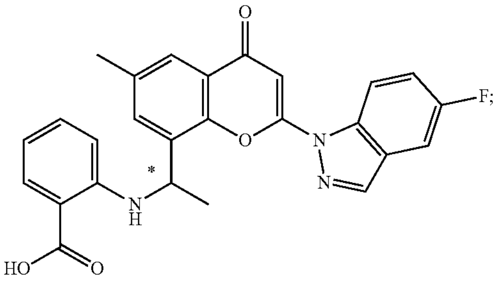
-continued
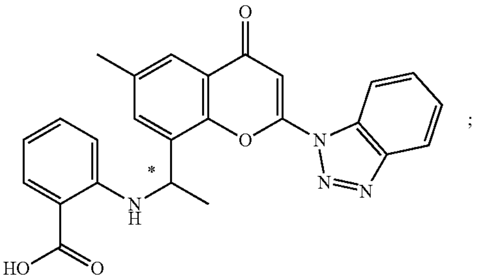
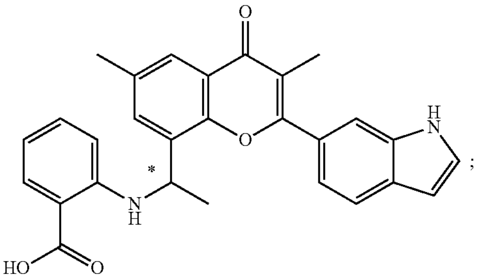
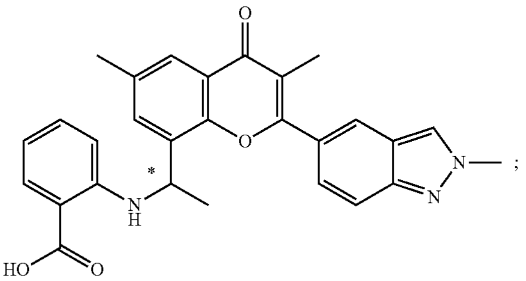
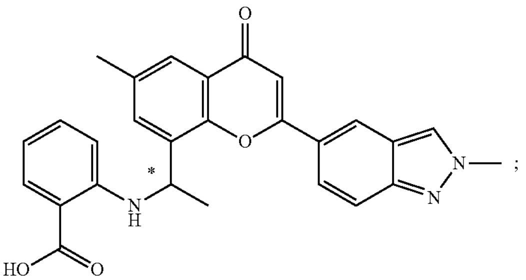
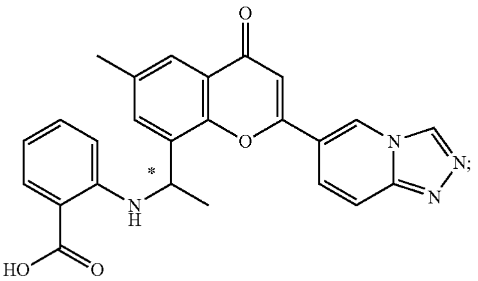
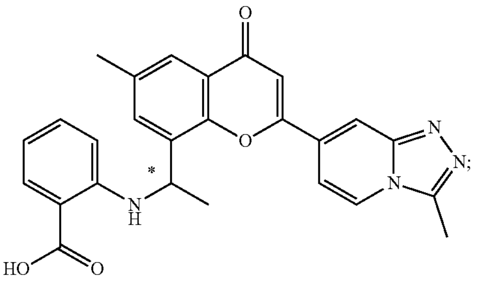

-continued
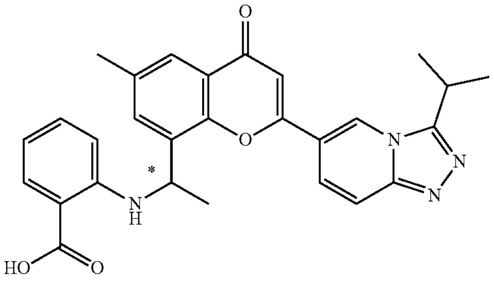
;
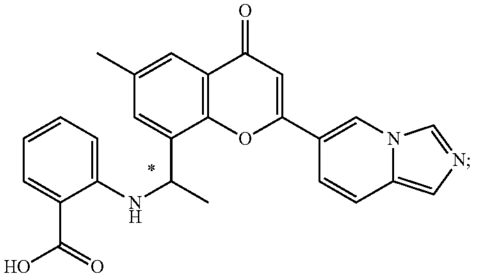
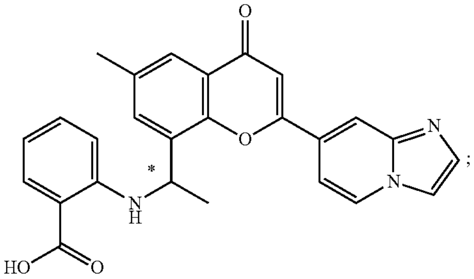
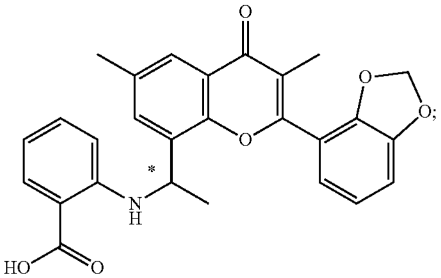
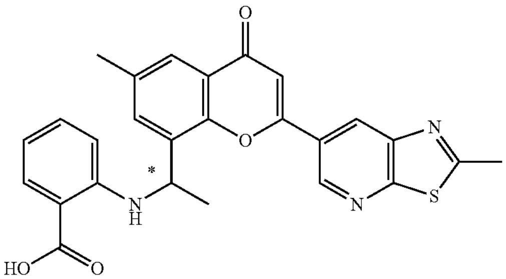
;
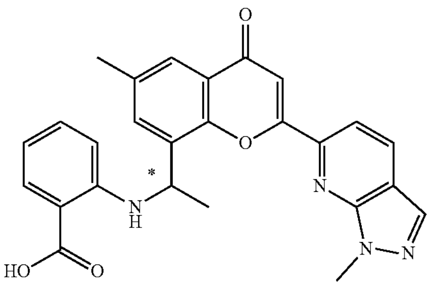
; and
-continued
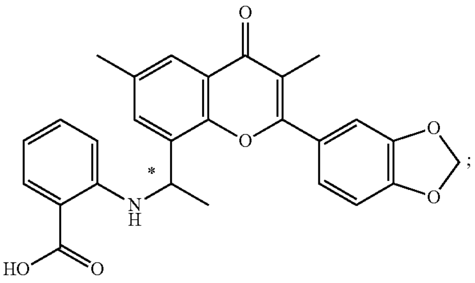
or a pharmaceutically acceptable salt of any of the foregoing;
wherein the bond at the * position is as represented,
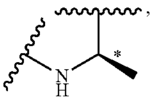
, or
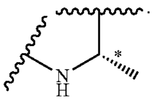
In yet a further compound of Formula (I), the compound is selected from:
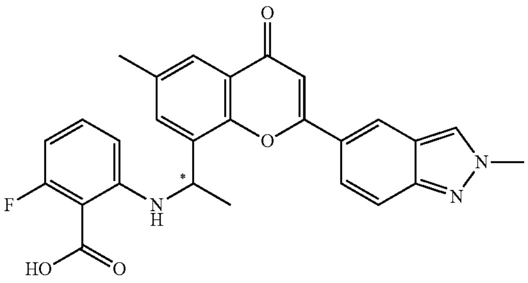
;
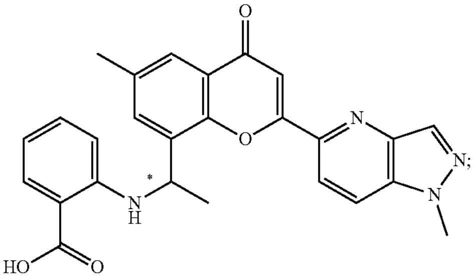
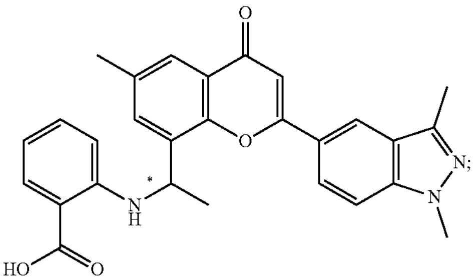

-continued
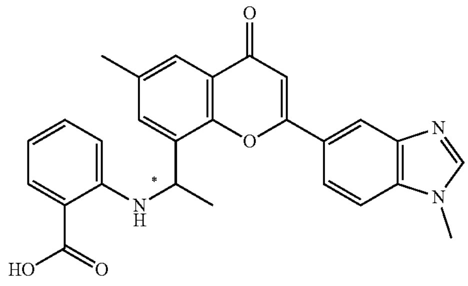
;
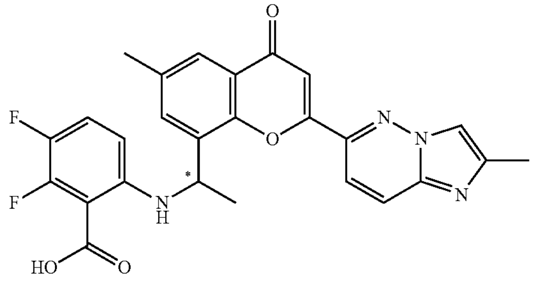
;
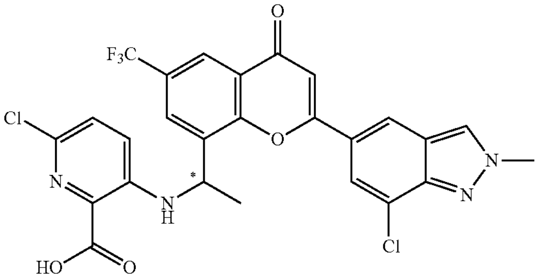
;
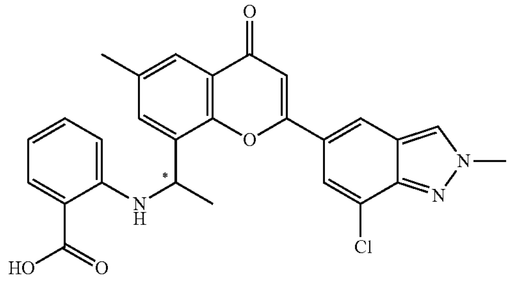
;
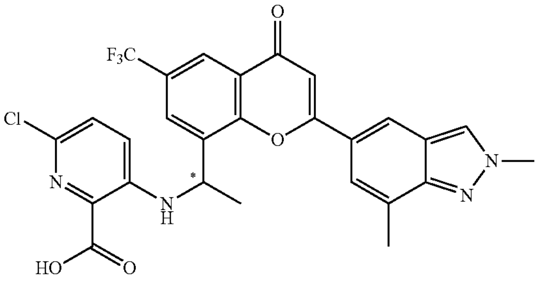
;
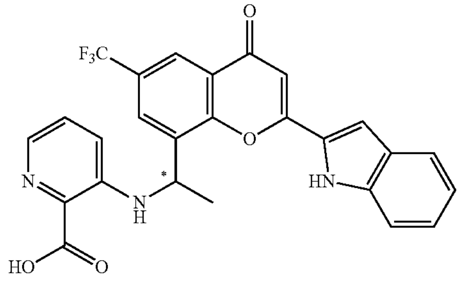
;
-continued
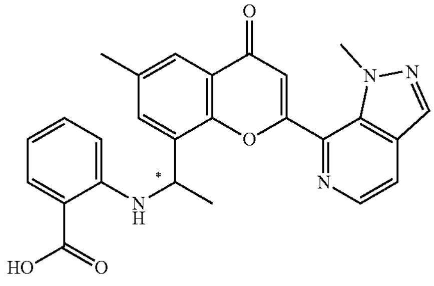
;
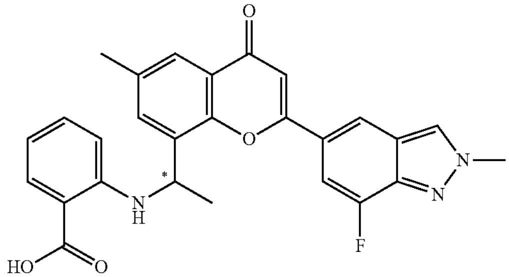
;
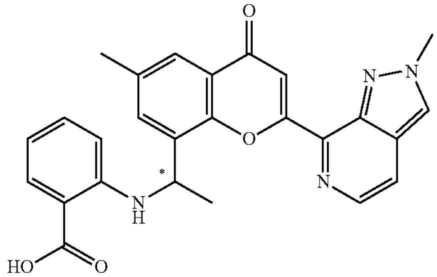
;
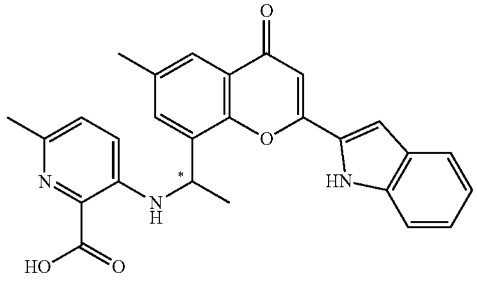
;
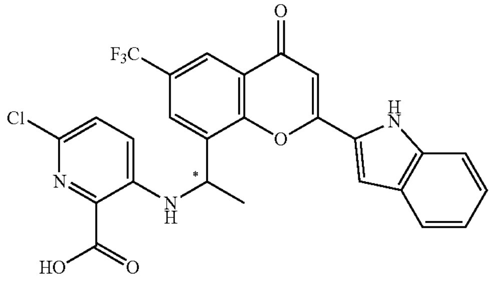
;
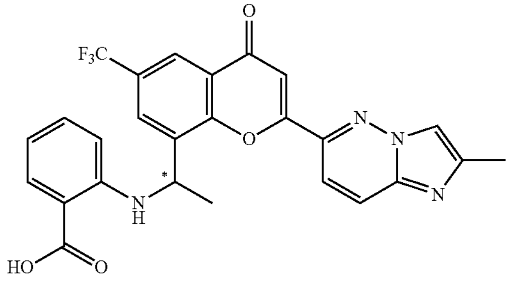
;

-continued
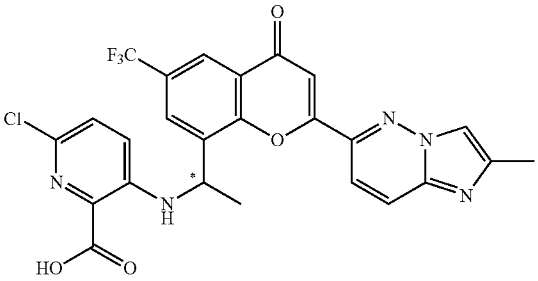
;
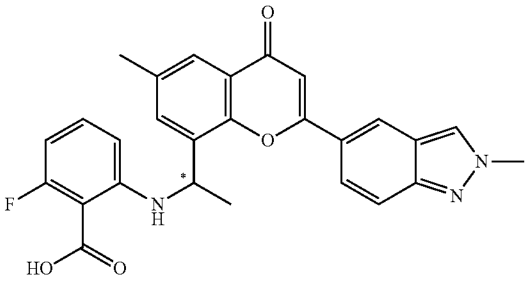
;
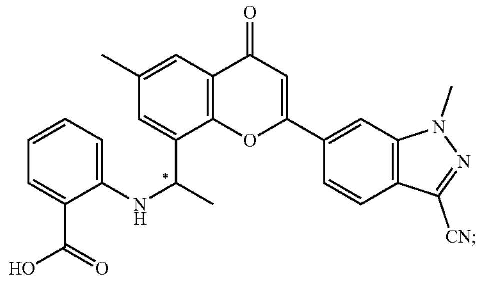
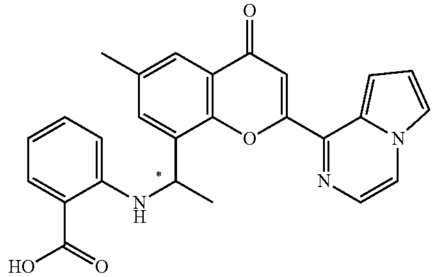
;
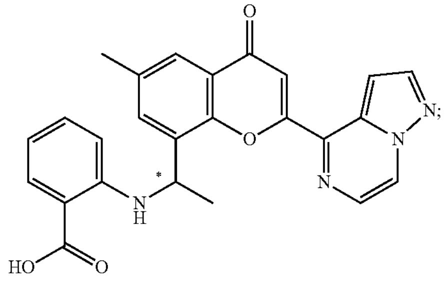
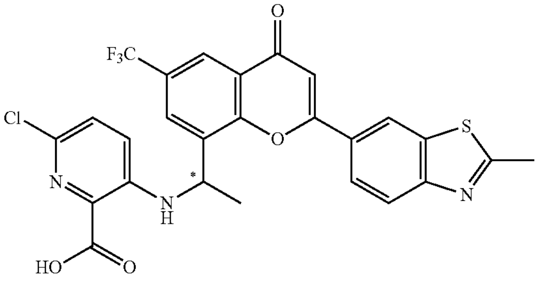
;
-continued
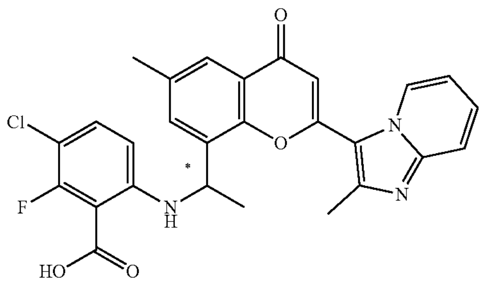
;
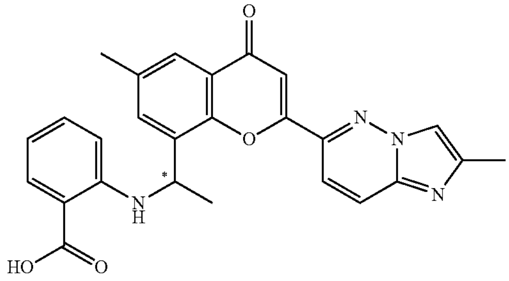
;
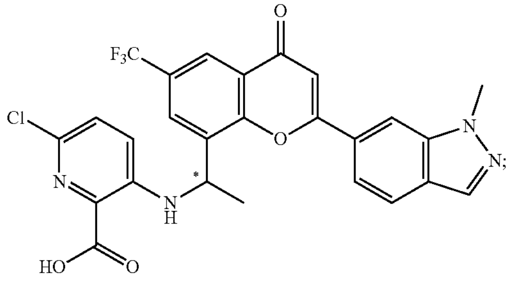
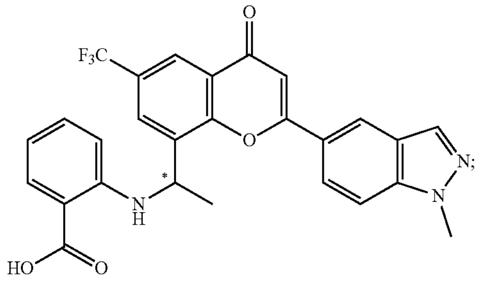
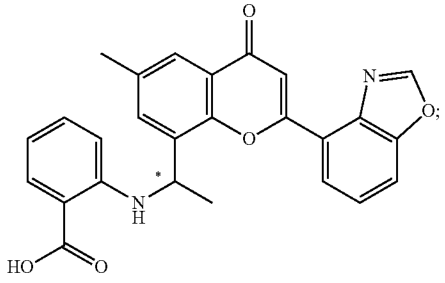
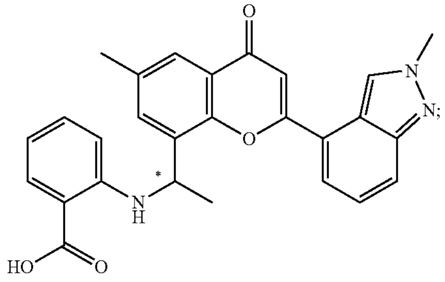

-continued
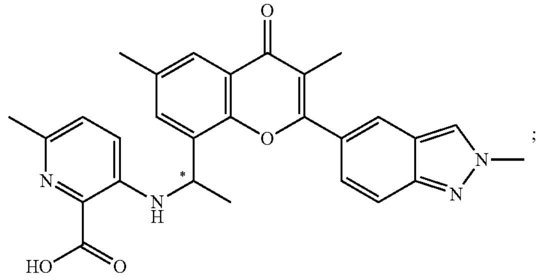
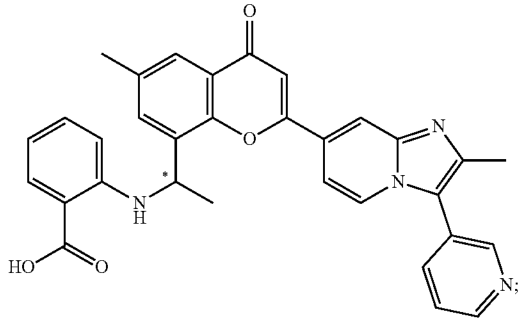
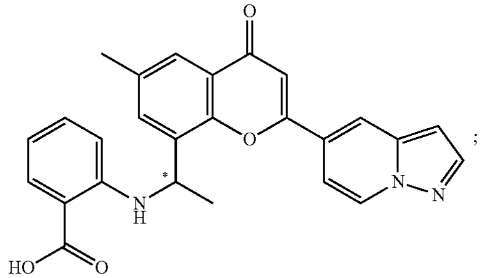
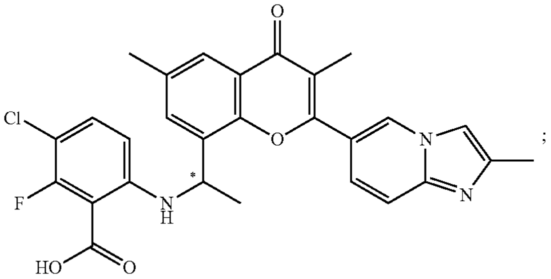
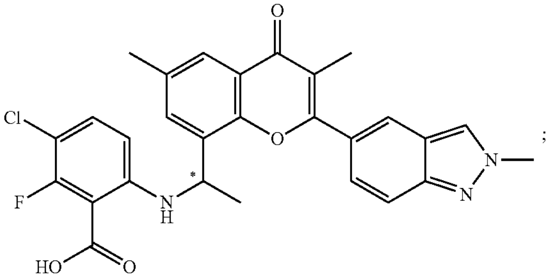
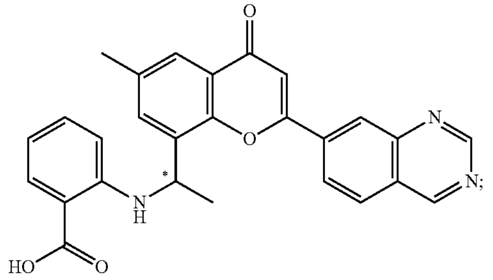
-continued
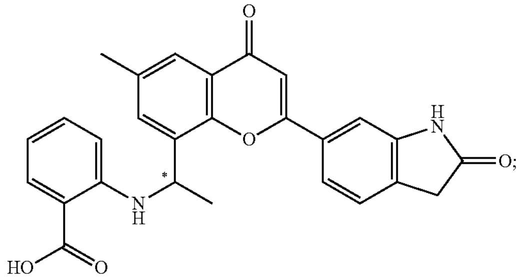
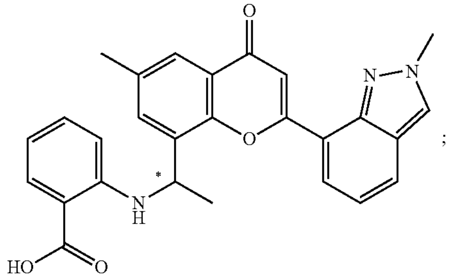
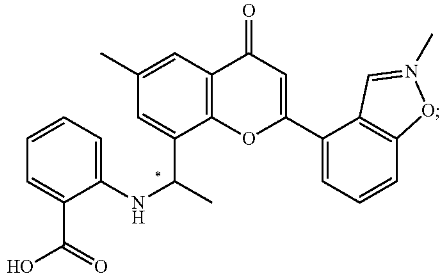
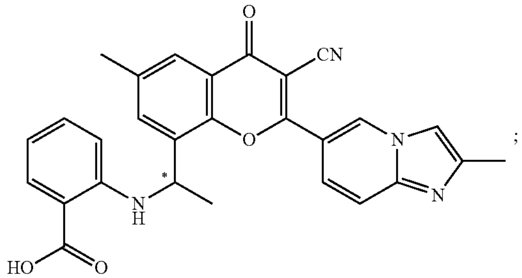
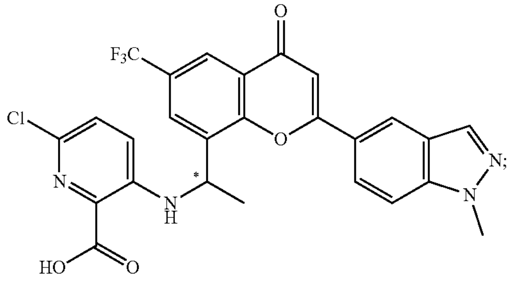
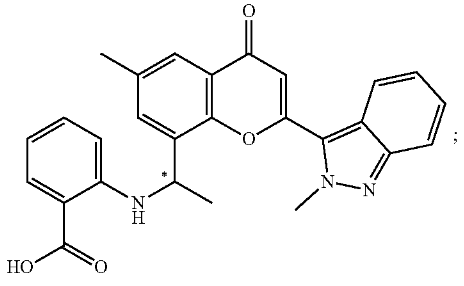

-continued
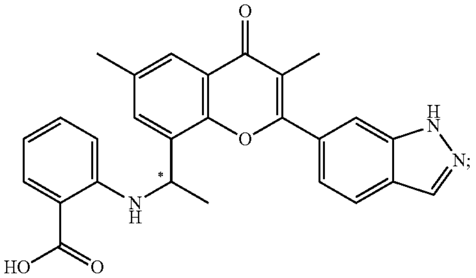
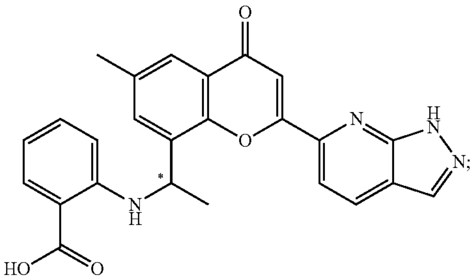
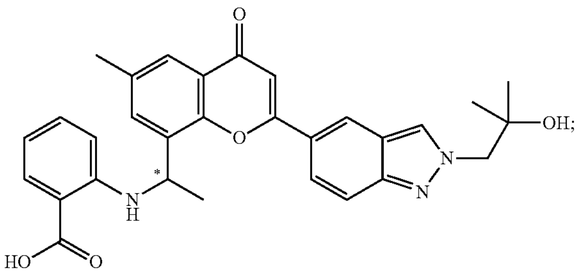
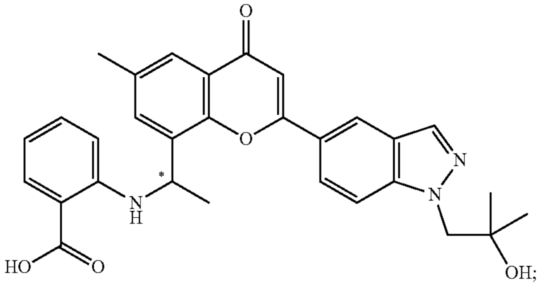
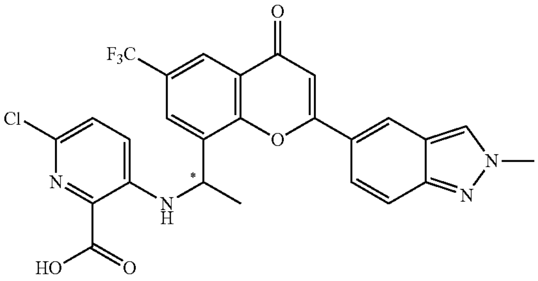
;
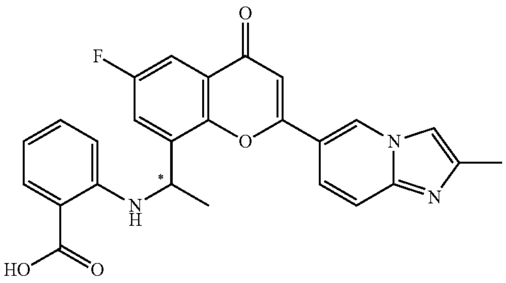
;
-continued
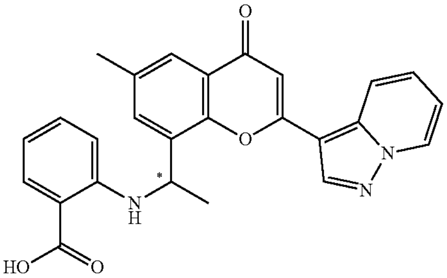
;
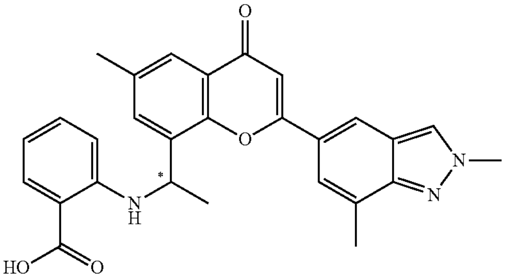
;
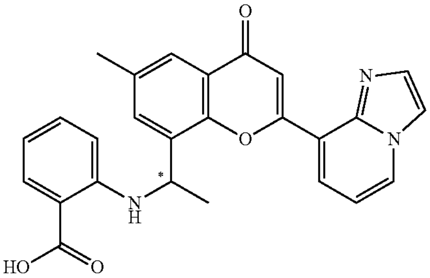
;
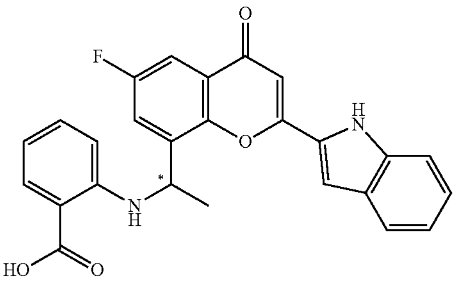
;
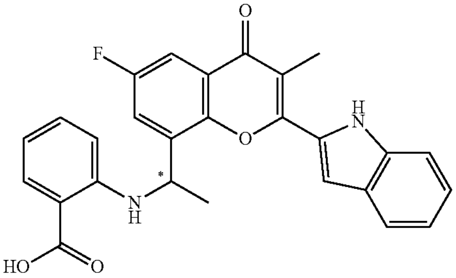
;
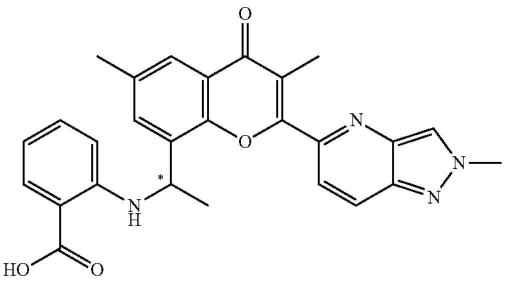
;

-continued
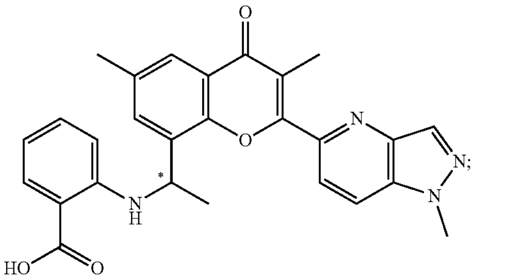
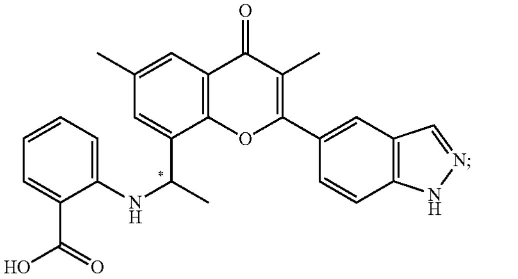
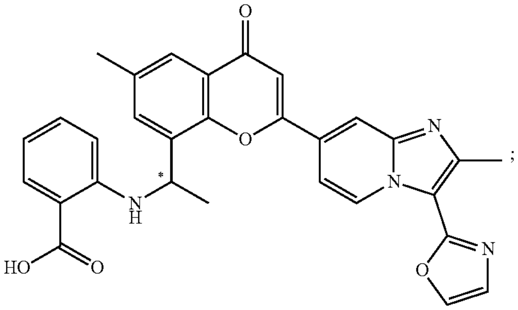
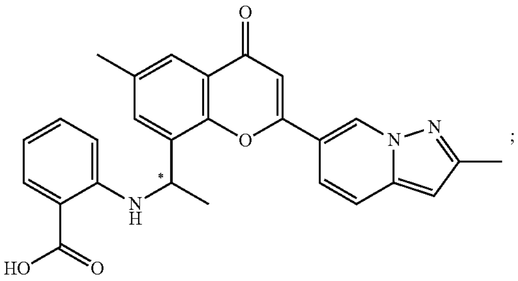
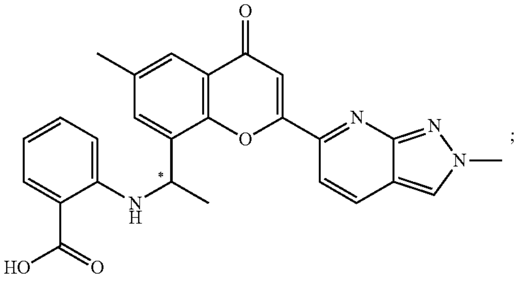
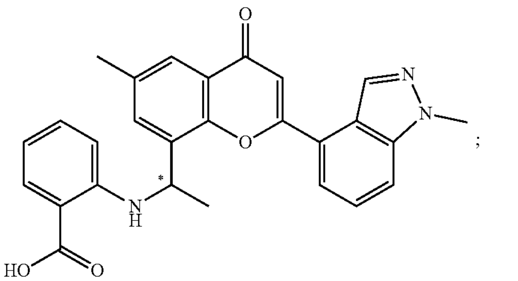
-continued
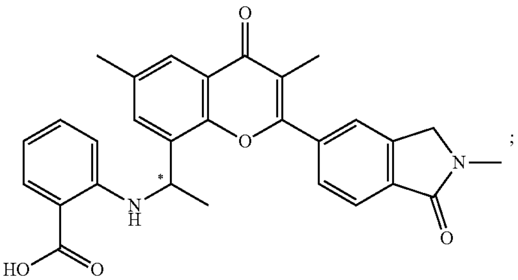
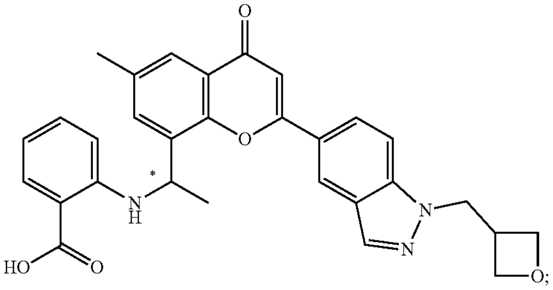
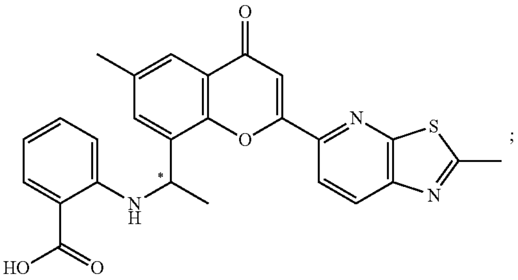
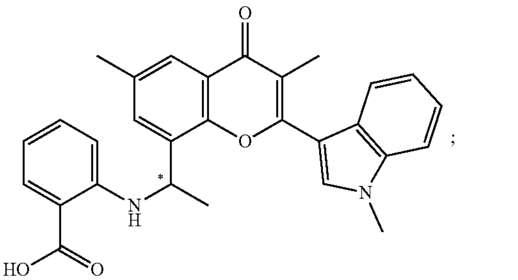
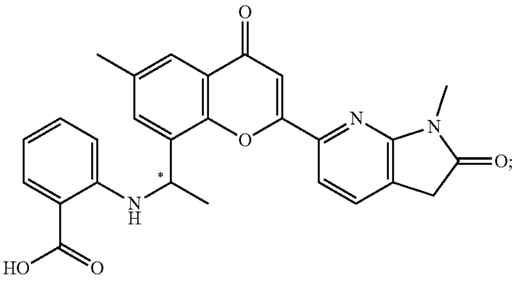
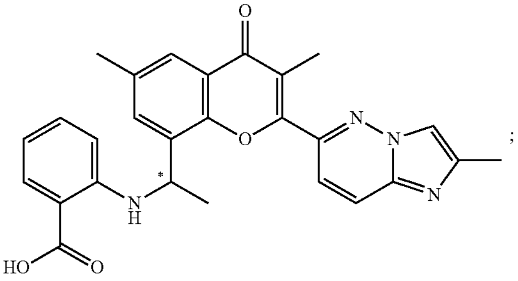

-continued
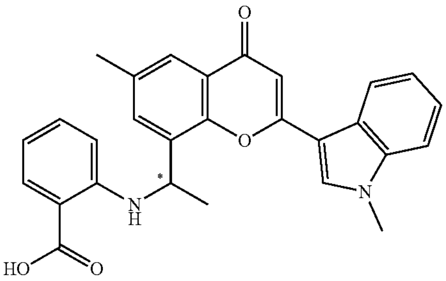
;
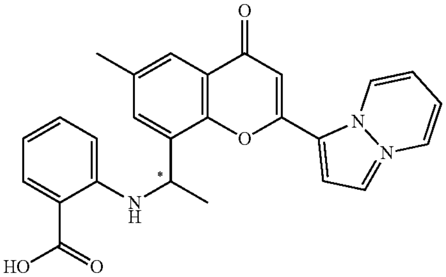
;
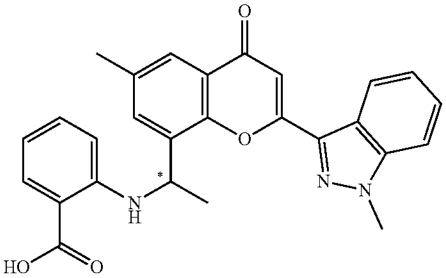
;
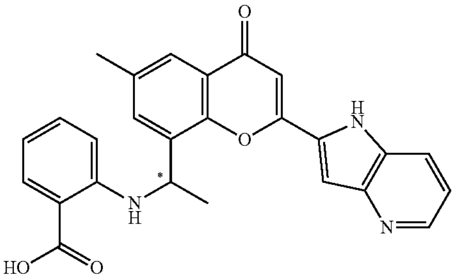
;
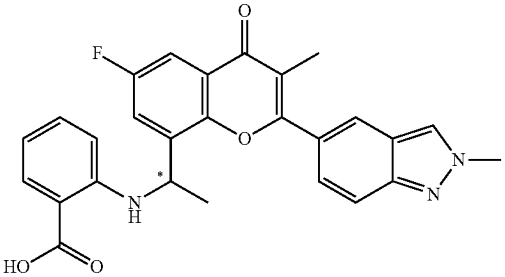
;
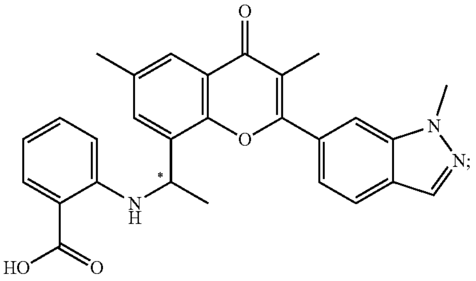
-continued
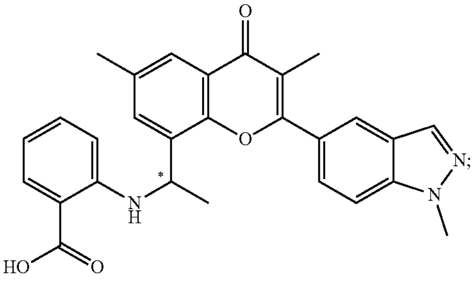
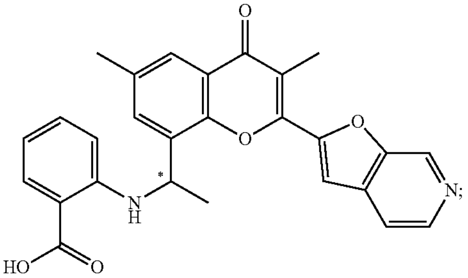
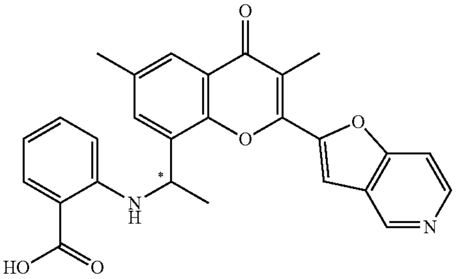
;
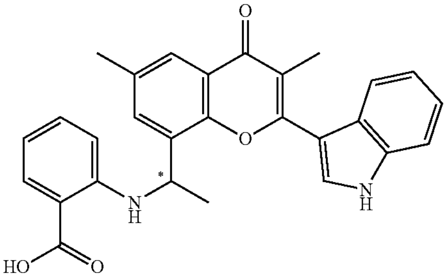
;
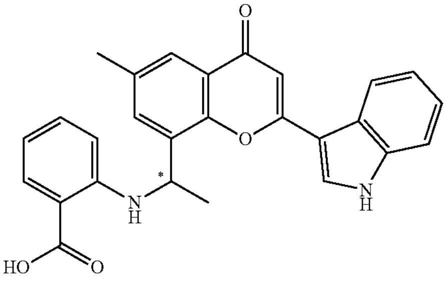
;
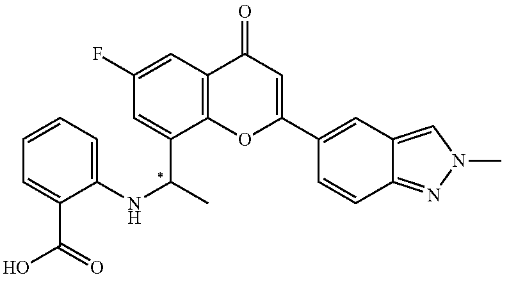
;

-continued
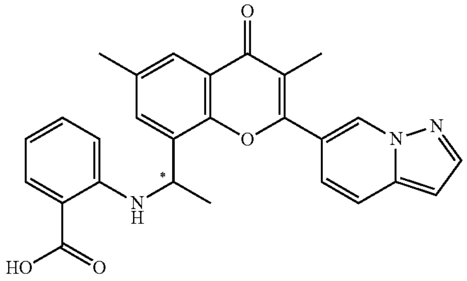
;
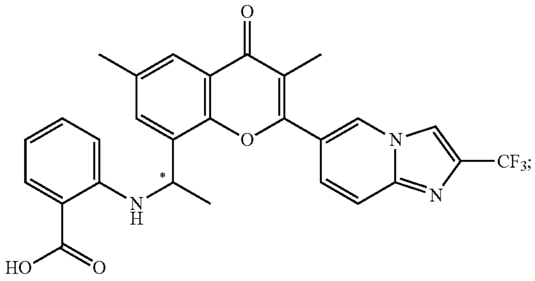
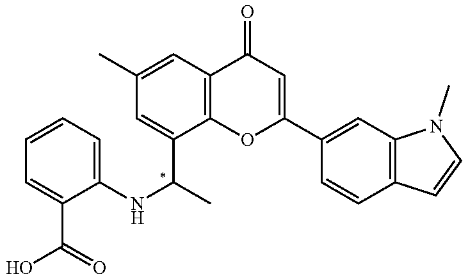
;
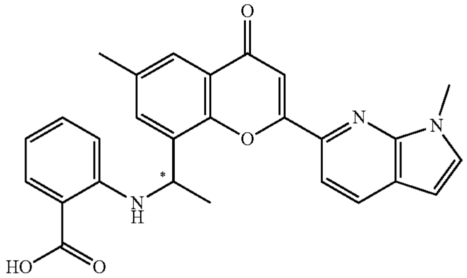
;
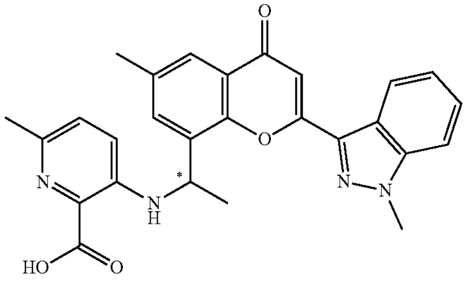
;
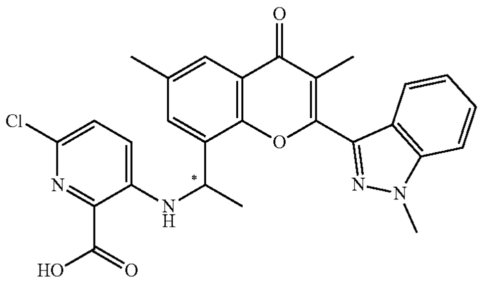
;
-continued
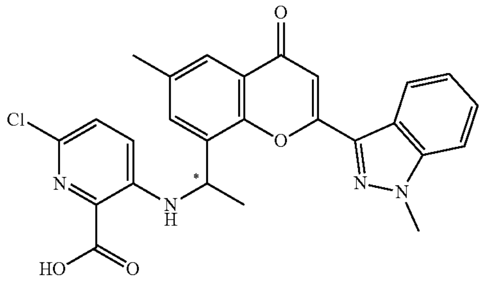
;
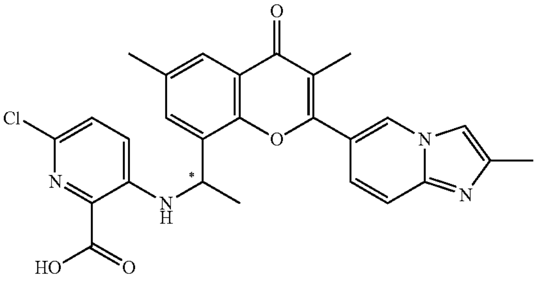
;
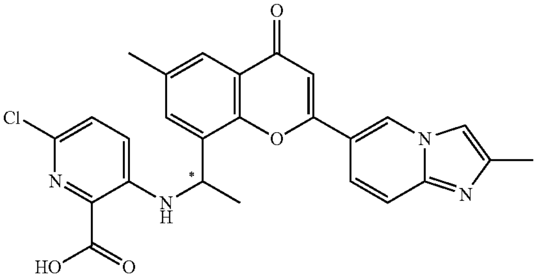
;
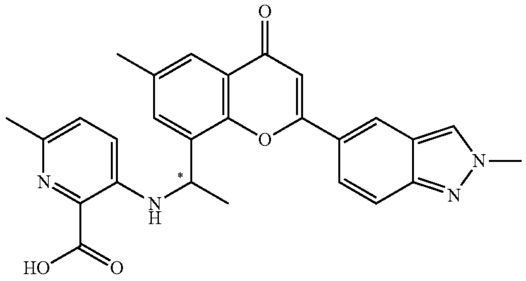
;
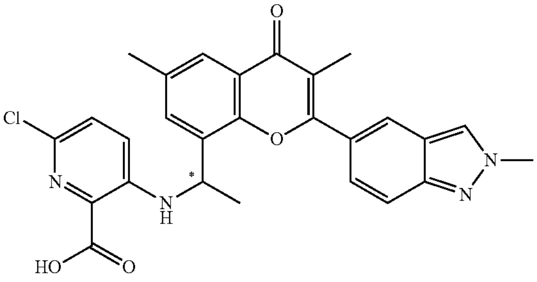
;
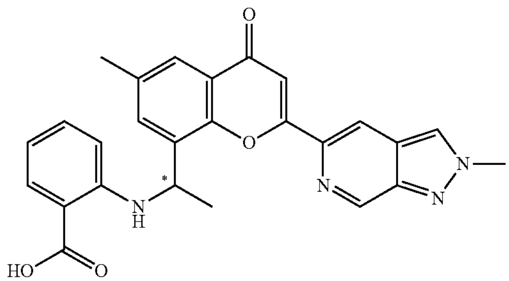
;

-continued

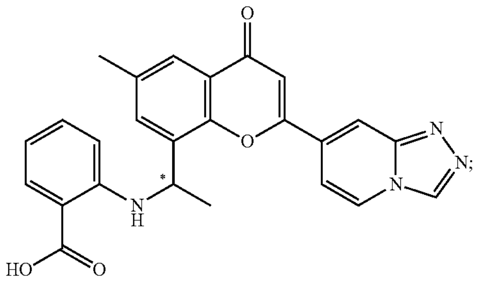

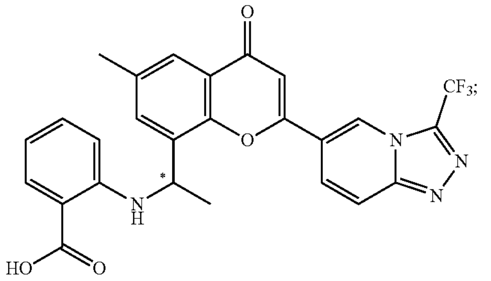

and

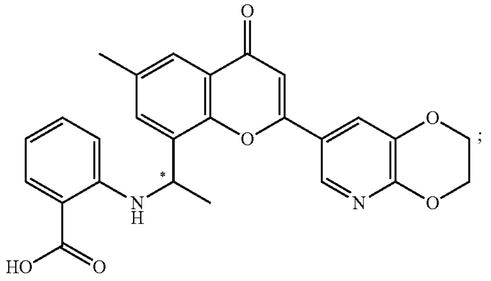

or a pharmaceutically acceptable salt of any of the foregoing;

wherein the bond at the * position is as represented,

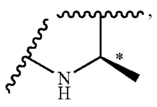

, or

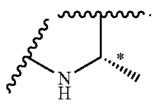

.

In yet a further compound of Formula (I), the compound is selected from:

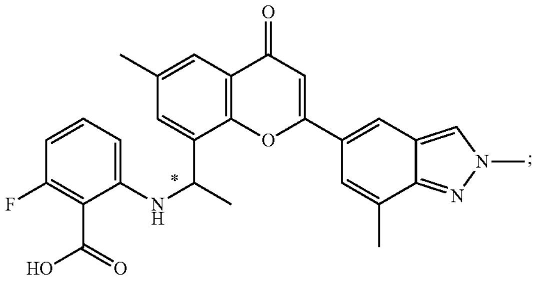

-continued

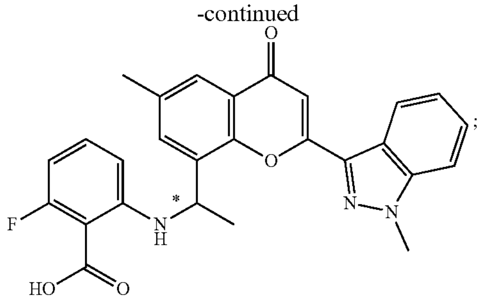

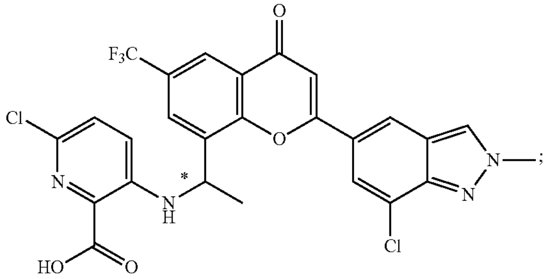

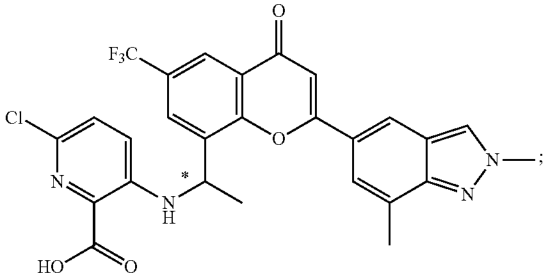

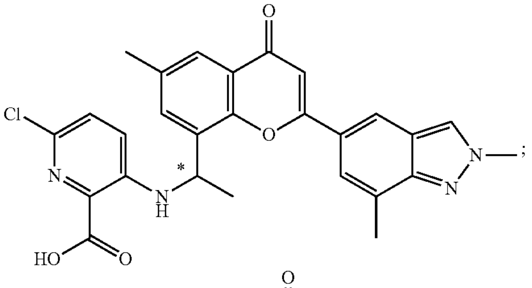

and

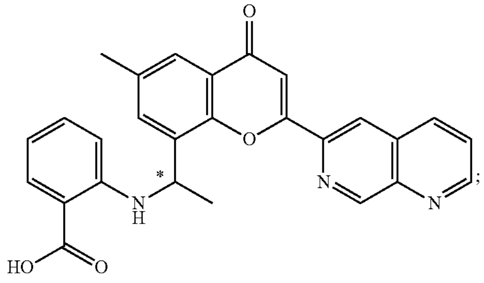

or a pharmaceutically acceptable salt of any of the foregoing;

wherein the bond at the * position is as represented,

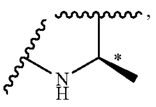

, or

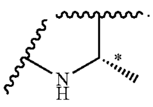

.

In yet a further compound of Formula (I), the compound is selected from:

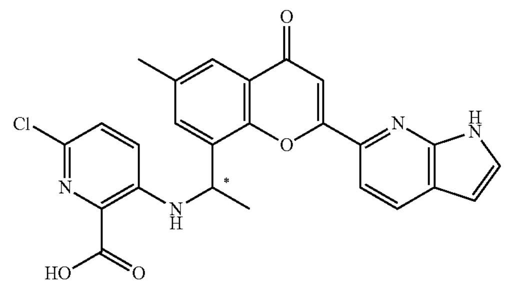
;
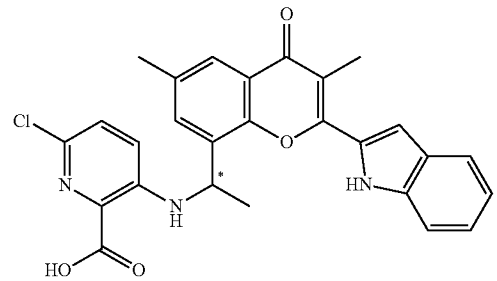
;
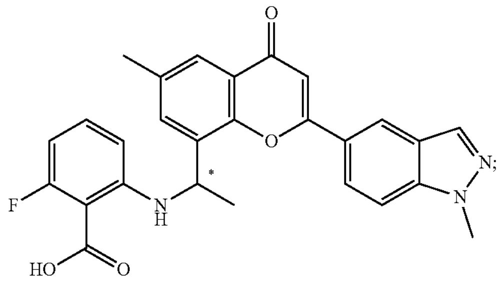
;
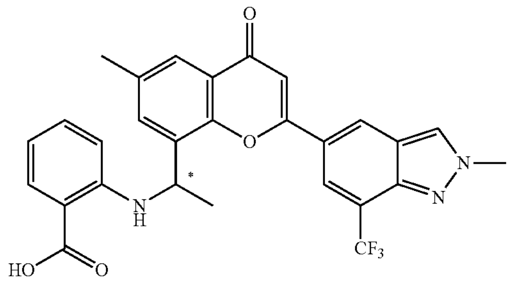
;
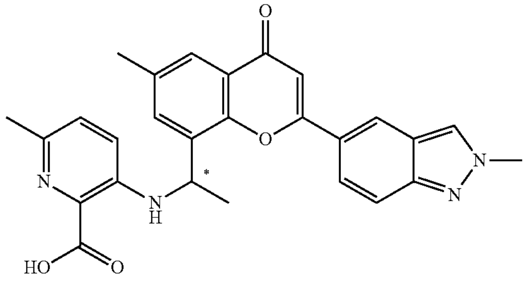
;
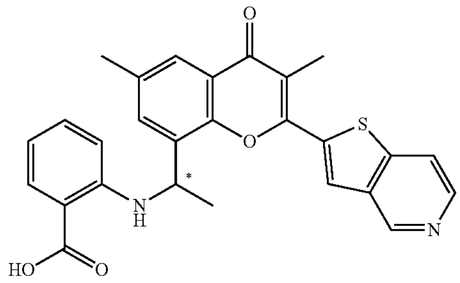
;
-continued
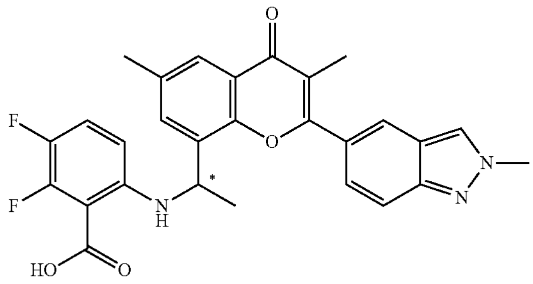
;
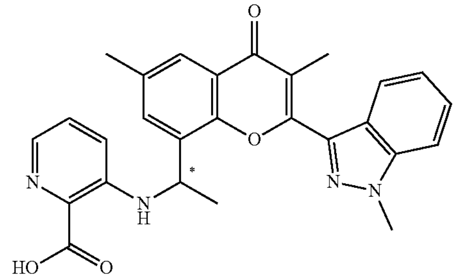
;
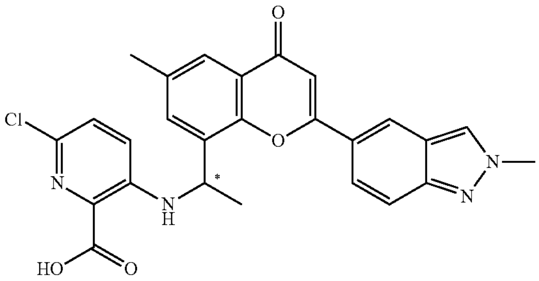
;
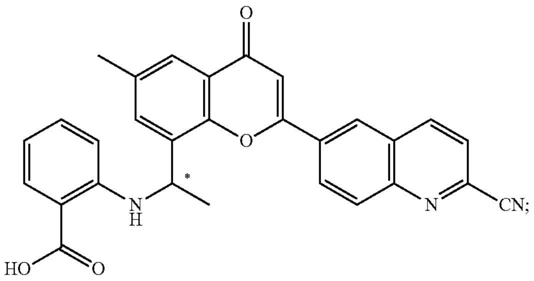
;
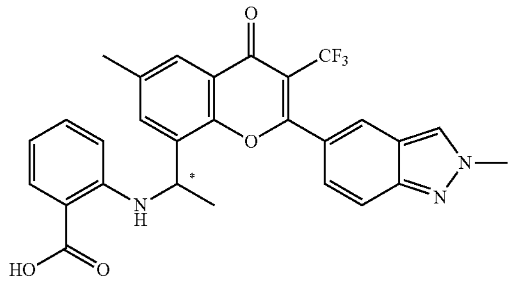
;
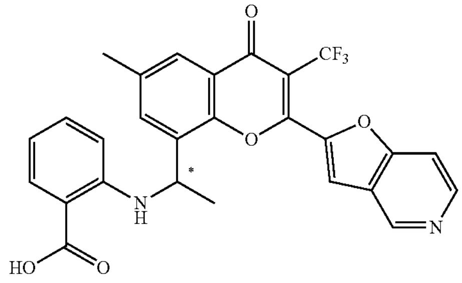
;

-continued
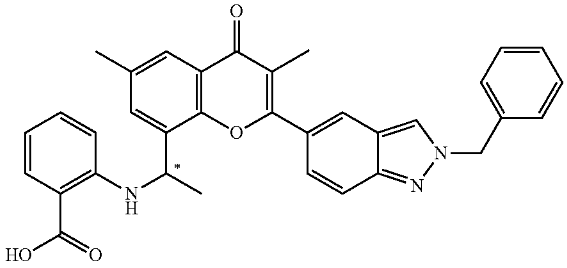
;
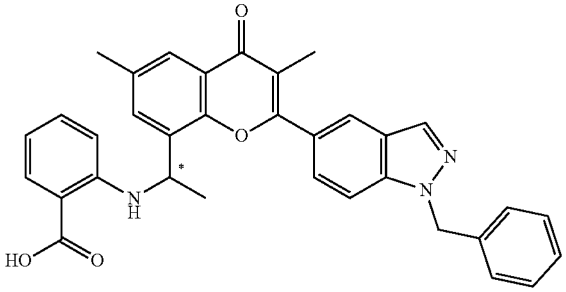
;
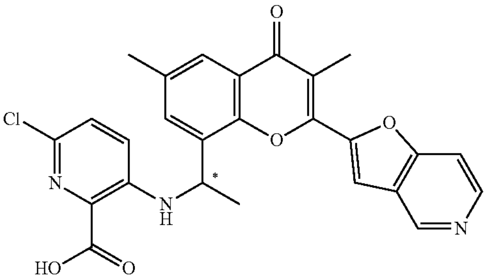
;
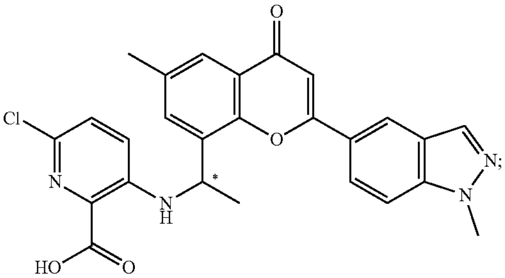
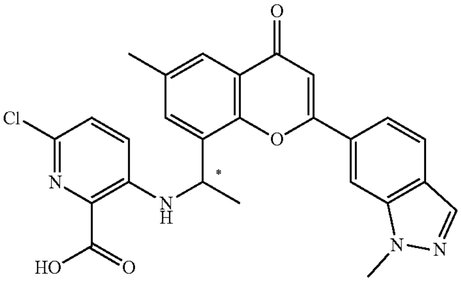
;
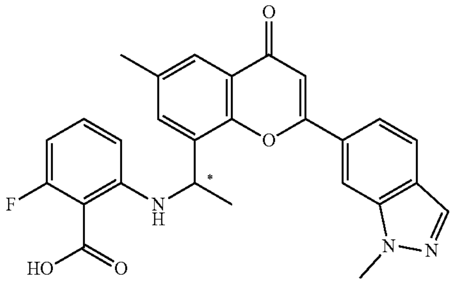
;
-continued
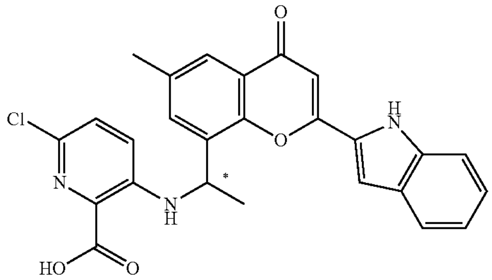
;
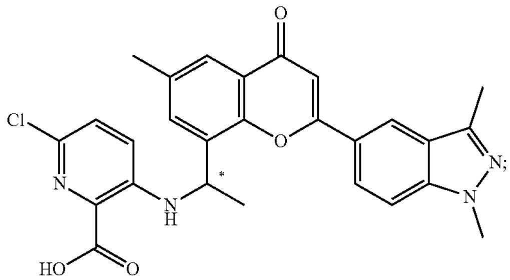
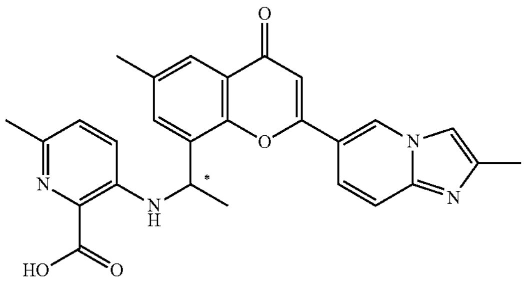
;
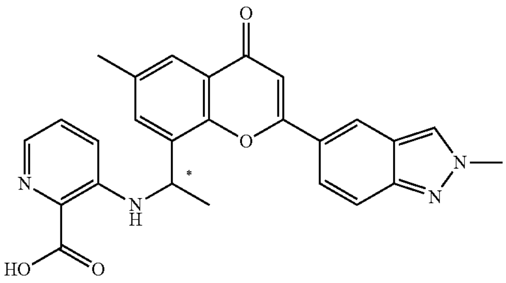
;
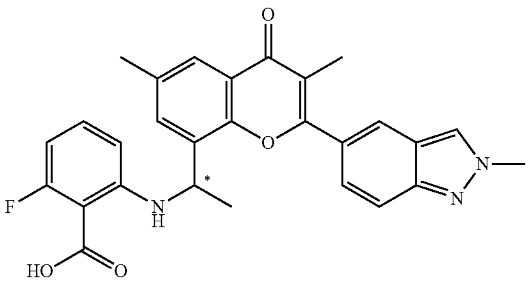
;
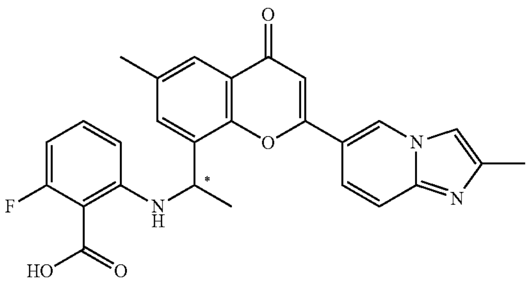
;

-continued
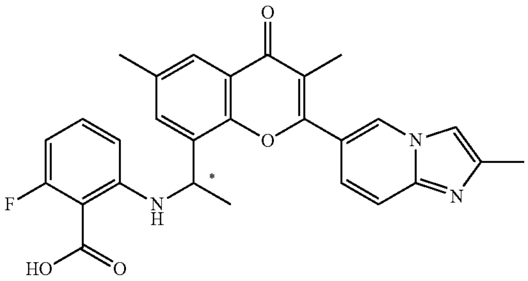
;
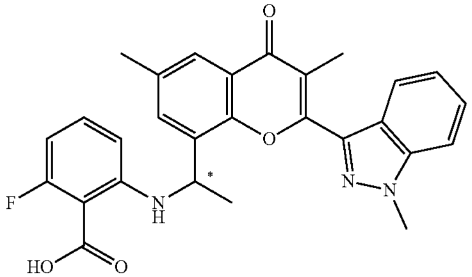
;
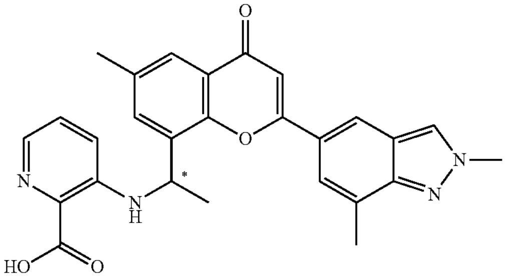
;
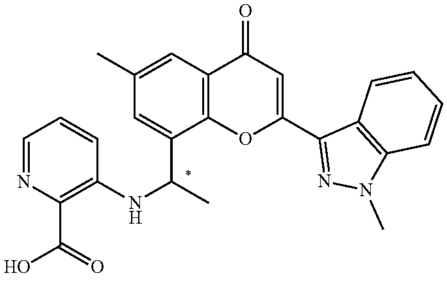
;
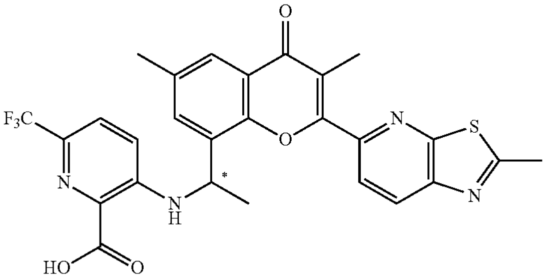
;
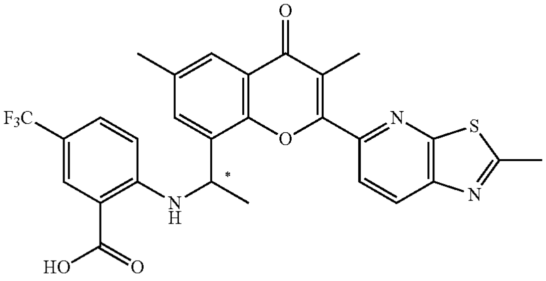
;
-continued
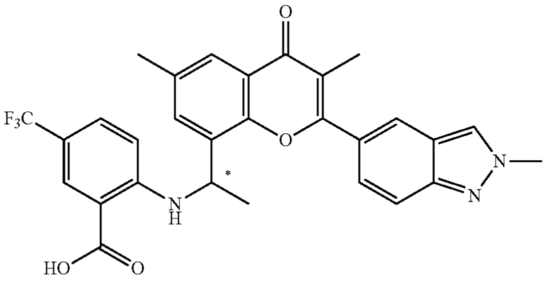
;
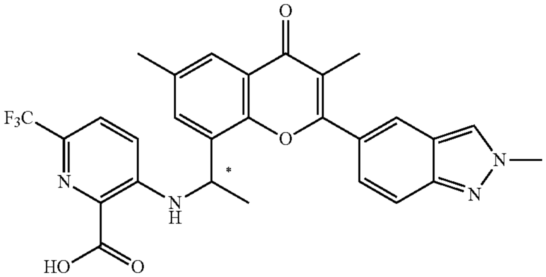
;
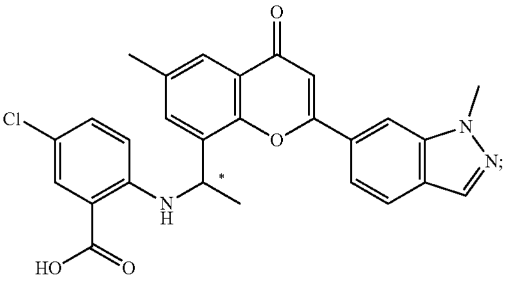
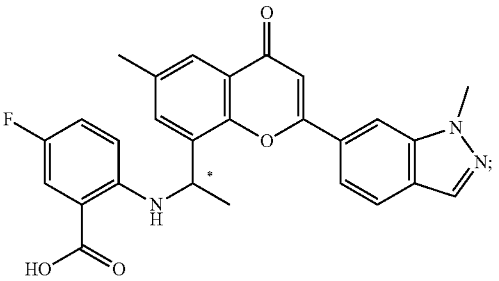
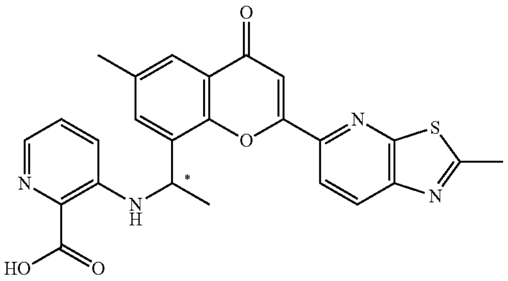
;
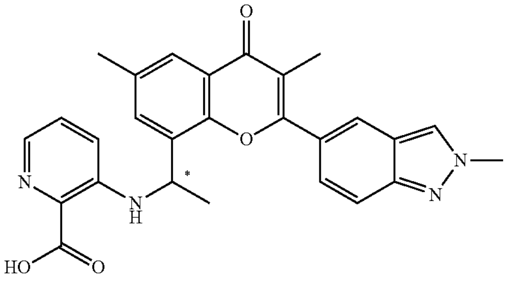
;

-continued
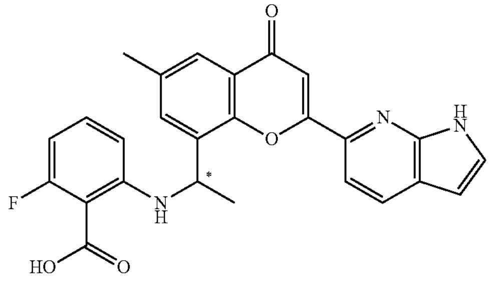
;
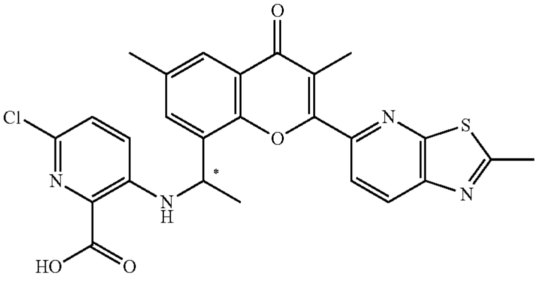
;
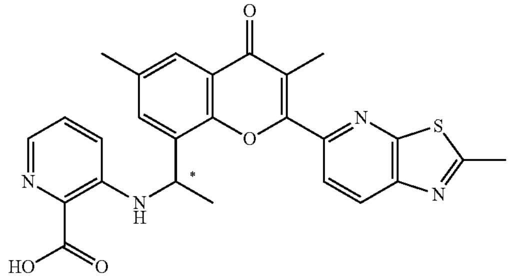
;
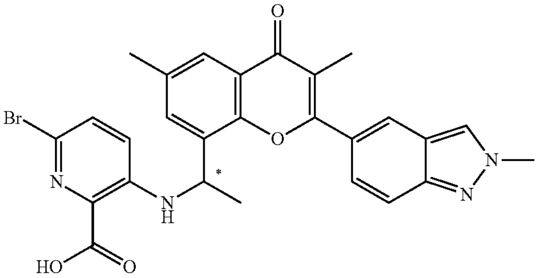
;
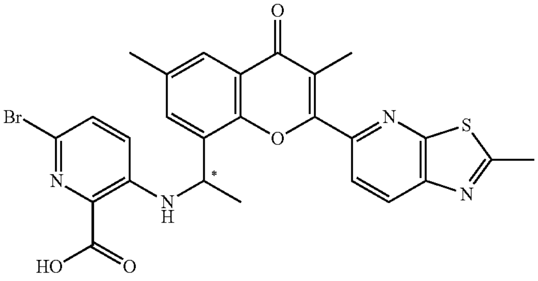
;
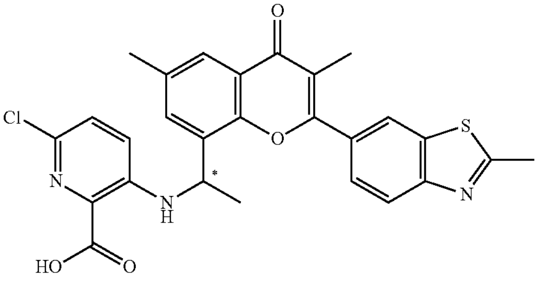
;
-continued
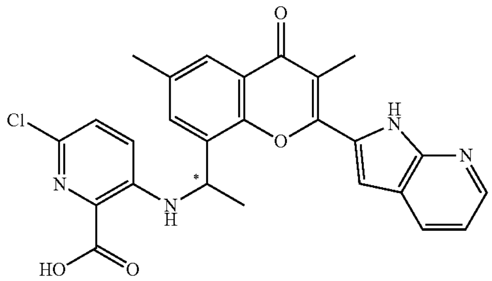
;
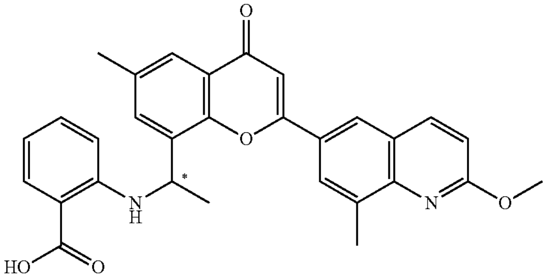
;
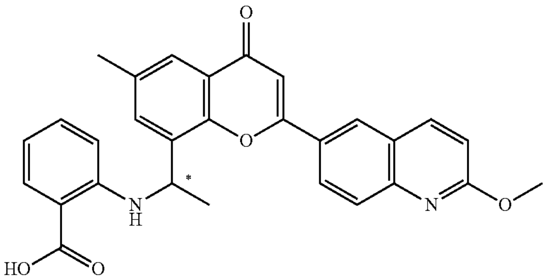
;
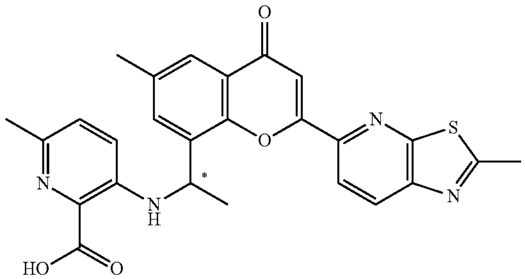
;
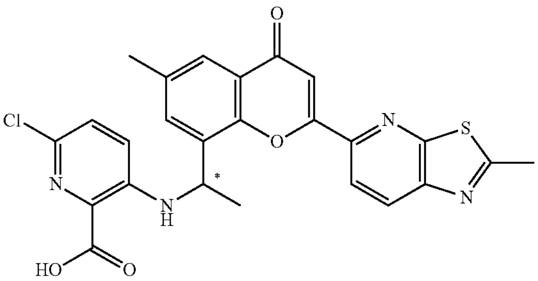
;
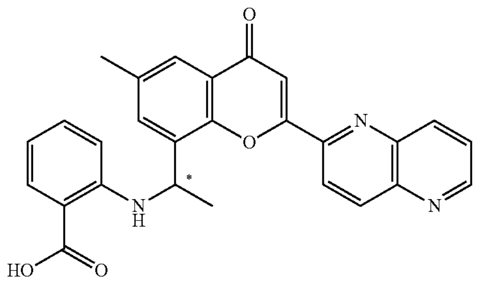
;

-continued
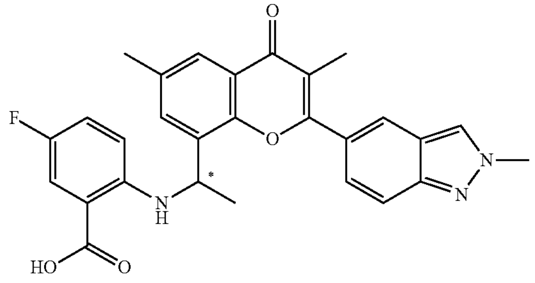
;
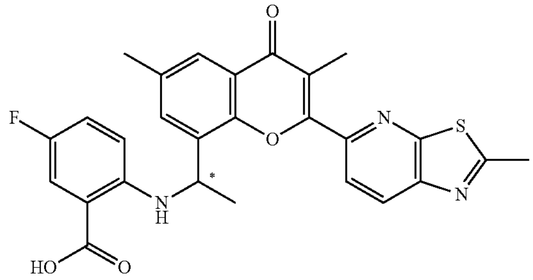
;
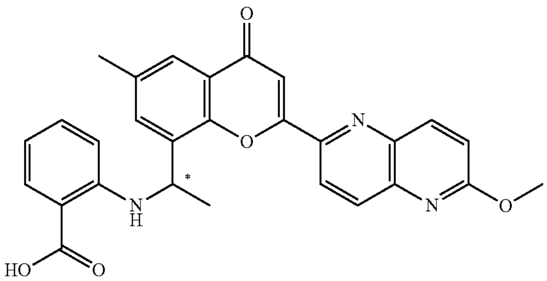
;
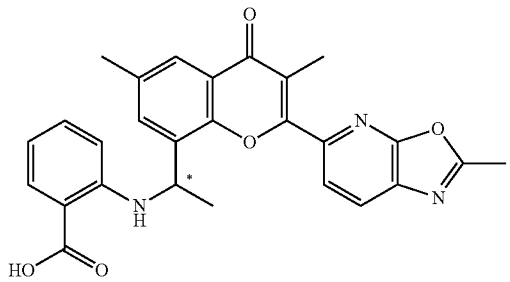
;
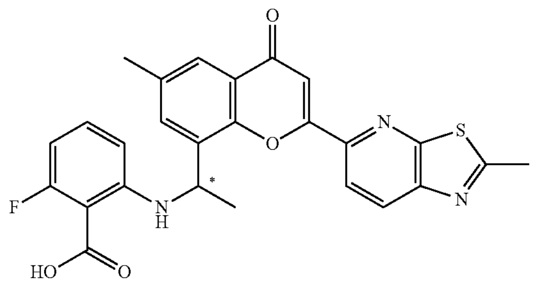
;
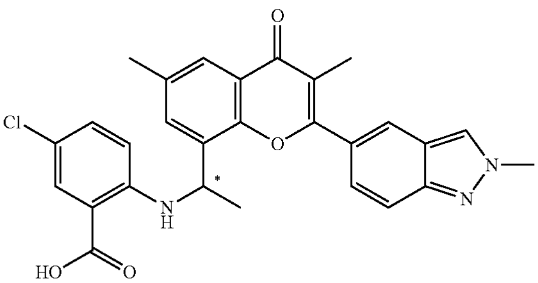
;
-continued
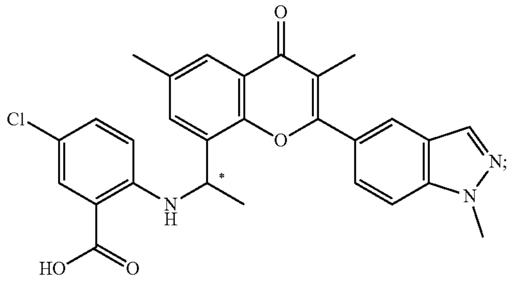
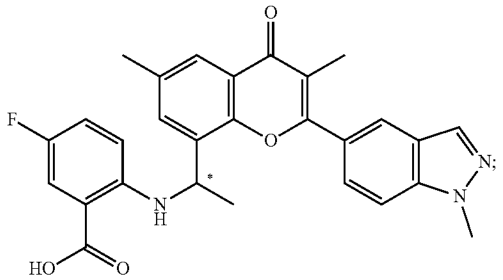
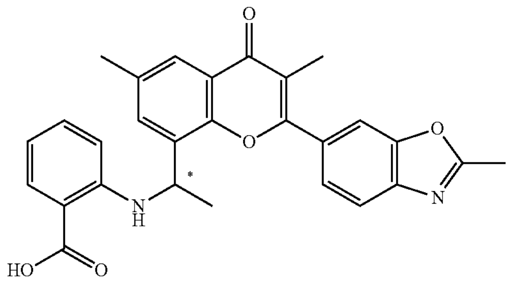
;
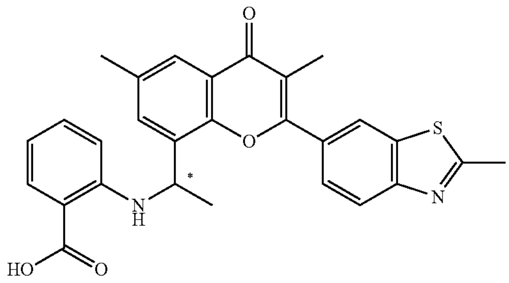
;
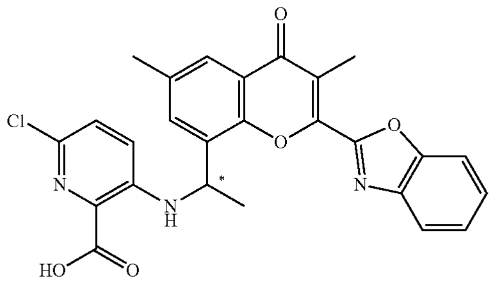
;
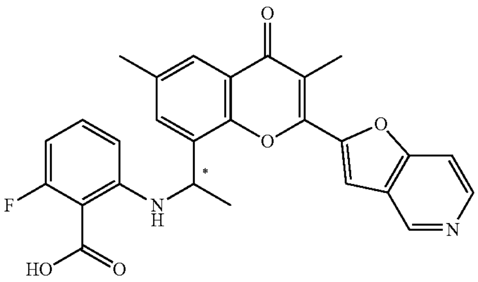
; and -continued

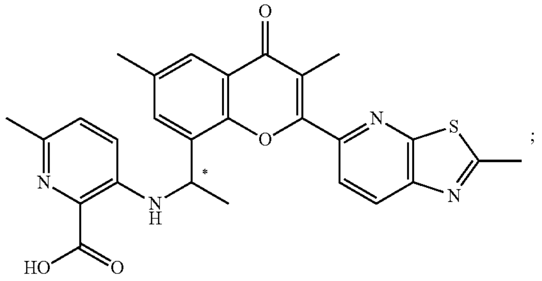

or a pharmaceutically acceptable salt of any of the foregoing;

wherein the bond at the * position is as represented,

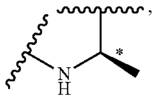

, or

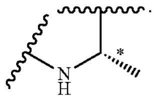

A further embodiment is a compound of Formula

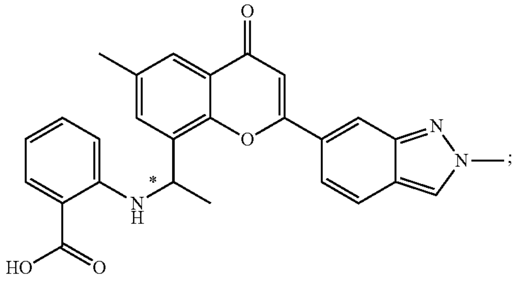 [SMILES: Cc1cc(C(C)Nc2ccccc2C(=O)O)c2oc(-c3ccc4cn(C)nc4c3)cc(=O)c2c1]

or pharmaceutically acceptable salt thereof. In yet a further embodiment, the bond at the * position is

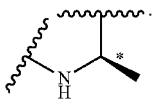

In yet a further embodiment, the bond at the * position is

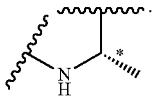

A further embodiment is a compound of Formula

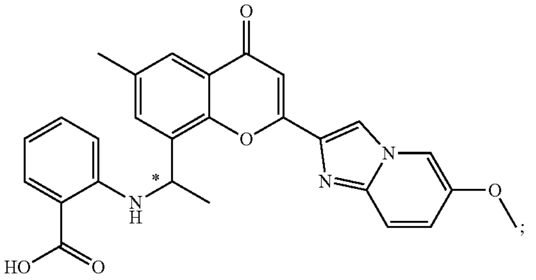 [SMILES: COc1ccc2nc(-c3cc(=O)c4cc(C)cc(C(C)Nc5ccccc5C(=O)O)c4o3)cn2c1]

or pharmaceutically acceptable salt thereof. In yet a further embodiment, the bond at the * position is

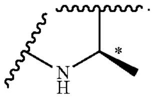 [SMILES: *N[C@@H](*)C]

In yet a further embodiment, the bond at the * position is

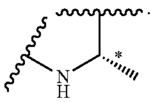

A further embodiment is a compound of Formula

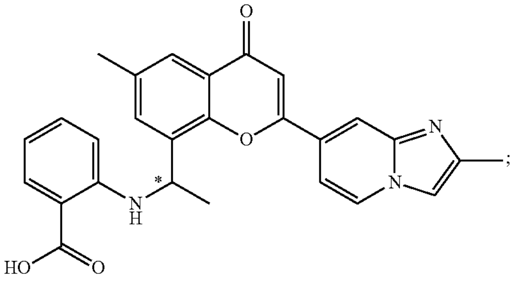 [SMILES: Cc1cc(C(C)Nc2ccccc2C(=O)O)c2oc(-c3ccn4cc(C)nc4c3)cc(=O)c2c1]

or pharmaceutically acceptable salt thereof. In yet a further embodiment, the bond at the * position is

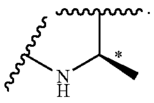

In yet a further embodiment, the bond at the * position is

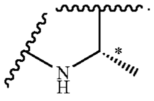

A further embodiment is a compound of Formula

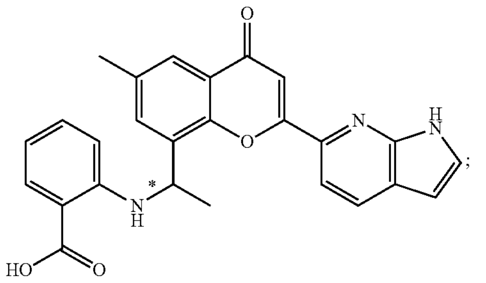 [SMILES: Cc1cc(C(C)Nc2ccccc2C(=O)O)c2oc(-c3ccc4cc[nH]c4n3)cc(=O)c2c1]

or pharmaceutically acceptable salt thereof. In yet a further embodiment, the bond at the * position is

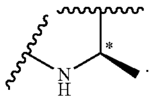 [SMILES: *N[C@@H](*)C]

In yet a further embodiment, the bond at the * position is

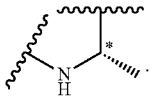

A further embodiment is a compound of Formula

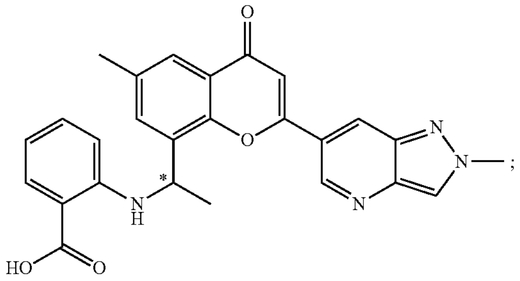 [SMILES: Cc1cc(C(C)Nc2ccccc2C(=O)O)c2oc(-c3cnc4cn(C)nc4c3)cc(=O)c2c1]

or pharmaceutically acceptable salt thereof. In yet a further embodiment, the bond at the * position is

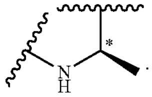

In yet a further embodiment, the bond at the * position is

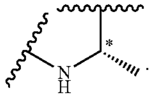

A further embodiment is a compound of Formula

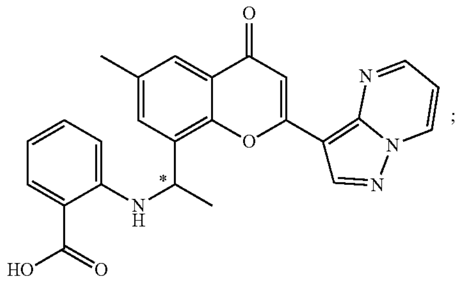 [SMILES: Cc1cc(C(C)Nc2ccccc2C(=O)O)c2oc(-c3cnn4cccnc34)cc(=O)c2c1]

or pharmaceutically acceptable salt thereof. In yet a further embodiment, the bond at the * position is

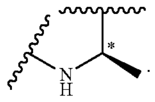 [SMILES: *N[C@@H](*)C]

In yet a further embodiment, the bond at the * position is

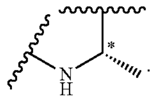 [SMILES: *N[C@H](*)C]

A further embodiment is a compound of Formula

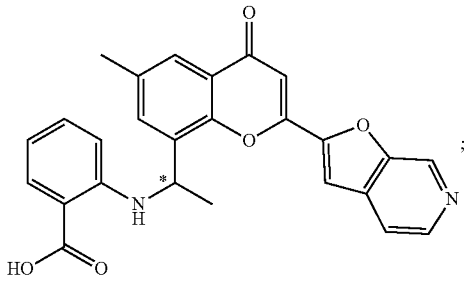 [SMILES: Cc1cc(C(C)Nc2ccccc2C(=O)O)c2oc(-c3cc4ccncc4o3)cc(=O)c2c1]

or pharmaceutically acceptable salt thereof. In yet a further embodiment, the bond at the * position is

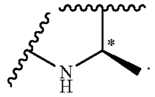 [SMILES: *N[C@@H](*)C]

In yet a further embodiment, the bond at the * position is

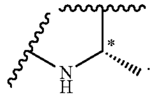

A further embodiment is a compound of Formula

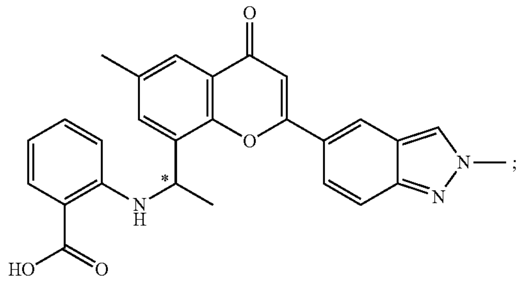 [SMILES: Cc1cc(C(C)Nc2ccccc2C(=O)O)c2oc(-c3ccc4nn(C)cc4c3)cc(=O)c2c1]

or pharmaceutically acceptable salt thereof. In yet a further embodiment, the bond at the * position is

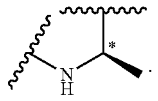

In yet a further embodiment, the bond at the * position is

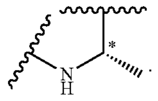

A further embodiment is a compound of Formula

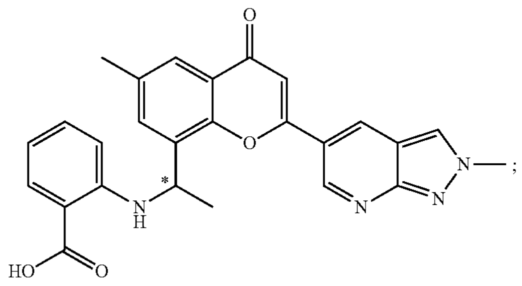 [SMILES: Cc1cc(C(C)Nc2ccccc2C(=O)O)c2oc(-c3cnc4nn(C)cc4c3)cc(=O)c2c1]

or pharmaceutically acceptable salt thereof. In yet a further embodiment, the bond at the * position is

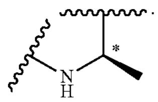 [SMILES: *N[C@@H](*)C]

In yet a further embodiment, the bond at the * position is

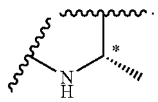

A further embodiment is a compound of Formula

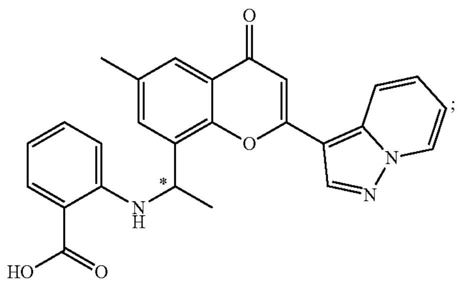 [SMILES: Cc1cc(C(C)Nc2ccccc2C(=O)O)c2oc(-c3cnn4ccccc34)cc(=O)c2c1]

or pharmaceutically acceptable salt thereof. In yet a further embodiment, the bond at the * position is

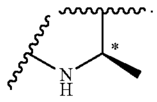

In yet a further embodiment, the bond at the * position is

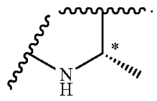

A further embodiment is a compound of Formula

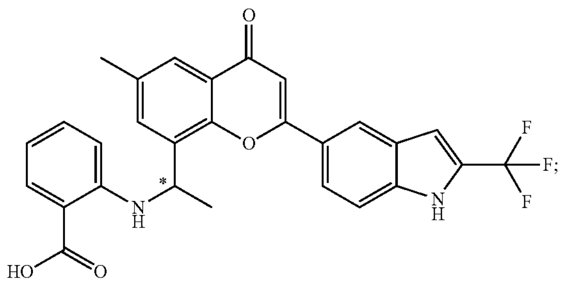 [SMILES: Cc1cc(C(C)Nc2ccccc2C(=O)O)c2oc(-c3ccc4[nH]c(C(F)(F)F)cc4c3)cc(=O)c2c1]

In yet a further embodiment, the bond at the * position is position is

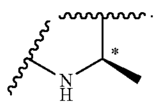 [SMILES: *N[C@@H](*)C]

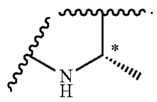 [SMILES: *N[C@H](*)C]

A further embodiment is a compound of Formula

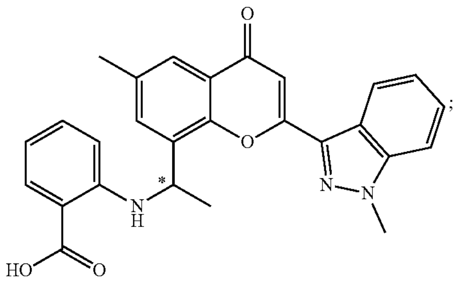 [SMILES: Cc1cc(C(C)Nc2ccccc2C(=O)O)c2oc(-c3nn(C)c4ccccc34)cc(=O)c2c1]

or pharmaceutically acceptable salt thereof. In yet a further embodiment, the bond at the * position is

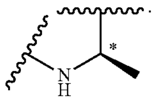 [SMILES: *N[C@@H](*)C]

In yet a further embodiment, the bond at the * position is

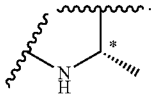 [SMILES: *N[C@H](*)C]

A further embodiment is a compound of Formula

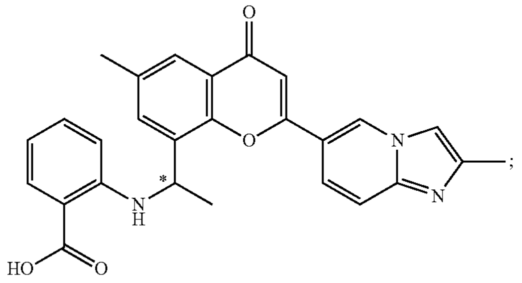

or pharmaceutically acceptable salt thereof. In yet a further embodiment, the bond at the * position is

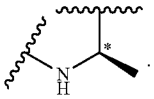

In yet a further embodiment, the bond at the * position is

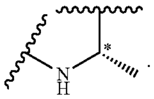

A further embodiment is a compound of Formula

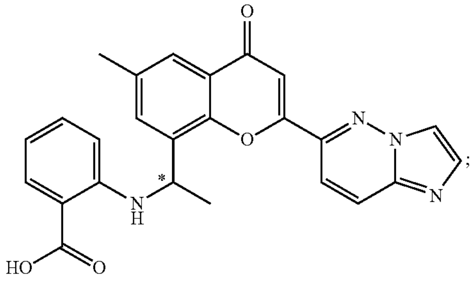 [SMILES: Cc1cc(C(C)Nc2ccccc2C(=O)O)c2oc(-c3ccc4nccn4n3)cc(=O)c2c1]

or pharmaceutically acceptable salt thereof. In yet a further embodiment, the bond at the * position is

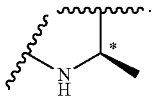 [SMILES: *N[C@@H](*)C]

In yet a further embodiment, the bond at the * position is

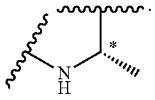

A further embodiment is a compound of Formula

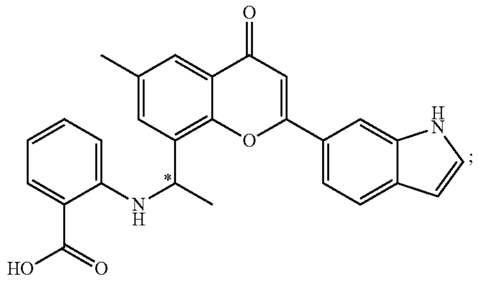 [SMILES: Cc1cc(C(C)Nc2ccccc2C(=O)O)c2oc(-c3ccc4cc[nH]c4c3)cc(=O)c2c1]

or pharmaceutically acceptable salt thereof. In yet a further embodiment, the bond at the * position is

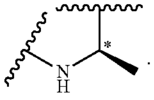 [SMILES: *N[C@@H](*)C]

In yet a further embodiment, the bond at the * position is

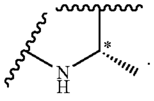

A further embodiment is a compound of Formula

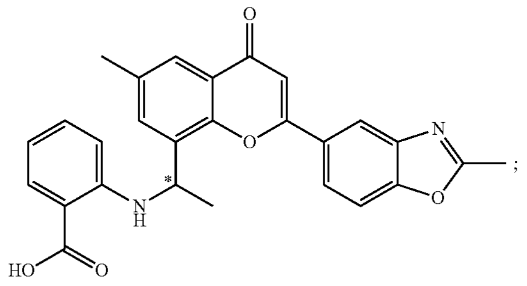 [SMILES: Cc1cc(C(C)Nc2ccccc2C(=O)O)c2oc(-c3ccc4oc(C)nc4c3)cc(=O)c2c1]

or pharmaceutically acceptable salt thereof. In yet a further embodiment, the bond at the * position is

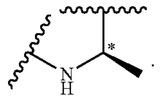

In yet a further embodiment, the bond at the * position is

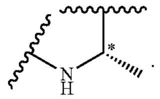

A further embodiment is a compound of Formula

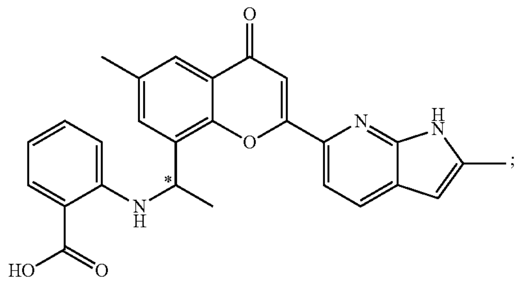 [SMILES: Cc1cc(C(C)Nc2ccccc2C(=O)O)c2oc(-c3ccc4cc(C)[nH]c4n3)cc(=O)c2c1]

or pharmaceutically acceptable salt thereof. In yet a further embodiment, the bond at the * position is

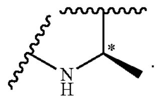 [SMILES: *N[C@@H](*)C]

In yet a further embodiment, the bond at the * position is

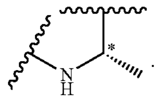

A further embodiment is a compound of Formula

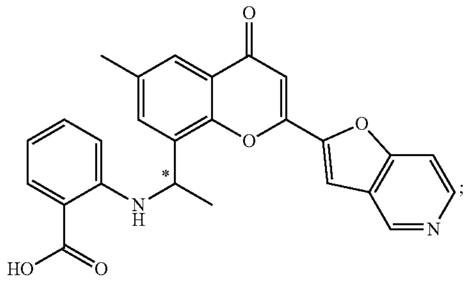 [SMILES: Cc1cc(C(C)Nc2ccccc2C(=O)O)c2oc(-c3cc4cnccc4o3)cc(=O)c2c1]

or pharmaceutically acceptable salt thereof. In yet a further embodiment, the bond at the * position is

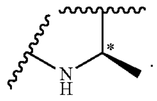 [SMILES: *N[C@@H](*)C]

In yet a further embodiment, the bond at the * position is

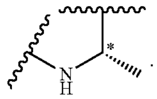

A further embodiment is a compound of Formula

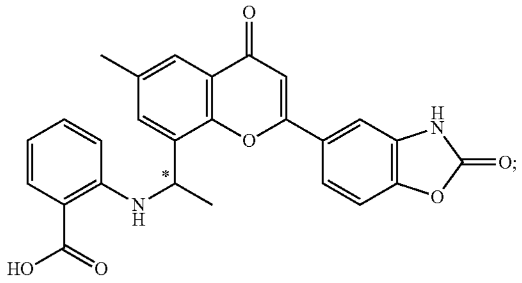 [SMILES: Cc1cc(C(C)Nc2ccccc2C(=O)O)c2oc(-c3ccc4oc(=O)[nH]c4c3)cc(=O)c2c1]

or pharmaceutically acceptable salt thereof. In yet a further embodiment, the bond at the * position is

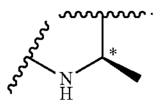 [SMILES: *N[C@@H](*)C]

In yet a further embodiment, the bond at the * position is

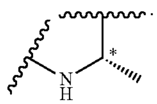

A further embodiment is a compound of Formula

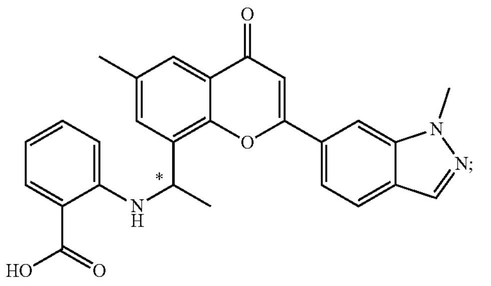 [SMILES: Cc1cc(C(C)Nc2ccccc2C(=O)O)c2oc(-c3ccc4cnn(C)c4c3)cc(=O)c2c1]

or pharmaceutically acceptable salt thereof. In yet a further embodiment, the bond at the * position is

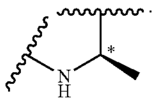

In yet a further embodiment, the bond at the * position is

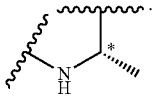

A further embodiment is a compound of Formula

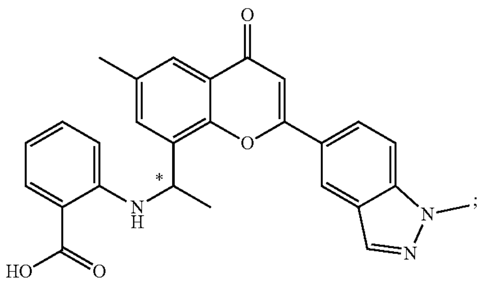 [SMILES: Cc1cc(C(C)Nc2ccccc2C(=O)O)c2oc(-c3ccc4c(cnn4C)c3)cc(=O)c2c1]

or pharmaceutically acceptable salt thereof. In yet a further embodiment, the bond at the * position is

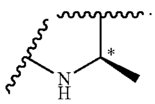 [SMILES: *N[C@@H](*)C]

In yet a further embodiment, the bond at the * position is

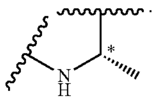

A further embodiment is a compound of Formula

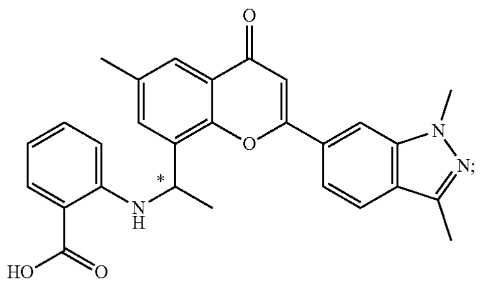 [SMILES: Cc1cc(C(C)Nc2ccccc2C(=O)O)c2oc(-c3ccc4c(C)nn(C)c4c3)cc(=O)c2c1]

or pharmaceutically acceptable salt thereof. In yet a further embodiment, the bond at the * position is

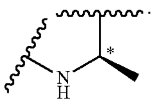 [SMILES: *N[C@@H](*)C]

In yet a further embodiment, the bond at the * position is

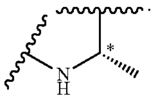

A further embodiment is a compound of Formula

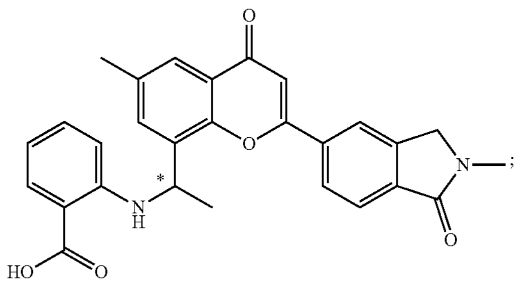 [SMILES: Cc1cc(C(C)Nc2ccccc2C(=O)O)c2oc(-c3ccc4c(c3)CN(C)C4=O)cc(=O)c2c1]

or pharmaceutically acceptable salt thereof. In yet a further embodiment, the bond at the * position is

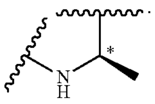 [SMILES: *N[C@@H](*)C]

In yet a further embodiment, the bond at the * position is

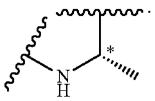 [SMILES: *N[C@H](*)C]

A further embodiment is a compound of Formula

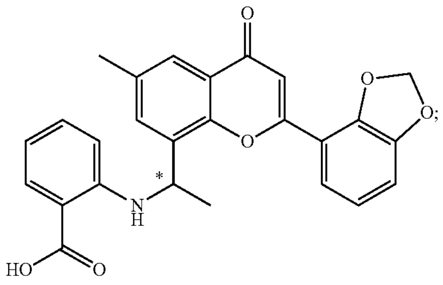 [SMILES: Cc1cc(C(C)Nc2ccccc2C(=O)O)c2oc(-c3cccc4c3OCO4)cc(=O)c2c1]

or pharmaceutically acceptable salt thereof. In yet a further embodiment, the bond at the * position is

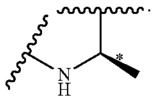 [SMILES: *N[C@@H](*)C]

In yet a further embodiment, the bond at the * position is

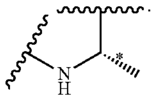 [SMILES: *N[C@H](*)C]

A further embodiment is a compound of Formula

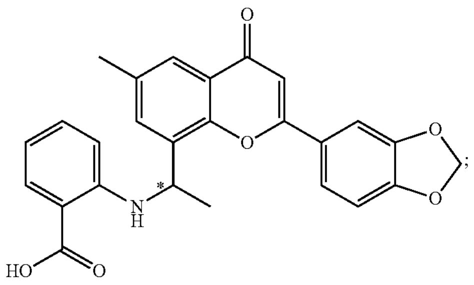 [SMILES: Cc1cc(C(C)Nc2ccccc2C(=O)O)c2oc(-c3ccc4c(c3)OCO4)cc(=O)c2c1]

or pharmaceutically acceptable salt thereof. In yet a further embodiment, the bond at the * position is

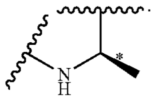 [SMILES: *N[C@@H](*)C]

In yet a further embodiment, the bond at the * position is

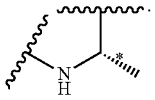 [SMILES: *N[C@H](*)C]

A further embodiment is a compound of Formula

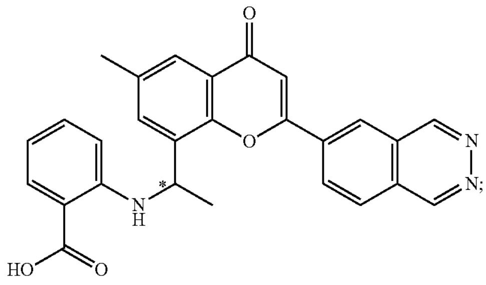 [SMILES: Cc1cc(C(C)Nc2ccccc2C(=O)O)c2oc(-c3ccc4cnncc4c3)cc(=O)c2c1]

or pharmaceutically acceptable salt thereof. In yet a further embodiment, the bond at the * position is

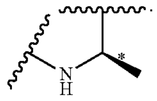 [SMILES: *N[C@@H](*)C]

In yet a further embodiment, the bond at the * position is

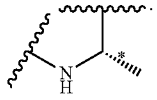 [SMILES: *N[C@H](*)C]

A further embodiment is a compound of Formula

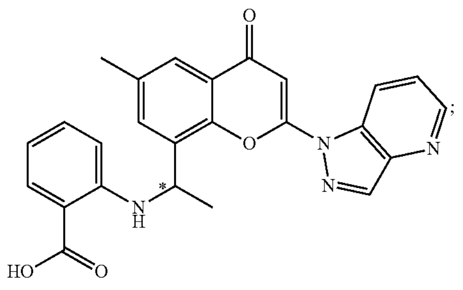 [SMILES: Cc1cc(C(C)Nc2ccccc2C(=O)O)c2oc(-n3ncc4ncccc43)cc(=O)c2c1]

or pharmaceutically acceptable salt thereof. In yet a further embodiment, the bond at the * position is

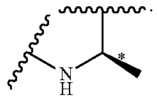 [SMILES: *N[C@@H](*)C]

In yet a further embodiment, the bond at the * position is

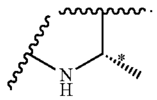 [SMILES: *N[C@H](*)C]

A further embodiment is a compound of Formula

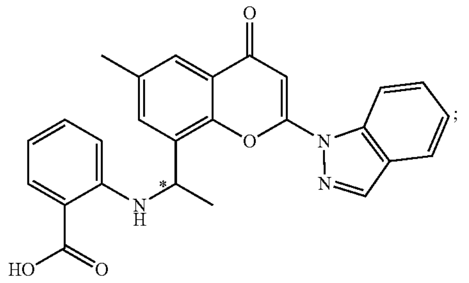 [SMILES: Cc1cc(C(C)Nc2ccccc2C(=O)O)c2oc(-n3ncc4ccccc43)cc(=O)c2c1]

or pharmaceutically acceptable salt thereof. In yet a further embodiment, the bond at the * position is

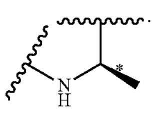 [SMILES: *N[C@@H](*)C]

In yet a further embodiment, the bond at the * position is

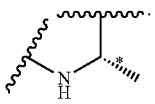

A further embodiment is a compound of Formula

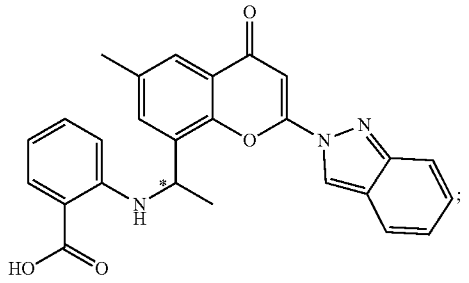 [SMILES: Cc1cc(C(C)Nc2ccccc2C(=O)O)c2oc(-n3cc4ccccc4n3)cc(=O)c2c1]

or pharmaceutically acceptable salt thereof. In yet a further embodiment, the bond at the * position is

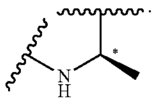 [SMILES: *N[C@@H](*)C]

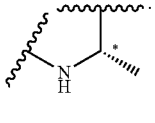 [SMILES: *N[C@H](*)C]

A further embodiment is a compound of Formula

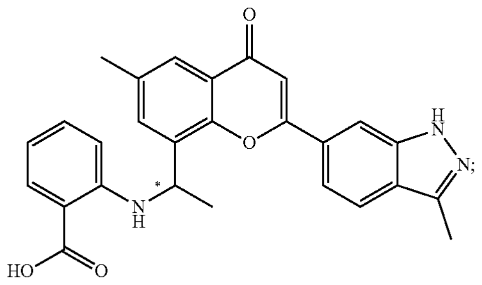 [SMILES: Cc1cc(C(C)Nc2ccccc2C(=O)O)c2oc(-c3ccc4c(C)n[nH]c4c3)cc(=O)c2c1]

or pharmaceutically acceptable salt thereof. In yet a further embodiment, the bond at the * position is

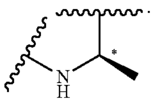 [SMILES: *N[C@@H](*)C]

In yet a further embodiment, the bond at the * position is

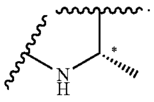

A further embodiment is a compound of Formula

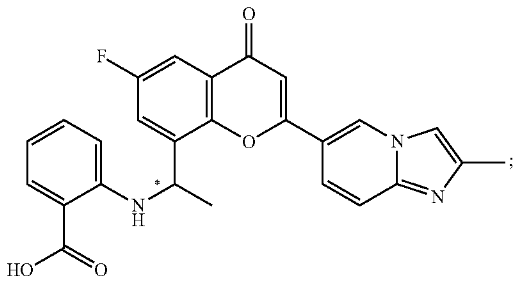 [SMILES: Cc1cn2cc(-c3cc(=O)c4cc(F)cc(C(C)Nc5ccccc5C(=O)O)c4o3)ccc2n1]

or pharmaceutically acceptable salt thereof. In yet a further embodiment, the bond at the * position is

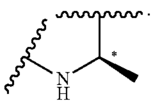 [SMILES: *N[C@@H](*)C]

In yet a further embodiment, the bond at the * position is

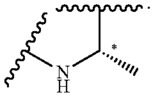

A further embodiment is a compound of

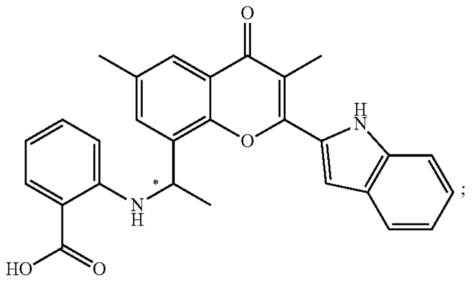 [SMILES: Cc1cc(C(C)Nc2ccccc2C(=O)O)c2oc(-c3cc4ccccc4[nH]3)c(C)c(=O)c2c1]

or pharmaceutically acceptable salt thereof. In yet a further embodiment, the bond at the * position is

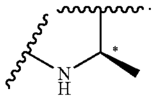 [SMILES: *N[C@@H](*)C]

In yet a further embodiment, the bond at the * position is

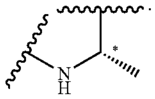

A further embodiment is a compound of Formula

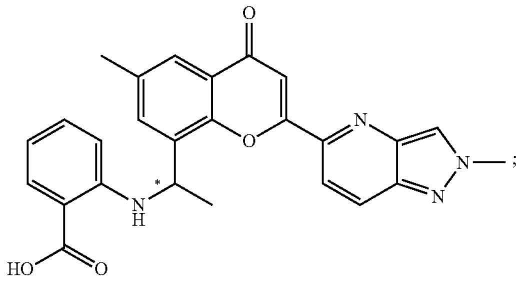

or pharmaceutically acceptable salt thereof. In yet a further embodiment, the bond at the * position is

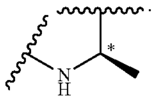

In yet a further embodiment, the bond at the * position is

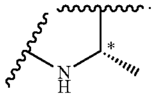

A further embodiment is a compound of Formula

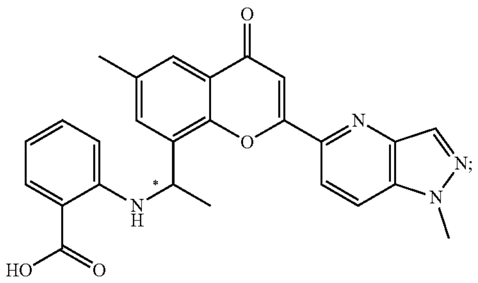 [SMILES: Cc1cc(C(C)Nc2ccccc2C(=O)O)c2oc(-c3ccc4c(cnn4C)n3)cc(=O)c2c1]

or pharmaceutically acceptable salt thereof. In yet a further embodiment, the bond at the * position is

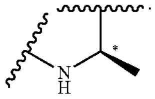 [SMILES: *N[C@@H](*)C]

In yet a further embodiment, the bond at the * position is

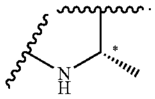

A further embodiment is a compound of Formula

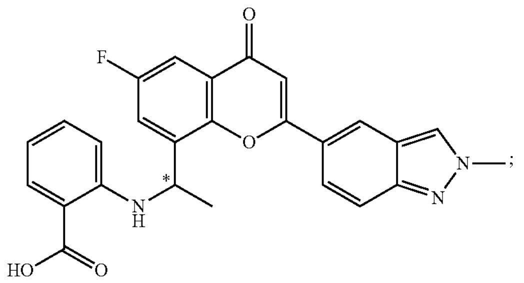 [SMILES: CC(Nc1ccccc1C(=O)O)c1cc(F)cc2c(=O)cc(-c3ccc4nn(C)cc4c3)oc12]

or pharmaceutically acceptable salt thereof. In yet a further embodiment, the bond at the * position is

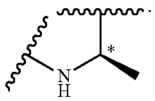 [SMILES: *N[C@@H](*)C]

In yet a further embodiment, the bond at the * position is

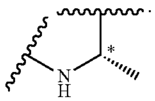

A further embodiment is a compound of Formula

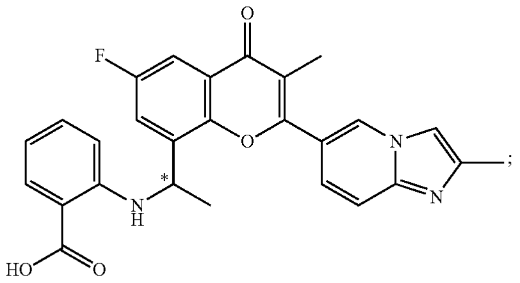 [SMILES: Cc1cn2cc(-c3oc4c(C(C)Nc5ccccc5C(=O)O)cc(F)cc4c(=O)c3C)ccc2n1]

or pharmaceutically acceptable salt thereof. In yet a further embodiment, the bond at the * position is

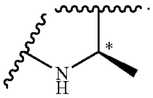 [SMILES: *N[C@@H](*)C]

In yet a further embodiment, the bond at the * position is

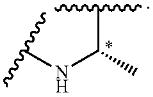

A further embodiment is a compound of Formula

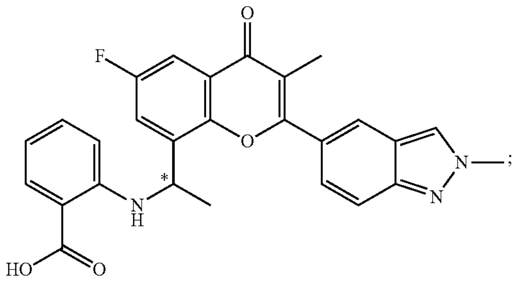 [SMILES: Cc1c(-c2ccc3nn(C)cc3c2)oc2c(C(C)Nc3ccccc3C(=O)O)cc(F)cc2c1=O]

or pharmaceutically acceptable salt thereof. In yet a further embodiment, the bond at the * position is

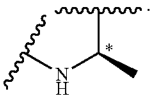 [SMILES: *N[C@@H](*)C]

In yet a further embodiment, the bond at the * position is

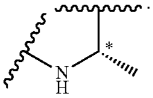

or pharmaceutically acceptable salt thereof. In yet a further embodiment, the bond at the * position is

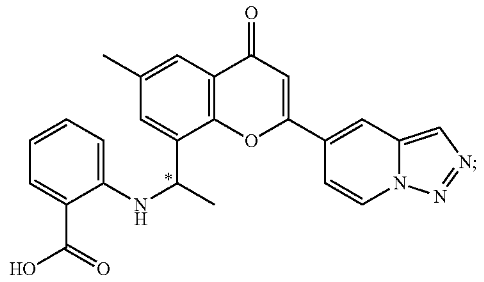 [SMILES: Cc1cc(C(C)Nc2ccccc2C(=O)O)c2oc(-c3ccn4nncc4c3)cc(=O)c2c1]

In yet a further embodiment, the bond at the * position is

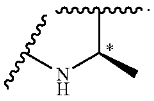

A further embodiment is a compound of Formula

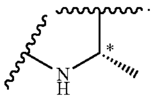 [SMILES: *N[C@H](*)C]

A further embodiment is a compound of Formula

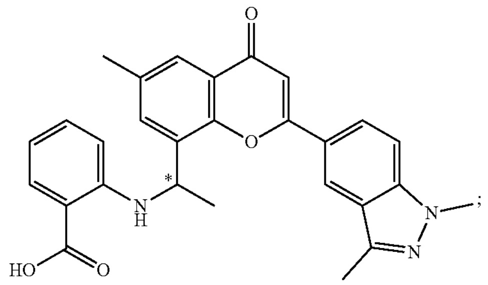 [SMILES: Cc1cc(C(C)Nc2ccccc2C(=O)O)c2oc(-c3ccc4c(c3)c(C)nn4C)cc(=O)c2c1]

or pharmaceutically acceptable salt thereof. In yet a further embodiment, the bond at the * position is

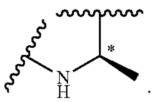 [SMILES: *N[C@@H](*)C]

In yet a further embodiment, the bond at the * position is

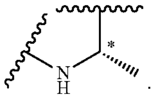 [SMILES: *N[C@H](*)C]

A further embodiment is a compound of Formula

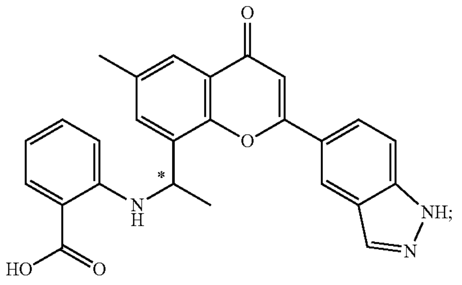 [SMILES: Cc1cc(C(C)Nc2ccccc2C(=O)O)c2oc(-c3ccc4[nH]ncc4c3)cc(=O)c2c1]

or pharmaceutically acceptable salt thereof. In yet a further embodiment, the bond at the * position is

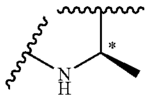
.

In yet a further embodiment, the bond at the * position is

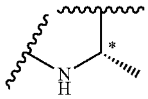
.

A further embodiment is a compound of Formula

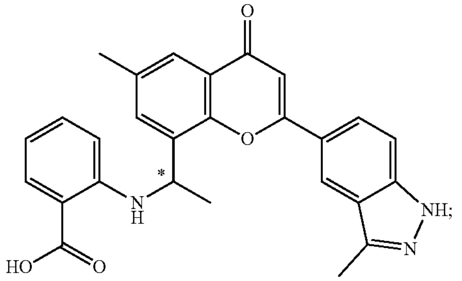 [SMILES: Cc1cc(C(C)Nc2ccccc2C(=O)O)c2oc(-c3ccc4[nH]nc(C)c4c3)cc(=O)c2c1]

or pharmaceutically acceptable salt thereof. In yet a further embodiment, the bond at the * position is

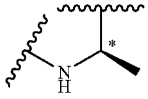
.

In yet a further embodiment, the bond at the * position is

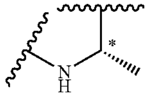
.

A further embodiment is a compound of Formula

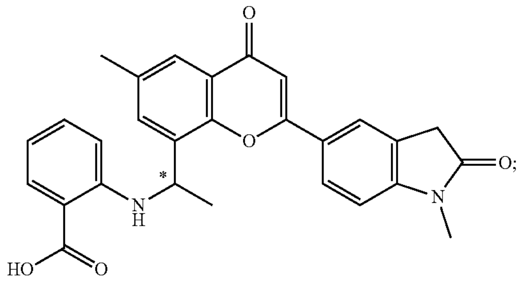 [SMILES: Cc1cc(C(C)Nc2ccccc2C(=O)O)c2oc(-c3ccc4c(c3)CC(=O)N4C)cc(=O)c2c1]

or pharmaceutically acceptable salt thereof. In yet a further embodiment, the bond at the * position is

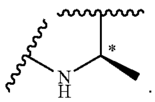 [SMILES: *N[C@@H](*)C]
.

In yet a further embodiment, the bond at the * position is

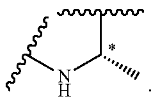 [SMILES: *N[C@H](*)C]
.

A further embodiment is a compound of Formula

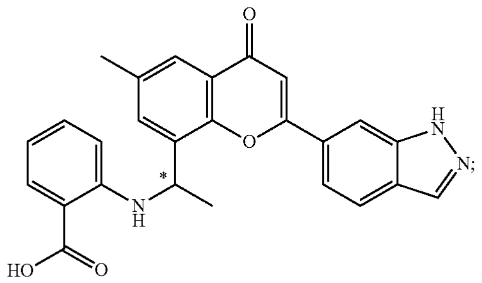 [SMILES: Cc1cc(C(C)Nc2ccccc2C(=O)O)c2oc(-c3ccc4cn[nH]c4c3)cc(=O)c2c1]

or pharmaceutically acceptable salt thereof. In yet a further embodiment, the bond at the * position is

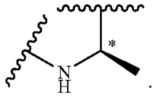 [SMILES: *N[C@@H](*)C]
.

In yet a further embodiment, the bond at the * position is

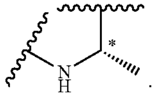 [SMILES: *N[C@H](*)C]
.

A further embodiment is a compound of Formula

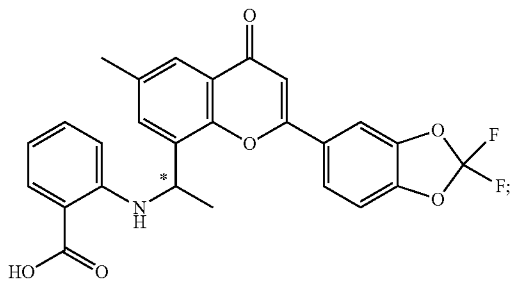 [SMILES: Cc1cc(C(C)Nc2ccccc2C(=O)O)c2oc(-c3ccc4c(c3)OC(F)(F)O4)cc(=O)c2c1]

or pharmaceutically acceptable salt thereof. In yet a further embodiment, the bond at the * position is

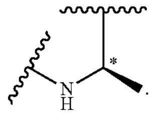 [SMILES: *N[C@@H](*)C]

In yet a further embodiment, the bond at the * position is

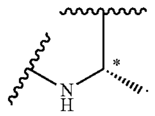 [SMILES: *N[C@H](*)C]

A further embodiment is a compound of Formula

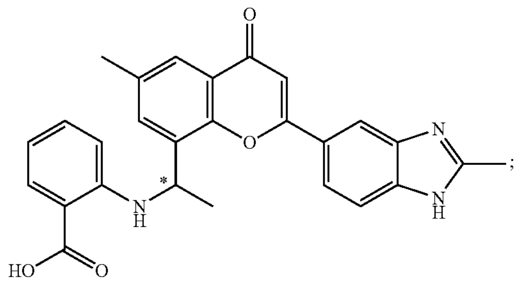 [SMILES: Cc1cc(C(C)Nc2ccccc2C(=O)O)c2oc(-c3ccc4[nH]c(C)nc4c3)cc(=O)c2c1]

or pharmaceutically acceptable salt thereof. In yet a further embodiment, the bond at the * position is

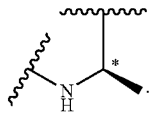

In yet a further embodiment, the bond at the * position is

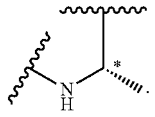

A further embodiment is a compound of Formula

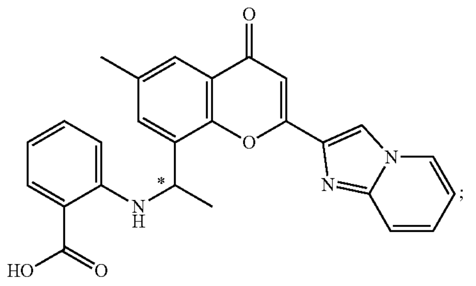 [SMILES: Cc1cc(C(C)Nc2ccccc2C(=O)O)c2oc(-c3cn4ccccc4n3)cc(=O)c2c1]

or pharmaceutically acceptable salt thereof. In yet a further embodiment, the bond at the * position is

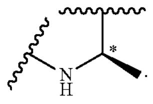 [SMILES: *N[C@@H](*)C]

In yet a further embodiment, the bond at the * position is

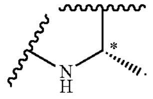

A further embodiment is a compound of Formula

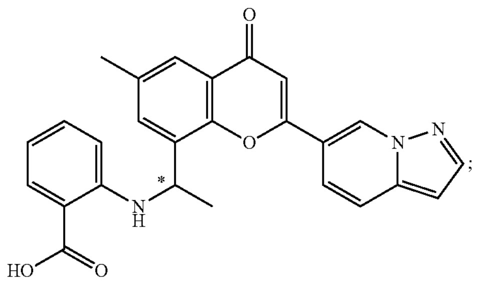 [SMILES: Cc1cc(C(C)Nc2ccccc2C(=O)O)c2oc(-c3ccc4ccnn4c3)cc(=O)c2c1]

or pharmaceutically acceptable salt thereof. In yet a further embodiment, the bond at the * position is

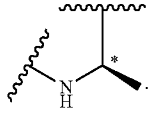 [SMILES: *N[C@@H](*)C]

In yet a further embodiment, the bond at the * position is

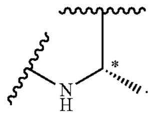 [SMILES: *N[C@H](*)C]

A further embodiment is a compound of Formula

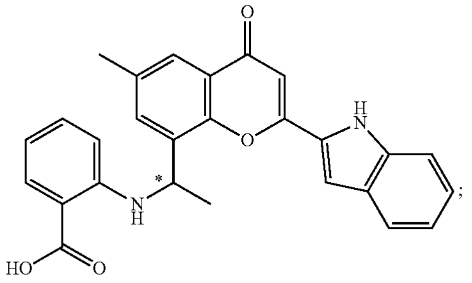 [SMILES: Cc1cc(C(C)Nc2ccccc2C(=O)O)c2oc(-c3cc4ccccc4[nH]3)cc(=O)c2c1]

or pharmaceutically acceptable salt thereof. In yet a further embodiment, the bond at the * position is

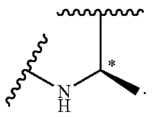 [SMILES: *N[C@@H](*)C]

In yet a further embodiment, the bond at the * position is

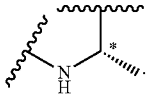

A further embodiment is a compound of Formula

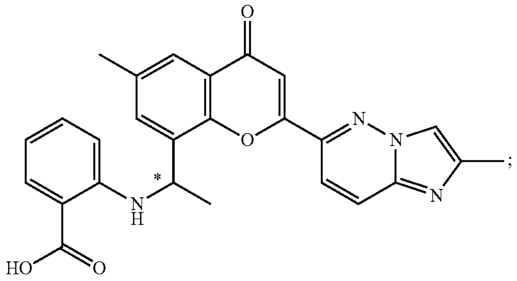 [SMILES: Cc1cc(C(C)Nc2ccccc2C(=O)O)c2oc(-c3ccc4nc(C)cn4n3)cc(=O)c2c1]

or pharmaceutically acceptable salt thereof. In yet a further embodiment, the bond at the position is

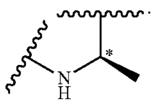 [SMILES: *N[C@@H](*)C]

In yet a further embodiment, the bond at the * position is

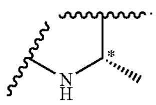 [SMILES: *N[C@H](*)C]

A further embodiment is a compound of Formula

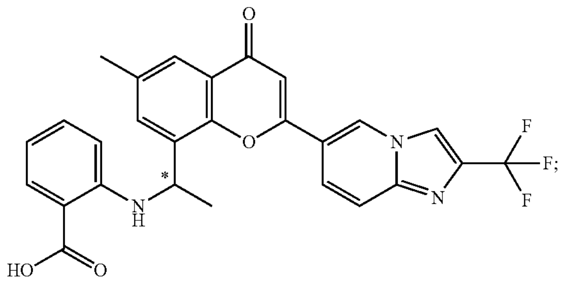 [SMILES: Cc1cc(C(C)Nc2ccccc2C(=O)O)c2oc(-c3ccc4nc(C(F)(F)F)cn4c3)cc(=O)c2c1]

or pharmaceutically acceptable salt thereof. In yet a further embodiment, the bond at the * position is

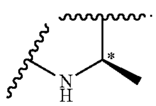 [SMILES: *N[C@@H](*)C]

In yet a further embodiment, the bond at the * position is

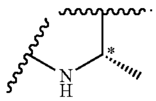 [SMILES: *N[C@H](*)C]

A further embodiment is a compound of Formula

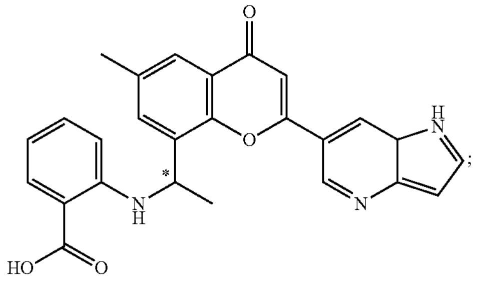

or pharmaceutically acceptable salt thereof. In yet a further embodiment, the bond at the * position is

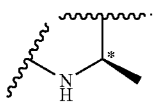 [SMILES: *N[C@@H](*)C]

In yet a further embodiment, the bond at the * position is

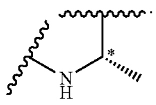 [SMILES: *N[C@H](*)C]

A further embodiment is a compound of Formula

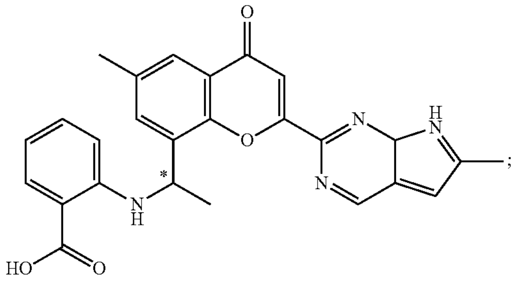

or pharmaceutically acceptable salt thereof. In yet a further embodiment, the bond at the position is

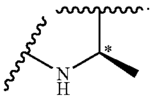 [SMILES: *N[C@@H](*)C]

In yet a further embodiment, the bond at the * position is

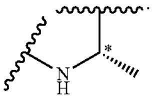 [SMILES: *N[C@H](*)C]

A further embodiment is a compound of Formula

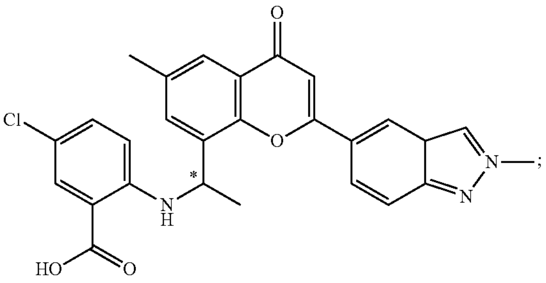

or pharmaceutically acceptable salt thereof. In yet a further embodiment, the bond at the * position is

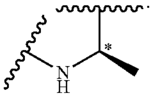 [SMILES: *N[C@@H](*)C]

In yet a further embodiment, the bond at the * position is

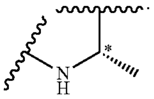 [SMILES: *N[C@H](*)C]

A further embodiment is a compound of Formula

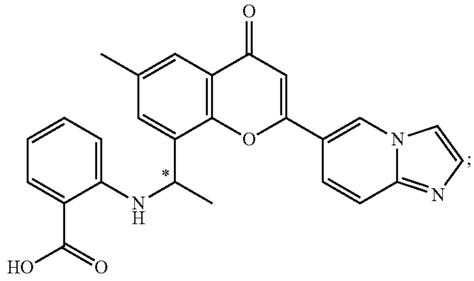 [SMILES: Cc1cc(C(C)Nc2ccccc2C(=O)O)c2oc(-c3ccc4nccn4c3)cc(=O)c2c1]

or pharmaceutically acceptable salt thereof. In yet a further embodiment, the bond at the * position is

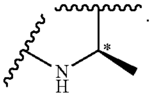

In yet a further embodiment, the bond at the * position is

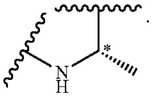

A further embodiment is a compound of Formula

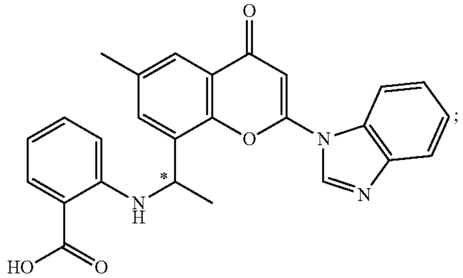 [SMILES: Cc1cc(C(C)Nc2ccccc2C(=O)O)c2oc(-n3cnc4ccccc43)cc(=O)c2c1]

or pharmaceutically acceptable salt thereof. In yet a further embodiment, the bond at the position is

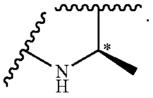

In yet a further embodiment, the bond at the * position is

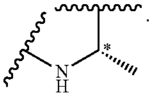

A further embodiment is a compound of Formula

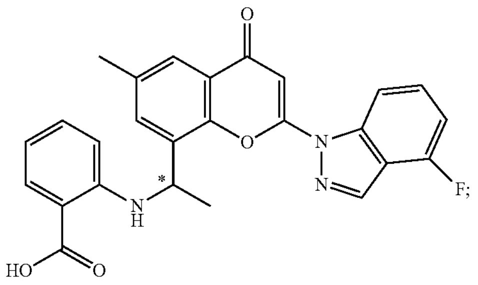 [SMILES: Cc1cc(C(C)Nc2ccccc2C(=O)O)c2oc(-n3ncc4c(F)cccc43)cc(=O)c2c1]

or pharmaceutically acceptable salt thereof. In yet a further embodiment, the bond at the * position is

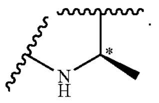 [SMILES: *N[C@@H](*)C]

In yet a further embodiment, the bond at the * position is

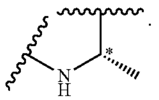

A further embodiment is a compound of Formula

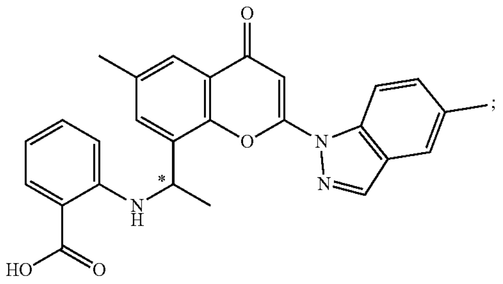 [SMILES: Cc1ccc2c(cnn2-c2cc(=O)c3cc(C)cc(C(C)Nc4ccccc4C(=O)O)c3o2)c1]

or pharmaceutically acceptable salt thereof. In yet a further embodiment, the bond at the position is

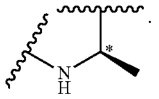 [SMILES: *N[C@@H](*)C]

In yet a further embodiment, the bond at the * position is

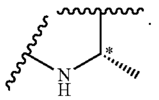

A further embodiment is a compound of Formula

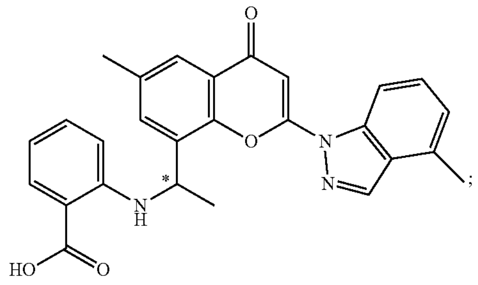 [SMILES: Cc1cc(C(C)Nc2ccccc2C(=O)O)c2oc(-n3ncc4c(C)cccc43)cc(=O)c2c1]

or pharmaceutically acceptable salt thereof. In yet a further embodiment, the bond at the position is

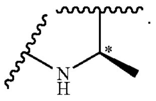

In yet a further embodiment, the bond at the * position is

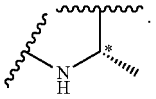

A further embodiment is a compound of Formula

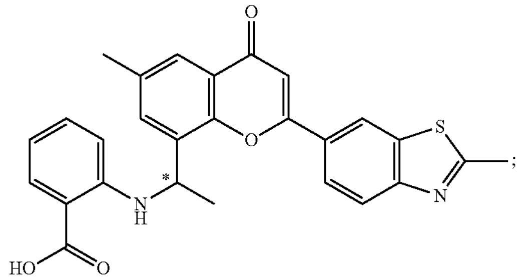

or pharmaceutically acceptable salt thereof. In yet a further embodiment, the bond at the * position is

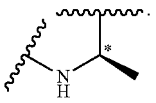 [SMILES: *N[C@@H](*)C]

In yet a further embodiment, the bond at the * position is

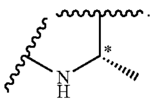 [SMILES: *N[C@H](*)C]

A further embodiment is a compound of Formula

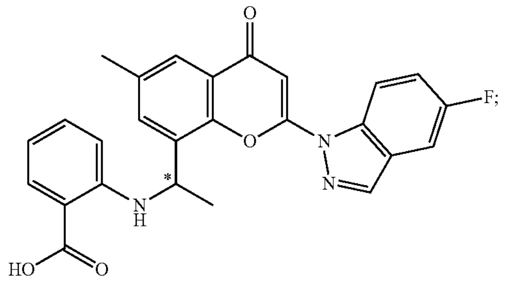 [SMILES: Cc1cc(C(C)Nc2ccccc2C(=O)O)c2oc(-n3ncc4cc(F)ccc43)cc(=O)c2c1]

or pharmaceutically acceptable salt thereof. In yet a further embodiment, the bond at the * position is

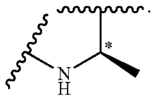 [SMILES: *N[C@@H](*)C]

In yet a further embodiment, the bond at the * position is

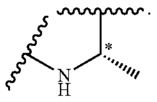 [SMILES: *N[C@H](*)C]

A further embodiment is a compound of Formula

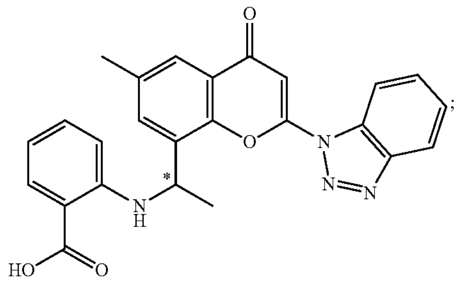 [SMILES: Cc1cc(C(C)Nc2ccccc2C(=O)O)c2oc(-n3nnc4ccccc43)cc(=O)c2c1]

or pharmaceutically acceptable salt thereof. In yet a further embodiment, the bond at the * position is

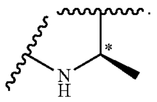 [SMILES: *N[C@@H](*)C]

In yet a further embodiment, the bond at the * position is

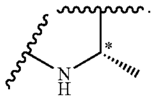

A further embodiment is a compound of Formula

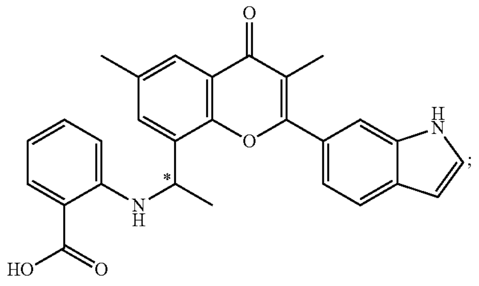 [SMILES: Cc1cc(C(C)Nc2ccccc2C(=O)O)c2oc(-c3ccc4cc[nH]c4c3)c(C)c(=O)c2c1]

or pharmaceutically acceptable salt thereof. In yet a further embodiment, the bond at the * position is

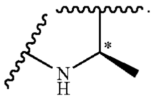 [SMILES: *N[C@@H](*)C]

In yet a further embodiment, the bond at the * position is

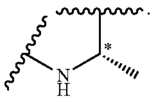 [SMILES: *N[C@H](*)C]

A further embodiment is a compound of Formula

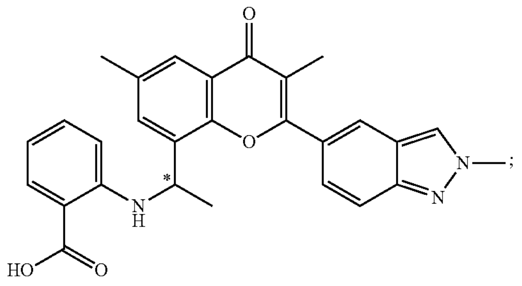

or pharmaceutically acceptable salt thereof. In yet a further embodiment, the bond at the * position is

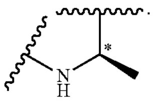 [SMILES: *N[C@@H](*)C]

In yet a further embodiment, the bond at the * position is

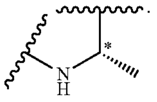

A further embodiment is a compound of Formula

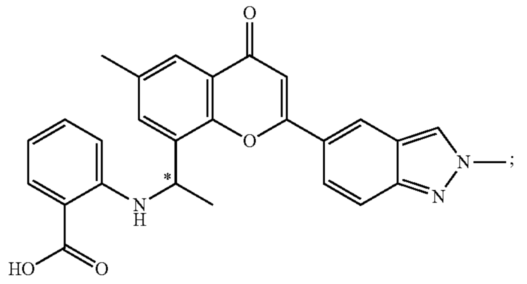

or pharmaceutically acceptable salt thereof. In yet a further embodiment, the bond at the * position is

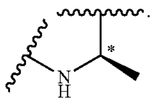

In yet a further embodiment, the bond at the * position is

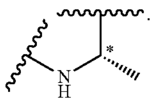 [SMILES: *N[C@H](*)C]

A further embodiment is a compound of Formula

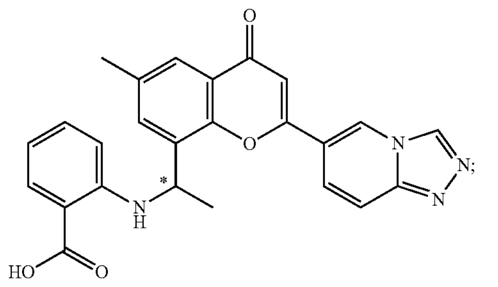 [SMILES: Cc1cc(C(C)Nc2ccccc2C(=O)O)c2oc(-c3ccc4nncn4c3)cc(=O)c2c1]

or pharmaceutically acceptable salt thereof. In yet a further embodiment, the bond at the * position is

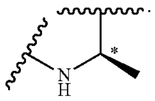

In yet a further embodiment, the bond at the * position is

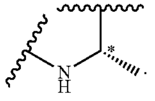 [SMILES: *N[C@H](*)C]

A further embodiment is a compound of Formula

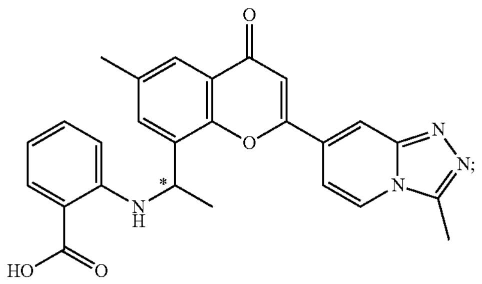 [SMILES: Cc1cc(C(C)Nc2ccccc2C(=O)O)c2oc(-c3ccn4c(C)nnc4c3)cc(=O)c2c1]

or pharmaceutically acceptable salt thereof. In yet a further embodiment, the bond at the * position is

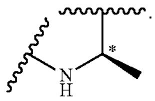 [SMILES: *N[C@@H](*)C]

In yet a further embodiment, the bond at the * position is

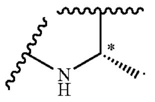

A further embodiment is a compound of Formula

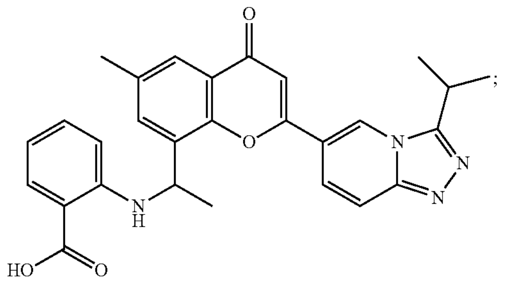 [SMILES: Cc1cc(C(C)Nc2ccccc2C(=O)O)c2oc(-c3ccc4nnc(C(C)C)n4c3)cc(=O)c2c1]

or pharmaceutically acceptable salt thereof. In yet a further embodiment, the bond at the * position is

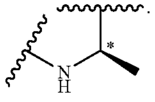

In yet a further embodiment, the bond at the * position is

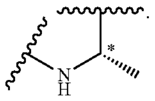

A further embodiment is a compound of Formula

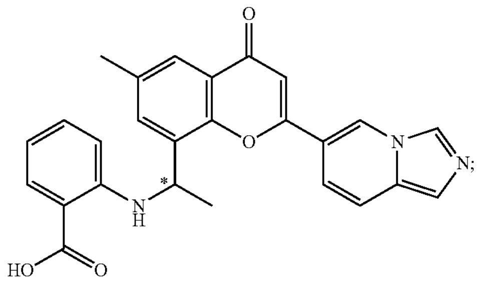

or pharmaceutically acceptable salt thereof. In yet a further embodiment, the bond at the position is

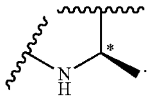

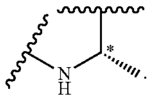

or pharmaceutically acceptable salt thereof. In yet a further embodiment, the bond at the * position is

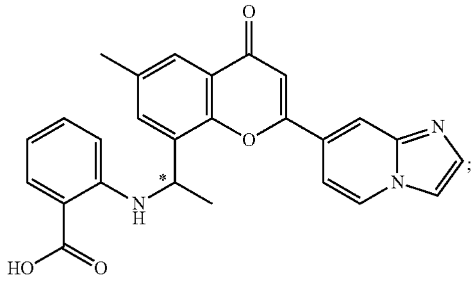 [SMILES: Cc1cc(C(C)Nc2ccccc2C(=O)O)c2oc(-c3ccn4ccnc4c3)cc(=O)c2c1]

In yet a further embodiment, the bond at the * position is

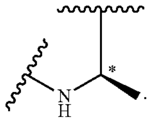 [SMILES: *N[C@@H](*)C]

In yet a further embodiment, the bond at the * position is

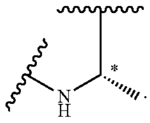 [SMILES: *N[C@H](*)C]

A further embodiment is a compound of Formula

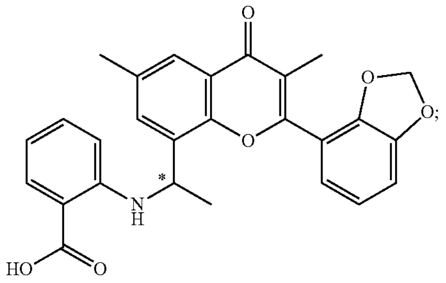 [SMILES: Cc1cc(C(C)Nc2ccccc2C(=O)O)c2oc(-c3cccc4c3OCO4)c(C)c(=O)c2c1]

or pharmaceutically acceptable salt thereof. In yet a further embodiment, the bond at the * position is

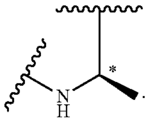 [SMILES: *N[C@@H](*)C]

In yet a further embodiment, the bond at the * position is

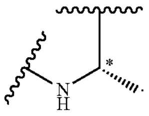 [SMILES: *N[C@H](*)C]

A further embodiment is a compound of Formula

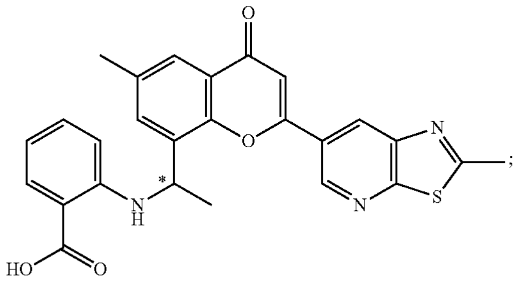 [SMILES: Cc1cc(C(C)Nc2ccccc2C(=O)O)c2oc(-c3cnc4sc(C)nc4c3)cc(=O)c2c1]

or pharmaceutically acceptable salt thereof. In yet a further embodiment, the bond at the * position is

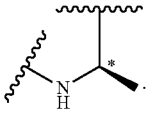 [SMILES: *N[C@@H](*)C]

In yet a further embodiment, the bond at the * position is

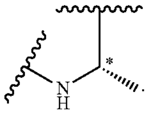 [SMILES: *N[C@H](*)C]

A further embodiment is a compound of Formula

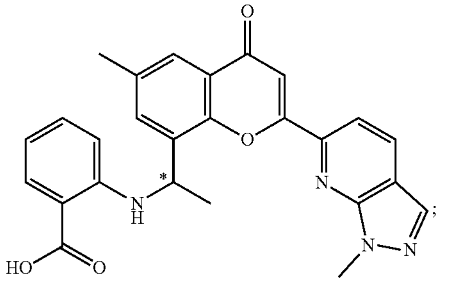 [SMILES: Cc1cc(C(C)Nc2ccccc2C(=O)O)c2oc(-c3ccc4cnn(C)c4n3)cc(=O)c2c1]

or pharmaceutically acceptable salt thereof. In yet a further embodiment, the bond at the * position is

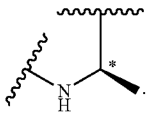 [SMILES: *N[C@@H](*)C]

In yet a further embodiment, the bond at the * position is

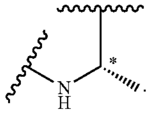

A further embodiment is a compound of Formula

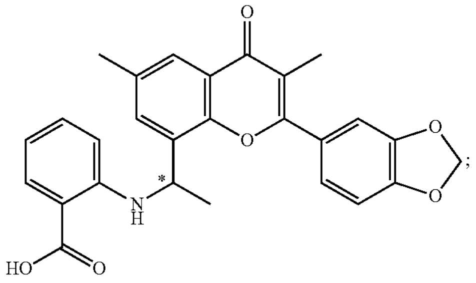 [SMILES: Cc1cc(C(C)Nc2ccccc2C(=O)O)c2oc(-c3ccc4c(c3)OCO4)c(C)c(=O)c2c1]

or pharmaceutically acceptable salt thereof. In yet a further embodiment, the bond at the * position is

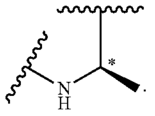

In yet a further embodiment, the bond at the * position is

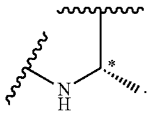 [SMILES: *N[C@H](*)C]

A further embodiment is a compound of Formula

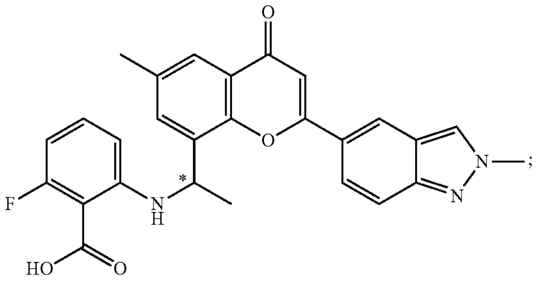 [SMILES: Cc1cc(C(C)Nc2cccc(F)c2C(=O)O)c2oc(-c3ccc4nn(C)cc4c3)cc(=O)c2c1]

or pharmaceutically acceptable salt thereof. In yet a further embodiment, the bond at the * position is

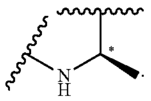 [SMILES: *N[C@@H](*)C]

In yet a further embodiment, the bond at the * position is

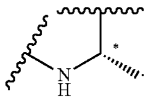 [SMILES: *N[C@H](*)C]

A further embodiment is a compound of Formula

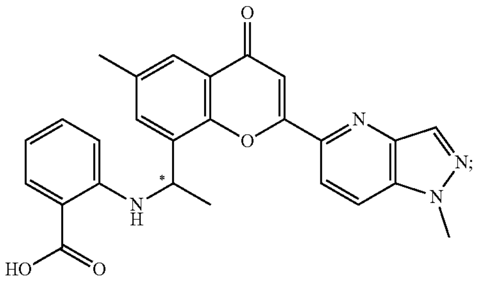 [SMILES: Cc1cc(C(C)Nc2ccccc2C(=O)O)c2oc(-c3ccc4c(cnn4C)n3)cc(=O)c2c1]

or pharmaceutically acceptable salt thereof. In yet a further embodiment, the bond at the * position is

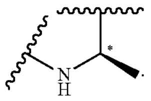 [SMILES: *N[C@@H](*)C]

In yet a further embodiment, the bond at the * position is

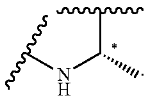

A further embodiment is a compound of Formula

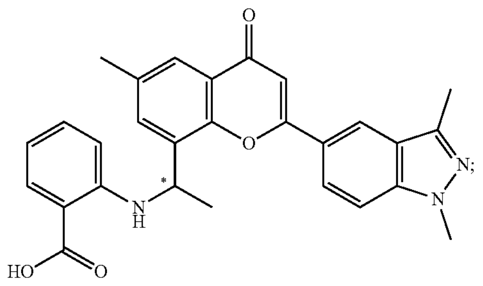 [SMILES: Cc1cc(C(C)Nc2ccccc2C(=O)O)c2oc(-c3ccc4c(c3)c(C)nn4C)cc(=O)c2c1]

or pharmaceutically acceptable salt thereof. In yet a further embodiment, the bond at the * position is

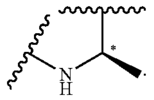

In yet a further embodiment, the bond at the * position is

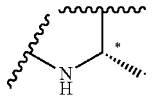

A further embodiment is a compound of Formula

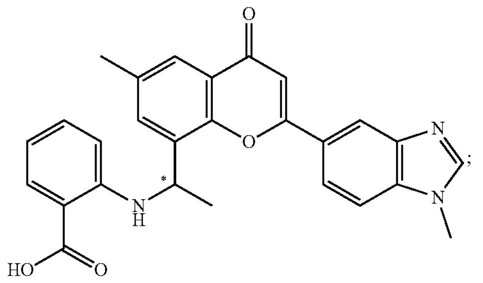 [SMILES: Cc1cc(C(C)Nc2ccccc2C(=O)O)c2oc(-c3ccc4c(c3)ncn4C)cc(=O)c2c1]

or pharmaceutically acceptable salt thereof. In yet a further embodiment, the bond at the * position is

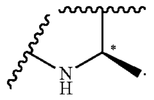 [SMILES: *N[C@@H](*)C]

In yet a further embodiment, the bond at the * position is

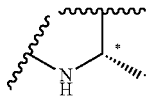 [SMILES: *N[C@H](*)C]

A further embodiment is a compound of Formula

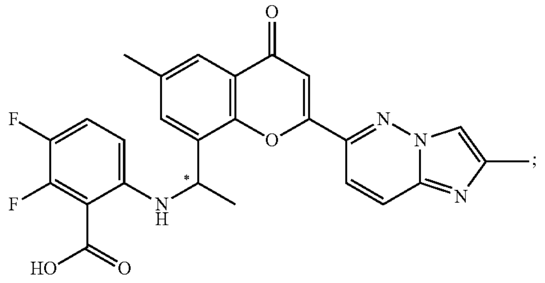 [SMILES: Cc1cc(C(C)Nc2ccc(F)c(F)c2C(=O)O)c2oc(-c3ccc4nc(C)cn4n3)cc(=O)c2c1]

or pharmaceutically acceptable salt thereof. In yet a further embodiment, the bond at the * position is

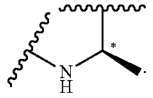 [SMILES: *N[C@@H](*)C]

In yet a further embodiment, the bond at the * position is

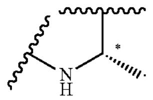 [SMILES: *N[C@H](*)C]

A further embodiment is a compound of Formula

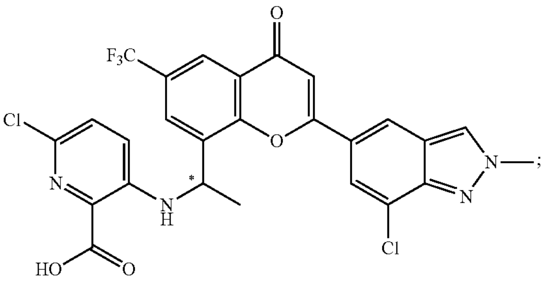

or pharmaceutically acceptable salt thereof. In yet a further embodiment, the bond at the position is

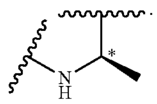 [SMILES: *N[C@@H](*)C]

In yet a further embodiment, the bond at the * position is

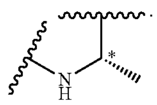

A further embodiment is a compound of Formula

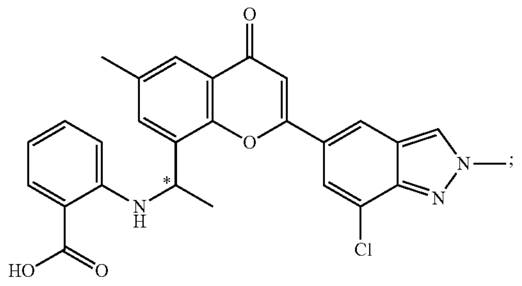

or pharmaceutically acceptable salt thereof. In yet a further embodiment, the bond at the position is

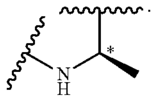

In yet a further embodiment, the bond at the * position is

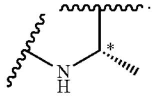

A further embodiment is a compound of Formula

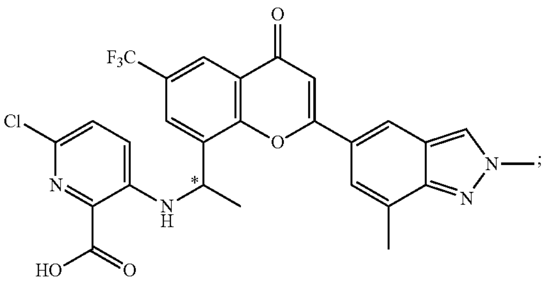 [SMILES: Cc1cc(-c2cc(=O)c3cc(C(F)(F)F)cc(C(C)Nc4ccc(Cl)nc4C(=O)O)c3o2)cc2cn(C)nc12]

or pharmaceutically acceptable salt thereof. In yet a further embodiment, the bond at the * position is

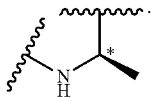

In yet a further embodiment, the bond at the * position is

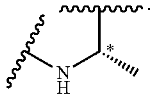

A further embodiment is a compound of Formula

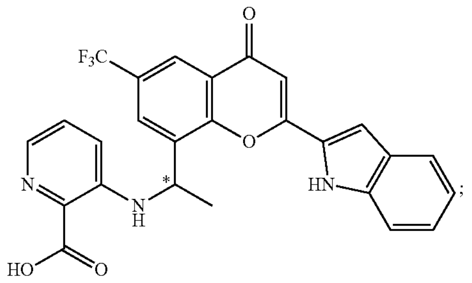

or pharmaceutically acceptable salt thereof. In yet a further embodiment, the bond at the * position is

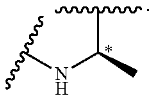 [SMILES: *N[C@@H](*)C]

In yet a further embodiment, the bond at the * position is

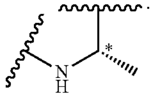 [SMILES: *N[C@H](*)C]

A further embodiment is a compound of Formula

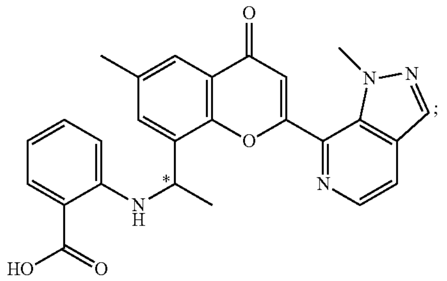

or pharmaceutically acceptable salt thereof. In yet a further embodiment, the bond at the * position is

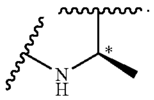 [SMILES: *N[C@@H](*)C]

In yet a further embodiment, the bond at the * position is

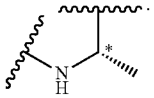 [SMILES: *N[C@H](*)C]

A further embodiment is a compound of Formula

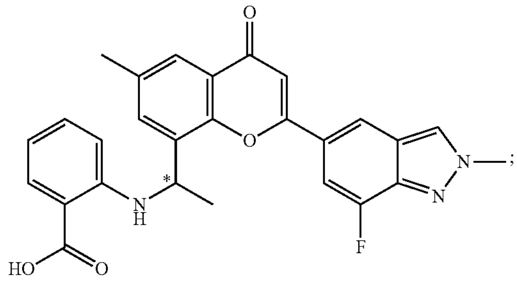 [SMILES: Cc1cc(C(C)Nc2ccccc2C(=O)O)c2oc(-c3cc(F)c4nn(C)cc4c3)cc(=O)c2c1]

;

or pharmaceutically acceptable salt thereof. In yet a further embodiment, the bond at the * position is

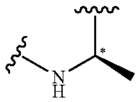

.

In yet a further embodiment, the bond at the * position is

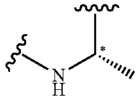

.

A further embodiment is a compound of Formula

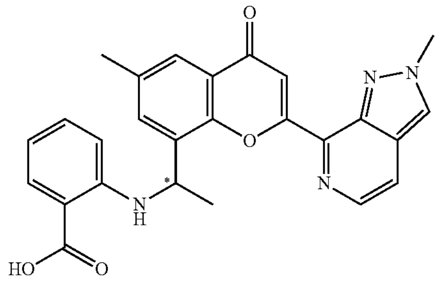

;

or pharmaceutically acceptable salt thereof. In yet a further embodiment, the bond at the * position is

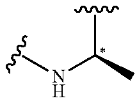

.

In yet a further embodiment, the bond at the * position is

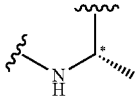

.

A further embodiment is a compound of Formula

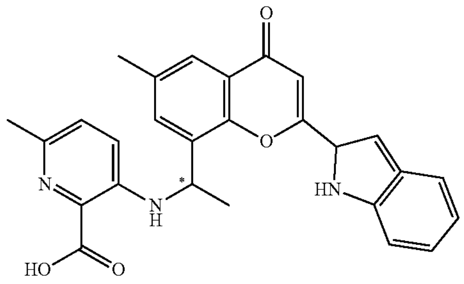

;

or pharmaceutically acceptable salt thereof. In yet a further embodiment, the bond at the * position is

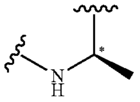

.

In yet a further embodiment, the bond at the * position is

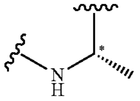

.

A further embodiment is a compound of Formula

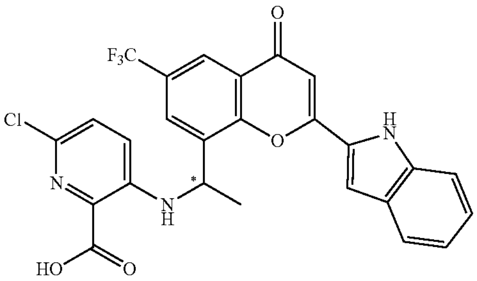

;

or pharmaceutically acceptable salt thereof. In yet a further embodiment, the bond at the * position is

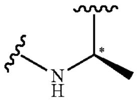

.

In yet a further embodiment, the bond at the * position is

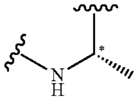

.

A further embodiment is a compound of Formula

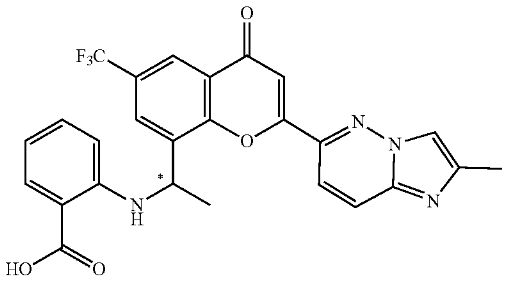

;

or pharmaceutically acceptable salt thereof. In yet a further embodiment, the bond at the * position is

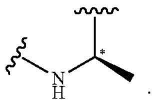

.

In yet a further embodiment, the bond at the * position is

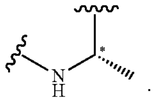

.

A further embodiment is a compound of Formula

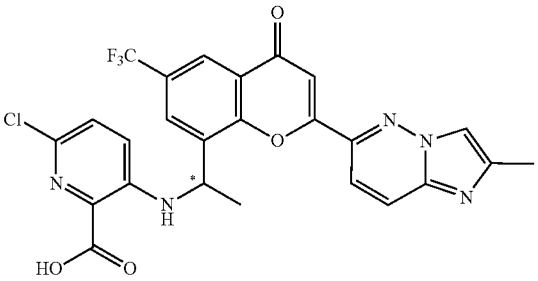

;

or pharmaceutically acceptable salt thereof. In yet a further embodiment, the bond at the * position is

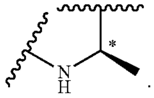 [SMILES: *N[C@@H](*)C]

.

In yet a further embodiment, the bond at the * position is

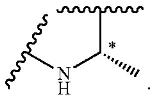

.

A further embodiment is a compound of Formula

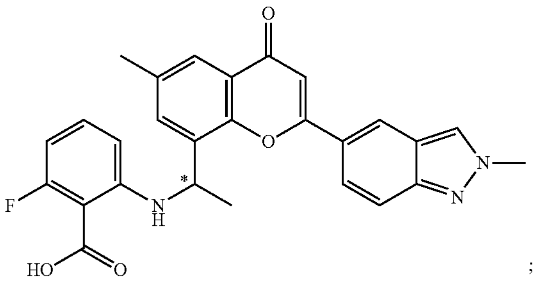 [SMILES: Cc1cc(C(C)Nc2cccc(F)c2C(=O)O)c2oc(-c3ccc4nn(C)cc4c3)cc(=O)c2c1]

;

or pharmaceutically acceptable salt thereof. In yet a further embodiment, the bond at the position is

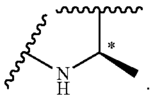 [SMILES: *N[C@@H](*)C]

.

In yet a further embodiment, the bond at the * position is,

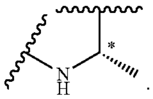

.

A further embodiment is a compound of Formula

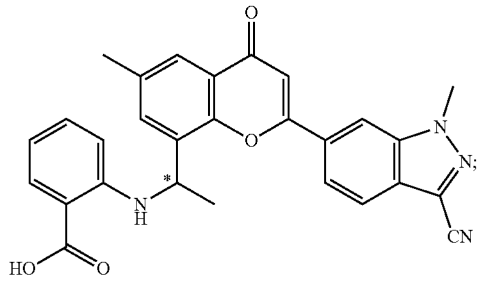 [SMILES: Cc1cc(C(C)Nc2ccccc2C(=O)O)c2oc(-c3ccc4c(C#N)nn(C)c4c3)cc(=O)c2c1]

or pharmaceutically acceptable salt thereof. In yet a further embodiment, the bond at the * position is

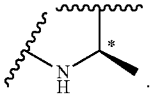 [SMILES: *N[C@@H](*)C]

.

In yet a further embodiment, the bond at the * position is

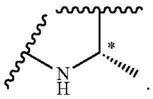

.

A further embodiment is a compound of Formula

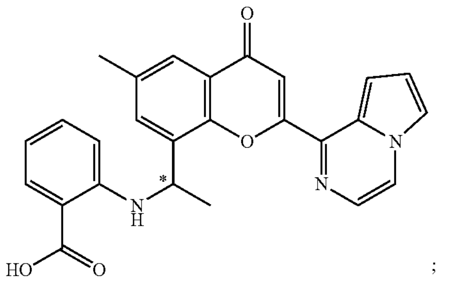 [SMILES: Cc1cc(C(C)Nc2ccccc2C(=O)O)c2oc(-c3nccn4cccc34)cc(=O)c2c1]

;

or pharmaceutically acceptable salt thereof. In yet a further embodiment, the bond at the * position is

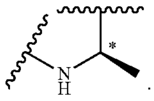 [SMILES: *N[C@@H](*)C]

.

In yet a further embodiment, the bond at the * position is

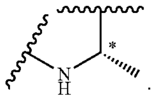

.

A further embodiment is a compound of Formula

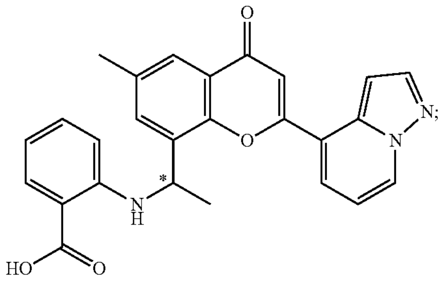 [SMILES: Cc1cc(C(C)Nc2ccccc2C(=O)O)c2oc(-c3cccn4nccc34)cc(=O)c2c1]

or pharmaceutically acceptable salt thereof. In yet a further embodiment, the bond at the position is

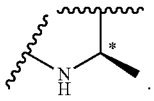 [SMILES: *N[C@@H](*)C]

.

In yet a further embodiment, the bond at the * position is

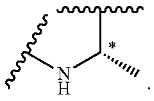

.

A further embodiment is a compound of Formula

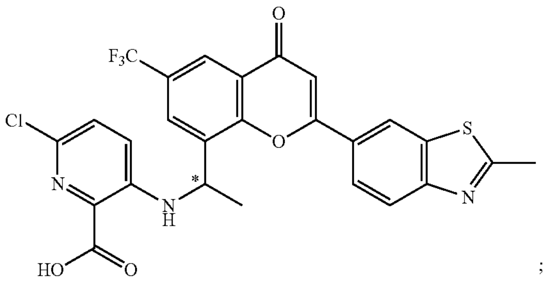 [SMILES: Cc1nc2ccc(-c3cc(=O)c4cc(C(F)(F)F)cc(C(C)Nc5ccc(Cl)nc5C(=O)O)c4o3)cc2s1]

;

or pharmaceutically acceptable salt thereof. In yet a further embodiment, the bond at the * position is

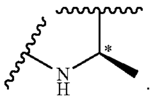 [SMILES: *N[C@@H](*)C]

.

In yet a further embodiment, the bond at the * position is

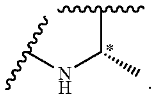 [SMILES: *N[C@H](*)C]

.

A further embodiment is a compound of Formula

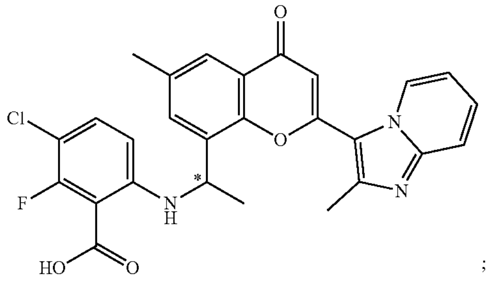 [SMILES: Cc1cc(C(C)Nc2ccc(Cl)c(F)c2C(=O)O)c2oc(-c3c(C)nc4ccccn34)cc(=O)c2c1]

;

or pharmaceutically acceptable salt thereof. In yet a further embodiment, the bond at the * position is

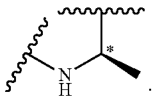 [SMILES: *N[C@@H](*)C]

.

In yet a further embodiment, the bond at the * position is

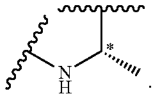 [SMILES: *N[C@H](*)C]

.

A further embodiment is a compound of Formula

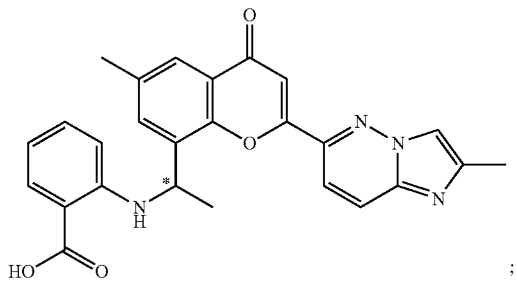 [SMILES: Cc1cc(C(C)Nc2ccccc2C(=O)O)c2oc(-c3ccc4nc(C)cn4n3)cc(=O)c2c1]
;

or pharmaceutically acceptable salt thereof. In yet a further embodiment, the bond at the position is

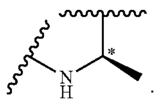
.

In yet a further embodiment, the bond at the * position is

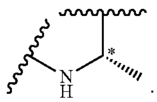
.

A further embodiment is a compound of Formula

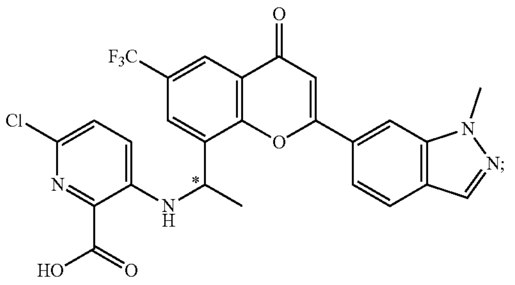 [SMILES: CC(Nc1ccc(Cl)nc1C(=O)O)c1cc(C(F)(F)F)cc2c(=O)cc(-c3ccc4cnn(C)c4c3)oc12]

or pharmaceutically acceptable salt thereof. In yet a further embodiment, the bond at the * position is

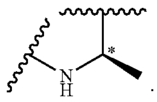 [SMILES: *N[C@@H](*)C]
.

In yet a further embodiment, the bond at the * position is

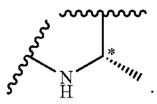
.

A further embodiment is a compound of Formula

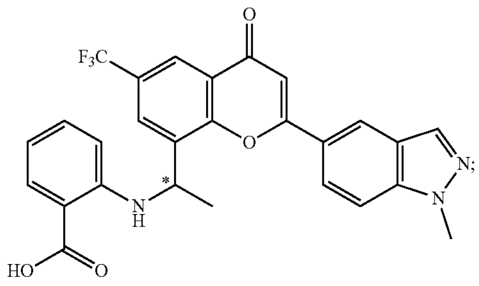 [SMILES: CC(Nc1ccccc1C(=O)O)c1cc(C(F)(F)F)cc2c(=O)cc(-c3ccc4c(cnn4C)c3)oc12]

or pharmaceutically acceptable salt thereof. In yet a further embodiment, the bond at the position is

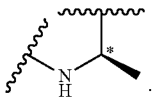
.

In yet a further embodiment, the bond at the * position is

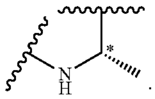 [SMILES: *N[C@H](*)C]
.

A further embodiment is a compound of Formula

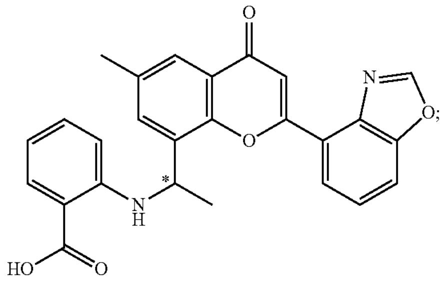 [SMILES: Cc1cc(C(C)Nc2ccccc2C(=O)O)c2oc(-c3cccc4ocnc34)cc(=O)c2c1]

or pharmaceutically acceptable salt thereof. In yet a further embodiment, the bond at the * position is

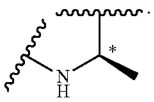 [SMILES: *N[C@@H](*)C]

In yet a further embodiment, the bond at the * position is

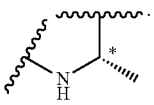 [SMILES: *N[C@H](*)C]

A further embodiment is a compound of Formula

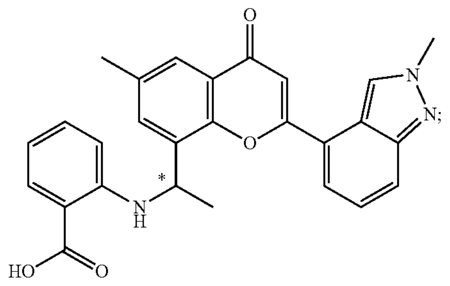 [SMILES: Cc1cc(C(C)Nc2ccccc2C(=O)O)c2oc(-c3cccc4nn(C)cc34)cc(=O)c2c1]

or pharmaceutically acceptable salt thereof. In yet a further embodiment, the bond at the position is

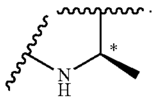 [SMILES: *N[C@@H](*)C]

In yet a further embodiment, the bond at the * position is

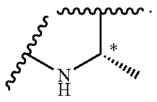

A further embodiment is a compound of Formula

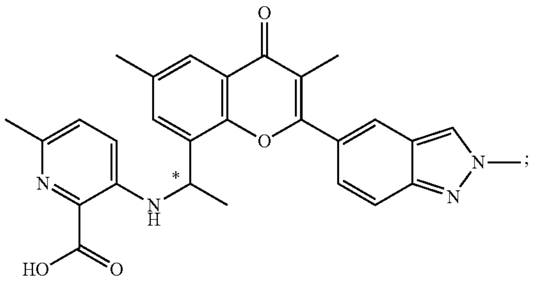

or pharmaceutically acceptable salt thereof. In yet a further embodiment, the bond at the * position is

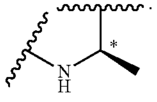 [SMILES: *N[C@@H](*)C]

In yet a further embodiment, the bond at the * position is

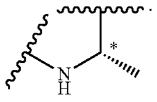 [SMILES: *N[C@H](*)C]

A further embodiment is a compound of Formula

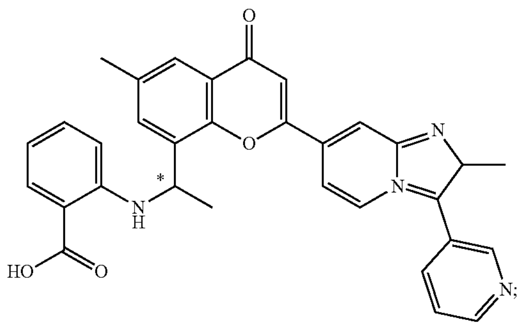

or pharmaceutically acceptable salt thereof. In yet a further embodiment, the bond at the * position is

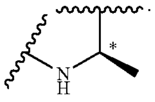 [SMILES: *N[C@@H](*)C]

In yet a further embodiment, the bond at the * position is

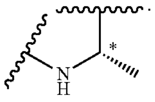

A further embodiment is a compound of Formula

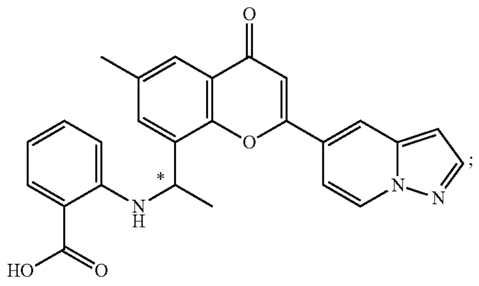 [SMILES: Cc1cc(C(C)Nc2ccccc2C(=O)O)c2oc(-c3ccn4nccc4c3)cc(=O)c2c1]

or pharmaceutically acceptable salt thereof. In yet a further embodiment, the bond at the * position is

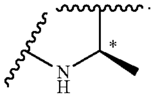 [SMILES: *N[C@@H](*)C]

In yet a further embodiment, the bond at the * position is

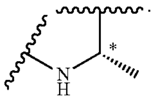

A further embodiment is a compound of Formula

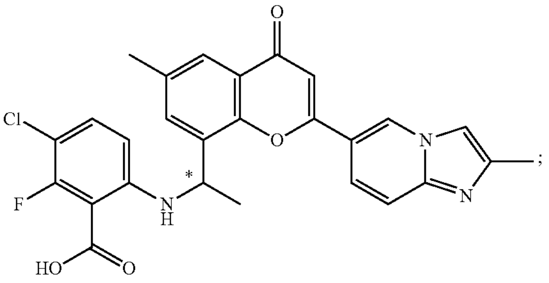

or pharmaceutically acceptable salt thereof. In yet a further embodiment, the bond at the * position is

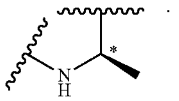 [SMILES: *N[C@@H](*)C]

In yet a further embodiment, the bond at the * position is

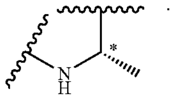

A further embodiment is a compound of Formula

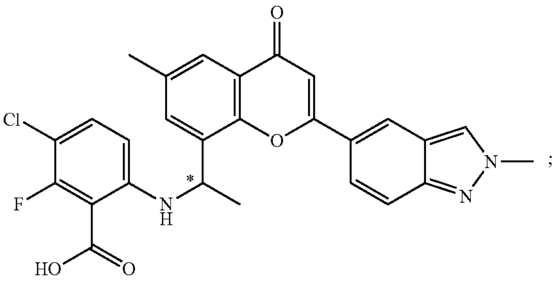 [SMILES: Cc1cc(C(C)Nc2ccc(Cl)c(F)c2C(=O)O)c2oc(-c3ccc4nn(C)cc4c3)cc(=O)c2c1]

or pharmaceutically acceptable salt thereof. In yet a further embodiment, the bond at the * position is

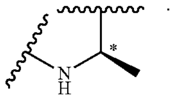 [SMILES: *N[C@@H](*)C]

In yet a further embodiment, the bond at the * position is,

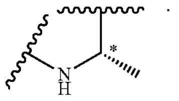 [SMILES: *N[C@H](*)C]

A further embodiment is a compound of Formula

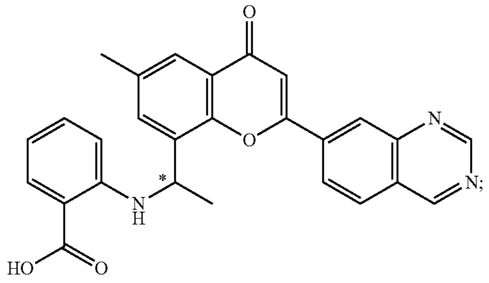 [SMILES: Cc1cc(C(C)Nc2ccccc2C(=O)O)c2oc(-c3ccc4cncnc4c3)cc(=O)c2c1]

or pharmaceutically acceptable salt thereof. In yet a further embodiment, the bond at the * position is

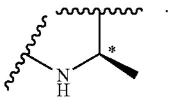 [SMILES: *N[C@@H](*)C]

In yet a further embodiment, the bond at the * position is

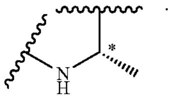

A further embodiment is a compound of Formula

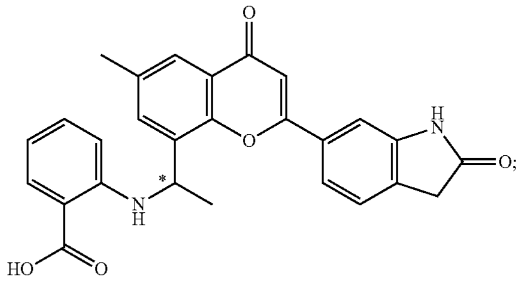 [SMILES: Cc1cc(C(C)Nc2ccccc2C(=O)O)c2oc(-c3ccc4c(c3)NC(=O)C4)cc(=O)c2c1]

or pharmaceutically acceptable salt thereof. In yet a further embodiment, the bond at the * position is

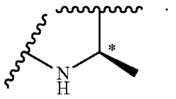 [SMILES: *N[C@@H](*)C]

In yet a further embodiment, the bond at the * position is

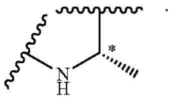 [SMILES: *N[C@H](*)C]

A further embodiment is a compound of Formula

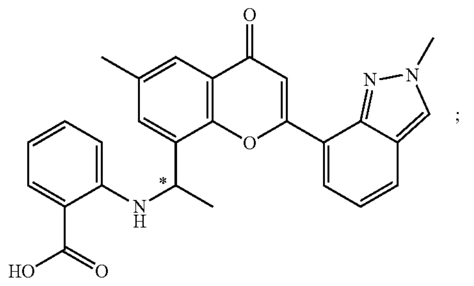 [SMILES: Cc1cc(C(C)Nc2ccccc2C(=O)O)c2oc(-c3cccc4cn(C)nc34)cc(=O)c2c1]

or pharmaceutically acceptable salt thereof. In yet a further embodiment, the bond at the * position is

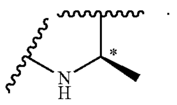 [SMILES: *N[C@@H](*)C]

In yet a further embodiment, the bond at the * position is

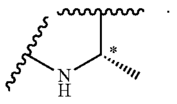 [SMILES: *N[C@H](*)C]

A further embodiment is a compound of Formula

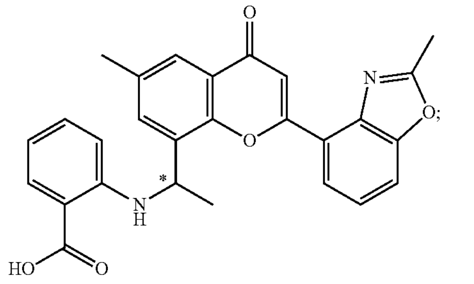 [SMILES: Cc1cc(C(C)Nc2ccccc2C(=O)O)c2oc(-c3cccc4oc(C)nc34)cc(=O)c2c1]

or pharmaceutically acceptable salt thereof. In yet a further embodiment, the bond at the * position is

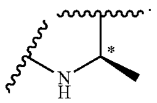

In yet a further embodiment, the bond at the * position is

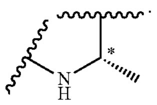

A further embodiment is a compound of Formula

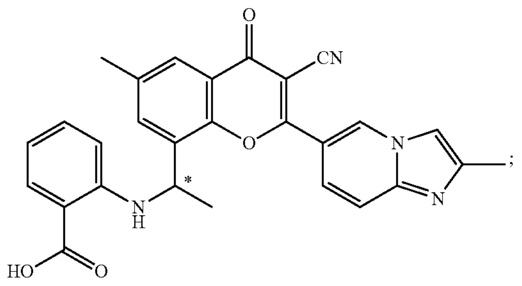 [SMILES: Cc1cc(C(C)Nc2ccccc2C(=O)O)c2oc(-c3ccc4nc(C)cn4c3)c(C#N)c(=O)c2c1]

or pharmaceutically acceptable salt thereof. In yet a further embodiment, the bond at the * position is

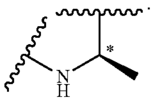

In yet a further embodiment, the bond at the * position is

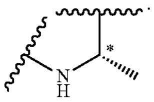

A further embodiment is a compound of Formula

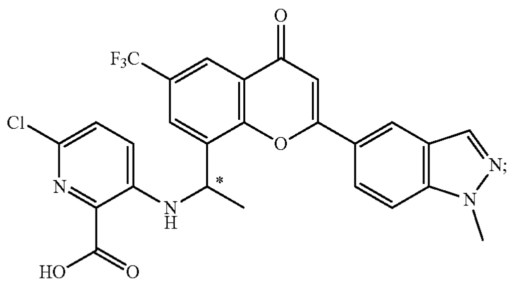 [SMILES: CC(Nc1ccc(Cl)nc1C(=O)O)c1cc(C(F)(F)F)cc2c(=O)cc(-c3ccc4c(cnn4C)c3)oc12]

or pharmaceutically acceptable salt thereof. In yet a further embodiment, the bond at the * position is

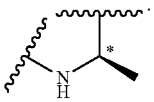

In yet a further embodiment, the bond at the * position is

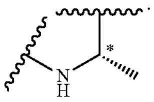

A further embodiment is a compound of Formula

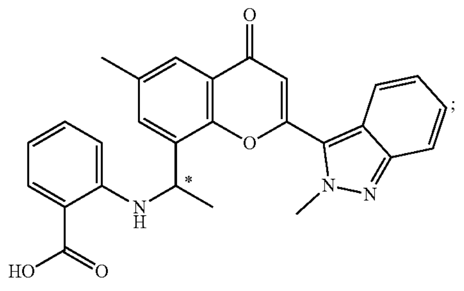 [SMILES: Cc1cc(C(C)Nc2ccccc2C(=O)O)c2oc(-c3c4ccccc4nn3C)cc(=O)c2c1]

or pharmaceutically acceptable salt thereof. In yet a further embodiment, the bond at the * position is

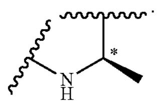

In yet a further embodiment, the bond at the * position is

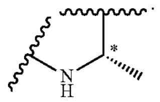

A further embodiment is a compound of Formula

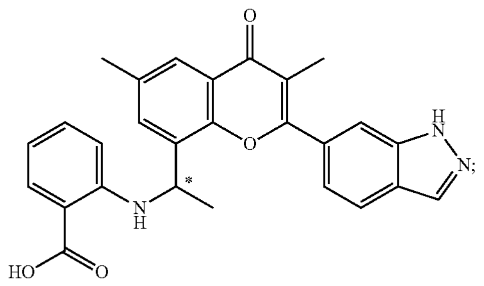 [SMILES: Cc1cc(C(C)Nc2ccccc2C(=O)O)c2oc(-c3ccc4cn[nH]c4c3)c(C)c(=O)c2c1]

or pharmaceutically acceptable salt thereof. In yet a further embodiment, the bond at the * position is

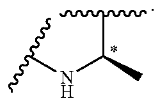

In yet a further embodiment, the bond at the * position is

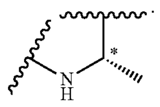

A further embodiment is a compound of Formula

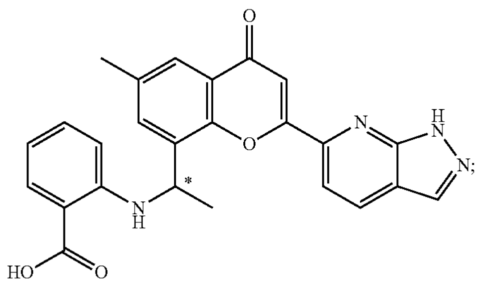 [SMILES: Cc1cc(C(C)Nc2ccccc2C(=O)O)c2oc(-c3ccc4cn[nH]c4n3)cc(=O)c2c1]

or pharmaceutically acceptable salt thereof. In yet a further embodiment, the bond at the * position is

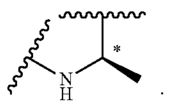 [SMILES: *N[C@@H](*)C]

In yet a further embodiment, the bond at the * position is

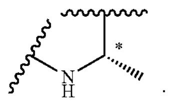

A further embodiment is a compound of Formula

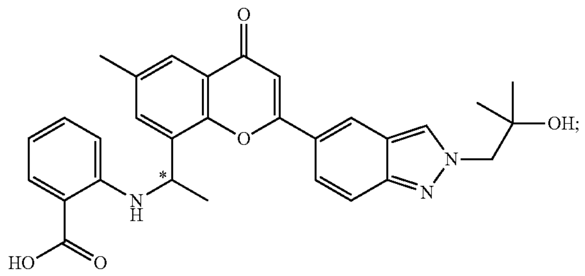 [SMILES: Cc1cc(C(C)Nc2ccccc2C(=O)O)c2oc(-c3ccc4nn(CC(C)(C)O)cc4c3)cc(=O)c2c1]

or pharmaceutically acceptable salt thereof. In yet a further embodiment, the bond at the * position is

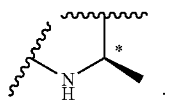 [SMILES: *N[C@@H](*)C]

In yet a further embodiment, the bond at the * position is

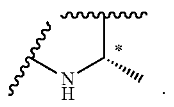 [SMILES: *N[C@H](*)C]

A further embodiment is a compound of Formula

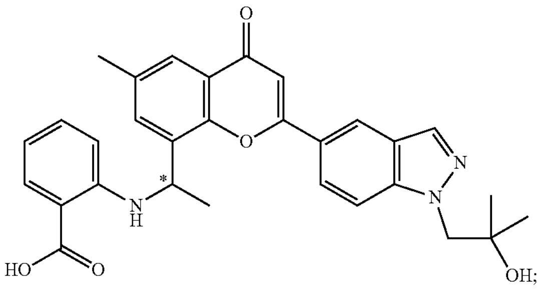 [SMILES: Cc1cc(C(C)Nc2ccccc2C(=O)O)c2oc(-c3ccc4c(cnn4CC(C)(C)O)c3)cc(=O)c2c1]

or pharmaceutically acceptable salt thereof. In yet a further embodiment, the bond at the * position is

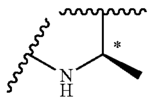
.

In yet a further embodiment, the bond at the * position is

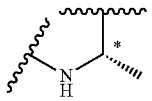
.

A further embodiment is a compound of Formula

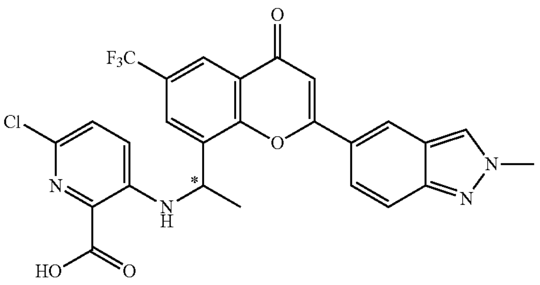
;

or pharmaceutically acceptable salt thereof. In yet a further embodiment, the bond at the * position is

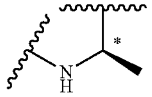
.

In yet a further embodiment, the bond at the * position is

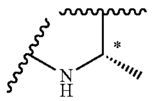
.

A further embodiment is a compound of Formula

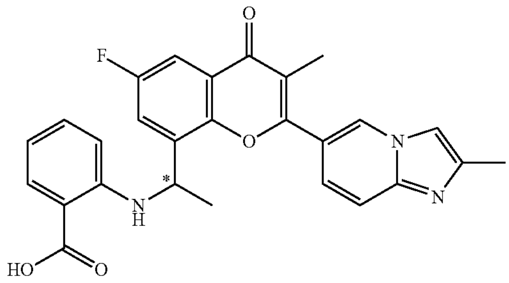
;

or pharmaceutically acceptable salt thereof. In yet a further embodiment, the bond at the * position is

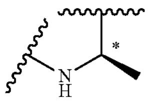
.

In yet a further embodiment, the bond at the * position is

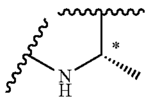
.

A further embodiment is a compound of Formula

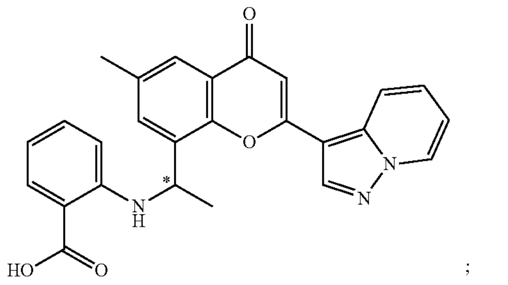 [SMILES: Cc1cc(C(C)Nc2ccccc2C(=O)O)c2oc(-c3cnn4ccccc34)cc(=O)c2c1]
;

or pharmaceutically acceptable salt thereof. In yet a further embodiment, the bond at the * position is

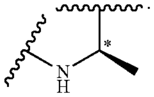

In yet a further embodiment, the bond at the * position is

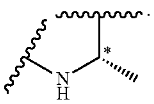

A further embodiment is a compound of Formula

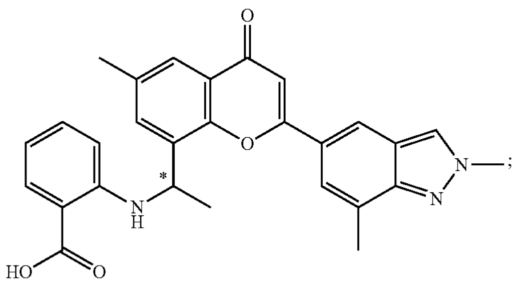 [SMILES: Cc1cc(C(C)Nc2ccccc2C(=O)O)c2oc(-c3cc(C)c4nn(C)cc4c3)cc(=O)c2c1]

or pharmaceutically acceptable salt thereof. In yet a further embodiment, the bond at the position is

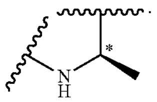 [SMILES: *N[C@@H](*)C]

In yet a further embodiment, the bond at the * position is

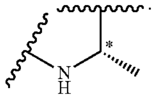

A further embodiment is a compound of Formula

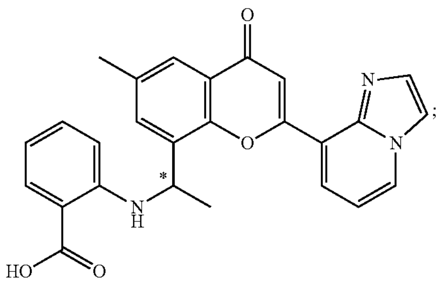 [SMILES: Cc1cc(C(C)Nc2ccccc2C(=O)O)c2oc(-c3cccn4ccnc34)cc(=O)c2c1]

or pharmaceutically acceptable salt thereof. In yet a further embodiment, the bond at the * position is

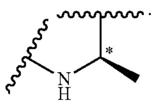

In yet a further embodiment, the bond at the * position is

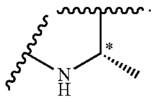

A further embodiment is a compound of Formula

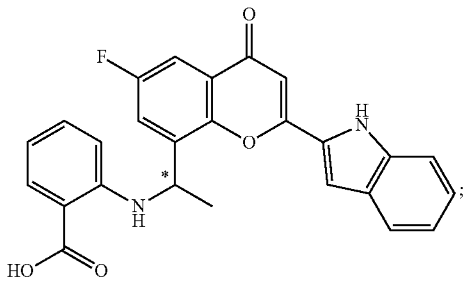 [SMILES: CC(Nc1ccccc1C(=O)O)c1cc(F)cc2c(=O)cc(-c3cc4ccccc4[nH]3)oc12]

or pharmaceutically acceptable salt thereof. In yet a further embodiment, the bond at the * position is

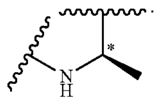

In yet a further embodiment, the bond at the * position is

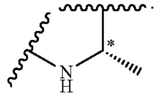

A further embodiment is a compound of Formula

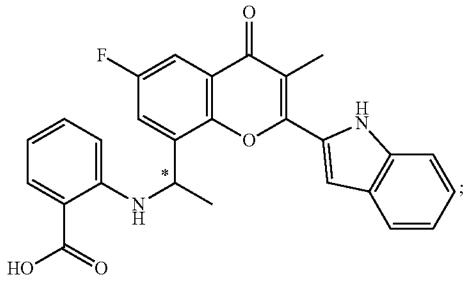 [SMILES: Cc1c(-c2cc3ccccc3[nH]2)oc2c(C(C)Nc3ccccc3C(=O)O)cc(F)cc2c1=O]

or pharmaceutically acceptable salt thereof. In yet a further embodiment, the bond at the * position is

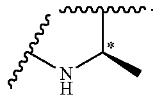

In yet a further embodiment, the bond at the * position is

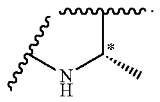

A further embodiment is a compound of Formula

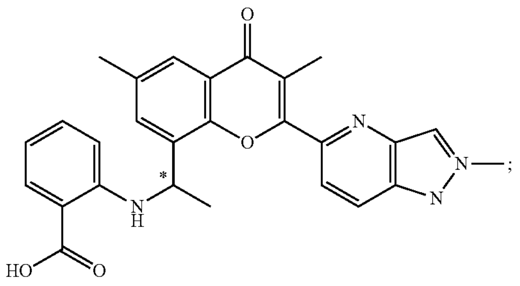

or pharmaceutically acceptable salt thereof. In yet a further embodiment, the bond at the * position is

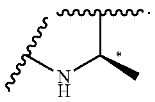

In yet a further embodiment, the bond at the * position is

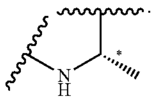

A further embodiment is a compound of Formula

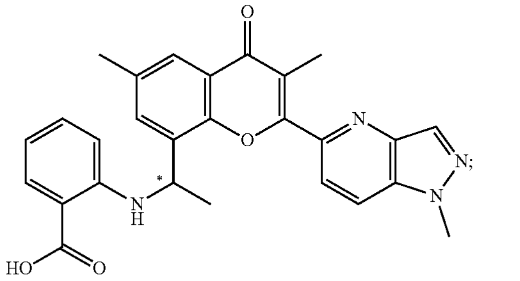 [SMILES: Cc1cc(C(C)Nc2ccccc2C(=O)O)c2oc(-c3ccc4c(cnn4C)n3)c(C)c(=O)c2c1]

or pharmaceutically acceptable salt thereof. In yet a further embodiment, the bond at the * position is

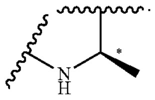

In yet a further embodiment, the bond at the * position is

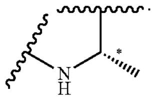

A further embodiment is a compound of Formula

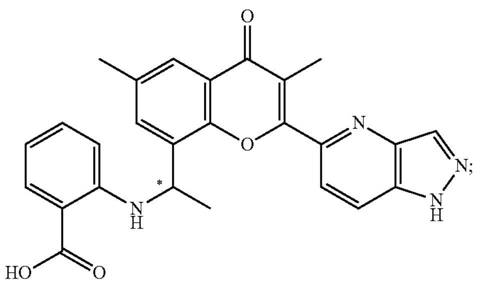 [SMILES: Cc1cc(C(C)Nc2ccccc2C(=O)O)c2oc(-c3ccc4[nH]ncc4n3)c(C)c(=O)c2c1]

or pharmaceutically acceptable salt thereof. In yet a further embodiment, the bond at the * position is

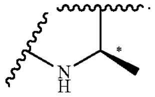

In yet a further embodiment, the bond at the * position is

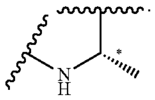

A further embodiment is a compound of Formula

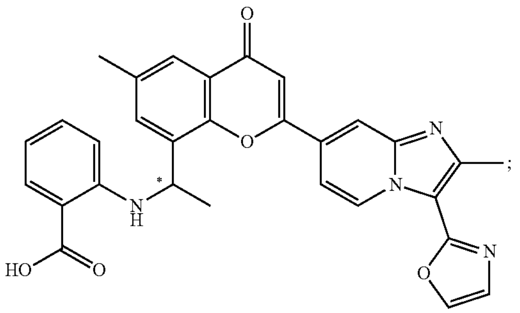 [SMILES: Cc1cc(C(C)Nc2ccccc2C(=O)O)c2oc(-c3ccn4c(-c5ncco5)c(C)nc4c3)cc(=O)c2c1]

or pharmaceutically acceptable salt thereof. In yet a further embodiment, the bond at the position is

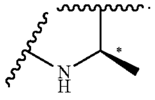 [SMILES: *N[C@@H](*)C]

In yet a further embodiment, the bond at the * position is

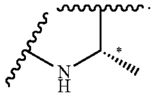

A further embodiment is a compound of Formula

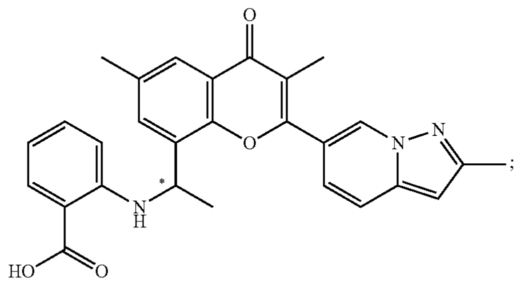 [SMILES: Cc1cc(C(C)Nc2ccccc2C(=O)O)c2oc(-c3ccc4cc(C)nn4c3)c(C)c(=O)c2c1]

or pharmaceutically acceptable salt thereof. In yet a further embodiment, the bond at the position is

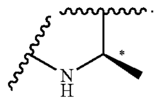

In yet a further embodiment, the bond at the * position is

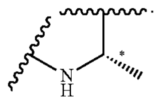

A further embodiment is a compound of Formula

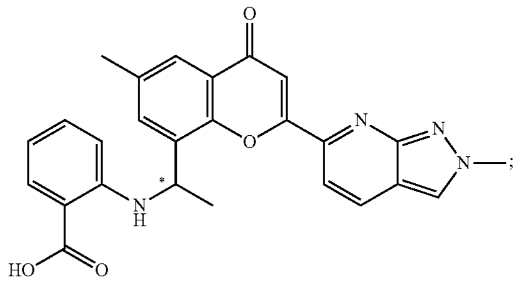 [SMILES: Cc1cc(C(C)Nc2ccccc2C(=O)O)c2oc(-c3ccc4cn(C)nc4n3)cc(=O)c2c1]

or pharmaceutically acceptable salt thereof. In yet a further embodiment, the bond at the * position is

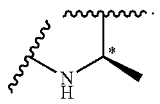

In yet a further embodiment, the bond at the * position is

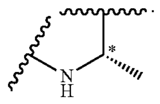

A further embodiment is a compound of Formula

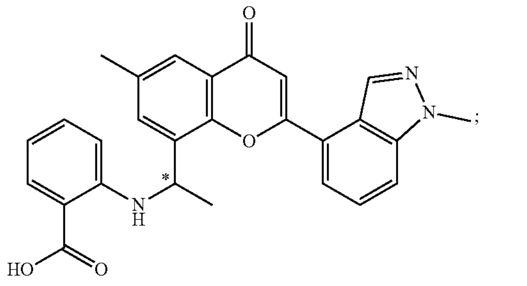 [SMILES: Cc1cc(C(C)Nc2ccccc2C(=O)O)c2oc(-c3cccc4c3cnn4C)cc(=O)c2c1]

or pharmaceutically acceptable salt thereof. In yet a further embodiment, the bond at the * position is

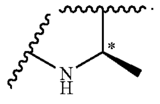

In yet a further embodiment, the bond at the * position is

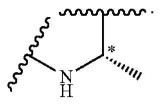

A further embodiment is a compound of Formula

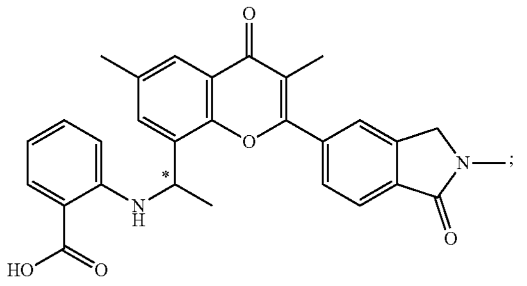 [SMILES: Cc1cc(C(C)Nc2ccccc2C(=O)O)c2oc(-c3ccc4c(c3)CN(C)C4=O)c(C)c(=O)c2c1]

or pharmaceutically acceptable salt thereof. In yet a further embodiment, the bond at the * position is

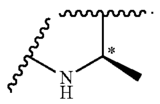 [SMILES: *N[C@@H](*)C]

In yet a further embodiment, the bond at the * position is

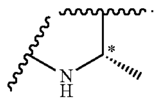

A further embodiment is a compound of Formula

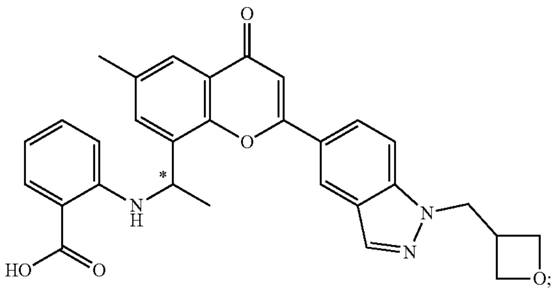 [SMILES: Cc1cc(C(C)Nc2ccccc2C(=O)O)c2oc(-c3ccc4c(cnn4CC4COC4)c3)cc(=O)c2c1]

or pharmaceutically acceptable salt thereof. In yet a further embodiment, the bond at the position is

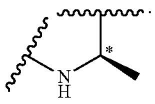 [SMILES: *N[C@@H](*)C]

In yet a further embodiment, the bond at the * position is

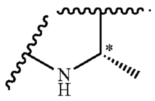

A further embodiment is a compound of Formula

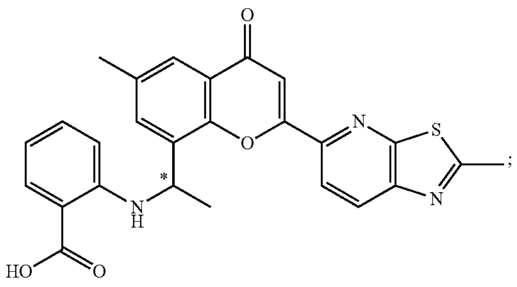 [SMILES: Cc1cc(C(C)Nc2ccccc2C(=O)O)c2oc(-c3ccc4nc(C)sc4n3)cc(=O)c2c1]

or pharmaceutically acceptable salt thereof. In yet a further embodiment, the bond at the * position is

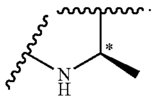 [SMILES: *N[C@@H](*)C]

In yet a further embodiment, the bond at the * position is

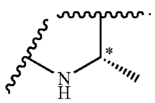

A further embodiment is a compound of Formula

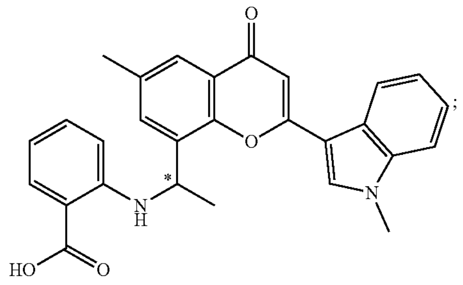 [SMILES: Cc1cc(C(C)Nc2ccccc2C(=O)O)c2oc(-c3cn(C)c4ccccc34)cc(=O)c2c1]

or pharmaceutically acceptable salt thereof. In yet a further embodiment, the bond at the * position is

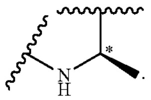 [SMILES: *N[C@@H](*)C]

In yet a further embodiment, the bond at the * position is

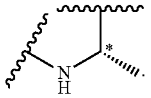 [SMILES: *N[C@H](*)C]

A further embodiment is a compound of Formula

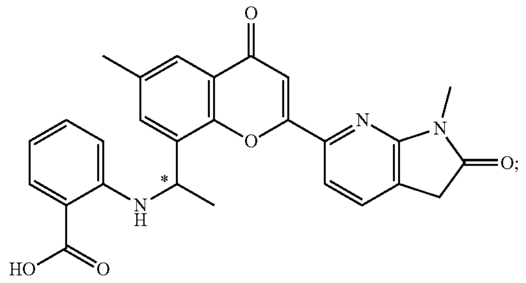 [SMILES: Cc1cc(C(C)Nc2ccccc2C(=O)O)c2oc(-c3ccc4c(n3)N(C)C(=O)C4)cc(=O)c2c1]

or pharmaceutically acceptable salt thereof. In yet a further embodiment, the bond at the * position is

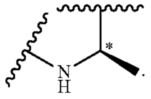 [SMILES: *N[C@@H](*)C]

In yet a further embodiment, the bond at the * position is

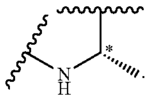 [SMILES: *N[C@H](*)C]

A further embodiment is a compound of Formula

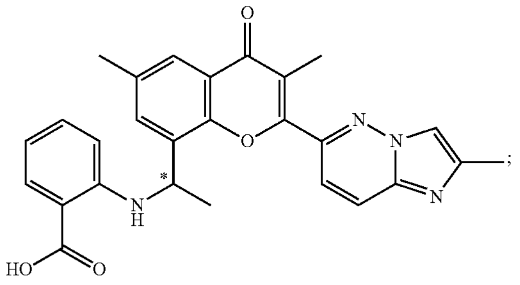

or pharmaceutically acceptable salt thereof. In yet a further embodiment, the bond at the * position is

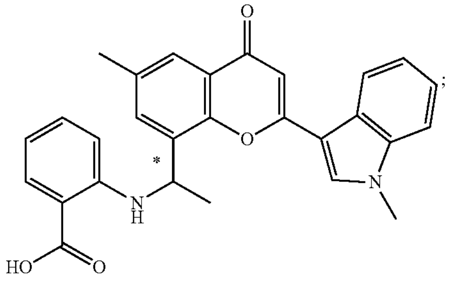 [SMILES: Cc1cc(C(C)Nc2ccccc2C(=O)O)c2oc(-c3cn(C)c4ccccc34)cc(=O)c2c1]

In yet a further embodiment, the bond at the * position is

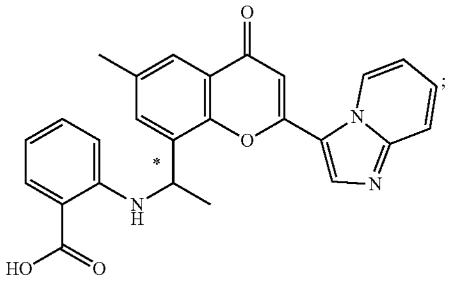 [SMILES: Cc1cc(C(C)Nc2ccccc2C(=O)O)c2oc(-c3cnc4ccccn34)cc(=O)c2c1]

A further embodiment is a compound of Formula

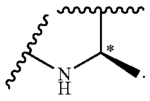 [SMILES: *N[C@@H](*)C]

or pharmaceutically acceptable salt thereof. In yet a further embodiment, the bond at the * position is

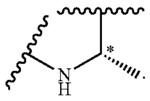 [SMILES: *N[C@H](*)C]

In yet a further embodiment, the bond at the * position is

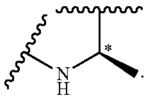 [SMILES: *N[C@@H](*)C]

A further embodiment is a compound of Formula

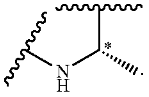 [SMILES: *N[C@H](*)C]

or pharmaceutically acceptable salt thereof. In yet a further embodiment, the bond at the * position is

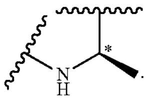 [SMILES: *N[C@@H](*)C]

In yet a further embodiment, the bond at the * position is

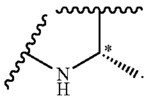 [SMILES: *N[C@H](*)C]

A further embodiment is a compound of Formula

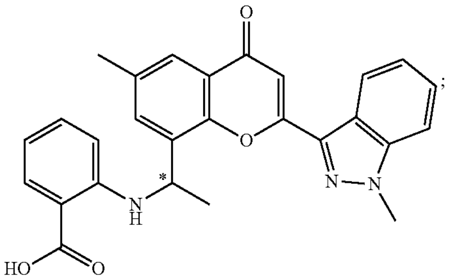 [SMILES: Cc1cc(C(C)Nc2ccccc2C(=O)O)c2oc(-c3nn(C)c4ccccc34)cc(=O)c2c1]

or pharmaceutically acceptable salt thereof. In yet a further embodiment, the bond at the * position is

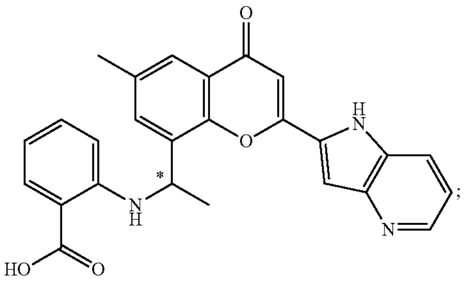 [SMILES: Cc1cc(C(C)Nc2ccccc2C(=O)O)c2oc(-c3cc4ncccc4[nH]3)cc(=O)c2c1]

In yet a further embodiment, the bond at the * position is

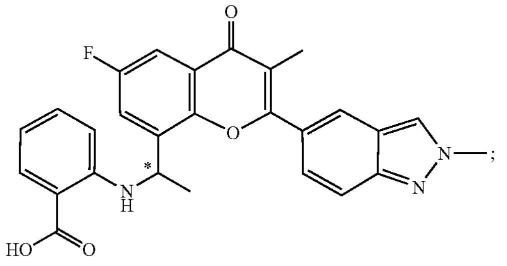 [SMILES: Cc1c(-c2ccc3nn(C)cc3c2)oc2c(C(C)Nc3ccccc3C(=O)O)cc(F)cc2c1=O]

A further embodiment is a compound of Formula

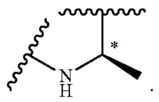

or pharmaceutically acceptable salt thereof. In yet a further embodiment, the bond at the * position is

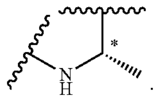

In yet a further embodiment, the bond at the * position is

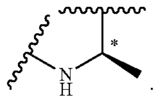 [SMILES: *N[C@@H](*)C]

A further embodiment is a compound of Formula

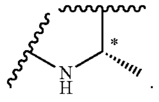

or pharmaceutically acceptable salt thereof. In yet a further embodiment, the bond at the * position is

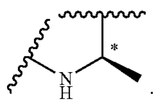

In yet a further embodiment, the bond at the * position is

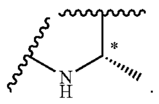

A further embodiment is a compound of Formula

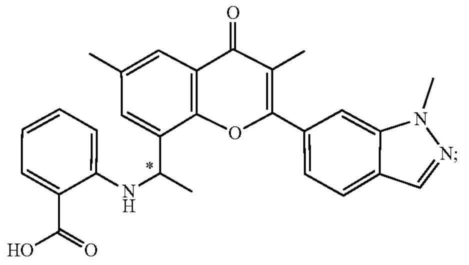 [SMILES: Cc1cc(C(C)Nc2ccccc2C(=O)O)c2oc(-c3ccc4cnn(C)c4c3)c(C)c(=O)c2c1]

or pharmaceutically acceptable salt thereof. In yet a further embodiment, the bond at the * position is

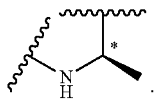 [SMILES: *N[C@@H](*)C]

In yet a further embodiment, the bond at the * position is

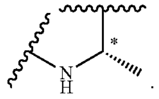

A further embodiment is a compound of Formula

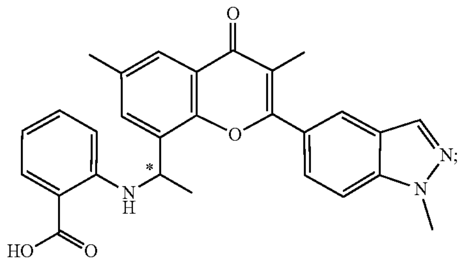 [SMILES: Cc1cc(C(C)Nc2ccccc2C(=O)O)c2oc(-c3ccc4c(cnn4C)c3)c(C)c(=O)c2c1]

or pharmaceutically acceptable salt thereof. In yet a further embodiment, the bond at the * position is

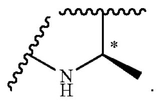 [SMILES: *N[C@@H](*)C]

In yet a further embodiment, the bond at the * position is

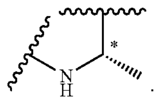

A further embodiment is a compound of Formula

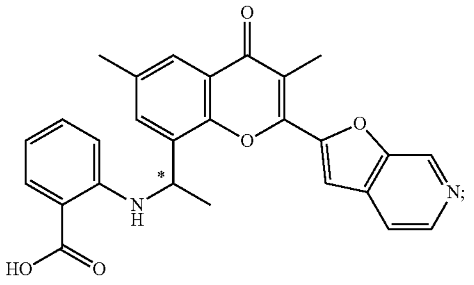 [SMILES: Cc1cc(C(C)Nc2ccccc2C(=O)O)c2oc(-c3cc4ccncc4o3)c(C)c(=O)c2c1]

or pharmaceutically acceptable salt thereof. In yet a further embodiment, the bond at the * position is

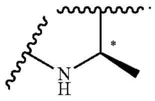 [SMILES: *N[C@@H](*)C]

In yet a further embodiment, the bond at the * position is

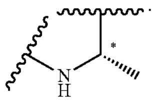

A further embodiment is a compound of Formula

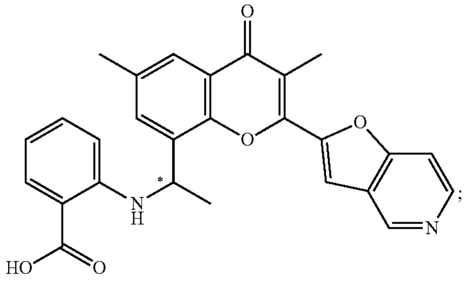 [SMILES: Cc1cc(C(C)Nc2ccccc2C(=O)O)c2oc(-c3cc4cnccc4o3)c(C)c(=O)c2c1]

or pharmaceutically acceptable salt thereof. In yet a further embodiment, the bond at the * position is

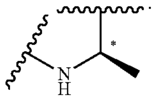

In yet a further embodiment, the bond at the * position is

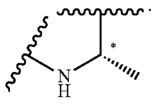

A further embodiment is a compound of Formula

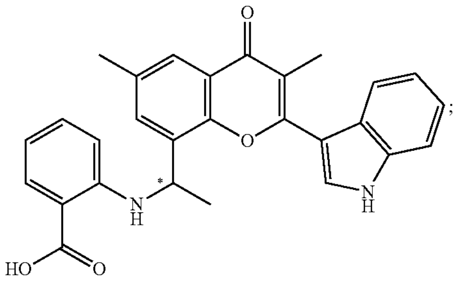 [SMILES: Cc1cc(C(C)Nc2ccccc2C(=O)O)c2oc(-c3c[nH]c4ccccc34)c(C)c(=O)c2c1]

or pharmaceutically acceptable salt thereof. In yet a further embodiment, the bond at the * position is

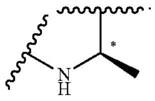

In yet a further embodiment, the bond at the * position is

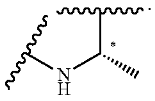

A further embodiment is a compound of Formula

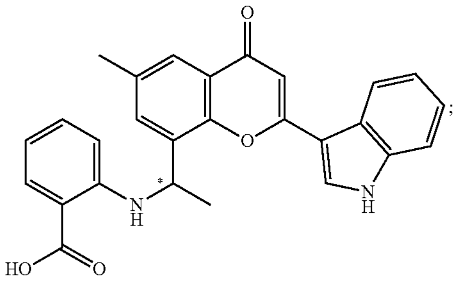 [SMILES: Cc1cc(C(C)Nc2ccccc2C(=O)O)c2oc(-c3c[nH]c4ccccc34)cc(=O)c2c1]

or pharmaceutically acceptable salt thereof. In yet a further embodiment, the bond at the * position is

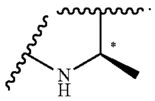 [SMILES: *N[C@@H](*)C]

In yet a further embodiment, the bond at the * position is

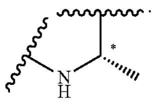

A further embodiment is a compound of Formula

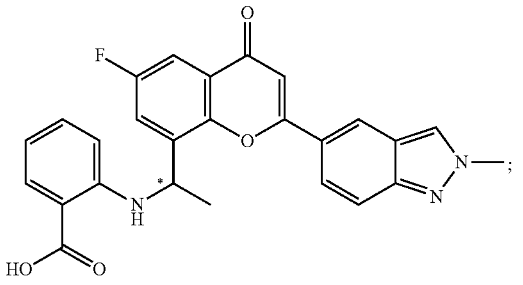

or pharmaceutically acceptable salt thereof. In yet a further embodiment, the bond at the position is

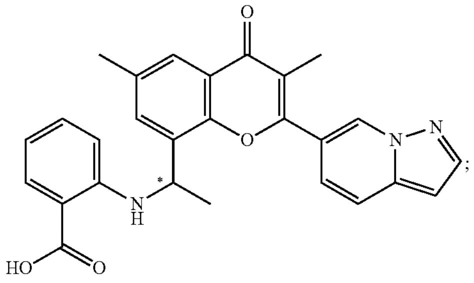 [SMILES: Cc1cc(C(C)Nc2ccccc2C(=O)O)c2oc(-c3ccc4ccnn4c3)c(C)c(=O)c2c1]

In yet a further embodiment, the bond at the * position is

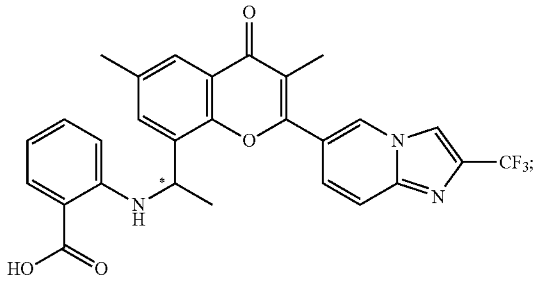 [SMILES: Cc1cc(C(C)Nc2ccccc2C(=O)O)c2oc(-c3ccc4nc(C(F)(F)F)cn4c3)c(C)c(=O)c2c1]

A further embodiment is a compound of Formula

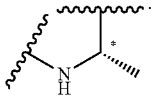

or pharmaceutically acceptable salt thereof. In yet a further embodiment, the bond at the * position is

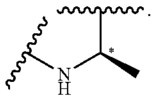 [SMILES: *N[C@@H](*)C]

In yet a further embodiment, the bond at the * position is

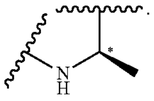 [SMILES: *N[C@@H](*)C]

A further embodiment is a compound of Formula

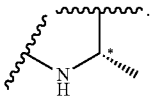

or pharmaceutically acceptable salt thereof. In yet a further embodiment, the bond at the * position is

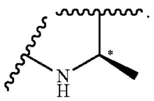 [SMILES: *N[C@@H](*)C]

In yet a further embodiment, the bond at the * position is

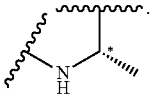

A further embodiment is a compound of Formula

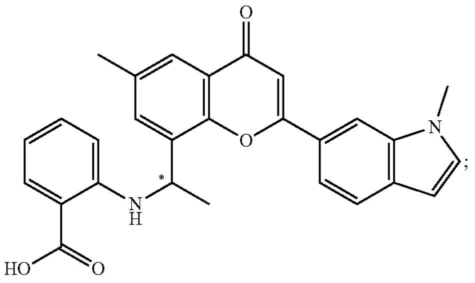 [SMILES: Cc1cc(C(C)Nc2ccccc2C(=O)O)c2oc(-c3ccc4ccn(C)c4c3)cc(=O)c2c1]

or pharmaceutically acceptable salt thereof. In yet a further embodiment, the bond at the * position is

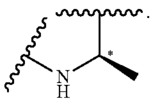 [SMILES: *N[C@@H](*)C]

In yet a further embodiment, the bond at the * position is

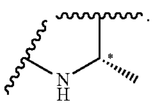

A further embodiment is a compound of Formula

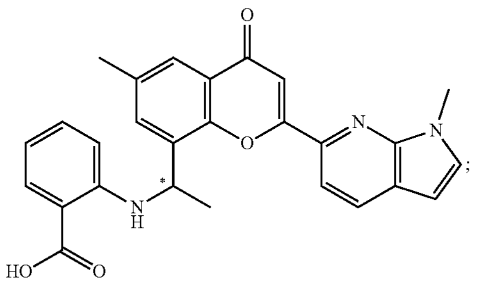 [SMILES: Cc1cc(C(C)Nc2ccccc2C(=O)O)c2oc(-c3ccc4ccn(C)c4n3)cc(=O)c2c1]

or pharmaceutically acceptable salt thereof. In yet a further embodiment, the bond at the * position is

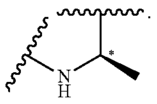 [SMILES: *N[C@@H](*)C]

In yet a further embodiment, the bond at the * position is

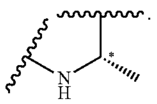

A further embodiment is a compound of Formula

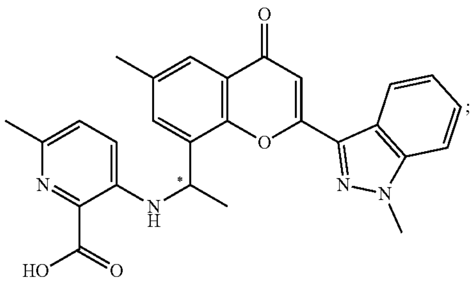 [SMILES: Cc1cc(C(C)Nc2ccc(C)nc2C(=O)O)c2oc(-c3nn(C)c4ccccc34)cc(=O)c2c1]

or pharmaceutically acceptable salt thereof. In yet a further embodiment, the bond at the * position is

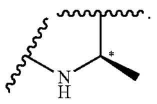 [SMILES: *N[C@@H](*)C]

In yet a further embodiment, the bond at the * position is

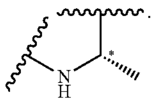

A further embodiment is a compound of Formula

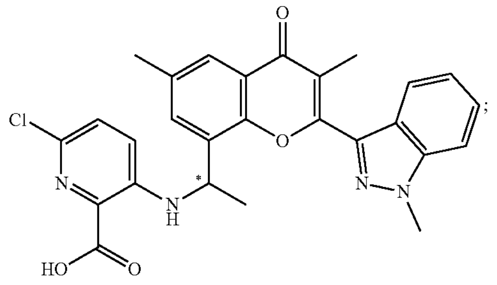 [SMILES: Cc1cc(C(C)Nc2ccc(Cl)nc2C(=O)O)c2oc(-c3nn(C)c4ccccc34)c(C)c(=O)c2c1]

or pharmaceutically acceptable salt thereof. In yet a further embodiment, the bond at the * position is

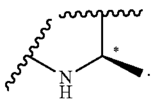 [SMILES: *N[C@@H](*)C]

In yet a further embodiment, the bond at the * position is

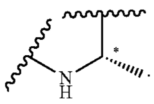

A further embodiment is a compound of Formula

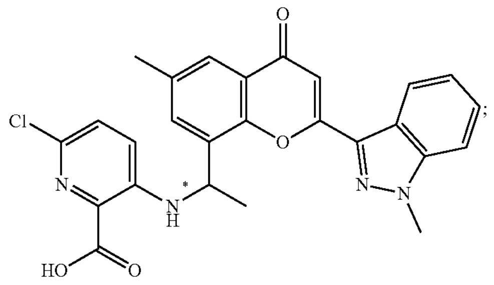 [SMILES: Cc1cc(C(C)Nc2ccc(Cl)nc2C(=O)O)c2oc(-c3nn(C)c4ccccc34)cc(=O)c2c1]

or pharmaceutically acceptable salt thereof. In yet a further embodiment, the bond at the * position is

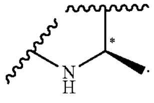 [SMILES: *N[C@@H](*)C]

In yet a further embodiment, the bond at the * position is

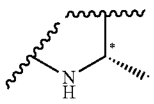 [SMILES: *N[C@H](*)C]

A further embodiment is a compound of Formula

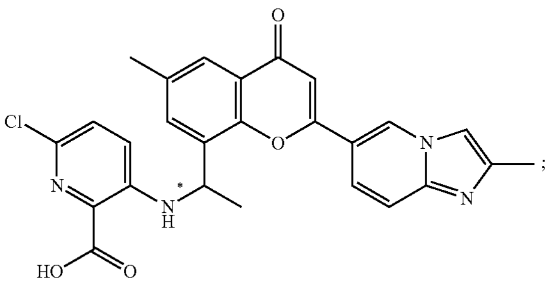 [SMILES: Cc1cc(C(C)Nc2ccc(Cl)nc2C(=O)O)c2oc(-c3ccc4nc(C)cn4c3)cc(=O)c2c1]

or pharmaceutically acceptable salt thereof. In yet a further embodiment, the bond at the * position is

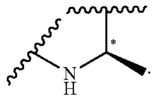 [SMILES: *N[C@@H](*)C]

In yet a further embodiment, the bond at the * position is

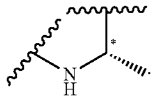

A further embodiment is a compound of Formula

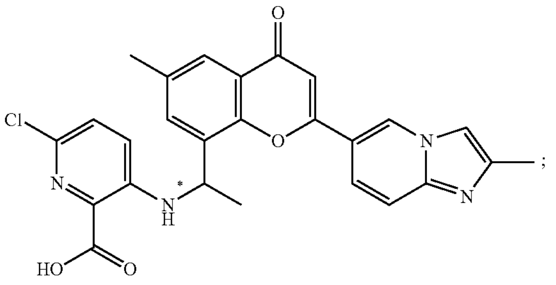 [SMILES: Cc1cc(C(C)Nc2ccc(Cl)nc2C(=O)O)c2oc(-c3ccc4nc(C)cn4c3)cc(=O)c2c1]

or pharmaceutically acceptable salt thereof. In yet a further embodiment, the bond at the * position is

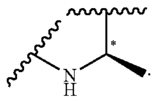 [SMILES: *N[C@@H](*)C]

In yet a further embodiment, the bond at the * position is

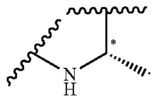

A further embodiment is a compound of Formula

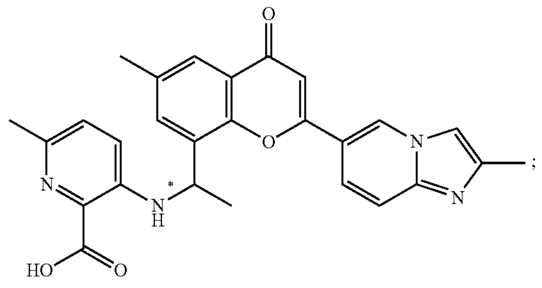

or pharmaceutically acceptable salt thereof. In yet a further embodiment, the bond at the * position is

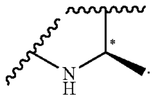 [SMILES: *N[C@@H](*)C]

In yet a further embodiment, the bond at the * position is

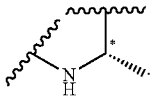 [SMILES: *N[C@H](*)C]

A further embodiment is a compound of Formula

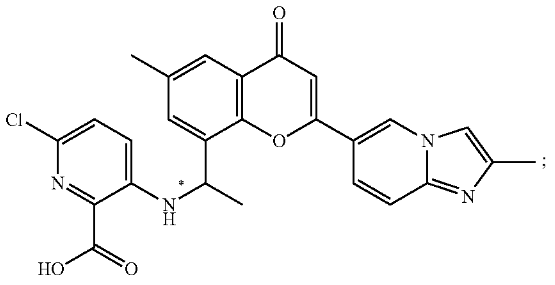 [SMILES: Cc1cc(C(C)Nc2ccc(Cl)nc2C(=O)O)c2oc(-c3ccc4nc(C)cn4c3)cc(=O)c2c1]

or pharmaceutically acceptable salt thereof. In yet a further embodiment, the bond at the * position is

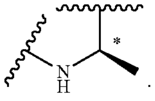 [SMILES: *N[C@@H](*)C]

In yet a further embodiment, the bond at the * position is

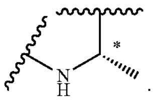

A further embodiment is a compound of Formula

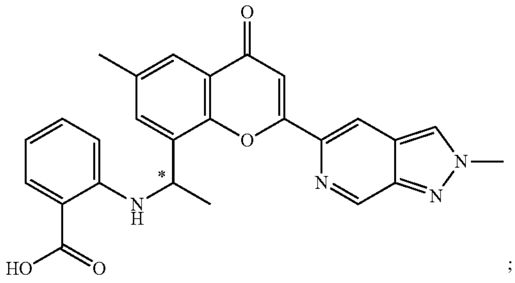 [SMILES: Cc1cc(C(C)Nc2ccccc2C(=O)O)c2oc(-c3cc4cn(C)nc4cn3)cc(=O)c2c1]

;

or pharmaceutically acceptable salt thereof. In yet a further embodiment, the bond at the position is

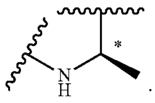 [SMILES: *N[C@@H](*)C]

.

In yet a further embodiment, the bond at the * position is

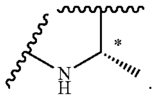 [SMILES: *N[C@H](*)C]

.

A further embodiment is a compound of Formula

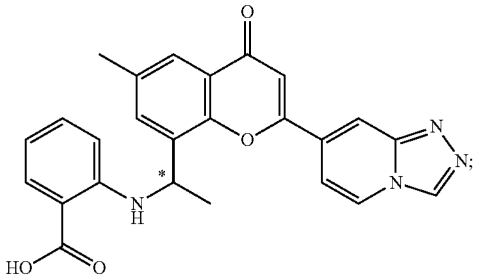 [SMILES: Cc1cc(C(C)Nc2ccccc2C(=O)O)c2oc(-c3ccn4cnnc4c3)cc(=O)c2c1]

or pharmaceutically acceptable salt thereof. In yet a further embodiment, the bond at the position is

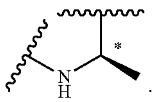 [SMILES: *N[C@@H](*)C]

.

In yet a further embodiment, the bond at the * position is

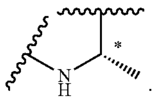

.

A further embodiment is a compound of Formula

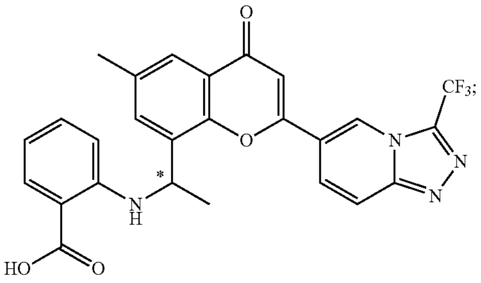 [SMILES: Cc1cc(C(C)Nc2ccccc2C(=O)O)c2oc(-c3ccc4nnc(C(F)(F)F)n4c3)cc(=O)c2c1]

or pharmaceutically acceptable salt thereof. In yet a further embodiment, the bond at the * position is

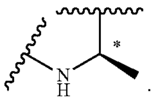 [SMILES: *N[C@@H](*)C]

.

In yet a further embodiment, the bond at the * position is

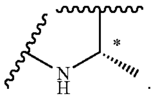 [SMILES: *N[C@H](*)C]

.

A further embodiment is a compound of Formula

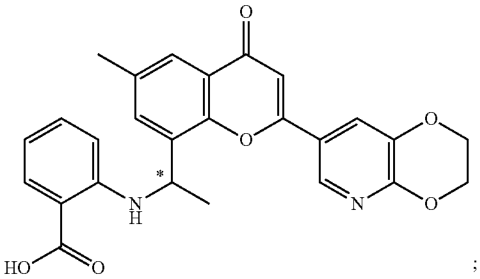 [SMILES: Cc1cc(C(C)Nc2ccccc2C(=O)O)c2oc(-c3cnc4c(c3)OCCO4)cc(=O)c2c1]

;

or pharmaceutically acceptable salt thereof. In yet a further embodiment, the bond at the position is

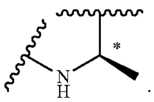 [SMILES: *N[C@@H](*)C]

.

In yet a further embodiment, the bond at the * position is

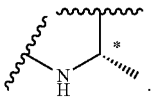

.

A further embodiment is a compound of Formula

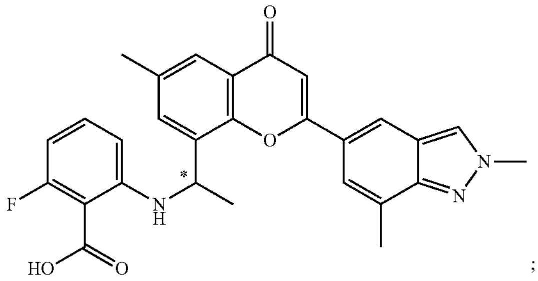 [SMILES: Cc1cc(C(C)Nc2cccc(F)c2C(=O)O)c2oc(-c3cc(C)c4nn(C)cc4c3)cc(=O)c2c1]

;

or pharmaceutically acceptable salt thereof. In yet a further embodiment, the bond at the * position is

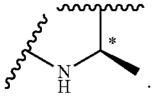 [SMILES: *N[C@@H](*)C]

.

In yet a further embodiment, the bond at the * position is

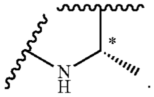 [SMILES: *N[C@H](*)C]

.

A further embodiment is a compound of Formula

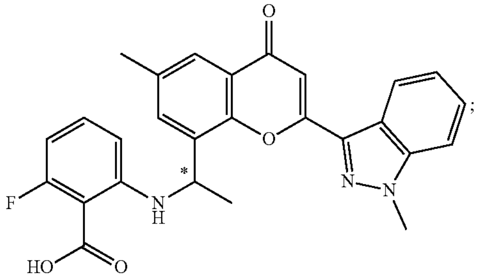 [SMILES: Cc1cc(C(C)Nc2cccc(F)c2C(=O)O)c2oc(-c3nn(C)c4ccccc34)cc(=O)c2c1]

;

or pharmaceutically acceptable salt thereof. In yet a further embodiment, the bond at the * position is

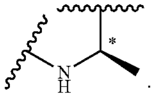 [SMILES: *N[C@@H](*)C]

.

In yet a further embodiment, the bond at the * position is

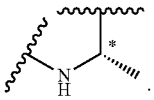 [SMILES: *N[C@H](*)C]

.

A further embodiment is a compound of Formula

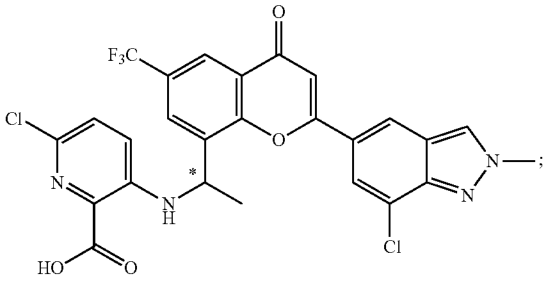 [SMILES: CC(Nc1ccc(Cl)nc1C(=O)O)c1cc(C(F)(F)F)cc2c(=O)cc(-c3cc(Cl)c4nn(C)cc4c3)oc12]

;

or pharmaceutically acceptable salt thereof. In yet a further embodiment, the bond at the * position is

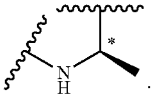 [SMILES: *N[C@@H](*)C]

.

In yet a further embodiment, the bond at the * position is

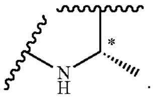 [SMILES: *N[C@H](*)C]

.

A further embodiment is a compound of Formula

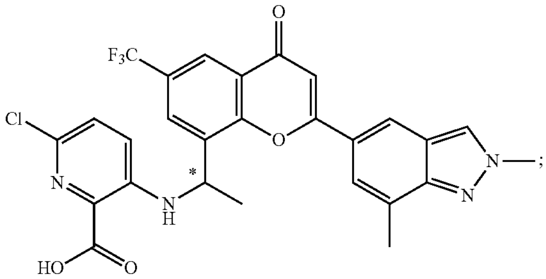 [SMILES: Cc1cc(-c2cc(=O)c3cc(C(F)(F)F)cc(C(C)Nc4ccc(Cl)nc4C(=O)O)c3o2)cc2cn(C)nc12]

;

or pharmaceutically acceptable salt thereof. In yet a further embodiment, the bond at the position is

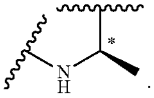 [SMILES: *N[C@@H](*)C]

.

In yet a further embodiment, the bond at the * position is

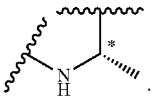

.

A further embodiment is a compound of Formula

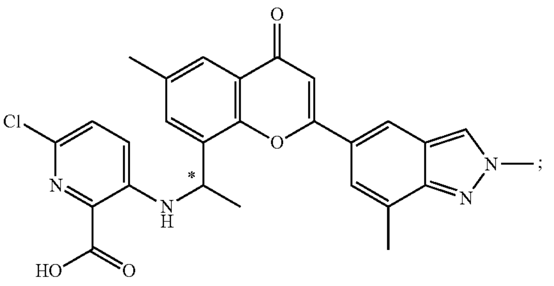 [SMILES: Cc1cc(C(C)Nc2ccc(Cl)nc2C(=O)O)c2oc(-c3cc(C)c4nn(C)cc4c3)cc(=O)c2c1]

or pharmaceutically acceptable salt thereof. In yet a further embodiment, the bond at the * position is

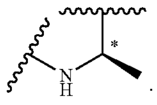 [SMILES: *N[C@@H](*)C]

In yet a further embodiment, the bond at the * position is

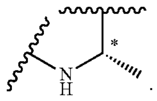 [SMILES: *N[C@H](*)C]

A further embodiment is a compound of Formula

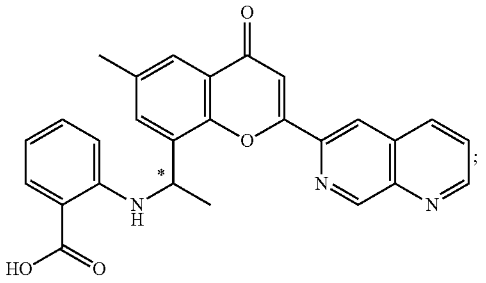 [SMILES: Cc1cc(C(C)Nc2ccccc2C(=O)O)c2oc(-c3cc4cccnc4cn3)cc(=O)c2c1]

or pharmaceutically acceptable salt thereof. In yet a further embodiment, the bond at the * position is

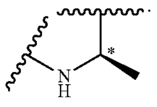 [SMILES: *N[C@@H](*)C]

In yet a further embodiment, the bond at the * position is

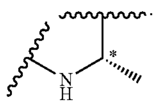

A further embodiment is a compound of Formula

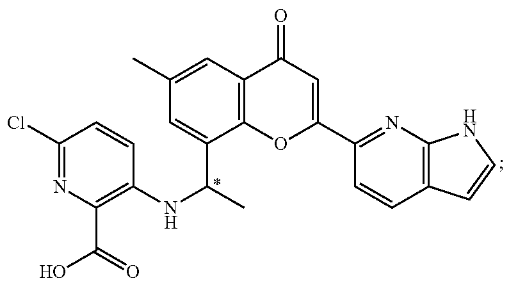 [SMILES: Cc1cc(C(C)Nc2ccc(Cl)nc2C(=O)O)c2oc(-c3ccc4cc[nH]c4n3)cc(=O)c2c1]

or pharmaceutically acceptable salt thereof. In yet a further embodiment, the bond at the * position is

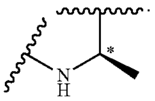 [SMILES: *N[C@@H](*)C]

In yet a further embodiment, the bond at the * position is

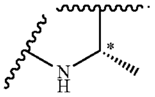

A further embodiment is a compound of Formula

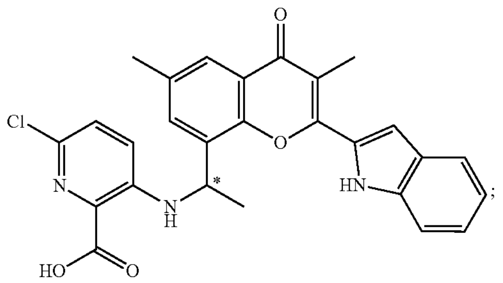 [SMILES: Cc1cc(C(C)Nc2ccc(Cl)nc2C(=O)O)c2oc(-c3cc4ccccc4[nH]3)c(C)c(=O)c2c1]

or pharmaceutically acceptable salt thereof. In yet a further embodiment, the bond at the position is

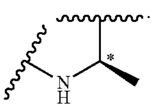 [SMILES: *N[C@@H](*)C]

In yet a further embodiment, the bond at the * position is

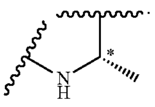

A further embodiment is a compound of Formula

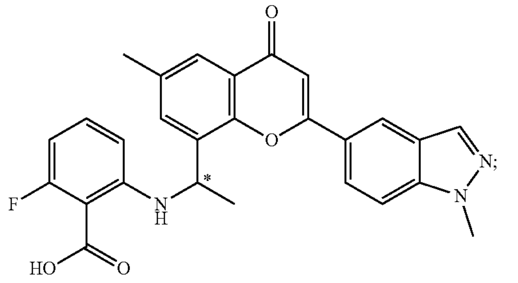 [SMILES: Cc1cc(C(C)Nc2cccc(F)c2C(=O)O)c2oc(-c3ccc4c(cnn4C)c3)cc(=O)c2c1]

or pharmaceutically acceptable salt thereof. In yet a further embodiment, the bond at the * position is

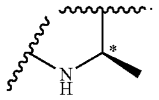 [SMILES: *N[C@@H](*)C]

In yet a further embodiment, the bond at the * position is

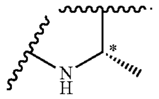

A further embodiment is a compound of Formula

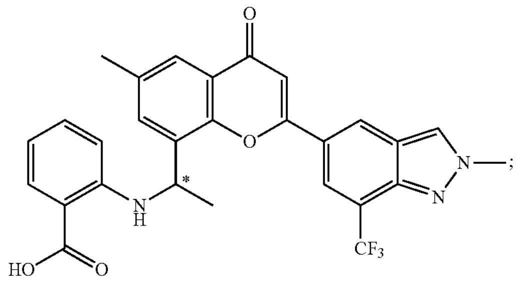

or pharmaceutically acceptable salt thereof. In yet a further embodiment, the bond at the * position is

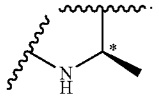 [SMILES: *N[C@@H](*)C]

In yet a further embodiment, the bond at the * position is

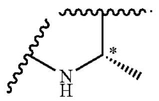 [SMILES: *N[C@H](*)C]

A further embodiment is a compound of Formula

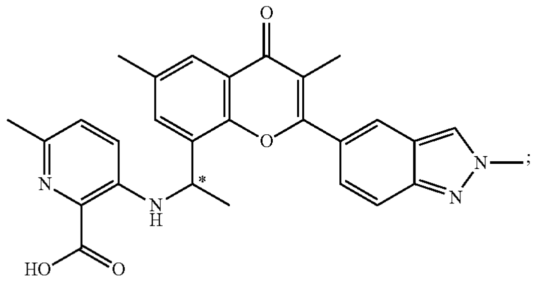

or pharmaceutically acceptable salt thereof. In yet a further embodiment, the bond at the * position is

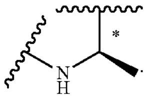 [SMILES: *N[C@@H](*)C]

In yet a further embodiment, the bond at the * position is

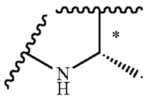

A further embodiment is a compound of Formula

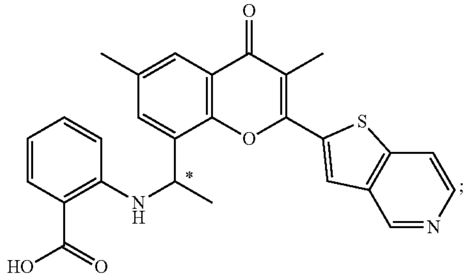 [SMILES: Cc1cc(C(C)Nc2ccccc2C(=O)O)c2oc(-c3cc4cnccc4s3)c(C)c(=O)c2c1]

or pharmaceutically acceptable salt thereof. In yet a further embodiment, the bond at the * position is

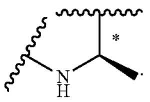 [SMILES: *N[C@@H](*)C]

In yet a further embodiment, the bond at the * position is

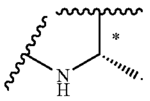

A further embodiment is a compound of Formula

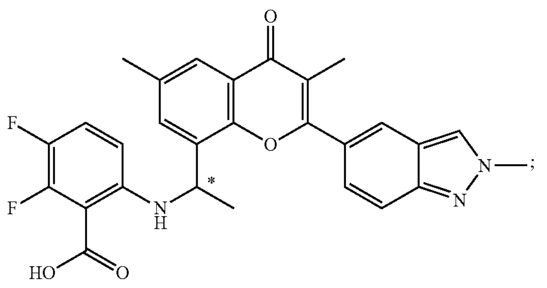 [SMILES: Cc1cc(C(C)Nc2ccc(F)c(F)c2C(=O)O)c2oc(-c3ccc4nn(C)cc4c3)c(C)c(=O)c2c1]

or pharmaceutically acceptable salt thereof. In yet a further embodiment, the bond at the * position is

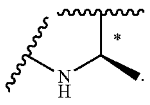 [SMILES: *N[C@@H](*)C]

In yet a further embodiment, the bond at the * position is

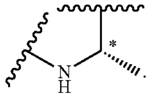 [SMILES: *N[C@H](*)C]

A further embodiment is a compound of Formula

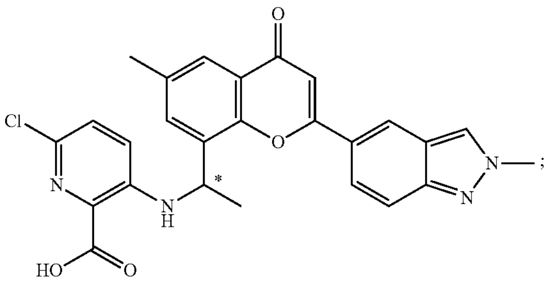 [SMILES: Cc1cc(C(C)Nc2ccc(Cl)nc2C(=O)O)c2oc(-c3ccc4nn(C)cc4c3)cc(=O)c2c1]

or pharmaceutically acceptable salt thereof. In yet a further embodiment, the bond at the * position is

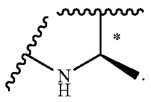 [SMILES: *N[C@@H](*)C]

In yet a further embodiment, the bond at the * position is

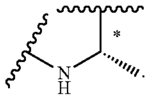 [SMILES: *N[C@H](*)C]

A further embodiment is a compound of Formula

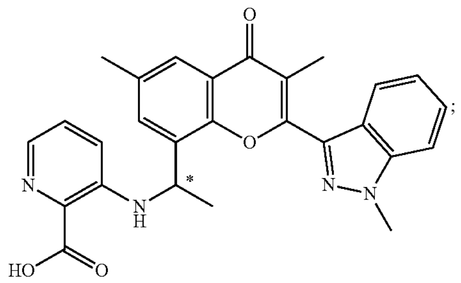

or pharmaceutically acceptable salt thereof. In yet a further embodiment, the bond at the * position is

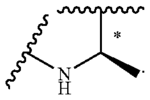

In yet a further embodiment, the bond at the * position is

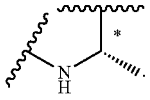

A further embodiment is a compound of Formula

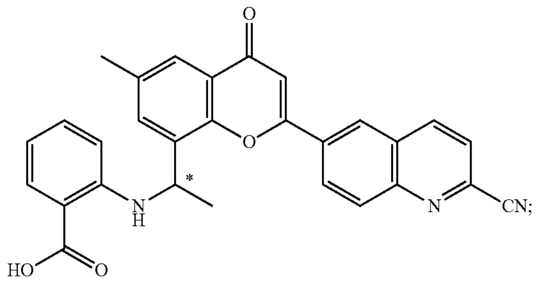 [SMILES: Cc1cc(C(C)Nc2ccccc2C(=O)O)c2oc(-c3ccc4nc(C#N)ccc4c3)cc(=O)c2c1]

or pharmaceutically acceptable salt thereof. In yet a further embodiment, the bond at the * position is

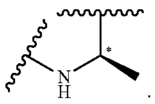 [SMILES: *N[C@@H](*)C]

In yet a further embodiment, the bond at the * position is

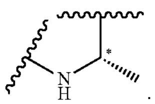 [SMILES: *N[C@H](*)C]

A further embodiment is a compound of Formula

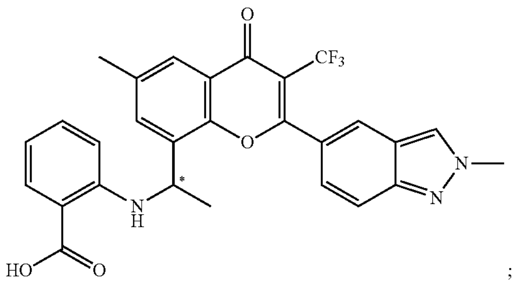 [SMILES: Cc1cc(C(C)Nc2ccccc2C(=O)O)c2oc(-c3ccc4nn(C)cc4c3)c(C(F)(F)F)c(=O)c2c1]

;

or pharmaceutically acceptable salt thereof. In yet a further embodiment, the bond at the position is

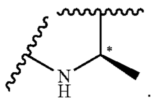 [SMILES: *N[C@@H](*)C]

.

In yet a further embodiment, the bond at the * position is

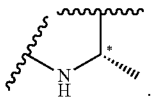 [SMILES: *N[C@H](*)C]

.

A further embodiment is a compound of Formula

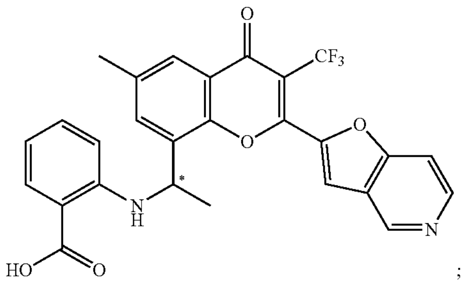 [SMILES: Cc1cc(C(C)Nc2ccccc2C(=O)O)c2oc(-c3cc4cnccc4o3)c(C(F)(F)F)c(=O)c2c1]

;

or pharmaceutically acceptable salt thereof. In yet a further embodiment, the bond at the * position is

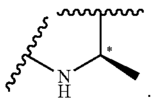 [SMILES: *N[C@@H](*)C]

.

In yet a further embodiment, the bond at the * position is

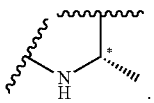 [SMILES: *N[C@H](*)C]

.

A further embodiment is a compound of Formula

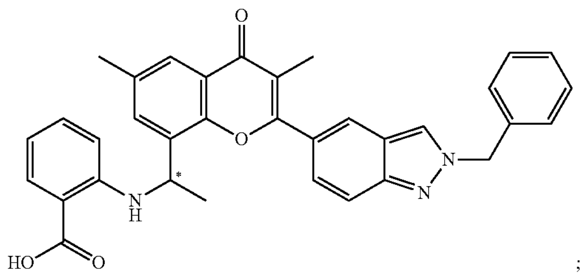 [SMILES: Cc1cc(C(C)Nc2ccccc2C(=O)O)c2oc(-c3ccc4nn(Cc5ccccc5)cc4c3)c(C)c(=O)c2c1]

;

or pharmaceutically acceptable salt thereof. In yet a further embodiment, the bond at the * position is

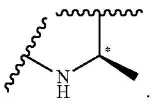 [SMILES: *N[C@@H](*)C]

.

In yet a further embodiment, the bond at the * position is

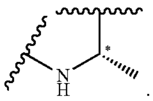 [SMILES: *N[C@H](*)C]

.

A further embodiment is a compound of Formula

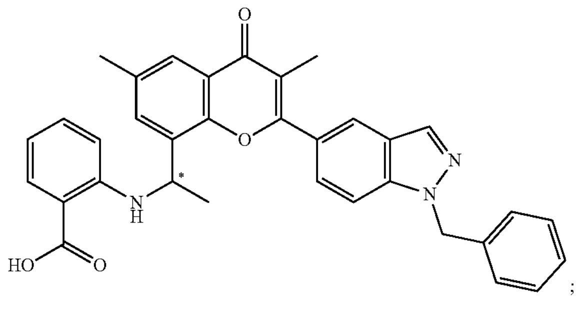 [SMILES: Cc1cc(C(C)Nc2ccccc2C(=O)O)c2oc(-c3ccc4c(cnn4Cc4ccccc4)c3)c(C)c(=O)c2c1]

;

or pharmaceutically acceptable salt thereof. In yet a further embodiment, the bond at the * position is

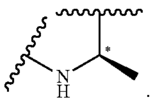 [SMILES: *N[C@@H](*)C]

.

In yet a further embodiment, the bond at the * position is

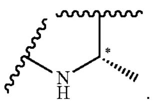 [SMILES: *N[C@H](*)C]

.

A further embodiment is a compound of Formula

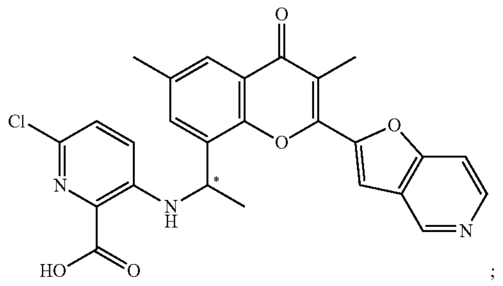 [SMILES: Cc1cc(C(C)Nc2ccc(Cl)nc2C(=O)O)c2oc(-c3cc4cnccc4o3)c(C)c(=O)c2c1]

;

or pharmaceutically acceptable salt thereof. In yet a further embodiment, the bond at the * position is

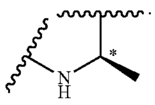 [SMILES: *N[C@@H](*)C]

In yet a further embodiment, the bond at the * position is

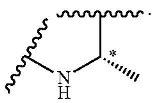

A further embodiment is a compound of Formula

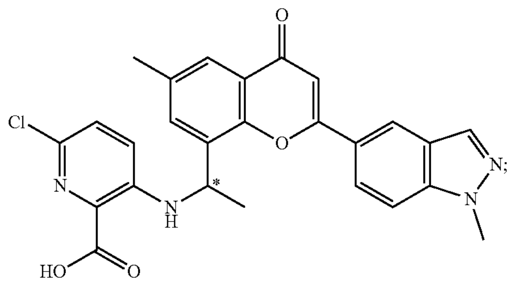 [SMILES: Cc1cc(C(C)Nc2ccc(Cl)nc2C(=O)O)c2oc(-c3ccc4c(cnn4C)c3)cc(=O)c2c1]

or pharmaceutically acceptable salt thereof. In yet a further embodiment, the bond at the * position is

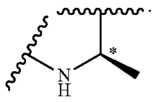

In yet a further embodiment, the bond at the * position is

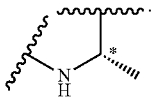

A further embodiment is a compound of Formula

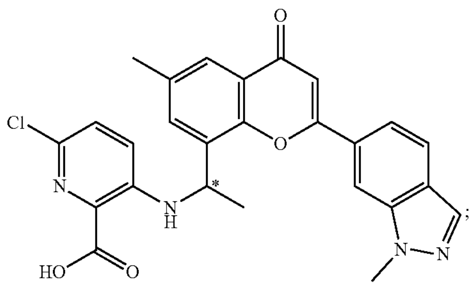 [SMILES: Cc1cc(C(C)Nc2ccc(Cl)nc2C(=O)O)c2oc(-c3ccc4cnn(C)c4c3)cc(=O)c2c1]

or pharmaceutically acceptable salt thereof. In yet a further embodiment, the bond at the position is

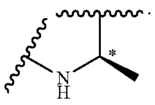

In yet a further embodiment, the bond at the * position is

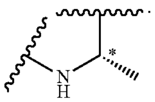

A further embodiment is a compound of Formula

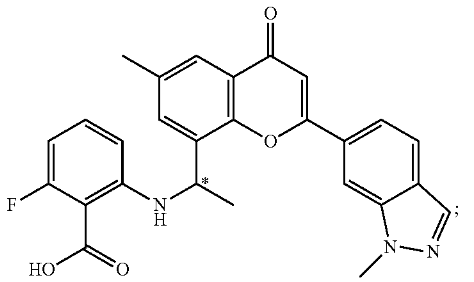 [SMILES: Cc1cc(C(C)Nc2cccc(F)c2C(=O)O)c2oc(-c3ccc4cnn(C)c4c3)cc(=O)c2c1]

or pharmaceutically acceptable salt thereof. In yet a further embodiment, the bond at the * position is

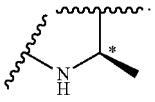 [SMILES: *N[C@@H](*)C]

In yet a further embodiment, the bond at the * position is

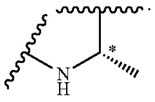

A further embodiment is a compound of Formula

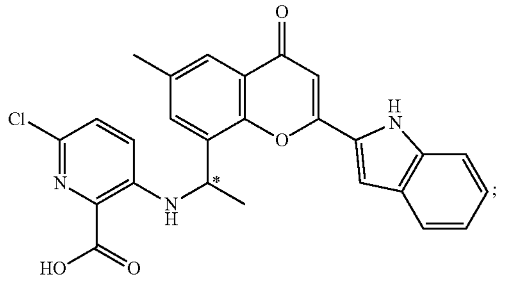

or pharmaceutically acceptable salt thereof. In yet a further embodiment, the bond at the * position is

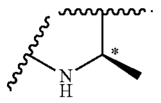 [SMILES: *N[C@@H](*)C]

In yet a further embodiment, the bond at the * position is

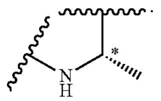

A further embodiment is a compound of Formula

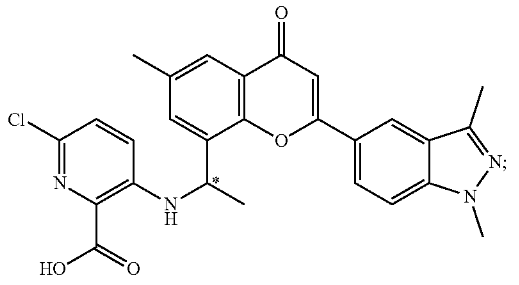 [SMILES: Cc1cc(C(C)Nc2ccc(Cl)nc2C(=O)O)c2oc(-c3ccc4c(c3)c(C)nn4C)cc(=O)c2c1]

or pharmaceutically acceptable salt thereof. In yet a further embodiment, the bond at the position is

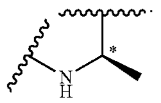

In yet a further embodiment, the bond at the * position is

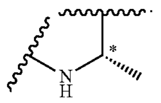

A further embodiment is a compound of Formula

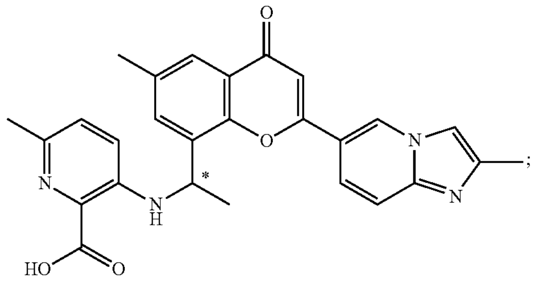

or pharmaceutically acceptable salt thereof. In yet a further embodiment, the bond at the * position is

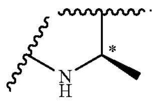

In yet a further embodiment, the bond at the * position is

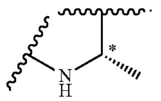 [SMILES: *N[C@H](*)C]

A further embodiment is a compound of Formula

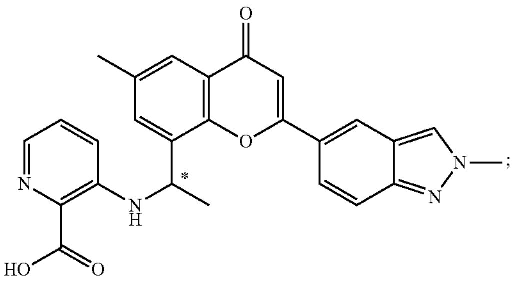

or pharmaceutically acceptable salt thereof. In yet a further embodiment, the bond at the * position is

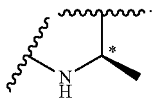

In yet a further embodiment, the bond at the * position is

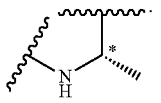

A further embodiment is a compound of Formula

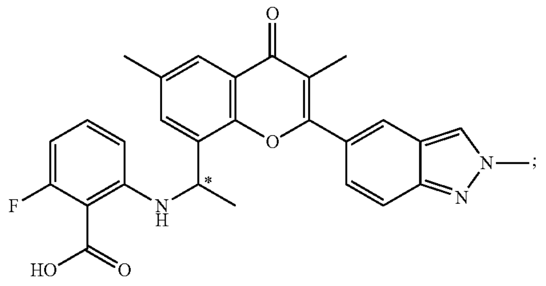 [SMILES: Cc1cc(C(C)Nc2cccc(F)c2C(=O)O)c2oc(-c3ccc4nn(C)cc4c3)c(C)c(=O)c2c1]

or pharmaceutically acceptable salt thereof. In yet a further embodiment, the bond at the position is

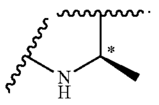 [SMILES: *N[C@@H](*)C]

In yet a further embodiment, the bond at the * position is

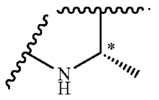

A further embodiment is a compound of Formula

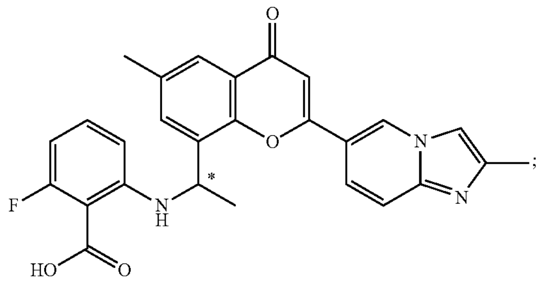 [SMILES: Cc1cc(C(C)Nc2cccc(F)c2C(=O)O)c2oc(-c3ccc4nc(C)cn4c3)cc(=O)c2c1]

or pharmaceutically acceptable salt thereof. In yet a further embodiment, the bond at the * position is

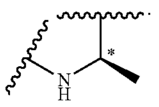

In yet a further embodiment, the bond at the * position is

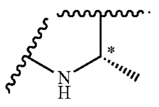

A further embodiment is a compound of Formula

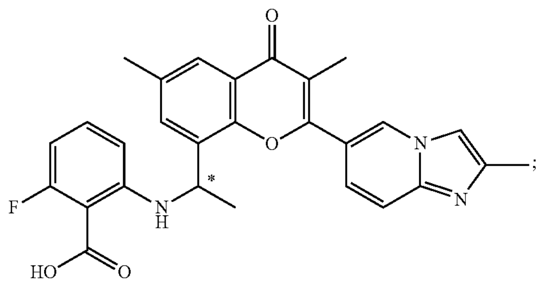 [SMILES: Cc1cc(C(C)Nc2cccc(F)c2C(=O)O)c2oc(-c3ccc4nc(C)cn4c3)c(C)c(=O)c2c1]

or pharmaceutically acceptable salt thereof. In yet a further embodiment, the bond at the * position is

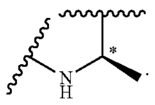 [SMILES: *N[C@@H](*)C]

In yet a further embodiment, the bond at the * position is

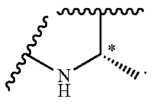

A further embodiment is a compound of Formula

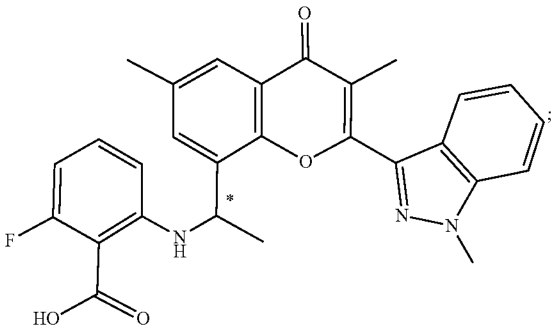 [SMILES: Cc1cc(C(C)Nc2cccc(F)c2C(=O)O)c2oc(-c3nn(C)c4ccccc34)c(C)c(=O)c2c1]

or pharmaceutically acceptable salt thereof. In yet a further embodiment, the bond at the * position is

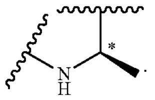 [SMILES: *N[C@@H](*)C]

In yet a further embodiment, the bond at the * position is

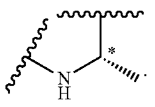

A further embodiment is a compound of Formula

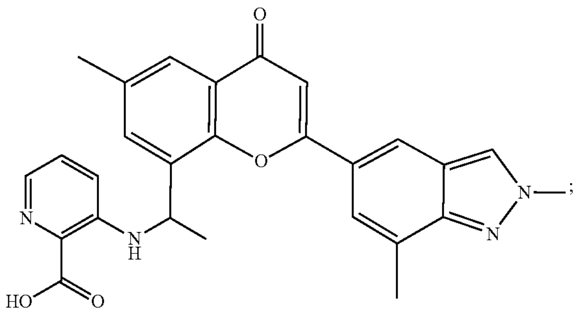 [SMILES: Cc1cc(C(C)Nc2cccnc2C(=O)O)c2oc(-c3cc(C)c4nn(C)cc4c3)cc(=O)c2c1]

or pharmaceutically acceptable salt thereof. In yet a further embodiment, the bond at the * position is

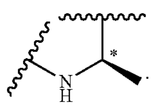 [SMILES: *N[C@@H](*)C]

In yet a further embodiment, the bond at the * position is

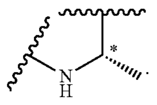 [SMILES: *N[C@H](*)C]

A further embodiment is a compound of Formula

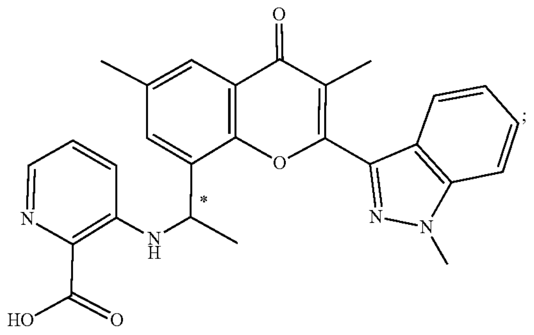 [SMILES: Cc1cc(C(C)Nc2cccnc2C(=O)O)c2oc(-c3nn(C)c4ccccc34)c(C)c(=O)c2c1]

or pharmaceutically acceptable salt thereof. In yet a further embodiment, the bond at the * position is

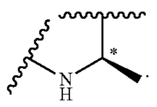 [SMILES: *N[C@@H](*)C]

In yet a further embodiment, the bond at the * position is

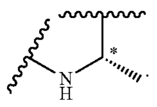 [SMILES: *N[C@H](*)C]

A further embodiment is a compound of Formula

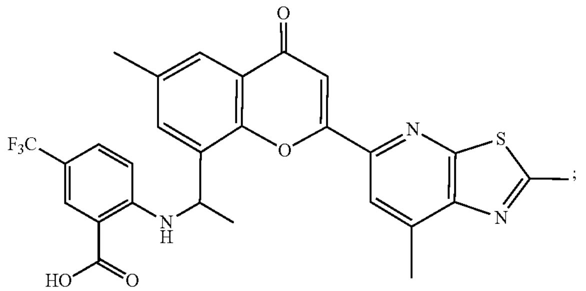 [SMILES: Cc1cc(C(C)Nc2ccc(C(F)(F)F)cc2C(=O)O)c2oc(-c3cc(C)c4nc(C)sc4n3)cc(=O)c2c1]

or pharmaceutically acceptable salt thereof. In yet a further embodiment, the bond at the * position is

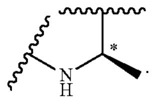 [SMILES: *N[C@@H](*)C]

In yet a further embodiment, the bond at the * position is

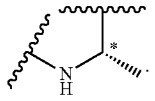 [SMILES: *N[C@H](*)C]

A further embodiment is a compound of Formula

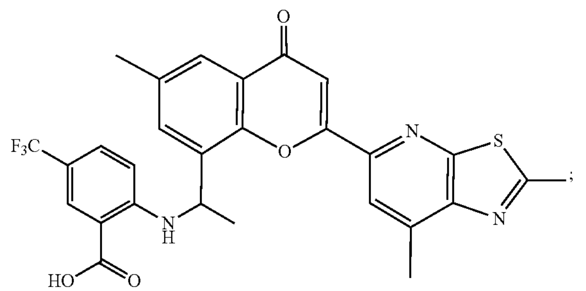 [SMILES: Cc1cc(C(C)Nc2ccc(C(F)(F)F)cc2C(=O)O)c2oc(-c3cc(C)c4nc(C)sc4n3)cc(=O)c2c1]

or pharmaceutically acceptable salt thereof. In yet a further embodiment, the bond at the position is

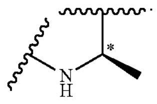 [SMILES: *N[C@@H](*)C]

In yet a further embodiment, the bond at the * position is

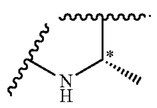 [SMILES: *N[C@H](*)C]

A further embodiment is a compound of Formula

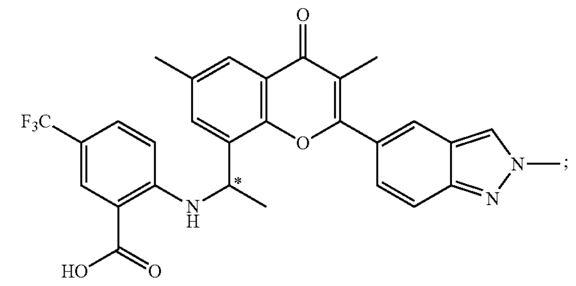 [SMILES: Cc1cc(C(C)Nc2ccc(C(F)(F)F)cc2C(=O)O)c2oc(-c3ccc4nn(C)cc4c3)c(C)c(=O)c2c1]

or pharmaceutically acceptable salt thereof. In yet a further embodiment, the bond at the * position is

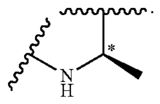 [SMILES: *N[C@@H](*)C]

In yet a further embodiment, the bond at the * position is

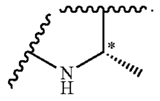

A further embodiment is a compound of Formula

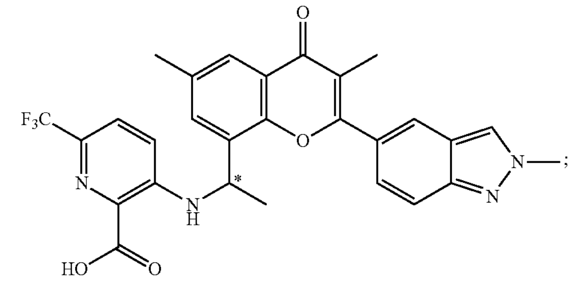 [SMILES: Cc1cc(C(C)Nc2ccc(C(F)(F)F)nc2C(=O)O)c2oc(-c3ccc4nn(C)cc4c3)c(C)c(=O)c2c1]

or pharmaceutically acceptable salt thereof. In yet a further embodiment, the bond at the * position is

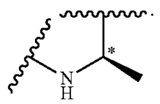 [SMILES: *N[C@@H](*)C]

In yet a further embodiment, the bond at the * position is

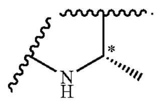 [SMILES: *N[C@H](*)C]

A further embodiment is a compound of Formula

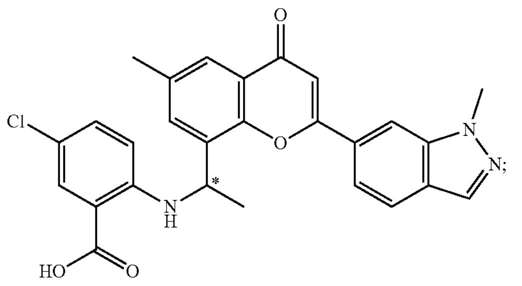 [SMILES: Cc1cc(C(C)Nc2ccc(Cl)cc2C(=O)O)c2oc(-c3ccc4cnn(C)c4c3)cc(=O)c2c1]

or pharmaceutically acceptable salt thereof. In yet a further embodiment, the bond at the * position is

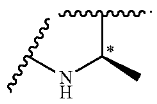 [SMILES: *N[C@@H](*)C]

In yet a further embodiment, the bond at the * position is

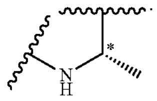 [SMILES: *N[C@H](*)C]

A further embodiment is a compound of Formula

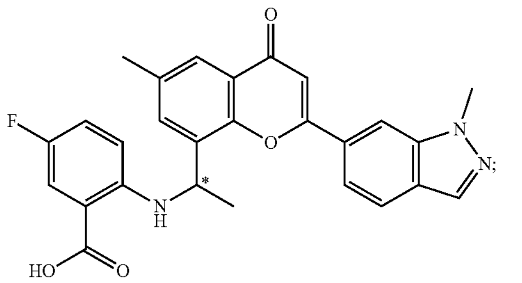 [SMILES: Cc1cc(C(C)Nc2ccc(F)cc2C(=O)O)c2oc(-c3ccc4cnn(C)c4c3)cc(=O)c2c1]

or pharmaceutically acceptable salt thereof. In yet a further embodiment, the bond at the * position is

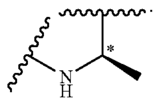 [SMILES: *N[C@@H](*)C]

In yet a further embodiment, the bond at the * position is

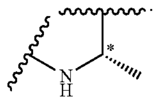

A further embodiment is a compound of Formula

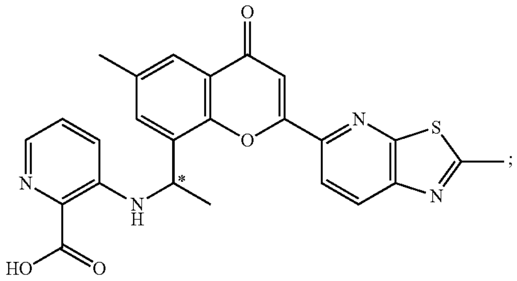

or pharmaceutically acceptable salt thereof. In yet a further embodiment, the bond at the * position is

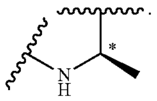 [SMILES: *N[C@@H](*)C]

In yet a further embodiment, the bond at the * position is

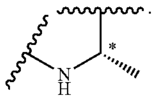

A further embodiment is a compound of Formula

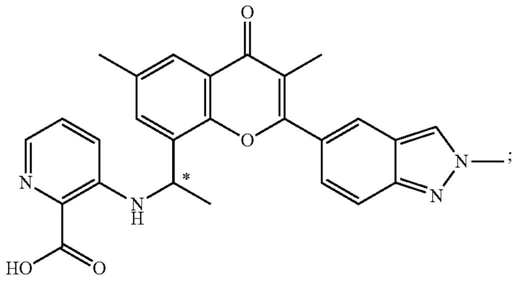 [SMILES: Cc1cc(C(C)Nc2cccnc2C(=O)O)c2oc(-c3ccc4nn(C)cc4c3)c(C)c(=O)c2c1]

or pharmaceutically acceptable salt thereof. In yet a further embodiment, the bond at the position is

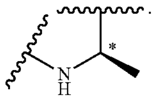 [SMILES: *N[C@@H](*)C]

In yet a further embodiment, the bond at the * position is

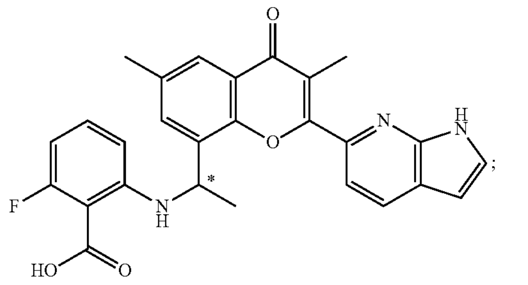 [SMILES: Cc1cc(C(C)Nc2cccc(F)c2C(=O)O)c2oc(-c3ccc4cc[nH]c4n3)c(C)c(=O)c2c1]

A further embodiment is a compound of Formula

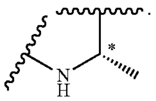

or pharmaceutically acceptable salt thereof. In yet a further embodiment, the bond at the * position is

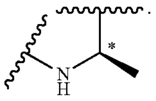 [SMILES: *N[C@@H](*)C]

In yet a further embodiment, the bond at the * position is

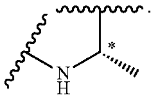

A further embodiment is a compound of Formula

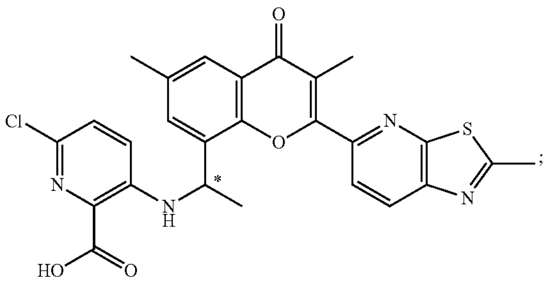 [SMILES: Cc1cc(C(C)Nc2ccc(Cl)nc2C(=O)O)c2oc(-c3ccc4nc(C)sc4n3)c(C)c(=O)c2c1]

or pharmaceutically acceptable salt thereof. In yet a further embodiment, the bond at the position is

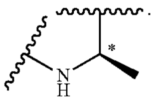

In yet a further embodiment, the bond at the * position is

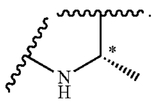

A further embodiment is a compound of Formula

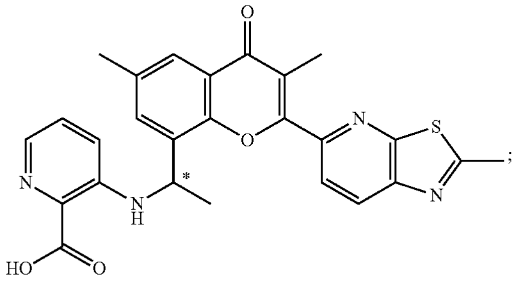 [SMILES: Cc1cc(C(C)Nc2cccnc2C(=O)O)c2oc(-c3ccc4nc(C)sc4n3)c(C)c(=O)c2c1]

or pharmaceutically acceptable salt thereof. In yet a further embodiment, the bond at the * position is

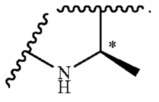 [SMILES: *N[C@@H](*)C]

In yet a further embodiment, the bond at the * position is

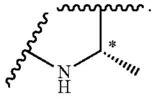

A further embodiment is a compound of Formula

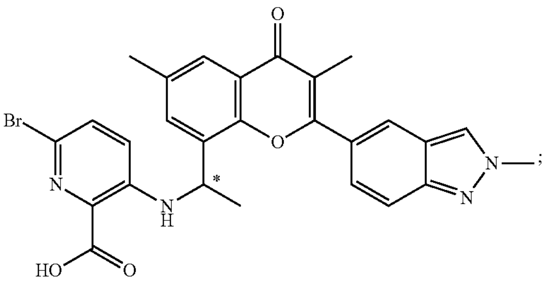 [SMILES: Cc1cc(C(C)Nc2ccc(Br)nc2C(=O)O)c2oc(-c3ccc4nn(C)cc4c3)c(C)c(=O)c2c1]

or pharmaceutically acceptable salt thereof. In yet a further embodiment, the bond at the position is

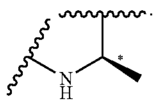 [SMILES: *N[C@@H](*)C]

In yet a further embodiment, the bond at the * position is

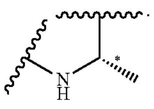 [SMILES: *N[C@H](*)C]

A further embodiment is a compound of Formula

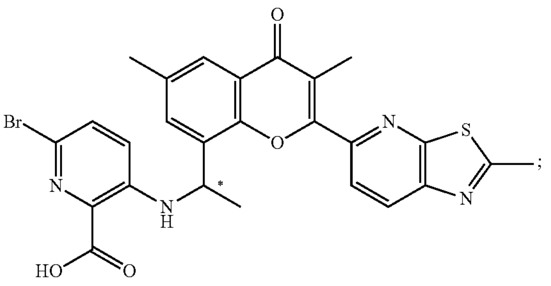 [SMILES: Cc1cc(C(C)Nc2ccc(Br)nc2C(=O)O)c2oc(-c3ccc4nc(C)sc4n3)c(C)c(=O)c2c1]

or pharmaceutically acceptable salt thereof. In yet a further embodiment, the bond at the * position is

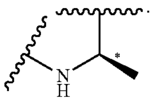 [SMILES: *N[C@@H](*)C]

In yet a further embodiment, the bond at the * position is

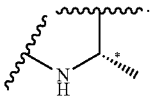

A further embodiment is a compound of Formula

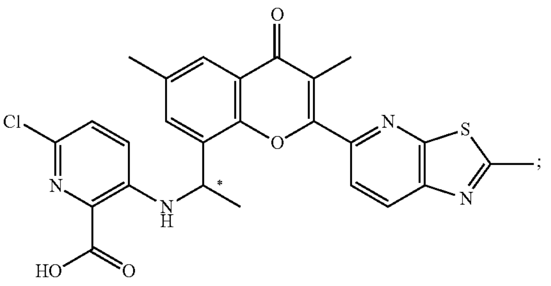 [SMILES: Cc1cc(C(C)Nc2ccc(Cl)nc2C(=O)O)c2oc(-c3ccc4nc(C)sc4n3)c(C)c(=O)c2c1]

or pharmaceutically acceptable salt thereof. In yet a further embodiment, the bond at the position is

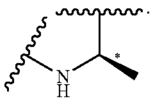 [SMILES: *N[C@@H](*)C]

In yet a further embodiment, the bond at the * position is

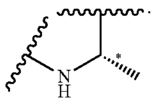

A further embodiment is a compound of Formula

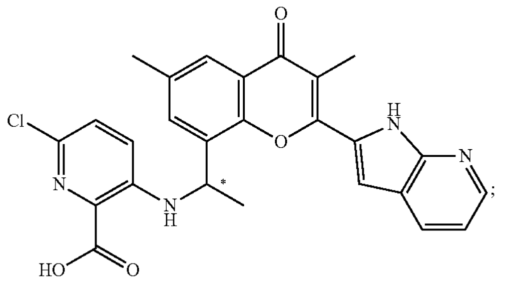 [SMILES: Cc1cc(C(C)Nc2ccc(Cl)nc2C(=O)O)c2oc(-c3cc4cccnc4[nH]3)c(C)c(=O)c2c1]

or pharmaceutically acceptable salt thereof. In yet a further embodiment, the bond at the * position is

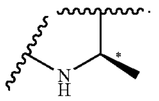 [SMILES: *N[C@@H](*)C]

In yet a further embodiment, the bond at the * position is

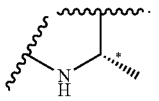

A further embodiment is a compound of Formula

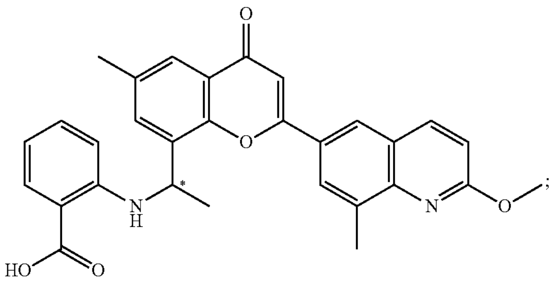 [SMILES: COc1ccc2cc(-c3cc(=O)c4cc(C)cc(C(C)Nc5ccccc5C(=O)O)c4o3)cc(C)c2n1]

or pharmaceutically acceptable salt thereof. In yet a further embodiment, the bond at the * position is

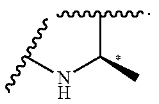

In yet a further embodiment, the bond at the * position is,

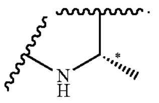

A further embodiment is a compound of Formula

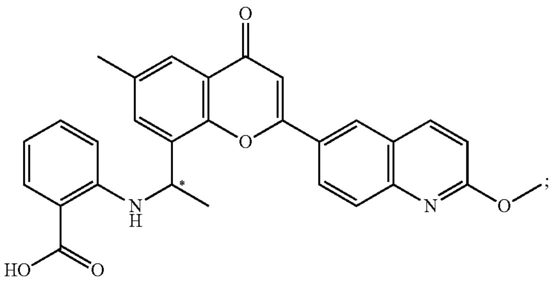

or pharmaceutically acceptable salt thereof. In yet a further embodiment, the bond at the * position is

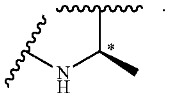 [SMILES: *N[C@@H](*)C]

In yet a further embodiment, the bond at the * position is

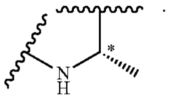 [SMILES: *N[C@H](*)C]

A further embodiment is a compound of Formula

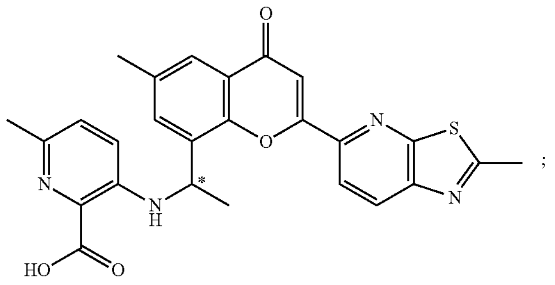

or pharmaceutically acceptable salt thereof. In yet a further embodiment, the bond at the * position is

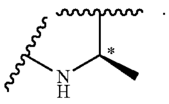 [SMILES: *N[C@@H](*)C]

In yet a further embodiment, the bond at the * position is

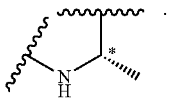 [SMILES: *N[C@H](*)C]

A further embodiment is a compound of Formula

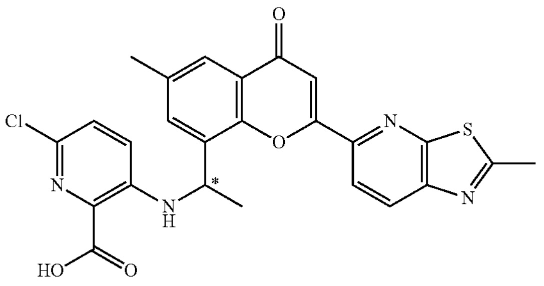
;

or pharmaceutically acceptable salt thereof. In yet a further embodiment, the bond at the position is

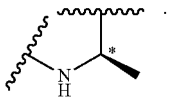 [SMILES: *N[C@@H](*)C]

In yet a further embodiment, the bond at the * position is

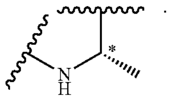

A further embodiment is a compound of Formula

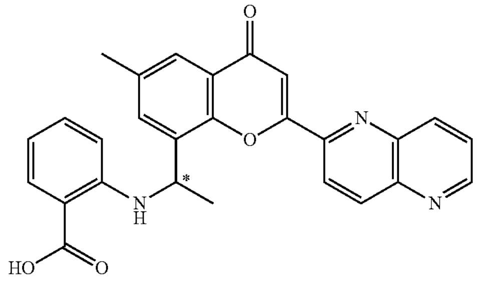
;

or pharmaceutically acceptable salt thereof. In yet a further embodiment, the bond at the * position is

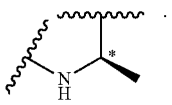 [SMILES: *N[C@@H](*)C]

In yet a further embodiment, the bond at the * position is

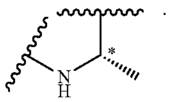 [SMILES: *N[C@H](*)C]

A further embodiment is a compound of Formula

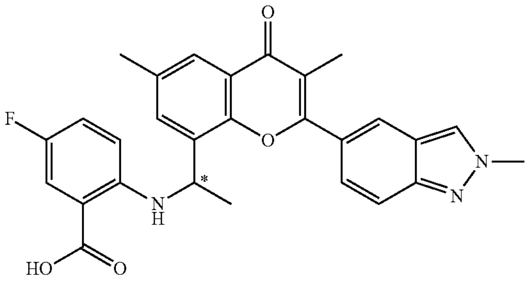
;

or pharmaceutically acceptable salt thereof. In yet a further embodiment, the bond at the * position is

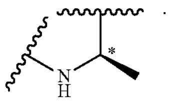 [SMILES: *N[C@@H](*)C]

In yet a further embodiment, the bond at the * position is

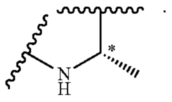 [SMILES: *N[C@H](*)C]

A further embodiment is a compound of Formula

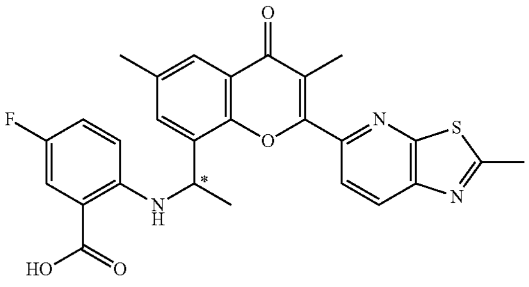
;

or pharmaceutically acceptable salt thereof. In yet a further embodiment, the bond at the * position is

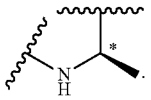 [SMILES: *N[C@@H](*)C]

In yet a further embodiment, the bond at the * position is

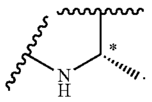

A further embodiment is a compound of Formula

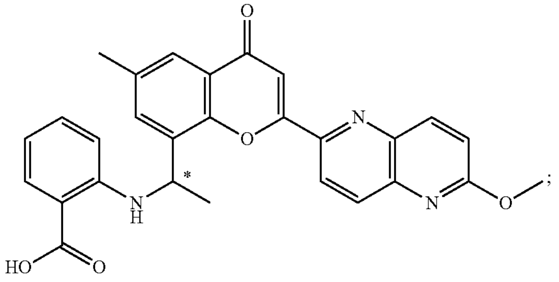 [SMILES: COc1ccc2nc(-c3cc(=O)c4cc(C)cc(C(C)Nc5ccccc5C(=O)O)c4o3)ccc2n1]

or pharmaceutically acceptable salt thereof. In yet a further embodiment, the bond at the position is

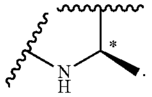 [SMILES: *N[C@@H](*)C]

In yet a further embodiment, the bond at the * position is

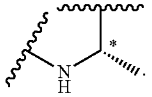

A further embodiment is a compound of Formula

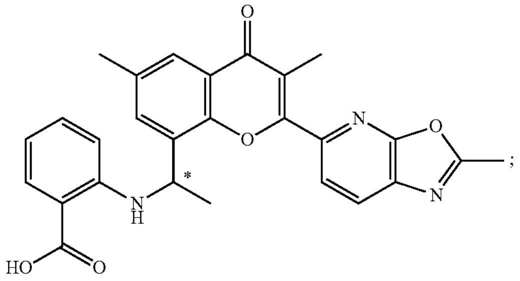 [SMILES: Cc1cc(C(C)Nc2ccccc2C(=O)O)c2oc(-c3ccc4nc(C)oc4n3)c(C)c(=O)c2c1]

or pharmaceutically acceptable salt thereof. In yet a further embodiment, the bond at the * position is

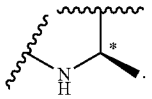 [SMILES: *N[C@@H](*)C]

In yet a further embodiment, the bond at the * position is

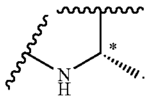 [SMILES: *N[C@H](*)C]

A further embodiment is a compound of Formula

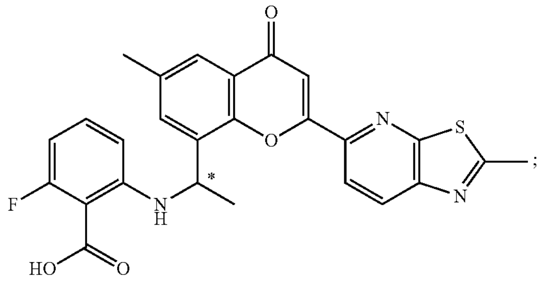 [SMILES: Cc1cc(C(C)Nc2cccc(F)c2C(=O)O)c2oc(-c3ccc4nc(C)sc4n3)cc(=O)c2c1]

or pharmaceutically acceptable salt thereof. In yet a further embodiment, the bond at the * position is

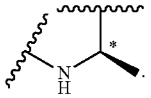 [SMILES: *N[C@@H](*)C]

In yet a further embodiment, the bond at the * position is

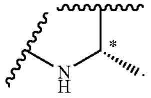 [SMILES: *N[C@H](*)C]

A further embodiment is a compound of Formula

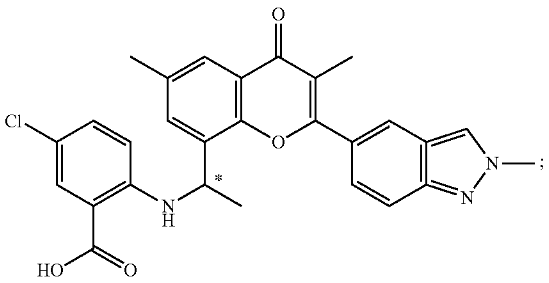

or pharmaceutically acceptable salt thereof. In yet a further embodiment, the bond at the * position is

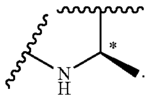 [SMILES: *N[C@@H](*)C]

In yet a further embodiment, the bond at the * position is

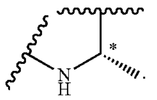

A further embodiment is a compound of Formula

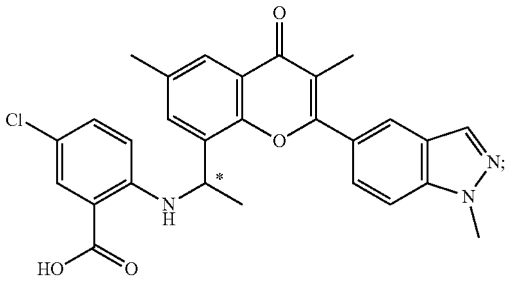 [SMILES: Cc1cc(C(C)Nc2ccc(Cl)cc2C(=O)O)c2oc(-c3ccc4c(cnn4C)c3)c(C)c(=O)c2c1]

or pharmaceutically acceptable salt thereof. In yet a further embodiment, the bond at the position is

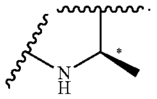 [SMILES: *N[C@@H](*)C]

In yet a further embodiment, the bond at the * position is

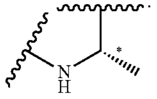 [SMILES: *N[C@H](*)C]

A further embodiment is a compound of Formula

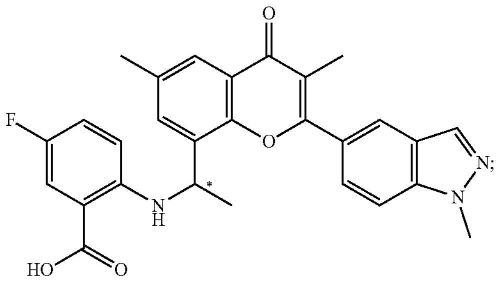 [SMILES: Cc1cc(C(C)Nc2ccc(F)cc2C(=O)O)c2oc(-c3ccc4c(cnn4C)c3)c(C)c(=O)c2c1]

or pharmaceutically acceptable salt thereof. In yet a further embodiment, the bond at the * position is

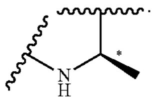 [SMILES: *N[C@@H](*)C]

In yet a further embodiment, the bond at the * position is

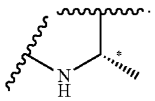

A further embodiment is a compound of Formula

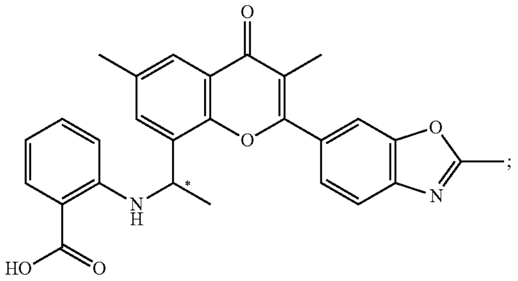

or pharmaceutically acceptable salt thereof. In yet a further embodiment, the bond at the * position is

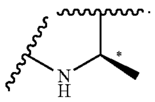

In yet a further embodiment, the bond at the * position is

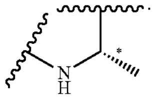

A further embodiment is a compound of Formula

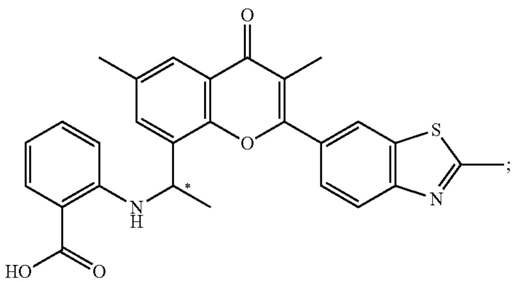 [SMILES: Cc1cc(C(C)Nc2ccccc2C(=O)O)c2oc(-c3ccc4nc(C)oc4c3)c(C)c(=O)c2c1]

or pharmaceutically acceptable salt thereof. In yet a further embodiment, the bond at the * position is

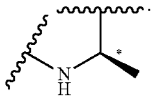 [SMILES: *N[C@@H](*)C]

In yet a further embodiment, the bond at the * position is

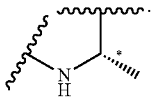

A further embodiment is a compound of Formula

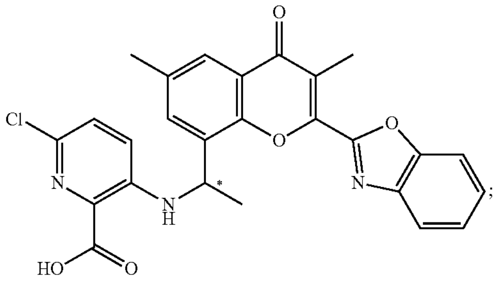 [SMILES: Cc1cc(C(C)Nc2ccc(Cl)nc2C(=O)O)c2oc(-c3nc4ccccc4o3)c(C)c(=O)c2c1]

or pharmaceutically acceptable salt thereof. In yet a further embodiment, the bond at the position is

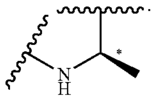 [SMILES: *N[C@@H](*)C]

In yet a further embodiment, the bond at the * position is

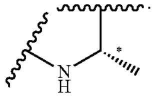

A further embodiment is a compound of Formula

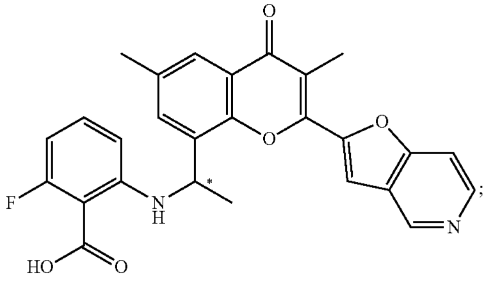 [SMILES: Cc1cc(C(C)Nc2cccc(F)c2C(=O)O)c2oc(-c3cc4cnccc4o3)c(C)c(=O)c2c1]

or pharmaceutically acceptable salt thereof. In yet a further embodiment, the bond at the * position is

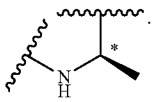 [SMILES: *N[C@@H](*)C]

In yet a further embodiment, the bond at the * position is

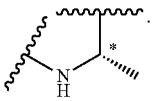

A further embodiment is a compound of Formula

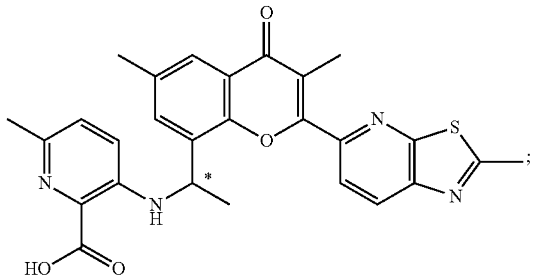

or pharmaceutically acceptable salt thereof. In yet a further embodiment, the bond at the * position is

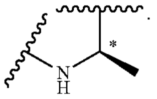 [SMILES: *N[C@@H](*)C]

In yet a further embodiment, the bond at the * position is

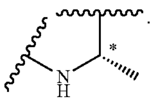 [SMILES: *N[C@H](*)C]

A pharmaceutically acceptable salt of a compound of the present invention is, for example, an acid-addition salt of a compound of the invention, which is sufficiently basic, for example, an acid-addition salt with, for example, an inorganic or organic acid, for example hydrochloric, hydrobromic, sulfuric, phosphoric, trifluoroacetic, formic, citric, methane sulfonate or maleic acid. In addition, a pharmaceutically acceptable salt of a compound of the present invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, diethylamine, trimethylamine, piperidine, morpholine or tris-(2-hydroxyethyl)amine. Pharmaceutically acceptable salts, and common methodology for preparing them are well known in the art (see, e.g., P. Stahl, et al. *Handbook of Pharmaceutical Salts: Properties, Selection, and Use,* 2$^{nd}$ Revised Edition (Wiley-VCH, 2011); S. M. Berge, et al., "Pharmaceutical Salts," *Journal of Pharmaceutical Sciences*, Vol. 66, No. 1, January 1977).

Further representative "pharmaceutically acceptable salts" include, e.g., water-soluble, and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium, calcium edetate, camsylate, carbonate, chloride, citrate, clavulanate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate, pantothenate, phosphate/diphosphate, picrate, polygalacturonate, propionate, p-toluenesulfonate, salicylate, stearate, subacetate, succinate, sulfate, sulfosalicylate, tannate, tartrate, teoclate, tosylate, triethiodide, and valerate salts.

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention can be synthesized by following the steps outlined in General Schemes 1, 2, 3, and 4 which comprise different sequences of assembling intermediates or compounds. Starting materials are either commercially available or made by known procedures in the reported literature or as illustrated below.

Scheme 1

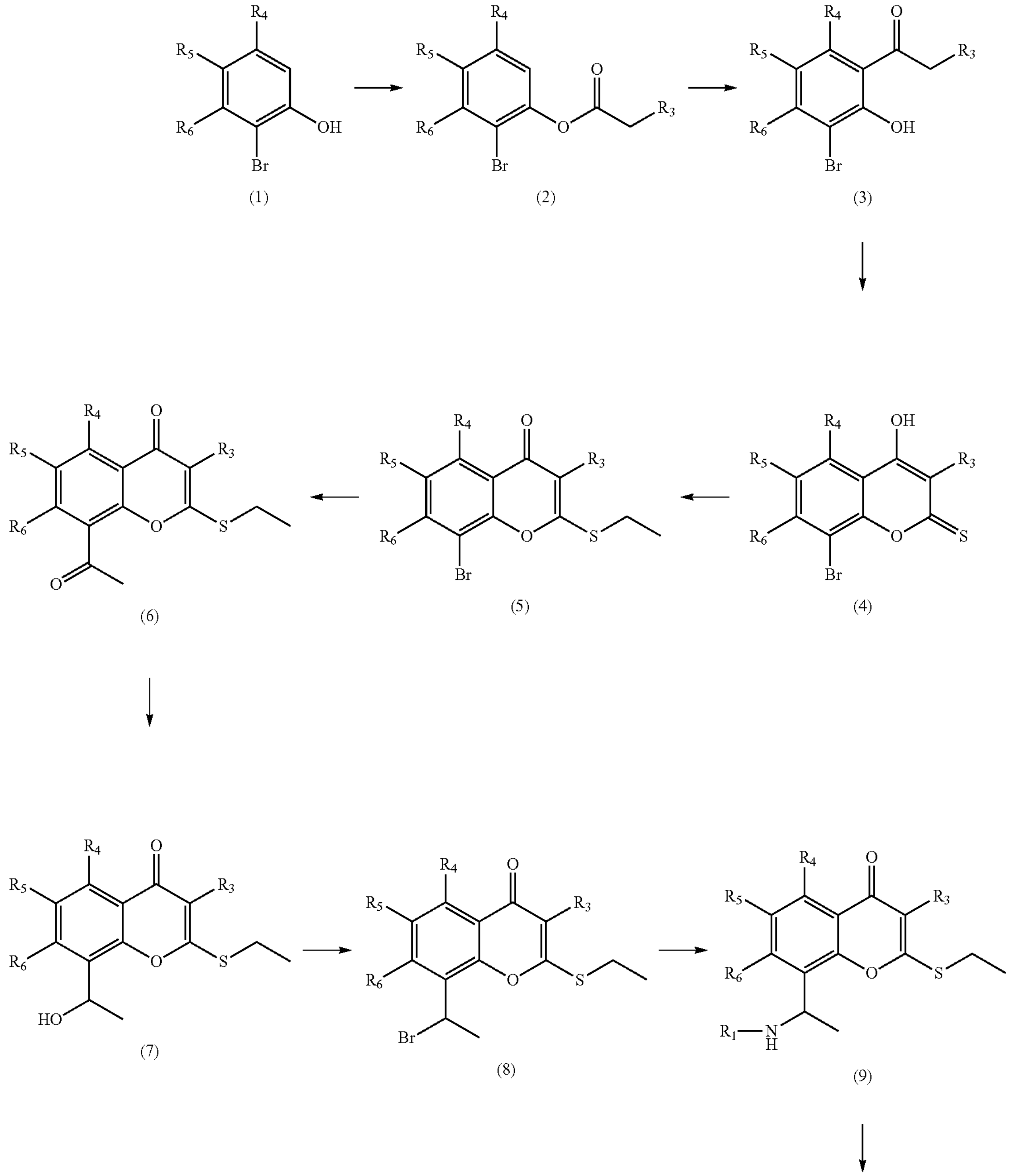

-continued

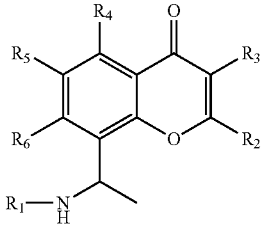

(I)

Scheme 1 depicts the preparation of compounds of Formula (I), where R is —H, $R_7$ is methyl, and $R_8$ is —H. Acylation of substituted phenol (1) can provide ester (2). Ester (2) can undergo rearrangement under Lewis acid (e.g., $AlCl_3$) or Brønsted acid (e.g., triflic acid) conditions to provide hydroxy aryl ketone (3). Basic deprotonation of ketone (3) in the presence of carbon disulfide can provide the bicyclic chromene-2-thione (4).

Alkylation of thione (4) under basic conditions can afford thiolether (5). Phenyl bromide (5) can be acylated via palladium catalysis to produce acyl chromen-4-one (6). Exemplary palladium catalysis conditions may include phenyl bromide (5), about 5-10 mol % $PdCl_2(Ph_3)_2$ and about 1.2 eq tributyl(1-ethoxyvinyl)stannane in about 30-35 equivalents dioxane at 95° C. for about 16 hours. Aryl ketone (6) can be reduced to hydroxy compound (7) with a reagent such as sodium borohydride. Use of a halogenating agent such as phosphorus tribromide can be used to convert hydroxy compound (7) to the halo compound (8).

Halo compound (8) can be used to alkylate an arylamine or heteroarylamine to give amine (9). Thiolether (9) can be converted to compounds of Formula (I) using transition metal catalysis to couple bicyclic boronic acids, boronic esters, or other coupling partners, followed by hydrolysis of an ester if present on $R_1$.

Scheme 2

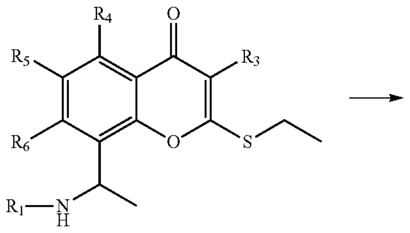

(9)

-continued

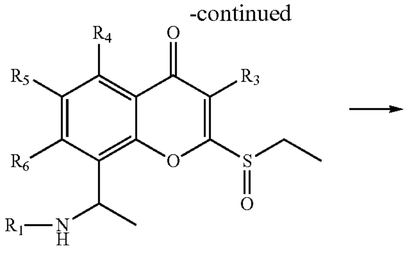

(10)

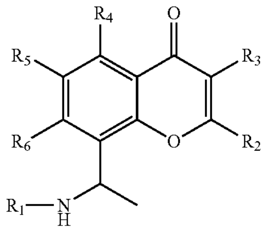

(I)

Scheme 2 depicts another preparation of compounds of Formula (I), where R is —H, $R_7$ is methyl, and $R_8$ is —H. Oxidation of thiolether (9) with an oxidant such as m-CPBA can give sulfoxide (10). Sulfoxide (10) can be converted to compounds of Formula (I) by substitution with various bicyclic heteroaryl amines followed by hydrolysis of an ester if present on $R_1$.

Scheme 3

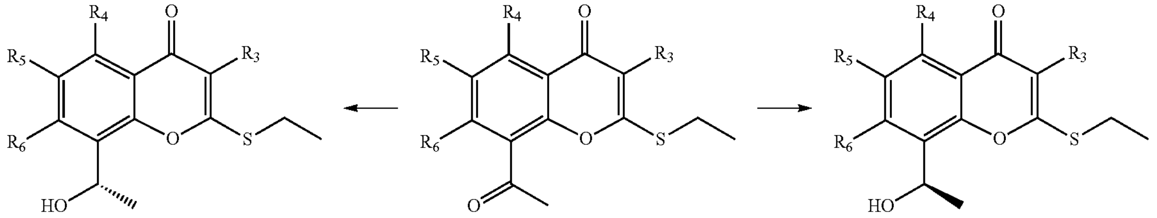

(11) (6) (13)

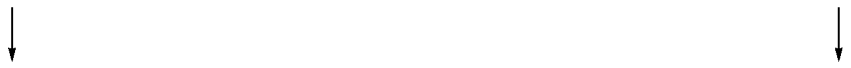

-continued

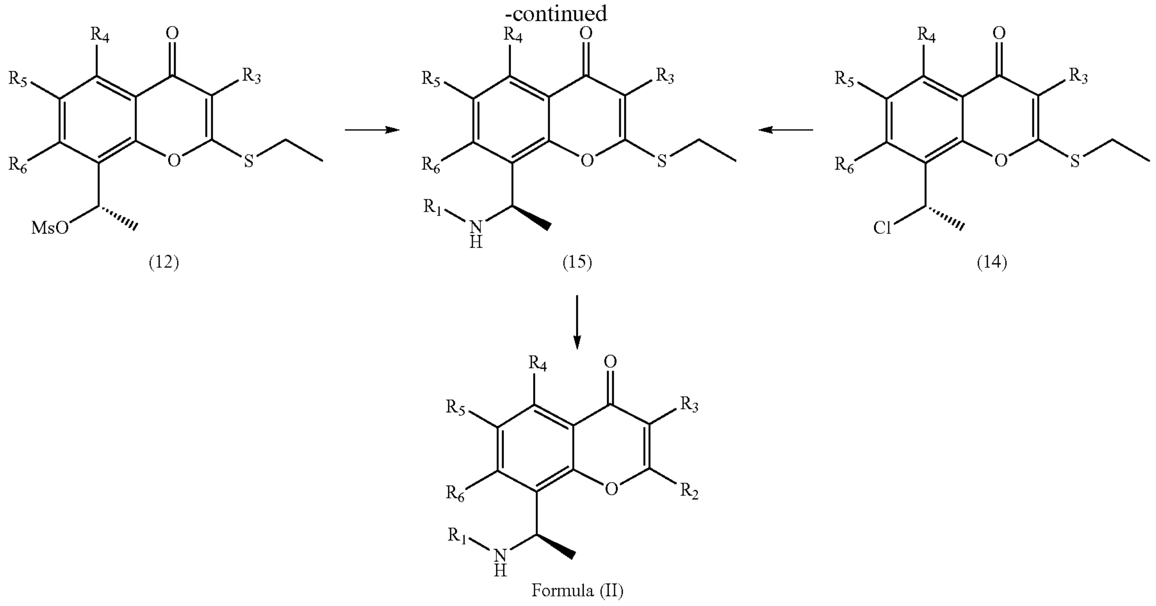

(12) (15) (14)

Formula (II)

Scheme 3 depicts the preparation of compounds of Formula (II) where R is —H, $R_7$ is methyl, and $R_8$ is —H. Ketone (6) can be reduced to hydroxy compound (11) with a chiral catalyst such as the Noyori catalyst. The hydroxyl group in compound (11) can be converted into a leaving group with methanesulfonic anhydride or methanesulfonyl chloride to give mesylate (12). Mesylate (12) can be used to alkylate an arylamine or heteroarylamine to give amine (15). Thiolether (15) can be converted to compounds of Formula (II) using transition metal catalysis to couple bicyclic heteroaryl boronic acids, bicyclic heteroaryl boronate esters, or other coupling partners, followed by hydrolysis of the ester if present on $R_1$.

Scheme 3 also depicts the preparation of compounds of Formula (II) where R is —H, $R_7$ is methyl, and $R_8$ is —H. Ketone (6) can be reduced to hydroxy compound (13) with a chiral catalyst such as the Noyori catalyst. The hydroxyl group in compound (13) can be converted with chlorinating agents such as 2,4,6-trichloro-1,3,5-triazine to chloride (14). Chloride (14) can be used to alkylate an arylamine or heteroarylamine to give amine (15). Thiolether (15) can be converted to compounds of Formula (II) using transition metal catalysis to couple bicyclic heteroaryl boronic acids, bicyclic heteroaryl boronate esters, or other coupling partners, followed by hydrolysis of an ester if present on $R_1$.

Scheme 4

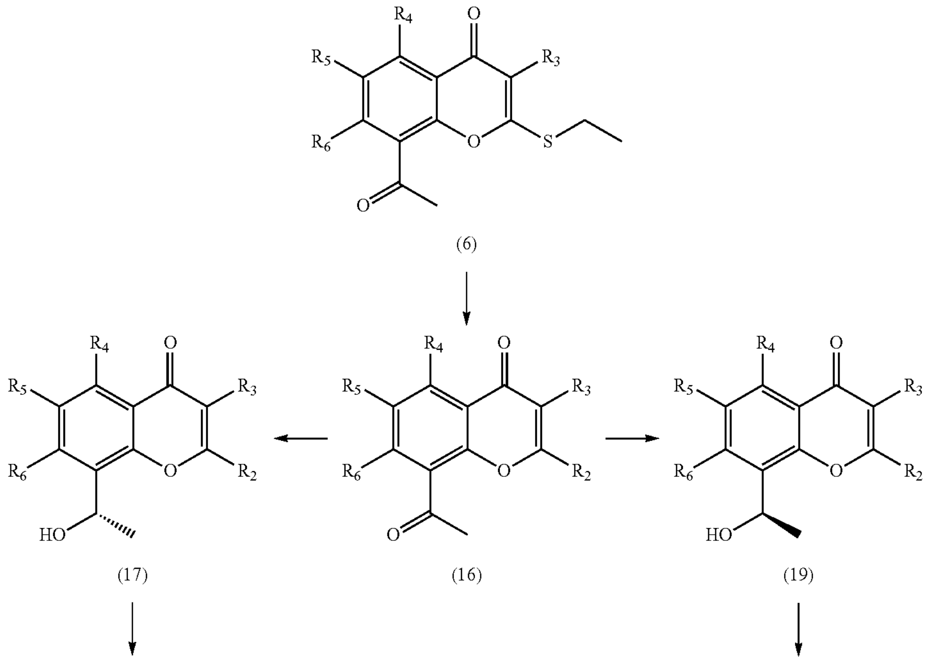

(6)

(17) (16) (19)

-continued

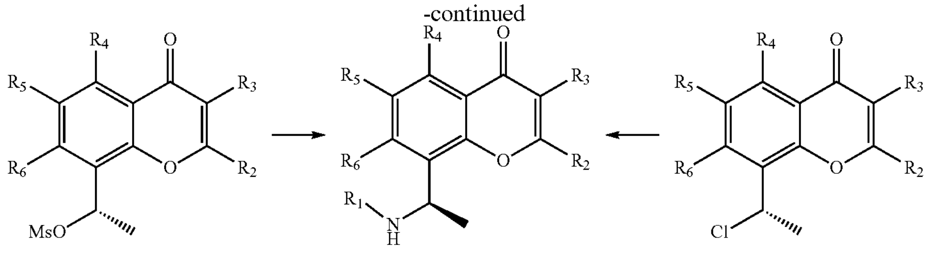

(18) Formula (II) (20)

Scheme 4 depicts an alternative preparation of compounds of Formula (II) where R is —H, $R_7$ is methyl, and $R_8$ is —H. Thiolether (6) can be converted to 2-substituted chromenone (16) using transition metal catalysis to couple bicyclic heteroaryl boronic acids, bicyclic heteroaryl boronate esters, or other coupling partners. Ketone (16) can be reduced to hydroxy compound (17) with a chiral catalyst such as the Noyori catalyst. The hydroxyl compound (17) can be converted into a leaving group with methanesulfonic anhydride or methanesulfonyl chloride to give mesylate (18). Mesylate (18) can be used to alkylate an arylamine or heteroarylamine to give compounds of Formula (II) after hydrolysis of the ester present on $R_1$.

Alternatively, ketone (16) can be reduced to hydroxy compound (19) with a chiral catalyst such as the Noyori catalyst. The hydroxyl group can be converted to chloride (20) with a chlorinating agent such as 2,4,6-trichloro-1,3,5-triazine. Chloride (20) can then be used to alkylate an arylamine or heteroarylamine to give compounds of Formula (II) after hydrolysis of an ester present if present on $R_1$.

Pharmaceutical Compositions

In some aspects, the present disclosure provides a pharmaceutical composition comprising a compound of Formula (I), (II), or (III) as an active ingredient. In some embodiments, the present disclosure provides a pharmaceutical composition comprising a compound of Formula (I), (II), or (III), or a pharmaceutically acceptable salt thereof, and one or more pharmaceutically acceptable carriers or excipients.

As used herein, the term "composition" is intended to encompass a product comprising the specified ingredients in the specified amounts, as well as any product which results, directly or indirectly, from combination of the specified ingredients in the specified amounts.

The compounds of Formula (I), (II), or (III) can be formulated for oral administration in forms such as tablets, capsules (each of which includes sustained release or timed release formulations), pills, powders, granules, elixirs, tinctures, suspensions, syrups and emulsions. The compounds of Formula (I), (II), or (III) can also be formulated for intravenous (bolus or in fusion), intraperitoneal, topical, subcutaneous, intramuscular or transdermal (e.g., patch) administration, all using forms well known to those of ordinary skill in the pharmaceutical arts.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

According to a further aspect of the disclosure there is provided a pharmaceutical composition which comprises a compound any one of the Formulae disclosed herein, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more coloring, sweetening, flavoring and/or preservative agents.

Methods of Use

In some aspects, the present disclosure provides a method of modulating PI3K (e.g., PI3Kα) activity (e.g., in vitro or in vivo), comprising contacting a cell with a therapeutically effective amount of a compound of Formula (I), (II), or (III), or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a method of treating a disease or disorder disclosed herein in a subject in need thereof, comprising administering to the subject a therapeutically effective amount of a compound of Formula (I), (II), or (III), or a pharmaceutically acceptable salt thereof, or a pharmaceutical composition of the present disclosure.

In some embodiments, the disease or disorder is associated with an implicated PI3K activity. In some embodiments, the disease or disorder is a disease or disorder in which PI3K activity is implicated.

In some embodiments, the disease or disorder is a cancer.

In some embodiments, the cancer is selected from acute lymphoblastic leukemia (ALL), acute myeloid leukemia (AML), adrenocortical carcinoma, aids-related cancers, aids-related lymphoma, anal cancer, astrocytoma, basal cell carcinoma, bile duct cancer, bladder cancer, bone cancer, osteosarcoma, malignant fibrous histiocytoma, brain tumors, breast cancer, bronchial tumors, Burkitt lymphoma, carcinoid tumor, cancer of unknown primary, cardiac (heart) tumors, atypical teratoid/rhabdoid tumor, primary CNS lymphoma, cervical cancer, cholangiocarcinoma, chordoma, chronic lymphocytic leukemia (CLL), chronic myelogenous leukemia (CIVIL), colorectal cancer, craniopharyngioma, cutaneous t-cell lymphoma, mycosis fungoides, Sezary syndrome, ductal carcinoma in situ (DCIS), embryonal tumors, medulloblastoma, endometrial cancer, ependymoma, esophageal cancer, esthesioneuroblastoma, Ewing sarcoma, extracranial germ cell tumor, extragonadal germ cell tumor, fallopian tube cancer, gallbladder cancer, gastric cancer, gastrointestinal carcinoid tumor, malignant gastrointestinal stromal tumors (GIST), germ cell tumors, gestational trophoblastic disease, hairy cell leukemia, head and neck cancer, hepatocellular cancer, Langerhans cell histiocytosis, Hodgkin lymphoma, islet cell tumors, pancreatic neuroendocrine tumors, Kaposi sarcoma, kidney cancer, laryngeal cancer, leukemia, liver cancer, lung cancer, lymphoma, male breast cancer, intraocular melanoma, Merkel cell carcinoma, malignant mesothelioma, metastatic cancer, metastatic squamous neck cancer, midline tract carcinoma with nut gene changes, mouth cancer, multiple endocrine neoplasia syndromes, multiple myeloma/plasma cell neoplasms, myelodysplastic syndromes, myelodysplastic neoplasms, myeloproliferative neoplasms, chronic myeloproliferative neoplasm, nasal cavity and paranasal sinus cancer, nasopharyngeal cancer, neuroblastoma, non-Hodgkin lymphoma, non-small cell lung cancer, oral cancer, lip and oral cavity cancer, oropharyngeal cancer, malignant fibrous histiocytoma of bone, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, multiple myeloma, pleuropulmonary blastoma, primary central nervous system (CNS) lymphoma, primary peritoneal cancer, prostate cancer, rectal cancer, recurrent cancer, renal cell (kidney) cancer, retinoblastoma, rhabdomyosarcoma, salivary gland cancer, sarcoma, childhood vascular tumors, skin cancer, small cell lung cancer, small intestine cancer, soft tissue sarcoma, squamous cell carcinoma of the skin, testicular cancer, oropharyngeal cancer, hypopharyngeal cancer, thymoma, thymic carcinoma, thyroid cancer, tracheobronchial tumors, transitional cell cancer of the renal pelvis and ureter, urethral cancer, uterine sarcoma, vaginal cancer, vascular tumors, vulvar cancer, and Wilms tumor.

In some embodiments, the cancer is Endometrial cancer, Breast cancer, Oesophageal squamous-cell cancer, Cervical squamous-cell carcinoma, Cervical adenocarcinoma, Colorectal adenocarcinoma, Bladder Urothelial Carcinoma, Glioblastoma, Ovarian cancer, Non-small-cell Lung cancer, Esophagogastric cancer, Nerve-sheath tumor, Head and neck squamous-cell carcinoma, Melanoma, Esophagogastric adenocarcinoma, Soft-tissue sarcoma, Prostate cancer, Fibrolamellar carcinoma, Hepatocellular carcinoma, Diffuse glioma, Colorectal cancer, Pancreatic cancer, Cholangiocarcinoma, B-cell lymphoma, Mesothelioma, Adrenocortical carcinoma, Renal non-clear-cell carcinoma, Renal clear-cell carcinoma, Germ-cell carcinoma, Thymic tumor, Pheochromocytoma, Miscellaneous neuroepithelial tumor, thyroid cancer, leukemia, or encapsulated glioma.

In some embodiments, the cancer is a breast cancer, a prostate cancer, or a brain cancer.

In some embodiments, the cancer is a breast cancer. In some embodiments, the cancer is a prostate cancer. In some embodiments, the cancer is a brain cancer.

In some embodiments, the breast cancer is metastatic breast cancer. In some embodiments, the breast cancer is ductal carcinoma in situ (DCIS). In some embodiments, the breast cancer is invasive ductal carcinoma. In some embodiments, the breast cancer is triple negative breast cancer. In some embodiments, the breast cancer is medullary carcinoma. In some embodiments, the breast cancer is tubular carcinoma. In some embodiments, the breast cancer is mucinous carcinoma. In some embodiments, the breast cancer is Paget disease of the breast or nipple. In some embodiments, the breast cancer is inflammatory breast cancer (IBC). In some embodiments, the breast cancer is hormone receptor-positive (HR+), human epidermal growth factor receptor 2-negative (HER2-) advanced or metastatic breast cancer.

In some embodiments, the prostate cancer is an adenocarcinoma. In some embodiments, the prostate cancer is a small cell carcinoma. In some embodiments, the prostate cancer is a neuroendocrine tumor. In some embodiments, the prostate cancer is a transitional cell carcinoma. In some embodiments, the prostate cancer is a sarcoma.

In some embodiments, the brain cancer is an acoustic neuroma. In some embodiments, the brain cancer is an astrocytoma. In some embodiments, the brain cancer is a brain metastasis. In some embodiments, the brain cancer is choroid plexus carcinoma. In some embodiments, the brain cancer is craniopharyngioma. In some embodiments, the brain cancer is an embryonal tumor. In some embodiments, the brain cancer is an ependymoma. In some embodiments, the brain cancer is a glioblastoma. In some embodiments, the brain cancer is a glioma. In some embodiments, the brain cancer is a medulloblastoma. In some embodiments, the brain cancer is a meningioma. In some embodiments, the brain cancer is an oligodendroglioma. In some embodiments, the brain cancer is a pediatric brain tumor. In some embodiments, the brain cancer is a pineoblastoma. In some embodiments, the brain cancer is a pituitary tumor.

In some embodiments, the disease or disorder associated with PI3K includes, but is not limited to, CLOVES syndrome (congenial lipomatous overgrowth, vascular malformations, epidermal naevi, scoliosis/skeletal and spinal syndrome), PIK3CA-related overgrowth syndrome (PROS), breast cancer, brain cancer, prostate cancer, endometrial cancer, gastric cancer, leukemia, lymphoma, sarcoma, colorectal cancer, lung cancer, ovarian cancer, skin cancer, or head and neck cancer.

In some embodiments, the diseases or disorder associated with PI3K is CLOVES syndrome (congenital lipomatous overgrowth, vascular malformations, epidermal naevi, scoliosis/skeletal and spinal syndrome).

In some embodiments, the disease or disorder associated with PI3K is PIK3CA-related overgrowth syndrome (PROS).

In some embodiments, the disease or disorder associated with PI3K is breast cancer, brain cancer, prostate cancer, endometrial cancer, gastric cancer, leukemia, lymphoma, sarcoma, colorectal cancer, lung cancer, ovarian cancer, skin cancer, or head and neck cancer.

In some embodiments, the disease or disorder associated with PI3K is a breast neoplasm, a thyroid neoplasm, an ovarian neoplasm, non-small-cell lung carcinoma, an endometrial neoplasm, or a pancreatic neoplasm. In some embodiments, the disease or disorder associated with PI3K is a breast neoplasm. In some embodiments, the disease or disorder associated with PI3K is a thyroid neoplasm. In some embodiments, the disease or disorder associated with PI3K is an ovarian neoplasm. In some embodiments, the disease or disorder associated with PI3K is non-small-cell lung carcinoma. In some embodiments, the disease or disorder associated with PI3K is an endometrial neoplasm. In some embodiments, the disease or disorder associated with PI3K is a pancreatic neoplasm.

In some embodiments, the disease or disorder associated with PI3K is breast cancer, brain cancer, prostate cancer, endometrial cancer, gastric cancer, colorectal cancer, lung cancer, ovarian cancer, skin cancer, or head and neck cancer.

In some embodiments, the disease or disorder associated with PI3K is leukemia, lymphoma, or sarcoma.

In some embodiments, the cancer is endometrial cancer, head and neck cancer, or a sarcoma.

In some embodiments, the cancer is endometrial cancer. In some embodiments the cancer is head and neck cancer. In some embodiments, the cancer is a sarcoma.

In some embodiments, the sarcoma is soft tissue sarcoma, osteosarcoma, chondrosarcoma, Ewing sarcoma, hemangioendothelioma, angiosarcoma, fibrosarcoma, myofibrosarcoma, chordoma, adamantinoma, liposarcoma, leiomyosarcoma, malignant peripheral nerve sheath tumor, rhabdomyosarcoma, synovial sarcoma, or malignant solitary fibrous tumor.

In some embodiments, the sarcoma is soft tissue sarcoma. In some embodiments the soft tissue sarcoma is liposarcoma, atypical lipomatous tumor, dermatofibrosarcoma protuberans, malignant solitary fibrous tumor, inflammatory myofibroblastic tumor, low-grade myofibroblastic sarcoma, fibrosarcoma, myxofibrosarcoma, low-grade fibromyxoid sarcoma, giant cell tumor of soft tissues, leiomyosarcoma, malignant glomus tumor, rhabdomyosarcoma, hemangioendothelioma, angiosarcoma of soft tissue, extraskeletal osteosarcoma, gastrointestinal stromal tumor, malignant gastrointestinal stromal tumor (GIST), malignant peripheral nerve sheath tumor, malignant Triton tumor, malignant granular cell tumor, malignant ossifying fibromyxoid tumor, stromal sarcoma, myoepithelial carcinoma, malignant phosphaturic mesenchymal tumor, synovial sarcoma, epithelioid sarcoma, alveolar soft part sarcoma, clear cell sarcoma of soft tissue, extraskeletal myxoid chondrosarcoma, extraskeletal Ewing sarcoma, desmoplastic small round cell tumor, extrarenal rhabdoid tumor, perivascular epithelioid cell tumor, intimal sarcoma, undifferentiated spindle cell sarcoma, undifferentiated pleomorphic sarcoma, undifferentiated round cell sarcoma, undifferentiated epithelioid sarcoma, or undifferentiated sarcoma, not otherwise specified.

In some aspects, the present disclosure provides a method of treating or preventing a cancer in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a method of treating a cancer in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a method of treating or preventing a breast cancer in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a method of treating a breast cancer in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a method of treating or preventing a prostate cancer in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a method of treating a prostate cancer in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a method of treating or preventing a brain cancer in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a method of treating a brain cancer in a subject in need thereof, comprising administering to the subject a therapeutically effective amount of a compound of Formula (I), (II), or (III), or a pharmaceutically acceptable salt thereof, or a pharmaceutical composition of the present disclosure.

In some aspects, the present disclosure provides a compound of Formula (I), (II), or (III), or a pharmaceutically acceptable salt thereof for use in therapy.

In some aspects, the present disclosure provides a compound of Formula (I), (II), or (III), or a pharmaceutically acceptable salt thereof for use in modulating PI3K (e.g., PI3Kα) activity (e.g., in vitro or in vivo).

In some aspects, the present disclosure provides a compound of Formula (I), (II), or (III), or a pharmaceutically acceptable salt thereof for use in treating or preventing a disease or disorder disclosed herein.

In some aspects, the present disclosure provides a compound of Formula (I), (II), or (III), or a pharmaceutically acceptable salt thereof for use in treating a disease or disorder disclosed herein.

In some aspects, the present disclosure provides a compound of Formula (I), (II), or (III), or a pharmaceutically acceptable salt thereof for use in treating or preventing a cancer.

In some aspects, the present disclosure provides a compound of Formula (I), (II), or (III), or a pharmaceutically acceptable salt thereof for use in treating a cancer.

In some aspects, the present disclosure provides a compound of Formula (I), (II), or (III), or a pharmaceutically acceptable salt thereof for use in treating or preventing a breast cancer.

In some aspects, the present disclosure provides a compound of Formula (I), (II), or (III), or a pharmaceutically acceptable salt thereof for use in treating a breast cancer.

In some aspects, the present disclosure provides a compound of Formula (I), (II), or (III), or a pharmaceutically acceptable salt thereof for use in treating or preventing a prostate cancer.

In some aspects, the present disclosure provides a compound of Formula (I), (II), or (III), or a pharmaceutically acceptable salt thereof for use in treating a prostate cancer.

In some aspects, the present disclosure provides a compound of Formula (I), (II), or (III), or a pharmaceutically acceptable salt thereof for use in treating or preventing a brain cancer.

In some aspects, the present disclosure provides a compound of Formula (I), (II), or (III), or a pharmaceutically acceptable salt thereof for use in treating a brain cancer.

In some aspects, the present disclosure provides use of a compound of Formula (I), (II), or (III), or a pharmaceutically acceptable salt thereof in the manufacture of a medicament for modulating PI3K (e.g., PI3Kα) activity (e.g., in vitro or in vivo).

In some aspects, the present disclosure provides use of a compound of Formula (I), (II), or (III), or a pharmaceutically acceptable salt thereof in the manufacture of a medicament for treating or preventing a disease or disorder disclosed herein.

In some aspects, the present disclosure provides use of a compound of Formula (I), (II), or (III), or a pharmaceutically acceptable salt thereof in the manufacture of a medicament for treating a disease or disorder disclosed herein.

In some aspects, the present disclosure provides use of a compound of Formula (I), (II), or (III), or a pharmaceutically acceptable salt thereof in the manufacture of a medicament for treating or preventing a cancer in a subject in need thereof.

In some aspects, the present disclosure provides use of a compound of Formula (I), (II), or (III), or a pharmaceutically acceptable salt thereof in the manufacture of a medicament for treating a cancer in a subject in need thereof.

In some aspects, the present disclosure provides use of a compound of Formula (I), (II), or (III), or a pharmaceutically acceptable salt thereof in the manufacture of a medicament for treating or preventing a breast cancer in a subject in need thereof.

In some aspects, the present disclosure provides use of a compound of Formula (I), (II), or (III), or a pharmaceutically acceptable salt thereof in the manufacture of a medicament for treating a breast cancer in a subject in need thereof.

In some aspects, the present disclosure provides use of a compound of Formula (I), (II), or (III), or a pharmaceutically acceptable salt thereof in the manufacture of a medicament for treating or preventing a prostate cancer in a subject in need thereof.

In some aspects, the present disclosure provides use of a compound of Formula (I), (II), or (III), or a pharmaceutically acceptable salt thereof in the manufacture of a medicament for treating a prostate cancer in a subject in need thereof.

In some aspects, the present disclosure provides use of a compound of Formula (I), (II), or (III), or a pharmaceutically acceptable salt thereof in the manufacture of a medicament for treating or preventing a brain cancer in a subject in need thereof.

In some aspects, the present disclosure provides use of a compound of Formula (I), (II), or (III), or a pharmaceutically acceptable salt thereof in the manufacture of a medicament for treating a brain cancer in a subject in need thereof.

The present disclosure provides compounds that function as modulators of PI3K activity. The present disclosure therefore provides a method of modulating PI3K activity in vitro or in vivo, said method comprising contacting a cell with a therapeutically effective amount of a compound, or a pharmaceutically acceptable salt thereof, as defined herein.

In some embodiments, PI3K modulation is inhibition of PI3K.

In some embodiments, the PI3K inhibitor is a PI3Kα inhibitor. In some embodiments, the PI3K inhibitor is a PI3Kα H1047R mutant inhibitor.

Effectiveness of compounds of the disclosure can be determined by industry-accepted assays/disease models according to standard practices of elucidating the same as described in the art and are found in the current general knowledge.

The present disclosure also provides a method of treating a disease or disorder in which PI3K activity is implicated in a patient in need of such treatment, said method comprising administering to said patient a therapeutically effective amount of a compound, or a pharmaceutically acceptable salt thereof, or a pharmaceutical composition as defined herein.

Routes of Administration

The compounds of Formula (I), (II), or (III), or pharmaceutical compositions comprising these compounds may be administered to a subject by any convenient route of administration, whether systemically/peripherally or topically (i.e., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

EXAMPLES

Exemplary compounds of Formula (I), (II), and (III) are synthesized and tested in the examples. It is understood that compounds of Formula (I), (II), and (III) may be converted to the corresponding pharmaceutically acceptable salts of the compounds using routine techniques in the art (e.g., by saponification of an ester to the carboxylic acid salt, or by hydrolyzing an amide to form a corresponding carboxylic acid and then converting the carboxylic acid to a carboxylic acid salt).

Nuclear magnetic resonance (NMR) spectra were recorded at 400 MHz or 300 MHz as stated and at 300.3 K unless otherwise stated; the chemical shifts (S) are reported in parts per million (ppm). Spectra were recorded using a Bruker or Varian instrument with 8, 16 or 32 scans.

LC-MS chromatograms and spectra were recorded using an Agilent 1200 or Shimadzu LC-20 AD&MS 2020 instrument using a C-18 column such as a Luna-C18 2.0×30 mm or Xbridge Shield RPC18 2.1×50 mm. Injection volumes were 0.7-8.0 μl and the flow rates were typically 0.8 or 1.2 ml/min. Detection methods were diode array (DAD) or evaporative light scattering (ELSD) as well as positive ion electrospray ionization. MS range was 100-1000 Da. Solvents were gradients of water and acetonitrile both containing a modifier (typically 0.01-0.04%) such as trifluoroacetic acid or ammonium carbonate.

ABBREVIATIONS

AcOH/HOAc Acetic Acid

ADP Adenosine diphosphate

ATP Adenosine triphosphate
$CDCl_3$ Chloroform-d
DCM Dichloromethane
DIEA N,N-diisopropylethylamine
DMF N,N-dimethylformamide
DMSO dimethylsulfoxide
DMSO-$d_6$ Hexadeuterodimethylsulfoxide
eq. equivalents
EtI Ethyl iodide
EtOAc ethyl acetate
h hour(s)
HEPES 4-(2-hydroxyethyl)-1-piperazineethanesulfonic acid
$^1$H NMR Proton nuclear magnetic resonance spectroscopy
LC-MS Liquid chromatography-mass spectrometry
MeOH Methanol
min minute(s)
NaHMDS Sodium bis(trimethylsilyl)amide
PIP2 Phosphatidylinositol 4,5-bisphosphate
$PPh_3$ triphenylphosphine
ppm parts per million
rt room temperature
TFA trifluoroacetic acid
THE Tetrahydrofuran
Ti(i-PrO)$_4$ Titanium(IV) isopropoxide Intermediate 1: (2-Bromo-4-methyl-phenyl)acetate

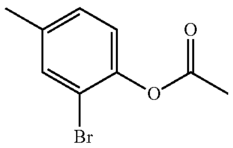

A DCM (2.4 L) mixture of 2-bromo-4-methyl-phenol (300 g, 1.6 mol) and pyridine (152 g, 1.92 mol) at 0° C. was treated with acetyl chloride (151 g, 1.92 mol) and stirred at 25° C. for 16 h. The mixture was diluted with water (1500 mL), pH adjusted to 5 with HCl (2 M aqueous), and extracted with DCM (3×500 mL). The combined organic extracts were washed with brine (2×250 mL), dried over $Na_2SO_4$, filtered, and concentrated to give the product as an oil (400 g, crude). $^1$H NMR (400 MHz, $CDCl_3$) δ ppm 2.24 (s, 3H), 2.25 (s, 3H), 6.91 (d, J=8.4 Hz, 1H), 7.01-7.02 (m, 1H), 7.33 (s, 1H).

The following compounds in Table 1 were made in a similar way as described for Intermediate 1.

TABLE 1

| Int # | Chemical Name | Structure | MS ES+ m/z |
|---|---|---|---|
| 96 | (2-Bromo-4-methyl-phenyl) propanoate | 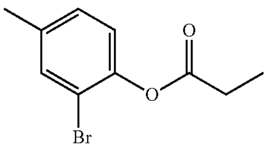 | |

Intermediate 2: 1-(3-Bromo-2-hydroxy-5-methyl-phenyl)ethanone

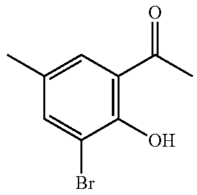

A mixture of (2-bromo-4-methyl-phenyl)acetate (50 g, 218 mmol) and $AlCl_3$ (102 g, 764 mmol) was degassed and purged with $N_2$ three times and stirred at 140° C. for 1 h. After cooling to rt, the reaction was diluted with DCM (30 mL) and dropped into 150 mL of water at 0° C. The mixture was filtered and the aqueous phase extracted with DCM (2×150 mL). The combined organic extracts were washed with brine, dried over anhydrous $Na_2SO_4$, filtered, and concentrated. The residue was triturated with petroleum ether (2×150 mL) to give the product as a solid (30 g, 52%). $^1$H NMR (400 MHz, $CDCl_3$) δ ppm 2.30 (s, 3H), 2.68 (s, 3H), 7.73 (s, 1H), 7.33 (s, 1H), 12.64 (s, 1H).

Intermediate 97: 1-(3-Bromo-2-hydroxy-5-methyl-phenyl)propan-1-one

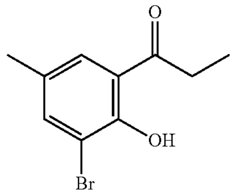

A mixture of (2-bromo-4-methyl-phenyl) propanoate (2328 g, 9.58 mol) and $AlCl_3$ (1430 g, 10.73 mol) was heated to 120° C. and stirred for 1 h to give a brown gum. The reaction mixture was cooled to 25° C., diluted with water (11.6 L), and stirred for 30 min. Hydrogen chloride (12 M, 1160 mL) was added dropwise and the reaction stirred for another 30 min. The mixture was extracted with ethyl acetate (11.6 L×2). The combined organics were washed with water (2328 mL), collected, and concentrated. The residue was triturated with n-heptane (3492 mL) and filtered to give the product (1700 g, yield: 73.0%) as a yellow solid.

Intermediate 98: 1-[3-Bromo-2-hydroxy-5-(trifluoromethyl)phenyl]ethanone

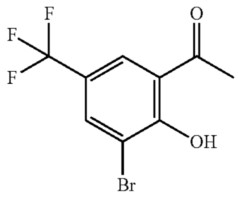

A mixture of 1-[2-hydroxy-5-(trifluoromethyl)phenyl] ethanone (24.87 g, 121.8 mmol) and sodium acetate (11.99 g, 146.2 mmol) in 125 mL of acetic acid was treated dropwise with bromine (20.44 g, 127.9 mmol). After stirring at rt for 1 h, the reaction was treated with 10 mL of saturated aqueous sodium thiosulfate. Diluted the thin suspension with −300 mL of water with vigorous stirring and then removed the product (32 g, 93%) as a white solid after drying. $^1$H NMR (400 MHz, $CDCl_3$) δ ppm 2.75 (s, 3H), 8.00 (m, 2H), 13.31 (s, 1H).

The following compounds in Table 2 were made in a similar way as described for Intermediate 98.

TABLE 2

| Int # | Chemical Name | Structure | MS ES+ m/z |
|---|---|---|---|
| 99 | 1-(3-Bromo-5-fluoro-2-hydroxy-phenyl)ethanone | 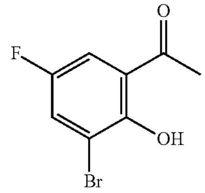 | 233 [M + H]$^+$ |

Intermediate 3: 8-Bromo-4-hydroxy-6-methyl-chromene-2-thione

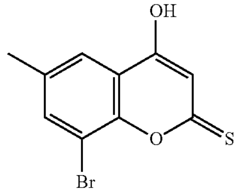

A solution of 1-(3-bromo-2-hydroxy-5-methyl-phenyl) ethanone (65 g, 284 mmol) in THE (800 mL) was treated with NaHMDS (851 mL, 1 M) at −50° C. over 30 min, allowed to warm to between −5° C. and 0° C., and stirred for 1 h. The reaction was cooled to −20° C. and treated with $CS_2$ (64.8 g, 851 mmol) dropwise over 1 h, allowed to warm to 25° C., and stirred for another 16 h. The reaction was quenched with $H_2SO_4$ (800 mL, 15%) at −50° C. over 1 h, allowed to warm to rt, and extracted with EtOAc (2×1 L). The combined organic extracts were washed with brine (1 L), dried over anhydrous $Na_2SO_4$, filtered, and concentrated. The residue was triturated with EtOAc (0.5 L) to give the product as a solid (210 g crude, 64%, purity ~76%).

The following compounds in Table 3 were made in a similar way as described for Intermediate 3.

TABLE 3

| Int # | Chemical Name | Structure | MS ES+ m/z |
|---|---|---|---|
| 100 | 8-Bromo-4-hydroxy-3,6-dimethyl-chromene-2-thione | 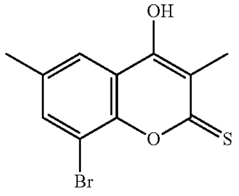 | |

Intermediate 101: 8-Bromo-4-hydroxy-6-(trifluoromethyl)chromene-2-thione

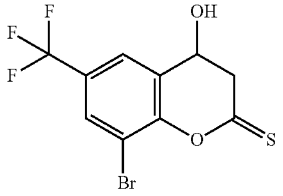 [SMILES: OC1CC(=S)Oc2c(Br)cc(C(F)(F)F)cc21]

A mixture of potassium tert-butoxide (20.57 g, 23.1 mL, 183.28 mmol) in 50 mL of THF was treated dropwise with a solution of 1-[3-bromo-2-hydroxy-5-(trifluoromethyl)phenyl]ethanone (17.29 g, 61.09 mmol) and carbon disulfide (6.05 g, 79.42 mmol) in 50 mL of THF. After addition was complete, the reaction was stirred at rt for 16 h. The reaction was diluted with 400 mL of water, the pH adjusted to 3 with 2M aqueous HCl, and extracted 3 times with 500 mL of ethyl acetate. The organics were combined, washed with brine, dried over $Na_2SO_4$, filtered, and concentrated. The residue was triturated with dichloromethane and the product (9.63 g, 46%) removed by filtration. MS ES+ m/z 325 [M+H]$^-$.

The following compounds in Table 4 were made in a similar way as described for Intermediate 101.

TABLE 4

| Int # | Chemical Name | Structure | MS ES+ m/z |
|---|---|---|---|
| 102 | 8-Bromo-6-fluoro-4-hydroxy-chromene-2-thione | 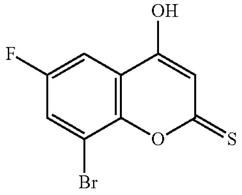 [SMILES: Oc1cc(=S)oc2c(Br)cc(F)cc12] | 275/277 [M + H]$^+$ |

Intermediate 4: 8-Bromo-2-ethylsulfanyl-6-methyl-chromen-4-one

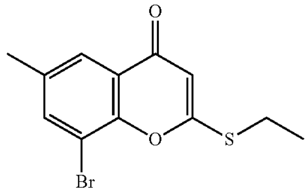 [SMILES: CCSc1cc(=O)c2cc(C)cc(Br)c2o1]

A mixture of 8-bromo-4-hydroxy-6-methyl-chromene-2-thione (20.0 g, 73.8 mmol), EtI (46 g, 295 mmol), and $K_2CO_3$ (12.2 g, 88.5 mmol) in acetone (200 mL) was stirred at 60° C. for 3 h. When the reaction had cooled to rt, the mixture was diluted with water (200 mL) and extracted with DCM (2×200 mL). The combined organic extracts were concentrated and purified via silica gel chromatography eluted with 20%-40% EtOAc in petroleum ether to give the product as a gum. $^1$H NMR (400 MHz, $CDCl_3$) δ ppm 1.51 (t, J=7.2 Hz, 3H), 2.45 (s, 3H), 3.22 (q, J=7.2 Hz, 2H), 6.32 (s, 1H), 7.70 (s, 1H), 7.93 (s, 1H).

The following compounds in Table 5 were made in a similar way as described for Intermediate 4.

TABLE 5

| Int # | Chemical Name | Structure | MS ES+ m/z |
|---|---|---|---|
| 103 | 8-Bromo-2-ethylsulfanyl-3,6-dimethyl-chromen-4-one | 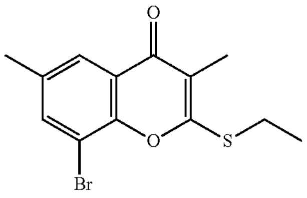 [SMILES: CCSc1oc2c(Br)cc(C)cc2c(=O)c1C] | |
| 104 | 8-Bromo-2-ethylsulfanyl-6-(trifluoromethyl)-chromen-4-one | 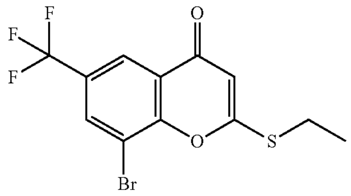 [SMILES: CCSc1cc(=O)c2cc(C(F)(F)F)cc(Br)c2o1] | 353/355 $[M + H]^+$ |
| 105 | 8-Bromo-2-ethylsulfanyl-6-fluoro-chromen-4-one | 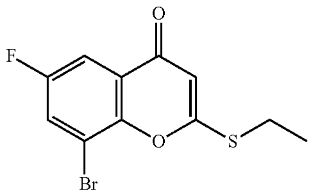 [SMILES: CCSc1cc(=O)c2cc(F)cc(Br)c2o1] | 303/305 $[M + H]^+$ |

Intermediate 5: 8-Acetyl-2-ethylsulfanyl-6-methyl-chromen-4-one

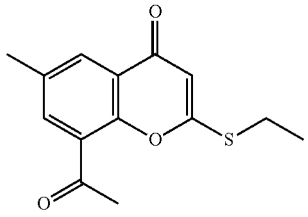 [SMILES: CCSc1cc(=O)c2cc(C)cc(C(C)=O)c2o1]

A mixture of 8-bromo-2-ethylsulfanyl-6-methyl-chromen-4-one (9.00 g, 30.0 mmol), tributyl(1-ethoxyvinyl)tin (13.3 g, 36.8 mmol), and $Pd(PPh_3)_2Cl_2$ (2.11 g, 3.01 mmol) in 1,4-dioxane (90 mL) was stirred at 95° C. for 16 h. After cooling to 50° C., HCl (30 mL, 1 M) was added to the mixture and stirred at 50° C. for 0.5 h. When cooled to rt, the mixture was treated with saturated aqueous KF (100 mL), stirred for 0.5 h, and then filtered. The filter cake was washed with EtOAc (3×40 mL). The filtrate was extracted with EtOAc (2×80 mL). The combined organic extracts were concentrated and purified via silica gel chromatography eluted with 0%-60% EtOAc in petroleum ether to give the product as a solid (5.8 g, 60%). MS ES+ m/z 263 $[M+H]^+$.

The following compounds in Table 6 were made in a similar way as described for Intermediate 5.

TABLE 6

| Int # | Chemical Name | Structure | MS ES+ m/z |
|---|---|---|---|
| 106 | 8-Acetyl-2-ethylsulfanyl-3,6-dimethyl-chromen-4-one | 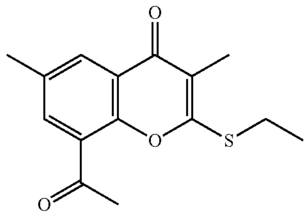 [SMILES: CCSc1oc2c(C(C)=O)cc(C)cc2c(=O)c1C] | |

TABLE 6-continued

| Int # | Chemical Name | Structure | MS ES+ m/z |
|---|---|---|---|
| 107 | 8-Acetyl-2-ethylsulfanyl-6-(trifluoromethyl)-chromen-4-one | 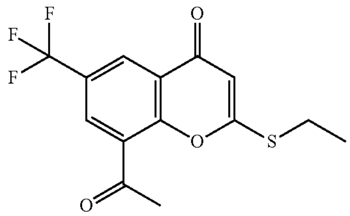 [SMILES: CCSc1cc(=O)c2cc(C(F)(F)F)cc(C(C)=O)c2o1] | 317 [M + H]$^+$ |
| 108 | 8-Acetyl-2-ethylsulfanyl-6-fluoro-chromen-4-one | 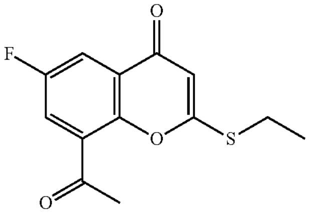 [SMILES: CCSc1cc(=O)c2cc(F)cc(C(C)=O)c2o1] | Product does not ionize well. |
| 109 | 8-Acetyl-2-ethylsulfanyl-6-fluoro-3-methyl-chromen-4-one | 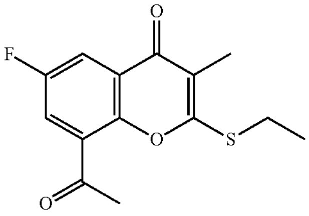 [SMILES: CCSc1oc2c(C(C)=O)cc(F)cc2c(=O)c1C] | |

Intermediate 110: (NE)-N-[1-[2-Ethylsulfanyl-4-oxo-6-(trifluoromethyl)chromen-8-yl]ethylidene]-2-methyl-propane-2-sulfinamide

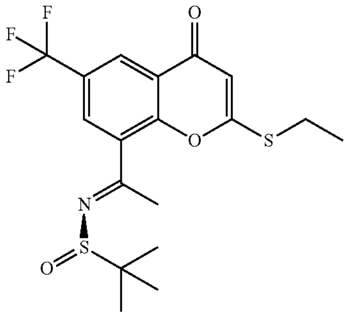

A solution of 8-acetyl-2-ethylsulfanyl-6-(trifluoromethyl) chromen-4-one (1 g, 3 mmol) in THE (15 mL) was treated with (R)-(+)-2-methylpropane-2-sulphinamide (0.80 g, 6 mmol) and titanium isopropoxide (4 g, 4 mL, 10 mmol). The reaction was sealed and heated at 80° C. overnight. The reaction was concentrated and purified by silica gel chromatography eluted with 0% to 50% ethyl acetate in heptane to give the product (1.30 g, 99%) as a pale, yellow oil. MS ES+ m/z 420 [M+H]$^+$.

The following compounds in Table 7 were made in a similar way as described for Intermediate 110.

TABLE 7

| Int # | Chemical Name | Structure | MS ES+ m/z |
|---|---|---|---|
| 285 | (NE)-N-[1-(2-Ethylsulfanyl-6-methyl-4-oxo-chromen-8-yl)ethylidene]-2-methyl-propane-2-sulfinamide | 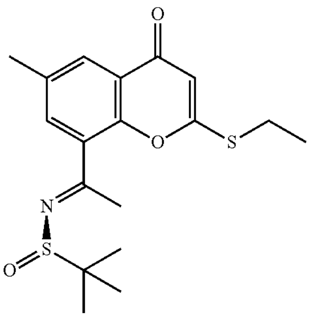 | 366 [M + H]$^+$ |

TABLE 7-continued

| Int # | Chemical Name | Structure | MS ES+ m/z |
|---|---|---|---|
| 286 | (NE)-N-[1-(2-Ethylsulfanyl-3,6-dimethyl-4-oxo-chromen-8-yl)ethylidene]-2-methyl-propane-2-sulfinamide | 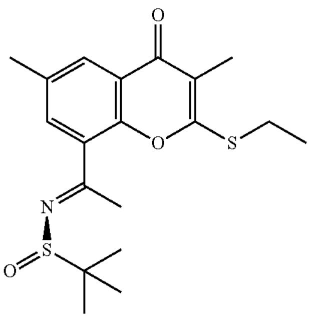 | 380 [M + H]$^+$ |

Intermediate 287: (NE,R)—N-[1-(2-Ethylsulfanyl-3,6-dimethyl-4-oxo-chromen-8-yl)ethylidene]-2-methyl-propane-2-sulfinamide

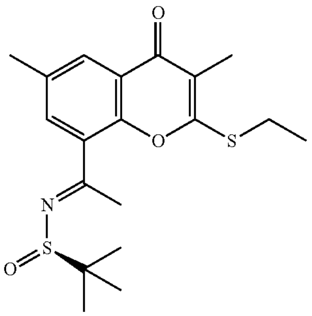 [SMILES: CCSc1oc2c(/C(C)=N/[S@](=O)C(C)(C)C)cc(C)cc2c(=O)c1C]

A mixture of 8-acetyl-2-ethylsulfanyl-3,6-dimethyl-chromen-4-one (50 g, 0.18 mol) in 500 mL of toluene was treated with (R)-2-methylpropane-2-sulfinamide (32.7 g, 0.27 mol) and titanium ethoxide (82.1 g, 0.36 mol) in one portion. The reaction was heated at 80° C. for 24 h. The reaction was allowed to cool to rt and then taken on to the reduction step without workup or purification.

Intermediate 111: N-[(1R)-1-[2-Ethylsulfanyl-4-oxo-6-(trifluoromethyl)chromen-8-yl]ethyl]-2-methyl-propane-2-sulfinamide

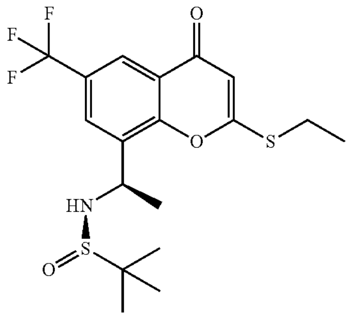

A solution of (NE)-N-[1-[2-ethylsulfanyl-4-oxo-6-(trifluoromethyl)chromen-8-yl]ethylidene]-2-methyl-propane-2-sulfinamide (6.72 g, 16 mmol) in methanol (100 mL) was treated with cerium(III) chloride heptahydrate (2.98 g, 8.01 mmol) and cooled to −70° C. When cold, the reaction was treated with sodium borohydride (1.21 g, 32 mmol) in one portion and allowed to stir at −70° C. After 2 h, the reaction was quenched with saturated aqueous ammonium chloride and extracted with dichloromethane. The organics were collected, concentrated, and the residue purified by silica gel chromatography eluted with 30% to 90% ethyl acetate in heptane. The diastereomers were then separated by reversed phase chromatography (C18) eluted with 15% to 70% acetonitrile in water (with 10 mM ammonium carbonate and 10% methanol) to give the product (1.67 g, 25%). MS ES+ m/z 422 [M+H]$^+$.

The following compounds in Table 8 were made in a similar way as described for Intermediate 111.

TABLE 8

| Int # | Chemical Name | Structure | MS ES+ m/z |
|---|---|---|---|
| 288 | (R)-N-[(1R)-1-(2-Ethylsulfanyl-6-methyl-4-oxo-chromen-8-yl)ethyl]-2-methyl-propane-2-sulfinamide | 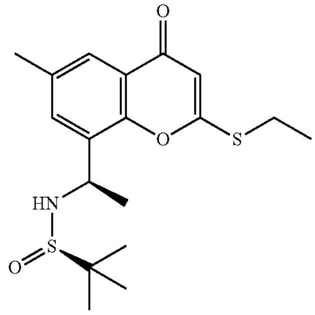 [SMILES: CCSc1cc(=O)c2cc(C)cc([C@@H](C)N[S@](=O)C(C)(C)C)c2o1] | 368 $[M + H]^+$ |
| 289 | (R)-N-[(1R)-1-(2-Ethylsulfanyl-3,6-dimethyl-4-oxo-chromen-8-yl)ethyl]-2-methyl-propane-2-sulfinamide | 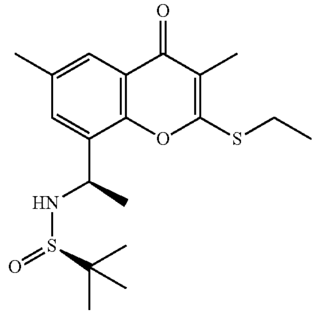 [SMILES: CCSc1oc2c([C@@H](C)N[S@](=O)C(C)(C)C)cc(C)cc2c(=O)c1C] | 382 $[M + H]^+$ |

Intermediate 290: (R)—N-[(1R)-1-(2-Ethylsulfanyl-3,6-dimethyl-4-oxo-chromen-8-yl)ethyl]-2-methyl-propane-2-sulfinamide

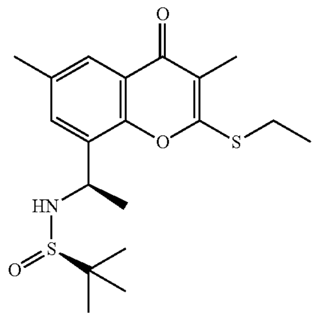 [SMILES: CCSc1oc2c([C@@H](C)N[S@](=O)C(C)(C)C)cc(C)cc2c(=O)c1C]

The toluene solution of (NE,R)—N-[1-(2-ethylsulfanyl-3,6-dimethyl-4-oxo-chromen-8-yl)ethylidene]-2-methyl-propane-2-sulfinamide (0.18 mol) was cooled to between −10° C. and 0° C. and treated in portions with sodium borohydride (20.4 g, 0.54 mmol) keeping the internal temperature below 0° C. After stirring at −10° C. and 0° C. for 1 h, the reaction was quenched with saturated aqueous $NH_4Cl$. The resulting white slurry was filtered through Celite and the solids washed with THF. The filtrate was washed with brine and the organic layer concentrated onto silica gel. The material was purified by chromatography to give the product (26 g, 37% over two steps). MS ES+ m/z 382 $[M+H]^+$.

Intermediate 112: tert-Butyl 2-[8-acetyl-4-oxo-6-(trifluoromethyl)chromen-2-yl]indole-1-carboxylate

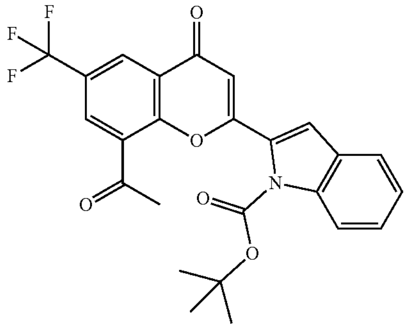 [SMILES: CC(=O)c1cc(C(F)(F)F)cc2c(=O)cc(-c3cc4ccccc4n3C(=O)OC(C)(C)C)oc12]

8-Acetyl-2-ethylsulfanyl-6-(trifluoromethyl)chromen-4-one (0.50 g, 1.58 mmol), (1-tert-butoxycarbonylindol-2-yl) boronic acid (1.03 g, 3.95 mmol), tetrakis(triphenylphosphine)palladium(0) (0.27 g, 0.24 mmol), copper(I) thiophene-2-carboxylate (0.66 g, 3.48 mmol), and cesium carbonate (1.03 g, 3.16 mmol) were combined in 1,4-dioxane (8 mL). The reaction was degassed with argon gas for 5 min and then stirred at 90° C. overnight. The reaction was concentrated and the residue purified by silica gel chromatography eluted with 0% to 100% ethyl acetate in heptane to give the product (0.25 g, 34%). MS ES+ m/z 472 $[M+H]^+$.

Intermediate 291: 8-Acetyl-3,6-dimethyl-2-pyrazolo[1,5-a]pyridin-6-yl-chromen-4-one

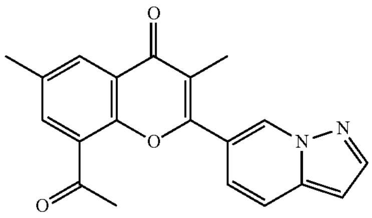 [SMILES: CC(=O)c1cc(C)cc2c(=O)c(C)c(-c3ccc4ccnn4c3)oc12]

8-Acetyl-2-ethylsulfanyl-3,6-dimethyl-chromen-4-one (3.0 g, 10.86 mmol), 6-(4,4,5,5-tetramethyl-1,3,2-dioxaborolan-2-yl)pyrazolo[1,5-a]pyridine (2.64 g, 10.82 mmol), copper(I) thiophene-2-carboxylic acid (3.12 g, 16.28 mmol) and tetrakis(triphenylphosphine)palladium(0) were suspended in EtOH (30 mL), flushed with $N_2$ gas for 1 min, and heated at reflux for 18 h. After cooling to rt, the reaction was treated with 50 mL of 1M aqueous HCl and extracted with 100 mL of EtOAc. The organic layer was washed with brine, concentrated, and the residue purified by silica gel chromatography eluted with 50% EtOAc in heptane. The resulting solid was triturated with AcCN to give the product as a light yellow solid (2.50 g, 69%) after filtration. MS ES+ m/z 333 [M+H]+.

Intermediate 113: 8-Acetyl-2-ethylsulfinyl-6-(trifluoromethyl)chromen-4-one

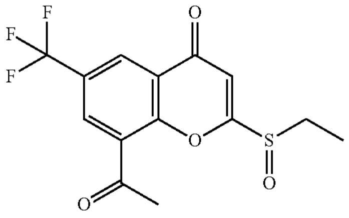 [SMILES: CCS(=O)c1cc(=O)c2cc(C(F)(F)F)cc(C(C)=O)c2o1]

8-Acetyl-2-ethylsulfanyl-6-(trifluoromethyl)chromen-4-one (5.07 g, 16.01 mmol) was dissolved in dichloromethane (80 mL) and cooled in an ice bath. When cold, the reaction was treated with solid mCPBA (5.38 g, 77%, 24.02 mmol) and allowed to stir at 0° C. After 90 min, the reaction was diluted with 100 mL of dichloromethane, 50 mL of water, and 50 mL of saturated sodium thiosulfate solution. The layers were separated and the remaining aqueous layer extracted twice with dichloromethane. The organic layers were combined, washed with brine, collected, dried over $MgSO_4$, filtered, and concentrated. The residue was purified by silica gel chromatography eluted with 0% to 100% ethyl acetate in heptane to give the product (3.36 g, 63%) as a white solid. MS ES+ m/z 333 $[M+H]^+$.

Intermediate 114: 8-Acetyl-2-bromo-6-(trifluoromethyl)chromen-4-one

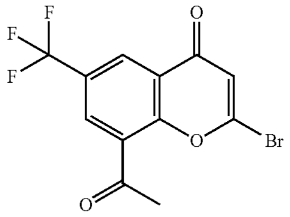 [SMILES: CC(=O)c1cc(C(F)(F)F)cc2c(=O)cc(Br)oc12]

8-Acetyl-2-ethylsulfinyl-6-(trifluoromethyl)chromen-4-one (3.28 g, 9.87 mmol) in 165 mL of dichloromethane was treated with N-benzyl-N,N,N-triethylammonium bromide (1.34 g, 4.94 mmol) and hydrogen bromide (8.32 g, 48% wt, 49.35 mmol) and allowed to stir at rt. After 2 h, another 2 mL of hydrogen bromide was added and stirring continued at rt. After 2 h, the reaction was neutralized with saturated aqueous sodium bicarbonate and the layers separated. The remaining aqueous layer was extracted twice with fresh dichloromethane. The organics were combined, washed with brine, collected, dried over $MgSO_4$, filtered, and concentrated. The residue was purified by silica gel chromatography eluted with 0% to 35% ethyl acetate in heptane to give the product (2.75 g, 83%) as a white solid. MS ES+ m/z 335 $[M+H]^+$.

The following compounds in Table 9 were made in a similar way as described for Intermediate 114.

TABLE 9

| Int # | Chemical Name | Structure | MS ES+ m/z |
|---|---|---|---|
| 115 | tert-Butyl 2-[1-(2-bromo-6-methyl-4-oxo-chromen-8-yl)ethylamino]benzoate, Isomer 2 | 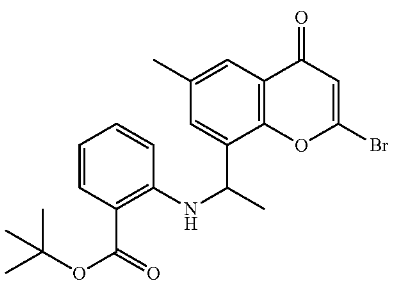 [SMILES: Cc1cc(C(C)Nc2ccccc2C(=O)OC(C)(C)C)c2oc(Br)cc(=O)c2c1] | 458/460 $[M + H]^+$ |

Intermediate 6: 2-Ethylsulfanyl-8-(1-hydroxyethyl)-6-methyl-chromen-4-one

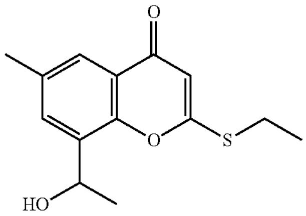 [SMILES: CCSc1cc(=O)c2cc(C)cc(C(C)O)c2o1]

A solution of 8-acetyl-2-ethylsulfanyl-6-methyl-chromen-4-one (8.30 g, 31.6 mmol) in DCM (30 mL) and MeOH (30 mL) was treated with $NaBH_4$ (1.32 g, 34.8 mmol) in portions at 0° C., and stirred at 15° C. for 1 h. The mixture was diluted with water (50 mL) and extracted with DCM (2×100 mL). The combined organic extracts were washed with brine (80 mL), dried over anhydrous $Na_2SO_4$, filtered, and concentrated. The residue was purified via silica gel chromatography eluted with 0%-4% MeOH in DCM to give the product as a solid (6.0 g, 60%). MS ES+ m/z 265 $[M+H]^+$.

The following compounds in Table 10 were made in a similar way as described for Intermediate 6.

TABLE 10

| Int # | Chemical Name | Structure | MS ES+ m/z |
|---|---|---|---|
| 116 | 2-Ethylsulfanyl-8-(1-hydroxyethyl)-6-(trifluoromethyl)-chromen-4-one | 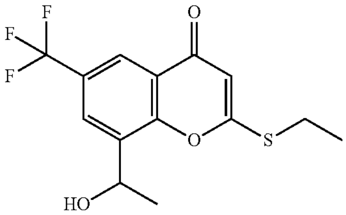 [SMILES: CCSc1cc(=O)c2cc(C(F)(F)F)cc(C(C)O)c2o1] | 319 $[M + H]^+$ |
| 117 | 2-Ethylsulfanyl-6-fluoro-8-(1-hydroxyethyl)-chromen-4-one | 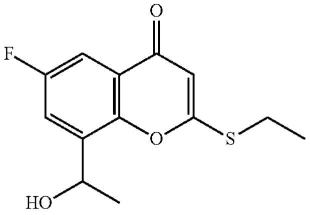 [SMILES: CCSc1cc(=O)c2cc(F)cc(C(C)O)c2o1] | 269 $[M + H]^+$ |
| 118 | 2-Ethylsulfanyl-6-fluoro-8-(1-hydroxyethyl)-3-methyl-chromen-4-one | 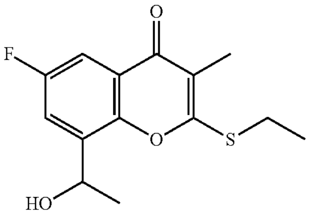 [SMILES: CCSc1oc2c(C(C)O)cc(F)cc2c(=O)c1C] | |
| 119 | tert-Butyl 2-[8-(1-hydroxyethyl)-4-oxo-6-(trifluoromethyl)-chromen-2-yl]indole-1-carboxylate | 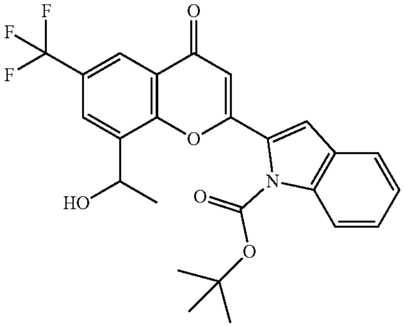 [SMILES: CC(O)c1cc(C(F)(F)F)cc2c(=O)cc(-c3cc4ccccc4n3C(=O)OC(C)(C)C)oc12] | 474 $[M + H]^+$ |

TABLE 10-continued

| Int # | Chemical Name | Structure | MS ES+ m/z |
|---|---|---|---|
| 120 | 2-Ethylsulfanyl-8-(1-hydroxyethyl)-3,6-dimethyl-chromen-4-one | 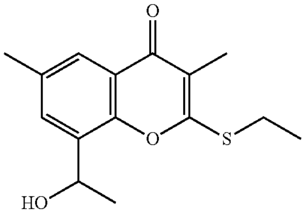 [SMILES: CCSc1oc2c(C(C)O)cc(C)cc2c(=O)c1C] | |

Intermediate 121: 2-Ethylsulfanyl-8-(1-hydroxyethyl)-6-methyl-chromen-4-one

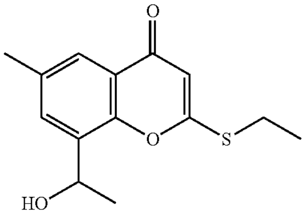 [SMILES: CCSc1cc(=O)c2cc(C)cc(C(C)O)c2o1]

A stirring solution of 8-acetyl-2-ethylsulfanyl-6-methyl-chromen-4-one (34.65 g, 132.1 mmol) in dichloromethane (520 mL) was treated with triethylamine (26.7 g, 264.2 mmol) and formic acid (18.2 g, 396.3 mmol). Added RuCl (p-cymene)[(S,S)-Ts-DPEN] (CAS 192139-90-5, 0.82 g, 1.32 mmol) as a solid, cooled the reaction in an ice bath, and purged the reaction with argon gas. After stirring at 0° C. for about 5 min, removed the reaction from the ice bath and allowed the reaction to stir and gradually warm to rt. After stirring overnight at rt, diluted the reaction with ethyl acetate and water to give a thick mixture which was stirred overnight. Filtered the mixture and washed the solids with water and heptane to give the product (28.75 g, 82.3%) as a light tan solid. MS ES+ m/z 265 $[M+H]^+$.

The following compounds in Table 11 were made in a similar way as described for Intermediate 121.

TABLE 11

| Int # | Chemical Name | Structure | MS ES+ m/z |
|---|---|---|---|
| 122 | 2-Bromo-8-(1-hydroxyethyl)-6-(trifluoromethyl)-chromen-4-one | 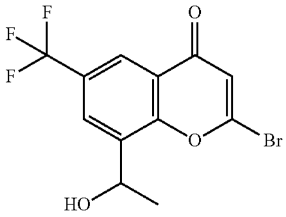 [SMILES: CC(O)c1cc(C(F)(F)F)cc2c(=O)cc(Br)oc12] | 337 $[M + H]^+$ |
| 123 | 2-Ethylsulfanyl-8-(1-hydroxyethyl)-6-(trifluoromethyl)-chromen-4-one | 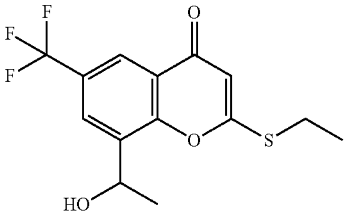 [SMILES: CCSc1cc(=O)c2cc(C(F)(F)F)cc(C(C)O)c2o1] | |

Intermediate 292: 8-[(1R)-1-Hydroxyethyl]-3,6-dimethyl-2-pyrazolo[1,5-a]pyridin-6-yl-chromen-4-one

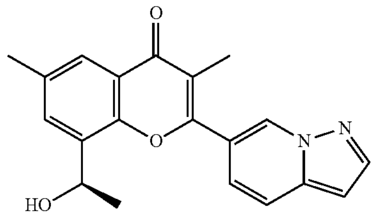 [SMILES: Cc1cc([C@@H](C)O)c2oc(-c3ccc4ccnn4c3)c(C)c(=O)c2c1]

A DCM solution (20 mL) of 8-acetyl-3,6-dimethyl-2-pyrazolo[1,5-a]pyridin-6-yl-chromen-4-one (2.0 g, 6.02 mmol) under a $N_2$ atmosphere was cooled to around −5° C. When cold, added RuCl(p-cymene)[(R,R)-Ts-DPEN] (CAS 192139-92-7, 0.19 g, 0.30 mmol) and formic acid (0.86 g, 17.99 mmol) in one portion. DBU (2.74 g, 17.99 mmol) was then added dropwise keeping the internal temperature below 0° C. After addition was complete, the reaction was stirred at rt for 18 h. The reaction was diluted with 10 mL of DCM, washed with water and brine, and the organic layer concentrated. The resulting residue was purified by silica gel chromatography eluted with 50% ethyl acetate in heptane to give the product (1.70 g, 84%) as a light yellow solid. MS ES+ m/z 335 $[M+H]^+$.

Intermediate 293: 8-[(1S)-1-Chloroethyl]-3,6-dimethyl-2-pyrazolo[1,5-a]pyridin-6-yl-chromen-4-one

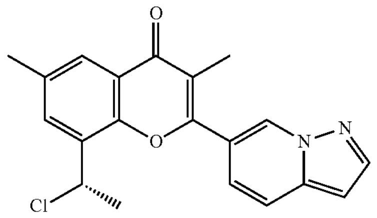 [SMILES: Cc1cc([C@H](C)Cl)c2oc(-c3ccc4ccnn4c3)c(C)c(=O)c2c1]

Cyanuric chloride (0.11 g, 5.63 mmol) was added to DMF (0.1 mL) and stirred at rt for 30 min. A DCM solution (5 mL) of 8-[(1R)-1-hydroxyethyl]-3,6-dimethyl-2-pyrazolo[1,5-a]pyridin-6-yl-chromen-4-one (1.70 g, 5.08 mmol) was added in portions and the resulting mixture stirred at rt for 4 h. The reaction was treated with 10 mL of saturated aqueous $Na_2CO_3$ and extracted with 30 mL of DCM. The organic layer was washed with brine, collected, and concentrated. The residue was purified by silica gel chromatography eluted with 50% EtOAc in heptane to give the product (0.80 g, 44%, 65% ee) as a light yellow solid. MS ES+ m/z 353 $[M+H]^+$.

Intermediate 124: 1-(2-Ethylsulfanyl-6-methyl-4-oxo-chromen-8-yl)ethyl methanesulfonate

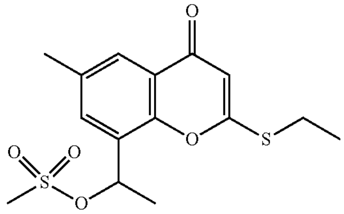 [SMILES: CCSc1cc(=O)c2cc(C)cc(C(C)OS(C)(=O)=O)c2o1]

2-Ethylsulfanyl-8-(1-hydroxyethyl)-6-methyl-chromen-4-one (8.0 g, 30.3 mmol) was dissolved in dichloromethane (35 mL), treated with triethylamine (4.59 g, 45.4 mmol), and cooled in an ice bath. When cold, the solution was treated dropwise over 10 min with methanesulfonic anhydride (6.33 g, 36.3 mmol). After 2 h, the reaction was diluted with 120 mL of dichloromethane, 75 mL of water, and 75 mL of saturated aqueous sodium bicarbonate in a separatory funnel. After removal of the organic layer, the remaining aqueous layer was re-extracted twice with dichloromethane. The organic layers were combined, dried over $MgSO_4$, filtered, and concentrated to provide the product (10.04 g, 97%) as a tan solid which was used without purification.

The following compounds in Table 12 were made in a similar way as described for Intermediate 124.

TABLE 12

| Int # | Chemical Name | Structure | MS ES+ m/z |
|---|---|---|---|
| 125 | 1-[2-Ethylsulfanyl-4-oxo-6-(trifluoromethyl)-chromen-8-yl]ethyl methanesulfonate | 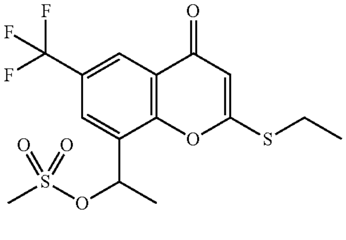 [SMILES: CCSc1cc(=O)c2cc(C(F)(F)F)cc(C(C)OS(C)(=O)=O)c2o1] | 397 $[M + H]^+$ |
| 126 | 1-[2-Bromo-4-oxo-6-(trifluoromethyl)-chromen-8-yl]ethyl methanesulfonate | 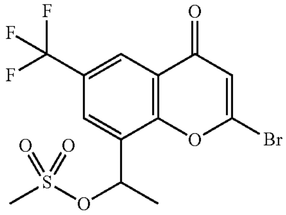 [SMILES: CC(OS(C)(=O)=O)c1cc(C(F)(F)F)cc2c(=O)cc(Br)oc12] | 415 $[M + H]^+$ |

Intermediate 127: 8-(1-Azidoethyl)-2-ethylsulfanyl-6-methyl-chromen-4-one

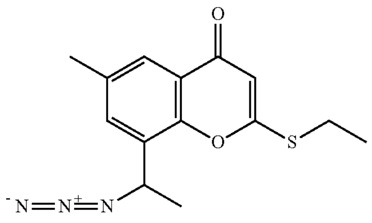

A solution of 1-(2-ethylsulfanyl-6-methyl-4-oxo-chromen-8-yl)ethyl methanesulfonate (5.0 g, 14.6 mmol) in anhydrous dimethyl sulfoxide (50 mL) was treated with solid sodium azide (1.14 g, 17.5 mmol) and warmed to 80° C. After 2 h, the reaction was diluted with water to form a thick white suspension. Extracted 3 times with ethyl acetate. The combined organics were washed with brine, collected, dried over $Na_2SO_4$ and $MgSO_4$, filtered, and concentrated to provide the product (4.3 g, 100%) as a pale amber oil which was used without purification.

Intermediate 128: 8-(1-Aminoethyl)-2-ethylsulfanyl-6-methyl-chromen-4-one

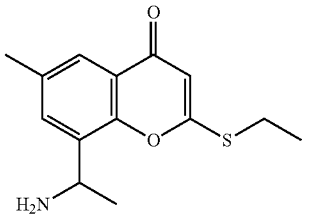 [SMILES: CCSc1cc(=O)c2cc(C)cc(C(C)N)c2o1]

8-(1-Azidoethyl)-2-ethylsulfanyl-6-methyl-chromen-4-one (4.3 g, 15.0 mmol) was dissolved in THF (75 mL) and water (25 mL), treated with polymer bound triphenylphosphine (~3 mmol/g, 7.85 g, 29.9 mmol), and stirred at 60° C. After 6 h, the reaction was filtered and the resin washed with 50 mL of THF and 30 mL of 50% MeOH in dichloromethane. The filtrate was concentrated to provide the product (3.95 g, 95%) as a light orange oil that crystallized overnight. MS ES+ m/z 264 $[M+H]^+$.

Intermediate 129: 8-[(1R)-1-Aminoethyl]-2-ethylsulfanyl-6-(trifluoromethyl)chromen-4-one

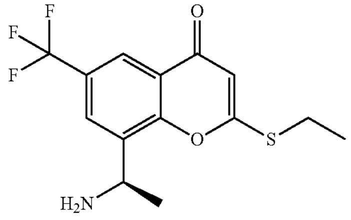 [SMILES: CCSc1cc(=O)c2cc(C(F)(F)F)cc([C@@H](C)N)c2o1]

A solution of N-[(1R)-1-[2-ethylsulfanyl-4-oxo-6-(trifluoromethyl)chromen-8-yl]ethyl]-2-methyl-propane-2-sulfinamide (1.63 g, 3.87 mmol) in dichloromethane (25 mL) was treated with 4M aqueous HCl (5.97 g, 3.87 mL, 15.5 mmol) and allowed to stir overnight at rt. The pH of the reaction was neutralized with saturated aqueous sodium bicarbonate (200 mL) and extracted with 20% isopropanol in chloroform until the product had been completely extracted. The organics were combined, dried over $MgSO_4$, filtered, and concentrated. The residue was passed through an SCX-2 column to remove non-polar impurities and then purified by silica gel chromatography eluted with 10% to 20% methanol in dichloromethane followed by 30% 1M $NH_3$ in MeOH in dichloromethane to obtain the product (0.71 g 58%). MS ES+ m/z 318 $[M+H]^+$.

The following compounds in Table 13 were made in a similar way as described for Intermediate 129.

TABLE 13

| Int # | Chemical Name | Structure | MS ES+ m/z |
|---|---|---|---|
| 294 | 8-[(1R)-1-Aminoethyl]-2-ethylsulfanyl-6-methyl-chromen-4-one | 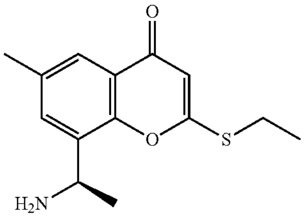 [SMILES: CCSc1cc(=O)c2cc(C)cc([C@@H](C)N)c2o1] | 264 $[M + H]^+$ |
| 295 | 8-[(1R)-1-Aminoethyl]-2-ethylsulfanyl-3,6-dimethyl-chromen-4-one | 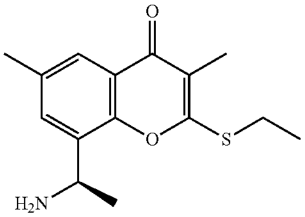 | 278 $[M + H]^+$ |

Intermediate 296: 8-[(1R)-1-aminoethyl]-2-ethylsulfanyl-3,6-dimethyl-chromen-4-one

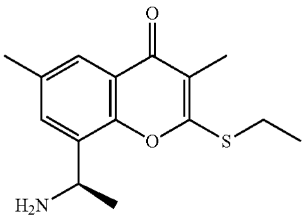 [SMILES: CCSc1oc2c([C@@H](C)N)cc(C)cc2c(=O)c1C]

A solution of (R)—N-[(1R)-1-(2-ethylsulfanyl-3,6-dimethyl-4-oxo-chromen-8-yl)ethyl]-2-methyl-propane-2-sulfinamide (20 g, 52.4 mmol) in THE (200 mL) was treated dropwise with 12 M aqueous HCl (2 eq) and allowed to stir at rt. After 1 h, the reaction was concentrated, the residue dissolved in water and extracted with MTBE. The pH of the aqueous phase was adjusted to between 9 and 10 with 1M aqueous NaOH and extracted with EtOAc. The organic layer was washed with brine, dried over $MgSO_4$, filtered, and concentrated to give the product (12.6 g, 87%) as a white solid. MS ES+ m/z 278 $[M+H]^+$.

Intermediate 297: 8-[(1R)-1-Aminoethyl]-2-ethylsulfanyl-6-methyl-chromen-4-one

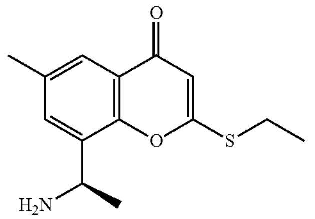 [SMILES: CCSc1cc(=O)c2cc(C)cc([C@@H](C)N)c2o1]

Pyridoxal 5'-phosphate monohydrate (200 mg, 0.81 mmol) was added to a mixture of PBS buffer pentan-3-amine (38.12 mmol, 600 mL) and ATA-154 (transaminase enzyme, 5 g) at rt until dissolved. Added a solution of 8-acetyl-2-ethylsulfanyl-6-methyl-chromen-4-one (10 g, 38.12 mmol) in DMSO (300 mL) and stirred the reaction at 45° C. for 72 h. The pH of the reaction was adjusted to 3 with 2 M aqueous HCl and extracted with EtOAc (2×500 mL). The pH of the aqueous layer was then adjusted to 10 with 1 M KOH and extracted with EtOAc (3×500 mL). The combined organic layers were washed with brine (3×500 mL), dried over $Na_2SO_4$, filtered, and concentrated. The resulting residue was purified by silica gel chromatography eluted with 0% to 2% MeOH in DCM to give the product (6 g, 60%) as a yellow solid. MS ES+ m/z 264 $[M+H]^+$.

Intermediate 298: tert-Butyl N-[(1R)-1-(2-ethylsulfanyl-3,6-dimethyl-4-oxo-chromen-8-yl)ethyl]carbamate

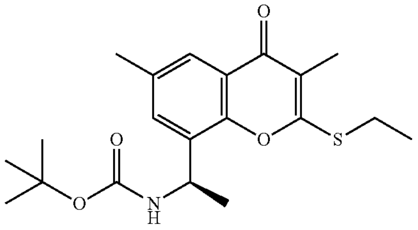 [SMILES: CCSc1oc2c([C@@H](C)NC(=O)OC(C)(C)C)cc(C)cc2c(=O)c1C]

A mixture of 8-[(1R)-1-aminoethyl]-2-ethylsulfanyl-3,6-dimethyl-chromen-4-one (2.5 g, 9.0 mmol) and diisopropylethylamine (2.0 g, 16 mmol) in dichloromethane (40 mL) was treated with di-tert-butyl dicarbonate (3.0 g, 14 mmol) and stirred overnight at rt. Concentrated the reaction and purified the residue by silica gel chromatography eluted with 0% to 100% EtOAc in heptane to give the product (2.5 g, 73%). MS ES+ m/z 378 $[M+H]^+$.

The following compounds in Table 14 were made in a similar way as described for Intermediate—.

TABLE 14

| Int # | Chemical Name | Structure | MS ES+ m/z |
|---|---|---|---|
| 299[1] | tert-Butyl N-[(1R)-1-(2-ethylsulfanyl-6-methyl-4-oxo-chromen-8-yl)ethyl]carbamate | 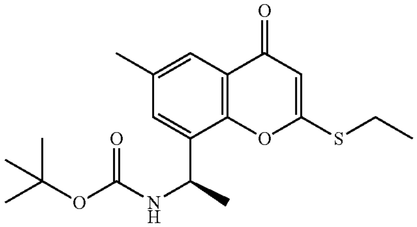 [SMILES: CCSc1cc(=O)c2cc(C)cc([C@@H](C)NC(=O)OC(C)(C)C)c2o1] | 364 $[M + H]^+$ |

[1]Triethylamine used as the base for this reaction.

Intermediate 300: tert-Butyl N-[(1R)-1-[3,6-dimethyl-2-(2-methylindazol-5-yl)-4-oxo-chromen-8-yl]ethyl]carbamate

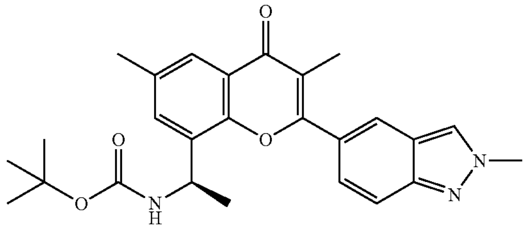 [SMILES: Cc1cc([C@@H](C)NC(=O)OC(C)(C)C)c2oc(-c3ccc4nn(C)cc4c3)c(C)c(=O)c2c1]

A mixture of tert-butyl N-[(1R)-1-(2-ethylsulfanyl-3,6-dimethyl-4-oxo-chromen-8-yl)ethyl]carbamate (500 mg, 1.32 mmol), (2-methylindazol-5-yl)boronic acid (466 mg, 2.65 mmol), copper(I) thiophene-2-carboxylate (758 mg, 3.97 mmol), cesium carbonate (1.29 g, 1.99 mmol), and tetrakis(triphenylphosphine)palladium(0) (765 mg, 0.66 mmol) in 10 mL of 2-methyltetrahydrofuran was degassed for 5 min with argon and then stirred at 90° C. for 16 h. Cooled the reaction to rt, diluted with EtOAc, and purified by silica gel chromatography eluted with EtOAc in heptane to give the product (250 mg, 42%) as a white solid. MS ES+ m/z 448 $[M+H]^+$.

Intermediate 301: tert-Butyl N-[(1R)-1-[3,6-dimethyl-2-(1-methylindazol-3-yl)-4-oxo-chromen-8-yl]ethyl]carbamate

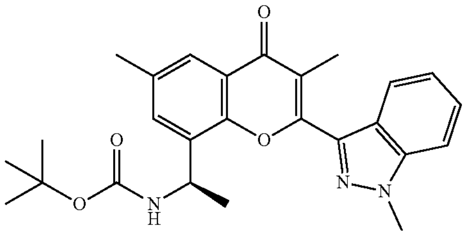 [SMILES: Cc1cc([C@@H](C)NC(=O)OC(C)(C)C)c2oc(-c3nn(C)c4ccccc34)c(C)c(=O)c2c1]

A mixture of tert-butyl N-[(1R)-1-(2-ethyl sulfanyl-3,6-dimethyl-4-oxo-chromen-8-yl)ethyl]carbamate (300 mg, 0.79 mmol), 3-bromo-1-methyl-indazole (503.19 mg, 2.38 mmol), bis(pinacolato)diboron (1.21 g, 4.77 mmol), copper (I) thiophene-2-carboxylate (606.17 mg, 3.18 mmol), cesium carbonate (1.29 g, 3.97 mmol), RuPhos Pd G3 (199.40 mg, 0.24 mmol), and XPhos Pd G3 (201.80 mg, 0.24 mmol) in 1,4-dioxane (6 mL) and water (0.1 mL) was stirred at 100° C. for 52 h. Allowed the reaction to cool to rt, concentrated, and purified the residue by silica gel chromatography eluted with 0% to 30% EtOAc in petroleum ether to give the crude product (650 mg) as a white solid. MS ES+ m/z 448 $[M+H]^+$.

The following compounds in Table 15 were made in a similar way as described for Intermediate 301.

TABLE 15

| Int # | Chemical Name | Structure | MS ES+ m/z |
|---|---|---|---|
| 302 | tert-Butyl N-[(1R)-1-[3,6-dimethyl-4-oxo-2-(1H-pyrrolo[2,3-b]pyridin-2-yl)chromen-8-yl]ethyl]carbamate | 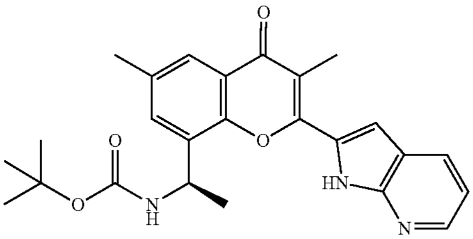 [SMILES: Cc1cc([C@@H](C)NC(=O)OC(C)(C)C)c2oc(-c3cc4cccnc4[nH]3)c(C)c(=O)c2c1] | 434 $[M + H]^+$ |

Intermediate 303: tert-Butyl N-[(1R)-1-[3,6-dimethyl-2-(2-methylthiazolo[5,4-b]pyridin-5-yl)-4-oxo-chromen-8-yl]ethyl]carbamate

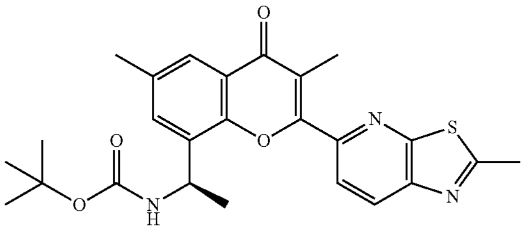 [SMILES: Cc1cc([C@@H](C)NC(=O)OC(C)(C)C)c2oc(-c3ccc4nc(C)sc4n3)c(C)c(=O)c2c1]

A mixture of tert-butyl N-[(1R)-1-(2-ethyl sulfanyl-3,6-dimethyl-4-oxo-chromen-8-yl)ethyl]carbamate (700 mg, 1.85 mmol), 5-chloro-2-methyl-thiazolo[5,4-b]pyridine (513.59 mg, 2.78 mmol), bis(pinacolato)diboron (1.18 g, 4.64 mmol), copper(I) thiophene-2-carboxylate (1.06 g, 5.56 mmol), BrettPhos Pd G3 (168.09 mg, 0.18 mmol), sodium tert-butoxide (891.03 mg, 9.27 mmol), and [1,3-bis(diphenylphosphino)propane]dichloronickel(II) (100.51 mg, 0.18 mmol) in 20 mL if 1,4-dioxane was stirred at 100° C. under $N_2$ for 20 h. The reaction was allowed to cool to rt, filtered, and the solids washed with 10 mL of dichloromethane. The filtrate was concentrated and the residue purified by silica gel chromatography eluted with 0% to 35% EtOAc in petroleum ether to give the product (300 mg, 35%) as a light yellow solid. MS ES+m/z 466 $[M+H]^+$.

The following compounds in Table 16 were made in a similar way as described for Intermediate 303.

TABLE 16

| Int # | Chemical Name | Structure | MS ES+ m/z |
|---|---|---|---|
| 304 | tert-Butyl N-[(1R)-1-[6-methyl-2-(2-methylthiazolo[5,4-b]pyridin-5-yl)-4-oxo-chromen-8-yl]ethyl]carbamate | 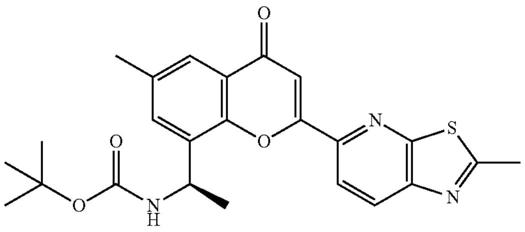 [SMILES: Cc1cc([C@@H](C)NC(=O)OC(C)(C)C)c2oc(-c3ccc4nc(C)sc4n3)cc(=O)c2c1] | 452 [M + H]$^+$ |

Intermediate 305: 8-[(1R)-1-Aminoethyl]-3,6-dimethyl-2-(2-methylindazol-5-yl)chromen-4-one

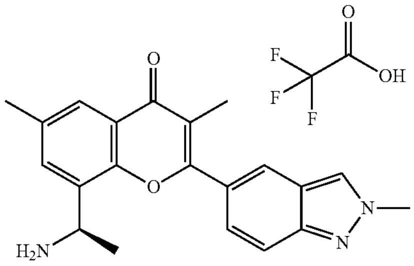

A mixture of tert-butyl N-[(1R)-1-[3,6-dimethyl-2-(2-methylindazol-5-yl)-4-oxo-chromen-8-yl]ethyl]carbamate (250 mg, 0.56 mmol) in dichloromethane (2 mL) was treated with 2 mL of TFA and stirred at rt for 2 h. Concentrated the reaction and purified the residue by reversed phase chromatography eluted with AcCN (0.1% TFA) in water (0.1% TFA) to give the product (200 mg, 103%) as a white solid. MS ES+ m/z 348 [M+H]$^+$.

The following compounds in Table 17 were made in a similar way as described for Intermediate 305.

TABLE 17

| Int # | Chemical Name | Structure | MS ES+ m/z |
|---|---|---|---|
| 306 | 8-[(1R)-1-Aminoethyl]-3,6-dimethyl-2-(1-methylindazol-3-yl)chromen-4-one | 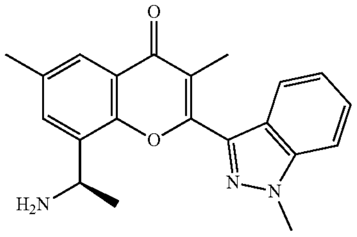 [SMILES: Cc1cc([C@@H](C)N)c2oc(-c3nn(C)c4ccccc34)c(C)c(=O)c2c1] | 348 [M + H]$^+$ |
| 307 | 8-[(1R)-1-Aminoethyl]-3,6-dimethyl-2-(2-methylthiazolo[5,4-b]pyridin-5-yl)chromen-4-one | 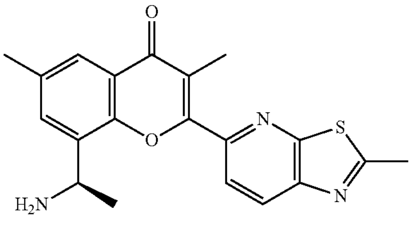 | 366 [M + H]$^+$ |
| 308 | 8-[(1R)-1-Aminoethyl]-3,6-dimethyl-2-(1H-pyrrolo[2,3-b]pyridin-2-yl)chromen-4-one | 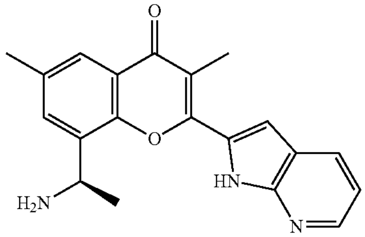 [SMILES: Cc1cc([C@@H](C)N)c2oc(-c3cc4cccnc4[nH]3)c(C)c(=O)c2c1] | 334 [M + H]$^+$ |

TABLE 17-continued

| Int # | Chemical Name | Structure | MS ES+ m/z |
|---|---|---|---|
| 309 | 8-[(1R)-1-Aminoethyl]-6-methyl-2-(2-methylthiazolo[5,4-b]pyridin-5-yl)chromen-4-one | 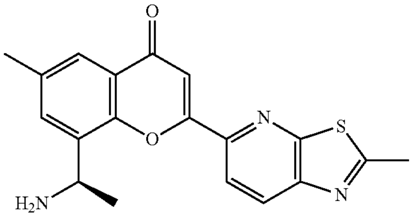 | 352 $[M + H]^+$ |

Intermediate 7: 8-(1-Bromoethyl)-2-ethylsulfanyl-6-methyl-chromen-4-one

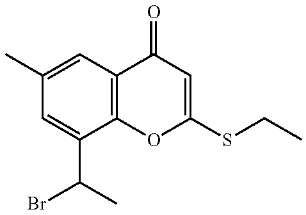 [SMILES: CCSc1cc(=O)c2cc(C)cc(C(C)Br)c2o1]

A mixture of 2-ethylsulfanyl-8-(1-hydroxyethyl)-6-methyl-chromen-4-one (5.50 g, 20.8 mmol) in DCM (50 mL) was treated dropwise with $PBr_3$ (16.9 g, 62.4 mmol) at 0° C., then stirred at 30° C. for 4 h. The reaction was quenched with water (20 mL) at 0° C. and the pH adjusted to 8 with saturated aqueous $NaHCO_3$. The mixture was extracted with DCM (2×80 mL). The combined organic extracts were washed with brine, dried over anhydrous $Na_2SO_4$, filtered, and concentrated to give the product as an oil (4.7 g, 61%). MS ES+ m/z 329 $[M+2+H]^+$.

The following compounds in Table 18 were made in a similar way as described for Intermediate 7.

TABLE 18

| Int # | Chemical Name | Structure | MS ES+ m/z |
|---|---|---|---|
| 130 | 8-(1-Bromoethyl)-2-ethylsulfanyl-6-fluoro-chromen-4-one | 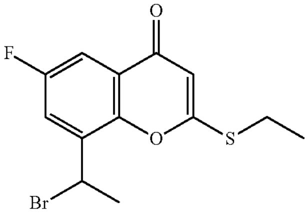 [SMILES: CCSc1cc(=O)c2cc(F)cc(C(C)Br)c2o1] | 331 $[M + H]^+$ |
| 131 | 8-(1-Bromoethyl)-2-ethylsulfanyl-6-fluoro-3-methyl-chromen-4-one | 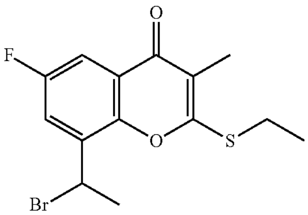 [SMILES: CCSc1oc2c(C(C)Br)cc(F)cc2c(=O)c1C] | |
| 132 | 8-(1-Bromoethyl)-2-(1H-indol-2-yl)-6-(trifluoromethyl)-chromen-4-one | 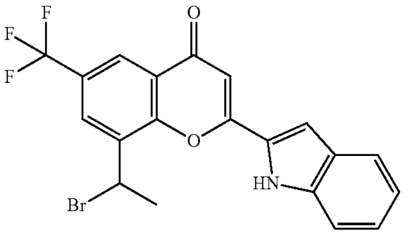 [SMILES: CC(Br)c1cc(C(F)(F)F)cc2c(=O)cc(-c3cc4ccccc4[nH]3)oc12] | |

TABLE 18-continued

| Int # | Chemical Name | Structure | MS ES+ m/z |
|---|---|---|---|
| 133 | 8-(1-Bromoethyl)-2-ethylsulfanyl-3,6-dimethyl-chromen-4-one | 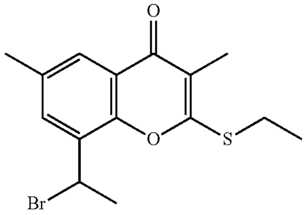 [SMILES: CCSc1oc2c(C(C)Br)cc(C)cc2c(=O)c1C] | |

Intermediate 8 and Intermediate 9: 2-[1-(2-Ethyl sulfanyl-6-methyl-4-oxo-chromen-8-yl)ethylamino] benzoic acid, Isomer 1 and Isomer 2

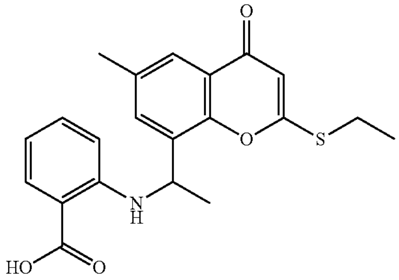 [SMILES: CCSc1cc(=O)c2cc(C)cc(C(C)Nc3ccccc3C(=O)O)c2o1]

A mixture of 8-(1-bromoethyl)-2-ethylsulfanyl-6-methyl-chromen-4-one (10 g, 31 mmol) and 2-aminobenzoic acid (8.38 g, 61.1 mmol) in DMF (70 mL) was stirred at 80° C. for 2 h. The reaction mixture was diluted with DCM (200 mL) and water (500 mL) and the pH adjusted to 11 with aq. NaOH (2 M). After removal of the organic layer, the aqueous layer was washed with MTBE (200 mL×2) and the pH adjusted to 3 with aq. HCl (2 M) to give a solid. After stirring for 0.5 h, the mixture was filtered and the filter cake was purified by chiral SFC using a Daicel ChiralCel OJ-H (250×30 mm; 5 μm) column using a gradient of 5%-50% MeOH with 0.1% aq $NH_3$ in $CO_2$ to give isomer 1 (5.4 g; 45%, 99.7% ee) and isomer 2 (4.9 g, 41%, 99.6% ee). MS ES+ m/z 384 $[M+H]^+$.

Intermediate 134 and Intermediate 135: 2-[1-(2-Ethylsulfanyl-3,6-dimethyl-4-oxo-chromen-8-yl) ethylamino]benzoic acid, Isomer 1 and Isomer 2

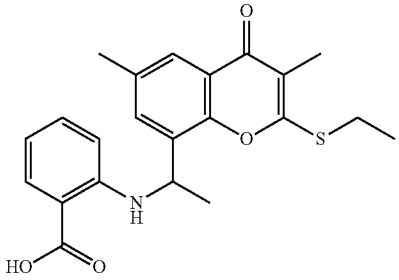 [SMILES: CCSc1oc2c(C(C)Nc3ccccc3C(=O)O)cc(C)cc2c(=O)c1C]

A mixture of 8-(1-bromoethyl)-2-ethylsulfanyl-3,6-dimethyl-chromen-4-one (330.0 g, 0.97 mol) in DMF (2.6 L) was treated with 2-aminobenzoic acid (132.6 g, 0.97 mol). The reaction mixture was stirred at 80° C. for 12 h to give a yellow solution. The mixture was added dropwise to $H_2O$ (6.6 L) and stirred at 20-25° C. for 1 h. This mixture was filtered and the cake was washed with ACN (1650 ml). Removed the product (330.0 g, racemate) as a yellow solid. The obtained racemate was used for chiral resolution to give Peak 1 (135.0 g) and Peak 2 (145.0 g).

Intermediate 10: 2-[1-(2-Ethylsulfinyl-6-methyl-4-oxo-chromen-8-yl)ethylamino]benzoic acid, Isomer 2

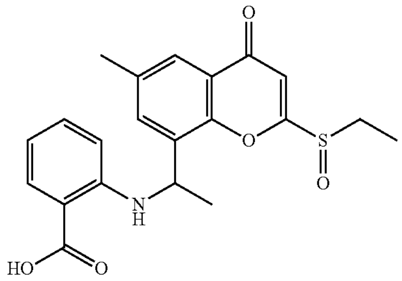 [SMILES: CCS(=O)c1cc(=O)c2cc(C)cc(C(C)Nc3ccccc3C(=O)O)c2o1]

A mixture of 2-[1-(2-ethylsulfanyl-6-methyl-4-oxo-chromen-8-yl)ethylamino]benzoic acid, Isomer 2 (850 mg, 2.22 mmol) in DCM (10 mL) was treated with m-CPBA (585 mg, 2.88 mmol, 85% purity) under $N_2$ at 0° C. The reaction was stirred at 25° C. for 2 h. The mixture was quenched with saturated $Na_2S_2O_3$ (10 mL) at 0° C. and the aqueous layer extracted with EtOAc (2×20 mL). The combined organic layers were washed with brine (3×20 mL), dried over anhydrous $Na_2SO_4$, filtered, and concentrated. The residue was purified via silica gel chromatography eluted with 0%-80% EtOAc in petroleum ether to give the product as a solid (410 mg, 42%). MS ES+ m/z 400 $[M+H]^+$.

Intermediate 136: 6-Bromo-1-tetrahydropyran-2-yl-indazole

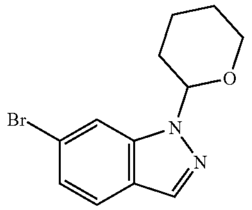

6-Bromo-1H-indazole (10.0 g, 50.8 mmol) and 3,4-dihydro-2H-pyran (8.54 g, 102 mmol) were dissolved in 100 mL of ethyl acetate, treated with methanesulfonic acid (0.49 g, 5.08 mmol), and stirred at 80° C. overnight. The dark reaction was allowed to cool to rt, diluted with 110 mL of ethyl acetate, and washed with water. The aqueous layer was re-extracted twice with 75 mL of ethyl acetate. The organics were dried over $Na_2SO_4$, filtered, and concentrated. The resulting thick oil was purified by silica gel chromatography eluted with 0% to 50% ethyl acetate in heptane giving a pale yellow solid (9.95 g, 70%). MS ES+ m/z 281/283 $[M+H]^+$.

The following compounds in Table 19 were made in a similar way as described for Intermediate 136.

TABLE 19

| Int # | Chemical Name | Structure | MS ES+ m/z |
|---|---|---|---|
| 137[a] | 6-Bromo-1-tetrahydropyran-2-yl-pyrazolo[3,4-b]pyridine | 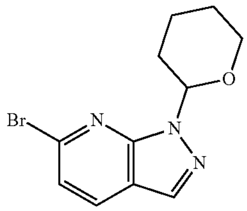 [SMILES: Brc1ccc2cnn(C3CCCCO3)c2n1] | Taken on to next step without MS being taken. |

[a]p-Toluenesulfonic acid used instead of methanesulfonic acid.

Intermediate 275: 6-Chloro-3-fluoro-pyridine-2-carbonyl chloride

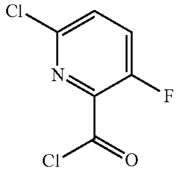 [SMILES: O=C(Cl)c1nc(Cl)ccc1F]

A mixture of 6-chloro-3-fluoro-pyridine-2-carboxylic acid (3.0 g, 17.09 mmol) in 60 mL of dichloromethane was treated with DMF (0.12 g, 1.71 mmol) and oxalyl chloride (4.34 g, 34.18 mmol) and stirred under nitrogen gas for 1.5 h. The reaction was concentrated and the residue (3.3 g, 100%) used in the next synthetic step without purification.

Intermediate 276: tert-Butyl 6-chloro-3-fluoro-pyridine-2-carboxylate

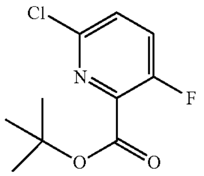

A mixture of 6-chloro-3-fluoro-pyridine-2-carbonyl chloride (3.3 g, 17.01 mmol) in 8 mL of THE was treated with pyridine (1.61 g, 20.41 mmol) and 2-methylpropan-2-ol (2.52 g, 34.02 mmol) and stirred under nitrogen at 25° C. for 2 h. The yellow suspension was concentrated and purified by silica gel chromatography eluted with 0% to 10% ethyl acetate in petroleum ether to give the product (3.6 g, 91%) as a colorless oil. $^1H$ NMR (400 MHz, DMSO-d6) δ ppm 1.61 (s, 9H), 7.42-7.46 (m, 1H), 7.47-7.52 (m, 1H).

Intermediate 277: Methyl 2,6-difluorobenzoate

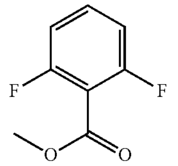

A mixture of 2,6-difluorobenzoic acid (5.8 g, 36.69 mmol) in 58 mL of methanol was treated with sulfuric acid (0.36 g, 3.67 mmol) and stirred at 65° C. for 18 h. The reaction was concentrated and the residue dissolved in 80 mL of dichloromethane. The organic layer was washed with saturated aqueous sodium bicarbonate, collected, dried over $Na_2SO_4$, filtered, and concentrated giving the product (5.08 g, 80%) as a yellow oil. $^1H$ NMR (400 MHz, $CDCl_3$) δ ppm 3.95 (s, 3H), 6.93-6.98 (m, 2H), 7.39-7.44 (m, 1H).

The following compounds in Table 20 were made in a similar way as described for Intermediate 277.

TABLE 20

| Int # | Chemical Name | Structure | MS ES+ m/z |
|---|---|---|---|
| 307 | Methyl 6-chloro-3-fluoro-pyridine-2-carboxylate | 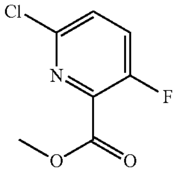 | 190 $[M + H]^+$ |
| 308 | Methyl 3-fluoropyridine-2-carboxylate | 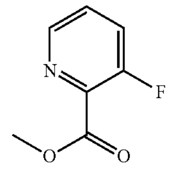 | |

Intermediate 138: tert-Butyl 2,3,6-trifluorobenzoate

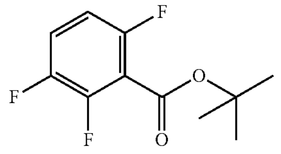 [SMILES: CC(C)(C)OC(=O)c1c(F)ccc(F)c1F]

2,3,6-Trifluorobenzoic acid (5.0 g, 28.4 mmol) was dissolved in toluene (50 mL), carefully treated with 2-tert-butyl-1,3-diisopropyl-isourea (22.8 g, 114 mmol) dropwise over 20 min, and then warmed to 65° C. After 15 min, the reaction was allowed to cool and diluted with 100 mL of water. Extracted 2 times with 75 mL of ethyl acetate. The organics were collected, dried over $Na_2SO_4$, filtered, and concentrated to an oil. The oil was purified by silica gel chromatography eluted with 0% to 75% ethyl acetate in heptanes to give the product (6.3 g, 94%) as an amber oil. $^{1}H$ NMR (400 MHz, DMSO-d6) δ ppm 1.55 (s, 9H) 7.29 (tdd, 1H) 7.72 (qd, J=9.56, 5.07 Hz, 1H).

The following compounds in Table 21 were made in a similar way as described for Intermediate 138.

TABLE 21

| Int # | Chemical Name | Structure | MS ES+ m/z |
|---|---|---|---|
| 139 | tert-Butyl 3-amino-6-chloro-pyridine-2-carboxylate | 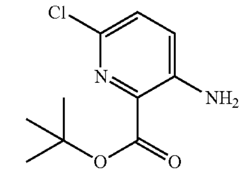 | |
| 140 | tert-Butyl 3-bromo-6-methyl-pyridine-2-carboxylate | 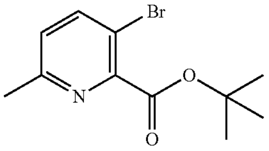 | |
| 141 | tert-Butyl 2-amino-6-fluoro-benzoate | 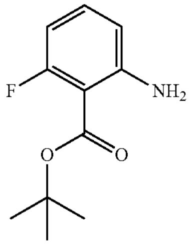 | 156 [MH − tBu]$^+$ |
| 309 | tert-Butyl 3-bromo-6-chloro-pyridine-2-carboxylate | 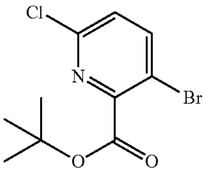 | |
| 310 | tert-Butyl 6-bromo-2,3-difluoro-benzoate | 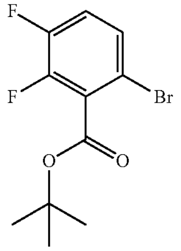 [SMILES: CC(C)(C)OC(=O)c1c(Br)ccc(F)c1F] | |
| 311 | tert-Butyl 3-fluoropyridine-2-carboxylate | 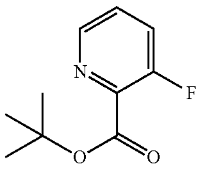 | |

Intermediate 312: Methyl 3-fluoro-6-(trifluoromethyl)pyridine-2-carboxylate

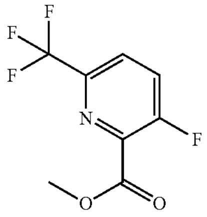

A mixture of 2-bromo-3-fluoro-6-(trifluoromethyl)pyridine (2.5 g, 10.25 mmol) in MeOH (50 mL) was treated with 1,1'-bis(diphenylphosphino)ferrocene (1.14 g, 2.05 mmol), diacetoxypalladium (0.46 g, 2.05 mmol), and triethylamine (3.11 g, 30.74 mmol). After purging the reaction 3 times with carbon monoxide, the reaction was stirred at 70° C. under 50 psi carbon monoxide for 16 h. The reaction was concentrated, diluted with 30 mL of water, and extracted with ethyl acetate (2×30 mL). The organic layers were combined, washed with brine (10 mL), dried over $Na_2SO_4$, filtered, and concentrated. The residue was purified by silica gel chromatography eluted with 0% to 13% EtOAc in petroleum ether to give the product (1.8 g, 79%) as a white solid. MS ES+ m/z 224 $[M+H]^+$.

Intermediate 11: tert-Butyl 2-[1-(2-ethylsulfanyl-6-methyl-4-oxo-chromen-8-yl)ethylamino]benzoate

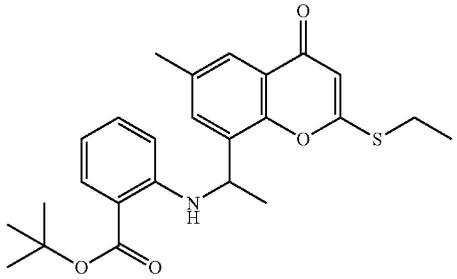 [SMILES: CCSc1cc(=O)c2cc(C)cc(C(C)Nc3ccccc3C(=O)OC(C)(C)C)c2o1]

8-(1-Bromoethyl)-2-ethylsulfanyl-6-methyl-chromen-4-one (25.0 g, 76.4 mmol), tert-butyl 2-aminobenzoate (29.5 g, 153 mmol) and DIEA (14.8 g, 20.0 mL, 115 mmol) were combined with DMF (150 mL) in a 500 mL round bottom flask and stirred at 80° C. for about 17.5 h. After cooling to rt, the reaction was partially concentrated to −100 mL, poured into 1.1 L of water, and extracted with EtOAc (2×350 mL). The combined organic layers were washed with brine (400 mL). The combined aqueous layers were re-extracted with fresh EtOAc. The organic layers were combined, dried over anhydrous $Na_2SO_4$, filtered, and concentrated to give a thick oil. Purified the oil via silica gel chromatography eluted with 0%-10% EtOAc in DCM to provide an off-white foam. Triturated with heptanes/DCM and washed with heptanes to give the product as a white solid (27.1 g, 81%). MS ES+ m/z 440 $[M+H]^+$.

The following compounds in Table 22 were made in a similar way as described for Intermediate 11.

TABLE 22

| Int # | Chemical Name | Structure | MS ES+ m/z |
|---|---|---|---|
| 142 | tert-Butyl 2-[1-(2-ethylsulfanyl-6-fluoro-4-oxo-chromen-8-yl)ethylamino]benzoate | 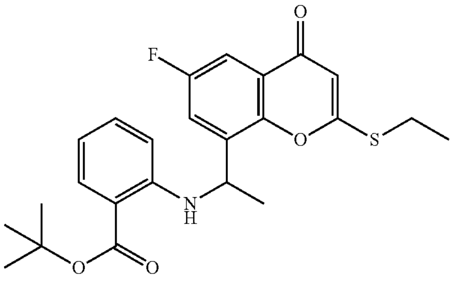 [SMILES: CCSc1cc(=O)c2cc(F)cc(C(C)Nc3ccccc3C(=O)OC(C)(C)C)c2o1] | |
| 143 | tert-Butyl 6-[1-(2-ethylsulfanyl-6-methyl-4-oxo-chromen-8-yl)ethylamino]-2,3-difluoro-benzoate | 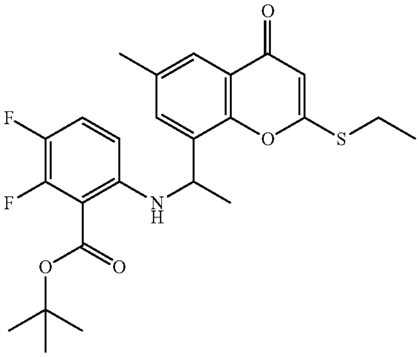 [SMILES: CCSc1cc(=O)c2cc(C)cc(C(C)Nc3ccc(F)c(F)c3C(=O)OC(C)(C)C)c2o1] | 476 [M + H]$^+$ |
| 144 | tert-Butyl 2-[1-(2-ethylsulfanyl-6-methyl-4-oxo-chromen-8-yl)ethylamino]-6-fluoro-benzoate | 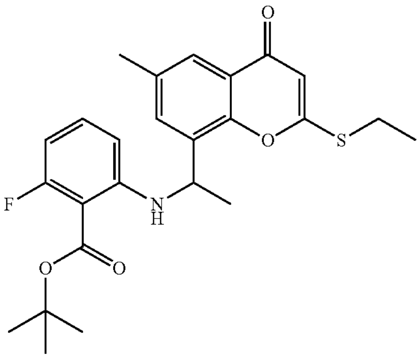 [SMILES: CCSc1cc(=O)c2cc(C)cc(C(C)Nc3cccc(F)c3C(=O)OC(C)(C)C)c2o1] | 458 [M + H]$^+$ |
| 145 | Methyl 3-chloro-6-[1-(2-ethylsulfanyl-6-methyl-4-oxo-chromen-8-yl)ethylamino]-2-fluoro-benzoate, Isomer 2 | 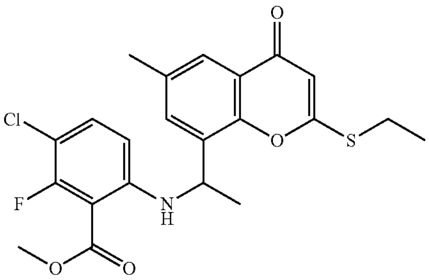 [SMILES: CCSc1cc(=O)c2cc(C)cc(C(C)Nc3ccc(Cl)c(F)c3C(=O)OC)c2o1] | 450 [M + H]$^+$ |
| 278 | tert-Butyl 6-chloro-3-[1-[2-(2,7-dimethylindazol-5-yl)-6-methyl-4-oxo-chromen-8-yl]ethylamino]pyridine-2-carboxylate, Isomer 2 | 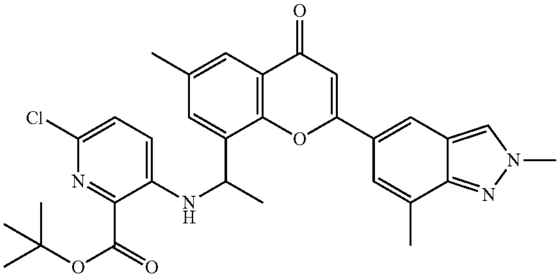 | 475 [M + H]$^+$ |

TABLE 22-continued

| Int # | Chemical Name | Structure | MS ES+ m/z |
|---|---|---|---|
| 279 | Methyl 2-[1-(2-ethylsulfanyl-6-methyl-4-oxo-chromen-8-yl)ethylamino]-6-fluoro-benzoate, Isomer 2 | 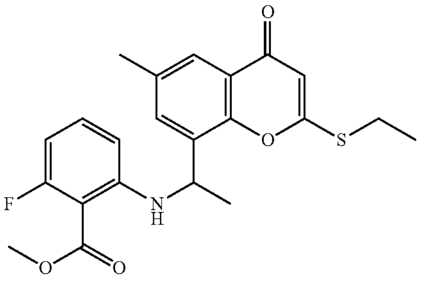 [SMILES: CCSc1cc(=O)c2cc(C)cc(C(C)Nc3cccc(F)c3C(=O)OC)c2o1] | 416 $[M + H]^+$ |

Intermediate 146: tert-Butyl 6-chloro-3-[1-[2-ethylsulfanyl-4-oxo-6-(trifluoromethyl)chromen-8-yl]ethylamino]pyridine-2-carboxylate

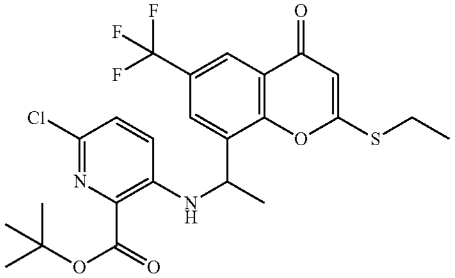 [SMILES: CCSc1cc(=O)c2cc(C(F)(F)F)cc(C(C)Nc3ccc(Cl)nc3C(=O)OC(C)(C)C)c2o1]

A suspension of 1-[2-ethylsulfanyl-4-oxo-6-(trifluoromethyl)chromen-8-yl]ethyl methanesulfonate (14 g, 35.32 mmol) and tert-butyl 3-amino-6-chloro-pyridine-2-carboxylate (16.10 g, 70.63 mmol) in 64 mL of toluene was treated with diisopropylethylamine (13.69 g, 105.90 mmol) and then heated to 110° C. After 12 h, the reaction was cooled to 10-20° C. and stirred for 1 h. The resulting suspension was filtered and the solids washed with 30 mL aliquots of methyl tert-butyl ether until no product remained in the filter cake. The filtrate was concentrated and purified by silica gel chromatography eluted with a gradient of 15:1 to 8:1 heptane/ethyl acetate to give the product (14.5 g, 77%) as a white solid.

Intermediate 147: tert-Butyl 2-[1-(2-ethyl sulfanyl-6-fluoro-3-methyl-4-oxo-chromen-8-yl)ethylamino]benzoate

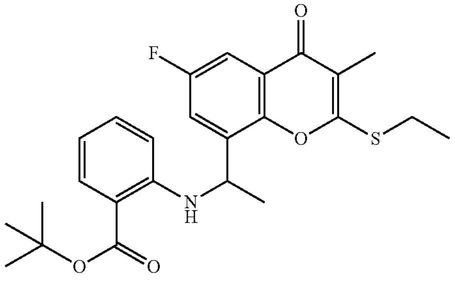 [SMILES: CCSc1oc2c(C(C)Nc3ccccc3C(=O)OC(C)(C)C)cc(F)cc2c(=O)c1C]

8-(1-Bromoethyl)-2-ethylsulfanyl-6-fluoro-3-methyl-chromen-4-one (70 g, 203 mmol) and tert-butyl 2-aminobenzoate (43.1 g, 223 mmol) were dissolved in 700 mL of chloroform, treated with pyridine (17.6 g, 223 mmol), and stirred at 80° C. for 54 h. The reaction was concentrated and the crude residue suspended in 2-methyltetrahydrofuran, placed in an ultrasonic bath for 30 min, and filtered. This process was repeated 3 more times. The filtrates were concentrated and the residue triturated with n-heptane for 30 min. The product (44.0 g, 47%) was removed by filtration and washed with heptane.

Intermediate 148 and Intermediate 149: tert-Butyl 2-[1-(2-ethylsulfanyl-6-fluoro-3-methyl-4-oxo-chromen-8-yl)ethylamino]benzoate, Isomer 1 and Isomer 2

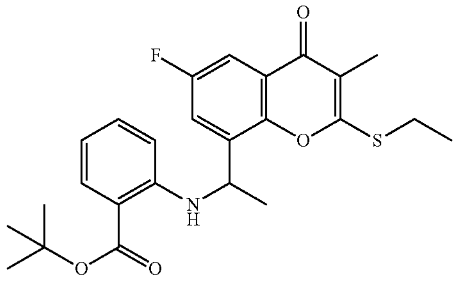 [SMILES: CCSc1oc2c(C(C)Nc3ccccc3C(=O)OC(C)(C)C)cc(F)cc2c(=O)c1C]

tert-Butyl 2-[1-(2-ethylsulfanyl-6-fluoro-3-methyl-4-oxo-chromen-8-yl)ethylamino]benzoate was separated by preparative SFC using a Chiralpak AS (300×50 mm I.D., 10 um) column eluted with 20% ethanol in $CO_2$ to give Isomer 1 (22.12 g) and Isomer 2 (22.33 g) as yellow solids.

Intermediate 150: tert-Butyl 6-chloro-3-[[(1R)-1-[2-ethylsulfanyl-4-oxo-6-(trifluoromethyl)chromen-8-yl]ethyl]amino]pyridine-2-carboxylate

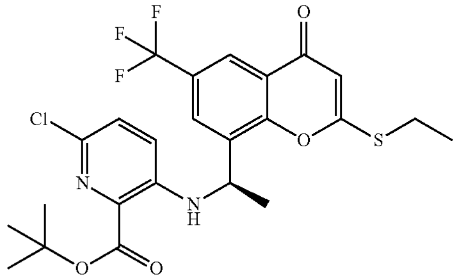 [SMILES: CCSc1cc(=O)c2cc(C(F)(F)F)cc([C@@H](C)Nc3ccc(Cl)nc3C(=O)OC(C)(C)C)c2o1]

A mixture of 8-[(1R)-1-aminoethyl]-2-ethylsulfanyl-6-(trifluoromethyl)chromen-4-one (0.98 g, 3.10 mmol), tert-butyl 6-chloro-3-fluoro-pyridine-2-carboxylate (1.44 g, 6.20 mmol), and diisopropylethylamine (0.80 g, 6.20 mmol) in N-methylpyrrolidine (12 mL) was heated in a microwave reactor at 120° C. for 24 hr. The reaction was cooled, diluted with water, and extracted twice with ethyl acetate. The organics were combined, dried over $Na_2SO_4$, filtered, and concentrated. The residue was purified by silica gel chromatography eluted with 0% to 45% ethyl acetate in heptane to give the product (0.40 g, 24%) as a colorless foam. MS ES+ m/z 473 $[MH-^tBu]^+$.

The following compounds in Table 23 were made in a similar way as described for Intermediate 150.

TABLE 23

| Int # | Chemical Name | Structure | MS ES+ m/z |
|---|---|---|---|
| 313[1] | Methyl 6-chloro-3-[[(1R)-1-(2-ethylsulfanyl-6-methyl-4-oxo-chromen-8-yl)ethyl]amino]pyridine-2-carboxylate | 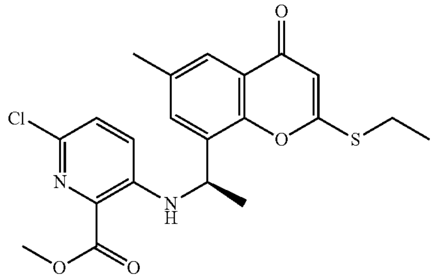 [SMILES: CCSc1cc(=O)c2cc(C)cc([C@@H](C)Nc3ccc(Cl)nc3C(=O)OC)c2o1] | 433 $[M + H]^+$ |
| 314[2] | Methyl 3-[[(1R)-1-(2-ethylsulfanyl-6-methyl-4-oxo-chromen-8-yl)ethyl]amino]pyridine-2-carboxylate | 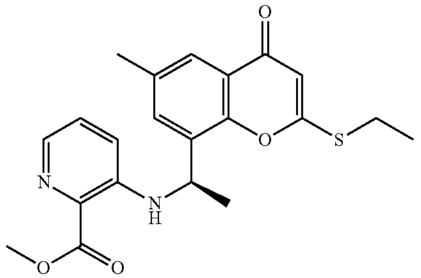 [SMILES: CCSc1cc(=O)c2cc(C)cc([C@@H](C)Nc3cccnc3C(=O)OC)c2o1] | 399 $[M + H]^+$ |
| 315[2] | Methyl 2-[[(1R)-1-(2-ethylsulfanyl-3,6-dimethyl-4-oxo-chromen-8-yl)ethyl]amino]-6-fluoro-benzoate | 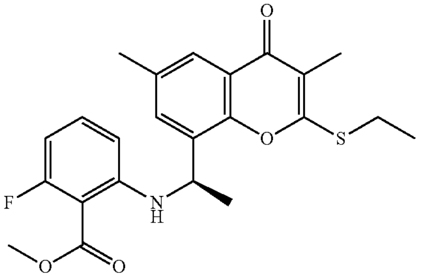 [SMILES: CCSc1oc2c([C@@H](C)Nc3cccc(F)c3C(=O)OC)cc(C)cc2c(=O)c1C] | 500 $[M + H]^+$ |
| 316[2] | tert-Butyl 6-chloro-3-[1-(2-ethylsulfanyl-6-methyl-4-oxo-chromen-8-yl)ethylamino]pyridine-2-carboxylate | 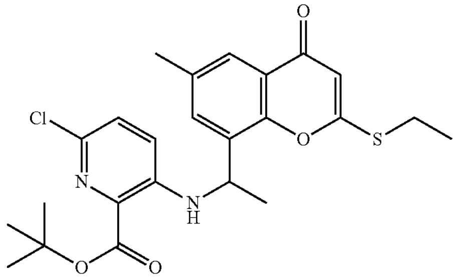 [SMILES: CCSc1cc(=O)c2cc(C)cc(C(C)Nc3ccc(Cl)nc3C(=O)OC(C)(C)C)c2o1] | 475 $[M + H]^+$ |

TABLE 23-continued

| Int # | Chemical Name | Structure | MS ES+ m/z |
|---|---|---|---|
| 317[2] | Methyl 3-[[(1R)-1-(2-ethylsulfanyl-3,6-dimethyl-4-oxo-chromen-8-yl)ethyl]amino]-6-(trifluoromethyl)pyridine-2-carboxylate | 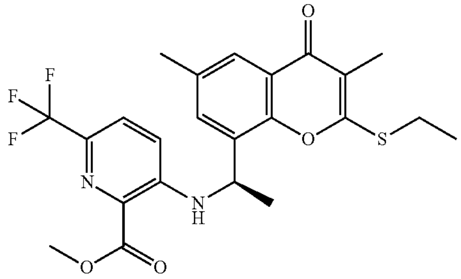 | 481 [M + H]$^+$ |
| 318[2] | Methyl 2-[[(1R)-1-(2-ethylsulfanyl-3,6-dimethyl-4-oxo-chromen-8-yl)ethyl]amino]-5-(trifluoromethyl)benzoate | 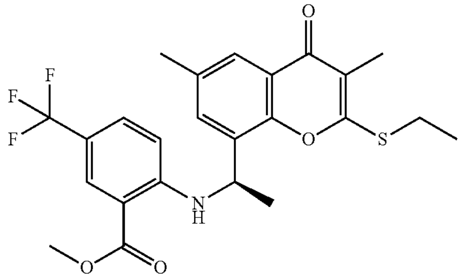 [SMILES: CCSc1oc2c([C@@H](C)Nc3ccc(C(F)(F)F)cc3C(=O)OC)cc(C)cc2c(=O)c1C] | 480 [M + H]$^+$ |
| 319[2] | tert-Butyl 2-[1-(2-ethylsulfanyl-6-methyl-4-oxo-chromen-8-yl)ethylamino]-6-fluoro-benzoate, Isomer 2 | 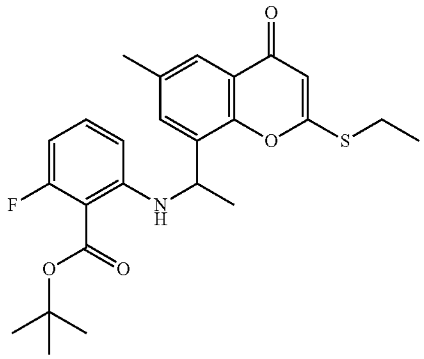 [SMILES: CCSc1cc(=O)c2cc(C)cc(C(C)Nc3cccc(F)c3C(=O)OC(C)(C)C)c2o1] | 458 [M + H]$^+$ |
| 320[2] | Methyl 2-[[(1R)-1-(2-ethylsulfanyl-6-methyl-4-oxo-chromen-8-yl)ethyl]amino]-6-fluoro-benzoate | 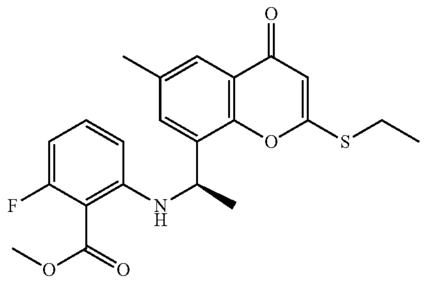 [SMILES: CCSc1cc(=O)c2cc(C)cc([C@@H](C)Nc3cccc(F)c3C(=O)OC)c2o1] | 416 [M + H]$^+$ |
| 321[2] | tert-Butyl 6-chloro-3-[[(1R)-1-(2-ethylsulfanyl-3,6-dimethyl-4-oxo-chromen-8-yl)ethyl]amino]pyridine-2-carboxylate | 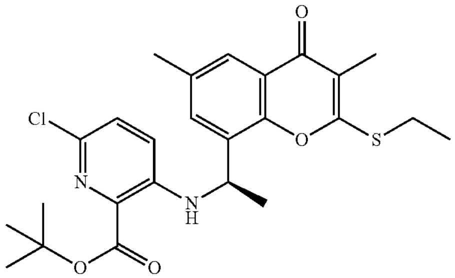 [SMILES: CCSc1oc2c([C@@H](C)Nc3ccc(Cl)nc3C(=O)OC(C)(C)C)cc(C)cc2c(=O)c1C] | 490 [M + H]$^+$ |

TABLE 23-continued

| Int # | Chemical Name | Structure | MS ES+ m/z |
|---|---|---|---|
| 322[2] | tert-Butyl 2-[[(1R)-1-(2-ethylsulfanyl-3,6-dimethyl-4-oxo-chromen-8-yl)ethyl]amino]-6-fluoro-benzoate | 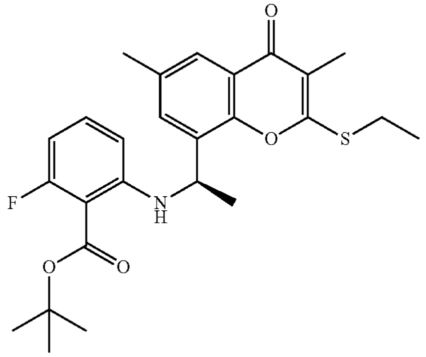 [SMILES: CCSc1oc2c([C@@H](C)Nc3cccc(F)c3C(=O)OC(C)(C)C)cc(C)cc2c(=O)c1C] | 472 [M + H]$^+$ |
| 323[2] | Methyl 3-[[(1R)-1-(2-ethylsulfanyl-6-methyl-4-oxo-chromen-8-yl)ethyl]amino]pyridine-2-carboxylate | 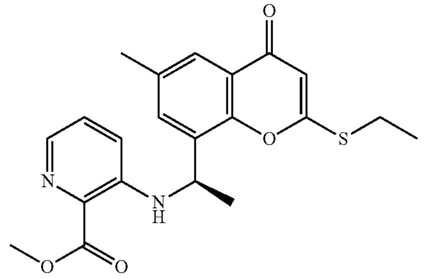 [SMILES: CCSc1cc(=O)c2cc(C)cc([C@@H](C)Nc3cccnc3C(=O)OC)c2o1] | 399 [M + H]$^+$ |
| 324[2,3] | tert-Butyl 3-[[(1R)-1-[3,6-dimethyl-2-(1-methylindazol-3-yl)-4-oxo-chromen-8-yl]ethyl]amino]pyridine-2-carboxylate | 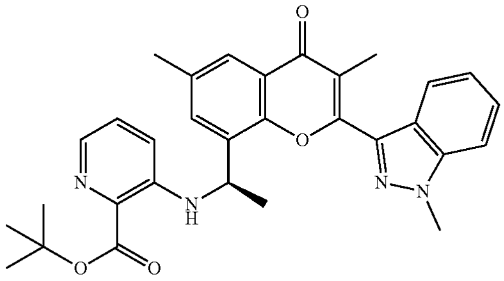 [SMILES: Cc1cc([C@@H](C)Nc2cccnc2C(=O)OC(C)(C)C)c2oc(-c3nn(C)c4ccccc34)c(C)c(=O)c2c1] | 525 [M + H]$^+$ |
| 325[2,3] | Methyl 6-chloro-3-[[(1R)-1-[3,6-dimethyl-2-(2-methylthiazolo[5,4-b]pyridin-5-yl)-4-oxo-chromen-8-yl]ethyl]amino]pyridine-2-carboxylate | 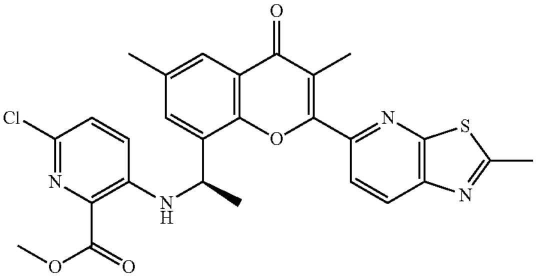 [SMILES: COC(=O)c1nc(Cl)ccc1N[C@H](C)c1cc(C)cc2c(=O)c(C)c(-c3ccc4nc(C)sc4n3)oc12] | 535 [M + H]$^+$ |
| 326[2,3] | Methyl 3-[[(1R)-1-[3,6-dimethyl-2-(2-methylthiazolo[5,4-b]pyridin-5-yl)-4-oxo-chromen-8-yl]ethyl]amino]pyridine-2-carboxylate | 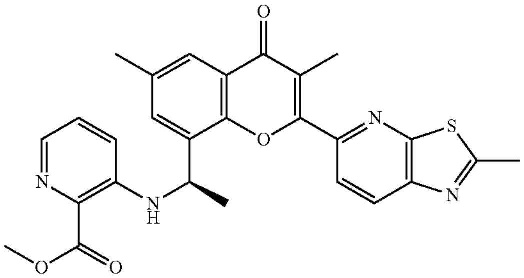 | 501 [M + H]$^+$ |

TABLE 23-continued

| Int # | Chemical Name | Structure | MS ES+ m/z |
|---|---|---|---|
| 327[1,3] | Methyl 6-bromo-3-[[(1R)-1-[3,6-dimethyl-2-(2-methylindazol-5-yl)-4-oxo-chromen-8-yl]ethyl]amino]pyridine-2-carboxylate | 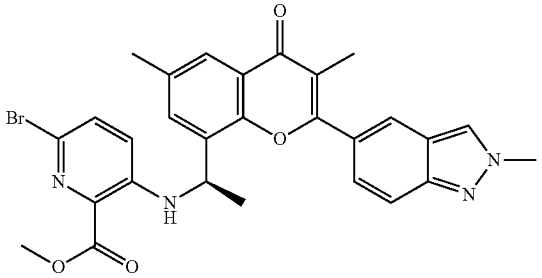 [SMILES: COC(=O)c1nc(Br)ccc1N[C@H](C)c1cc(C)cc2c(=O)c(C)c(-c3ccc4nn(C)cc4c3)oc12] | 563 $[M + H]^+$ |
| 328[2,3] | Methyl 6-bromo-3-[[(1R)-1-[3,6-dimethyl-2-(2-methylthiazolo[5,4-b]pyridin-5-yl)-4-oxo-chromen-8-yl]ethyl]amino]pyridine-2-carboxylate | 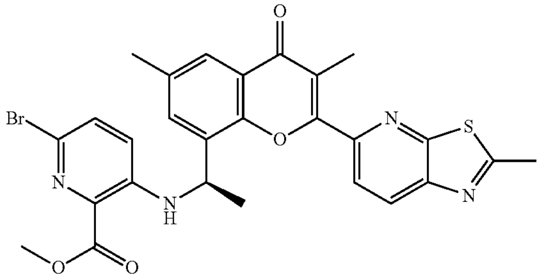 [SMILES: COC(=O)c1nc(Br)ccc1N[C@H](C)c1cc(C)cc2c(=O)c(C)c(-c3ccc4nc(C)sc4n3)oc12] | 581 $[M + H]^+$ |
| 329[2] | Methyl 6-chloro-3-[[(1R)-1-(2-ethylsulfanyl-3,6-dimethyl-4-oxo-chromen-8-yl)ethyl]amino]pyridine-2-carboxylate | 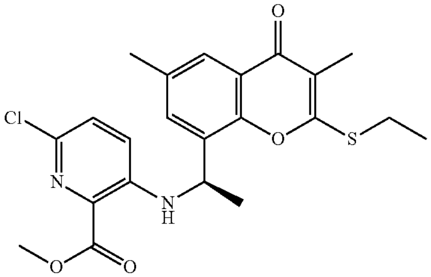 [SMILES: CCSc1oc2c([C@@H](C)Nc3ccc(Cl)nc3C(=O)OC)cc(C)cc2c(=O)c1C] | 447 $[M + H]^+$ |
| 330[2,3] | Methyl 6-chloro-3-[[(1R)-1-[3,6-dimethyl-4-oxo-2-(1H-pyrrolo[2,3-b]pyridin-2-yl)chromen-8-yl]ethyl]amino]pyridine-2-carboxylate | 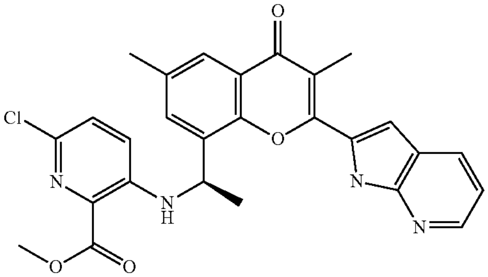 | 503 $[M + H]^+$ |
| 331[2] | Methyl 6-chloro-3-[[(1R)-1-[6-methyl-2-(2-methylthiazolo[5,4-b]pyridin-5-yl)-4-oxo-chromen-8-yl]ethyl]amino]pyridine-2-carboxylate | 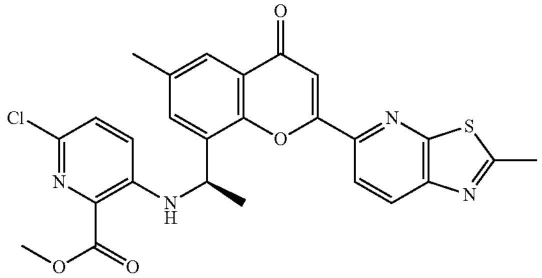 [SMILES: COC(=O)c1nc(Cl)ccc1N[C@H](C)c1cc(C)cc2c(=O)cc(-c3ccc4nc(C)sc4n3)oc12] | 521 $[M + H]^+$ |

[1]DMF used as the solvent in this reaction.

[2]DMSO used as the solvent in this reaction.

[3]Triethylamine used as the base in this reaction.

Intermediate 151: tert-Butyl 3-[1-(2-ethylsulfanyl-6-methyl-4-oxo-chromen-8-yl)ethylamino]-6-methyl-pyridine-2-carboxylate

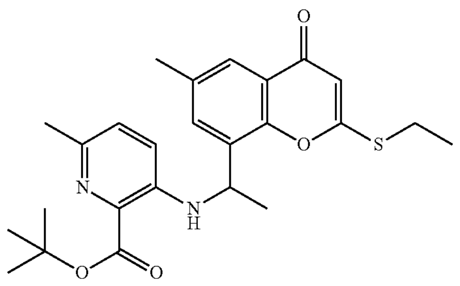 [SMILES: CCSc1cc(=O)c2cc(C)cc(C(C)Nc3ccc(C)nc3C(=O)OC(C)(C)C)c2o1]

8-(1-Aminoethyl)-2-ethylsulfanyl-6-methyl-chromen-4-one (0.55 g, 2.09 mmol), tert-butyl 3-bromo-6-methyl-pyridine-2-carboxylate (0.80 g, 2.92 mmol), tris(dibenzylideneacetone)dipalladium(0) (0.13 g, 0.15 mmol), Xantphos (0.25 g, 0.44 mmol), and cesium carbonate (1.09 g, 3.34 mmol) were combined in toluene (20 mL), degassed with argon for 5 min, and heated at 80° C. for 16 h. The reaction was diluted with 10 mL of dichloromethane and purified by silica gel chromatography eluted with 0% to 100% ethyl acetate in heptane to give the product (0.42 g, 44%). MS ES+ m/z 455 $[M+H]^+$.

The following compounds in Table 24 were made in a similar way as described for Intermediate 151.

TABLE 24

| Int # | Chemical Name | Structure | MS ES+ m/z |
|---|---|---|---|
| 332 | tert-Butyl 6-chloro-3-[[(1R)-1-(2-ethylsulfanyl-3,6-dimethyl-4-oxo-chromen-8-yl)ethyl]amino]pyridine-2-carboxylate | 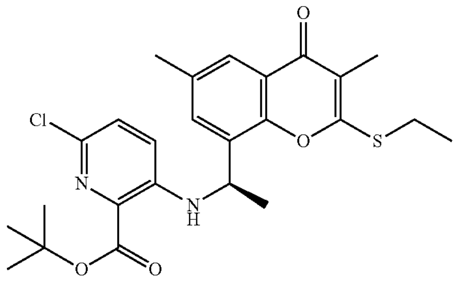 [SMILES: CCSc1oc2c([C@@H](C)Nc3ccc(Cl)nc3C(=O)OC(C)(C)C)cc(C)cc2c(=O)c1C] | 489 $[M + H]^+$ |
| 333 | Methyl 5-chloro-2-[[(1R)-1-(2-ethylsulfanyl-6-methyl-4-oxo-chromen-8-yl)ethyl]amino]benzoate | 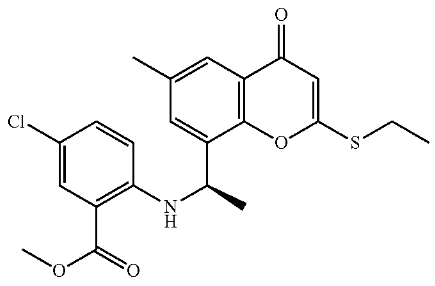 | 432 $[M + H]^+$ |
| 334 | Methyl 2-[[(1R)-1-(2-ethylsulfanyl-6-methyl-4-oxo-chromen-8-yl)ethyl]amino]-5-fluoro-benzoate | 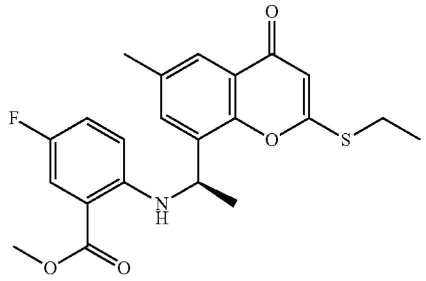 [SMILES: CCSc1cc(=O)c2cc(C)cc([C@@H](C)Nc3ccc(F)cc3C(=O)OC)c2o1] | 416 $[M + H]^+$ |

TABLE 24-continued

| Int # | Chemical Name | Structure | MS ES+ m/z |
|---|---|---|---|
| 335 | tert-Butyl 3-[[(1R)-1-[3,6-dimethyl-2-(2-methylindazol-5-yl)-4-oxo-chromen-8-yl]ethyl]amino]-6-methyl-pyridine-2-carboxylate | 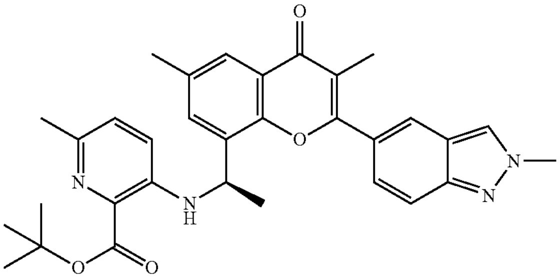 [SMILES: Cc1cc([C@@H](C)Nc2ccc(C)nc2C(=O)OC(C)(C)C)c2oc(-c3ccc4nn(C)cc4c3)c(C)c(=O)c2c1] | 539 [M + H]$^+$ |
| 336[1] | tert-Butyl 6-[[(1R)-1-[3,6-dimethyl-2-(2-methylindazol-5-yl)-4-oxo-chromen-8-yl]ethyl]amino]-2,3-difluoro-benzoate | 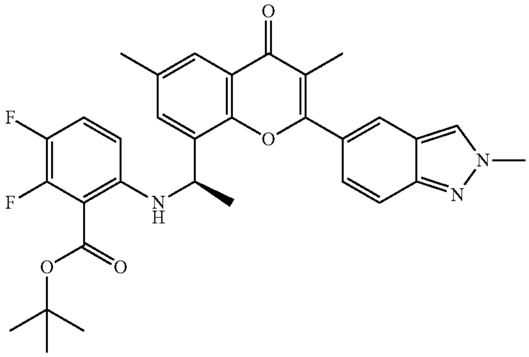 [SMILES: Cc1cc([C@@H](C)Nc2ccc(F)c(F)c2C(=O)OC(C)(C)C)c2oc(-c3ccc4nn(C)cc4c3)c(C)c(=O)c2c1] | 560 [M + H]$^+$ |

[1]DavePhos and sodium tert-butoxide usee instead of Xantphos and cesium carbonte.

Intermediate 12: Methyl 2-[1-(2-ethyl sulfanyl-6-methyl-4-oxo-chromen-8-yl)ethylamino]benzoate

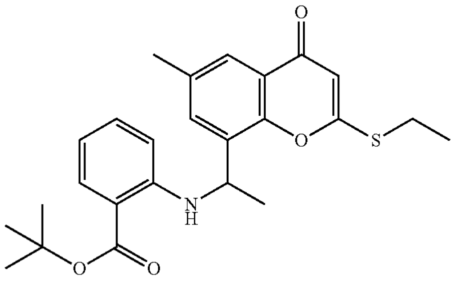 [SMILES: CCSc1cc(=O)c2cc(C)cc(C(C)Nc3ccccc3C(=O)OC(C)(C)C)c2o1]

A mixture of 8-(1-bromoethyl)-2-ethylsulfanyl-6-methyl-chromen-4-one (4.00 g, 12.2 mmol) and methyl 2-amino-benzoate (3.70 g, 24.5 mmol) in DMF (30 mL) was stirred at 80° C. for 8 h. When cooled to rt, the mixture was diluted with water (100 mL) and extracted with EtOAc (3×80 mL). The combined extract was washed with brine (3×100 mL), dried over anhydrous $Na_2SO_4$, filtered, concentrated. The residue was purified by silica gel chromatography eluted with 0%-27% EtOAc in petroleum ether to give the product (4.5 g, 84%) as a solid. MS ES+ m/z 398 [M+H]$^+$.

The following compounds in Table 25 were made in a similar way as described for Intermediate 12.

TABLE 25

| Int # | Chemical Name | Structure | MS ES+ m/z |
|---|---|---|---|
| 152 | Methyl 3-[1-[2-bromo-4-oxo-6-(trifluoromethyl)chromen-8-yl]ethylamino]-6-chloro-pyridine-2-carboxylate | 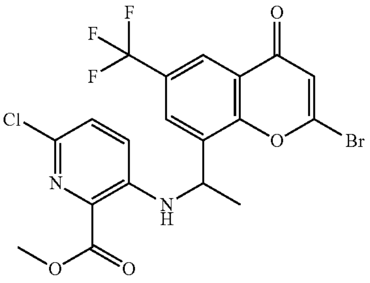 [SMILES: COC(=O)c1nc(Cl)ccc1NC(C)c1cc(C(F)(F)F)cc2c(=O)cc(Br)oc12] | 505/507 [M + H]$^+$ |

Intermediate 337: 2-[[(1R)-1-(2-Ethylsulfanyl-3,6-dimethyl-4-oxo-chromen-8-yl)ethyl]amino]-5-fluoro-benzoic acid

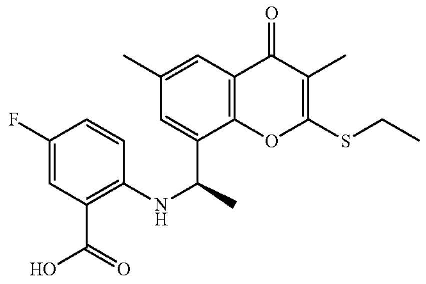 [SMILES: CCSc1oc2c([C@@H](C)Nc3ccc(F)cc3C(=O)O)cc(C)cc2c(=O)c1C]

A mixture of 8-[(1R)-1-aminoethyl]-2-ethylsulfanyl-3,6-dimethyl-chromen-4-one (500 mg, 1.80 mmol), 5-fluoro-2-iodo-benzoic acid (959 mg, 3.61 mmol), copper(I) iodide (34.33 mg, 0.18 mmol), 2-(methylamino)acetic acid (32.12 mg, 0.36 mmol), and potassium carbonate (498.25 mg, 3.61 mmol) in DMSO (5 mL) was stirred at 90° C. under $N_2$ for 12 h. After cooling to rt, the reaction was diluted with 50 mL of water and extracted with EtOAc (2×50 mL). The combined organic layers were washed with brine (2×50 mL), dried over $Na_2SO_4$, filtered, and concentrated. The reside was purified by silica gel chromatography eluted with 0% to 30% EtOAc in petroleum ether to give the product (204 mg, 20%) as a yellow oil. MS ES+ m/z 416 $[M+H]^+$.

Intermediate 338: 5-Chloro-2-[[(1R)-1-(2-ethylsulfanyl-3,6-dimethyl-4-oxo-chromen-8-yl)ethyl]amino]benzoic acid

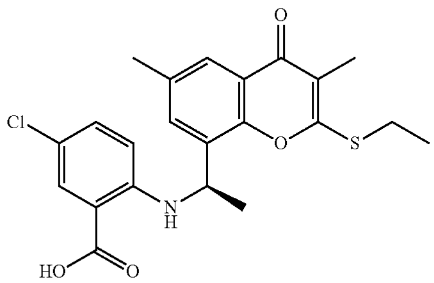 [SMILES: CCSc1oc2c([C@@H](C)Nc3ccc(Cl)cc3C(=O)O)cc(C)cc2c(=O)c1C]

A mixture of 8-[(1R)-1-aminoethyl]-2-ethylsulfanyl-3,6-dimethyl-chromen-4-one (400 mg, 1.44 mmol), 5-chloro-2-iodo-benzoic acid (814.65 mg, 2.88 mmol), potassium carbonate (797.21 mg, 5.77 mmol) and copper powder (183.27 mg, 2.88 mmol) in 6 mL of DMF was stirred at 100° C. for 12 h. Cooled the reaction to rt and adjusted the pH to 3 with 2M aqueous HCl. Extracted with EtOAc (3×20 mL), combined the organic layers, dried over $Na_2SO_4$, filtered, and concentrated. The resulting residue was purified by silica gel chromatography eluted with 0% to 30% EtOAc in petroleum ether to give the product (280 mg, 39%) as a yellow solid. MS ES+ m/z 432 $[M+H]^+$.

The following compounds in Table 26 were made in a similar way as described for Intermediate 338.

TABLE 26

| Int # | Chemical Name | Structure | MS ES+ m/z |
|---|---|---|---|
| 339 | 2-[[(1R)-1-(2-Ethylsulfanyl-6-methyl-4-oxo-chromen-8-yl)ethyl]amino]-6-fluoro-benzoic acid | 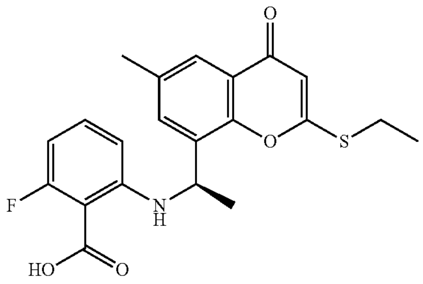 [SMILES: CCSc1cc(=O)c2cc(C)cc([C@@H](C)Nc3cccc(F)c3C(=O)O)c2o1] | 402 $[M + H]^+$ |
| 340 | 2-[[(1R)-1-(2-Ethylsulfanyl-3,6-dimethyl-4-oxo-chromen-8-yl)ethyl]amino]benzoic acid | 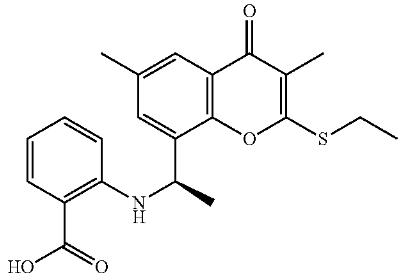 [SMILES: CCSc1oc2c([C@@H](C)Nc3ccccc3C(=O)O)cc(C)cc2c(=O)c1C] | 398 $[M + H]^+$ |

Intermediate 153: 7-Chloro-2-methyl-3-(3-pyridyl) imidazo[1,2-a]pyridine

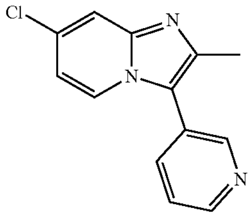 [SMILES: Cc1nc2cc(Cl)ccn2c1-c1cccnc1]

A mixture of 7-chloro-2-methyl-imidazo[1,2-a]pyridine (0.40 g, 2.40 mmol), 3-bromopyridine (0.46 g, 2.88 mmol), palladium(II) acetate (0.054 g, 0.24 mmol), triphenylphosphine (0.13 g, 0.48 mmol), and cesium carbonate (1.25 g, 3.84 mmol) in 8 mL of 1,4-dioxane was stirred at 100° C. for 16 h. The dark reaction was cooled, combined with another similar reaction, and concentrated. The residue was purified by silica gel chromatography eluted with 0% to 85% ethyl acetate in petroleum ether to give the product (0.48 g, 68%) as a light yellow solid. MS ES+ m/z 244 $[M+H]^+$.

Intermediate 154 and 155: 7-Bromo-1-methyl-pyrazolo[3,4-c]pyridine and 7-bromo-2-methyl-pyrazolo [3,4-c]pyridine

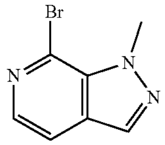

and

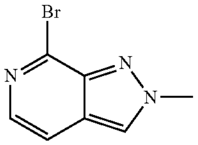

7-Bromo-1H-pyrazolo[3,4-c]pyridine (0.5 g, 2.52 mmol) was dissolved in THE (5 mL) and treated with sodium hydride (0.20 g, 60% wt, 5.05 mmol). Allowed the reaction to stir at rt for 30 min and then cooled in an ice bath. When cold, treated the reaction with iodomethane (1.36 g, 9.59 mmol) dropwise and then removed the bath and allowed to stir at rt. After 1 h, quenched the reaction with ice water and extracted with ethyl acetate. The organics were washed with brine, collected, dried over $MgSO_4$, filtered, and concentrated. The residue was purified by reversed phase chromatography (C-18 column) giving 7-bromo-1-methyl-pyrazolo [3,4-c]pyridine (0.02 g, 3.5%) and 7-bromo-2-methyl-pyrazolo[3,4-c]pyridine (0.30 g, 53%). MS ES+ m/z 212/214 $[M+H]^+$.

The following compounds in Table 27 were made in a similar way as described for Intermediate 154 and 155.

TABLE 27

| Int # | Chemical Name | Structure | MS ES+ m/z |
|---|---|---|---|
| 156 | 6-Bromo-1-methyl-indazole-3-carbonitrile | 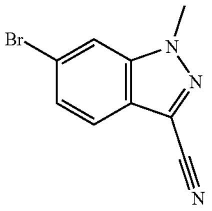 | 236 $[M + H]^+$ |
| 157 | 6-Bromo-2-methyl-indazole-3-carbonitrile | 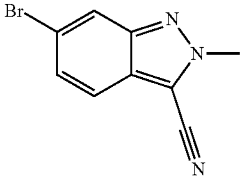 | 236 $[M + H]^+$ |
| 158 | 5-Bromo-1-methyl-pyrazolo[4,3-b]pyridine | 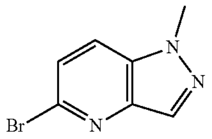 | 212 $[M + H]^+$ |
| 159 | 5-Bromo-2-methyl-pyrazolo[4,3-b]pyridine | 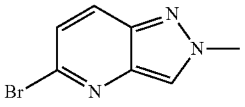 | 212 $[M + H]^+$ |
| 160 | 5-Bromo-1-(oxetan-3-ylmethyl)indazole | 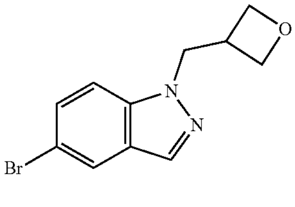 [SMILES: Brc1ccc2c(cnn2CC2COC2)c1] | 267 $[M + H]^+$ |

TABLE 27-continued

| Int # | Chemical Name | Structure | MS ES+ m/z |
|---|---|---|---|
| 161[a] | 6-Bromo-1-methyl-3H-pyrrolo[2,3-b]pyridin-2-one | 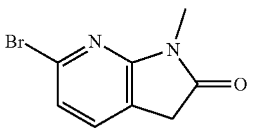 | 227/229 $[M + H]^+$ |
| 162 | 6-Bromo-1-methyl-pyrrolo[2,3-b]pyridine | 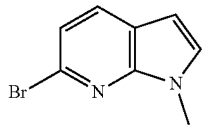 | 213 $[M + H]^+$ |

[a]Dimethyl sulfate used as the methylating reagent.

Intermediate 341: 5-Bromo-2-methyl-7-(trifluoromethyl)indazole

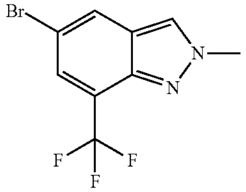

A suspension of 5-bromo-7-(trifluoromethyl)-1H-indazole (0.55 g, 2.07 mmol) in EtOAc (10 mL) was treated with trimethyloxonium tetrafluoroborate (0.92 g, 6.20 mmol) and stirred at rt for 16 h. Quenched the reaction with saturated aqueous sodium bicarbonate and extracted with EtOAc (3×15 mL). The combined organic layers were dried over $Na_2SO_4$, filtered, and concentrated. The crude residue was purified by silica gel chromatography eluted with a gradient of EtOAc in heptane to obtain the product (0.25 g, 44%) as a light yellow solid. MS ES+ m/z 279/281 $[M+H]^+$.

Intermediate 163: N-(6-Bromo-2-chloro-3-pyridyl)acetamide

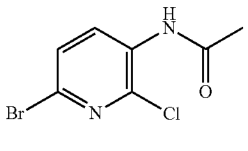

A suspension of 6-bromo-2-chloro-pyridin-3-amine (2.47 g, 11.92 mmol) and triethylamine (1.21 g, 11.92 mmol) in dichloromethane (12 mL) was slowly treated with acetyl chloride (1.05 g, 13.41 mmol) dropwise at rt. Allowed the resulting solution to stir at rt for 16 h. Added another 0.24 mL of acetyl chloride and stirred at rt for 6 h. Adjusted the pH to 7 with 8 mL of saturated aqueous sodium bicarbonate. Diluted with water and extracted three times with dichloromethane. The organics were combined, dried over $MgSO_4$, filtered, and concentrated. The residue was purified by silica gel chromatography eluted with 0% to 60% ethyl acetate in heptane to give the product (2.16 g, 73%). MS ES+ m/z 249/251 $[M+H]^+$.

Intermediate 164: 5-Bromo-2-methyl-thiazolo[5,4-b]pyridine

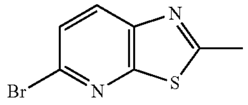

A suspension of N-(6-bromo-2-chloro-3-pyridyl)acetamide (2.16 g, 8.66 mmol) in toluene (16 mL) was treated with Lawesson's reagent (2.10 g, 5.19 mmol) and the reaction heated to 110° C. After 4 h, the reaction was allowed to cool, concentrated, and purified by silica gel chromatography eluted with 0% to 40% ethyl acetate in heptane to give the product (1.25 g, 63%). MS ES+ m/z 229/231 $[M+H]^+$.

Intermediate 342: 6-Bromo-2-methoxy-8-methyl-quinoline

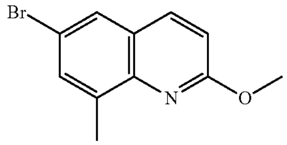

A mixture of 6-bromo-2-chloro-8-methyl-quinoline (330 mg, 1.29 mmol) and sodium methoxide (694.97 mg, 12.86 mmol) in 8 mL of methanol was stirred at 80° C. for 40 h. The reaction was allowed to cool to rt and concentrated. The residue was diluted with 20 mL of dichloromethane and water. After removal of the organic layer, the remaining aqueous layer was re-extracted with dichloromethane (3×20 mL). The combined organic layers were washed with 40 mL of brine, dried over $Na_2SO_4$, filtered, and concentrated. The residue was purified by silica gel chromatography eluted with 0% to 2% EtOAc in petroleum ether to give the product (300 mg, 90%) as a white solid. MS ES+ m/z 254 $[M+H]^+$.

Intermediate 13: 2-Methyl-6-(4,4,5,5-tetramethyl-1,3,2-dioxaborolan-2-yl)pyrazolo[4,3-b]pyridine

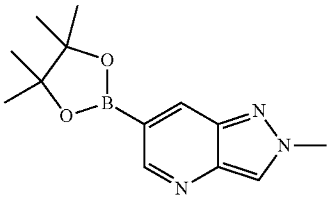

A suspension of 6-bromo-2-methyl-pyrazolo[4,3-b]pyridine (193 mg, 0.91 mmol), bis(pinacolato)diboron (347 mg, 1.37 mmol), and potassium acetate (268 mg, 2.73 mmol) in 5 mL of 1,4-dioxane was flushed with argon gas. Treated the suspension with [1,1'-bis(diphenylphosphino)ferrocene]dichloropalladium(II) complex with DCM (74.2 mg, 0.091 mmol) as a solid and flushed the mixture with argon gas. Stirred the reaction at 100° C. for 2.25 h. The reaction was cooled to room temperature, filtered through celite, and the celite washed with ethyl acetate. The filtrate was concentrated and used in the next reaction without purification.

The following compounds in Table 28 were made in a similar way as described for Intermediate 13.

TABLE 28

| Int # | Chemical Name | Structure | MS ES+ m/z |
|---|---|---|---|
| 14 | (6-Methoxyimidazo[1,2-a]pyridin-2-yl)boronic acid | 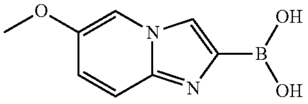 | 193 [M + H]$^+$ |
| 15 | 6-(4,4,5,5-Tetramethyl-1,3,2-dioxaborolan-2-yl)-1H-pyrrolo[2,3-b]pyridine | 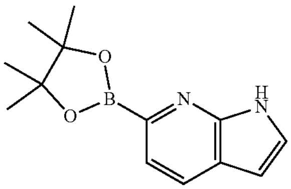 [SMILES: CC1(C)OB(c2ccc3cc[nH]c3n2)OC1(C)C] | 245 [M + H]$^+$ |
| 55 | 2-Methyl-6-(4,4,5,5-tetramethyl-1,3,2-dioxaborolan-2-yl)imidazo[1,2-b]pyridazine | 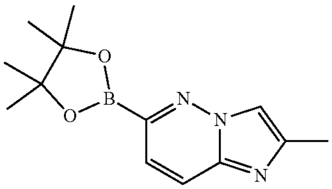 | Material does not ionize well |
| 56 | 6-(4,4,5,5-Tetramethyl-1,3,2-dioxaborolan-2-yl)-2-(trifluoromethyl)imidazo[1,2-a]pyridine | 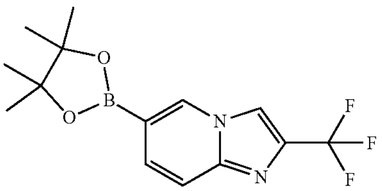 [SMILES: CC1(C)OB(c2ccc3nc(C(F)(F)F)cn3c2)OC1(C)C] | 313 [M + H]$^+$ |
| 57 | 6-(4,4,5,5-Tetramethyl-1,3,2-dioxaborolan-2-yl)-1H-pyrrolo[3,2-b]pyridine | 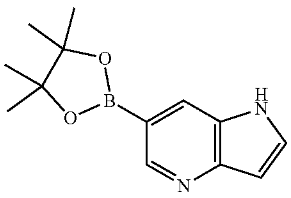 [SMILES: CC1(C)OB(c2cnc3cc[nH]c3c2)OC1(C)C] | 245 [M + H]$^+$ |
| 58 | 6-Methyl-2-(4,4,5,5-tetramethyl-1,3,2-dioxaborolan-2-yl)-7H-pyrrolo[2,3-d]pyrimidine | 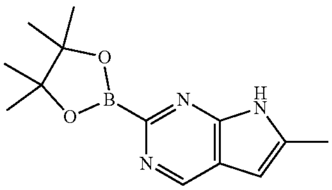 | Material does not ionize well |

TABLE 28-continued

| Int # | Chemical Name | Structure | MS ES+ m/z |
|---|---|---|---|
| 59 | 3-Methyl-7-(4,4,5,5-tetramethyl-1,3,2-dioxaborolan-2-yl)-[1,2,4]triazolo[4,3-a]pyridine | 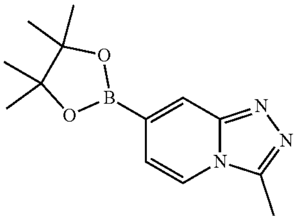 | 178 Degradation to boronic acid in MS |
| 60 | 3-Isopropyl-6-(4,4,5,5-tetramethyl-1,3,2-dioxaborolan-2-yl)-[1,2,4]triazolo[4,3-a]pyridine | 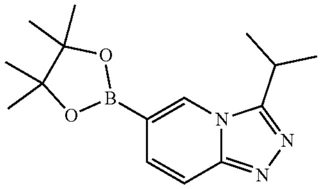 | 206 Degradation to boronic acid in MS |
| 61 | 2-Methyl-6-(4,4,5,5-tetramethyl-1,3,2-dioxaborolan-2-yl)thiazolo[5,4-b]pyridine | 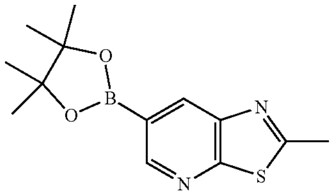 | Reagent taken on to coupling without LC/MS taken |
| 62 | 1-Methyl-6-(4,4,5,5-tetramethyl-1,3,2-dioxaborolan-2-yl)pyrazolo[3,4-b]pyridine | 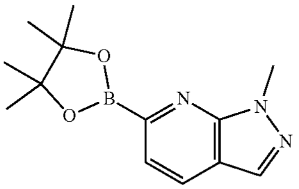 | 178 Degradation to boronic acid in MS |
| 165 | 7-Chloro-2-methyl-5-(4,4,5,5-tetramethyl-1,3,2-dioxaborolan-2-yl)indazole | 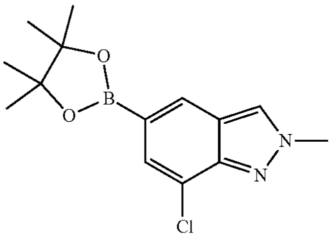 | 293 $[M + H]^+$ |
| 166[a] | 2-Methyl-3-(3-pyridyl)-7-(4,4,5,5-tetramethyl-1,3,2-dioxaborolan-2-yl)imidazo[1,2-a]pyridine | 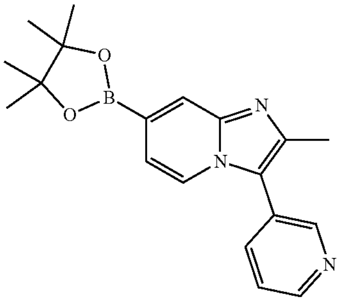 | 254 Degradation to boronic acid in MS |
| 167 | 5-(4,4,5,5-Tetramethyl-1,3,2-dioxaborolan-2-yl)pyrazolo[1,5-a]pyridine | 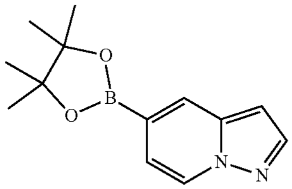 [SMILES: CC1(C)OB(c2ccn3nccc3c2)OC1(C)C] | 245 $[M + H]^+$ |

TABLE 28-continued

| Int # | Chemical Name | Structure | MS ES+ m/z |
|---|---|---|---|
| 168 | 1-Tetrahydropyran-2-yl-6-(4,4,5,5-tetramethyl-1,3,2-dioxaborolan-2-yl)indazole | 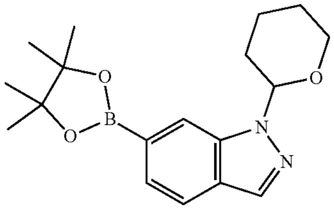 [SMILES: CC1(C)OB(c2ccc3cnn(C4CCCCO4)c3c2)OC1(C)C] | 329 [M + H]$^+$ |
| 169 | 2-Methyl-6-(4,4,5,5-tetramethyl-1,3,2-dioxaborolan-2-yl)pyrazolo[1,5-a]pyridine | 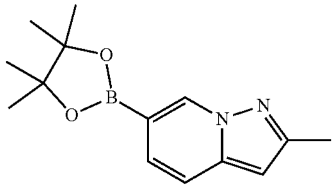 | 259 [M + H]$^+$ |
| 170 | (2-Methylthiazolo[5,4-b]pyridin-5-yl)boronic acid | 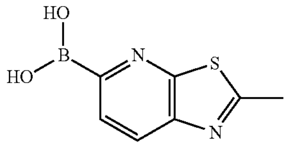 | 195 [M + H]$^+$ |
| 171 | (1-Methyl-2-oxo-3H-pyrrolo[2,3-b]pyridin-6-yl)boronic acid | 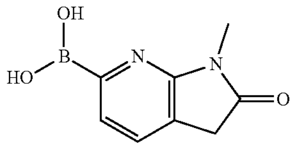 | 193 [M + H]$^+$ |
| 172[a] | 2,7-Dimethyl-5-(4,4,5,5-tetramethyl-1,3,2-dioxaborolan-2-yl)indazole | 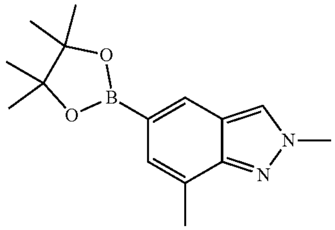 | 273 [M + H]$^+$ |
| 173 | 1-Methyl-6-(4,4,5,5-tetramethyl-1,3,2-dioxaborolan-2-yl)pyrrolo[2,3-b]pyridine | 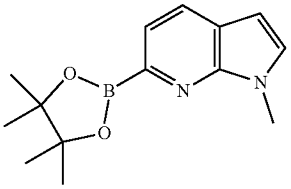 [SMILES: Cn1ccc2ccc(B3OC(C)(C)C(C)(C)O3)nc21] | Does not ionize well. |
| 174[a] | (1-Methylindazol-3-yl)boronic acid | 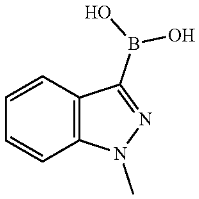 | 177 [M + H]$^+$ |

TABLE 28-continued

| Int # | Chemical Name | Structure | MS ES+ m/z |
|---|---|---|---|
| 175[a] | 2-Methyl-6-(4,4,5,5-tetramethyl-1,3,2-dioxaborolan-2-yl)imidazo[1,2-a]pyridine | 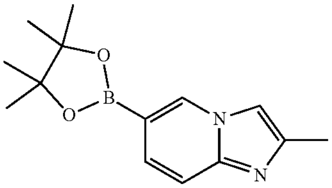 | Degradation to boronic acid in MS |
| 176[a] | [1,2,4]Triazolo[4,3-a]pyridin-7-ylboronic acid | 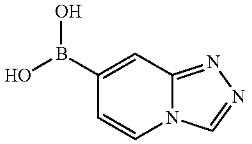 | 164 [M + H]+ |
| 177[b] | 6-(4,4,5,5-Tetramethyl-1,3,2-dioxaborolan-2-yl)-3-(trifluoromethyl)-[1,2,4]triazolo[4,3-a]pyridine | 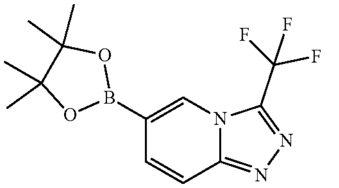 | 232 Degradation to boronic acid in MS |
| 178 | 7-(4,4,5,5-Tetramethyl-1,3,2-dioxaborolan-2-yl)-2,3-dihydro-[1,4]dioxino[2,3-b]pyridine | 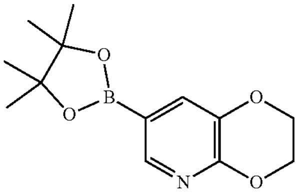 [SMILES: CC1(C)OB(c2cnc3c(c2)OCCO3)OC1(C)C] | 264 [M + H]+ |
| 343 | 2-Methyl-6-(4,4,5,5-tetramethyl-1,3,2-dioxaborolan-2-yl)-1,3-benzothiazole | 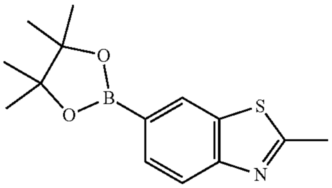 | 276 [M + H]+ |

[a]Reaction used tris(dibenzylideneacetone)dipalladium(0) and tricyclohexylphosphine as the catalyst.
[b]Reaction used triphenylphosphine and palladium(II) acetate as the catalyst.

Intermediate 16: Furo[2,3-c]pyridin-2-ylboronic acid

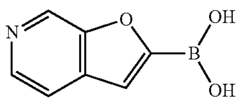 [SMILES: OB(O)c1cc2ccncc2o1]

A 20 mL vial was charged with 4-iodopyridin-3-ol (1.0 g, 4.53 mmol), ethyneboronic acid MIDA ester (1.06 g, 5.88 mmol), bis(triphenylphosphino)-palladium(II) chloride (158.8 mg, 0.23 mmol), triphenylphosphine (118.7 mg, 0.45 mmol), copper(I) iodide (86.2 mg, 0.45 mmol) and DMF (7 mL). The reaction was evacuated and flushed with argon gas three times and 1,1,3,3-tetramethylguanidine (625 mg, 5.43 mmol) added as a solid. The reaction was stirred at 63° C. for 22 h. Cooled the reaction to rt, diluted with water, and extracted 3× with ethyl acetate. The combined organic phases were washed with brine, collected, dried over anhydrous $MgSO_4$, filtered, and concentrated to dryness. The residue was purified via silica gel chromatography eluted with 0%-15% MeOH in DCM to produce a solid. The solid was taken up in EtOH and stirred at 85° C. for 30 min, cooled, and filtered. The filtrate was concentrated to dryness to give the product (530 mg, 71%) which was taken on to the coupling reaction without further purification.

The following compounds in Table 29 were made in a similar way as described for Intermediate 16.

TABLE 29

| Int # | Chemical Name | Structure | MS ES+ m/z |
|---|---|---|---|
| 17 | Furo[3,2-c]pyridin-2-ylboronic acid | 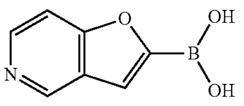 [SMILES: OB(O)c1cc2cnccc2o1] | Reagent taken on to coupling reaction without purification. |

Intermediate 179: 5-Bromo-7-fluoro-2-methyl-indazole

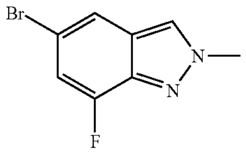

5-Bromo-7-fluoro-1H-indazole (0.55 g, 2.55 mmol) was suspended in ethyl acetate (10 mL) and treated with trimethyloxonium tetrafluoroborate as a solid in one portion. The reaction was allowed to stir at rt. After stirring overnight, added another portion of trimethyloxonium tetrafluoroborate (1.13 g, 7.64 mmol) and stirred overnight at rt. Carefully quenched the reaction with saturated aqueous sodium bicarbonate and extracted with ethyl acetate. The organics were washed with brine, collected, dried over $MgSO_4$, filtered, and concentrated. The residue was purified by silica gel chromatography eluted with 0% to 30% ethyl acetate in heptane to give the product (1.26 g, 55%). MS ES+ m/z 229 $[M+H]^+$.

Intermediate 180 and Intermediate 181: 1-(5-Bromoindazol-1-yl)-2-methyl-propan-2-ol and 1-(5-bromoindazol-2-yl)-2-methyl-propan-2-ol

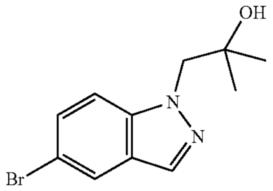

and

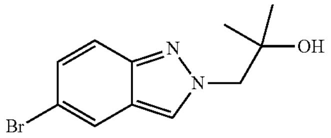

5-Bromo-1H-indazole (1.0 g, 5 mmol) was dissolved in 12 mL of DMF and treated sequentially with cesium carbonate (3.0 g, 10 mmol) and 1-chloro-2-methylpropan-2-ol (0.6 g, 6 mmol). The microwave tube was sealed and the reaction heated at 100° C. for 40 min. The reaction was filtered through celite and solids washed with ethyl acetate. The filtrate was concentrated and the residue purified by silica gel chromatography eluted with 50% to 75% ethyl acetate in heptane to give 1-(5-bromoindazol-1-yl)-2-methyl-propan-2-ol (0.45 g, 30%) and 1-(5-bromoindazol-2-yl)-2-methyl-propan-2-ol (0.52 g, 40%). MS ES+ m/z 269 $[M+H]^+$.

Intermediate 182: 2-(7-Bromo-2-methyl-imidazo[1,2-a]pyridin-3-yl)-4,5-dihydrooxazole

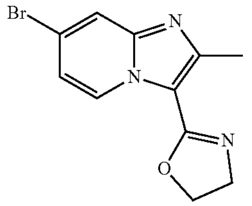 [SMILES: Cc1nc2cc(Br)ccn2c1C1=NCCO1]

A solution of 7-bromo-2-methyl-imidazo[1,2-a]pyridine-3-carboxylic acid (0.54 g, 2.12 mmol) in dichloromethane (3 mL) and thionyl chloride (1.76 g, 14.8 mmol) was treated with 1 drop of pyridine and the reaction heated to 50° C. After 2 h, the reaction was allowed to cool and concentrated. The residue was dissolved in 5 mL of dichloromethane and treated with ethanolamine (0.26 g, 4.23 mmol) dissolved in 1 mL of dichloromethane. The reaction was stirred at rt for 3 h to produce a suspension. The suspension was diluted with 5 mL of saturated aqueous sodium bicarbonate and 5 mL of dichloromethane. After shaking well, the solid was removed by filtration and the solid washed with water, dichloromethane, and dried. This solid was suspended in 10 mL of dichloromethane and treated with thionyl chloride (0.16 mL) and the mixture stirred vigorously for 2 h. The mixture was concentrated and triturated with toluene giving the product (0.54 g, 91%). MS ES+ m/z 280/282 $[M+H]^+$.

Intermediate 183: 2-(7-Bromo-2-methyl-imidazo[1,2-a]pyridin-3-yl)oxazole

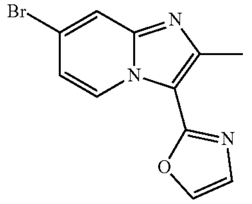 [SMILES: Cc1nc2cc(Br)ccn2c1-c1ncco1]

2-(7-Bromo-2-methyl-imidazo[1,2-a]pyridin-3-yl)-4,5-dihydrooxazole (0.10 g, 0.38 mmol) was dissolved in toluene (5 mL) and treated with manganese(II) dioxide (0.13 g, 1.5 mmol) and heated to 85° C. After 20 h, the reaction was cooled, solids removed by filtration, and the solids washed with methanol. The filtrate was concentrated and the residue purified by silica gel chromatography eluted with a gradient of methanol in dichloromethane and then a second column eluted with a gradient of ethyl acetate in heptane to give the product (0.003 g, 3%). MS ES+ m/z 278/280 $[M+H]^+$.

Intermediate 18: tert-Butyl 2-[1-[6-methyl-2-(2-methylpyrazolo[4,3-b]pyridin-6-yl)-4-oxo-chromen-8-yl]ethylamino]benzoate

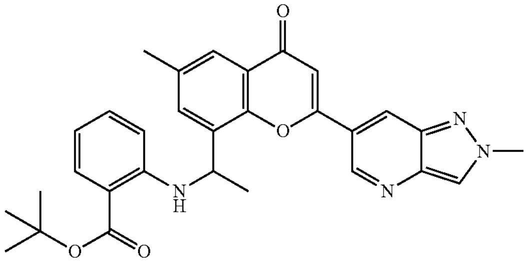 [SMILES: Cc1cc(C(C)Nc2ccccc2C(=O)OC(C)(C)C)c2oc(-c3cnc4cn(C)nc4c3)cc(=O)c2c1]

A 20 mL vial was charged with tert-butyl 2-[1-(2-ethylsulfanyl-6-methyl-4-oxo-chromen-8-yl)ethylamino]benzoate (200 mg, 0.46 mmol), 2-methyl-6-(4,4,5,5-tetramethyl-1,3,2-dioxaborolan-2-yl)pyrazolo[4,3-b]pyridine (236 mg, 0.91 mmol), zinc(II) acetate (167 mg, 0.91 mmol), copper(I) thiophene-2-carboxylate (174 mg, 0.91 mmol), water (30 μL, 1%), and THE (3 mL). Flushed the mixture with argon gas and added tris(dibenzylideneacetone)dipalladium(0) (41.7 mg, 0.046 mmol) and tri(2-furyl)phosphine (42.3 mg, 0.18 mmol) as solids. Flushed the mixture with argon gas and stirred the reaction at 75° C. for 5 days. The reaction was diluted with ethyl acetate and filtered through celite. The filtrate was concentrated and the residue purified via silica gel chromatography eluted with 0%-100% ethyl acetate in heptanes to give the product as a yellow solid (103 mg, 44%). MS ES+ m/z 511 $[M+H]^+$.

The following compounds in Table 30 were made in a similar way as described for Intermediate 18.

TABLE 30

| Int # | Chemical Name | Structure | MS ES+ m/z |
|---|---|---|---|
| 19 | tert-Butyl 2-[1-[6-methyl-2-(2-methyl-1-oxo-isoindolin-5-yl)-4-oxo-chromen-8-yl]ethylamino]benzoate | 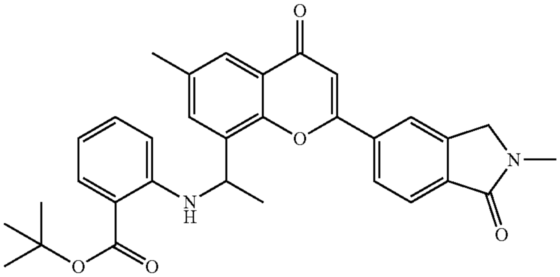 [SMILES: Cc1cc(C(C)Nc2ccccc2C(=O)OC(C)(C)C)c2oc(-c3ccc4c(c3)CN(C)C4=O)cc(=O)c2c1] | 525 $[M + H]^+$ |
| 20 | tert-Butyl 2-[1-(6-methyl-4-oxo-2-pyrazolo[1,5-a]pyrimidin-3-yl-chromen-8-yl)ethylamino]benzoate | 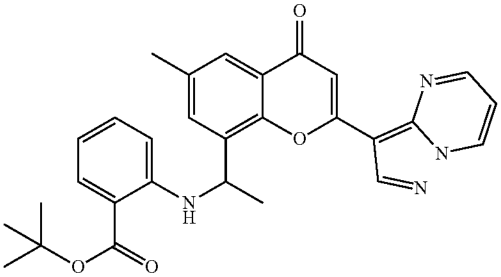 [SMILES: Cc1cc(C(C)Nc2ccccc2C(=O)OC(C)(C)C)c2oc(/C(C=N)=C3\N=CC=CN3)cc(=O)c2c1] | 497 $[M + H]^+$ |
| 21 | tert-Butyl 2-[1-(2-furo[2,3-c]pyridin-2-yl-6-methyl-4-oxo-chromen-8-yl)ethylamino]benzoate | 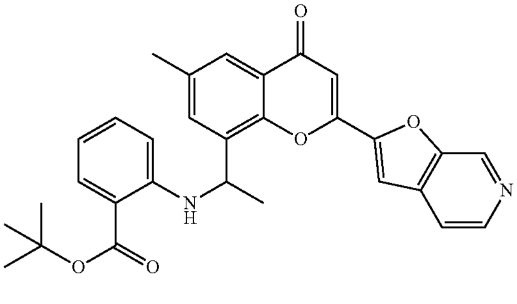 [SMILES: Cc1cc(C(C)Nc2ccccc2C(=O)OC(C)(C)C)c2oc(-c3cc4ccncc4o3)cc(=O)c2c1] | 497 $[M + H]^+$ |

TABLE 30-continued

| Int # | Chemical Name | Structure | MS ES+ m/z |
|---|---|---|---|
| 22 | tert-Butyl 2-[1-[6-methyl-2-(2-methylpyrazolo[3,4-b]pyridin-5-yl)-4-oxo-chromen-8-yl]ethylamino]benzoate | 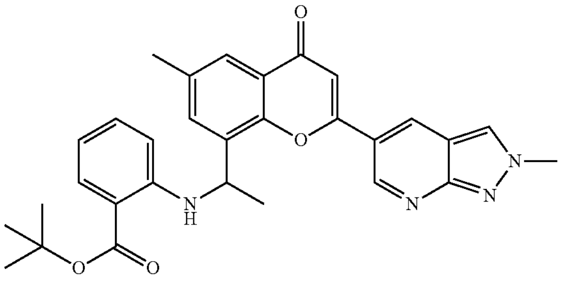 | 511 $[M + H]^+$ |
| 23 | tert-Butyl 2-[1-(6-methyl-4-oxo-2-pyrazolo[1,5-a]pyridin-3-yl-chromen-8-yl)ethylamino]benzoate | 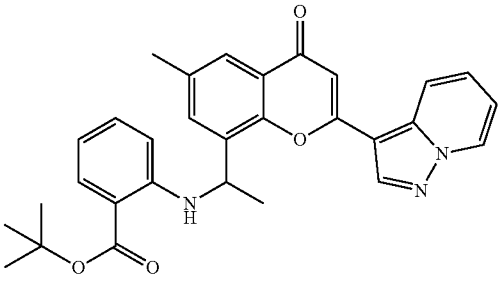 [SMILES: Cc1cc(C(C)Nc2ccccc2C(=O)OC(C)(C)C)c2oc(-c3cnn4ccccc34)cc(=O)c2c1] | 496 $[M + H]^+$ |
| 24 | tert-Butyl 2-[1-[6-methyl-4-oxo-2-[2-(trifluoromethyl)-1H-indol-5-yl]chromen-8-yl]ethylamino]benzoate | 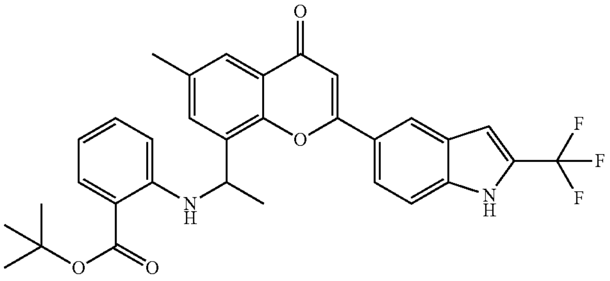 [SMILES: Cc1cc(C(C)Nc2ccccc2C(=O)OC(C)(C)C)c2oc(-c3ccc4[nH]c(C(F)(F)F)cc4c3)cc(=O)c2c1] | 563 $[M + H]^+$ |
| 25 | tert-Butyl 2-[1-[6-methyl-2-(1-methylindazol-3-yl)-4-oxo-chromen-8-yl]ethylamino]benzoate | 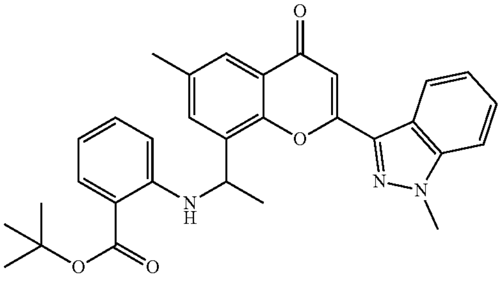 [SMILES: Cc1cc(C(C)Nc2ccccc2C(=O)OC(C)(C)C)c2oc(-c3nn(C)c4ccccc34)cc(=O)c2c1] | 510 $[M + H]^+$ |
| 26 | tert-Butyl 2-[1-[6-methyl-2-(2-methylindazol-5-yl)-4-oxo-chromen-8-yl]ethylamino]benzoate | 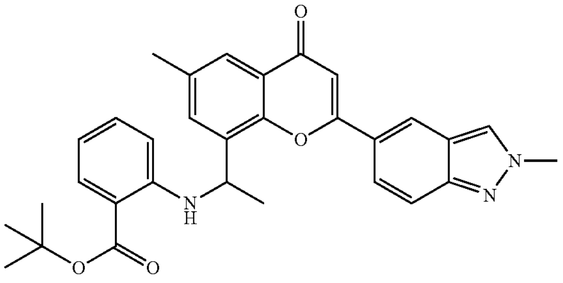 | 310 $[M + H]^+$ |

TABLE 30-continued

| Int # | Chemical Name | Structure | MS ES+ m/z |
|---|---|---|---|
| 27 | tert-Butyl 2-[1-[6-methyl-4-oxo-2-(1H-pyrrolo[2,3-b]pyridin-6-yl)chromen-8-yl]ethylamino]benzoate | 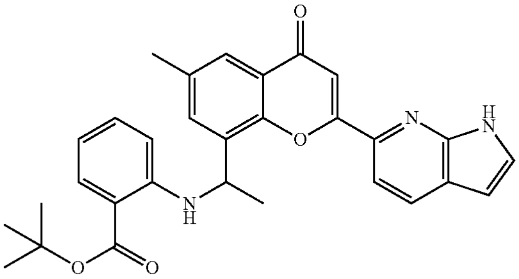 [SMILES: Cc1cc(C(C)Nc2ccccc2C(=O)OC(C)(C)C)c2oc(-c3ccc4cc[nH]c4n3)cc(=O)c2c1] | 496 [M + H]+ |
| 28 | tert-Butyl 2-[1-(2-imidazo[1,2-b]pyridazin-6-yl-6-methyl-4-oxo-chromen-8-yl)ethylamino]benzoate | 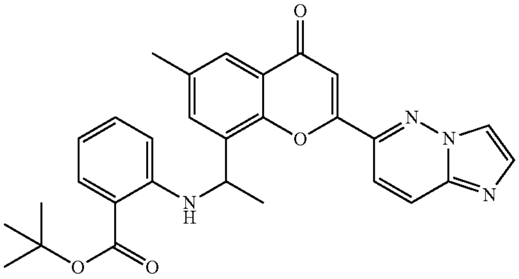 [SMILES: Cc1cc(C(C)Nc2ccccc2C(=O)OC(C)(C)C)c2oc(-c3ccc4nccn4n3)cc(=O)c2c1] | 497 [M + H]+ |
| 29 | tert-Butyl 2-[1-[6-methyl-2-(2-methylimidazo[1,2-a]pyridin-6-yl)-4-oxo-chromen-8-yl]ethylamino]benzoate | 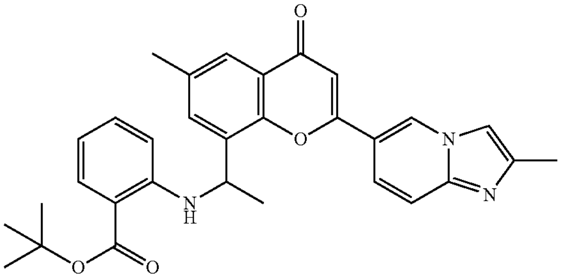 [SMILES: Cc1cc(C(C)Nc2ccccc2C(=O)OC(C)(C)C)c2oc(-c3ccc4nc(C)cn4c3)cc(=O)c2c1] | 510 [M + H]+ |
| 30 | tert-Butyl 2-[1-[2-(1H-indol-6-yl)-6-methyl-4-oxo-chromen-8-yl]ethylamino]benzoate | 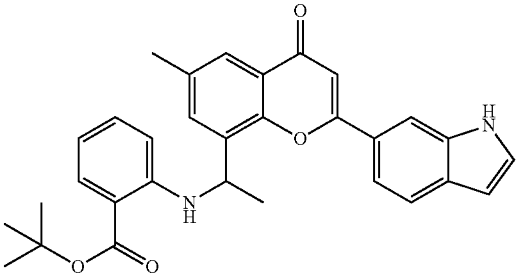 [SMILES: Cc1cc(C(C)Nc2ccccc2C(=O)OC(C)(C)C)c2oc(-c3ccc4cc[nH]c4c3)cc(=O)c2c1] | 495 [M + H]+ |
| 184 | tert-Butyl 2,3-difluoro-6-[1-[6-methyl-2-(2-methylimidazo[1,2-b]pyridazin-6-yl)-4-oxo-chromen-8-yl]ethylamino]benzoate | 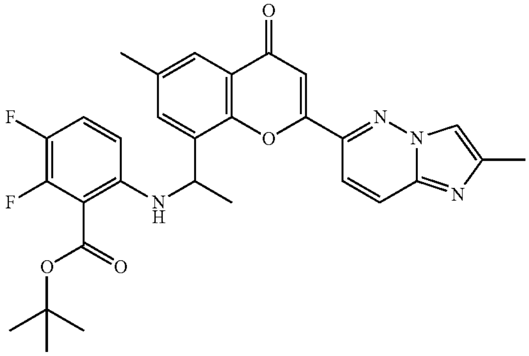 [SMILES: Cc1cc(C(C)Nc2ccc(F)c(F)c2C(=O)OC(C)(C)C)c2oc(-c3ccc4nc(C)cn4n3)cc(=O)c2c1] | 547 [M + H]+ |

TABLE 30-continued

| Int # | Chemical Name | Structure | MS ES+ m/z |
|---|---|---|---|
| 344 | tert-Butyl 2-fluoro-6-[1-[6-methyl-2-(1-methylindazol-5-yl)-4-oxo-chromen-8-yl]ethylamino]benzoate, Isomer 2 | 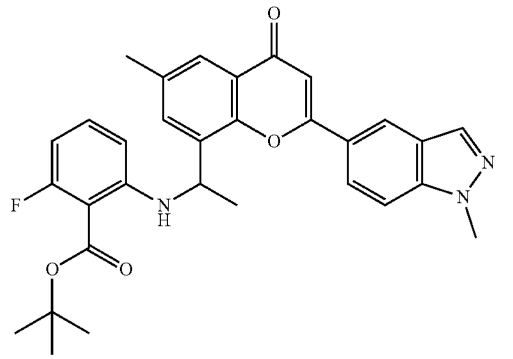 [SMILES: Cc1cc(C(C)Nc2cccc(F)c2C(=O)OC(C)(C)C)c2oc(-c3ccc4c(cnn4C)c3)cc(=O)c2c1] | 528 [M + H]+ |
| 345 | tert-Butyl 2-fluoro-6-[1-[6-methyl-2-(1-methylindazol-6-yl)-4-oxo-chromen-8-yl]ethylamino]benzoate | 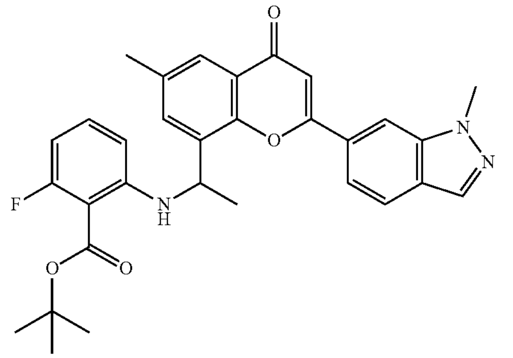 [SMILES: Cc1cc(C(C)Nc2cccc(F)c2C(=O)OC(C)(C)C)c2oc(-c3ccc4cnn(C)c4c3)cc(=O)c2c1] | 528 [M + H]+ |
| 346 | Methyl 5-chloro-2-[[(1R)-1-[6-methyl-2-(1-methylindazol-6-yl)-4-oxo-chromen-8-yl]ethyl]amino]benzoate | 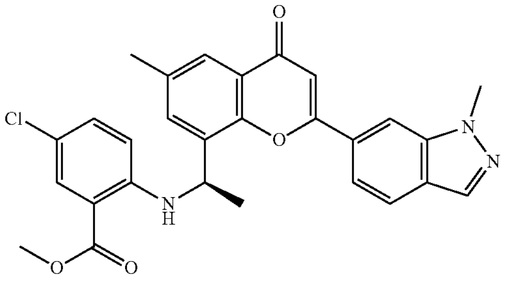 [SMILES: COC(=O)c1cc(Cl)ccc1N[C@H](C)c1cc(C)cc2c(=O)cc(-c3ccc4cnn(C)c4c3)oc12] | 502 [M + H]+ |
| 347 | Methyl 5-fluoro-2-[[(1R)-1-[6-methyl-2-(1-methylindazol-6-yl)-4-oxo-chromen-8-yl]ethyl]amino]benzoate | 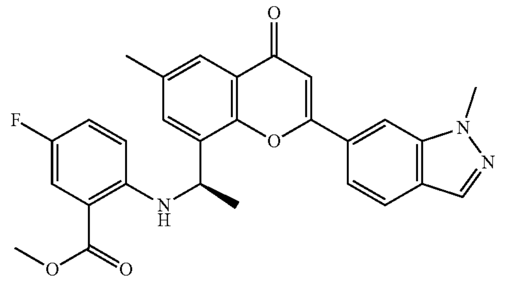 [SMILES: COC(=O)c1cc(F)ccc1N[C@H](C)c1cc(C)cc2c(=O)cc(-c3ccc4cnn(C)c4c3)oc12] | 486 [M + H]+ |

TABLE 30-continued

| Int # | Chemical Name | Structure | MS ES+ m/z |
|---|---|---|---|
| 348 | tert-Butyl 2-[8-[1-[(2-tert-butoxycarbonyl-6-chloro-3-pyridyl)amino]ethyl]-6-methyl-4-oxo-chromen-2-yl]indole-1-carboxylate | 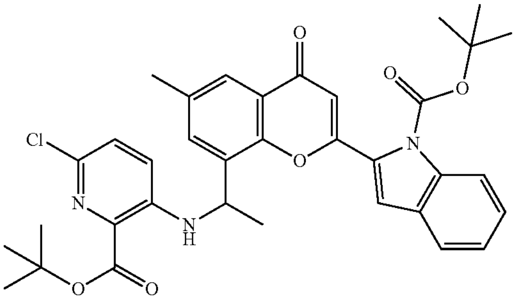 [SMILES: Cc1cc(C(C)Nc2ccc(Cl)nc2C(=O)OC(C)(C)C)c2oc(-c3cc4ccccc4n3C(=O)OC(C)(C)C)cc(=O)c2c1] | 630 [M + H]+ |
| 349 | tert-Butyl 6-chloro-3-[1-[2-(1,3-dimethylindazol-5-yl)-6-methyl-4-oxo-chromen-8-yl]ethylamino]pyridine-2-carboxylate | 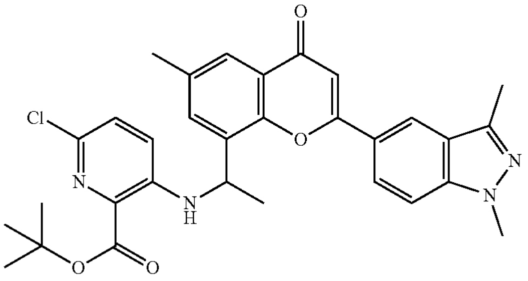 [SMILES: Cc1cc(C(C)Nc2ccc(Cl)nc2C(=O)OC(C)(C)C)c2oc(-c3ccc4c(c3)c(C)nn4C)cc(=O)c2c1] | 559 [M + H]+ |
| 350 | tert-Butyl 2-[[(1R)-1-(3,6-dimethyl-4-oxo-2-thieno[3,2-c]pyridin-2-yl-chromen-8-yl)ethyl]amino]benzoate | 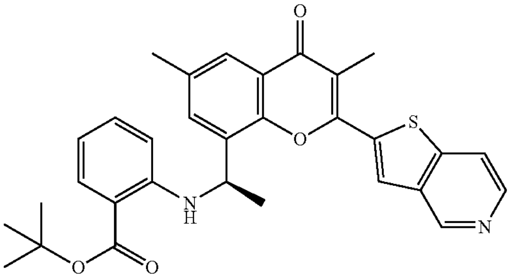 [SMILES: Cc1cc([C@@H](C)Nc2ccccc2C(=O)OC(C)(C)C)c2oc(-c3cc4cnccc4s3)c(C)c(=O)c2c1] | 527 [M + H]+ |
| 351 | tert-Butyl 6-chloro-3-[1-[6-methyl-2-(2-methylindazol-5-yl)-4-oxo-chromen-8-yl]ethylamino]pyridine-2-carboxylate | 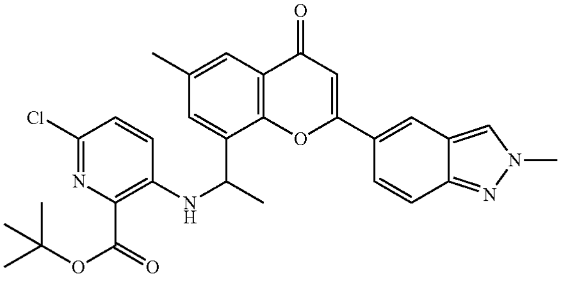 [SMILES: Cc1cc(C(C)Nc2ccc(Cl)nc2C(=O)OC(C)(C)C)c2oc(-c3ccc4nn(C)cc4c3)cc(=O)c2c1] | 545 [M + H]+ |

Intermediate 31 and Intermediate 32: Methyl 2-[1-(2-ethyl sulfanyl-6-methyl-4-oxo-chromen-8-yl) ethylamino]benzoate, Isomer 1 and Isomer 2

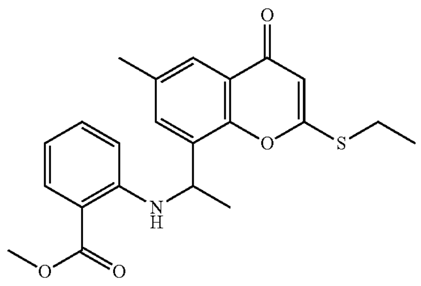 [SMILES: CCSc1cc(=O)c2cc(C)cc(C(C)Nc3ccccc3C(=O)OC)c2o1]

Methyl 2-[1-(2-ethylsulfanyl-6-methyl-4-oxo-chromen-8-yl)ethylamino]benzoate (13 g, 32.7 mmol) was separated into component isomers using a DAICEL Chiralpak AS (250×50 mm; 10 μm) column eluted with 30% EtOH with 0.1% $NH_4OH$ in $CO_2$ to give isomer 1 (4.3 g, 33%) and isomer 2 (5.6 g, 42%) as white solids. MS ES+ m/z 398 $[M+H]^+$.

Intermediate 33: Methyl 2-[1-[2-(1,3-benzodioxol-4-yl)-6-methyl-4-oxo-chromen-8-yl]ethylamino] benzoate, Isomer 2

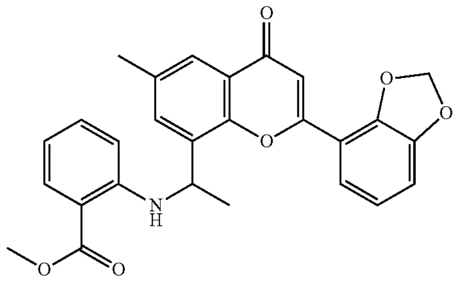 [SMILES: COC(=O)c1ccccc1NC(C)c1cc(C)cc2c(=O)cc(-c3cccc4c3OCO4)oc12]

A mixture of methyl 2-[1-(2-ethyl sulfanyl-6-methyl-4-oxo-chromen-8-yl)ethylamino]benzoate, Isomer 2 (120.00 mg, 301.90 μmol), 1,3-benzodioxol-4-ylboronic acid (150.29 mg, 905.69 μmol), copper(I) thiophene-2-carboxylate (115.14 mg, 603.79 μmol), tetrakis(triphenylphosphine) palladium(0) (34.89 mg, 30.19 μmol), and cesium carbonate (295.09 mg, 905.69 μmol) in DMF (3 mL) was stirred at 110° C. under nitrogen for 16 h to give a suspension. The reaction was cooled to rt, filtered, and then concentrated. The residue was purified by silica gel chromatography eluted with 0%-25% ethyl acetate in petroleum ether to give the product as a light yellow solid (72 mg, 52.1%). MS ES+ m/z 458 $[M+H]^+$.

The following compounds in Table 31 were made in a similar way as described for Intermediate 33.

TABLE 31

| Int # | Chemical Name | Structure | MS ES+ m/z |
|---|---|---|---|
| 34 | 2-[1-(6-Methyl-4-oxo-2-phthalazin-6-yl-chromen-8-yl)ethylamino]benzoic acid, Isomer 2 | 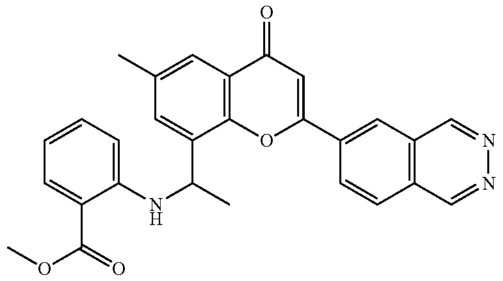 [SMILES: COC(=O)c1ccccc1NC(C)c1cc(C)cc2c(=O)cc(-c3ccc4cnncc4c3)oc12] | 466 $[M + H]^+$ |
| 35 | 2-[1-[2-(1,3-Benzodioxol-5-yl)-6-methyl-4-oxo-chromen-8-yl]ethylamino]benzoic acid, Isomer 2 | 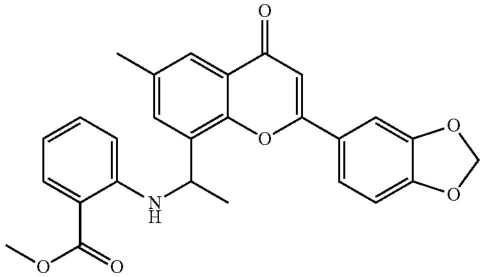 [SMILES: COC(=O)c1ccccc1NC(C)c1cc(C)cc2c(=O)cc(-c3ccc4c(c3)OCO4)oc12] | 458 $[M + H]^+$ |

Intermediate 36 and Intermediate 37: tert-Butyl 2-[1-(2-ethylsulfanyl-6-methyl-4-oxo-chromen-8-yl)ethylamino]benzoate, Isomer 1 and Isomer 2

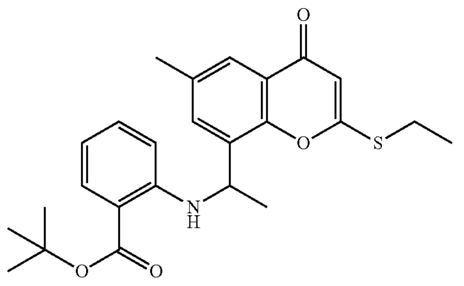

tert-Butyl 2-[1-(2-ethylsulfanyl-6-methyl-4-oxo-chromen-8-yl)ethylamino]benzoate (22.04 g, 50.14 mmol) was separated into component isomers using a Chiralcel OJ column (8×34 cm; 20 micron) eluted with 100% MeOH with 0.2% DMEA to give isomer 1 (wet 11.3 g) and isomer 2 (wet 12.9 g). MS ES+ m/z 440 $[M+H]^+$.

Intermediate 185 and Intermediate 186: tert-Butyl 6-chloro-3-[1-[2-ethylsulfanyl-4-oxo-6-(trifluoromethyl)chromen-8-yl]ethylamino]pyridine-2-carboxylate, Isomer 1 and Isomer 2

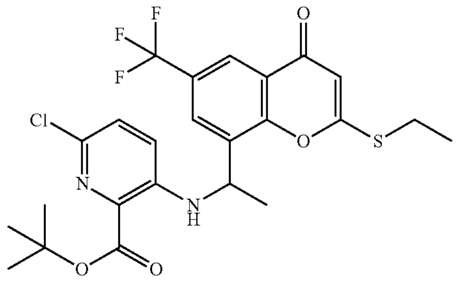 [SMILES: CCSc1cc(=O)c2cc(C(F)(F)F)cc(C(C)Nc3ccc(Cl)nc3C(=O)OC(C)(C)C)c2o1]

tert-Butyl 6-chloro-3-[1-[2-ethylsulfanyl-4-oxo-6-(trifluoromethyl)chromen-8-yl]ethylamino]pyridine-2-carboxylate was separated into Isomer 1 and Isomer 2 by SFC chromatography using a ChiralCel OJ column (50×250 mm ID; 10 μm) eluted with 15% MeOH (with 0.1% $NH_4OH$) in $CO_2$ as the mobile phase.

Intermediate 187: tert-Butyl 2-[1-(2-ethyl sulfanyl-3-iodo-6-methyl-4-oxo-chromen-8-yl)ethylamino]benzoate, Isomer 2

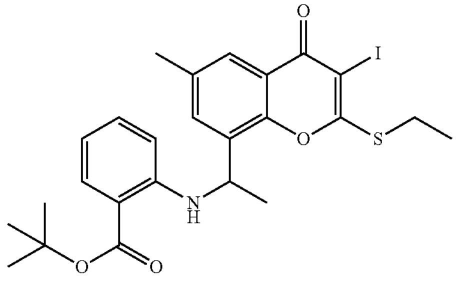 [SMILES: CCSc1oc2c(C(C)Nc3ccccc3C(=O)OC(C)(C)C)cc(C)cc2c(=O)c1I]

A dry flask equipped with a stir bar and septum was flushed with argon gas and charged with tert-butyl 2-[1-(2-ethylsulfanyl-6-methyl-4-oxo-chromen-8-yl)ethylamino]benzoate, Isomer 2 (1.00 g, 2.27 mmol) and 2 mL of dry THF. The reaction was cooled in an ice bath. When cold, 2,2,6,6-tetramethylpiperidinylzinc chloride lithium chloride complex (1M in THF, 1.93 g, 6.82 mmol) was added dropwise via addition funnel over 30 min. After addition was complete, the reaction was stirred at 0° C. After 1 h, iodine dissolved in dry THF (1M, 2.73 mL, 2.73 mmol) was added dropwise via addition funnel. After addition was complete, the reaction was stirred at 0° C. After 1 h, the reaction was cooled to −40° C. and quenched with methanol (10 mL). Added 50 mL of an ammonium chloride/ammonia solution (aqueous 2M solution; 50 mL) and stirred the reaction at rt for 2 h. Extracted three times with 300 mL of dichloromethane. The organics were combined, washed with aqueous sodium carbonate, collected, dried over $Na_2SO_4$, filtered, and concentrated. The residue was purified by reverse phase chromatography (C18) eluted with 0% to 80% acetonitrile (with 0.1% TFA) in water (with 0.1% TFA) to give the product (0.90 g, 66%). MS ES+ m/z 566 $[M+H]^+$.

Intermediate 188: tert-Butyl 2-[1-(3-cyano-2-ethylsulfanyl-6-methyl-4-oxo-chromen-8-yl)ethylamino]benzoate, Isomer 2

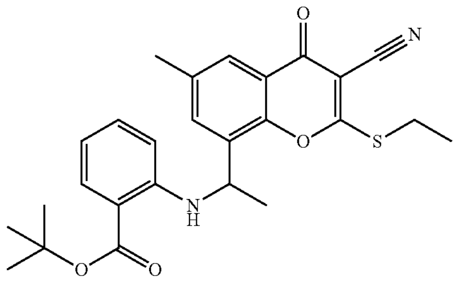 [SMILES: CCSc1oc2c(C(C)Nc3ccccc3C(=O)OC(C)(C)C)cc(C)cc2c(=O)c1C#N]

tert-Butyl 2-[1-(2-ethylsulfanyl-3-iodo-6-methyl-4-oxo-chromen-8-yl)ethylamino]benzoate, Isomer 2 (0.65 g, 1.15 mmol) and copper(I) cyanide (0.52 g, 5.77 mmol) were suspended in 12 mL of DMF and heated at 100° C. for 18 h. The reaction was allowed to cool and treated with saturated aqueous sodium bicarbonate (10 mL). The reaction was extracted three times with 5 mL of dichloromethane. The organics were combined, dried over $Na_2SO_4$, filtered, and concentrated. The residue was purified by silica gel chromatography eluted with 0% to 20% dichloromethane in ethyl acetate to give the product (0.42 g, 79%). MS ES+ m/z 465 $[M+H]^+$.

Intermediate 352: tert-Butyl 2-[1-[2-ethylsulfanyl-6-methyl-4-oxo-3-(trifluoromethyl)chromen-8-yl]ethylamino]benzoate, Isomer 2

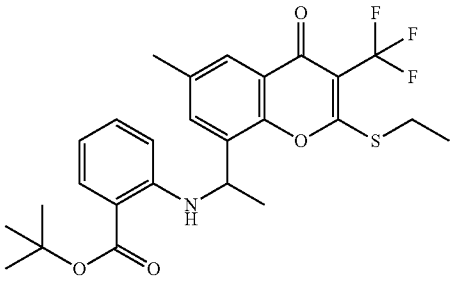 [SMILES: CCSc1oc2c(C(C)Nc3ccccc3C(=O)OC(C)(C)C)cc(C)cc2c(=O)c1C(F)(F)F]

A mixture of tert-butyl 2-[1-(2-ethylsulfanyl-3-iodo-6-methyl-4-oxo-chromen-8-yl)ethylamino]benzoate, isomer 2 (830 mg, 1.47 mmol), methyl difluoro(fluorosulfonyl)acetate (1.41 g, 7.34 mmol), and copper(I) iodide (335 mg, 1.76 mmol) in DMF (10 mL) were stirred at 70° C. for 18 h. The reaction was cooled to rt, quenched with saturated aqueous ammonium chloride (1 mL), and extracted with DCM (2×1 mL). The combined organic layers were dried over $Na_{2504}$, filtered, and concentrated. The residue was purified by silica gel chromatography eluted with 0% to 20% EtOAc in DCM to give the product (508 mg, 68%) as an orange oil. MS ES+ m/z 508 $[M+H]^+$.

Intermediate 189: tert-Butyl 2-[1-(2-ethyl sulfinyl-6-methyl-4-oxo-chromen-8-yl)ethylamino]benzoate, Isomer 2

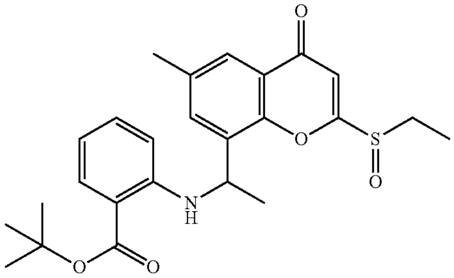 [SMILES: CCS(=O)c1cc(=O)c2cc(C)cc(C(C)Nc3ccccc3C(=O)OC(C)(C)C)c2o1]

tert-Butyl 2-[1-(2-ethylsulfanyl-6-methyl-4-oxo-chromen-8-yl)ethylamino]benzoate, Isomer 2 (3.2 g, 7.28 mmol) was dissolved in dichloromethane (30 mL), treated with saturated aqueous sodium bicarbonate (30 mL), and cooled in an ice bath. When cold, the reaction was treated with mCPBA (1.8 g, 77% wt, 8.0 mmol) as a solid and stirring continued at 0° C. After 1.5 h, poured the reaction into 50 mL of saturated aqueous sodium bicarbonate and brine and extracted three times with ethyl acetate. The organics were collected, washed with aqueous sodium thiosulfate, water, and brine, dried over $MgSO_4$, filtered, and concentrated. The residue was purified by silica gel chromatography eluted with 0% to 70% ethyl acetate in heptane to give the product (2.48 g, 75%) as a yellow foam. MS ES+ m/z 456 $[M+H]^+$.

The following compounds in Table 32 were made in a similar way as described for Intermediate 189.

TABLE 32

| Int # | Chemical Name | Structure | MS ES+ m/z |
|---|---|---|---|
| 280 | Methyl 2-[1-(2-ethylsulfinyl-6-methyl-4-oxo-chromen-8-yl)ethylamino]-6-fluoro-benzoate, Isomer 2 | 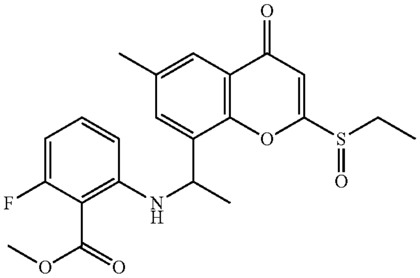 [SMILES: CCS(=O)c1cc(=O)c2cc(C)cc(C(C)Nc3cccc(F)c3C(=O)OC)c2o1] | 432 $[M + H]^+$ |
| 353 | Methyl 3-[1-(2-ethylsulfinyl-6-methyl-4-oxo-chromen-8-yl)ethylamino]pyridine-2-carboxylate, Isomer 2 | 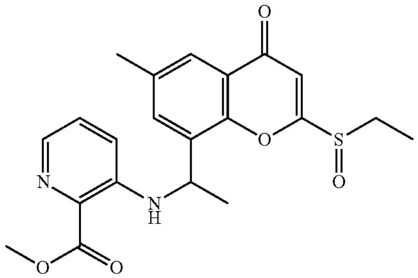 [SMILES: CCS(=O)c1cc(=O)c2cc(C)cc(C(C)Nc3cccnc3C(=O)OC)c2o1] | 415 $[M + H]^+$ |

TABLE 32-continued

| Int # | Chemical Name | Structure | MS ES+ m/z |
|---|---|---|---|
| 354 | Methyl 3-[[(1R)-1-(2-ethylsulfinyl-6-methyl-4-oxo-chromen-8-yl)ethyl]amino]pyridine-2-carboxylate | 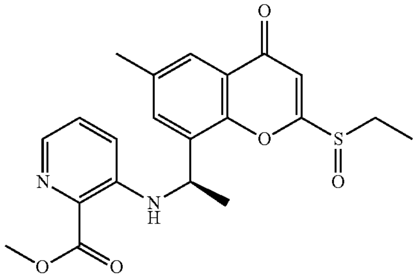 [SMILES: CCS(=O)c1cc(=O)c2cc(C)cc([C@@H](C)Nc3cccnc3C(=O)OC)c2o1] | 415 [M + H]+ |
| 355 | Methyl 2-[[(1R)-1-(2-ethylsulfinyl-6-methyl-4-oxo-chromen-8-yl)ethyl]amino]-6-fluoro-benzoate | 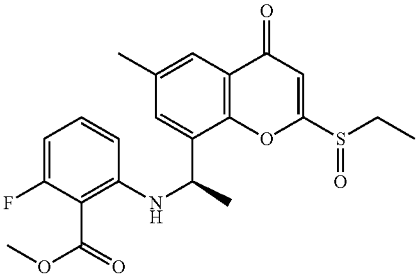 [SMILES: CCS(=O)c1cc(=O)c2cc(C)cc([C@@H](C)Nc3cccc(F)c3C(=O)OC)c2o1] | 432 [M + H]+ |

Intermediate 190: tert-Butyl 2-[1-(2-bromo-6-methyl-4-oxo-chromen-8-yl)ethylamino]benzoate, Isomer 2

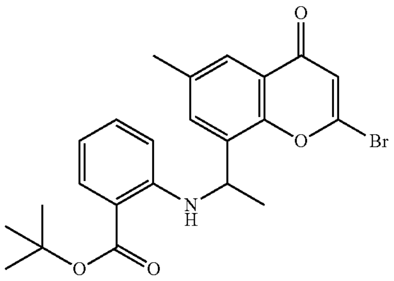 [SMILES: Cc1cc(C(C)Nc2ccccc2C(=O)OC(C)(C)C)c2oc(Br)cc(=O)c2c1]

tert-Butyl 2-[1-(2-ethylsulfinyl-6-methyl-4-oxo-chromen-8-yl)ethylamino]benzoate, Isomer 2 (2.48 g, 5.44 mmol) was suspended in 1,4-dioxane (80 mL) and treated with benzyltriethylammonium bromide (0.74 g, 2.72 mmol). The suspension was then treated with hydrogen bromide (4.59 g, 48 wt %, 27.22 mmol) and stirred at rt. After 30 min, added another aliquot of hydrogen bromide (4.59 g, 48 wt %, 27.22 mmol) and stirred at rt. After stirring 30 min, the pH of the reaction was adjusted to 7 with 100 mL of saturated, aqueous sodium bicarbonate. Poured the reaction into brine (100 mL) and extracted 3 times with ethyl acetate. The combined organic layers were washed with brine, dried over $MgSO_4$, filtered, and concentrated. The crude residue was purified by silica gel chromatography eluted with 0% to 25% ethyl acetate in heptane to give the product as a yellow foam (616 mg, 25%). MS ES+ m/z 458/460 $[M+H]^+$.

The following compounds in Table 33 were made in a similar way as described for Intermediate 190.

TABLE 33

| Int # | Chemical Name | Structure | MS ES+ m/z |
|---|---|---|---|
| 281 | Methyl 2-[1-(2-bromo-6-methyl-4-oxo-chromen-8-yl)ethylamino]-6-fluoro-benzoate | 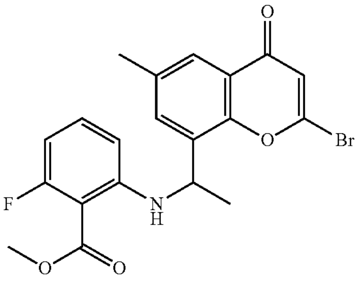 [SMILES: COC(=O)c1c(F)cccc1NC(C)c1cc(C)cc2c(=O)cc(Br)oc12] | |

TABLE 33-continued

| Int # | Chemical Name | Structure | MS ES+ m/z |
|---|---|---|---|
| 356 | Methyl 3-[[(1R)-1-(2-bromo-6-methyl-4-oxo-chromen-8-yl)ethyl]amino]pyridine-2-carboxylate | 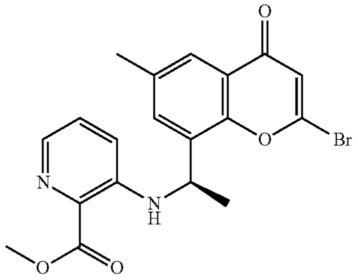 [SMILES: COC(=O)c1ncccc1N[C@H](C)c1cc(C)cc2c(=O)cc(Br)oc12] | 419 [M + H]$^+$ |
| 357 | Methyl 3-[[(1R)-1-(2-bromo-6-methyl-4-oxo-chromen-8-yl)ethyl]amino]pyridine-2-carboxylate | 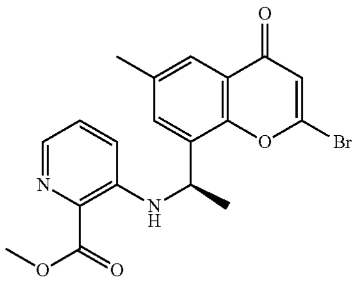 [SMILES: COC(=O)c1ncccc1N[C@H](C)c1cc(C)cc2c(=O)cc(Br)oc12] | 419 [M + H]$^+$ |
| 358 | Methyl 2-[[(1R)-1-(2-bromo-6-methyl-4-oxo-chromen-8-yl)ethyl]amino]-6-fluoro-benzoate | 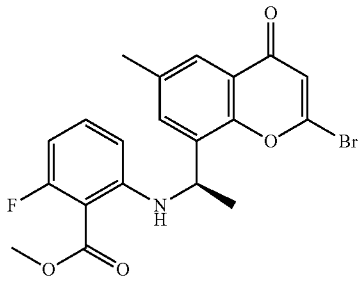 [SMILES: COC(=O)c1c(F)cccc1N[C@H](C)c1cc(C)cc2c(=O)cc(Br)oc12] | 435 [M + H]$^+$ |

Intermediate 38: tert-Butyl 2-[1-[6-methyl-2-(2-methylindazol-6-yl)-4-oxo-chromen-8-yl]ethyl-amino]benzoate, Isomer 2

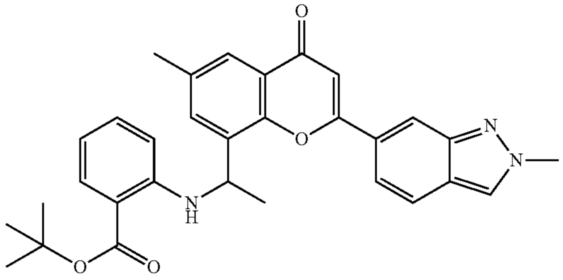 [SMILES: Cc1cc(C(C)Nc2ccccc2C(=O)OC(C)(C)C)c2oc(-c3ccc4cn(C)nc4c3)cc(=O)c2c1]

A 20 mL vial was charged with tert-butyl 2-[1-(2-ethyl-sulfanyl-6-methyl-4-oxo-chromen-8-yl)ethylamino]benzoate, Isomer 2 (100 mg, 0.23 mmol), 2-methyl-6-(4,4,5,5-tetramethyl-1,3,2-dioxaborolan-2-yl)indazole (117 mg, 0.46 mmol), copper(I) thiophene-2-carboxylate (86.8 mg, 0.46 mmol), tris(dibenzylideneacetone)dipalladium(0) (20.8 mg, 0.023 mmol), tri(2-furyl)phosphine (26.4 mg, 0.11 mmol), zinc(II) acetate (83.5 mg, 0.46 mmol), and degassed THE (5 mL). The reaction was flushed with argon gas and stirred at 75° C. for 16 h. After cooling to rt, the reaction was filtered and concentrated. The residue was purified using silica gel chromatography eluted with 10%-100% ethyl acetate in heptanes to give the product (20.5 mg, 18%). MS ES+ m/z 510 [M+H]$^+$.

The following compounds in Table 34 were made in a similar way as described for Intermediate 38.

TABLE 34

| Int # | Chemical Name | Structure | MS ES+ m/z |
|---|---|---|---|
| 39 | tert-Butyl 2-[1-[2-(6-methoxyimidazo[1,2-a]pyridin-2-yl)-6-methyl-4-oxo-chromen-8-yl]ethylamino]benzoate, Isomer 2 | 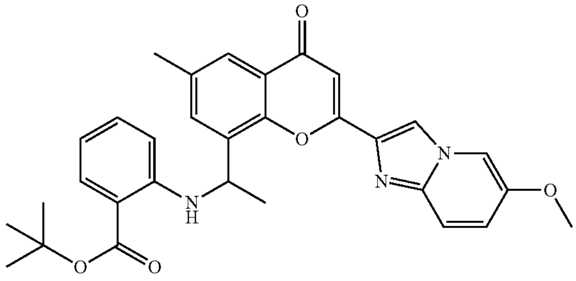 [SMILES: COc1ccc2nc(-c3cc(=O)c4cc(C)cc(C(C)Nc5ccccc5C(=O)OC(C)(C)C)c4o3)cn2c1] | 526 [M + H]+ |
| 40 | tert-Butyl 2-[1-[6-methyl-2-(2-methylimidazo[1,2-a]pyridin-7-yl)-4-oxo-chromen-8-yl]ethylamino]benzoate, Isomer 2 | 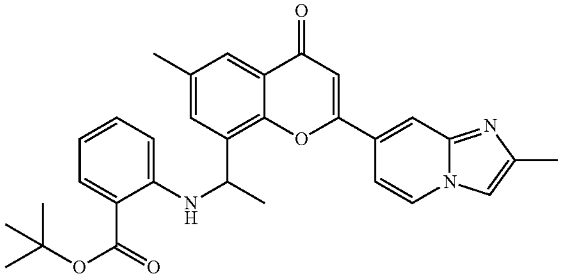 [SMILES: Cc1cc(C(C)Nc2ccccc2C(=O)OC(C)(C)C)c2oc(-c3ccn4cc(C)nc4c3)cc(=O)c2c1] | 510 [M + H]+ |
| 41 | tert-Butyl 2-[1-[6-methyl-4-oxo-2-(1H-pyrrolo[2,3-b]pyridin-6-yl)chromen-8-yl]ethylamino]benzoate, Isomer 2 | 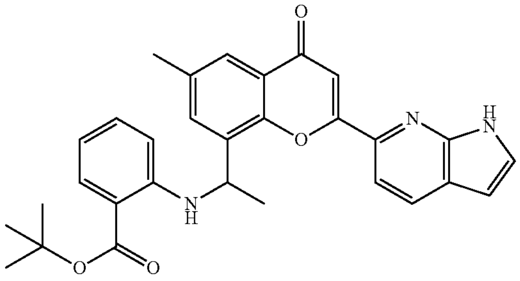 [SMILES: Cc1cc(C(C)Nc2ccccc2C(=O)OC(C)(C)C)c2oc(-c3ccc4cc[nH]c4n3)cc(=O)c2c1] | 496 [M + H]+ |
| 42 | tert-Butyl 2-[1-[6-methyl-2-(2-methylindazol-5-yl)-4-oxo-chromen-8-yl]ethylamino]benzoate, Isomer 2 | 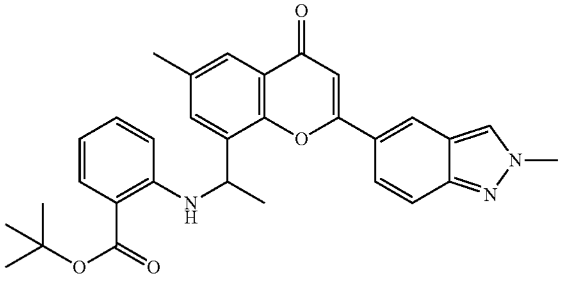 [SMILES: Cc1cc(C(C)Nc2ccccc2C(=O)OC(C)(C)C)c2oc(-c3ccc4nn(C)cc4c3)cc(=O)c2c1] | 510 [M + H]+ |
| 43 | tert-Butyl 2-[1-[6-methyl-2-(2-methyl-1,3-benzoxazol-5-yl)-4-oxo-chromen-8-yl]ethylamino]benzoate, Isomer 2 | 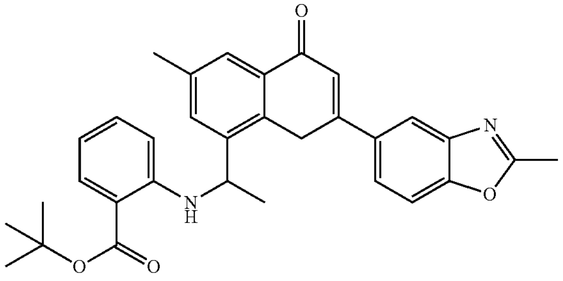 | 511 [M + H]+ |

TABLE 34-continued

| Int # | Chemical Name | Structure | MS ES+ m/z |
|---|---|---|---|
| 44 | tert-Butyl 2-[1-[6-methyl-2-(2-methyl-1H-pyrrolo[2,3-b]pyridin-6-yl)-4-oxo-chromen-8-yl]ethylamino]benzoate, Isomer 2 | 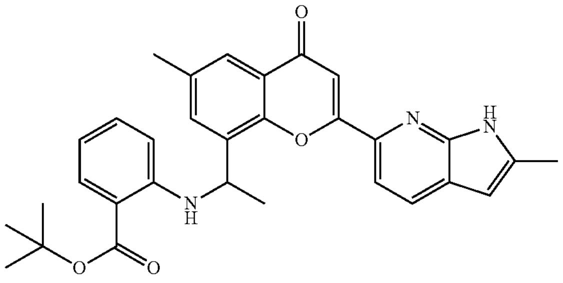 [SMILES: Cc1cc(C(C)Nc2ccccc2C(=O)OC(C)(C)C)c2oc(-c3ccc4cc(C)[nH]c4n3)cc(=O)c2c1] | 510 [M + H]$^+$ |
| 45 | tert-Butyl 2-[1-[2-(1H-indol-6-yl)-6-methyl-4-oxo-chromen-8-yl]ethylamino]benzoate, Isomer 2 | 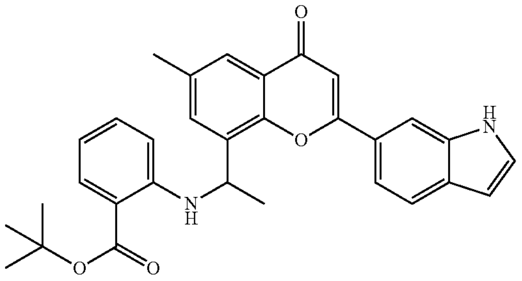 [SMILES: Cc1cc(C(C)Nc2ccccc2C(=O)OC(C)(C)C)c2oc(-c3ccc4cc[nH]c4c3)cc(=O)c2c1] | 495 [M + H]$^+$ |
| 46 | tert-Butyl 2-[1-(2-furo[3,2-c]pyridin-2-yl-6-methyl-4-oxo-chromen-8-yl)ethylamino]benzoate, Isomer 2 | 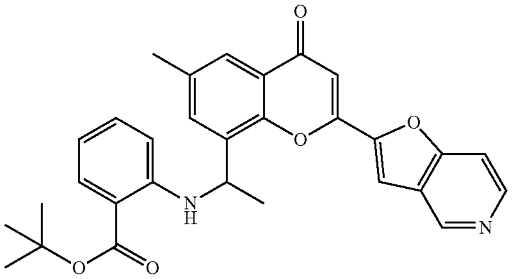 [SMILES: Cc1cc(C(C)Nc2ccccc2C(=O)OC(C)(C)C)c2oc(-c3cc4cnccc4o3)cc(=O)c2c1] | 497 [M + H]$^+$ |
| 47 | tert-Butyl 2-[1-[6-methyl-2-(1-methylindazol-3-yl)-4-oxo-chromen-8-yl]ethylamino]benzoate, Isomer 2 | 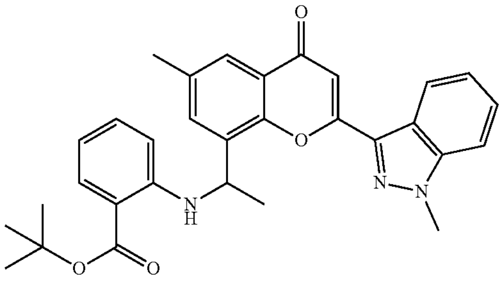 [SMILES: Cc1cc(C(C)Nc2ccccc2C(=O)OC(C)(C)C)c2oc(-c3nn(C)c4ccccc34)cc(=O)c2c1] | 510 [M + H]$^+$ |
| 48 | tert-Butyl 2-[1-[6-methyl-2-(2-methylimidazo[1,2-a]pyridin-6-yl)-4-oxo-chromen-8-yl]ethylamino]benzoate, Isomer 2 | 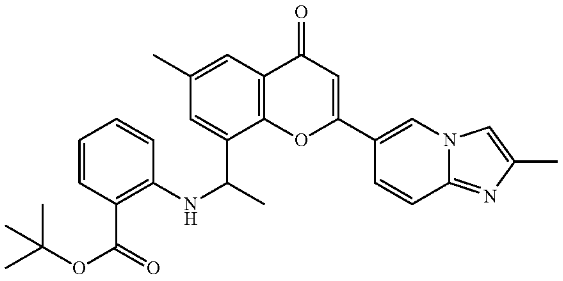 [SMILES: Cc1cc(C(C)Nc2ccccc2C(=O)OC(C)(C)C)c2oc(-c3ccc4nc(C)cn4c3)cc(=O)c2c1] | 510 [M + H]$^+$ |

TABLE 34-continued

| Int # | Chemical Name | Structure | MS ES+ m/z |
|---|---|---|---|
| 49 | tert-Butyl 2-[1-[6-methyl-4-oxo-2-(2-oxo-3H-1,3-benzoxazol-5-yl)chromen-8-yl]ethylamino]benzoate, Isomer 2 | 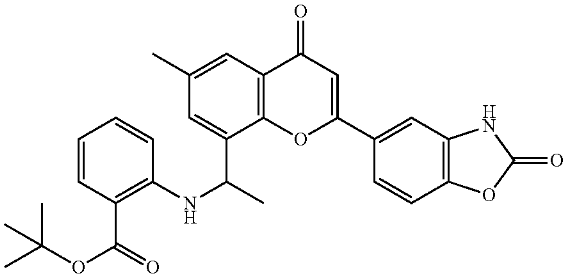 [SMILES: Cc1cc(C(C)Nc2ccccc2C(=O)OC(C)(C)C)c2oc(-c3ccc4oc(=O)[nH]c4c3)cc(=O)c2c1] | 513 $[M + H]^+$ |
| 50 | tert-Butyl 2-[1-[6-methyl-2-(1-methylindazol-6-yl)-4-oxo-chromen-8-yl]ethylamino]benzoate, Isomer 2 | 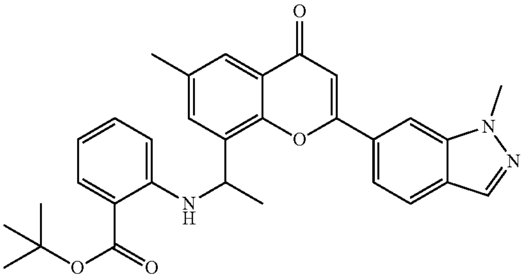 [SMILES: Cc1cc(C(C)Nc2ccccc2C(=O)OC(C)(C)C)c2oc(-c3ccc4cnn(C)c4c3)cc(=O)c2c1] | 510 $[M + H]^+$ |
| 51 | tert-Butyl 2-[1-[6-methyl-2-(1-methylindazol-5-yl)-4-oxo-chromen-8-yl]ethylamino]benzoate, Isomer 2 | 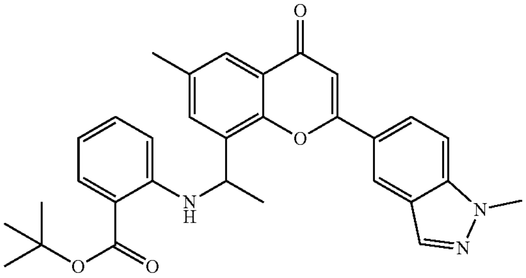 [SMILES: Cc1cc(C(C)Nc2ccccc2C(=O)OC(C)(C)C)c2oc(-c3ccc4c(cnn4C)c3)cc(=O)c2c1] | 510 $[M + H]^+$ |
| 52 | tert-Butyl 2-[1-[2-(1,3-dimethylindazol-6-yl)-6-methyl-4-oxo-chromen-8-yl]ethylamino]benzoate, Isomer 2 | 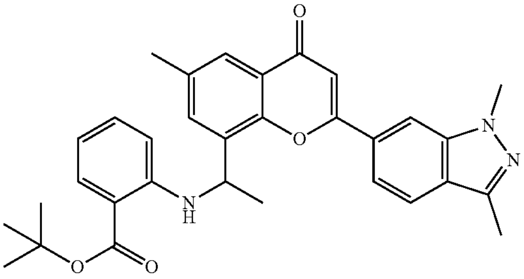 | 524 $[M + H]^+$ |
| 53 | tert-Butyl 2-[1-(6-methyl-4-oxo-2-pyrazolo[1,5-a]pyridin-3-yl-chromen-8-yl)ethylamino]benzoate, Isomer 2 | 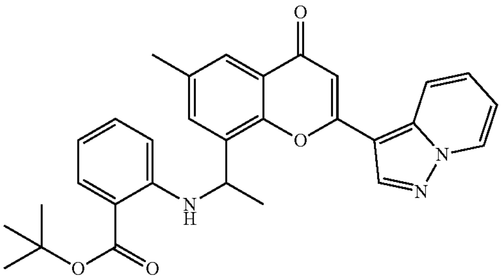 [SMILES: Cc1cc(C(C)Nc2ccccc2C(=O)OC(C)(C)C)c2oc(-c3cnn4ccccc34)cc(=O)c2c1] | 496 $[M + H]^+$ |

TABLE 34-continued

| Int # | Chemical Name | Structure | MS ES+ m/z |
|---|---|---|---|
| 54 | tert-Butyl 2-[1-[6-methyl-2-(3-methyl-1H-indazol-6-yl)-4-oxo-chromen-8-yl]ethylamino]benzoate, Isomer 2 | 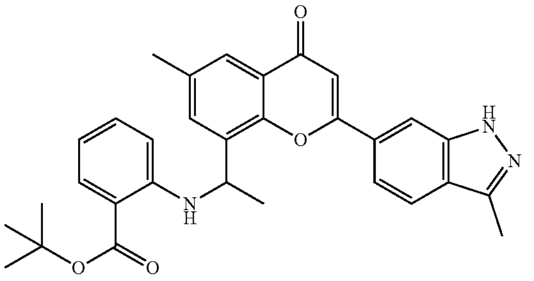 [SMILES: Cc1cc(C(C)Nc2ccccc2C(=O)OC(C)(C)C)c2oc(-c3ccc4c(C)n[nH]c4c3)cc(=O)c2c1] | 510 [M + H]+ |
| 63 | tert-Butyl 2-[1-[6-fluoro-2-(2-methylimidazo[1,2-a]pyridin-6-yl)-4-oxo-chromen-8-yl]ethylamino]benzoate, Isomer 2 | 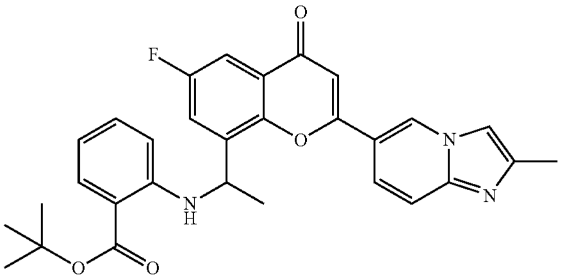 [SMILES: Cc1cn2cc(-c3cc(=O)c4cc(F)cc(C(C)Nc5ccccc5C(=O)OC(C)(C)C)c4o3)ccc2n1] | 514 [M + H]+ |
| 64 | tert-Butyl 2-[1-[6-fluoro-2-(2-methylindazol-5-yl)-4-oxo-chromen-8-yl]ethylamino]benzoate, Isomer 2 | 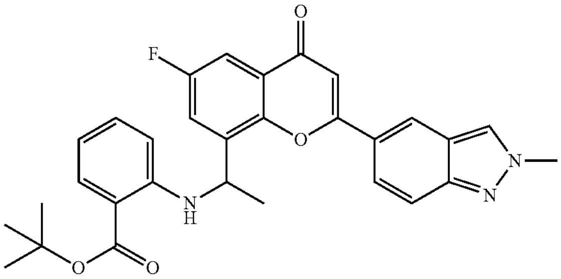 | 514 [M + H]+ |
| 65 | tert-Butyl 2-[1-[6-fluoro-3-methyl-2-(2-methylimidazo[1,2-a]pyridin-6-yl)-4-oxo-chromen-8-yl]ethylamino]benzoate, Isomer 2 | 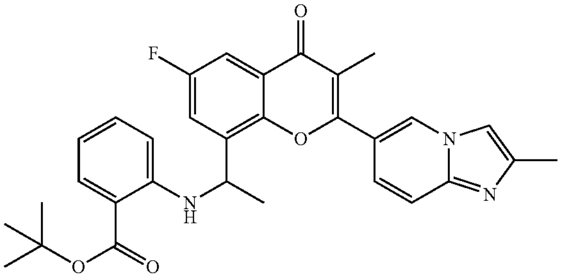 [SMILES: Cc1cn2cc(-c3oc4c(C(C)Nc5ccccc5C(=O)OC(C)(C)C)cc(F)cc4c(=O)c3C)ccc2n1] | 528 [M + H]+ |
| 66 | tert-Butyl 2-[1-[6-fluoro-3-methyl-2-(2-methylindazol-5-yl)-4-oxo-chromen-8-yl]ethylamino]benzoate, Isomer 2 | 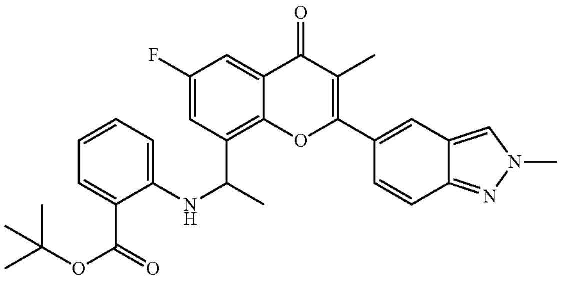 [SMILES: Cc1c(-c2ccc3nn(C)cc3c2)oc2c(C(C)Nc3ccccc3C(=O)OC(C)(C)C)cc(F)cc2c1=O] | 528 [M + H]+ |

TABLE 34-continued

| Int # | Chemical Name | Structure | MS ES+ m/z |
|---|---|---|---|
| 67 | tert-Butyl 2-[1-[6-methyl-4-oxo-2-(triazolo[1,5-a]pyridin-5-yl)chromen-8-yl]ethylamino]benzoate, Isomer 2 | 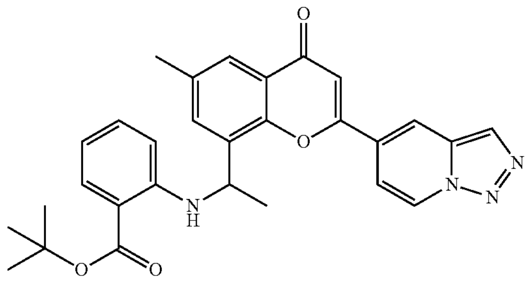 [SMILES: Cc1cc(C(C)Nc2ccccc2C(=O)OC(C)(C)C)c2oc(-c3ccn4nncc4c3)cc(=O)c2c1] | 497 [M + H]$^+$ |
| 68 | tert-Butyl 2-[1-[2-(1,3-dimethylindazol-5-yl)-6-methyl-4-oxo-chromen-8-yl]ethylamino]benzoate, Isomer 2 | 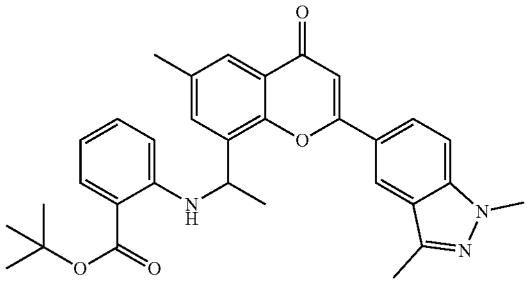 [SMILES: Cc1cc(C(C)Nc2ccccc2C(=O)OC(C)(C)C)c2oc(-c3ccc4c(c3)c(C)nn4C)cc(=O)c2c1] | 524 [M + H]$^+$ |
| 69 | tert-Butyl 2-[1-[2-(1H-indazol-5-yl)-6-methyl-4-oxo-chromen-8-yl]ethylamino]benzoate, Isomer 2 | 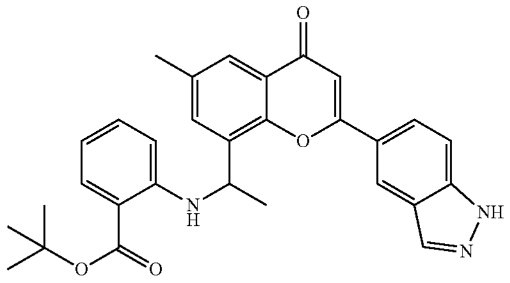 [SMILES: Cc1cc(C(C)Nc2ccccc2C(=O)OC(C)(C)C)c2oc(-c3ccc4[nH]ncc4c3)cc(=O)c2c1] | 496 [M + H]$^+$ |
| 70 | tert-Butyl 2-[1-[6-methyl-2-(3-methyl-1H-indazol-5-yl)-4-oxo-chromen-8-yl]ethylamino]benzoate, Isomer 2 | 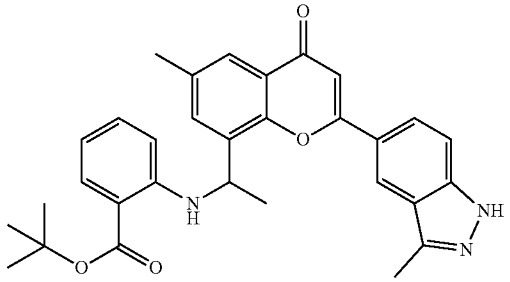 [SMILES: Cc1cc(C(C)Nc2ccccc2C(=O)OC(C)(C)C)c2oc(-c3ccc4[nH]nc(C)c4c3)cc(=O)c2c1] | 510 [M + H]$^+$ |
| 71 | tert-Butyl 2-[1-[6-methyl-2-(1-methyl-2-oxo-indolin-5-yl)-4-oxo-chromen-8-yl]ethylamino]benzoate, Isomer 2 | 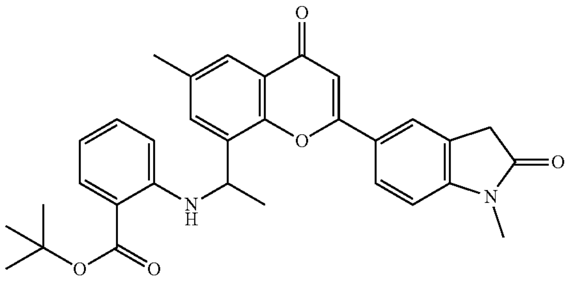 [SMILES: Cc1cc(C(C)Nc2ccccc2C(=O)OC(C)(C)C)c2oc(-c3ccc4c(c3)CC(=O)N4C)cc(=O)c2c1] | 525 [M + H]$^+$ |

TABLE 34-continued

| Int # | Chemical Name | Structure | MS ES+ m/z |
|---|---|---|---|
| 72 | tert-Butyl 2-[1-[2-(1H-indazol-6-yl)-6-methyl-4-oxo-chromen-8-yl]ethylamino]benzoate, Isomer 2 | 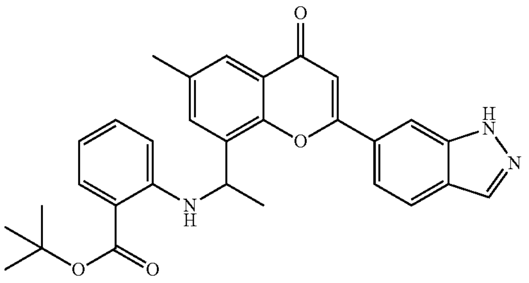 [SMILES: Cc1cc(C(C)Nc2ccccc2C(=O)OC(C)(C)C)c2oc(-c3ccc4cn[nH]c4c3)cc(=O)c2c1] | 496 $[M + H]^+$ |
| 73 | tert-Butyl 2-[1-[2-(2,2-difluoro-1,3-benzodoxol-5-yl)-6-methyl-4-oxo-chromen-8-yl]ethylamino]benzoate, Isomer 2 | 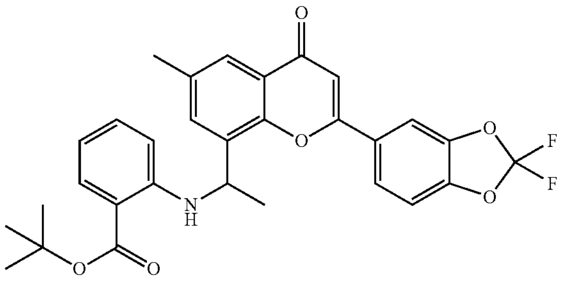 [SMILES: Cc1cc(C(C)Nc2ccccc2C(=O)OC(C)(C)C)c2oc(-c3ccc4c(c3)OC(F)(F)O4)cc(=O)c2c1] | 536 $[M + H]^+$ |
| 74 | tert-Butyl 2-[1-[6-methyl-2-(2-methyl-1H-benzimidazol-5-yl)-4-oxo-chromen-8-yl]ethylamino]benzoate, Isomer 2 | 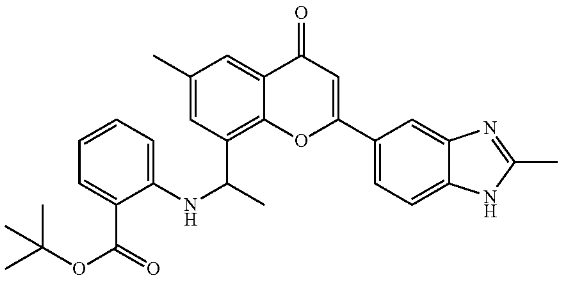 [SMILES: Cc1cc(C(C)Nc2ccccc2C(=O)OC(C)(C)C)c2oc(-c3ccc4[nH]c(C)nc4c3)cc(=O)c2c1] | 510 $[M + H]^+$ |
| 75 | tert-Butyl 2-[1-(6-methyl-4-oxo-2-pyrazolo[1,5-a]pyridin-6-yl-chromen-8-yl)ethylamino]benzoate, Isomer 2 | 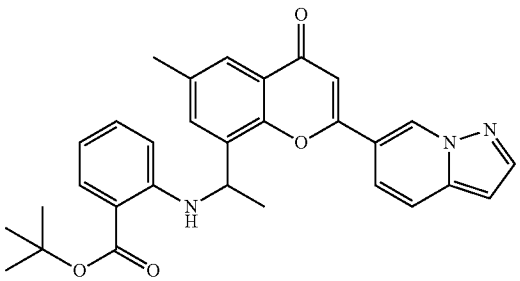 [SMILES: Cc1cc(C(C)Nc2ccccc2C(=O)OC(C)(C)C)c2oc(-c3ccc4ccnn4c3)cc(=O)c2c1] | 496 $[M + H]^+$ |
| 76 | tert-Butyl 2-[8-[1-(2-tert-butoxycarbonylanilino)ethyl]-6-methyl-4-oxo-chromen-2-yl]indole-1-carboxylate, Isomer 2 | 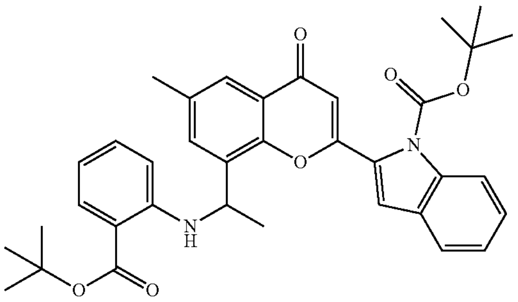 | 595 $[M + H]^+$ |

TABLE 34-continued

| Int # | Chemical Name | Structure | MS ES+ m/z |
|---|---|---|---|
| 77 | tert-Butyl 2-[1-[6-methyl-4-oxo-2-[2-(trifluoromethyl)imidazo[1,2-a]pyridin-6-yl]chromen-8-yl]ethylamino]benzoate, Isomer 2 | 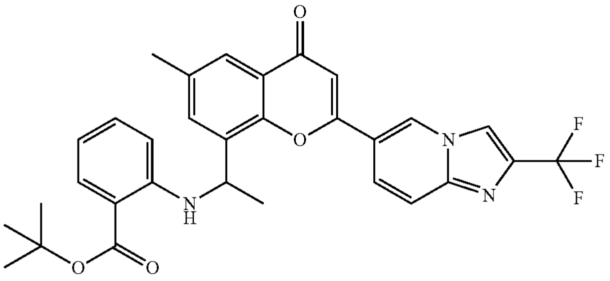 [SMILES: Cc1cc(C(C)Nc2ccccc2C(=O)OC(C)(C)C)c2oc(-c3ccc4nc(C(F)(F)F)cn4c3)cc(=O)c2c1] | 564 [M + H]+ |
| 78 | tert-Butyl 2-[1-[6-methyl-4-oxo-2-(1H-pyrrolo[3,2-b]pyridin-6-yl)chromen-8-yl]ethylamino]benzoate, Isomer 2 | 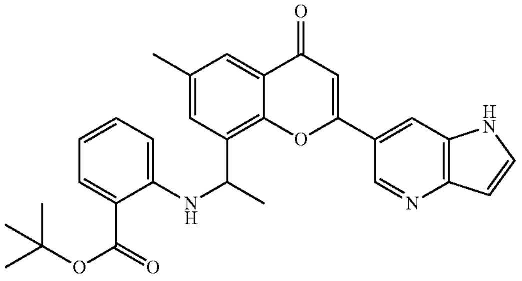 [SMILES: Cc1cc(C(C)Nc2ccccc2C(=O)OC(C)(C)C)c2oc(-c3cnc4cc[nH]c4c3)cc(=O)c2c1] | 496 [M + H]+ |
| 79 | tert-Butyl 2-[1-[6-methyl-2-(6-methyl-7H-pyrrolo[2,3-d]pyrimidin-2-yl)-4-oxo-chromen-8-yl]ethylamino]benzoate, Isomer 2 | 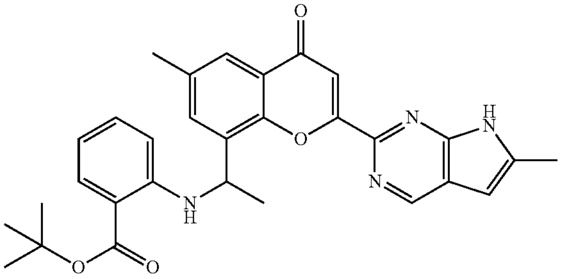 [SMILES: Cc1cc(C(C)Nc2ccccc2C(=O)OC(C)(C)C)c2oc(-c3ncc4cc(C)[nH]c4n3)cc(=O)c2c1] | 511 [M + H]+ |
| 80 | tert-Butyl 2-[1-(2-imidazo[1,2-a]pyridin-6-yl-6-methyl-4-oxo-chromen-8-yl)ethylamino]benzoate, Isomer 2 | 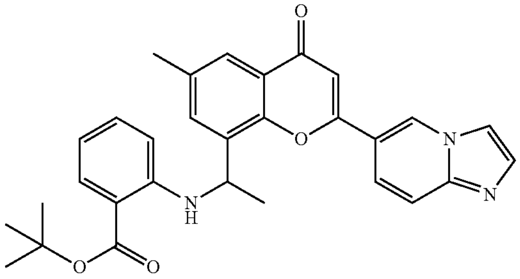 [SMILES: Cc1cc(C(C)Nc2ccccc2C(=O)OC(C)(C)C)c2oc(-c3ccc4nccn4c3)cc(=O)c2c1] | 496 [M + H]+ |
| 81 | tert-Butyl 2-[1-[6-methyl-2-(2-methyl-1,3-benzothiazol-6-yl)-4-oxo-chromen-8-yl]ethylamino]benzoate, Isomer 2 | 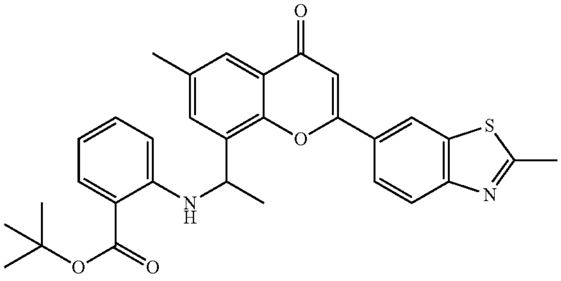 [SMILES: Cc1cc(C(C)Nc2ccccc2C(=O)OC(C)(C)C)c2oc(-c3ccc4nc(C)sc4c3)cc(=O)c2c1] | 527 [M + H]+ |

TABLE 34-continued

| Int # | Chemical Name | Structure | MS ES+ m/z |
|---|---|---|---|
| 82 | tert-Butyl 2-[1-[6-methyl-4-oxo-2-([1,2,4]triazolo[4,3-a]pyridin-6-yl)chromen-8-yl]ethylamino]benzoate, Isomer 2 | 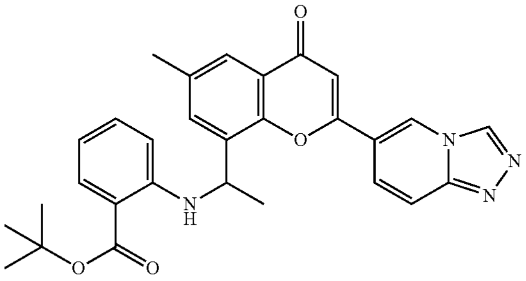 [SMILES: Cc1cc(C(C)Nc2ccccc2C(=O)OC(C)(C)C)c2oc(-c3ccc4nncn4c3)cc(=O)c2c1] | 497 [M + H]$^+$ |
| 83 | tert-Butyl 2-[1-[6-methyl-2-(3-methyl-[1,2,4]triazolo[4,3-a]pyridin-7-yl)-4-oxo-chromen-8-yl]ethylamino]benzoate, Isomer 2 | 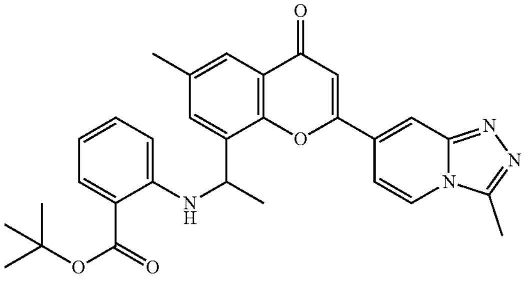 [SMILES: Cc1cc(C(C)Nc2ccccc2C(=O)OC(C)(C)C)c2oc(-c3ccn4c(C)nnc4c3)cc(=O)c2c1] | 511 [M + H]$^+$ |
| 84 | tert-Butyl 2-[1-[2-(3-isopropyl-[1,2,4]triazolo[4,3-a]pyridin-6-yl)-6-methyl-4-oxo-chromen-8-yl]ethylamino]benzoate, Isomer 2 | 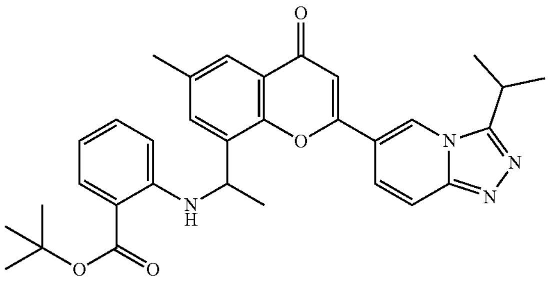 [SMILES: Cc1cc(C(C)Nc2ccccc2C(=O)OC(C)(C)C)c2oc(-c3ccc4nnc(C(C)C)n4c3)cc(=O)c2c1] | 539 [M + H]$^+$ |
| 191 | tert-Butyl 2-[8-[1-[(2-tert-butoxycarbonyl-6-chloro-3-pyridyl)amino]ethyl]-4-oxo-6-(trifluoromethyl)chromen-2-yl]indole-1-carboxylate, Isomer 2 | 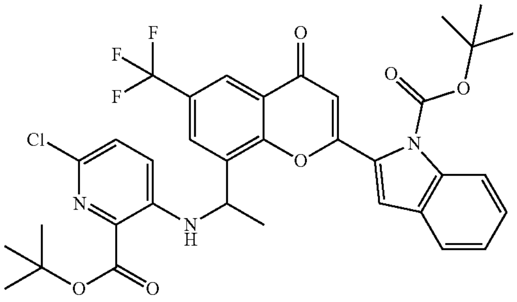 [SMILES: CC(Nc1ccc(Cl)nc1C(=O)OC(C)(C)C)c1cc(C(F)(F)F)cc2c(=O)cc(-c3cc4ccccc4n3C(=O)OC(C)(C)C)oc12] | 628 [M + H]$^+$ |
| 192 | tert-Butyl 2-[1-[2-(2-methylimidazo[1,2-b]pyridazin-6-yl)-4-oxo-6-(trifluoromethyl)chromen-8-yl]ethylamino]benzoate, Isomer 2 | 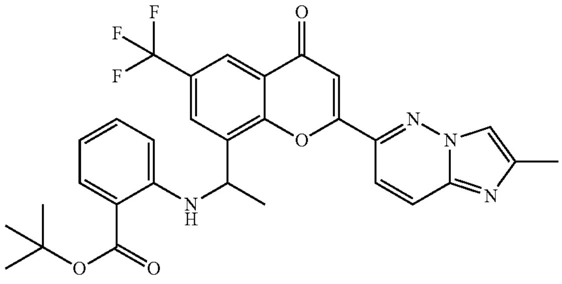 [SMILES: Cc1cn2nc(-c3cc(=O)c4cc(C(F)(F)F)cc(C(C)Nc5ccccc5C(=O)OC(C)(C)C)c4o3)ccc2n1] | 565 [M + H]$^+$ |

TABLE 34-continued

| Int # | Chemical Name | Structure | MS ES+ m/z |
|---|---|---|---|
| 193 | tert-Butyl 2-fluoro-6-[1-[6-methyl-2-(2-methylindazol-5-yl)-4-oxo-chromen-8-yl]ethylamino]benzoate | 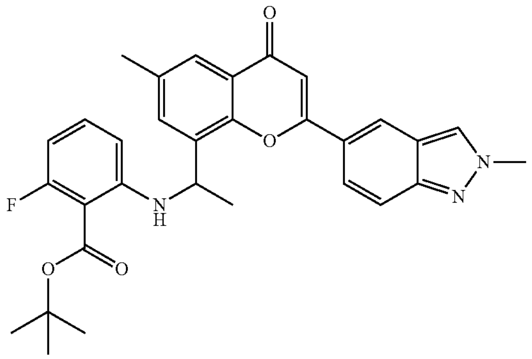 [SMILES: Cc1cc(C(C)Nc2cccc(F)c2C(=O)OC(C)(C)C)c2oc(-c3ccc4nn(C)cc4c3)cc(=O)c2c1] | 528 $[M + H]^+$ |
| 194 | tert-Butyl 2-[1-[6-methyl-2-(2-methylimidazo[1,2-b]pyridazin-6-yl)-4-oxo-chromen-8-yl]ethylamino]benzoate, Isomer 2 | 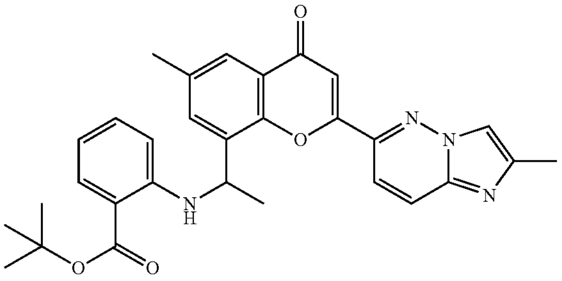 [SMILES: Cc1cc(C(C)Nc2ccccc2C(=O)OC(C)(C)C)c2oc(-c3ccc4nc(C)cn4n3)cc(=O)c2c1] | 511 $[M + H]^+$ |
| 195 | tert-Butyl 6-chloro-3-[1-[2-(1-methylindazol-6-yl)-4-oxo-6-(trifluoromethyl)chromen-8-yl]ethylamino]pyridine-2-carboxylate, Isomer 2 | 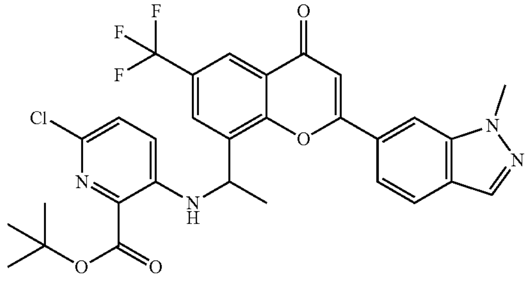 [SMILES: CC(Nc1ccc(Cl)nc1C(=O)OC(C)(C)C)c1cc(C(F)(F)F)cc2c(=O)cc(-c3ccc4cnn(C)c4c3)oc12] | 543 $[M + H]^+$ |
| 196 | tert-Butyl 2-[1-[2-(1-methylindazol-5-yl)-4-oxo-6-(trifluoromethyl)chromen-8-yl]ethylamino]benzoate, Isomer 2 | 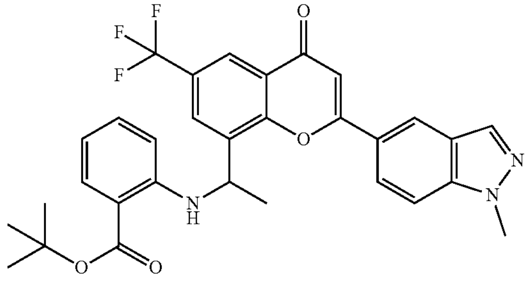 [SMILES: CC(Nc1ccccc1C(=O)OC(C)(C)C)c1cc(C(F)(F)F)cc2c(=O)cc(-c3ccc4c(cnn4C)c3)oc12] | 564 $[M + H]^+$ |
| 197 | tert-Butyl 2-[1-[2-(1,3-benzoxazol-4-yl)-6-methyl-4-oxo-chromen-8-yl]ethylamino]benzoate, Isomer 2 | 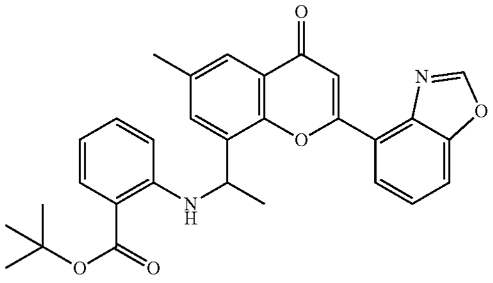 [SMILES: Cc1cc(C(C)Nc2ccccc2C(=O)OC(C)(C)C)c2oc(-c3cccc4ocnc34)cc(=O)c2c1] | 497 $[M + H]^+$ |

TABLE 34-continued

| Int # | Chemical Name | Structure | MS ES+ m/z |
|---|---|---|---|
| 198 | tert-Butyl 2-[1-[6-methyl-2-(2-methylindazol-4-yl)-4-oxo-chromen-8-yl]ethylamino]benzoate, Isomer 2 | 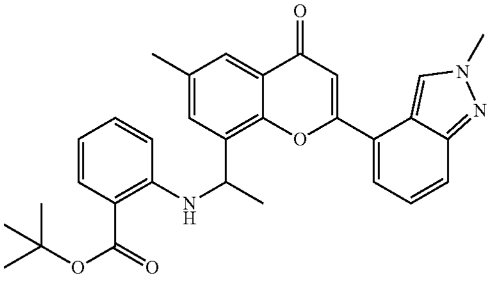 [SMILES: Cc1cc(C(C)Nc2ccccc2C(=O)OC(C)(C)C)c2oc(-c3cccc4nn(C)cc34)cc(=O)c2c1] | 510 $[M+H]^+$ |
| 199 | tert-Butyl 2-[1-[6-methyl-2-(2-methylindazol-7-yl)-4-oxo-chromen-8-yl]ethylamino]benzoate, Isomer 2 | 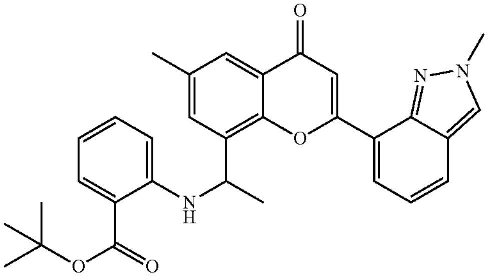 [SMILES: Cc1cc(C(C)Nc2ccccc2C(=O)OC(C)(C)C)c2oc(-c3cccc4cn(C)nc34)cc(=O)c2c1] | 510 $[M+H]^+$ |
| 200 | tert-Butyl 2-[1-[6-methyl-2-(2-methyl-1,3-benzoxazol-4-yl)-4-oxo-chromen-8-yl]ethylamino]benzoate, Isomer 2 | 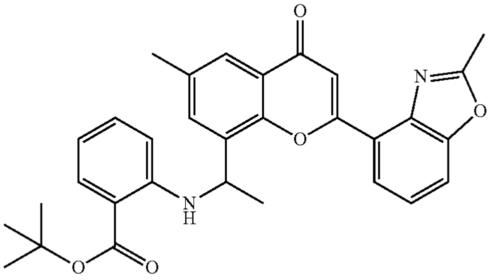 [SMILES: Cc1cc(C(C)Nc2ccccc2C(=O)OC(C)(C)C)c2oc(-c3cccc4oc(C)nc34)cc(=O)c2c1] | 511 $[M+H]^+$ |
| 201 | tert-Butyl 2-[1-[3-cyano-6-methyl-2-(2-methylimidazo[1,2-a]pyridin-6-yl)-4-oxo-chromen-8-yl]ethylamino]benzoate, Isomer 2 | 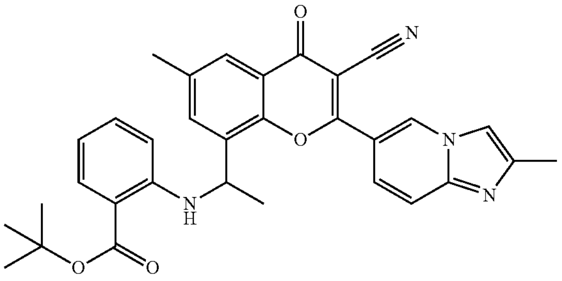 [SMILES: Cc1cc(C(C)Nc2ccccc2C(=O)OC(C)(C)C)c2oc(-c3ccc4nc(C)cn4c3)c(C#N)c(=O)c2c1] | 535 $[M+H]^+$ |
| 202 | tert-Butyl 2-[1-[3,6-dimethyl-4-oxo-2-(1-tetrahydropyran-2-ylindazol-6-yl)chromen-8-yl]ethylamino]benzoate, Isomer 2 | 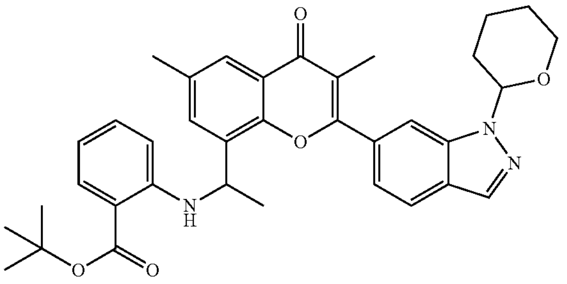 [SMILES: Cc1cc(C(C)Nc2ccccc2C(=O)OC(C)(C)C)c2oc(-c3ccc4cnn(C5CCCCO5)c4c3)c(C)c(=O)c2c1] | 594 [M + H]+ |

TABLE 34-continued

| Int # | Chemical Name | Structure | MS ES+ m/z |
|---|---|---|---|
| 203 | tert-Butyl 2-[1-[6-fluoro-3-methyl-2-(2-methylimidazo[1,2-a]pyridin-6-yl)-4-oxo-chromen-8-yl]ethylamino]benzoate, Isomer 2 | 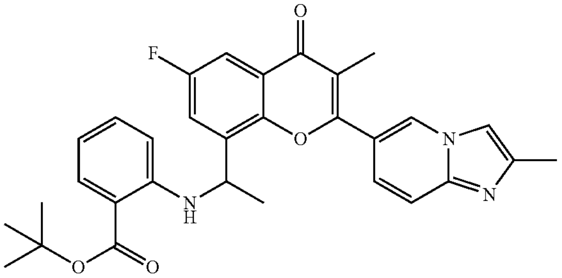 [SMILES: Cc1cn2cc(-c3oc4c(C(C)Nc5ccccc5C(=O)OC(C)(C)C)cc(F)cc4c(=O)c3C)ccc2n1] | 528 $[M + H]^+$ |
| 204 | tert-Butyl 2-[1-(6-methyl-4-oxo-2-pyrazolo[1,5-a]pyridin-3-yl-chromen-8-yl)ethylamino]benzoate, Isomer 2 | 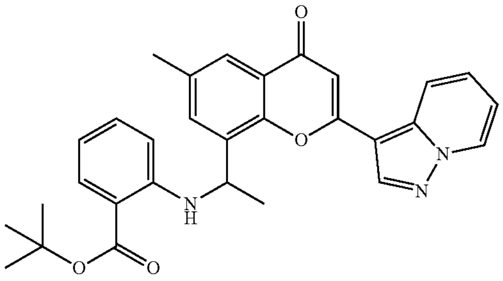 [SMILES: Cc1cc(C(C)Nc2ccccc2C(=O)OC(C)(C)C)c2oc(-c3cnn4ccccc34)cc(=O)c2c1] | 496 $[M + H]^+$ |
| 205 | tert-Butyl 2-[8-[1-(2-tert-butoxycarbonylanilino)ethyl]-6-fluoro-4-oxo-chromen-2-yl]indole-1-carboxylate, Isomer 2 | 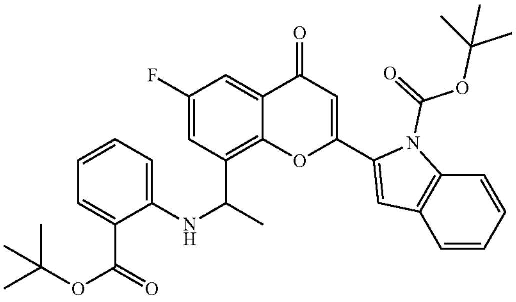 | 599 $[M + H]^+$ |
| 206 | tert-Butyl 2-[8-[1-(2-tert-butoxycarbonylanilino)ethyl]-6-fluoro-3-methyl-4-oxo-chromen-2-yl]indole-1-carboxylate, Isomer 2 | 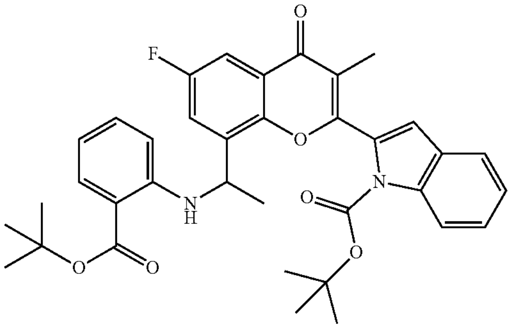 [SMILES: Cc1c(-c2cc3ccccc3n2C(=O)OC(C)(C)C)oc2c(C(C)Nc3ccccc3C(=O)OC(C)(C)C)cc(F)cc2c1=O] | 613 $[M + H]^+$ |
| 207 | tert-Butyl 2-[1-[3,6-dimethyl-4-oxo-2-(1-tetrahydropyran-2-ylindazol-5-yl)chromen-8-yl]ethylamino]benzoate, Isomer 2 | 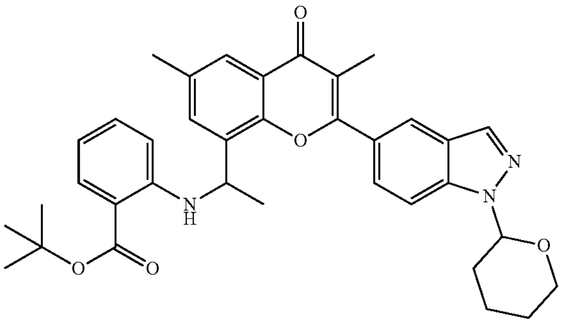 [SMILES: Cc1cc(C(C)Nc2ccccc2C(=O)OC(C)(C)C)c2oc(-c3ccc4c(cnn4C4CCCCO4)c3)c(C)c(=O)c2c1] | 594 $[M + H]^+$ |

TABLE 34-continued

| Int # | Chemical Name | Structure | MS ES+ m/z |
|---|---|---|---|
| 208 | tert-Butyl 2-[1-[6-methyl-2-(1-methylindazol-4-yl)-4-oxo-chromen-8-yl]ethylamino]benzoate, Isomer 2 | 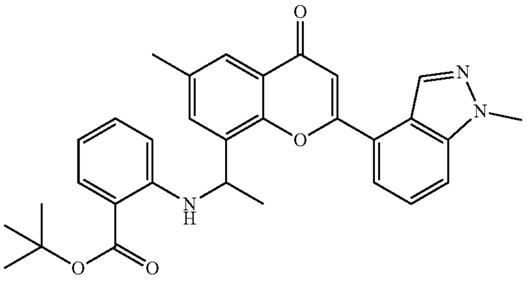 | 510 [M + H]+ |
| 209 | tert-Butyl 2-[1-[3,6-dimethyl-2-(2-methyl-1-oxo-isoindolin-5-yl)-4-oxo-chromen-8-yl]ethylamino]benzoate, Isomer 2 | 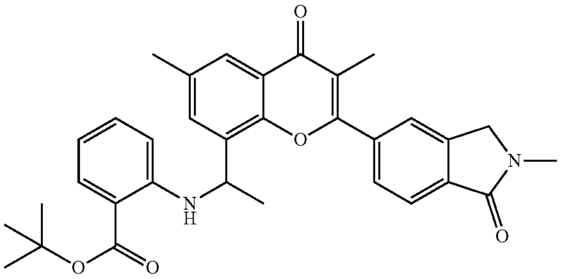 [SMILES: Cc1cc(C(C)Nc2ccccc2C(=O)OC(C)(C)C)c2oc(-c3ccc4c(c3)CN(C)C4=O)c(C)c(=O)c2c1] | 539 [M + H]+ |
| 210 | tert-Butyl 2-[1-[3,6-dimethyl-2-(1-methylindol-3-yl)-4-oxo-chromen-8-yl]ethylamino]benzoate, Isomer 2 | 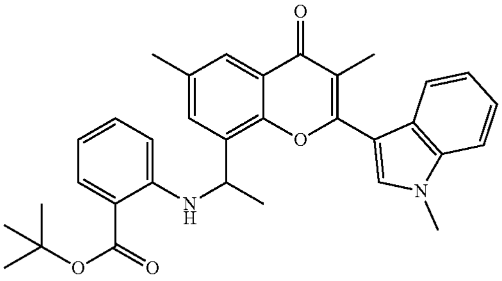 [SMILES: Cc1cc(C(C)Nc2ccccc2C(=O)OC(C)(C)C)c2oc(-c3cn(C)c4ccccc34)c(C)c(=O)c2c1] | 523 [M + H]+ |
| 211 | tert-Butyl 2-[1-[3,6-dimethyl-2-(2-methylimidazo[1,2-b]pyridazin-6-yl)-4-oxo-chromen-8-yl]ethylamino]benzoate, Isomer 2 | 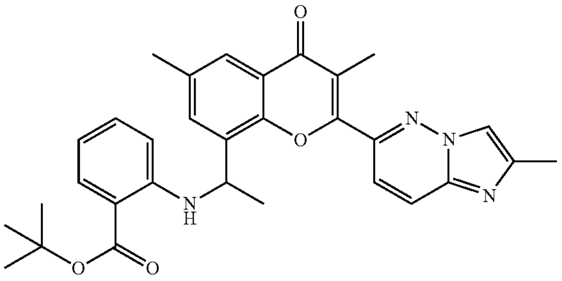 [SMILES: Cc1cc(C(C)Nc2ccccc2C(=O)OC(C)(C)C)c2oc(-c3ccc4nc(C)cn4n3)c(C)c(=O)c2c1] | 525 [M + H]+ |
| 212 | tert-Butyl 2-[1-[6-methyl-2-(1-methylindol-3-yl)-4-oxo-chromen-8-yl]ethylamino]benzoate, Isomer 2 | 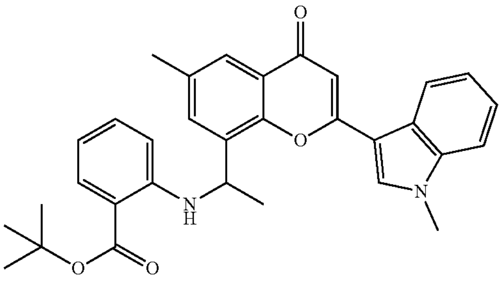 [SMILES: Cc1cc(C(C)Nc2ccccc2C(=O)OC(C)(C)C)c2oc(-c3cn(C)c4ccccc34)cc(=O)c2c1] | 509 [M + H]+ |

TABLE 34-continued

| Int # | Chemical Name | Structure | MS ES+ m/z |
|---|---|---|---|
| 213 | tert-Butyl 2-[1-[3,6-dimethyl-2-(1-methylindazol-3-yl)-4-oxo-chromen-8-yl]ethylamino]benzoate, Isomer 2 | 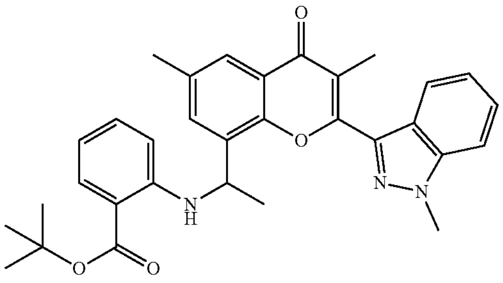 [SMILES: Cc1cc(C(C)Nc2ccccc2C(=O)OC(C)(C)C)c2oc(-c3nn(C)c4ccccc34)c(C)c(=O)c2c1] | 524 [M + H]+ |
| 214 | tert-Butyl 2-[1-[6-fluoro-3-methyl-2-(2-methylindazol-5-yl)-4-oxo-chromen-8-yl]ethylamino]benzoate, Isomer 2 | 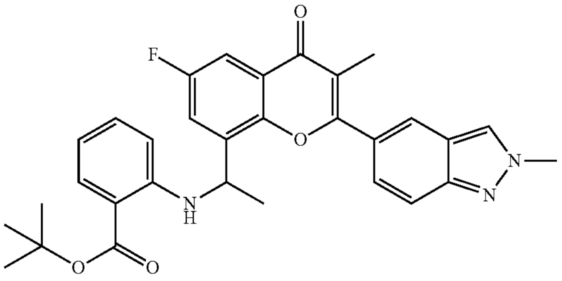 [SMILES: Cc1c(-c2ccc3nn(C)cc3c2)oc2c(C(C)Nc3ccccc3C(=O)OC(C)(C)C)cc(F)cc2c1=O] | 528 [M + H]+ |
| 215 | tert-Butyl 2-[1-[3,6-dimethyl-2-(1-methylindazol-6-yl)-4-oxo-chromen-8-yl]ethylamino]benzoate, Isomer 2 | 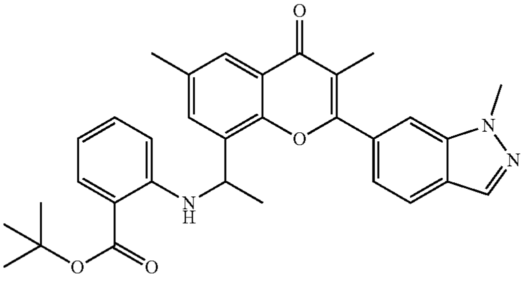 [SMILES: Cc1cc(C(C)Nc2ccccc2C(=O)OC(C)(C)C)c2oc(-c3ccc4cnn(C)c4c3)c(C)c(=O)c2c1] | 524 [M + H]+ |
| 216 | tert-Butyl 2-[1-[3,6-dimethyl-2-(1-methylindazol-5-yl)-4-oxo-chromen-8-yl]ethylamino]benzoate, Isomer 2 | 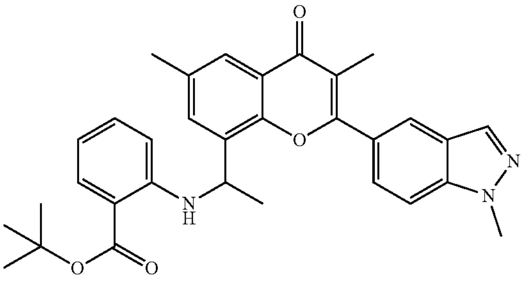 [SMILES: Cc1cc(C(C)Nc2ccccc2C(=O)OC(C)(C)C)c2oc(-c3ccc4c(cnn4C)c3)c(C)c(=O)c2c1] | 524 [M + H]+ |
| 217 | tert-Butyl 2-[1-(2-furo[2,3-c]pyridin-2-yl-3,6-dimethyl-4-oxo-chromen-8-yl)ethylamino]benzoate, Isomer 2 | 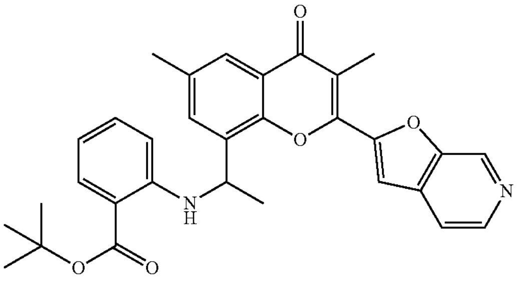 | 511 [M + H]+ |

TABLE 34-continued

| Int # | Chemical Name | Structure | MS ES+ m/z |
|---|---|---|---|
| 218 | tert-Butyl 2-[1-(2-furo[2,3-c]pyridin-2-yl-6-methyl-4-oxo-chromen-8-yl)ethylamino]benzoate, Isomer 2 | 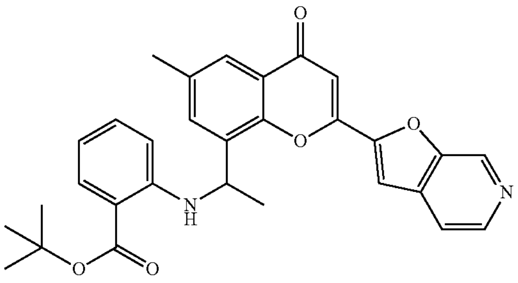 [SMILES: Cc1cc(C(C)Nc2ccccc2C(=O)OC(C)(C)C)c2oc(-c3cc4ccncc4o3)cc(=O)c2c1] | 497 [M + H]+ |
| 219 | tert-Butyl 2-[1-(2-furo[3,2-c]pyridin-2-yl-3,6-dimethyl-4-oxo-chromen-8-yl)ethylamino]benzoate, Isomer 2 | 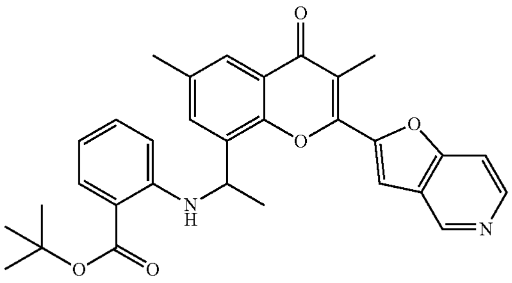 [SMILES: Cc1cc(C(C)Nc2ccccc2C(=O)OC(C)(C)C)c2oc(-c3cc4cnccc4o3)c(C)c(=O)c2c1] | 511 [M + H]+ |
| 220 | tert-Butyl 3-[8-[1-(2-tert-butoxycarbonylanilino)ethyl]-3,6-dimethyl-4-oxo-chromen-2-yl]indole-1-carboxylate, Isomer 2 | 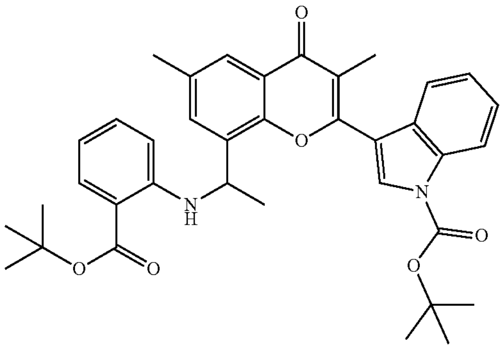 [SMILES: Cc1cc(C(C)Nc2ccccc2C(=O)OC(C)(C)C)c2oc(-c3cn(C(=O)OC(C)(C)C)c4ccccc34)c(C)c(=O)c2c1] | 609 [M + H]+ |
| 221 | tert-Butyl 3-[8-[1-(2-tert-butoxycarbonylanilino)ethyl]-6-methyl-4-oxo-chromen-2-yl]indole-1-carboxylate, Isomer 2 | 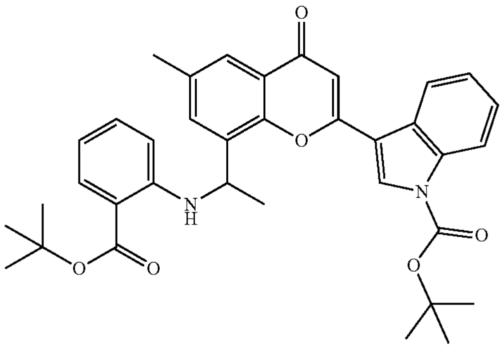 [SMILES: Cc1cc(C(C)Nc2ccccc2C(=O)OC(C)(C)C)c2oc(-c3cn(C(=O)OC(C)(C)C)c4ccccc34)cc(=O)c2c1] | 595 [M + H]+ |
| 222 | tert-Butyl 2-[1-[6-fluoro-2-(2-methylindazol-5-yl)-4-oxo-chromen-8-yl]ethylamino]benzoate, Isomer 1 | 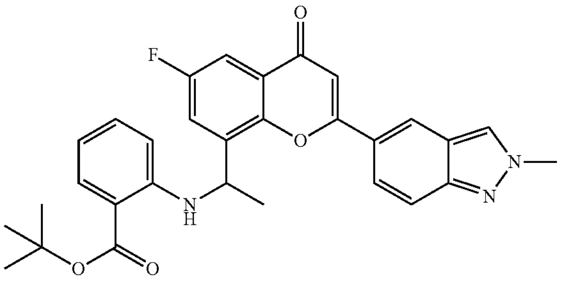 | 514 [M + H]+ |

TABLE 34-continued

| Int # | Chemical Name | Structure | MS ES+ m/z |
|---|---|---|---|
| 223 | tert-Butyl 2-[1-(3,6-dimethyl-4-oxo-2-pyrazolo[1,5-a]pyridin-6-yl-chromen-8-yl)ethylamino]benzoate, Isomer 2; 2,2,2-trifluoroacetic acid | 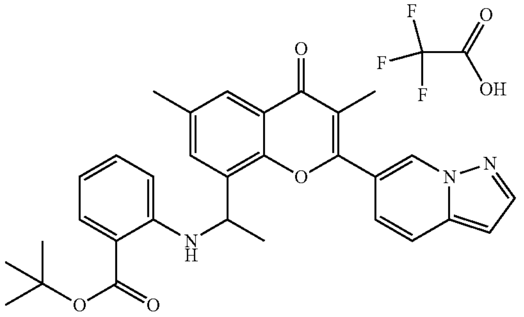 | 510 $[M + H]^+$ |
| 224 | tert-Butyl 2-[1-[6-methyl-4-oxo-2-([1,2,4]triazolo[4,3-a]pyridin-7-yl)chromen-8-yl]ethylamino]benzoate, Isomer 2 | 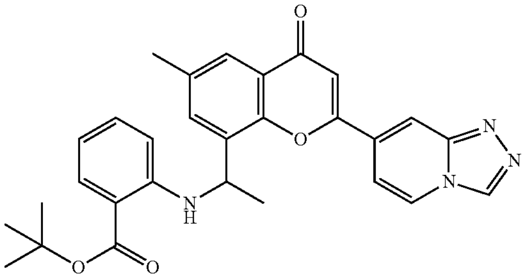 [SMILES: Cc1cc(C(C)Nc2ccccc2C(=O)OC(C)(C)C)c2oc(-c3ccn4cnnc4c3)cc(=O)c2c1] | 497 $[M + H]^+$ |
| 225 | tert-Butyl 2-[1-[2-(2,3-dihydro-[1,4]dioxino[2,3-b]pyridin-7-yl)-6-methyl-4-oxo-chromen-8-yl]ethylamino]benzoate, Isomer 2 | 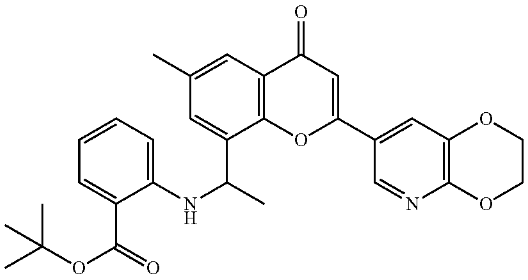 [SMILES: Cc1cc(C(C)Nc2ccccc2C(=O)OC(C)(C)C)c2oc(-c3cnc4c(c3)OCCO4)cc(=O)c2c1] | 515 $[M + H]^+$ |
| 359 | tert-Butyl 2-[1-[6-methyl-2-(2-methylindazol-5-yl)-4-oxo-3-(trifluoromethyl)chromen-8-yl]ethylamino]benzoate, Isomer 2 | 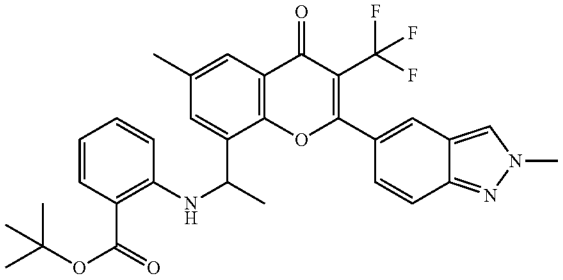 [SMILES: Cc1cc(C(C)Nc2ccccc2C(=O)OC(C)(C)C)c2oc(-c3ccc4nn(C)cc4c3)c(C(F)(F)F)c(=O)c2c1] | 578 $[M + H]^+$ |
| 360 | tert-Butyl 2-[1-[2-furo[3,2-c]pyridin-2-yl-6-methyl-4-oxo-3-(trifluoromethyl)chromen-8-yl]ethylamino]benzoate, Isomer 2 | 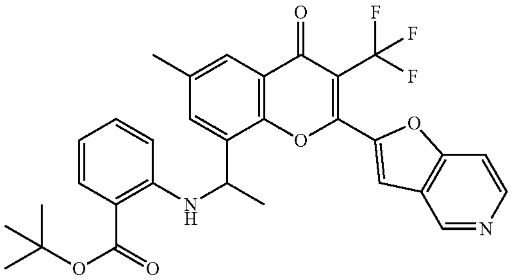 [SMILES: Cc1cc(C(C)Nc2ccccc2C(=O)OC(C)(C)C)c2oc(-c3cc4cnccc4o3)c(C(F)(F)F)c(=O)c2c1] | 565 $[M + H]^+$ |

Intermediate 226: tert-Butyl 2-[1-(6-methyl-4-oxo-2-pyrazolo[1,5-a]pyridin-5-yl-chromen-8-yl)ethylamino]benzoate, Isomer 2

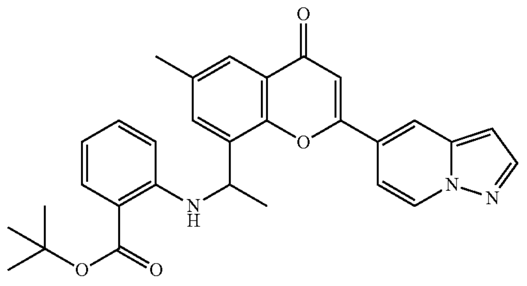 [SMILES: Cc1cc(C(C)Nc2ccccc2C(=O)OC(C)(C)C)c2oc(-c3ccn4nccc4c3)cc(=O)c2c1]

A mixture of tert-butyl 2-[1-(2-ethyl sulfanyl-6-methyl-4-oxo-chromen-8-yl)ethylamino]benzoate, Isomer 2 (0.10 g, 0.23 mmol), 5-(4,4,5,5-tetramethyl-1,3,2-dioxaborolan-2-yl)pyrazolo[1,5-a]pyridine (0.17 g, 0.68 mmol), copper(I) thiophene-2-carboxylate (0.13 g, 0.68 mmol), cesium carbonate (0.22 g, 0.68 mmol), and tris(dibenzylideneacetone) dipalladium(0) (0.02 g, 0.02 mmol) in 2 mL of 2-methyltetrahydrofuran was stirred at 85° C. for 12 h. The dark reaction was cooled, filtered, and concentrated. The residue was purified by silica gel chromatography eluted with 0% to 100% ethyl acetate in petroleum ether to give the product (0.12 g, 87%) as a yellow solid. MS ES+ m/z 496 $[M+H]^+$.

Intermediate 85: tert-Butyl 2-[8-[1-(2-tert-butoxycarbonylanilino)ethyl]-3,6-dimethyl-4-oxo-chromen-2-yl]indole-1-carboxylate, Isomer 2

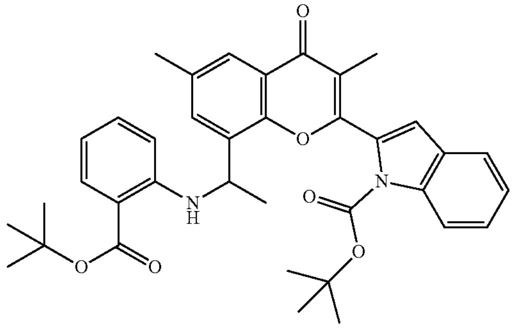 [SMILES: Cc1cc(C(C)Nc2ccccc2C(=O)OC(C)(C)C)c2oc(-c3cc4ccccc4n3C(=O)OC(C)(C)C)c(C)c(=O)c2c1]

tert-Butyl 2-[1-(2-ethylsulfanyl-3,6-dimethyl-4-oxo-chromen-8-yl)ethylamino]benzoate, Isomer 2 (150 mg, 331 μmol), tert-butyl 2-(4,4,5,5-tetramethyl-1,3,2-dioxaborolan-2-yl)-1H-indole-1-carboxylate (227 mg, 661 μmol), (2-dicyclohexylphosphino-2',6'-diisopropoxy-1,1'-biphenyl)[2-(2'-amino-1,1'-biphenyl)]palladium(II) methanesulfonate (27.7 mg, 33.1 μmol), XPhos Pd G3 (28.0 mg, 33.1 μmol), copper(I) thiophene-2-carboxylate (189 mg, 992 μmol), and sodium tert-butoxide (127 mg, 1.32 mmol) were combined in 2-methyltetrahydrofuran (3 mL) with 3 drops of water and degassed using argon for 5 min. The reaction was allowed to stir at 100° C. for 16 h. After cooling, the reaction was diluted with 10 mL of dichloromethane/silica gel. The mixture was concentrated and purified via silica gel chromatography using a gradient of 0% to 100% ethyl acetate in heptanes to give the product (0.17 g, 84%) with some starting material impurities. MS ES+ m/z 609 $[M+H]^+$.

The following compounds in Table 35 were made in a similar way as described for Intermediate 85.

TABLE 35

| Int # | Chemical Name | Structure | MS ES+ m/z |
|---|---|---|---|
| 227 | tert-Butyl 2-[8-[1-[(2-tert-butoxycarbonyl-6-methyl-3-pyridyl)amino]ethyl]-6-methyl-4-oxo-chromen-2-yl]indole-1-carboxylate | 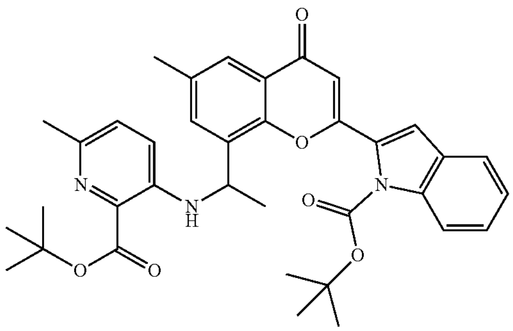 [SMILES: Cc1cc(C(C)Nc2ccc(C)nc2C(=O)OC(C)(C)C)c2oc(-c3cc4ccccc4n3C(=O)OC(C)(C)C)cc(=O)c2c1] | 610 $[M + H]^+$ |

Intermediate 86: tert-Butyl 2-[1-[6-methyl-2-(1-methylpyrazolo[4,3-b]pyridin-5-yl)-4-oxo-chromen-8-yl]ethylamino]benzoate, Isomer 2

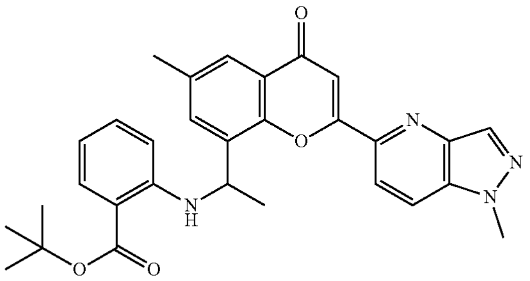 [SMILES: Cc1cc(C(C)Nc2ccccc2C(=O)OC(C)(C)C)c2oc(-c3ccc4c(cnn4C)n3)cc(=O)c2c1]

tert-Butyl 2-[1-(2-ethylsulfanyl-6-methyl-4-oxo-chromen-8-yl)ethylamino]benzoate, Isomer 2 (0.200 g, 455 μmol), 5-bromo-1-methyl-1H-pyrazolo[4,3-b]pyridine (193 mg, 910 μcool) XPhos G3 (38.1 mg, 45.5 μcool), RuPhos G3 (38.5 mg, 45.5 μmol), cesium carbonate (593 mg, 1.82 mmol), copper(I) thiophene-2-carboxylate (260 mg, 1.36 mmol), and bis(pinacolato)diboron (462 mg, 1.82 mmol) were combined in 1,4-dioxane (8 mL) and degassed using argon for 5 min. The reaction was allowed to stir at 100° C. for 16 h. After cooling, the reaction was diluted with 10 mL of dichloromethane/silica gel. The mixture was concentrated and purified via silica gel chromatography using a gradient of 0% to 100% ethyl acetate in heptanes to give the product (15 mg, 6.5%). MS ES+ m/z 511 $[M+H]^+$.

The following compounds in Table 36 were made in a similar way as described for Intermediate 86.

TABLE 36

| Int # | Chemical Name | Structure | MS ES+ m/z |
|---|---|---|---|
| 87 | tert-Butyl 2-[1-[6-methyl-2-(2-methylpyrazolo[4,3-b]pyridin-5-yl)-4-oxo-chromen-8-yl]ethylamino]benzoate, Isomer 2 | 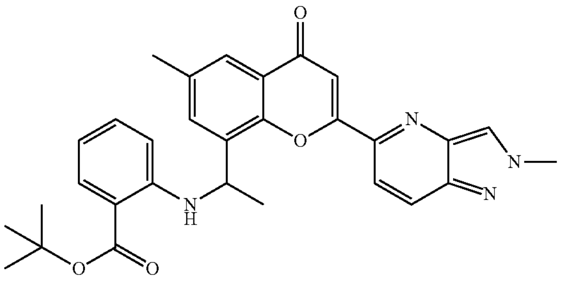 [SMILES: CN/C=C1/N=C(c2cc(=O)c3cc(C)cc(C(C)Nc4ccccc4C(=O)OC(C)(C)C)c3o2)C=CC1=N] | 511 $[M + H]^+$ |
| 228 | tert-Butyl 2-[1-[6-methyl-2-(1-methylpyrazolo[3,4-c]pyridin-7-yl)-4-oxo-chromen-8-yl]ethylamino]benzoate, Isomer 2 | 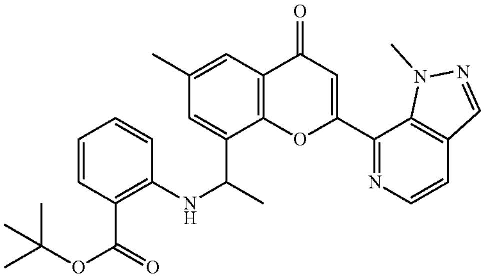 [SMILES: Cc1cc(C(C)Nc2ccccc2C(=O)OC(C)(C)C)c2oc(-c3nccc4cnn(C)c34)cc(=O)c2c1] | 511 $[M - H]^-$ |
| 229 | tert-Butyl 2-[1-[2-(7-fluoro-2-methyl-indazol-5-yl)-6-methyl-4-oxo-chromen-8-yl]ethylamino]benzoate, Isomer 2 | 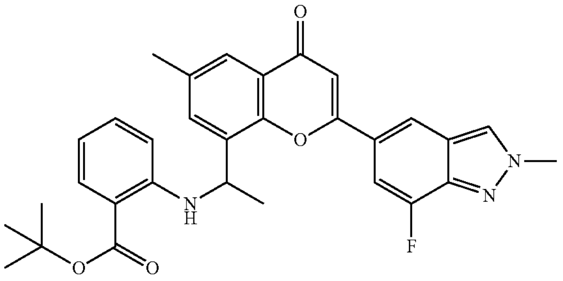 [SMILES: Cc1cc(C(C)Nc2ccccc2C(=O)OC(C)(C)C)c2oc(-c3cc(F)c4nn(C)cc4c3)cc(=O)c2c1] | 528 $[M + H]^+$ |

TABLE 36-continued

| Int # | Chemical Name | Structure | MS ES+ m/z |
|---|---|---|---|
| 230 | tert-Butyl 2-[1-[6-methyl-2-(2-methylpyrazolo[3,4-c]pyridin-7-yl)-4-oxo-chromen-8-yl]ethylamino]benzoate, Isomer 2 | 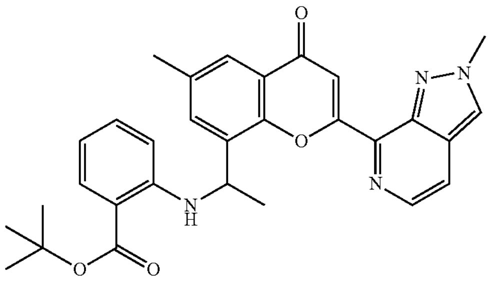 [SMILES: Cc1cc(C(C)Nc2ccccc2C(=O)OC(C)(C)C)c2oc(-c3nccc4cn(C)nc34)cc(=O)c2c1] | 511 [M + H]+ |
| 231[a] | tert-Butyl 6-chloro-3-[1-[2-(2-methylimidazo[1,2-b]pyridazin-6-yl)-4-oxo-6-(trifluoromethyl)chromen-8-yl]ethylamino]pyridine-2-carboxylate, Isomer 2 | 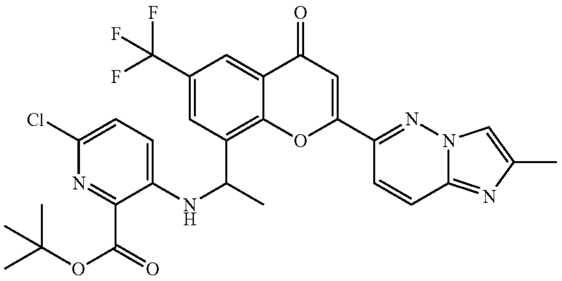 [SMILES: Cc1cn2nc(-c3cc(=O)c4cc(C(F)(F)F)cc(C(C)Nc5ccc(Cl)nc5C(=O)OC(C)(C)C)c4o3)ccc2n1] | 600 [M + H]+ |
| 232 | tert-Butyl 2-[1-[2-(3-cyano-1-methyl-indazol-6-yl)-6-methyl-4-oxo-chromen-8-yl]ethylamino]benzoate, Isomer 2 | 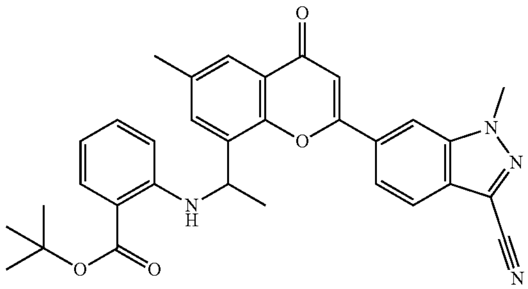 [SMILES: Cc1cc(C(C)Nc2ccccc2C(=O)OC(C)(C)C)c2oc(-c3ccc4c(C#N)nn(C)c4c3)cc(=O)c2c1] | 535 [M + H]+ |
| 233 | tert-Butyl 2-[1-(6-methyl-4-oxo-2-pyrrolo[1,2-a]pyrazin-1-yl-chromen-8-yl)ethylamino]benzoate, Isomer 2 | 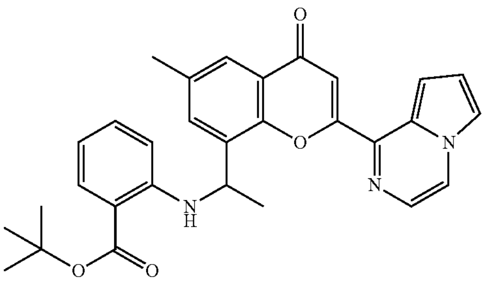 [SMILES: Cc1cc(C(C)Nc2ccccc2C(=O)OC(C)(C)C)c2oc(-c3nccn4cccc34)cc(=O)c2c1] | 496 [M + H]+ |
| 234 | tert-Butyl 2-[1-(6-methyl-4-oxo-2-pyrazolo[1,5-a]pyridin-4-yl-chromen-8-yl)ethylamino]benzoate, Isomer 2 | 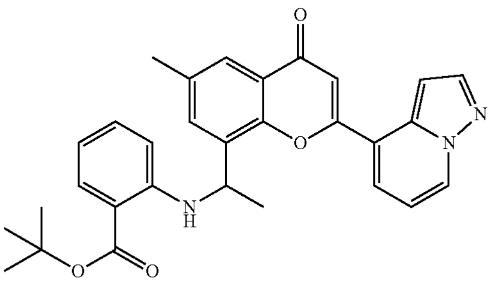 [SMILES: Cc1cc(C(C)Nc2ccccc2C(=O)OC(C)(C)C)c2oc(-c3cccn4nccc34)cc(=O)c2c1] | 396 [M + H]+ |

TABLE 36-continued

| Int # | Chemical Name | Structure | MS ES+ m/z |
|---|---|---|---|
| 235[a] | tert-Butyl 2-[1-[6-methyl-2-(2-methylindazol-3-yl)-4-oxo-chromen-8-yl]ethylamino]benzoate, Isomer 2 | 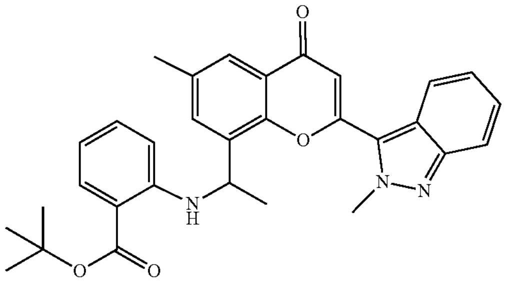 [SMILES: Cc1cc(C(C)Nc2ccccc2C(=O)OC(C)(C)C)c2oc(-c3c4ccccc4nn3C)cc(=O)c2c1] | 510 [M + H]+ |
| 236[b] | tert-Butyl 2-[1-[6-methyl-4-oxo-2-(1-tetrahydropyran-2-ylpyrazolo[3,4-b]pyridin-6-yl)chromen-8-yl]ethylamino]benzoate, Isomer 2 | 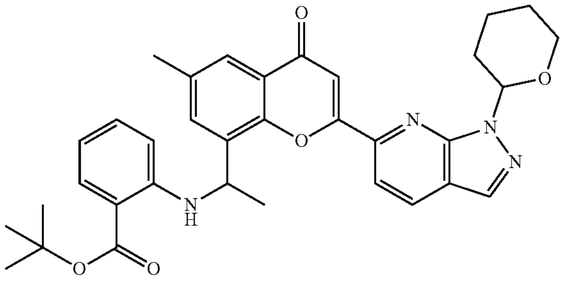 [SMILES: Cc1cc(C(C)Nc2ccccc2C(=O)OC(C)(C)C)c2oc(-c3ccc4cnn(C5CCCCO5)c4n3)cc(=O)c2c1] | 581 [M + H]+ |
| 237 | tert-Butyl 2-[1-(2-imidazo[1,2-a]pyridin-8-yl-6-methyl-4-oxo-chromen-8-yl)ethylamino]benzoate, Isomer 2 | 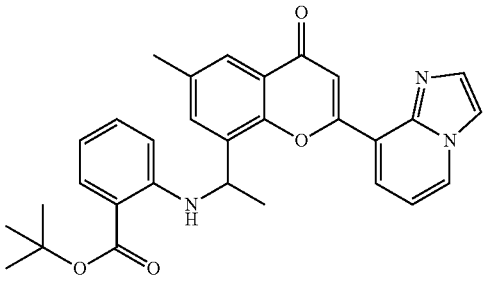 [SMILES: Cc1cc(C(C)Nc2ccccc2C(=O)OC(C)(C)C)c2oc(-c3cccn4ccnc34)cc(=O)c2c1] | 496 [M + H]+ |
| 238 | tert-Butyl 2-[1-[3,6-dimethyl-2-(2-methylpyrazolo[4,3-b]pyridin-5-yl)-4-oxo-chromen-8-yl]ethylamino]benzoate, Isomer 2 | 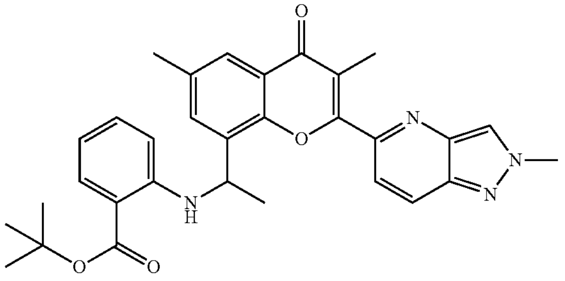 [SMILES: Cc1cc(C(C)Nc2ccccc2C(=O)OC(C)(C)C)c2oc(-c3ccc4nn(C)cc4n3)c(C)c(=O)c2c1] | 525 [M + H]+ |
| 239 | tert-Butyl 2-[1-[3,6-dimethyl-2-(1-methylpyrazolo[4,3-b]pyridin-5-yl)-4-oxo-chromen-8-yl]ethylamino]benzoate, Isomer 2 | 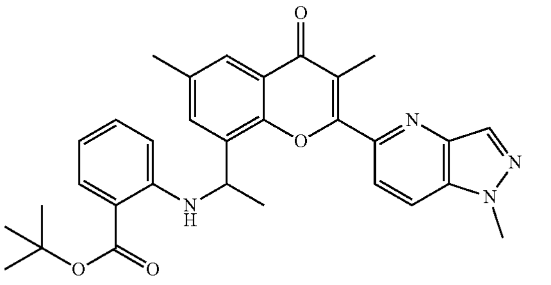 [SMILES: Cc1cc(C(C)Nc2ccccc2C(=O)OC(C)(C)C)c2oc(-c3ccc4c(cnn4C)n3)c(C)c(=O)c2c1] | 525 [M + H]+ |

TABLE 36-continued

| Int # | Chemical Name | Structure | MS ES+ m/z |
|---|---|---|---|
| 240[a] | tert-Butyl 2-[1-[6-methyl-2-(2-methyl-3-oxazol-2-yl-imidazo[1,2-a]pyridin-7-yl)-4-oxo-chromen-8-yl]ethylamino]benzoate, Isomer 2 | 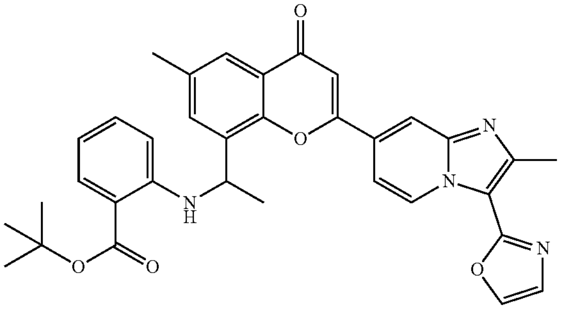 [SMILES: Cc1cc(C(C)Nc2ccccc2C(=O)OC(C)(C)C)c2oc(-c3ccn4c(-c5ncco5)c(C)nc4c3)cc(=O)c2c1] | 577 [M + H]+ |
| 241 | tert-Butyl 2-[1-[6-methyl-2-(2-methylpyrazolo[3,4-b]pyridin-6-yl)-4-oxo-chromen-8-yl]ethylamino]benzoate, Isomer 2 | 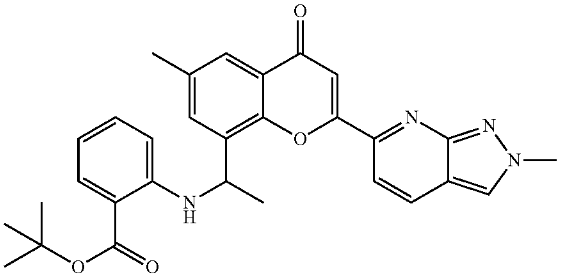 [SMILES: Cc1cc(C(C)Nc2ccccc2C(=O)OC(C)(C)C)c2oc(-c3ccc4cn(C)nc4n3)cc(=O)c2c1] | 511 [M + H]+ |
| 242[b] | tert-Butyl 2-[1-[6-methyl-2-[1-(oxetan-3-ylmethyl)indazol-5-yl]-4-oxo-chromen-8-yl]ethylamino]benzoate, Isomer 2 | 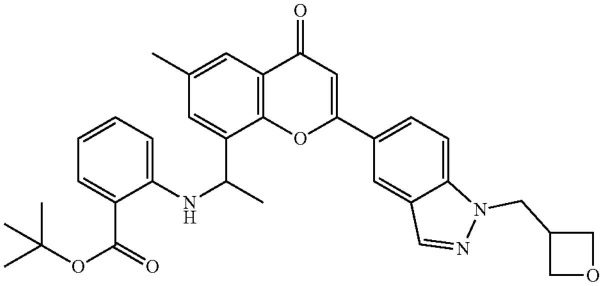 [SMILES: Cc1cc(C(C)Nc2ccccc2C(=O)OC(C)(C)C)c2oc(-c3ccc4c(cnn4CC4COC4)c3)cc(=O)c2c1] | 566 [M + H]+ |
| 243[b] | tert-Butyl 2-[1-(2-imidazo[1,2-a]pyridin-3-yl-6-methyl-4-oxo-chromen-8-yl)ethylamino]benzoate, Isomer 2 | 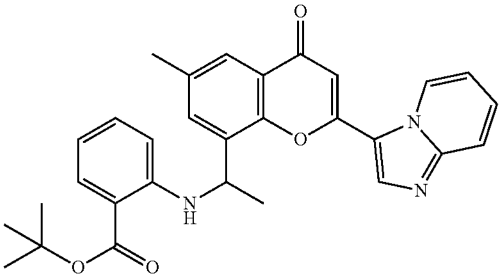 [SMILES: Cc1cc(C(C)Nc2ccccc2C(=O)OC(C)(C)C)c2oc(-c3cnc4ccccn34)cc(=O)c2c1] | 496 [M + H]+ |
| 282[b] | tert-Butyl 2-[1-[6-methyl-2-(1,7-naphthyridin-6-yl)-4-oxo-chromen-8-yl]ethylamino]benzoate, Isomer 2 | 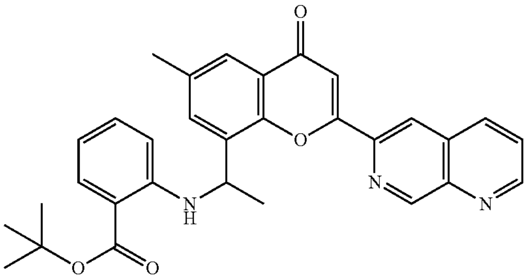 [SMILES: Cc1cc(C(C)Nc2ccccc2C(=O)OC(C)(C)C)c2oc(-c3cc4cccnc4cn3)cc(=O)c2c1] | 508 [M + H]+ |

TABLE 36-continued

| Int # | Chemical Name | Structure | MS ES+ m/z |
| --- | --- | --- | --- |
| 361 | tert-Butyl 6-chloro-3-[1-[6-methyl-4-oxo-2-(1H-pyrrolo[2,3-b]pyridin-6-yl)chromen-8-yl]ethylamino]pyridine-2-carboxylate | 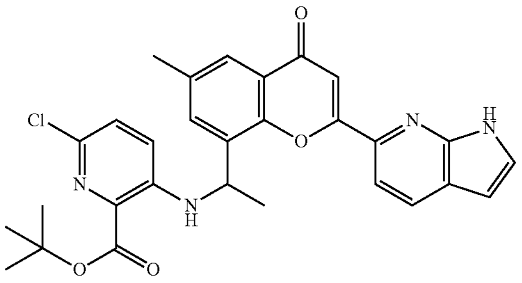 [SMILES: Cc1cc(C(C)Nc2ccc(Cl)nc2C(=O)OC(C)(C)C)c2oc(-c3ccc4cc[nH]c4n3)cc(=O)c2c1] | 531 [M + H]+ |
| 362 | tert-Butyl 2-[[(1R)-1-[6-methyl-2-[2-methyl-7-(trifluoromethyl)indazol-5-yl]-4-oxo-chromen-8-yl]ethyl]amino]benzoate | 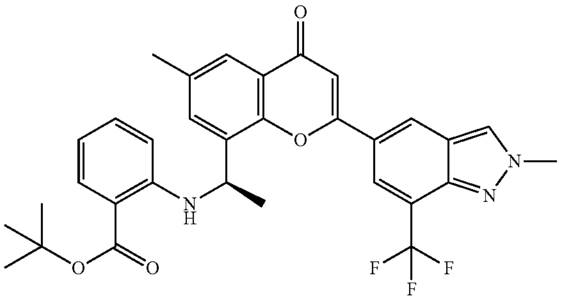 [SMILES: Cc1cc([C@@H](C)Nc2ccccc2C(=O)OC(C)(C)C)c2oc(-c3cc(C(F)(F)F)c4nn(C)cc4c3)cc(=O)c2c1] | 578 [M + H]+ |
| 363 | Methyl 2-[1-[6-methyl-2-(1,5-naphthyridin-2-yl)-4-oxo-chromen-8-yl]ethylamino]benzoate, Isomer 2 | 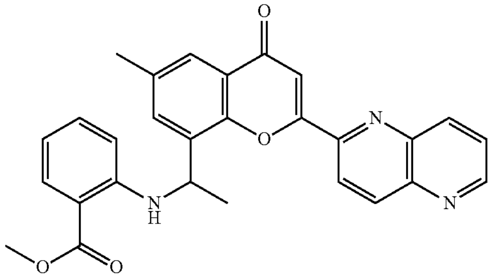 [SMILES: COC(=O)c1ccccc1NC(C)c1cc(C)cc2c(=O)cc(-c3ccc4ncccc4n3)oc12] | 466 [M + H]+ |
| 364 | Methyl 2-[[(1R)-1-[2-(2-methoxy-8-methyl-6-quinolyl)-6-methyl-4-oxo-chromen-8-yl]ethyl]amino]benzoate | 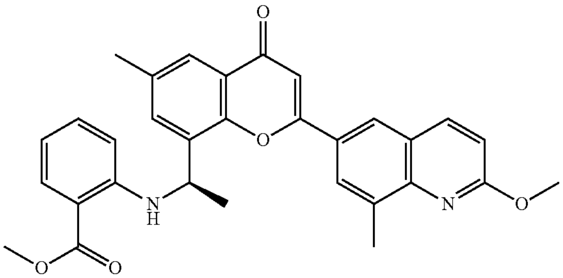 | 509 [M + H]+ |
| 365 | tert-Butyl 2-[[(1R)-1-[2-(2-benzylindazol-5-yl)-3,6-dimethyl-4-oxo-chromen-8-yl]ethyl]amino]benzoate | 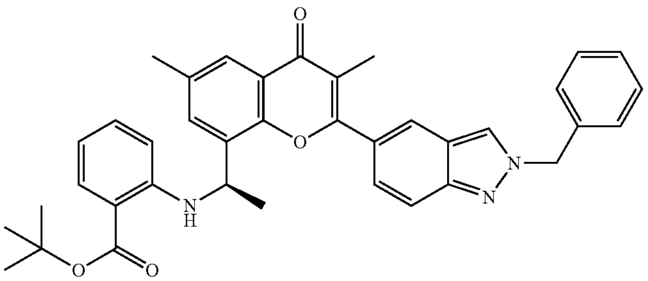 [SMILES: Cc1cc([C@@H](C)Nc2ccccc2C(=O)OC(C)(C)C)c2oc(-c3ccc4nn(Cc5ccccc5)cc4c3)c(C)c(=O)c2c1] | 600 [M + H]+ |

TABLE 36-continued

| Int # | Chemical Name | Structure | MS ES+ m/z |
|---|---|---|---|
| 366 | tert-Butyl 2-[[(1R)-1-[2-(1-benzylindazol-5-yl)-3,6-dimethyl-4-oxo-chromen-8-yl]ethyl]amino]benzoate | 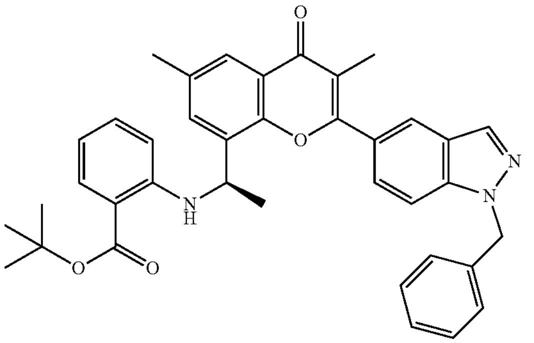 [SMILES: Cc1cc([C@@H](C)Nc2ccccc2C(=O)OC(C)(C)C)c2oc(-c3ccc4c(cnn4Cc4ccccc4)c3)c(C)c(=O)c2c1] | 600 $[M + H]^+$ |

[a]This reaction used RuPhos Pd G4 instead of RuPhos Pd G3.
[b]This reaction only used BrettPhos Pd G3 as the palladium catalyst.

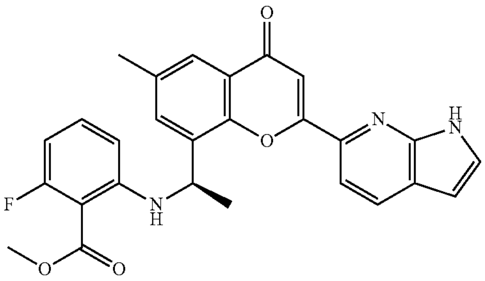 [SMILES: COC(=O)c1c(F)cccc1N[C@H](C)c1cc(C)cc2c(=O)cc(-c3ccc4cc[nH]c4n3)oc12]

A mixture of methyl 2-[[(1R)-1-(2-ethylsulfanyl-6-methyl-4-oxo-chromen-8-yl)ethyl]amino]-6-fluoro-benzoate (160 mg, 0.39 mmol), 6-bromo-1H-pyrrolo[2,3-b]pyridine (227.63 mg, 1.16 mmol), copper(I) thiophene-2-carboxylate (220.3 mg, 1.16 mmol), bis(pinacoloto)diboron (391.17 mg, 1.54 mmol), BrettPhos Pd G3 (69.82 mg, 0.08 mmol), sodium tert-butoxide (185.05 mg, 1.93 mmol), and [1,3-bis(diphenylphosphino)propane]dichloronickel(II) (41.75 mg, 0.08 mmol) in 6 mL of 1,4-dioxane was stirred at 100° C. for 18 h. Allowed the reaction to cool to rt, concentrated, and purified the residue by silica gel chromatography eluted with 0% to 40% EtOAc in petroleum ether to give the product (140 mg, 77%) as a green solid. MS ES+ m/z 472 $[M+H]^+$.

The following compounds in Table 37 were made in a similar way as described for Intermediate 367.

TABLE 37

| Int # | Chemical Name | Structure | MS ES+ m/z |
|---|---|---|---|
| 368 | Methyl 2-[[(1R)-1-[2-(2-methoxy-6-quinolyl)-6-methyl-4-oxo-chromen-8-yl]ethyl]amino]benzoate | 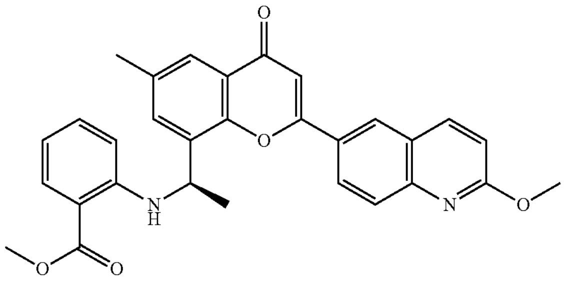 | 495 $[M + H]^+$ |
| 369 | tert-butyl 2-[1-[2-(2-cyano-6-quinolyl)-6-methyl-4-oxo-chromen-8-yl]ethylamino]benzoate, Isomer 2 | 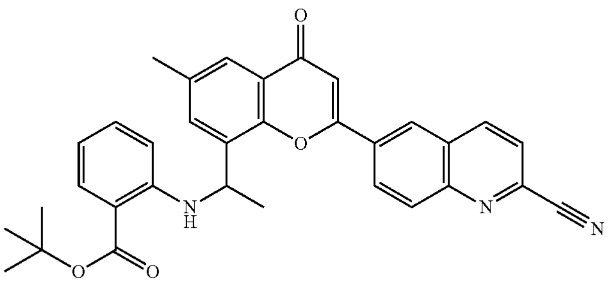 [SMILES: Cc1cc(C(C)Nc2ccccc2C(=O)OC(C)(C)C)c2oc(-c3ccc4nc(C#N)ccc4c3)cc(=O)c2c1] | 532 $[M + H]^+$ |

Intermediate 244: tert-Butyl 2-[1-[2-[2-(2-hydroxy-2-methyl-propyl)indazol-5-yl]-6-methyl-4-oxo-chromen-8-yl]ethyl amino]benzoate, Isomer 2

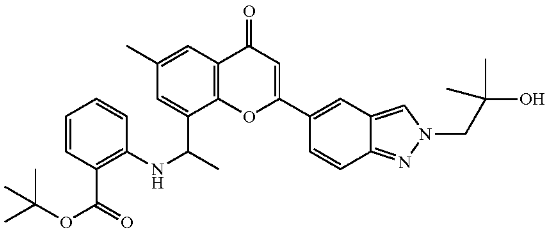 [SMILES: Cc1cc(C(C)Nc2ccccc2C(=O)OC(C)(C)C)c2oc(-c3ccc4nn(CC(C)(C)O)cc4c3)cc(=O)c2c1]

A mixture of tert-butyl 2-[1-(2-ethyl sulfanyl-6-methyl-4-oxo-chromen-8-yl)ethylamino]benzoate (0.20 g, 0.46 mmol), 1-(5-bromoindazol-2-yl)-2-methyl-propan-2-ol (0.26 g, 0.91 mmol), cesium carbonate (0.59 g, 1.82 mmol), bis(pinacolato)diboron (0.58 g, 2.27 mmol), BrettPhos Pd G3, and copper(I) thiophene-2-carboxylate (0.26 g, 1.36 mmol) in 5 mL of 1,4-dioxane was purged with nitrogen gas for 10 min, the pressure vessel sealed, and the reaction heated to 100° C. for 16 h. Reaction was not complete so cooled and charged with potassium acetate (3 eq), bis (pinacoloto)diboron (2 eq), and [1,1'-bis(diphenylphosphino)ferrocene]dichloropalladium(II) (0.15 eq) and purged the reaction with nitrogen gas for 15 min. The reaction was sealed and heated at 100° C. for another 24 h. The reaction was filtered through celite and the solids washed with 50% methanol in dichloromethane until all product retrieved. The filtrate was concentrated and the residue purified by silica gel chromatography eluted with 0% to 20% methanol in dichloromethane to give the product (0.06 g, 21%). MS ES+ m/z 568 $[M+H]^+$.

The following compounds in Table 38 were made in a similar way as described for Intermediate 244.

Intermediate 88: tert-Butyl 2-[1-(2-imidazo[1,2-a]pyridine-2-yl-6-methyl-4-oxo-chromen-8-yl)ethyl-amino]benzoate, Isomer 2

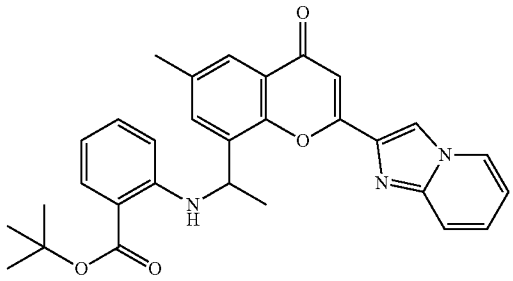

Transferred 2-bromoimidazo[1,2-a]pyridine (121 mg, 0.614 mmol) to a 20 mL vial and added THF (1 mL). Cooled the solution in an ice bath and when cool, added isopropy-lmagnesium(II) lithium chloride (1.3 M in THF, 85.9 mg, 0.455 mL, 0.591 mmol) via syringe and allowed to stir at 0° C. for 1 h. When the Grignard had formed, added it dropwise to a 0° C. solution of tert-butyl 2-[1-(2-ethyl sulfanyl-6-methyl-4-oxo-chromen-8-yl)ethylamino]benzoate, Isomer 2 (200 mg, 0.455 mmol) in 1 mL of 2-methyltetrahydrofuran. After stirring at 0° C. for 10 min, the reaction was stirred at 80° C. for ~48 h. Prepared fresh Grignard as described above and added into reaction that had been cooled back to 0° C. After 10 min at 0° C., stirred the reaction at 50° C. for 40 h. Quenched the reaction with saturated, aqueous ammonium chloride and stirred for 5 minutes. Diluted with water and extracted twice with ethyl acetate. The organic layers were combined, washed with brine, dried over $MgSO_4$, filtered, and concentrated to a residue. The residue was purified by silica gel chromatography using a gradient of 0% to 70% ethyl acetate in heptanes to give the product as a yellow solid (33.7 mg, 15%). MS ES+ m/z 496 $[M+H]^+$.

TABLE 38

| Int # | Chemical Name | Structure | MS ES+ m/z |
|---|---|---|---|
| 245 | tert-Butyl 2-[1-[2-[1-(2-hydroxy-2-methyl-propyl)indazol-5-yl]-6-methyl-4-oxo-chromen-8-yl]ethylamino]benzoate, Isomer 2 | 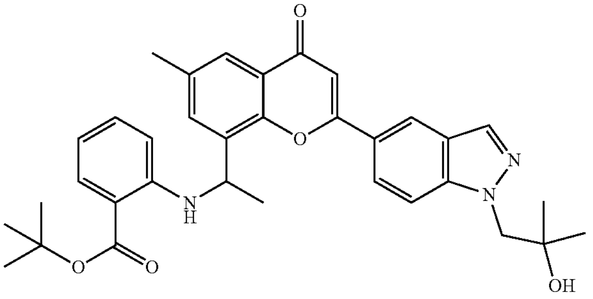 [SMILES: Cc1cc(C(C)Nc2ccccc2C(=O)OC(C)(C)C)c2oc(-c3ccc4c(cnn4CC(C)(C)O)c3)cc(=O)c2c1] | 568 $[M + H]^+$ |

Intermediate 89: tert-Butyl 2-[1-[6-methyl-2-(2-methylimidazo[1,2-b]pyridazin-6-yl)-4-oxo-chromen-8-yl]ethylamino]benzoate, Isomer 2

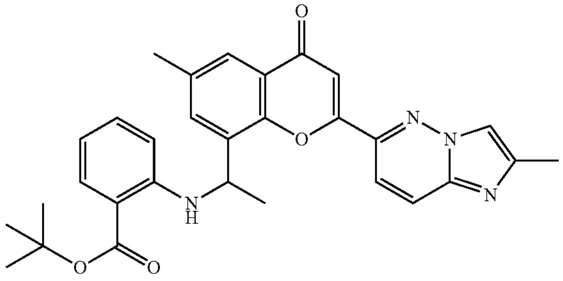 [SMILES: Cc1cc(C(C)Nc2ccccc2C(=O)OC(C)(C)C)c2oc(-c3ccc4nc(C)cn4n3)cc(=O)c2c1]

A mixture of tert-butyl 2-[1-(2-ethylsulfanyl-6-methyl-4-oxo-chromen-8-yl)ethylamino]benzoate, Isomer 2 (1.0 g, 2.27 mmol), 2-methyl-6-(4,4,5,5-tetramethyl-1,3,2-dioxaborolan-2-yl)imidazo[1,2-b]pyridazine (1.18 g, 4.55 mmol), BrettPhos Pd G3 (618.7 mg, 0.68 mmol), sodium tert-butoxide (0.66 mg, 6.82 mmol), and copper(I) thiophene-2-carboxylate (1.3 g, 6.82 mmol) in 2-methyltetrahydrofuran (20 mL) was stirred at 85° C. for 48 h. The black suspension was diluted with 30 mL of water and extracted with dichloromethane (3×100 mL), washed with brine, dried over $Na_2SO_4$, filtered, and concentrated. The residue was purified by silica gel chromatography using a gradient of 0% to 100% ethyl acetate in petroleum ether to give the product as a black oil (505 mg, 30%, 69% purity). MS ES+ m/z 511 $[M+H]^+$.

The following compounds in Table 39 were made in a similar way as described for Intermediate 89.

TABLE 39

| Int # | Chemical Name | Structure | MS ES+ m/z |
|---|---|---|---|
| 90 | tert-Butyl 2-[1-[6-methyl-2-(2-methylindazol-5-yl)-4-oxo-chromen-8-yl]ethylamino]benzoate, Isomer 2 | 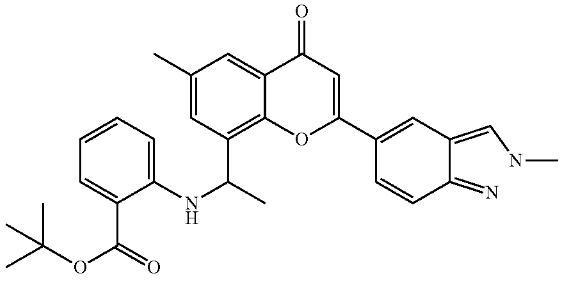 [SMILES: CN/C=C1/C=C(c2cc(=O)c3cc(C)cc(C(C)Nc4ccccc4C(=O)OC(C)(C)C)c3o2)C=CC1=N] | 510 $[M + H]^+$ |
| 91 | tert-Butyl 2-[1-(2-imidazo[1,5-a]pyridin-6-yl-6-methyl-4-oxo-chromen-8-yl)ethylamino]benzoate, Isomer 2 | 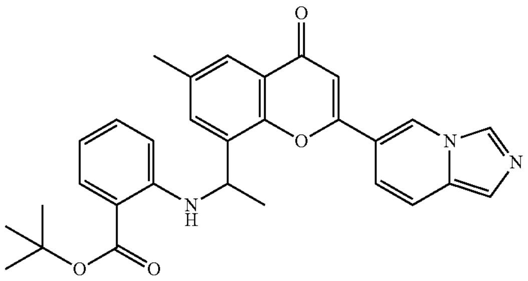 [SMILES: Cc1cc(C(C)Nc2ccccc2C(=O)OC(C)(C)C)c2oc(-c3ccc4cncn4c3)cc(=O)c2c1] | 496 $[M + H]^+$ |
| 92 | tert-Butyl 2-[1-(2-imidazo[1,2-a]pyridin-7-yl-6-methyl-4-oxo-chromen-8-yl)ethylamino]benzoate, Isomer 2 | 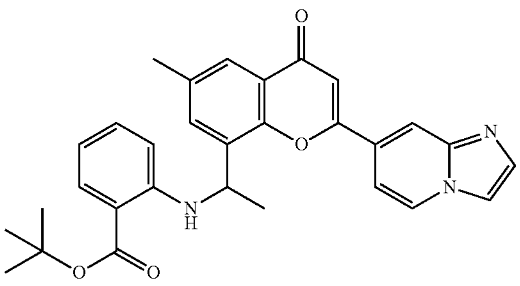 [SMILES: Cc1cc(C(C)Nc2ccccc2C(=O)OC(C)(C)C)c2oc(-c3ccn4ccnc4c3)cc(=O)c2c1] | 496 $[M + H]^+$ |

TABLE 39-continued

| Int # | Chemical Name | Structure | MS ES+ m/z |
| --- | --- | --- | --- |
| 93 | tert-Butyl 2-[1-[6-methyl-2-(2-methylthiazolo[5,4-b]pyridin-6-yl)-4-oxo-chromen-8-yl]ethylamino]benzoate, Isomer 2 | 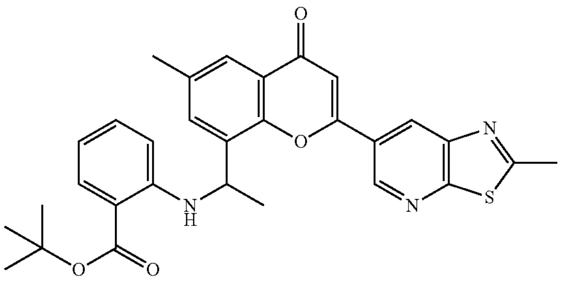 [SMILES: Cc1cc(C(C)Nc2ccccc2C(=O)OC(C)(C)C)c2oc(-c3cnc4sc(C)nc4c3)cc(=O)c2c1] | 528 $[M + H]^+$ |
| 94 | tert-Butyl 2-[1-[6-methyl-2-(1-methylpyrazolo[3,4-b]pyridin-6-yl)-4-oxo-chromen-8-yl]ethylamino]benzoate, Isomer 2 | 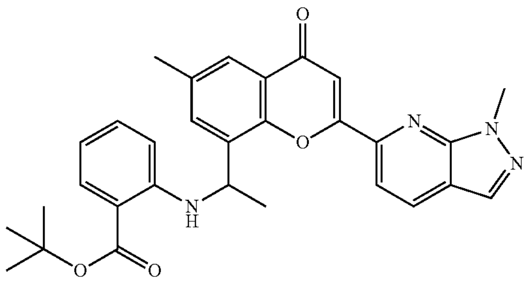 [SMILES: Cc1cc(C(C)Nc2ccccc2C(=O)OC(C)(C)C)c2oc(-c3ccc4cnn(C)c4n3)cc(=O)c2c1] | 511 $[M + H]^+$ |
| 246[a] | Methyl 3-chloro-2-fluoro-6-[1-[6-methyl-2-(2-methylimidazo[1,2-a]pyridin-6-yl)-4-oxo-chromen-8-yl]ethylamino]benzoate, Isomer 2 | 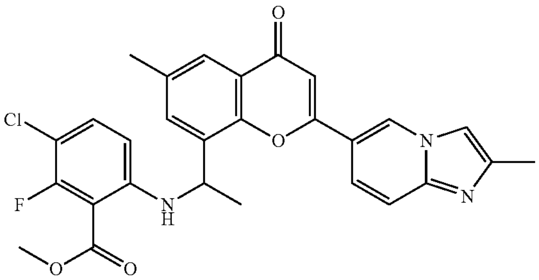 [SMILES: COC(=O)c1c(NC(C)c2cc(C)cc3c(=O)cc(-c4ccc5nc(C)cn5c4)oc23)ccc(Cl)c1F] | 520 $[M + H]^+$ |
| 247[a] | tert-Butyl 2-[1-[6-methyl-2-[2-methyl-3-(3-pyridyl)imidazo[1,2-a]pyridin-7-yl]-4-oxo-chromen-8-yl]ethylamino]benzoate, Isomer 2 | 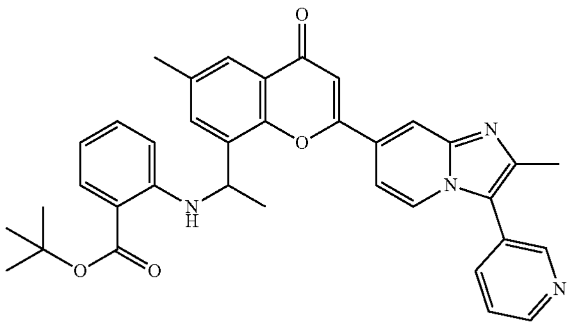 [SMILES: Cc1cc(C(C)Nc2ccccc2C(=O)OC(C)(C)C)c2oc(-c3ccn4c(-c5cccnc5)c(C)nc4c3)cc(=O)c2c1] | 587 $[M + H]^+$ |
| 248 | tert-Butyl 2-[1-[2-(2,7-dimethylindazol-5-yl)-6-methyl-4-oxo-chromen-8-yl]ethylamino]benzoate, Isomer 2 | 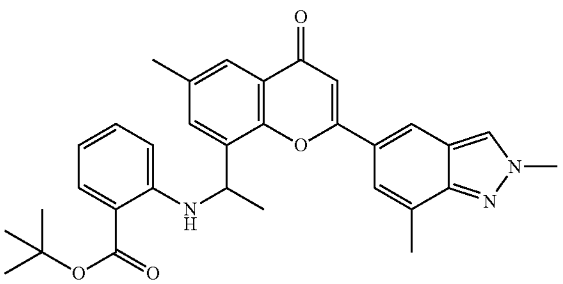 [SMILES: Cc1cc(C(C)Nc2ccccc2C(=O)OC(C)(C)C)c2oc(-c3cc(C)c4nn(C)cc4c3)cc(=O)c2c1] | 524 $[M + H]^+$ |

TABLE 39-continued

| Int # | Chemical Name | Structure | MS ES+ m/z |
|---|---|---|---|
| 249 | tert-Butyl 2-[1-[6-methyl-2-(1-methylindol-6-yl)-4-oxo-chromen-8-yl]ethylamino]benzoate, Isomer 2 | 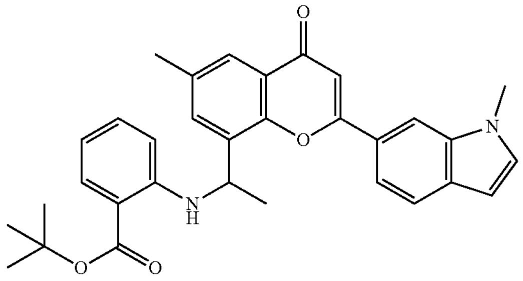 [SMILES: Cc1cc(C(C)Nc2ccccc2C(=O)OC(C)(C)C)c2oc(-c3ccc4ccn(C)c4c3)cc(=O)c2c1] | 509 [M + H]+ |
| 250[b] | tert-Butyl 2-[1-[6-methyl-2-(2-methylpyrazolo[3,4-c]pyridin-5-yl)-4-oxo-chromen-8-yl]ethylamino]benzoate | 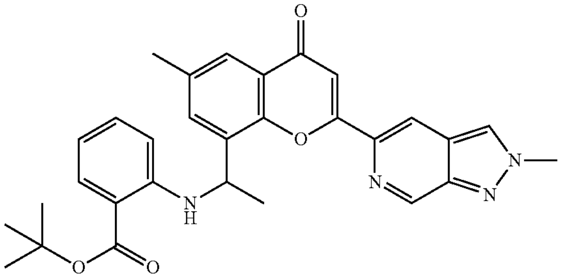 [SMILES: Cc1cc(C(C)Nc2ccccc2C(=O)OC(C)(C)C)c2oc(-c3cc4cn(C)nc4cn3)cc(=O)c2c1] | 511 [M + H]+ |
| 251 | tert-Butyl 2-[1-[6-methyl-4-oxo-2-[3-(trifluoromethyl)-[1,2,4]triazolo[4,3-a]pyridin-6-yl]chromen-8-yl]ethylamino]benzoate, Isomer 2 | 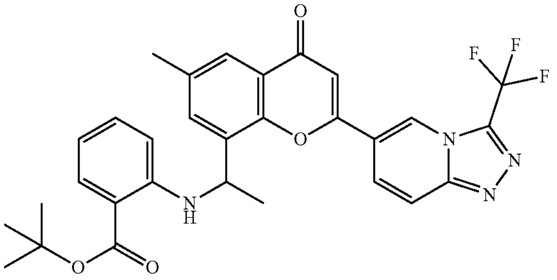 [SMILES: Cc1cc(C(C)Nc2ccccc2C(=O)OC(C)(C)C)c2oc(-c3ccc4nnc(C(F)(F)F)n4c3)cc(=O)c2c1] | 565 [M + H]+ |
| 252[b] | tert-Butyl 2-[1-[6-methyl-2-(1-methylpyrazolo[4,3-b]pyridin-5-yl)-4-oxo-chromen-8-yl]ethylamino]benzoate, Isomer 2 | 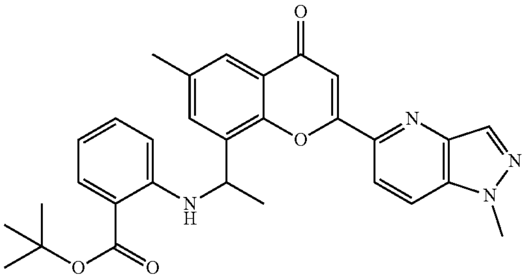 [SMILES: Cc1cc(C(C)Nc2ccccc2C(=O)OC(C)(C)C)c2oc(-c3ccc4c(cnn4C)n3)cc(=O)c2c1] | 511 [M + H]+ |
| 253 | tert-Butyl 2-[1-[2-(1,3-dimethylindazol-5-yl)-6-methyl-4-oxo-chromen-8-yl]ethylamino]benzoate, Isomer 2 | 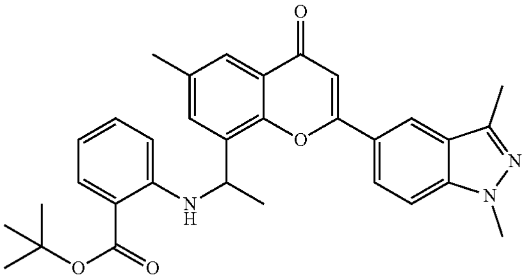 [SMILES: Cc1cc(C(C)Nc2ccccc2C(=O)OC(C)(C)C)c2oc(-c3ccc4c(c3)c(C)nn4C)cc(=O)c2c1] | 524 [M + H]+ |

TABLE 39-continued

| Int # | Chemical Name | Structure | MS ES+ m/z |
|---|---|---|---|
| -370 | Methyl 2-[[(1R)-1-[3,6-dimethyl-2-(2-methylindazol-5-yl)-4-oxo-chromen-8-yl]ethyl]amino]-6-fluoro-benzoate | 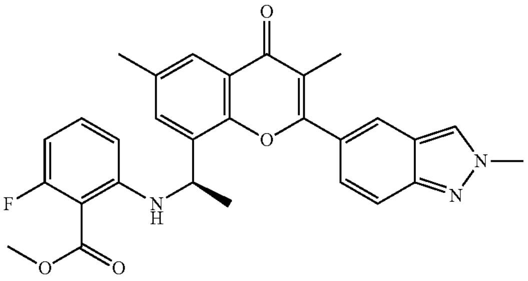 [SMILES: COC(=O)c1c(F)cccc1N[C@H](C)c1cc(C)cc2c(=O)c(C)c(-c3ccc4nn(C)cc4c3)oc12] | 500 $[M + H]^+$ |
| 371 | Methyl 2-[[(1R)-1-[3,6-dimethyl-2-(2-methylimidazo[1,2-a]pyridin-6-yl)-4-oxo-chromen-8-yl]ethyl]amino]-6-fluoro-benzoate | 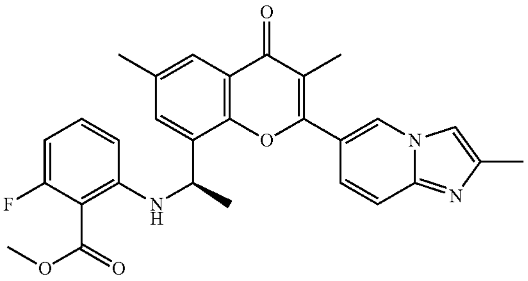 [SMILES: COC(=O)c1c(F)cccc1N[C@H](C)c1cc(C)cc2c(=O)c(C)c(-c3ccc4nc(C)cn4c3)oc12] | 500 $[M + H]^+$ |
| 372 | Methyl 2-[[(1R)-1-[3,6-dimethyl-2-(1-methylindazol-3-yl)-4-oxo-chromen-8-yl]ethyl]amino]-6-fluoro-benzoate | 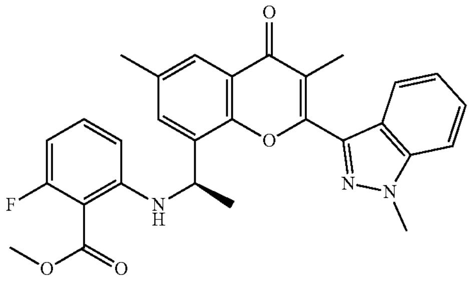 | 500 $[M + H]^+$ |
| 373 | Methyl 2-[[(1R)-1-[3,6-dimethyl-2-(2-methylindazol-5-yl)-4-oxo-chromen-8-yl]ethyl]amino]-5-(trifluoromethyl)benzoate | 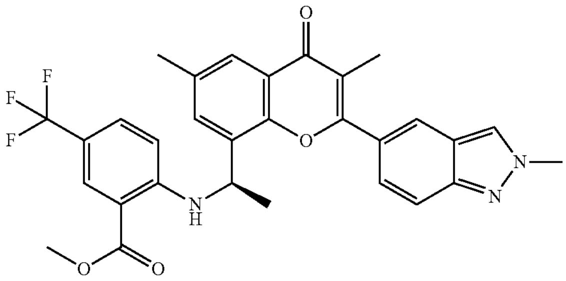 | 550 $[M + H]^+$ |

[a]Potassium carbonate used as the base instead of sodium tert-butoxide.

[b]Cesium carbonate used as the base instead of sodium tert-butoxide.

Intermediate 95: Methyl 6-chloro-3-[1-[6-methyl-2-(2-methylindazol-5-yl)-4-oxo-chromen-8-yl]ethyl-amino]pyridine-2-carboxylate, Isomer 2

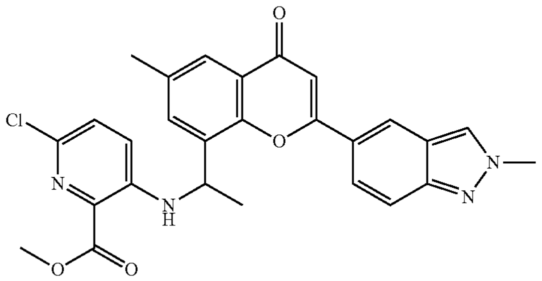

A mixture of methyl 6-chloro-3-[1-(2-ethylsulfanyl-6-methyl-4-oxo-chromen-8-yl)ethylamino]pyridine-2-carboxylate, Isomer 2 (300 mg, 0.69 mmol), 2-methyl-5-(4,4,5,5-tetramethyl-1,3,2-dioxaborolan-2-yl)indazole (358 mg, 1.39 mmol), copper(I) thiophene-2-carboxylate (396 mg, 2.08 mmol), tetrakis(triphenylphosphine)palladium(0) (80 mg, 0.069 mmol), and cesium carbonate (677 mg, 2.08 mmol) in 8 mL of 2-methyltetrahydrofuran was stirred at 85° C. under nitrogen gas for 50 h. The resulting brown suspension was concentrated, and the residue purified by silica gel chromatography using a gradient of 0% to 95% ethyl acetate in petroleum ether to give the product (120 mg, 34%) as a yellow solid. MS ES+ m/z 503 $[M+H]^+$.

The following compounds in Table 40 were made in a similar way as described for Intermediate 95.

TABLE 40

| Int # | Chemical Name | Structure | MS ES+ m/z |
|---|---|---|---|
| 254 | Methyl 6-Chloro-3-[1-[3,6-dimethyl-2-(2-methylindazol-5-yl)-4-oxo-chromen-8-yl]ethylamino]pyridine-2-carboxylate, Isomer 2 | 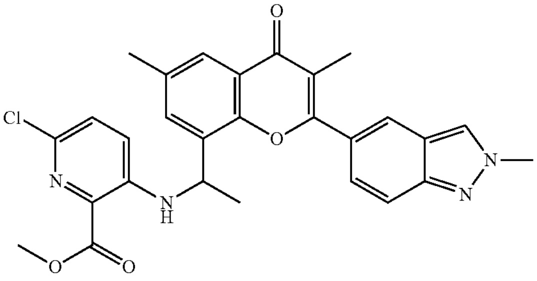 [SMILES: COC(=O)c1nc(Cl)ccc1NC(C)c1cc(C)cc2c(=O)c(C)c(-c3ccc4nn(C)cc4c3)oc12] | 517 $[M + H]^+$ |
| 255[a] | Methyl 3-Chloro-2-fluoro-6-[1-[6-methyl-2-(2-methylindazol-5-yl)-4-oxo-chromen-8-yl]ethylamino]benzoate, Isomer 2 | 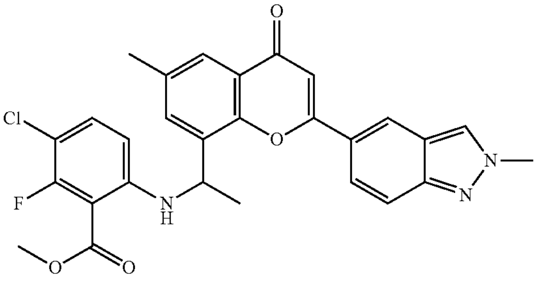 [SMILES: COC(=O)c1c(NC(C)c2cc(C)cc3c(=O)cc(-c4ccc5nn(C)cc5c4)oc23)ccc(Cl)c1F] | 520 $[M + H]^+$ |
| 256[b] | tert-Butyl 2-[1-[6-methyl-2-(1-methylpyrrolo[2,3-b]pyridin-6-yl)-4-oxo-chromen-8-yl]ethylamino]benzoate, Isomer 2 | 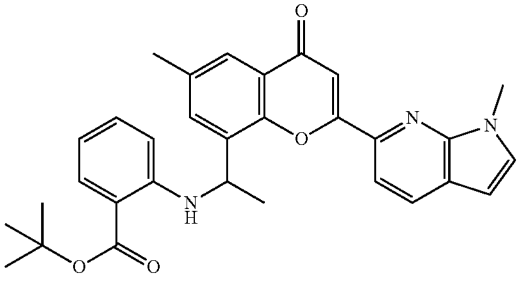 [SMILES: Cc1cc(C(C)Nc2ccccc2C(=O)OC(C)(C)C)c2oc(-c3ccc4ccn(C)c4n3)cc(=O)c2c1] | 510 $[M + H]^+$ |

TABLE 40-continued

| Int # | Chemical Name | Structure | MS ES+ m/z |
|---|---|---|---|
| 257 | Methyl 6-chloro-3-[1-[6-methyl-2-(1-methylindazol-3-yl)-4-oxo-chromen-8-yl]ethylamino]pyridine-2-carboxylate, Isomer 2 | 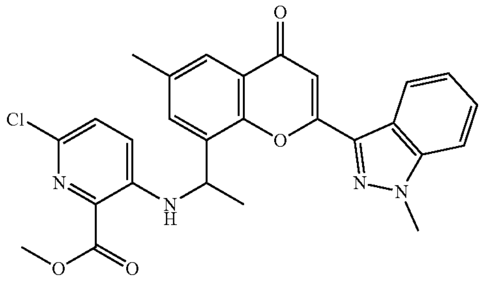 [SMILES: COC(=O)c1nc(Cl)ccc1NC(C)c1cc(C)cc2c(=O)cc(-c3nn(C)c4ccccc34)oc12] | 503 [M + H]+ |
| 258 | Methyl 6-chloro-3-[1-[3,6-dimethyl-2-(2-methylimidazo[1,2-a]pyridin-6-yl)-4-oxo-chromen-8-yl]ethylamino]pyridine-2-carboxylate, Isomer 2 | 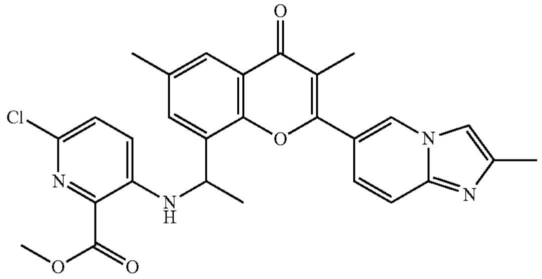 [SMILES: COC(=O)c1nc(Cl)ccc1NC(C)c1cc(C)cc2c(=O)c(C)c(-c3ccc4nc(C)cn4c3)oc12] | 517 [M + H]+ |
| 259 | Methyl 6-chloro-3-[1-[6-methyl-2-(2-methylimidazo[1,2-a]pyridin-6-yl)-4-oxo-chromen-8-yl]ethylamino]pyridine-2-carboxylate, Isomer 2 | 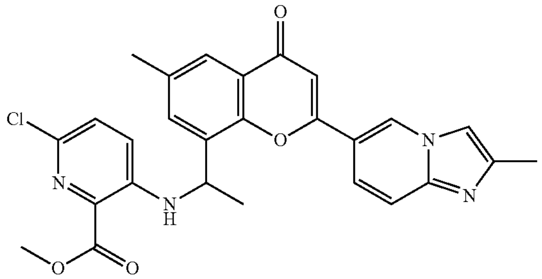 [SMILES: COC(=O)c1nc(Cl)ccc1NC(C)c1cc(C)cc2c(=O)cc(-c3ccc4nc(C)cn4c3)oc12] | 503 [M + H]+ |
| 260 | Methyl 6-chloro-3-[1-[3,6-dimethyl-2-(2-methylindazol-5-yl)-4-oxo-chromen-8-yl]ethylamino]pyridine-2-carboxylate, Isomer 2 | 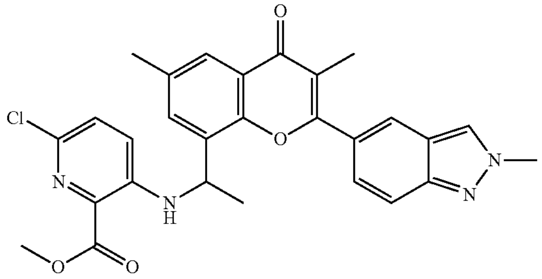 [SMILES: COC(=O)c1nc(Cl)ccc1NC(C)c1cc(C)cc2c(=O)c(C)c(-c3ccc4nn(C)cc4c3)oc12] | 517 [M + H]+ |
| 374 | tert-Butyl 2-[8-[(1R)-1-[(2-tert-butoxycarbonyl-6-chloro-3-pyridyl)amino]ethyl]-3,6-dimethyl-4-oxo-chromen-2-yl]indole-1-carboxylate | 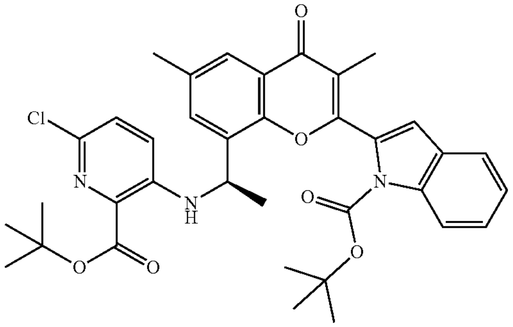 [SMILES: Cc1cc([C@@H](C)Nc2ccc(Cl)nc2C(=O)OC(C)(C)C)c2oc(-c3cc4ccccc4n3C(=O)OC(C)(C)C)c(C)c(=O)c2c1] | 644 [M + H]+ |

TABLE 40-continued

| Int # | Chemical Name | Structure | MS ES+ m/z |
|---|---|---|---|
| 375 | Methyl 3-[[(1R)-1-[3,6-dimethyl-2-(2-methylindazol-5-yl)-4-oxo-chromen-8-yl]ethyl]amino]-6-(trifluoromethyl)pyridine-2-carboxylate | 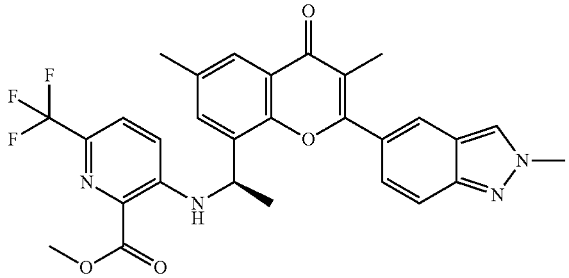 [SMILES: COC(=O)c1nc(C(F)(F)F)ccc1N[C@H](C)c1cc(C)cc2c(=O)c(C)c(-c3ccc4nn(C)cc4c3)oc12] | 551 $[M + H]^+$ |
| 376 | Methyl 6-chloro-3-[[(1R)-1-[3,6-dimethyl-2-(2-methyl-1,3-benzothiazol-6-yl)-4-oxo-chromen-8-yl]ethyl]amino]pyridine-2-carboxylate | 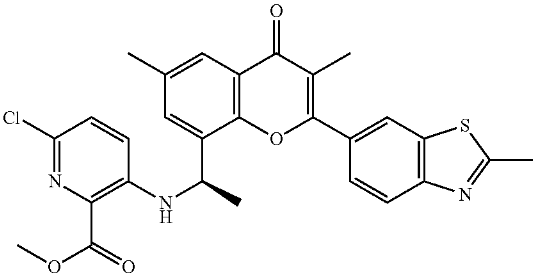 [SMILES: COC(=O)c1nc(Cl)ccc1N[C@H](C)c1cc(C)cc2c(=O)c(C)c(-c3ccc4nc(C)sc4c3)oc12] | 534 $[M + H]^+$ |

[a]Potassium fluoride (1 eq.) used as an additive in the reaction.

[b]Tris(dibenzylideneacetone)dipalladium(0) used as the catalyst instead of tetrakis(triplenylphosphine)palladium(0).

Intermediate 261: Methyl 3-[1-[3,6-dimethyl-2-(2-methylindazol-5-yl)-4-oxo-chromen-8-yl]ethylamino]-6-methyl-pyridine-2-carboxylate, Isomer 2

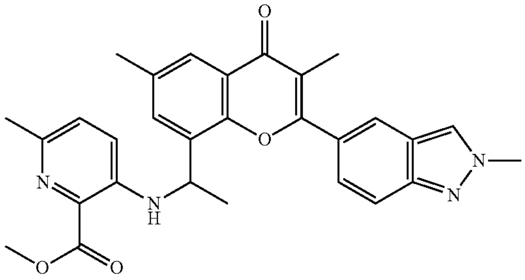

A mixture of methyl 6-chloro-3-[1-[3,6-dimethyl-2-(2-methylindazol-5-yl)-4-oxo-chromen-8-yl]ethylamino]pyridine-2-carboxylate, Isomer 2 (0.11 g, 0.21 mmol), methylboronic acid (0.025 g, 0.43 mmol), tetrakis (triphenylphosphine)palladium(0) (0.025 g, 0.021 mmol), and potassium carbonate (0.088 g, 0.64 mmol) in 2 mL of DMF was stirred at 100° C. under nitrogen for 4 h. The dark reaction was diluted with 20 mL of water and extracted 3 times with 20 mL of ethyl acetate. The organics were combined, washed with brine, collected, dried over $Na_2SO_4$, filtered and concentrated. The residue was purified by silica gel chromatography eluted with 0% to 100% ethyl acetate in petroleum ether to give the product (0.03 g, 28%) was a white solid. MS ES+ m/z 519 $[M+Na]^+$.

The following compounds in Table 41 were made in a similar way as described for Intermediate 261.

TABLE 41

| Int # | Chemical Name | Structure | MS ES+ m/z |
|---|---|---|---|
| 262 | Methyl 6-methyl-3-[1-[6-methyl-2-(1-methylindazol-3-yl)-4-oxo-chromen-8-yl]ethylamino]pyridine-2-carboxylate, Isomer 2 | 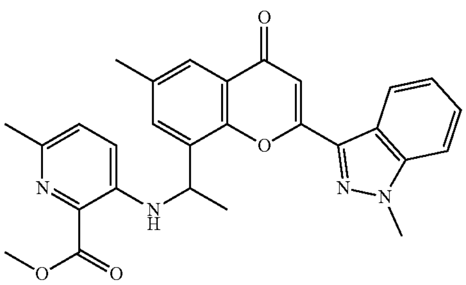 [SMILES: COC(=O)c1nc(C)ccc1NC(C)c1cc(C)cc2c(=O)cc(-c3nn(C)c4ccccc34)oc12] | 483 $[M + H]^+$ |

TABLE 41-continued

| Int # | Chemical Name | Structure | MS ES+ m/z |
|---|---|---|---|
| 263 | Methyl 6-methyl-3-[1-[6-methyl-2-(2-methylindazol-5-yl)-4-oxo-chromen-8-yl]ethylamino]pyridine-2-carboxylate, Isomer 2 | 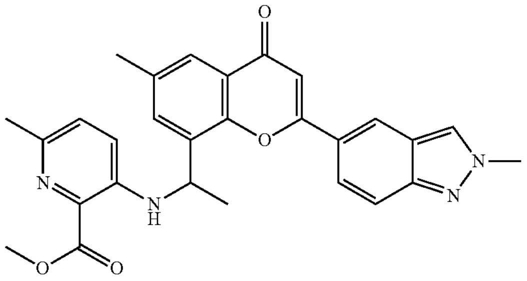 | 483 [M + H]$^+$ |

Intermediate 377: Ethyl 6-methyl-3-[1-[6-methyl-2-(2-methylimidazo[1,2-a]pyridin-6-yl)-4-oxo-chromen-8-yl]ethylamino]pyridine-2-carboxylate, Isomer 2

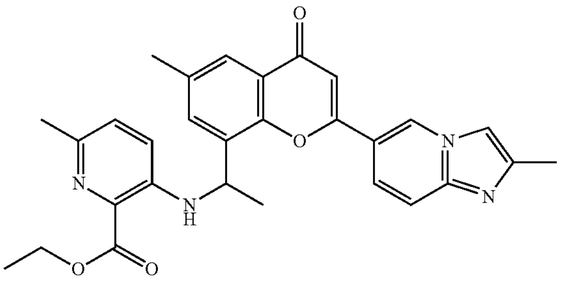

A toluene mixture (5 mL) of ethyl 6-chloro-3-[1-[6-methyl-2-(2-methylimidazo[1,2-a]pyridin-6-yl)-4-oxo-chromen-8-yl]ethylamino]pyridine-2-carboxylate [50 mg, 0.097 mmol, from synthesis of methyl 6-chloro-3-[1-[6-methyl-2-(2-methylimidazo[1,2-a]pyridin-6-yl)-4-oxo-chromen-8-yl]ethylamino]pyridine-2-carboxylate) was treated with Pd(dppf)$Cl_2$—$CH_2Cl_2$ (7.9 mg, 9.67 μmol) and dimethyl zinc (145.1 μL, 1M, 0.15 mmol) at 0° C. After stirring at 120° C. for 16 h, the reaction was cooled to 0° C., quenched with 0.5 mL of MeOH, and concentrated. The residue was diluted with 10 mL of dichloromethane, filtered, and concentrated with the residue being purified by prep-HPLC to give the product (17 mg, 35%) as an off-white solid after lyophilization. MS ES+ m/z 497 [M+H]$^+$.

The following compounds in Table 42 were made in a similar way as described for Intermediate 377.

TABLE 42

| Int # | Chemical Name | Structure | MS ES+ m/z |
|---|---|---|---|
| 378 | Methyl 6-methyl-3-[[(1R)-1-[6-methyl-2-(2-methylthiazolo[5,4-b]pyridin-5-yl)-4-oxo-chromen-8-yl]ethyl]amino]pyridine-2-carboxylate | 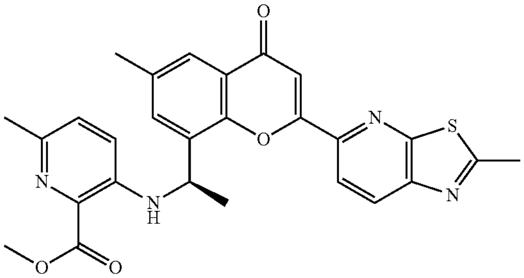 | 501 [M + H]$^+$ |

Intermediate 264: Methyl 6-chloro-3-[1-[2-(7-chloro-2-methyl-indazol-5-yl)-4-oxo-6-(trifluoromethyl)chromen-8 yl]ethylamino]pyridine-2-carboxylate

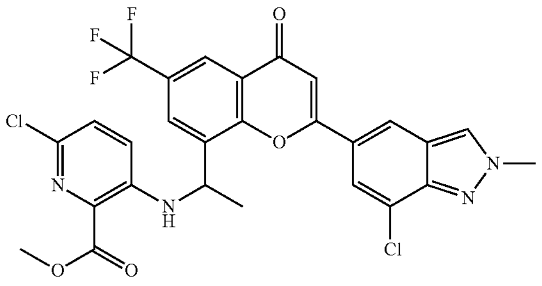

A suspension of methyl 3-[1-[2-bromo-4-oxo-6-(trifluoromethyl)chromen-8-yl]ethylamino]-6-chloro-pyridine-2-carboxylate (68.1 mg, 0.14 mmol), 7-chloro-2-methyl-5-(4,4,5,5-tetramethyl-1,3,2-dioxaborolan-2-yl)indazole (69 mg, 0.24 mmol), and potassium carbonate (65.1 mg, 0.47 mmol) in 1,4-dioxane (3 mL) and water (60 μL) was vacuum flushed three times with argon gas and then treated with solid [1,1'-bis(diphenylphosphino)ferrocene]dichloropalladium(II) complex with dichloromethane (11 mg, 0.0014 mmol) and vacuum flushed with argon gas three more times. Heated the reaction to 90° C. After 2 h, the reaction was cooled, filtered over celite/silica gel, and the solids rinsed with ethyl acetate. Concentrated the filtrate and the residue was purified by silica gel chromatography eluted with 0% to 100% ethyl acetate in heptane to give the product (60.5 mg, 76%) as a yellow solid. MS ES+ m/z 591 $[M+H]^+$.

The following compounds in Table 43 were made in a similar way as described for Intermediate 264.

TABLE 43

| Int # | Chemical Name | Structure | MS ES+ m/z |
|---|---|---|---|
| 265 | tert-Butyl 2-[1-[2-(7-chloro-2-methyl-indazol-5-yl)-6-methyl-4-oxo-chromen-8-yl]ethylamino]benzoate, Isomer 2 | 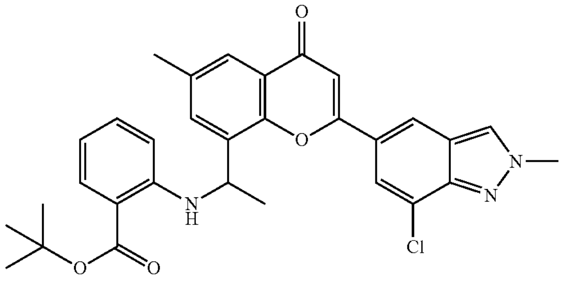 [SMILES: Cc1cc(C(C)Nc2ccccc2C(=O)OC(C)(C)C)c2oc(-c3cc(Cl)c4nn(C)cc4c3)cc(=O)c2c1] | 544 $[M + H]^+$ |
| 266 | Methyl 6-chloro-3-[1-[2-(2,7-dimethylindazol-5-yl)-4-oxo-6-(trifluoromethyl)chromen-8-yl]ethylamino]pyridine-2-carboxylate | 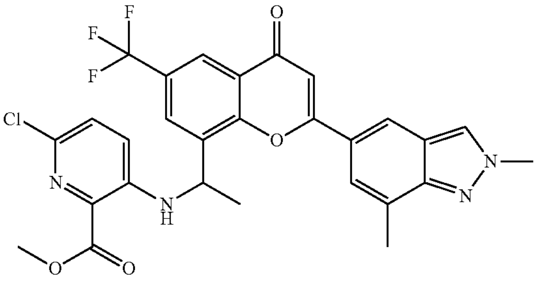 [SMILES: COC(=O)c1nc(Cl)ccc1NC(C)c1cc(C(F)(F)F)cc2c(=O)cc(-c3cc(C)c4nn(C)cc4c3)oc12] | 571 $[M + H]^+$ |
| 267[a] | tert-Butyl 2-[1-(6-methyl-4-oxo-2-quinazolin-7-yl-chromen-8-yl)ethylamino]benzoate, Isomer 2 | 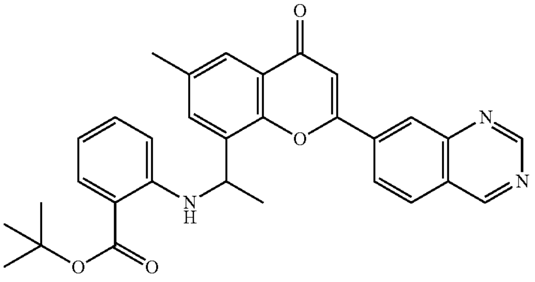 [SMILES: Cc1cc(C(C)Nc2ccccc2C(=O)OC(C)(C)C)c2oc(-c3ccc4cncnc4c3)cc(=O)c2c1] | 508 $[M + H]^+$ |

TABLE 43-continued

| Int # | Chemical Name | Structure | MS ES+ m/z |
|---|---|---|---|
| 268[a] | tert-Butyl 2-[1-[6-methyl-4-oxo-2-(2-oxoindolin-6-yl)chromen-8-yl]ethylamino]benzoate, Isomer 2 | 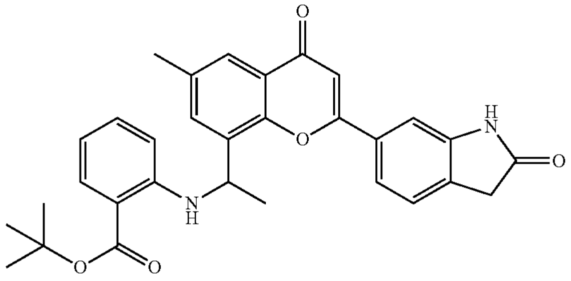 [SMILES: Cc1cc(C(C)Nc2ccccc2C(=O)OC(C)(C)C)c2oc(-c3ccc4c(c3)NC(=O)C4)cc(=O)c2c1] | 511 [M + H]$^+$ |
| 269[a] | tert-Butyl 2-[1-[2-(2,7-dimethylindazol-5-yl)-6-methyl-4-oxo-chromen-8-yl]ethylamino]benzoate, Isomer 2 | 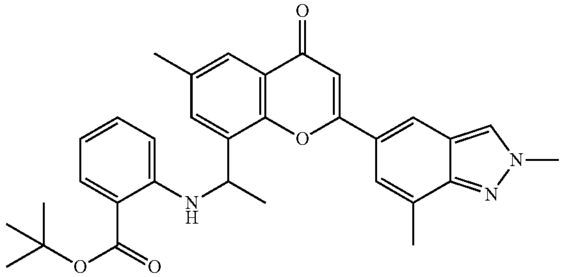 [SMILES: Cc1cc(C(C)Nc2ccccc2C(=O)OC(C)(C)C)c2oc(-c3cc(C)c4nn(C)cc4c3)cc(=O)c2c1] | 524 [M + H]$^+$ |
| 270[a] | tert-Butyl 2-[1-[6-methyl-2-(2-methylpyrazolo[1,5-a]pyridin-6-yl)-4-oxo-chromen-8-yl]ethylamino]benzoate, Isomer 2 | 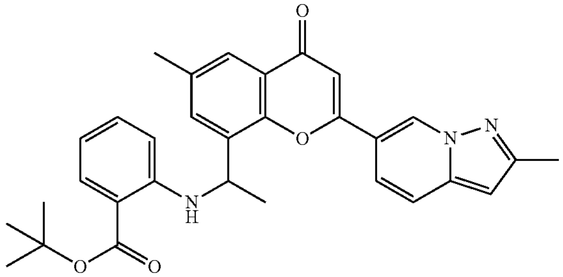 [SMILES: Cc1cc(C(C)Nc2ccccc2C(=O)OC(C)(C)C)c2oc(-c3ccc4cc(C)nn4c3)cc(=O)c2c1] | 510 [M + H]$^+$ |
| 271[a] | tert-Butyl 2-[1-[6-methyl-2-(2-methylthiazolo[5,4-b]pyridin-5-yl)-4-oxo-chromen-8-yl]ethylamino]benzoate, Isomer 2 | 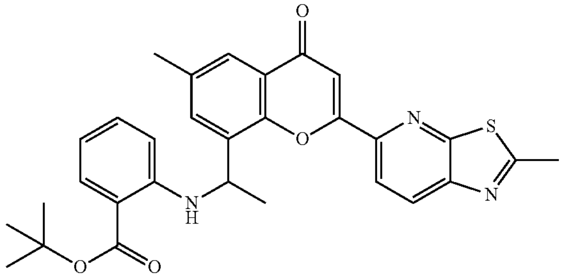 [SMILES: Cc1cc(C(C)Nc2ccccc2C(=O)OC(C)(C)C)c2oc(-c3ccc4nc(C)sc4n3)cc(=O)c2c1] | 528 [M + H]$^+$ |
| 272[a] | tert-Butyl 2-[1-[6-methyl-2-(1-methyl-2-oxo-3H-pyrrolo[2,3-b]pyridin-6-yl)-4-oxo-chromen-8-yl]ethylamino]benzoate, Isomer 2 | 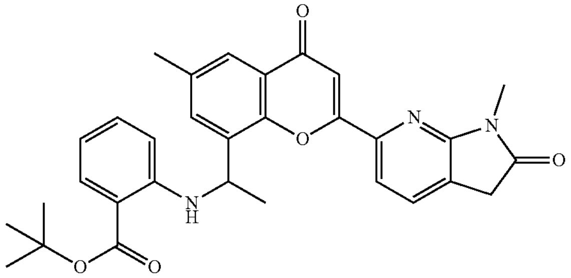 [SMILES: Cc1cc(C(C)Nc2ccccc2C(=O)OC(C)(C)C)c2oc(-c3ccc4c(n3)N(C)C(=O)C4)cc(=O)c2c1] | 526 [M + H]$^+$ |

TABLE 43-continued

| Int # | Chemical Name | Structure | MS ES+ m/z |
|---|---|---|---|
| 273[a] | tert-Butyl 2-[8-[1-(2-tert-butoxycarbonylanilino)ethyl]-6-methyl-4-oxo-chromen-2-yl]pyrrolo[3,2-b]pyridine-1-carboxylate, Isomer 2 | 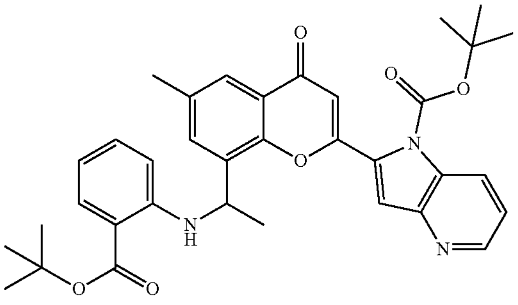 [SMILES: Cc1cc(C(C)Nc2ccccc2C(=O)OC(C)(C)C)c2oc(-c3cc4ncccc4n3C(=O)OC(C)(C)C)cc(=O)c2c1] | 596 [M + H]$^+$ |
| 274[a] | tert-Butyl 2-[1-[6-methyl-2-(1-methylbenzimidazol-5-yl)-4-oxo-chromen-8-yl]ethylamino]benzoate, Isomer 2 | 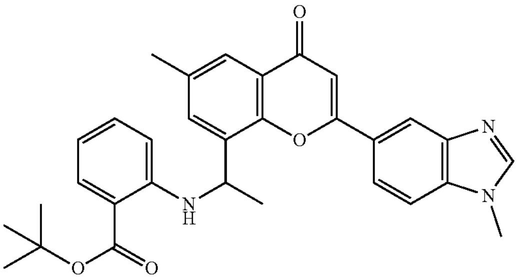 [SMILES: Cc1cc(C(C)Nc2ccccc2C(=O)OC(C)(C)C)c2oc(-c3ccc4c(c3)ncn4C)cc(=O)c2c1] | 510 [M + H]$^+$ |
| 283[a] | Methyl 2-fluoro-6-[1-[6-methyl-2-(1-methylindazol-3-yl)-4-oxo-chromen-8-yl]ethylamino]benzoate, Isomer 2 | 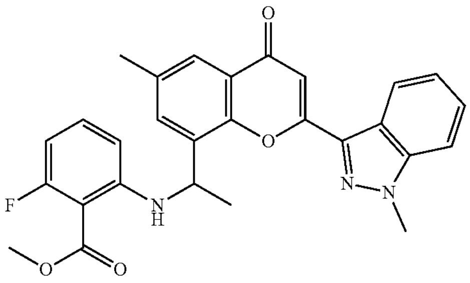 [SMILES: COC(=O)c1c(F)cccc1NC(C)c1cc(C)cc2c(=O)cc(-c3nn(C)c4ccccc34)oc12] | 486 [M + H]$^+$ |
| 284[a] | Methyl 2-[1-[2-(2,7-dimethylindazol-5-yl)-6-methyl-4-oxo-chromen-8-yl]ethylamino]-6-fluoro-benzoate, Isomer 2 | 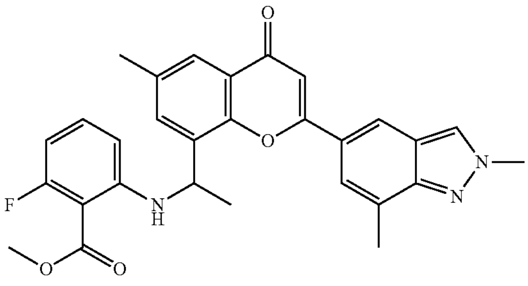 [SMILES: COC(=O)c1c(F)cccc1NC(C)c1cc(C)cc2c(=O)cc(-c3cc(C)c4nn(C)cc4c3)oc12] | 500 [M + H]$^+$ |
| 379[a] | Methyl 3-[[(1R)-1-[6-methyl-2-(2-methylindazol-5-yl)-4-oxo-chromen-8-yl]ethyl]amino]pyridine-2-carboxylate | 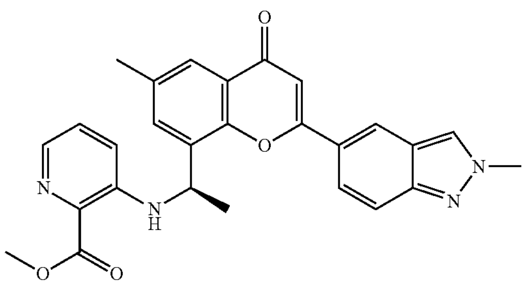 | 469 [M + H]$^+$ |

TABLE 43-continued

| Int # | Chemical Name | Structure | MS ES+ m/z |
|---|---|---|---|
| 380[a] | Methyl 2-fluoro-6-[[(1R)-1-[6-methyl-2-(2-methylimidazo[1,2-a]pyridin-6-yl)-4-oxo-chromen-8-yl]ethyl]amino]benzoate | 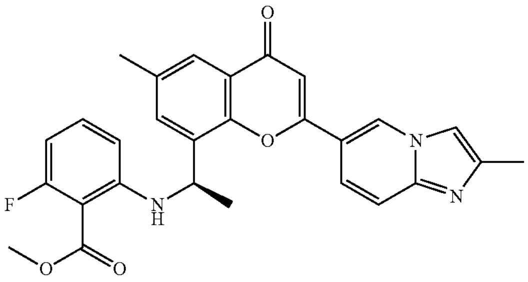 [SMILES: COC(=O)c1c(F)cccc1N[C@H](C)c1cc(C)cc2c(=O)cc(-c3ccc4nc(C)cn4c3)oc12] | 486 [M + H]$^+$ |
| 381[a] | Methyl 3-[[(1R)-1-[2-(2,7-dimethylindazol-5-yl)-6-methyl-4-oxo-chromen-8-yl]ethyl]amino]pyridine-2-carboxylate | 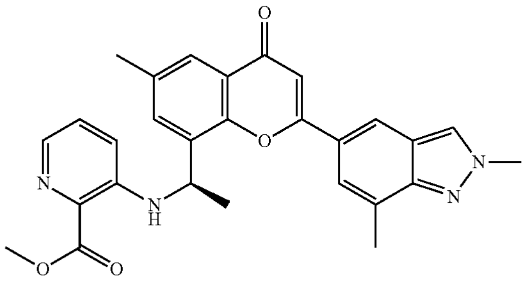 | 483 [M + H]$^+$ |
| 382[a] | Methyl 3-[[(1R)-1-[6-methyl-2-(1-methylindazol-3-yl)-4-oxo-chromen-8-yl]ethyl]amino]pyridine-2-carboxylate | 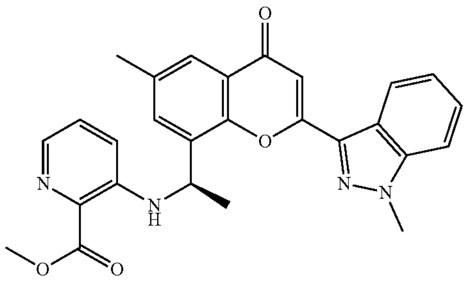 [SMILES: COC(=O)c1ncccc1N[C@H](C)c1cc(C)cc2c(=O)cc(-c3nn(C)c4ccccc34)oc12] | 469 [M + H]$^+$ |
| 383 | Methyl 3-[[(1R)-1-[3,6-dimethyl-2-(2-methylthiazolo[5,4-b]pyridin-5-yl)-4-oxo-chromen-8-yl]ethyl]amino]-6-(trifluoromethyl)pyridine-2-carboxylate | 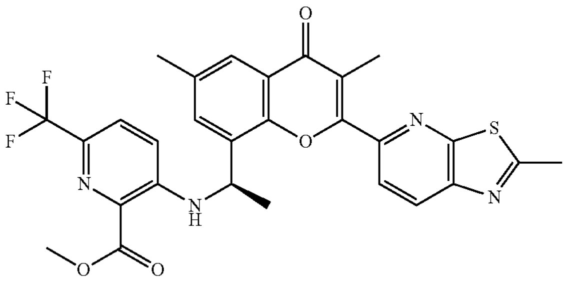 [SMILES: COC(=O)c1nc(C(F)(F)F)ccc1N[C@H](C)c1cc(C)cc2c(=O)c(C)c(-c3ccc4nc(C)sc4n3)oc12] | 569 [M + H]$^+$ |
| 384[b] | Methyl 2-[[(1R)-1-[3,6-dimethyl-2-(2-methylthiazolo[5,4-b]pyridin-5-yl)-4-oxo-chromen-8-yl]ethyl]amino]-5-(trifluoromethyl)benzoate | 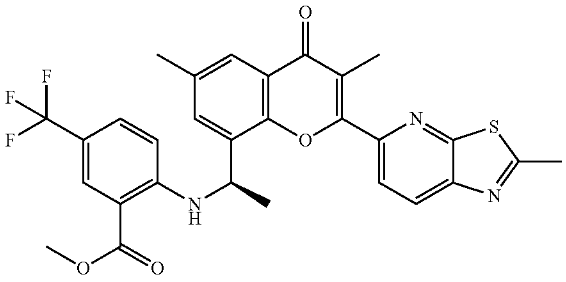 [SMILES: COC(=O)c1cc(C(F)(F)F)ccc1N[C@H](C)c1cc(C)cc2c(=O)c(C)c(-c3ccc4nc(C)sc4n3)oc12] | 568 [M + H]$^+$ |

[a]Xphos Pd G3 used as the palladium catalyst.

[b]Pd(dppf)$Cl_2$—$CH_2Cl_2$ and cesium carbons he used as the catalyst and base.

Intermediate 385: Methyl 3-[[(1R)-1-[6-methyl-2-(2-methylthiazolo[5,4-b]pyridin-5-yl)-4-oxo-chromen-8-yl]ethyl]amino]pyridine-2-carboxylate

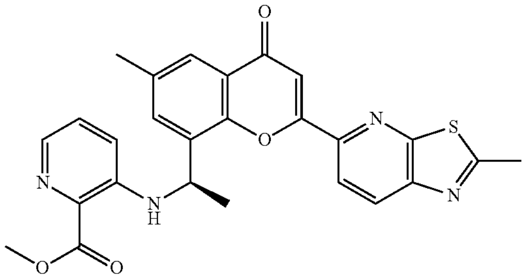

A mixture of 5-chloro-2-methyl-thiazolo[5,4-b]pyridine (203.56 mg, 1.1 mmol), bis(pinacolato)diboron (335.95 mg, 1.32 mmol), potassium acetate (540.98 mg, 5.51 mmol) in 3 mL of 1,4-dioxane was treated with [1,1'-bis(diphenylphosphino)ferrocene]dichloropalladium(II), complex with dichloromethane (90.03 mg, 0.11 mmol) and stirred at 100° C. for 7 h. The resulting black suspension was filtered and treated with methyl 3-[[(1R)-1-(2-bromo-6-methyl-4-oxo-chromen-8-yl)ethyl]amino]pyridine-2-carboxylate (46 mg, 0.11 mmol), cesium carbonate (107.76 mg, 0.33 mmol), [1,1'-bis(diphenylphosphino)ferrocene]dichloropalladium (II), complex with dichloromethane (27.01 mg, 0.03 mmol), and water (0.05 mL) and then stirred at 100° C. for 11 h. Allowed the reaction to cool to rt, concentrated, and purified by silica gel chromatography eluted with 0% to 25% EtOAc in petroleum ether to give the product (53.64 mg, 83%) as a white solid. MS ES+ m/z 487 $[M+H]^+$.

Intermediate 386: Methyl 3-[[(1R)-1-[3,6-dimethyl-2-(2-methylindazol-5-yl)-4-oxo-chromen-8-yl]ethyl]amino]pyridine-2-carboxylate

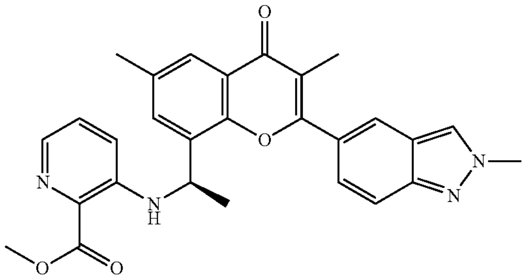

A solution of 8-[(1R)-1-aminoethyl]-3,6-dimethyl-2-(2-methylindazol-5-yl)chromen-4-one (150 mg, 0.43 mmol), methyl 3-fluoropyridine-2-carboxylate (200.94 mg, 1.30 mmol) in 4 mL of DMSO was treated with triethylamine (218.45 mg, 2.16 mmol) and stirred at 120° C. for 36 h. allowed the reaction to cool to rt and concentrated the reaction. Diluted the reaction with 20 mL of water and extracted with EtOAc (3×20 mL). The combined organic layers were washed with brine (3×20 mL), collected, dried over $Na_2SO_4$, filtered, concentrated, and purified by silica gel chromatography eluted with 0% to 5% MeOH in as the mobile phase to give the product (140 mg, 42%) as a yellow oil. MS ES+ m/z 483 $[M+H]^+$.

Example 1: 2-[1-[6-Methyl-2-(2-methylindazol-6-yl)-4-oxo-chromen-8-yl]ethylamino]benzoic acid, Isomer 2; 2,2,2-trifluoroacetic acid

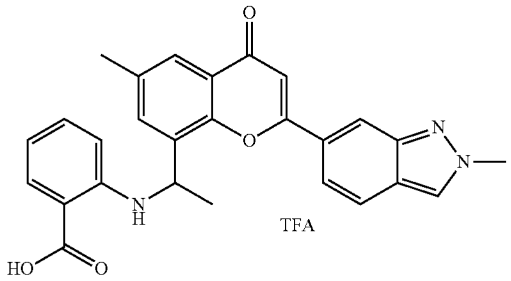 [SMILES: Cc1cc(C(C)Nc2ccccc2C(=O)O)c2oc(-c3ccc4cn(C)nc4c3)cc(=O)c2c1]

tert-Butyl 2-[1-[6-methyl-2-(2-methylindazol-6-yl)-4-oxo-chromen-8-yl]ethylamino]benzoate, Isomer 2 (20 mg, 0.04 mmol) was dissolved in DCM (2 mL) and treated with trifluoroacetic acid (2 mL). The solution was stirred at 30° C. for 16 h. The reaction was cooled to rt and concentrated. The residue was purified by reverse phase C-18 chromatography eluted with 0%-100% acetonitrile in water with 0.1% TFA to give the product (8 mg, 40%) as a trifluoroacetate salt. MS ES+ m/z 454 $[M+H]^+$.

The following compounds in Table 44 were made in a similar way as described for Example 1.

TABLE 44

| Ex # | Chemical Name | Structure | MS ES+ m/z |
|---|---|---|---|
| 2 | 2-[1-[2-(6-Methoxyimidazo[1,2-a]pyridin-2-yl)-6-methyl-4-oxo-chromen-8-yl]ethylamino]benzoic acid, Isomer 2; 2,2,2-trifluoroacetic acid | 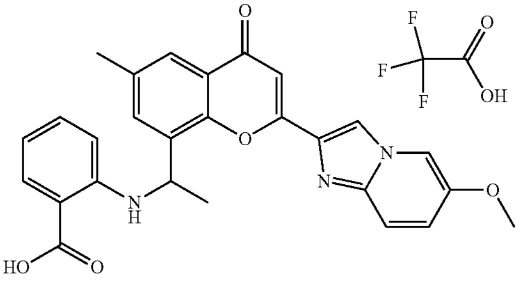 | 470 $[M + H]^+$ |

TABLE 44-continued

| Ex # | Chemical Name | Structure | MS ES+ m/z |
|---|---|---|---|
| 3 | 2-[1-[6-Methyl-2-(2-methylimidazo[1,2-a]pyridin-7-yl)-4-oxo-chromen-8-yl]ethylamino]benzoic acid, Isomer 2; 2,2,2-trifluoroacetic acid | 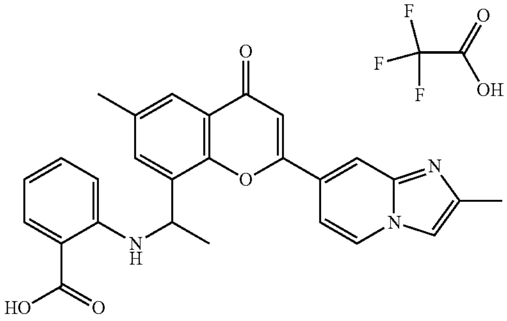 [SMILES: Cc1cc(C(C)Nc2ccccc2C(=O)O)c2oc(-c3ccn4cc(C)nc4c3)cc(=O)c2c1 ; O=C(O)C(F)(F)F] | 454 [M + H]+ |
| 4 | 2-[1-[6-Methyl-4-oxo-2-(1H-pyrrolo[2,3-b]pyridin-6-yl)chromen-8-yl]ethylamino]benzoic acid, Isomer 2; 2,2,2-trifluoroacetic acid | 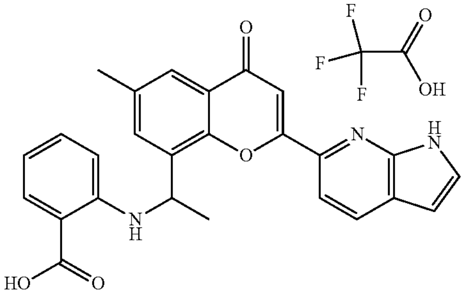 | 440 [M + H]+ |
| 5 | 2-[1-[6-Methyl-2-(2-methylpyrazolo[4,3-b]pyridin-6-yl)-4-oxo-chromen-8-yl]ethylamino]benzoic acid; 2,2,2-trifluoroacetic acid | 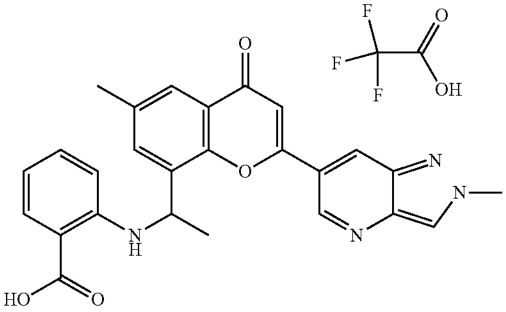 | 455 [M + H]+ |
| 6 | 2-[1-(6-Methyl-4-oxo-2-pyrazolo[1,5-a]pyrimidin-3-yl-chromen-8-yl)ethylamino]benzoic acid | 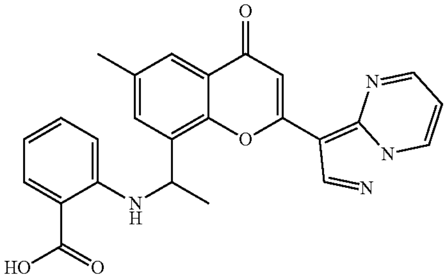 [SMILES: Cc1cc(C(C)Nc2ccccc2C(=O)O)c2oc(/C(C=N)=C3\N=CC=CN3)cc(=O)c2c1] | 441 [M + H]+ |
| 7 | 2-[1-(2-Furo[2,3-c]pyridin-2-yl-6-methyl-4-oxo-chromen-8-yl)ethylamino]benzoic acid; 2,2,2-trifluoroacetic acid | 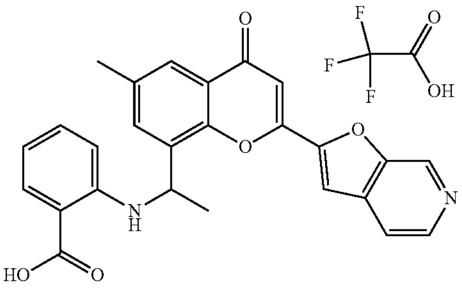 | 441 [M + H]+ |

TABLE 44-continued

| Ex # | Chemical Name | Structure | MS ES+ m/z |
|---|---|---|---|
| 8 | 2-[1-[6-Methyl-2-(2-methylindazol-5-yl)-4-oxo-chromen-8-yl]ethylamino]benzoic acid, Isomer 2; 2,2,2-trifluoroacetic acid | 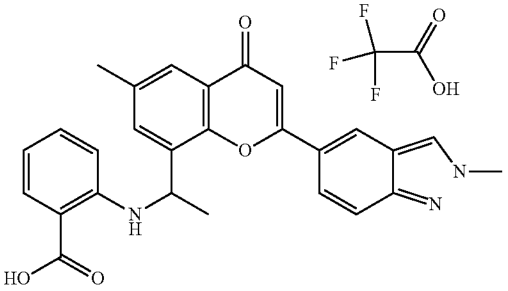 | 454 $[M + H]^+$ |
| 9 | 2-[1-[6-Methyl-2-(2-methylpyrazolo[3,4-b]pyridin-5-yl)-4-oxo-chromen-8-yl]ethylamino]benzoic acid; 2,2,2-trifluoroacetic acid | 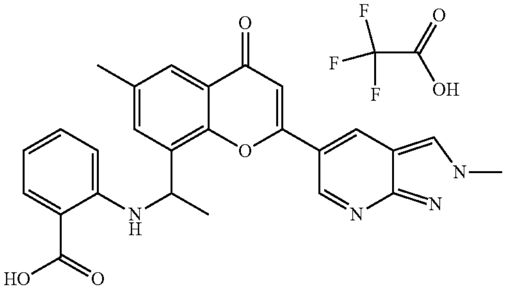 | 455 $[M + H]^+$ |
| 10 | 2-[1-(6-Methyl-4-oxo-2-pyrazolo[1,5-a]pyridin-3-yl-chromen-8-yl)ethylamino]benzoic acid; 2,2,2-trifluoroacetic acid | 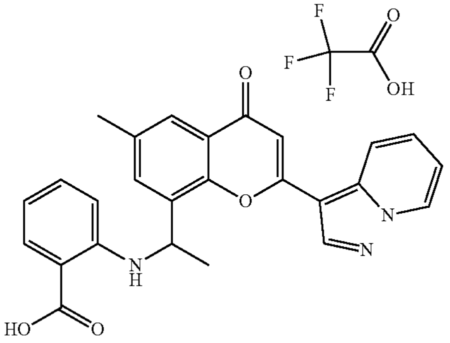 | 440 $[M + H]^+$ |
| 11 | 2-[1-[6-Methyl-4-oxo-2-[2-(trifluoromethyl)-1H-indol-5-yl]chromen-8-yl]ethylamino]benzoic acid; 2,2,2-trifluoroacetic acid | 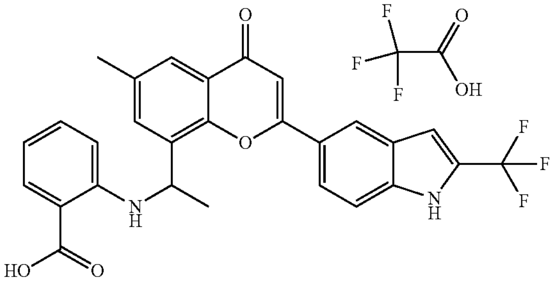 | 507 $[M + H]^+$ |
| 12 | 2-[1-[6-Methyl-2-(1-methylindazol-3-yl)-4-oxo-chromen-8-yl]ethylamino]benzoic acid; 2,2,2-trifluoroacetic acid | 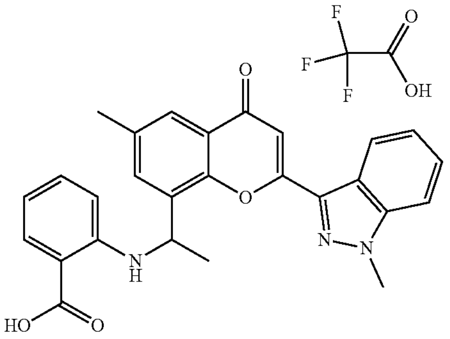 | 454 $[M + H]^+$ |

TABLE 44-continued

| Ex # | Chemical Name | Structure | MS ES+ m/z |
|---|---|---|---|
| 13 | 2-[1-[6-Methyl-2-(2-methylindazol-5-yl)-4-oxo-chromen-8-yl]ethylamino]benzoic acid | 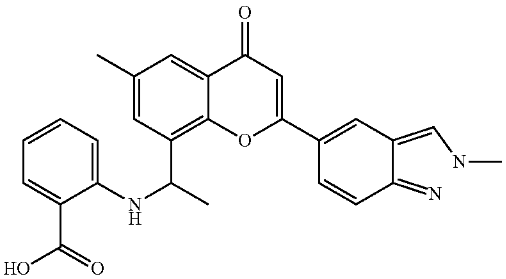 | 454 [M + H]+ |
| 14 | 2-[1-[6-Methyl-4-oxo-2-(1H-pyrrolo[2,3-b]pyridin-6-yl)chromen-8-yl]ethylamino]benzoic acid | 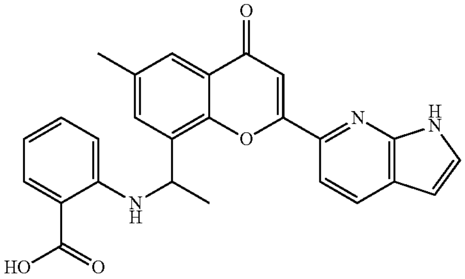 [SMILES: Cc1cc(C(C)Nc2ccccc2C(=O)O)c2oc(-c3ccc4cc[nH]c4n3)cc(=O)c2c1] | 440 [M + H]+ |
| 15 | 2-[1-(2-Imidazo[1,2-b]pyridazin-6-yl-6-methyl-4-oxo-chromen-8-yl)ethylamino]benzoic acid | 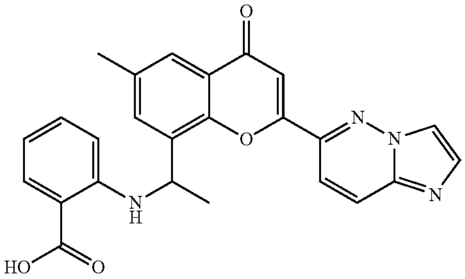 [SMILES: Cc1cc(C(C)Nc2ccccc2C(=O)O)c2oc(-c3ccc4nccn4n3)cc(=O)c2c1] | 441 [M + H]+ |
| 16 | 2-[1-[6-Methyl-2-(2-methylimidazo[1,2-a]pyridin-6-yl)-4-oxo-chromen-8-yl]ethylamino]benzoic acid; 2,2,2-trifluoroacetic acid | 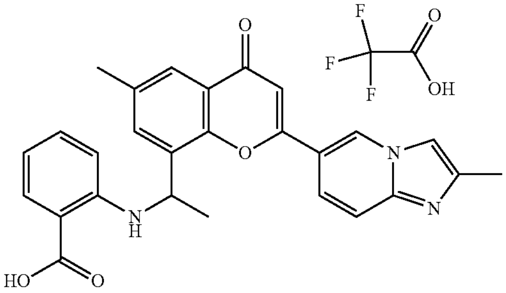 | 454 [M + H]+ |
| 17 | 2-[1-[6-Methyl-2-(2-methylimidazo[1,2-a]pyridin-6-yl)-4-oxo-chromen-8-yl]ethylamino]benzoic acid; 2,2,2-trifluoroacetic acid, Isomer 2 | 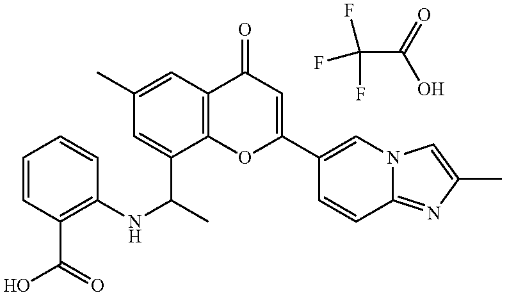 | 454 [M + H]+ |

TABLE 44-continued

| Ex # | Chemical Name | Structure | MS ES+ m/z |
|---|---|---|---|
| 18 | 2-[1-[2-(1H-Indol-6-yl)-6-methyl-4-oxo-chromen-8-yl]ethylamino]benzoic acid; 2,2,2-trifluoroacetic acid | 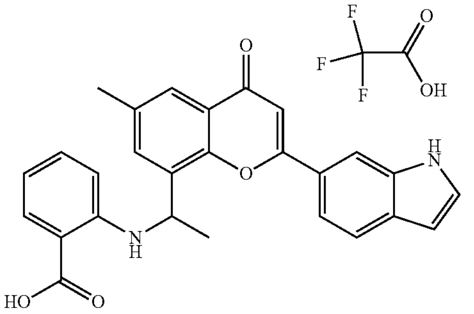 | 439 $[M + H]^+$ |
| 19 | 2-[1-[6-Methyl-2-(2-methyl-1,3-benzoxazol-5-yl)-4-oxo-chromen-8-yl]ethylamino]benzoic acid, Isomer 2; 2,2,2-trifluoroacetic acid | 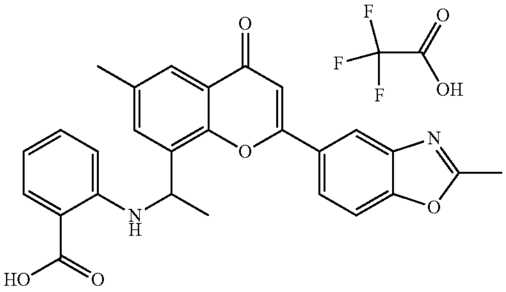 | 455 $[M + H]^+$ |
| 20 | 2-[1-[6-Methyl-2-(2-methyl-1H-pyrrolo[2,3-b]pyridin-6-yl)-4-oxo-chromen-8-yl]ethylamino]benzoic acid, Isomer 2; 2,2,2-trifluoroacetic acid | 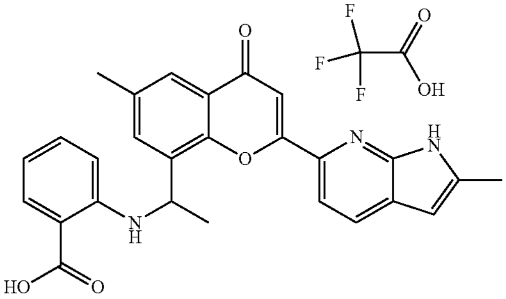 | 454 $[M + H]^+$ |
| 21 | 2-[1-[2-(1H-Indol-6-yl)-6-methyl-4-oxo-chromen-8-yl]ethylamino]benzoic acid, Isomer 2; 2,2,2-trifluoroacetic acid | 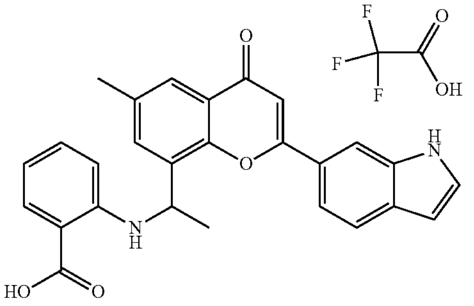 | 439 $[M + H]^+$ |
| 22 | 2-[1-(2-Furo[3,2-c]pyridin-2-yl-6-methyl-4-oxo-chromen-8-yl)ethylamino]benzoic acid, Isomer 2; 2,2,2-trifluoroacetic acid | 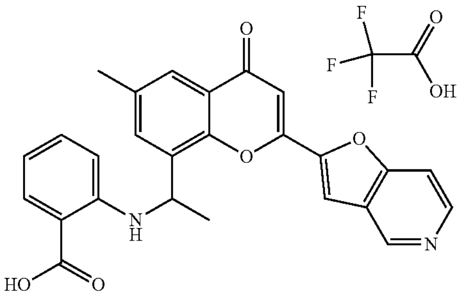 | 441 $[M + H]^+$ |

TABLE 44-continued

| Ex # | Chemical Name | Structure | MS ES+ m/z |
| --- | --- | --- | --- |
| 23 | 2-[1-[6-Methyl-2-(1-methylindazol-3-yl)-4-oxo-chromen-8-yl]ethylamino]benzoic acid, Isomer 2; 2,2,2-trifluoroacetic acid | 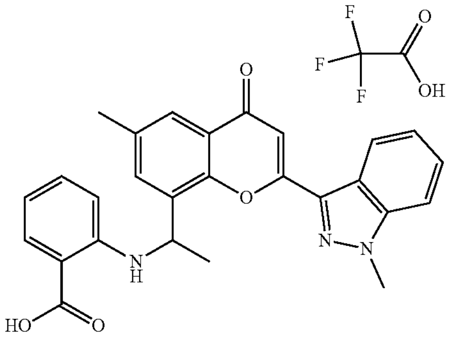 | 454 [M + H]$^+$ |
| 24 | 2-[1-[6-Methyl-4-oxo-2-(2-oxo-3H-1,3-benzoxazol-5-yl)chromen-8-yl]ethylamino]benzoic acid, Isomer 2; 2,2,2-trifluoroacetic acid | 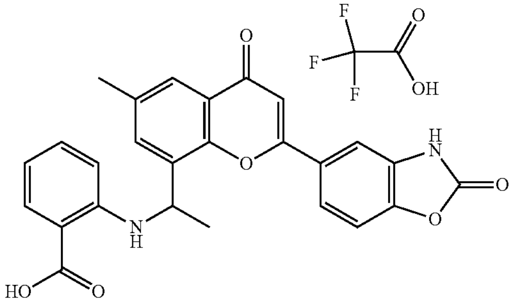 | 457 [M + H]$^+$ |
| 25 | 2-[1-[6-Methyl-2-(1-methylindazol-6-yl)-4-oxo-chromen-8-yl]ethylamino]benzoic acid, Isomer 2; 2,2,2-trifluoroacetic acid | 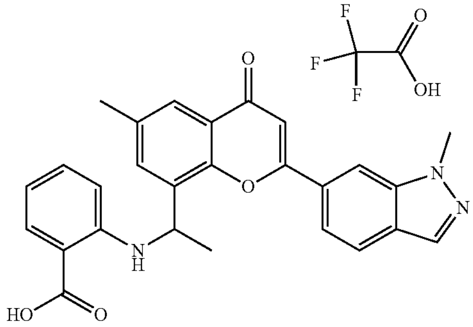 | 454 [M + H]$^+$ |
| 26 | 2-[1-[6-Methyl-2-(1-methylindazol-5-yl)-4-oxo-chromen-8-yl]ethylamino]benzoic acid, Isomer 2; 2,2,2-trifluoroacetic acid | 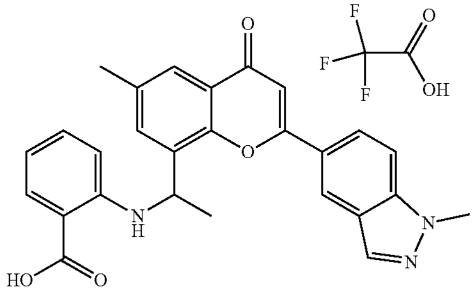 | 454 [M + H]$^+$ |

TABLE 44-continued

| Ex # | Chemical Name | Structure | MS ES+ m/z |
|---|---|---|---|
| 27 | 2-[1-[2-(1,3-Dimethylindazol-6-yl)-6-methyl-4-oxo-chromen-8-yl]ethylamino]benzoic acid, Isomer 2; 2,2,2-trifluoroacetic acid | 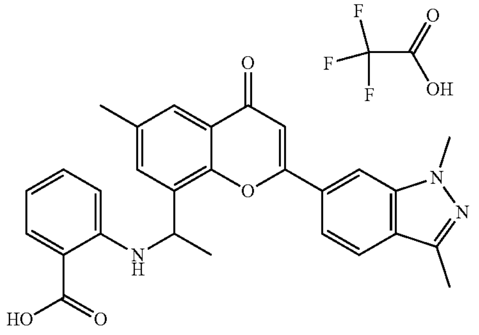 | 468 [M + H]+ |
| 28 | 2-[1-[6-Methyl-2-(3-methyl-1H-indazol-6-yl)-4-oxo-chromen-8-yl]ethylamino]benzoic acid, Isomer 2; 2,2,2-trifluoroacetic acid | 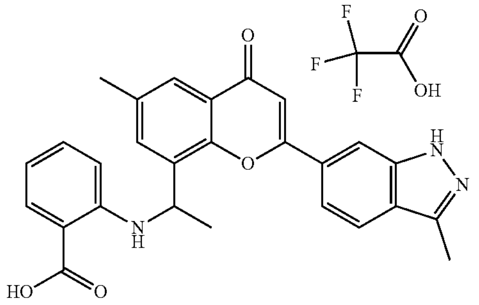 | 454 [M + H]+ |
| 29 | 2-[1-(6-Methyl-4-oxo-2-pyrazolo[1,5-a]pyridin-3-yl-chromen-8-yl)ethylamino]benzoic acid, Isomer 2; 2,2,2-trifluoroacetic acid | 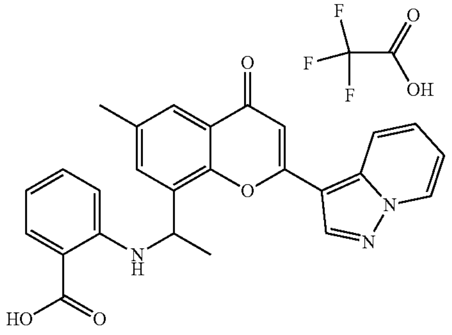 | 440 [M + H]+ |
| 51 | 2-[1-[6-Fluoro-2-(2-methylimidazo[1,2-a]pyridin-6-yl)-4-oxo-chromen-8-yl]ethylamino]benzoic acid, Isomer 2; 2,2,2-trifluoroacetic acid | 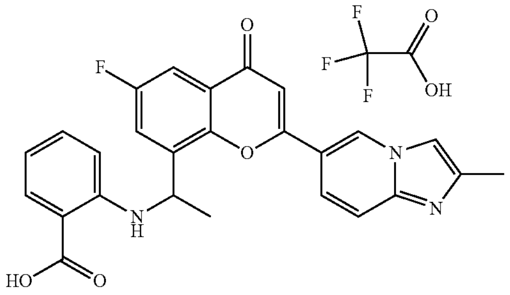 | 458 [M + H]+ |

TABLE 44-continued

| Ex # | Chemical Name | Structure | MS ES+ m/z |
|---|---|---|---|
| 52 | 2-[1-[2-(1H-Indol-2-yl)-3,6-dimethyl-4-oxo-chromen-8-yl]ethylamino]benzoic acid, Isomer 2; 2,2,2-trifluoroacetic acid | 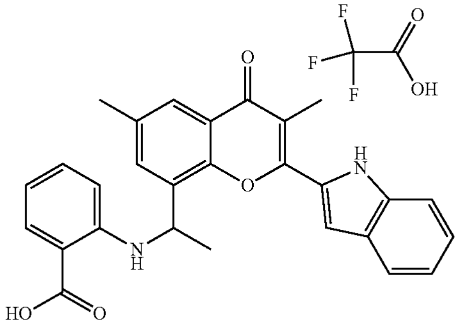 | 453 $[M + H]^+$ |
| 53 | 2-[1-[6-Methyl-2-(1-methylpyrazolo[4,3-b]pyridin-5-yl)-4-oxo-chromen-8-yl]ethylamino]benzoic acid, Isomer 2;2,2-trifluoroacetic acid | 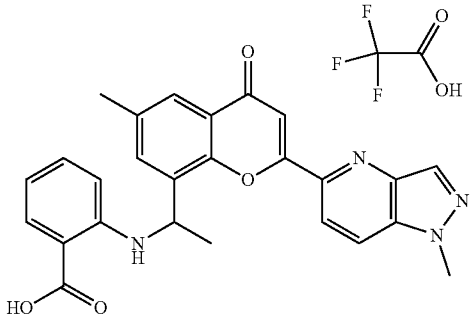 [SMILES: Cc1cc(C(C)Nc2ccccc2C(=O)O)c2oc(-c3ccc4c(cnn4C)n3)cc(=O)c2c1 ; O=C(O)C(F)(F)F] | 455 $[M + H]^+$ |
| 54 | 2-[1-[6-Methyl-2-(2-methylpyrazolo[4,3-b]pyridin-5-yl)-4-oxo-chromen-8-yl]ethylamino]benzoic acid, Isomer 2; 2,2,2-trifluoroacetic acid | 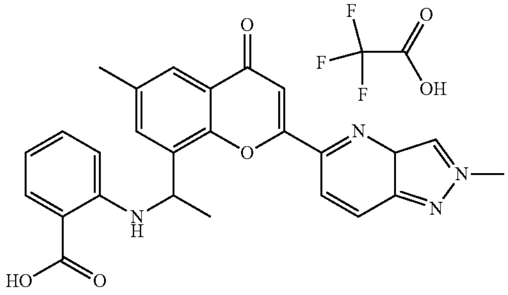 | 455 $[M + H]^+$ |
| 55 | 2-[1-[6-Fluoro-2-(2-methylindazol-5-yl)-4-oxo-chromen-8-yl]ethylamino]benzoic acid, Isomer 2 | 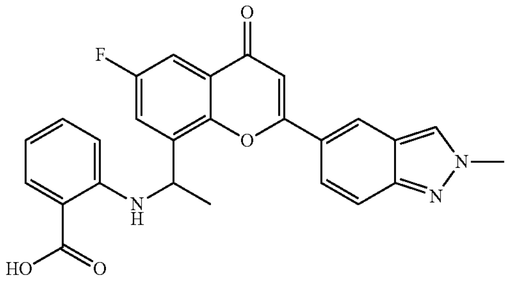 | 458 $[M + H]^+$ |
| 56 | 2-[1-[6-Fluoro-3-methyl-2-(2-methylimidazo[1,2-a]pyridin-6-yl)-4-oxo-chromen-8-yl]ethylamino]benzoic acid, Isomer 2; 2,2,2-trifluoroacetic acid | 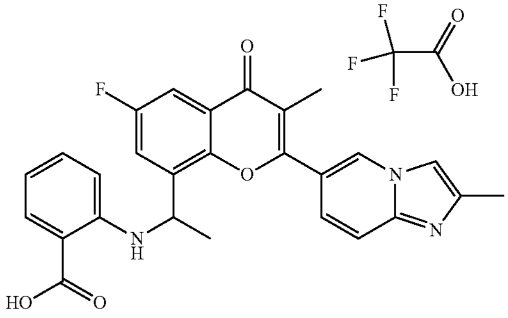 | 472 $[M + H]^+$ |

TABLE 44-continued

| Ex # | Chemical Name | Structure | MS ES+ m/z |
|---|---|---|---|
| 57 | 2-[1-[6-Fluoro-3-methyl-2-(2-methylindazol-5-yl)-4-oxo-chromen-8-yl]ethylamino]benzoic acid, Isomer 2; 2,2,2-trifluoroacetic acid | 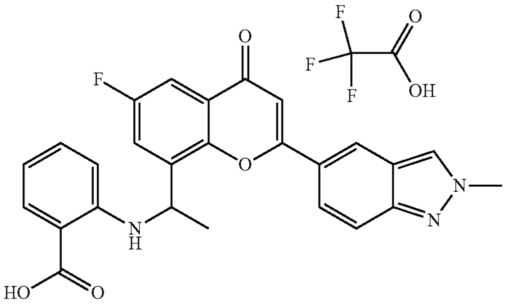 | 472 [M + H]+ |
| 58 | 2-[1-[6-Methyl-4-oxo-2-(triazolo[1,5-a]pyridin-5-yl)chromen-8-yl]ethylamino]benzoic acid, Isomer 2; 2,2,2-trifluoroacetic acid | 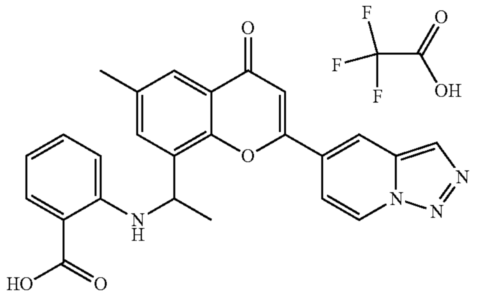 | 441 [M + H]+ |
| 59 | 2-[1-[2-(1,3-Dimethylindazol-5-yl)-6-methyl-4-oxo-chromen-8-yl]ethylamino]benzoic acid, Isomer 2; 2,2,2-trifluoroacetic acid | 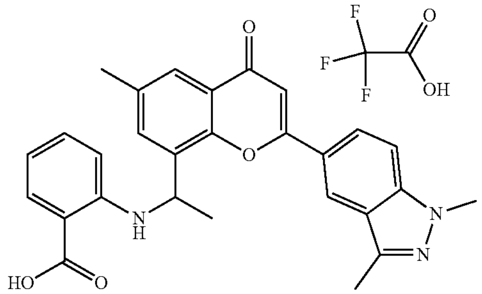 | 468 [M + H]+ |
| 60 | 2-[1-[2-(1H-Indazol-5-yl)-6-methyl-4-oxo-chromen-8-yl]ethylamino]benzoic acid, Isomer 2; 2,2,2-trifluoroacetic acid | 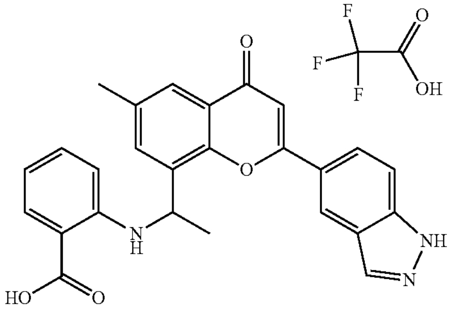 | 496 [M + H]+ |
| 61 | 2-[1-[6-Methyl-2-(3-methyl-1H-indazol-5-yl)-4-oxo-chromen-8-yl]ethylamino]benzoic acid, Isomer 2; 2,2,2-trifluoroacetic acid | 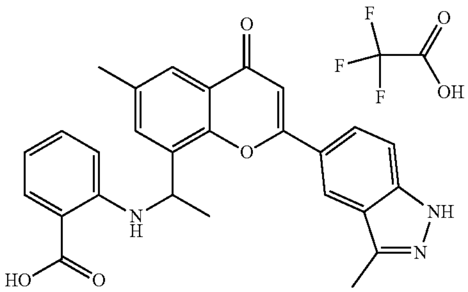 | 454 [M + H]+ |

TABLE 44-continued

| Ex # | Chemical Name | Structure | MS ES+ m/z |
|---|---|---|---|
| 62 | 2-[1-[6-Methyl-2-(1-methyl-2-oxo-indolin-5-yl)-4-oxo-chromen-8-yl]ethylamino]benzoic acid, Isomer 2; 2,2,2-trifluoroacetic acid | 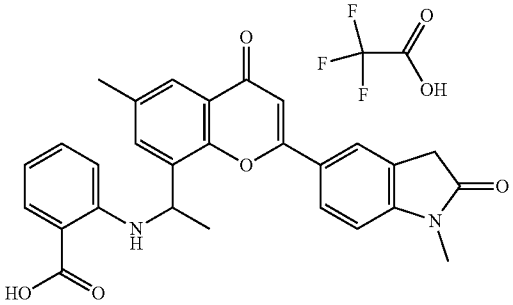 | 469 [M + H]+ |
| 63 | 2-[1-[2-(1H-Indazol-6-yl)-6-methyl-4-oxo-chromen-8-yl]ethylamino]benzoic acid, Isomer 2; 2,2,2-trifluoroacetic acid | 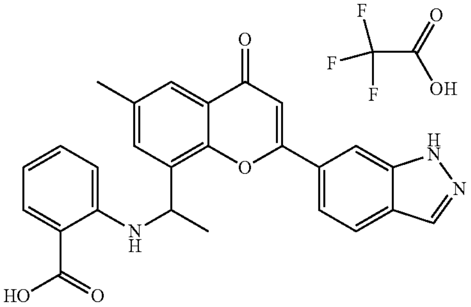 | 440 [M + H]+ |
| 64 | 2-[1-[2-(2,2-Difluoro-1,3-benzodioxol-5-yl)-6-methyl-4-oxo-chromen-8-yl]ethylamino]benzoic acid, Isomer 2; 2,2,2-trifluoroacetic acid | 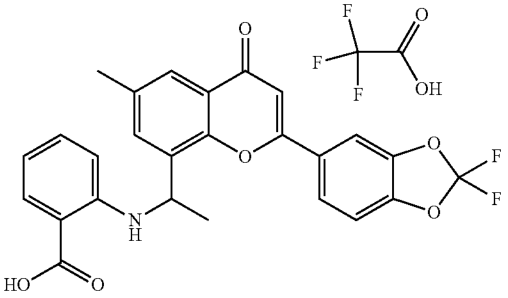 | 480 [M + H]+ |
| 65 | 2-[1-[6-Methyl-2-(2-methyl-1H-benzimidazol-5-yl)-4-oxo-chromen-8-yl]ethylamino]benzoic acid, Isomer 2; 2,2,2-trifluoroacetic acid | 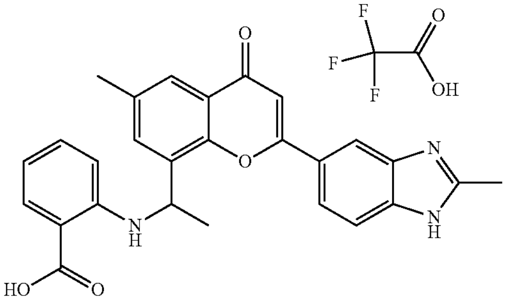 | 454 [M + H]+ |
| 66 | 2-[1-(2-Imidazo[1,2-a]pyridin-2-yl-6-methyl-4-oxo-chromen-8-yl)ethylamino]benzoic acid, Isomer 2; 2,2,2-trifluoroacetic acid | 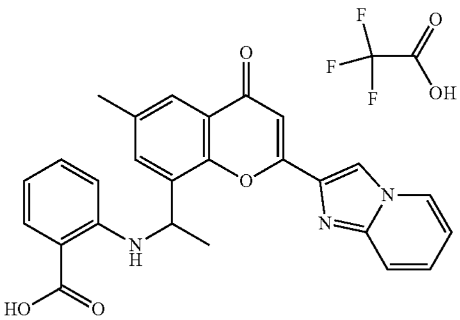 [SMILES: Cc1cc(C(C)Nc2ccccc2C(=O)O)c2oc(-c3cn4ccccc4n3)cc(=O)c2c1 ; O=C(O)C(F)(F)F] | 440 [M + H]+ |

TABLE 44-continued

| Ex # | Chemical Name | Structure | MS ES+ m/z |
|---|---|---|---|
| 67 | 2-[1-(6-Methyl-4-oxo-2-pyrazolo[1,5-a]pyridin-6-yl-chromen-8-yl)ethylamino]benzoic acid, Isomer 2; 2,2,2-trifluoroacetic acid | 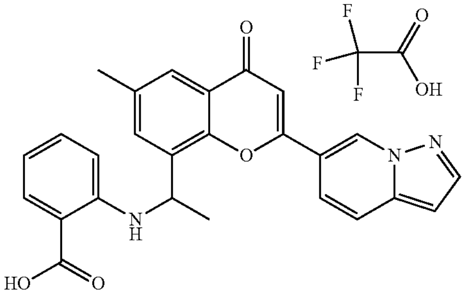 | 440 [M + H]+ |
| 68 | 2-[1-[2-(1H-Indol-2-yl)-6-methyl-4-oxo-chromen-8-yl]ethylamino]benzoic acid, Isomer 2; 2,2,2-trifluoroacetic acid | 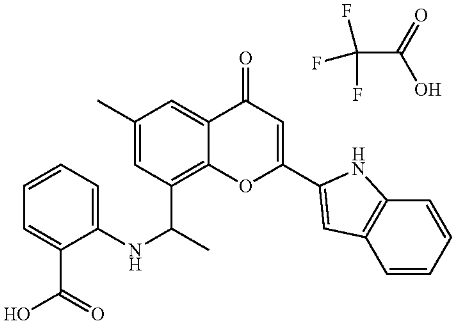 [SMILES: Cc1cc(C(C)Nc2ccccc2C(=O)O)c2oc(-c3cc4ccccc4[nH]3)cc(=O)c2c1 ; O=C(O)C(F)(F)F] | 439 [M + H]+ |
| 69 | 2-[1-[6-Methyl-2-(2-methylimidazo[1,2-b]pyridazin-6-yl)-4-oxo-chromen-8-yl]ethylamino]benzoic acid, Isomer 2 | 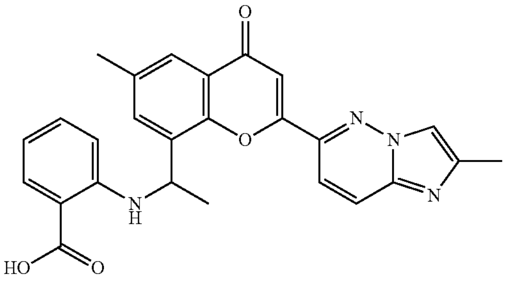 [SMILES: Cc1cc(C(C)Nc2ccccc2C(=O)O)c2oc(-c3ccc4nc(C)cn4n3)cc(=O)c2c1] | 455 [M + H]+ |
| 70 | 2-[1-[6-Methyl-4-oxo-2-[2-(trifluoromethyl)imidazo[1,2-a]pyridin-6-yl]chromen-8-yl]ethylamino]benzoic acid, Isomer 2; 2,2,2-trifluoroacetic acid | 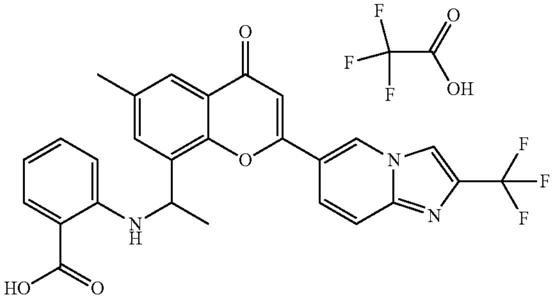 | 508 [M + H]+ |
| 71 | 2-[1-[6-Methyl-4-oxo-2-(1H-pyrrolo[3,2-b]pyridin-6-yl)chromen-8-yl]ethylamino]benzoic acid, Isomer 2; 2,2,2-trifluoroacetic acid | 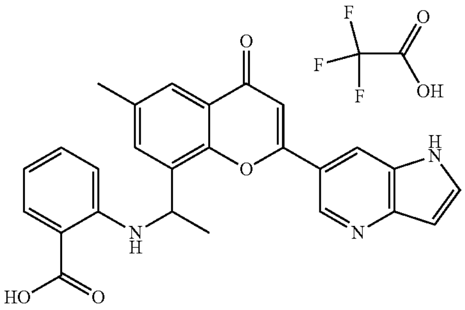 | 440 [M + H]+ |

TABLE 44-continued

| Ex # | Chemical Name | Structure | MS ES+ m/z |
|---|---|---|---|
| 72 | 2-[1-[6-Methyl-2-(6-methyl-7H-pyrrolo[2,3-d]pyrimidin-2-yl)-4-oxo-chromen-8-yl]ethylamino]benzoic acid, Isomer 2; 2,2,2-trifluoroacetic acid | 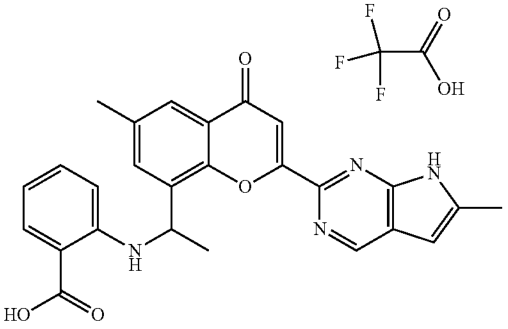 [SMILES: Cc1cc(C(C)Nc2ccccc2C(=O)O)c2oc(-c3ncc4cc(C)[nH]c4n3)cc(=O)c2c1 ; O=C(O)C(F)(F)F] | 455 $[M + H]^+$ |
| 73 | 2-[1-(2-Imidazo[1,2-a]pyridin-6-yl-6-methyl-4-oxo-chromen-8-yl)ethylamino]benzoic acid, Isomer 2; 2,2,2-trifluoroacetic acid | 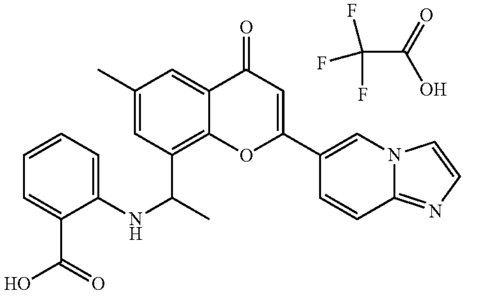 | 440 $[M + H]^+$ |
| 74 | 2-[1-[6-Methyl-2-(2-methyl-1,3-benzothiazol-6-yl)-4-oxo-chromen-8-yl]ethylamino]benzoic acid, Isomer 2; 2,2,2-trifluoroacetic acid | 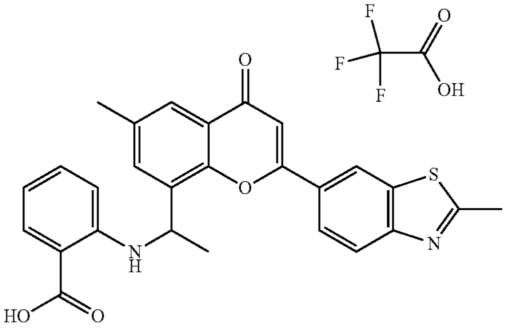 [SMILES: Cc1cc(C(C)Nc2ccccc2C(=O)O)c2oc(-c3ccc4nc(C)sc4c3)cc(=O)c2c1 ; O=C(O)C(F)(F)F] | 471 $[M + H]^+$ |
| 75 | 2-[1-[6-Methyl-2-(2-methylindazol-5-yl)-4-oxo-chromen-8-yl]ethylamino]benzoic acid, Isomer 2 | 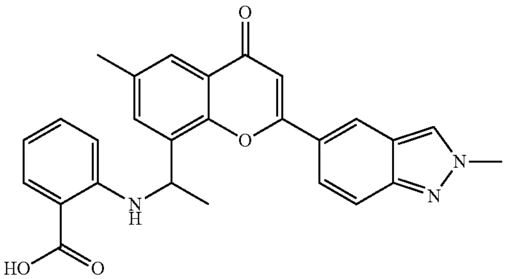 [SMILES: Cc1cc(C(C)Nc2ccccc2C(=O)O)c2oc(-c3ccc4nn(C)cc4c3)cc(=O)c2c1] | 454 $[M + H]^+$ |
| 76 | 2-[1-[6-Methyl-4-oxo-2-([1,2,4]triazolo[4,3-a]pyridin-6-yl)chromen-8-yl]ethylamino]benzoic acid, Isomer 2 | 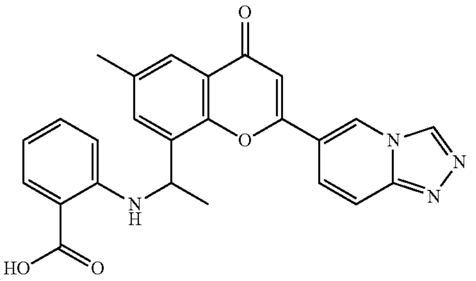 [SMILES: Cc1cc(C(C)Nc2ccccc2C(=O)O)c2oc(-c3ccc4nncn4c3)cc(=O)c2c1] | 441 $[M + H]^+$ |

TABLE 44-continued

| Ex # | Chemical Name | Structure | MS ES+ m/z |
|---|---|---|---|
| 77 | 2-[1-[6-Methyl-2-(3-methyl-[1,2,4]triazolo[4,3-a]pyridin-7-yl)-4-oxo-chromen-8-yl]ethylamino]benzoic acid, Isomer 2 | 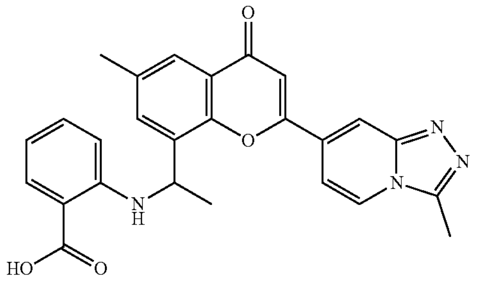 [SMILES: Cc1cc(C(C)Nc2ccccc2C(=O)O)c2oc(-c3ccn4c(C)nnc4c3)cc(=O)c2c1] | 455 [M + H]+ |
| 78 | 2-[1-[2-(3-Isopropyl-[1,2,4]triazolo[4,3-a]pyridin-6-yl)-6-methyl-4-oxo-chromen-8-yl]ethylamino]benzoic acid, Isomer 2 | 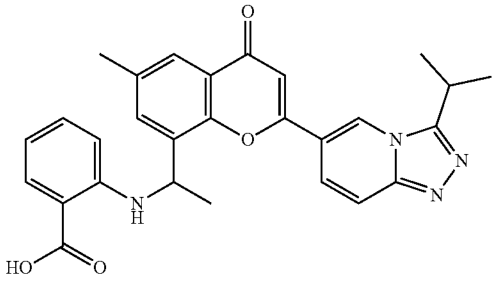 [SMILES: Cc1cc(C(C)Nc2ccccc2C(=O)O)c2oc(-c3ccc4nnc(C(C)C)n4c3)cc(=O)c2c1] | 483 [M + H]+ |
| 79 | 2-[1-(2-Imidazo[1,5-a]pyridin-6-yl-6-methyl-4-oxo-chromen-8-yl)ethylamino]benzoic acid, Isomer 2 | 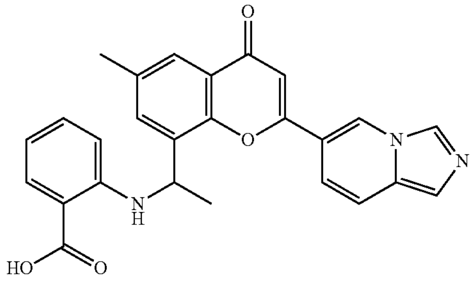 [SMILES: Cc1cc(C(C)Nc2ccccc2C(=O)O)c2oc(-c3ccc4cncn4c3)cc(=O)c2c1] | 440 [M + H]+ |
| 80 | 2-[1-(2-Imidazo[1,2-a]pyridin-7-yl-6-methyl-4-oxo-chromen-8-yl)ethylamino]benzoic acid, Isomer 2 | 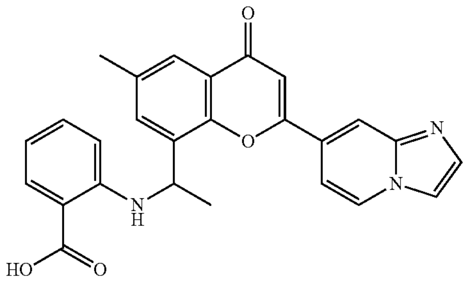 [SMILES: Cc1cc(C(C)Nc2ccccc2C(=O)O)c2oc(-c3ccn4ccnc4c3)cc(=O)c2c1] | 440 [M + H]+ |
| 81 | 2-[1-[6-Methyl-2-(2-methylthiazolo[5,4-b]pyridin-6-yl)-4-oxo-chromen-8-yl]ethylamino]benzoic acid, Isomer 2 | 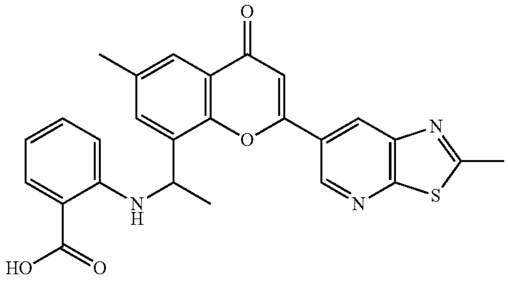 [SMILES: Cc1cc(C(C)Nc2ccccc2C(=O)O)c2oc(-c3cnc4sc(C)nc4c3)cc(=O)c2c1] | 472 [M + H]+ |

TABLE 44-continued

| Ex # | Chemical Name | Structure | MS ES+ m/z |
|---|---|---|---|
| 82 | 2-[1-[6-Methyl-2-(1-methylpyrazolo[3,4-b]pyridin-6-yl)-4-oxo-chromen-8-yl]ethylamino]benzoic acid, Isomer 2 | 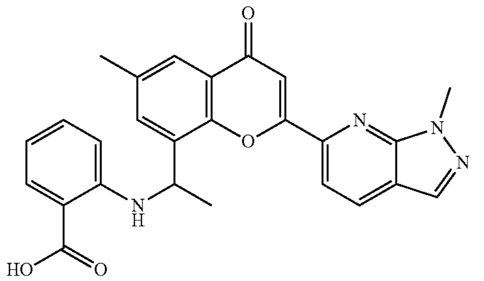 | 455 [M + H]+ |
| 94 | 2,3-Difluoro-6-[1-[6-methyl-2-(2-methylimidazo[1,2-b]pyridazin-6-yl)-4-oxo-chromen-8-yl]ethylamino]benzoic acid; 2,2,2-trifluoroacetic acid | 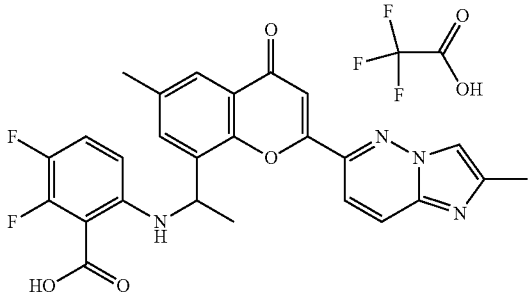 | 491 [M + H]+ |
| 95 | 2-[1-[2-(7-Chloro-2-methyl-indazol-5-yl)-6-methyl-4-oxo-chromen-8-yl]ethylamino]benzoic acid, Isomer 2; 2,2,2-trifluoroacetic acid | 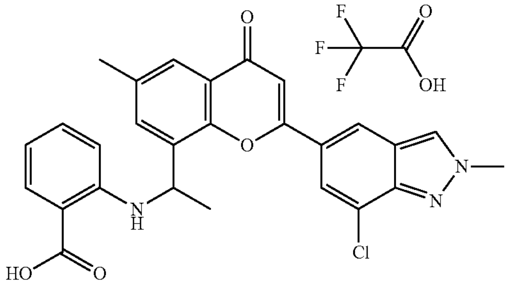 | 488 [M + H]+ |
| 96 | 2-[1-[6-Methyl-2-(1-methylpyrazolo[3,4-c]pyridin-7-yl)-4-oxo-chromen-8-yl]ethylamino]benzoic acid, Isomer 2; 2,2,2-trifluoroacetic acid | 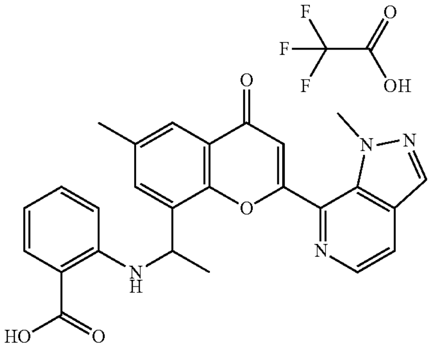 | 455 [M + H]+ |
| 97 | 2-[1-[2-(7-Fluoro-2-methyl-indazol-5-yl)-6-methyl-4-oxo-chromen-8-yl]ethylamino]benzoic acid, Isomer 2; 2,2,2-trifluoroacetic acid | 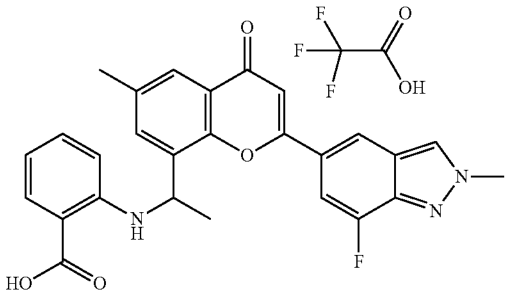 | 472 [M + H]+ |

TABLE 44-continued

| Ex # | Chemical Name | Structure | MS ES+ m/z |
|---|---|---|---|
| 98 | 2-[1-[6-Methyl-2-(2-methylpyrazolo[3,4-c]pyridin-7-yl)-4-oxo-chromen-8-yl]ethylamino]benzoic acid, Isomer 2; 2,2,2-trifluoroacetic acid | 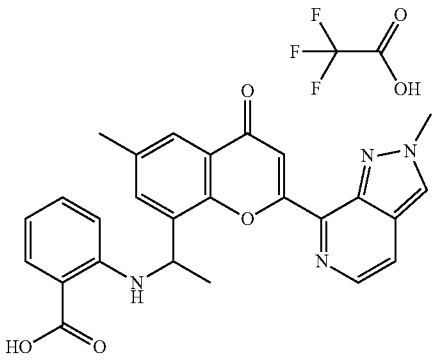 | 455 [M + H]+ |
| 99 | 3-[1-[2-(1H-Indol-2-yl)-6-methyl-4-oxo-chromen-8-yl]ethylamino]-6-methyl-pyridine-2-carboxylic acid; 2,2,2-trifluoroacetic acid | 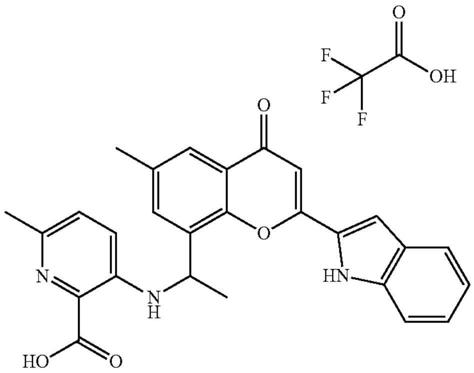 [SMILES: Cc1cc(C(C)Nc2ccc(C)nc2C(=O)O)c2oc(-c3cc4ccccc4[nH]3)cc(=O)c2c1 ; O=C(O)C(F)(F)F] | 454 [M + H]+ |
| 100 | 6-Chloro-3-[1-[2-(1H-indol-2-yl)-4-oxo-6-(trifluoromethyl)chromen-8-yl]ethylamino]pyridine-2-carboxylic acid, Isomer 2 | 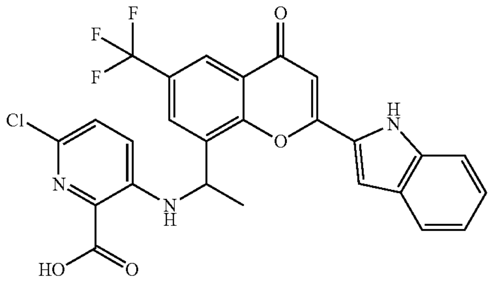 [SMILES: CC(Nc1ccc(Cl)nc1C(=O)O)c1cc(C(F)(F)F)cc2c(=O)cc(-c3cc4ccccc4[nH]3)oc12] | 528 [M + H]+ |
| 101[a] | 2-[1-[2-(2-Methylimidazo[1,2-b]pyridazin-6-yl)-4-oxo-6-(trifluoromethyl)chromen-8-yl]ethylamino]benzoic acid, Isomer 2 | 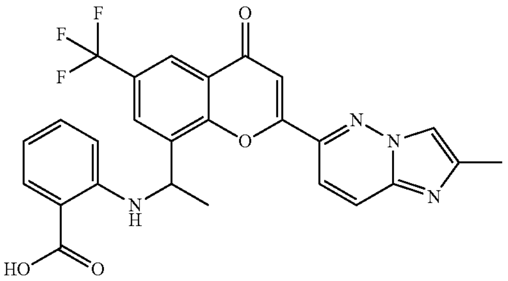 [SMILES: Cc1cn2nc(-c3cc(=O)c4cc(C(F)(F)F)cc(C(C)Nc5ccccc5C(=O)O)c4o3)ccc2n1] | 509 [M + H]+ |
| 102[a] | 6-Chloro-3-[1-[2-(2-methylimidazo[1,2-b]pyridazin-6-yl)-4-oxo-6-(trifluoromethyl)chromen-8-yl]ethylamino]pyridine-2-carboxylic acid, Isomer 2 | 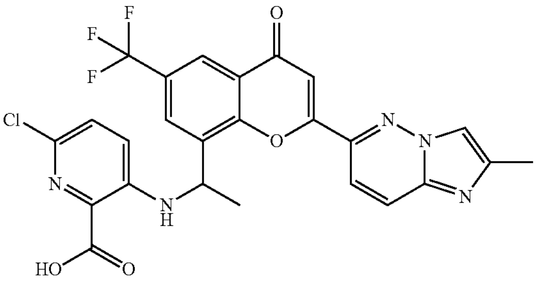 [SMILES: Cc1cn2nc(-c3cc(=O)c4cc(C(F)(F)F)cc(C(C)Nc5ccc(Cl)nc5C(=O)O)c4o3)ccc2n1] | 544 [M + H]+ |

TABLE 44-continued

| Ex # | Chemical Name | Structure | MS ES+ m/z |
|---|---|---|---|
| 103 | 2-Fluoro-6-[1-[6-methyl-2-(2-methylindazol-5-yl)-4-oxo-chromen-8-yl]ethylamino]benzoic acid; 2,2,2-trifluoroacetic acid | 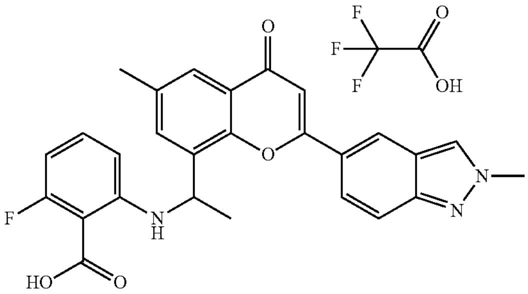 | 472 $[M + H]^+$ |
| 104 | 2-[1-[2-(3-Cyano-1-methyl-indazol-6-yl)-6-methyl-4-oxo-chromen-8-yl]ethylamino]benzoic acid, Isomer 2; 2,2,2-trifluoroacetic acid | 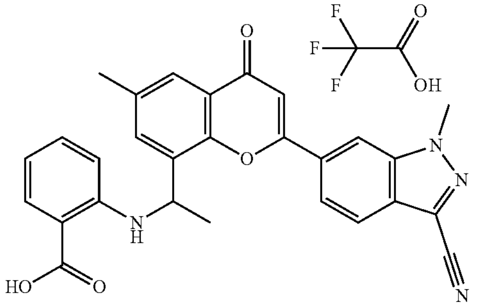 | 479 $[M + H]^+$ |
| 105 | 2-[1-(6-Methyl-4-oxo-2-pyrrolo[1,2-a]pyrazin-1-yl-chromen-8-yl)ethylamino]benzoic acid, Isomer 2; 2,2,2-trifluoroacetic acid | 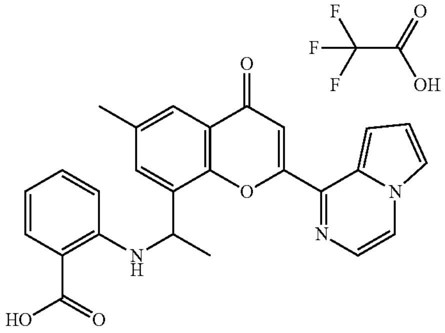 | 440 $[M + H]^+$ |
| 106 | 2-[1-(6-Methyl-4-oxo-2-pyrazolo[1,5-a]pyridin-4-yl-chromen-8-yl)ethylamino]benzoic acid, Isomer 2; 2,2,2-trifluoroacetic acid | 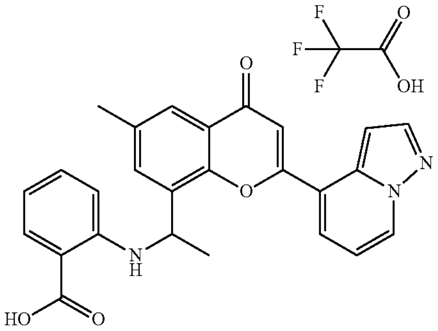 | 440 $[M + H]^+$ |

TABLE 44-continued

| Ex # | Chemical Name | Structure | MS ES+ m/z |
|---|---|---|---|
| 107 | 2-[1-[6-Methyl-2-(2-methylimidazo[1,2-b]pyridazin-6-yl)-4-oxo-chromen-8-yl]ethylamino]benzoic acid, Isomer 2; 2,2,2-trifluoroacetic acid | 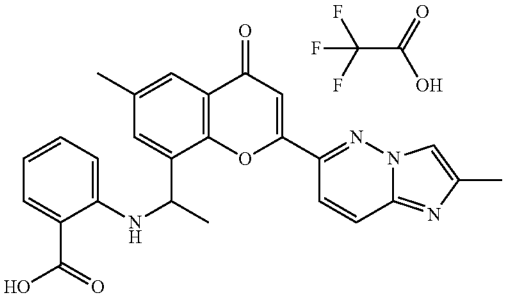 | 455 [M + H]+ |
| 108[a] | 6-Chloro-3-[1-[2-(1-methylindazol-6-yl)-4-oxo-6-(trifluoromethyl)chromen-8-yl]ethylamino]pyridine-2-carboxylic acid, Isomer 2 | 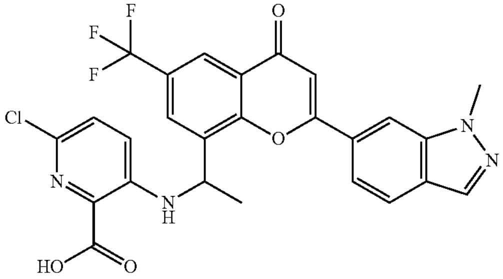 [SMILES: CC(Nc1ccc(Cl)nc1C(=O)O)c1cc(C(F)(F)F)cc2c(=O)cc(-c3ccc4cnn(C)c4c3)oc12] | 543 [M + H]+ |
| 109 | 2-[1-[2-(1-Methylindazol-5-yl)-4-oxo-6-(trifluoromethyl)chromen-8-yl]ethylamino]benzoic acid, Isomer 2 | 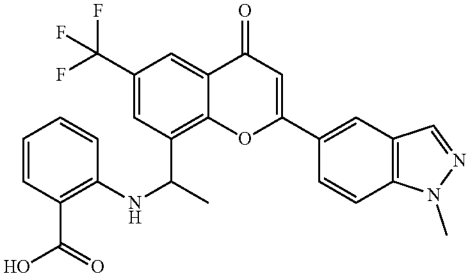 [SMILES: CC(Nc1ccccc1C(=O)O)c1cc(C(F)(F)F)cc2c(=O)cc(-c3ccc4c(cnn4C)c3)oc12] | 508 [M + H]+ |
| 110 | 2-[1-[2-(1,3-Benzoxazol-4-yl)-6-methyl-4-oxo-chromen-8-yl]ethylamino]benzoic acid, Isomer 2; 2,2,2-trifluoroacetic acid | 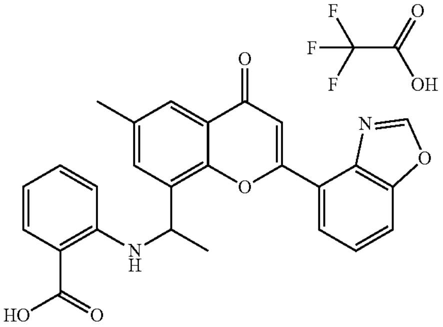 | 441 [M + H]+ |
| 111 | 2-[1-[6-Methyl-2-(2-methylindazol-4-yl)-4-oxo-chromen-8-yl]ethylamino]benzoic acid, Isomer 2; 2,2,2-trifluoroacetic acid | 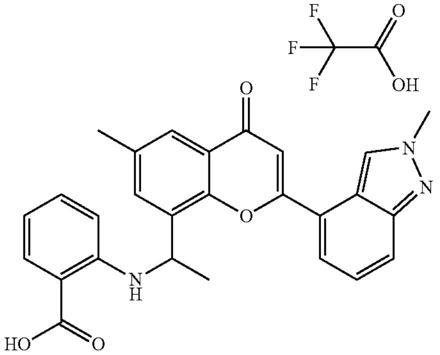 | 454 [M + H]+ |

TABLE 44-continued

| Ex # | Chemical Name | Structure | MS ES+ m/z |
|---|---|---|---|
| 112 | 2-[1-[6-Methyl-2-[2-methyl-3-(3-pyridyl)imidazo[1,2-a]pyridin-7-yl]-4-oxo-chromen-8-yl]ethylamino]benzoic acid, Isomer 2 | 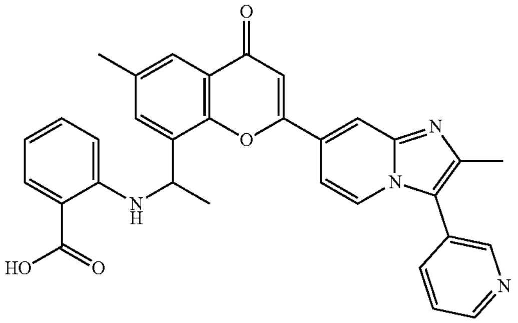 [SMILES: Cc1cc(C(C)Nc2ccccc2C(=O)O)c2oc(-c3ccn4c(-c5cccnc5)c(C)nc4c3)cc(=O)c2c1] | 531 [M + H]+ |
| 113 | 2-[1-(6-Methyl-4-oxo-2-pyrazolo[1,5-a]pyridin-5-yl-chromen-8-yl)ethylamino]benzoic acid, Isomer 2 | 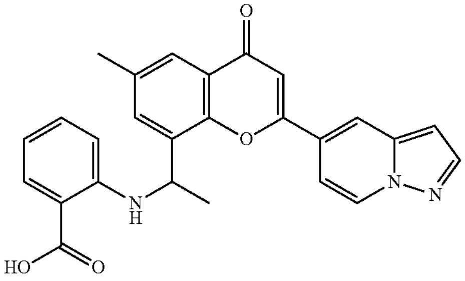 [SMILES: Cc1cc(C(C)Nc2ccccc2C(=O)O)c2oc(-c3ccn4nccc4c3)cc(=O)c2c1] | 440 [M + H]+ |
| 114 | 2-[1-(6-Methyl-4-oxo-2-quinazolin-7-yl-chromen-8-yl)ethylamino]benzoic acid, Isomer 2 | 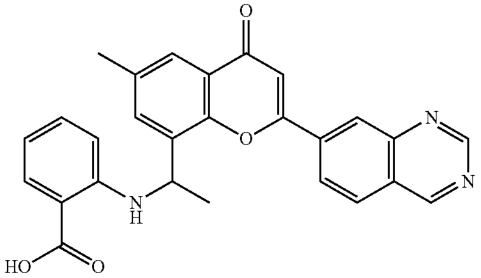 [SMILES: Cc1cc(C(C)Nc2ccccc2C(=O)O)c2oc(-c3ccc4cncnc4c3)cc(=O)c2c1] | 452 [M + H]+ |
| 115 | 2-[1-[6-Methyl-4-oxo-2-(2-oxoindolin-6-yl)chromen-8-yl]ethylamino]benzoic acid, Isomer 2; 2,2,2-trifluoroacetic acid | 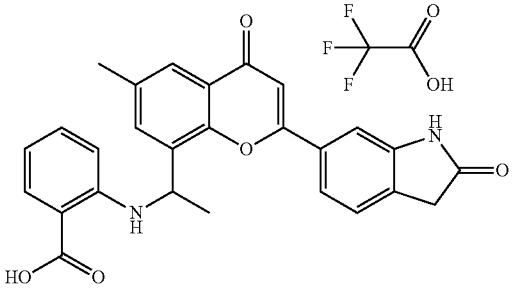 | 455 [M + H]+ |
| 116 | 2-[1-[6-Methyl-2-(2-methylindazol-7-yl)-4-oxo-chromen-8-yl]ethylamino]benzoic acid, Isomer 2; 2,2,2-trifluoroacetic acid | 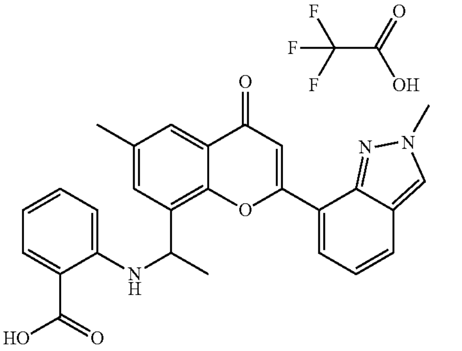 | 454 [M + H]+ |

TABLE 44-continued

| Ex # | Chemical Name | Structure | MS ES+ m/z |
|---|---|---|---|
| 117 | 2-[1-[6-Methyl-2-(2-methyl-1,3-benzoxazol-4-yl)-4-oxo-chromen-8-yl]ethylamino]benzoic acid, Isomer 2; 2,2,2-trifluoroacetic acid | 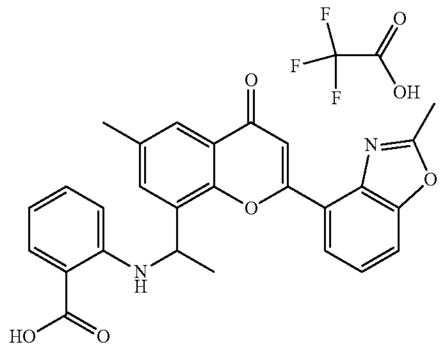 | 455 [M + H]+ |
| 118 | 2-[1-[3-Cyano-6-methyl-2-(2-methylimidazo[1,2-a]pyridin-6-yl)-4-oxo-chromen-8-yl]ethylamino]benzoic acid, Isomer 2; 2,2,2-trifluoroacetic acid | 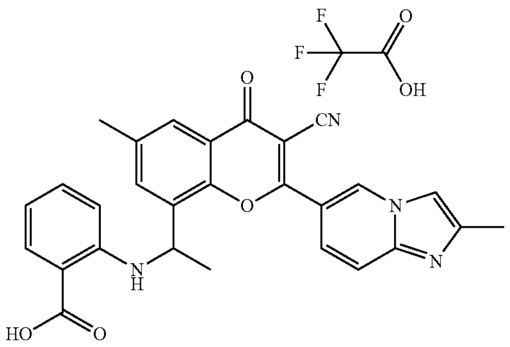 | 479 [M + H]+ |
| 119 | 2-[1-[6-Methyl-2-(2-methylindazol-3-yl)-4-oxo-chromen-8-yl]ethylamino]benzoic acid, Isomer 2; 2,2,2-trifluoroacetic acid | 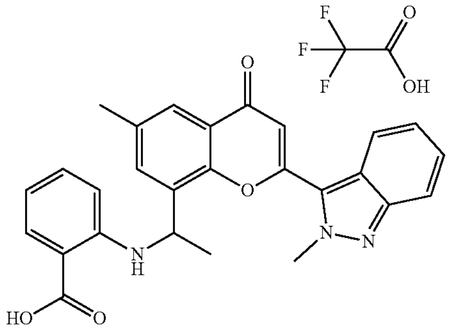 | 454 [M + H]+ |
| 120 | 2-[1-[2-(1H-Indazol-6-yl)-3,6-dimethyl-4-oxo-chromen-8-yl]ethylamino]benzoic acid, Isomer 2; 2,2,2-trifluoroacetic acid | 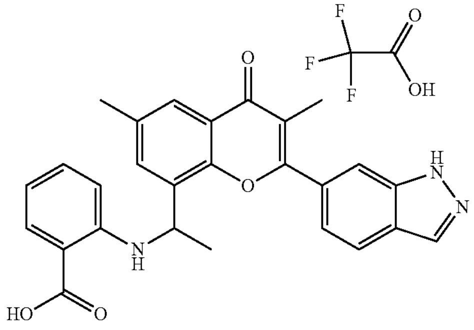 | 454 [M + H]+ |

TABLE 44-continued

| Ex # | Chemical Name | Structure | MS ES+ m/z |
|---|---|---|---|
| 121 | 2-[1-[6-Methyl-4-oxo-2-(1H-pyrazolo[3,4-b]pyridin-6-yl)chromen-8-yl]ethylamino]benzoic acid, Isomer 2 | 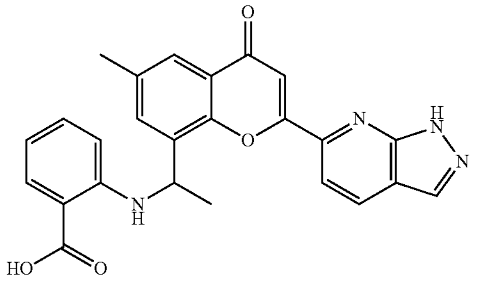 | 441 [M + H]+ |
| 122 | 2-[1-[2-[2-(2-Hydroxy-2-methyl-propyl)indazol-5-yl]-6-methyl-4-oxo-chromen-8-yl]ethylamino]benzoic acid, Isomer 2 | 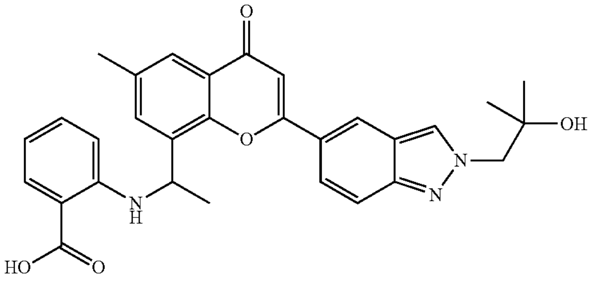 [SMILES: Cc1cc(C(C)Nc2ccccc2C(=O)O)c2oc(-c3ccc4nn(CC(C)(C)O)cc4c3)cc(=O)c2c1] | 512 [M + H]+ |
| 123 | 2-[1-[2-[1-(2-Hydroxy-2-methyl-propyl)indazol-5-yl]-6-methyl-4-oxo-chromen-8-yl]ethylamino]benzoic acid, Isomer 2 | 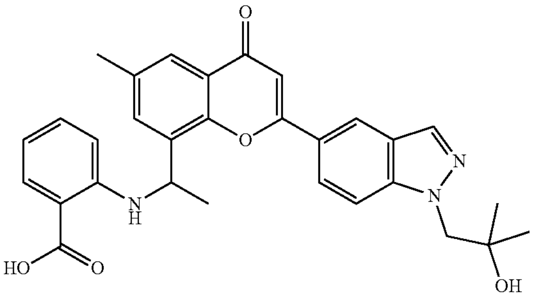 [SMILES: Cc1cc(C(C)Nc2ccccc2C(=O)O)c2oc(-c3ccc4c(cnn4CC(C)(C)O)c3)cc(=O)c2c1] | 512 [M + H]+ |
| 124 | 2-[1-[6-Fluoro-3-methyl-2-(2-methylimidazo[1,2-a]pyridin-6-yl)-4-oxo-chromen-8-yl]ethylamino]benzoic acid, Isomer 2; 2,2,2-trifluoroacetic acid | 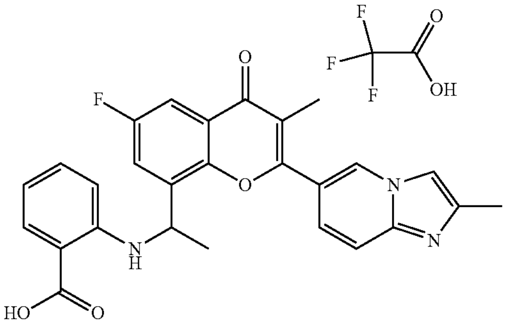 | 472 [M + H]+ |
| 125 | 2-[1-(6-Methyl-4-oxo-2-pyrazolo[1,5-a]pyridin-3-yl-chromen-8-yl)ethylamino]benzoic acid, Isomer 2; 2,2,2-trifluoroacetic acid | 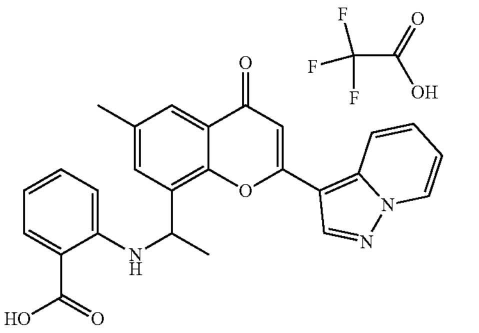 | 440 [M + H]+ |

TABLE 44-continued

| Ex # | Chemical Name | Structure | MS ES+ m/z |
|---|---|---|---|
| 126 | 2-[1-[2-(2,7-Dimethylindazol-5-yl)-6-methyl-4-oxo-chromen-8-yl]ethylamino]benzoic acid, Isomer 2; 2,2,2-trifluoroacetic acid | 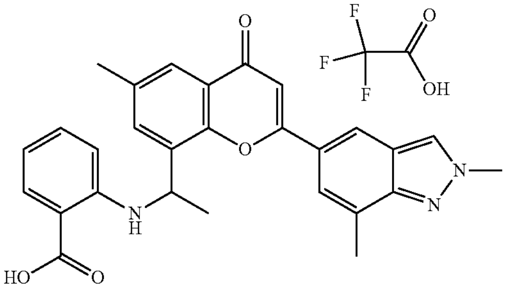 | 468 [M + H]+ |
| 127 | 2-[1-(2-Imidazo[1,2-a]pyridin-8-yl-6-methyl-4-oxo-chromen-8-yl)ethylamino]benzoic acid, Isomer 2; 2,2,2-trifluoroacetic acid | 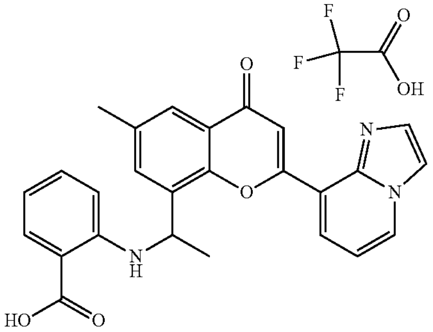 | 440 [M + H]+ |
| 128 | 2-[1-[6-Fluoro-2-(1H-indol-2-yl)-4-oxo-chromen-8-yl]ethylamino]benzoic acid, Isomer 2; 2,2,2-trifluoroacetic acid | 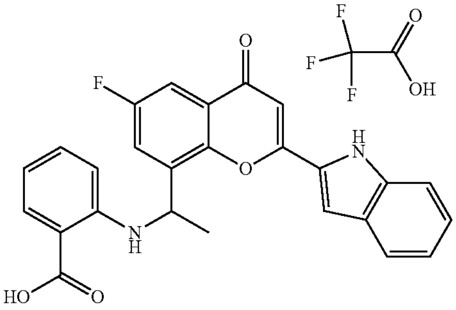 | 443 [M + H]+ |
| 129 | 2-[1-[6-Fluoro-2-(1H-indol-2-yl)-3-methyl-4-oxo-chromen-8-yl]ethylamino]benzoic acid, Isomer 2; 2,2,2-trifluoroacetic acid | 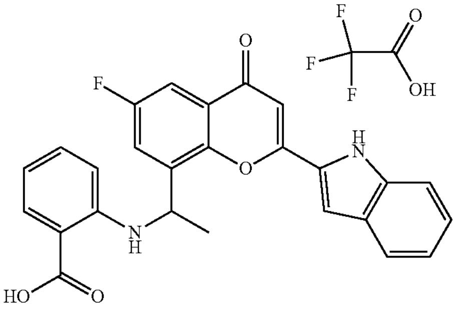 | 457 [M + H]+ |
| 130 | 2-[1-[3,6-Dimethyl-2-(2-methylpyrazolo[4,3-b]pyridin-5-yl)-4-oxo-chromen-8-yl]ethylamino]benzoic acid, Isomer 2; 2,2,2-trifluoroacetic acid | 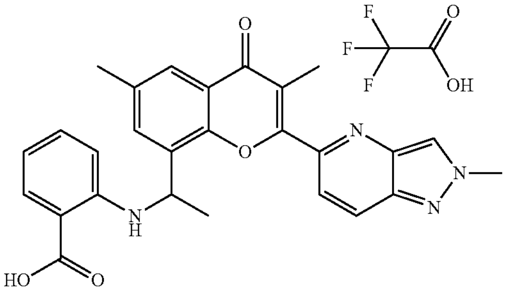 | 469 [M + H]+ |

TABLE 44-continued

| Ex # | Chemical Name | Structure | MS ES+ m/z |
|---|---|---|---|
| 131 | 2-[1-[3,6-Dimethyl-2-(1-methylpyrazolo[4,3-b]pyridin-5-yl)-4-oxo-chromen-8-yl]ethylamino]benzoic acid, Isomer 2; 2,2,2-trifluoroacetic acid | 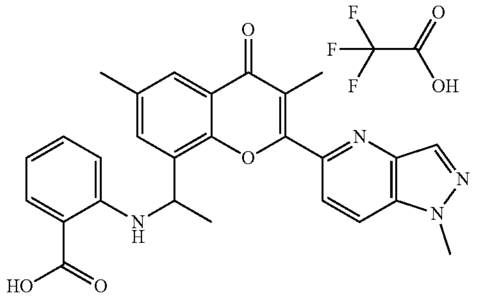 | 469 [M + H]+ |
| 132 | 2-[1-[2-(1H-Indazol-5-yl)-3,6-dimethyl-4-oxo-chromen-8-yl]ethylamino]benzoic acid, Isomer 2; 2,2,2-trifluoroacetic acid | 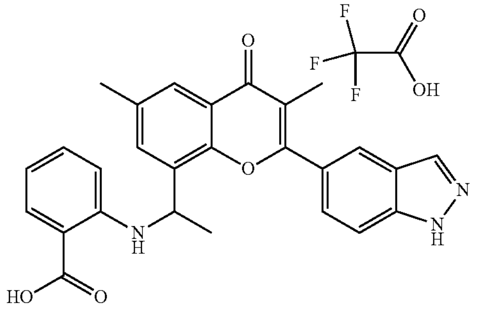 | 454 [M + H]+ |
| 133 | 2-[1-[6-Methyl-2-(2-methyl-3-oxazol-2-yl-imidazo[1,2-a]pyridin-7-yl)-4-oxo-chromen-8-yl]ethylamino]benzoic acid, Isomer 2; 2,2,2-trifluoroacetic acid | 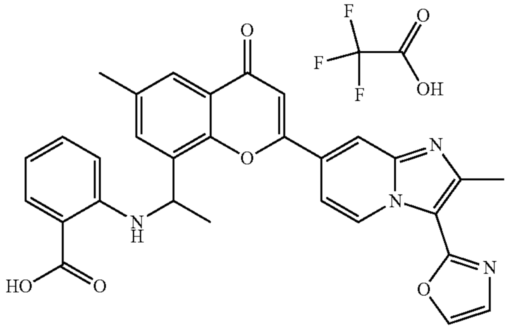 | 521 [M + H]+ |
| 134 | 2-[1-[6-Methyl-2-(2-methylpyrazolo[1,5-a]pyridin-6-yl)-4-oxo-chromen-8-yl]ethylamino]benzoic acid, Isomer 2; 2,2,2-trifluoroacetic acid | 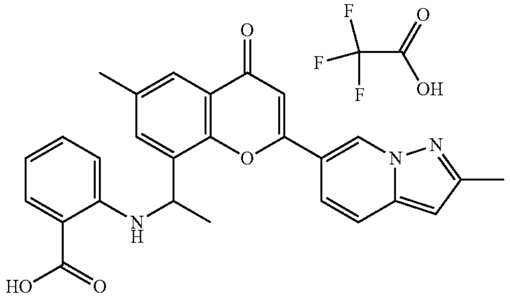 | 454 [M + H]+ |
| 135 | 2-[1-[6-Methyl-2-(2-methylpyrazolo[3,4-b]pyridin-6-yl)-4-oxo-chromen-8-yl]ethylamino]benzoic acid, Isomer 2; 2,2,2-trifluoroacetic acid | 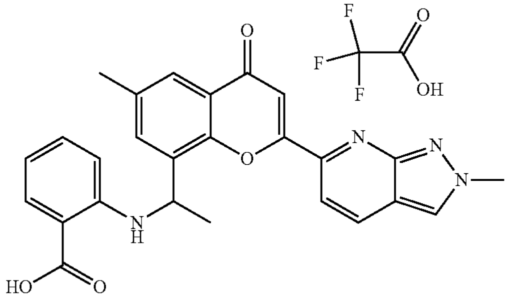 | 455 [M + H]+ |

TABLE 44-continued

| Ex # | Chemical Name | Structure | MS ES+ m/z |
|---|---|---|---|
| 136 | 2-[1-[6-Methyl-2-(1-methylindazol-4-yl)-4-oxo-chromen-8-yl]ethylamino]benzoic acid, Isomer 2; 2,2,2-trifluoroacetic acid | 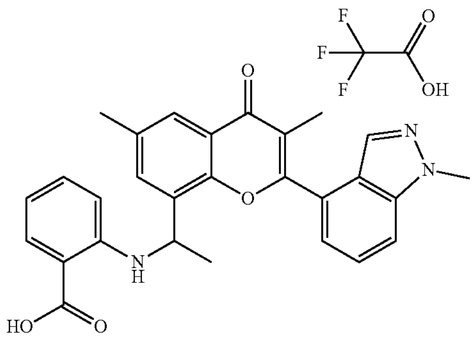 | 454 [M + H]+ |
| 137 | 2-[1-[3,6-Dimethyl-2-(2-methyl-1-oxo-isoindolin-5-yl)-4-oxo-chromen-8-yl]ethylamino]benzoic acid, Isomer 2; 2,2,2-trifluoroacetic acid | 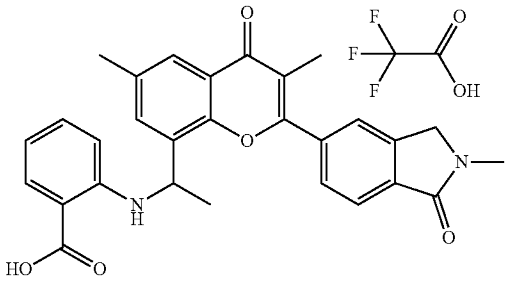 | 483 [M + H]+ |
| 138 | 2-[1-[6-Methyl-2-[1-(oxetan-3-ylmethyl)indazol-5-yl]-4-oxo-chromen-8-yl]ethylamino]benzoic acid, Isomer 2 | 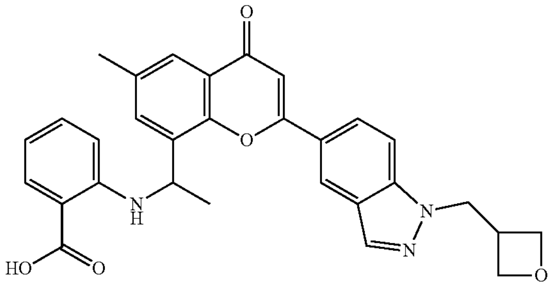 [SMILES: Cc1cc(C(C)Nc2ccccc2C(=O)O)c2oc(-c3ccc4c(cnn4CC4COC4)c3)cc(=O)c2c1] | 510 [M + H]+ |
| 139 | 2-[1-[6-Methyl-2-(2-methylthiazolo[5,4-b]pyridin-5-yl)-4-oxo-chromen-8-yl]ethylamino]benzoic acid, Isomer 2; 2,2,2-trifluoroacetic acid | 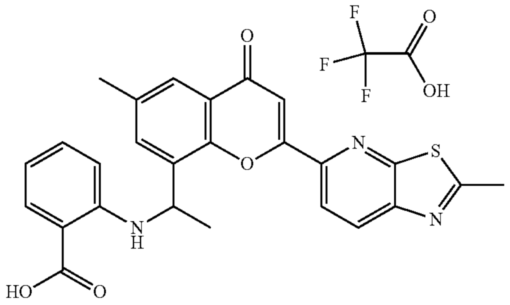 | 472 [M + H]+ |
| 140 | 2-[1-[3,6-Dimethyl-2-(1-methylindol-3-yl)-4-oxo-chromen-8-yl]ethylamino]benzoic acid, Isomer 2; 2,2,2-trifluoroacetic acid | 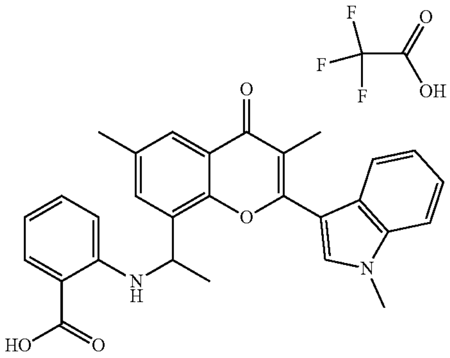 | 467 [M + H]+ |

TABLE 44-continued

| Ex # | Chemical Name | Structure | MS ES+ m/z |
|---|---|---|---|
| 141 | 2-[1-[6-Methyl-2-(1-methyl-2-oxo-3H-pyrrolo[2,3-b]pyridin-6-yl)-4-oxo-chromen-8-yl]ethylamino]benzoic acid, Isomer 2; 2,2,2-trifluoroacetic acid | 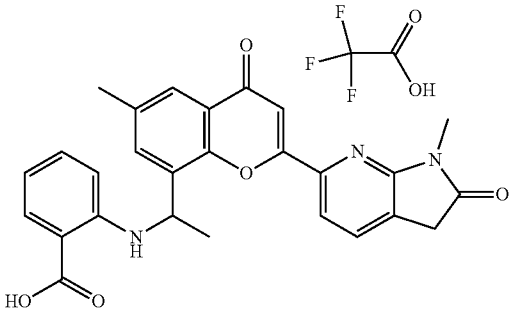 | 470 [M + H]$^+$ |
| 142 | 2-[1-[3,6-Dimethyl-2-(2-methylimidazo[1,2-b]pyridazin-6-yl)-4-oxo-chromen-8-yl]ethylamino]benzoic acid, Isomer 2; 2,2,2-trifluoroacetic acid | 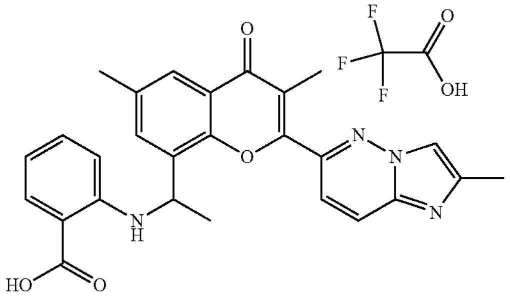 | 469 [M + H]$^+$ |
| 143 | 2-[1-[6-Methyl-2-(1-methylindol-3-yl)-4-oxo-chromen-8-yl]ethylamino]benzoic acid, Isomer 2; 2,2,2-trifluoroacetic acid | 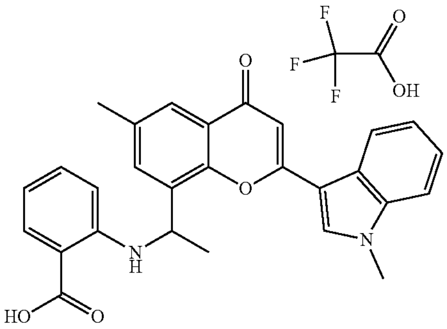 | 453 [M + H]$^+$ |
| 144 | 2-[1-[2-(2,7-Dimethylindazol-5-yl)-6-methyl-4-oxo-chromen-8-yl]ethylamino]benzoic acid, Isomer 2 | 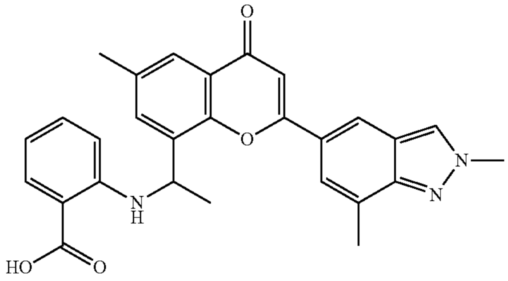 [SMILES: Cc1cc(C(C)Nc2ccccc2C(=O)O)c2oc(-c3cc(C)c4nn(C)cc4c3)cc(=O)c2c1] | 468 [M + H]$^+$ |
| 145 | 2-[1-(2-Imidazo[1,2-a]pyridin-3-yl-6-methyl-4-oxo-chromen-8-yl)ethylamino]benzoic acid, Isomer 2 | 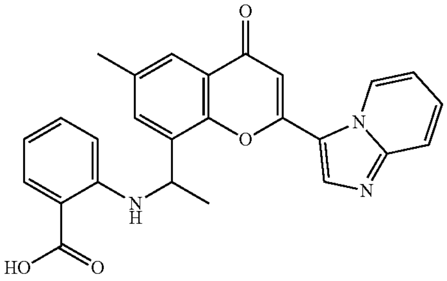 [SMILES: Cc1cc(C(C)Nc2ccccc2C(=O)O)c2oc(-c3cnc4ccccn34)cc(=O)c2c1] | 440 [M + H]$^+$ |

TABLE 44-continued

| Ex # | Chemical Name | Structure | MS ES+ m/z |
|---|---|---|---|
| 146 | 2-[1-[3,6-Dimethyl-2-(1-methylindazol-3-yl)-4-oxo-chromen-8-yl]ethylamino]benzoic acid, Isomer 2; 2,2,2-trifluoroacetic acid | 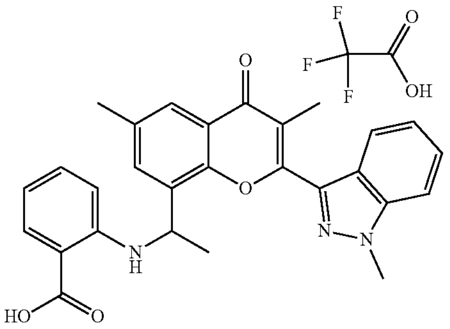 | 468 [M + H]+ |
| 147 | 2-[1-[6-Methyl-4-oxo-2-(1H-pyrrolo[3,2-b]pyridin-2-yl)chromen-8-yl]ethylamino]benzoic acid, Isomer 2; 2,2,2-trifluoroacetic acid | 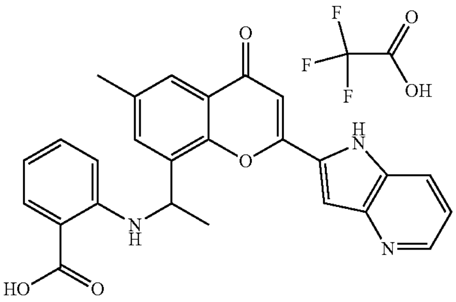 | 440 [M + H]+ |
| 148 | 2-[1-[6-Fluoro-3-methyl-2-(2-methylindazol-5-yl)-4-oxo-chromen-8-yl]ethylamino]benzoic acid, Isomer 2; 2,2,2-trifluoroacetic acid | 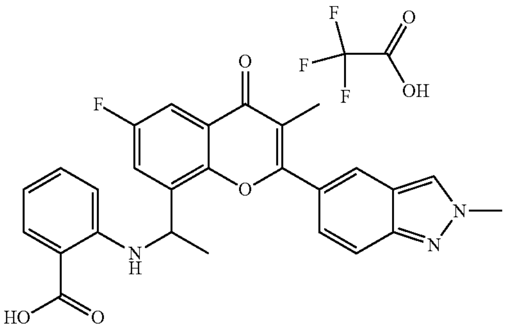 | 472 [M + H]+ |
| 149 | 2-[1-[3,6-Dimethyl-2-(1-methylindazol-6-yl)-4-oxo-chromen-8-yl]ethylamino]benzoic acid, Isomer 2; 2,2,2-trifluoroacetic acid | 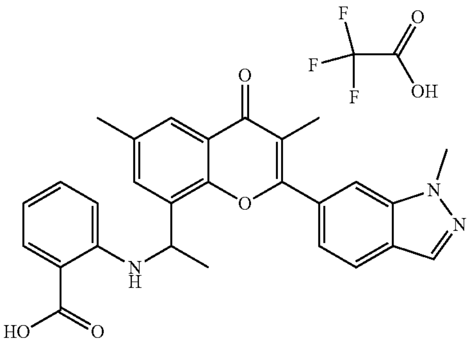 | 468 [M + H]+ |

TABLE 44-continued

| Ex # | Chemical Name | Structure | MS ES+ m/z |
|---|---|---|---|
| 150 | 2-[1-[3,6-Dimethyl-2-(1-methylindazol-5-yl)-4-oxo-chromen-8-yl]ethylamino]benzoic acid, Isomer 2; 2,2,2-trifluoroacetic acid | 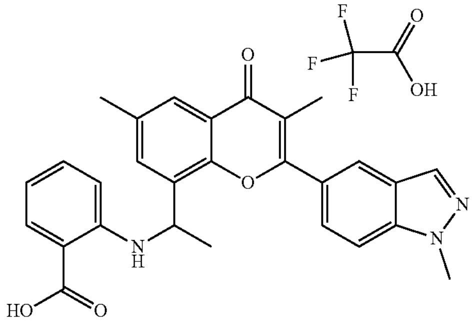 | 468 [M + H]$^+$ |
| 151 | 2-[1-(2-Furo[2,3-c]pyridin-2-yl-3,6-dimethyl-4-oxo-chromen-8-yl)ethylamino]benzoic acid, Isomer 2; 2,2,2-trifluoroacetic acid | 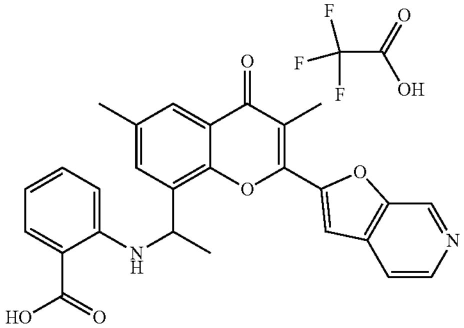 | 455 [M + H]$^+$ |
| 152 | 2-[1-(2-Furo[2,3-c]pyridin-2-yl-6-methyl-4-oxo-chromen-8-yl)ethylamino]benzoic acid; 2,2,2-trifluoroacetic acid | 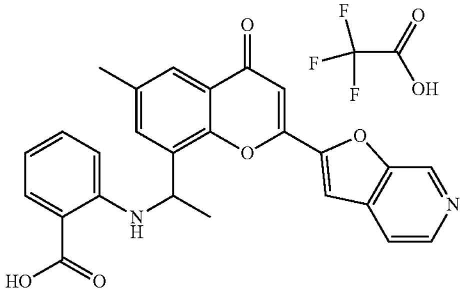 | 441 [M + H]$^+$ |
| 153 | 2-[1-(2-Furo[3,2-c]pyridin-2-yl-3,6-dimethyl-4-oxo-chromen-8-yl)ethylamino]benzoic acid, Isomer 2 | 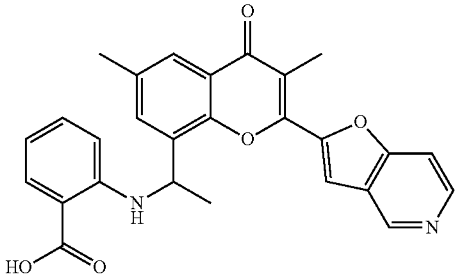 [SMILES: Cc1cc(C(C)Nc2ccccc2C(=O)O)c2oc(-c3cc4cnccc4o3)c(C)c(=O)c2c1] | 455 [M + H]$^+$ |
| 154 | 2-[1-[2-(1H-Indol-3-yl)-3,6-dimethyl-4-oxo-chromen-8-yl]ethylamino]benzoic acid, Isomer 2; 2,2,2-trifluoroacetic acid | 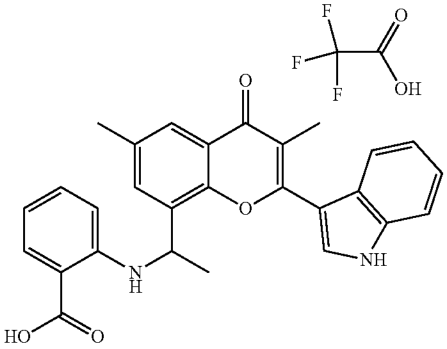 | 453 [M + H]$^+$ |

TABLE 44-continued

| Ex # | Chemical Name | Structure | MS ES+ m/z |
|---|---|---|---|
| 155 | 2-[1-[2-(1H-Indol-3-yl)-6-methyl-4-oxo-chromen-8-yl]ethylamino]benzoic acid, Isomer 2; 2,2,2-trifluoroacetic acid | 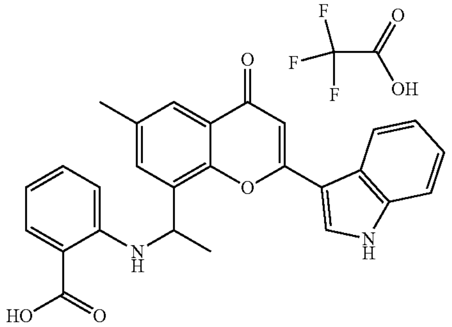 | 439 [M + H]+ |
| 156 | 2-[1-[6-Fluoro-2-(2-methylindazol-5-yl)-4-oxo-chromen-8-yl]ethylamino]benzoic acid, Isomer 1 | 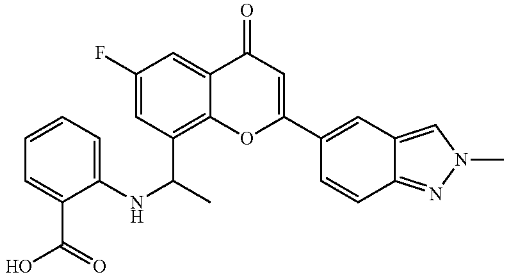 [SMILES: CC(Nc1ccccc1C(=O)O)c1cc(F)cc2c(=O)cc(-c3ccc4nn(C)cc4c3)oc12] | 458 [M + H]+ |
| 157 | 2-[1-(3,6-Dimethyl-4-oxo-2-pyrazolo[1,5-a]pyridin-6-yl-chromen-8-yl)ethylamino]benzoic acid, Isomer 2; 2,2,2-trifluoroacetic acid | 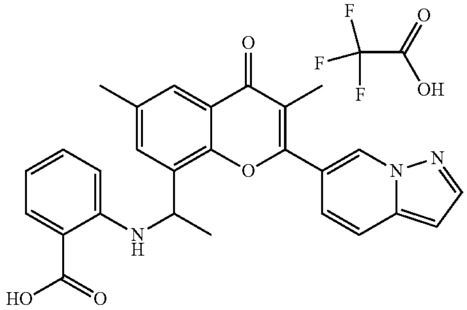 | 454 [M + H]+ |
| 158 | 2-[1-[6-Methyl-2-(1-methylindol-6-yl)-4-oxo-chromen-8-yl]ethylamino]benzoic acid, Isomer 2 | 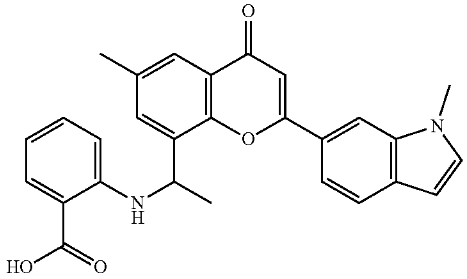 [SMILES: Cc1cc(C(C)Nc2ccccc2C(=O)O)c2oc(-c3ccc4ccn(C)c4c3)cc(=O)c2c1] | 453 [M + H]+ |
| 159 | 2-[1-[6-Methyl-2-(1-methylpyrrolo[2,3-b]pyridin-6-yl)-4-oxo-chromen-8-yl]ethylamino]benzoic acid, Isomer 2 | 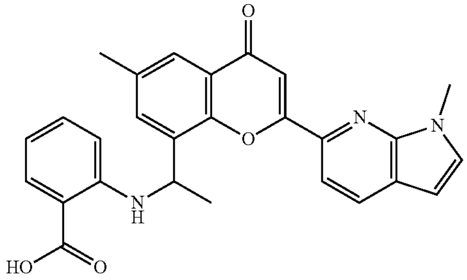 | 454 [M + H]+ |

TABLE 44-continued

| Ex # | Chemical Name | Structure | MS ES+ m/z |
|---|---|---|---|
| 160 | 2-[1-[6-Methyl-2-(2-methylpyrazolo[3,4-c]pyridin-5-yl)-4-oxo-chromen-8-yl]ethylamino]benzoic acid, Isomer 2 | 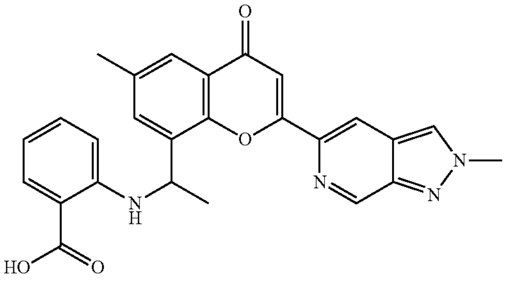 [SMILES: Cc1cc(C(C)Nc2ccccc2C(=O)O)c2oc(-c3cc4cn(C)nc4cn3)cc(=O)c2c1] | 455 [M + H]+ |
| 161 | 2-[1-[6-Methyl-4-oxo-2-([1,2,4]triazolo[4,3-a]pyridin-7-yl)chromen-8-yl]ethylamino]benzoic acid, Isomer 2 | 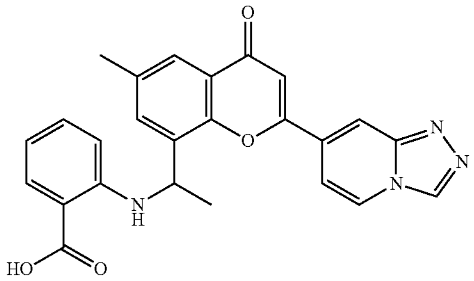 [SMILES: Cc1cc(C(C)Nc2ccccc2C(=O)O)c2oc(-c3ccn4cnnc4c3)cc(=O)c2c1] | 441 [M + H]+ |
| 162 | 2-[1-[6-Methyl-4-oxo-2-[3-(trifluoromethyl)-[1,2,4]triazolo[4,3-a]pyridin-6-yl]chromen-8-yl]ethylamino]benzoic acid, Isomer 2 | 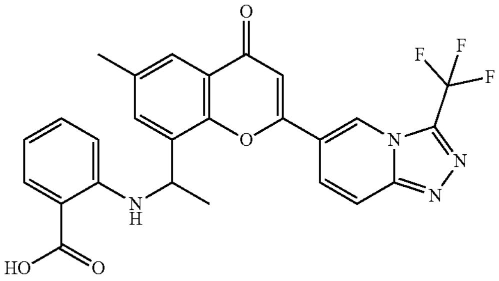 [SMILES: Cc1cc(C(C)Nc2ccccc2C(=O)O)c2oc(-c3ccc4nnc(C(F)(F)F)n4c3)cc(=O)c2c1] | 509 [M + H]+ |
| 163 | 2-[1-[2-(2,3-Dihydro-[1,4]dioxino[2,3-b]pyridin-7-yl)-6-methyl-4-oxo-chromen-8-yl]ethylamino]benzoic acid, Isomer 2 | 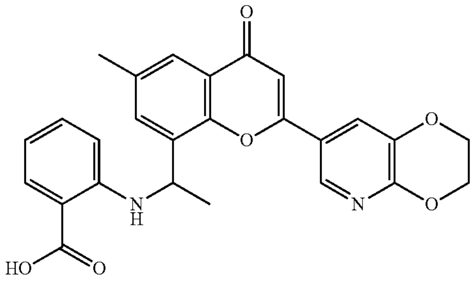 [SMILES: Cc1cc(C(C)Nc2ccccc2C(=O)O)c2oc(-c3cnc4c(c3)OCCO4)cc(=O)c2c1] | 459 [M + H]+ |
| 164 | 2-[1-[6-Methyl-2-(1-methylpyrazolo[4,3-b]pyridin-5-yl)-4-oxo-chromen-8-yl]ethylamino]benzoic acid, Isomer 2 | 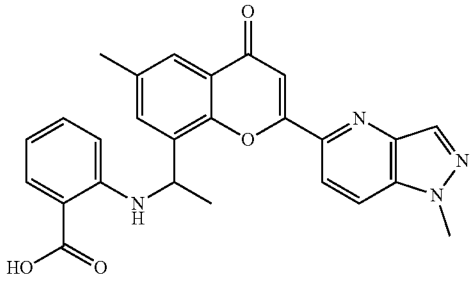 [SMILES: Cc1cc(C(C)Nc2ccccc2C(=O)O)c2oc(-c3ccc4c(cnn4C)n3)cc(=O)c2c1] | 455 [M + H]+ |

TABLE 44-continued

| Ex # | Chemical Name | Structure | MS ES+ m/z |
| --- | --- | --- | --- |
| 165 | 2-[1-[2-(1,3-Dimethylindazol-5-yl)-6-methyl-4-oxo-chromen-8-yl]ethylamino]benzoic acid, Isomer 2 | 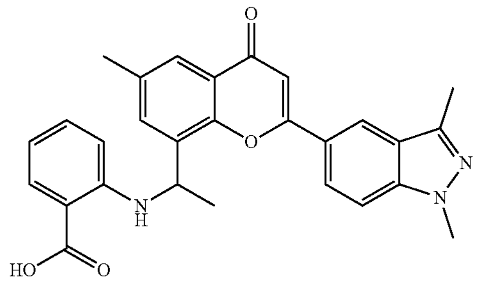 [SMILES: Cc1cc(C(C)Nc2ccccc2C(=O)O)c2oc(-c3ccc4c(c3)c(C)nn4C)cc(=O)c2c1] | 468 $[M + H]^+$ |
| 166 | 2-[1-[6-Methyl-2-(1-methylbenzimidazol-5-yl)-4-oxo-chromen-8-yl]ethylamino]benzoic acid, Isomer 2 | 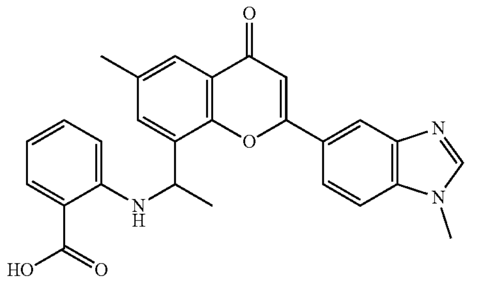 [SMILES: Cc1cc(C(C)Nc2ccccc2C(=O)O)c2oc(-c3ccc4c(c3)ncn4C)cc(=O)c2c1] | 454 $[M + H]^+$ |
| 187 | 2-[1-[6-Methyl-2-(1,7-naphthyridin-6-yl)-4-oxo-chromen-8-yl]ethylamino]benzoic acid, Isomer 2 | 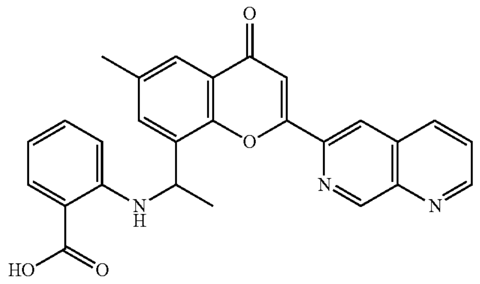 [SMILES: Cc1cc(C(C)Nc2ccccc2C(=O)O)c2oc(-c3cc4cccnc4cn3)cc(=O)c2c1] | 452 $[M + H]^+$ |
| 188 | 6-Chloro-3-[1-[2-(2,7-dimethylindazol-5-yl)-6-methyl-4-oxo-chromen-8-yl]ethylamino]pyridine-2-carboxylic acid, Isomer 2 | 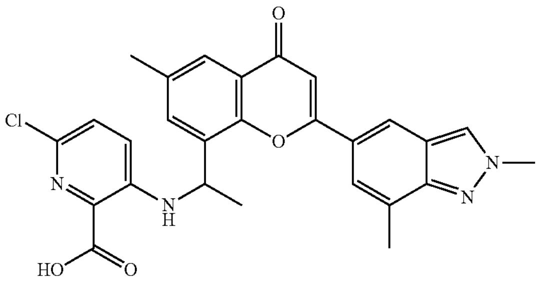 | 503 $[M + H]^+$ |
| 195 | 6-Chloro-3-[1-[6-methyl-4-oxo-2-(1H-pyrrolo[2,3-b]pyridin-6-yl)chromen-8-yl]ethylamino]pyridine-2-carboxylic acid; 2,2,2-trifluoroacetic acid | 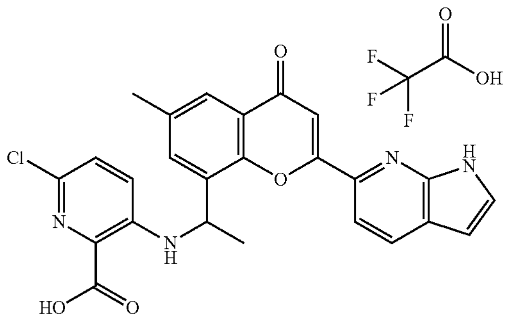 | 475 $[M + H]^+$ |

TABLE 44-continued

| Ex # | Chemical Name | Structure | MS ES+ m/z |
|---|---|---|---|
| 196 | 6-Chloro-3-[[(1R)-1-[2-(1H-indol-2-yl)-3,6-dimethyl-4-oxo-chromen-8-yl]ethyl]amino]pyridine-2-carboxylic acid; 2,2,2-trifluoroacetic acid | 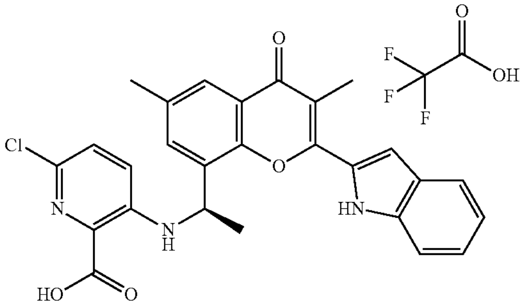 | 488 [M + H]$^+$ |
| 197 | 2-Fluoro-6-[[(1R)-1-[6-methyl-2-(1-methylindazol-5-yl)-4-oxo-chromen-8-yl]ethyl]amino]benzoic acid; 2,2,2-trifluoroacetic acid | 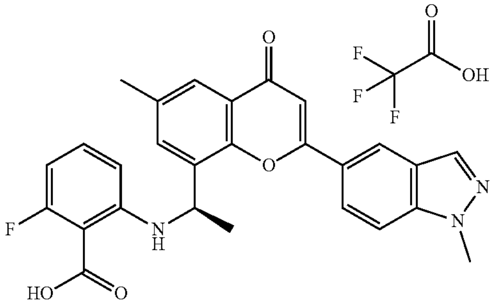 | 472 [M + H]$^+$ |
| 198 | 2-[[(1R)-1-[6-Methyl-2-[2-methyl-7-(trifluoromethyl)indazol-5-yl]-4-oxo-chromen-8-yl]ethyl]amino]benzoic acid; 2,2,2-trifluoroacetic acid | 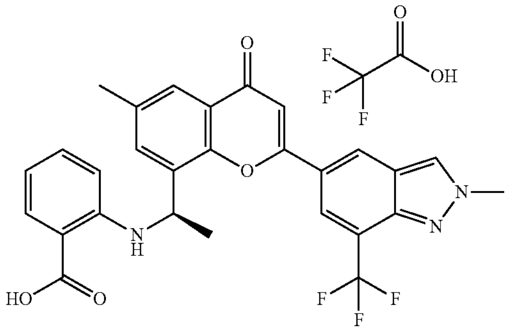 | 522 [M + H]$^+$ |
| 199 | 2-Fluoro-6-[1-[6-methyl-2-(1-methylindazol-6-yl)-4-oxo-chromen-8-yl]ethylamino]benzoic acid; 2,2,2-trifluoroacetic acid | 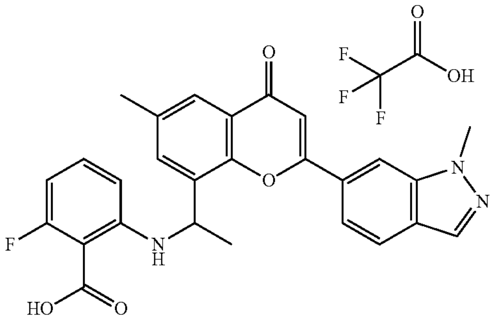 | 472 [M + H]$^+$ |
| 200 | 3-[[(1R)-1-[3,6-Dimethyl-2-(2-methylindazol-5-yl)-4-oxo-chromen-8-yl]ethyl]amino]-6-methyl-pyridine-2-carboxylic acid; 2,2,2-trifluoroacetic acid | 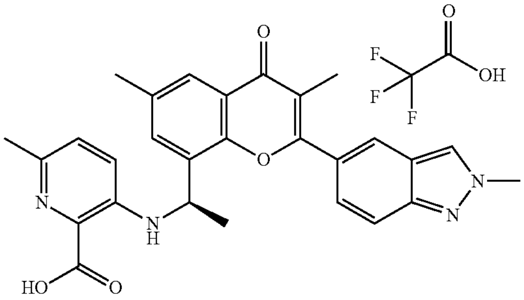 | 483 [M + H]$^+$ |

TABLE 44-continued

| Ex # | Chemical Name | Structure | MS ES+ m/z |
|---|---|---|---|
| 201 | 6-Chloro-3-[[(1R)-1-[2-(1H-indol-2-yl)-6-methyl-4-oxo-chromen-8-yl]ethyl]amino]pyridine-2-carboxylic acid; 2,2,2-trifluoroacetic acid | 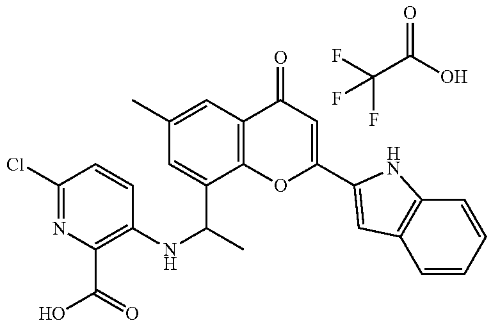 | 474 [M + H]$^+$ |
| 202 | 6-Chloro-3-[1-[2-(1,3-dimethylindazol-5-yl)-6-methyl-4-oxo-chromen-8-yl]ethylamino]pyridine-2-carboxylic acid; 2,2,2-trifluoroacetic acid | 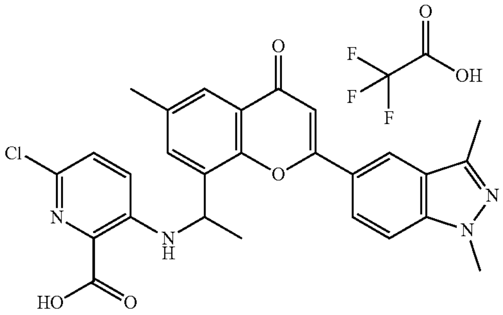 | 503 [M + H]$^+$ |
| 203 | 2-[[(1R)-1-(3,6-Dimethyl-4-oxo-2-thieno[3,2-c]pyridin-2-yl-chromen-8-yl)ethyl]amino]benzoic acid; 2,2,2-trifluoroacetic acid | 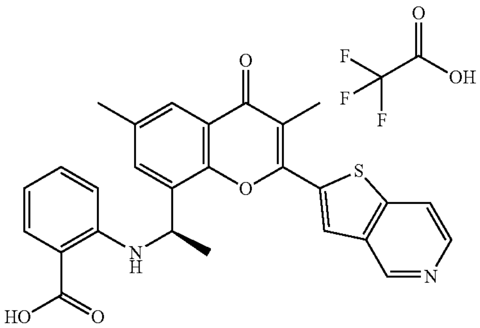 | 471 [M + H]$^+$ |
| 204 | 6-[[(1R)-1-[3,6-Dimethyl-2-(2-methylindazol-5-yl)-4-oxo-chromen-8-yl]ethyl]amino]-2,3-difluoro-benzoic acid | 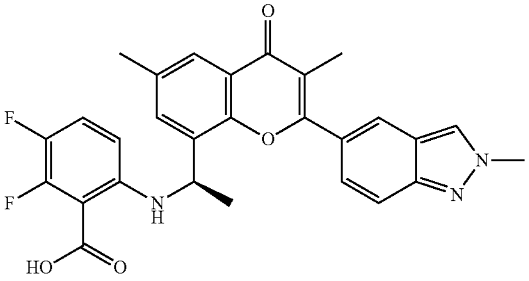 [SMILES: Cc1cc([C@@H](C)Nc2ccc(F)c(F)c2C(=O)O)c2oc(-c3ccc4nn(C)cc4c3)c(C)c(=O)c2c1] | 504 [M + H]$^+$ |
| 205 | 3-[[(1R)-1-[3,6-Dimethyl-2-(1-methylindazol-3-yl)-4-oxo-chromen-8-yl]ethyl]amino]pyridine-2-carboxylic acid | 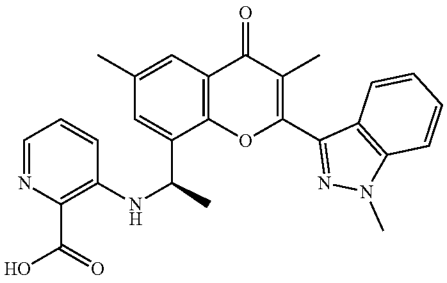 [SMILES: Cc1cc([C@@H](C)Nc2cccnc2C(=O)O)c2oc(-c3nn(C)c4ccccc34)c(C)c(=O)c2c1] | 469 [M + H]$^+$ |

TABLE 44-continued

| Ex # | Chemical Name | Structure | MS ES+ m/z |
| --- | --- | --- | --- |
| 206 | 6-Chloro-3-[1-[6-methyl-2-(2-methylindazol-5-yl)-4-oxo-chromen-8-yl]ethylamino]pyridine-2-carboxylic acid, Isomer 2; 2,2,2-trifluoroacetic acid | 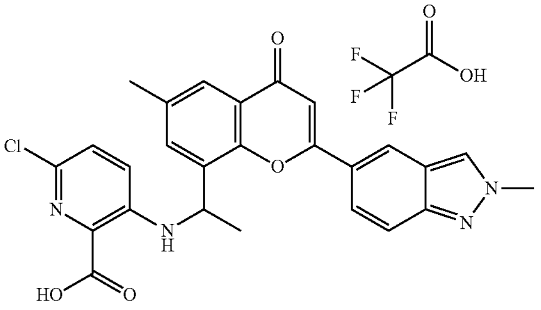 | 489 [M + H]$^+$ |
| 207 | 2-[1-[2-(2-Cyano-6-quinolyl)-6-methyl-4-oxo-chromen-8-yl]ethylamino]benzoic acid, Isomer 2 | 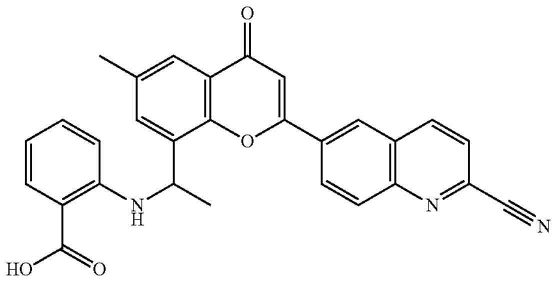 [SMILES: Cc1cc(C(C)Nc2ccccc2C(=O)O)c2oc(-c3ccc4nc(C#N)ccc4c3)cc(=O)c2c1] | 476 [M + H]$^+$ |
| 208 | 2-[1-[6-Methyl-2-(2-methylindazol-5-yl)-4-oxo-3-(trifluoromethyl)chromen-8-yl]ethylamino]benzoic acid, Isomer 2; 2,2,2-trifluoroacetic acid | 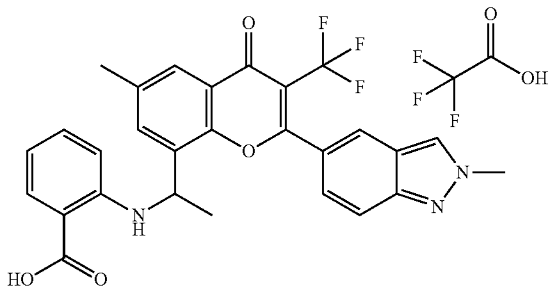 | 522 [M + H]$^+$ |
| 209 | 2-[[(1R)-1-[2-Furo[3,2-c]pyridin-2-yl-6-methyl-4-oxo-3-(trifluoromethyl)chromen-8-yl]ethyl]amino]benzoic acid; 2,2,2-trifluoroacetic acid | 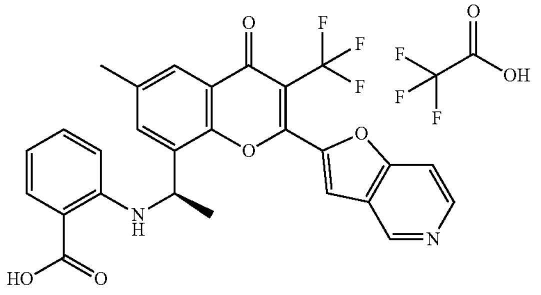 | 509 [M + H]$^+$ |
| 210 | 2-[[(1R)-1-[2-(2-Benzylindazol-5-yl)-3,6-dimethyl-4-oxo-chromen-8-yl]ethyl]amino]benzoic acid; 2,2,2-trifluoroacetic acid | 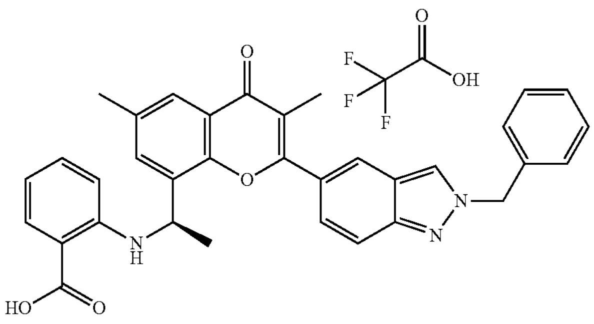 | 544 [M + H]$^+$ |

TABLE 44-continued

| Ex # | Chemical Name | Structure | MS ES+ m/z |
|---|---|---|---|
| 211 | 2-[[(1R)-1-[2-(1-Benzylindazol-5-yl)-3,6-dimethyl-4-oxo-chromen-8-yl]ethyl]amino]benzoic acid; 2,2,2-trifluoroacetic acid | 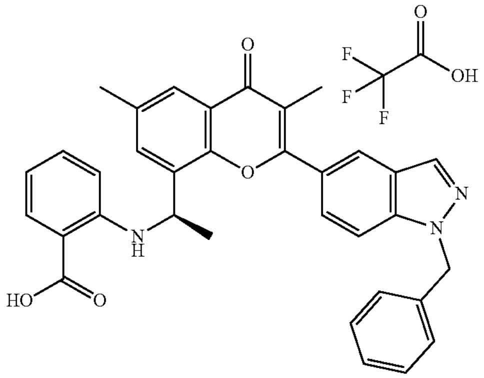 | 544 [M + H]+ |

[a]Purified via reversed phase chromatography using 10 mM aqueous ammonium bicarbonate (with 5% methanol)/acetonitrile.

Example 30: 2-[1-[6-Methyl-2-(2-methyl-1-oxo-isoindolin-5-yl)-4-oxo-chromen-8-yl]ethylamino] benzoic acid

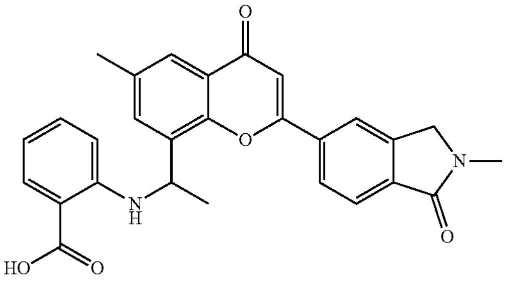 [SMILES: Cc1cc(C(C)Nc2ccccc2C(=O)O)c2oc(-c3ccc4c(c3)CN(C)C4=O)cc(=O)c2c1]

tert-Butyl 2-[1-[6-methyl-2-(2-methyl-1-oxo-isoindolin-5-yl)-4-oxo-chromen-8-yl]ethylamino]benzoate (130 mg, 0.25 mmol) was dissolved in DCM (1 mL) and treated with trifluoroacetic acid (2 mL). The reaction was stirred at 40° C. for 3 h. The reaction was cooled and directly purified on a C-18 reverse phase column eluted with 10%-100% acetonitrile in water with 0.1% trifluoroacetic acid to give the product (72 mg, 62%). MS ES+ m/z 469 $[M+H]^+$.

Example 167: 6-Chloro-3-[1-[2-(2-methyl-1,3-benzothiazol-6-yl)-4-oxo-6-(trifluoromethyl)chromen-8-yl]ethylamino]pyridine-2-carboxylic acid, Isomer 2; 2,2,2-trifluoroacetic acid

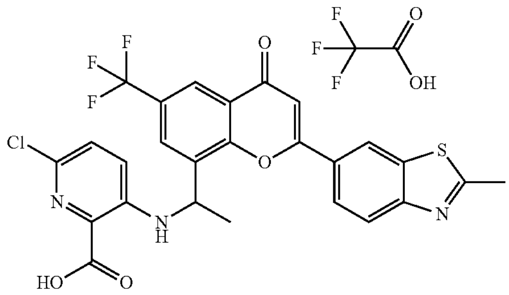

A mixture of tert-butyl 6-chloro-3-[1-[2-ethylsulfanyl-4-oxo-6-(trifluoromethyl)chromen-8-yl]ethylamino]pyridine-2-carboxylate (0.30 g, 0.57 mmol), (2-methyl-1,3-benzothiazol-6-yl)boronic acid (0.44 g, 2.27 mmol), zinc(II) acetate (0.21 g, 1.14 mmol), copper(I) thiophene-2-carboxylate (0.22 g, 1.14 mmol) in 3 mL of 1,4-dioxane was treated with tris(dibenzylideneacetone)dipalladium(0) (0.052 g, 0.057 mmol) and tri(2-furyl)phosphine (0.066 g, 0.028 mmol). The mixture was flushed with argon gas three times and heated at 85° C. for 18 h. The reaction was cooled and filtered through a celite/silica pad and rinsed with 10% methanol in ethyl acetate. The filtrate was concentrated, dissolved in trifluoroacetic acid (3 mL) and acetonitrile (2 mL) and purified on a C-18 column eluted with 10% to 100% acetonitrile in water (with 0.1% TFA) giving the product (6.6 mg, 1.7%). MS ES+ m/z 560 $[M+H]^+$.

The following compounds in Table 45 were made in a similar way as described for Example 167.

TABLE 45

| Ex # | Chemical Name | Structure | MS ES+ m/z |
|---|---|---|---|
| 168 | 6-Chloro-3-[1-[2-(1-methylindazol-5-yl)-4-oxo-6-(trifluoromethyl)chromen-8-yl]ethylamino]pyridine-2-carboxylic acid, Isomer 2 | 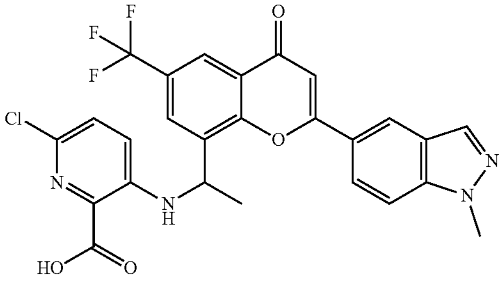 [SMILES: CC(Nc1ccc(Cl)nc1C(=O)O)c1cc(C(F)(F)F)cc2c(=O)cc(-c3ccc4c(cnn4C)c3)oc12] | 543 [M + H]+ |
| 169 | 6-Chloro-3-[[(1R)-1-[2-(2-methylindazol-5-yl)-4-oxo-6-(trifluoromethyl)chromen-8-yl]ethyl]amino]pyridine-2-carboxylic acid | 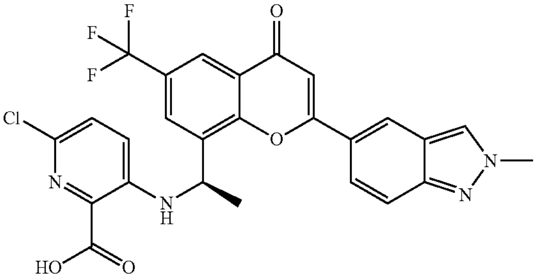 [SMILES: C[C@@H](Nc1ccc(Cl)nc1C(=O)O)c1cc(C(F)(F)F)cc2c(=O)cc(-c3ccc4nn(C)cc4c3)oc12] | 543 [M + H]+ |
| 212 | 6-Chloro-3-[1-[6-methyl-2-(1-methylindazol-5-yl)-4-oxo-chromen-8-yl]ethylamino]pyridine-2-carboxylic acid; 2,2,2-trifluoroacetic acid | 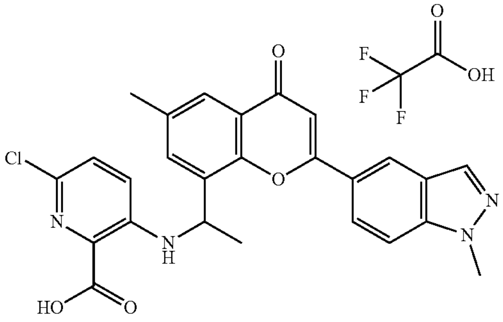 | 489 [M + H]+ |
| 213 | 6-Chloro-3-[1-[6-methyl-2-(1-methylindazol-6-yl)-4-oxo-chromen-8-yl]ethylamino]pyridine-2-carboxylic acid; 2,2,2-trifluoroacetic acid | 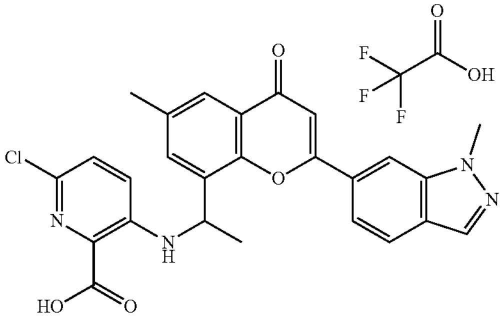 | 489 [M + H]+ |
| 214 | 6-Chloro-3-[[(1R)-1-(2-furo[3,2-c]pyridin-2-yl-3,6-dimethyl-4-oxo-chromen-8-yl)ethyl]amino]pyridine-2-carboxylic acid | 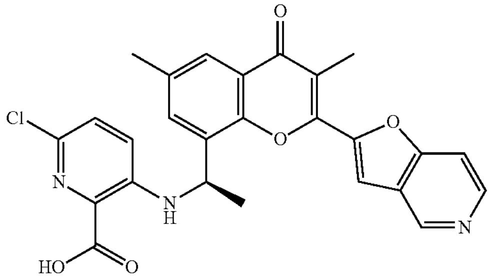 [SMILES: Cc1cc([C@@H](C)Nc2ccc(Cl)nc2C(=O)O)c2oc(-c3cc4cnccc4o3)c(C)c(=O)c2c1] | 490 [M + H]+ |

Example 170: 6-Chloro-3-[1-[3,6-dimethyl-2-(1-methylindazol-3-yl)-4-oxo-chromen-8-yl]ethylamino]pyridine-2-carboxylic acid, Isomer 2

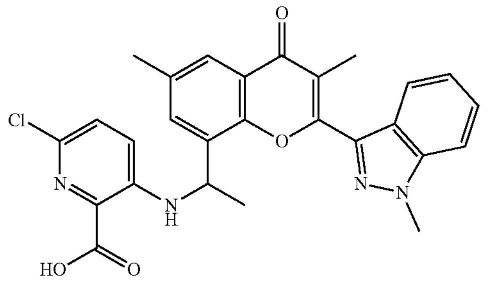 [SMILES: Cc1cc(C(C)Nc2ccc(Cl)nc2C(=O)O)c2oc(-c3nn(C)c4ccccc34)c(C)c(=O)c2c1]

A mixture of methyl 6-chloro-3-[1-(2-ethylsulfanyl-3,6-dimethyl-4-oxo-chromen-8-yl)ethylamino]pyridine-2-carboxylate, Isomer 2 (0.15 g, 0.34 mmol), 1-methylindazol-3-yl)boronic acid (0.18 g, 1.01 mmol), copper(I) thiophene-2-carboxylate (0.19 g, 1.01 mmol), tetrakis (triphenylphosphine)palladium(0) (0.039 g, 0.034 mmol), and cesium carbonate (0.44 g, 1.34 mmol) in 2-methyltetrahydrofuran (5 mL) was stirred at 85° C. under nitrogen gas for 40 h. Added another 0.18 g of 1-methylindazol-3-yl) boronic acid, 0.19 g of copper(I) thiophene-2-carboxylate, 0.039 g of tetrakis(triphenylphosphine)palladium(0), and 0.44 g of cesium carbonate and stirred at 85° C. for another 60 h. The reaction was allowed to cool and diluted with 20 mL each of water and dichloromethane. Adjusted the pH to ~2 with 2M aqueous hydrogen chloride and then 0.30 g of N-acetyl-L-cysteine was added and the reaction stirred at rt for 30 min. The reaction was filtered, the filtrate extracted 3 times with 30 mL of dichloromethane, and the organics collected and concentrated. The residue was purified by prep HPLC with ammonium hydroxide as an additive, concentrated to remove acetonitrile, the pH adjusted to 2 with 2M aqueous hydrogen chloride, extracted 3 times with 30 mL of dichloromethane, and the organics collected and concentrated. The residue was taken up in aqueous acetonitrile and lyophilized to give the product (3 mg, 1.6%) as a brown solid. MS ES+ m/z 503 $[M+H]^+$.

Example 31 and Example 32: 2-[1-[6-Methyl-2-(2-methyl-1-oxo-isoindolin-5-yl)-4-oxo-chromen-8-yl]ethylamino]benzoic acid, Isomer 1 and Isomer 2

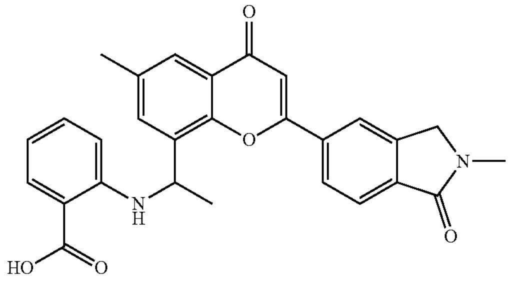 [SMILES: Cc1cc(C(C)Nc2ccccc2C(=O)O)c2oc(-c3ccc4c(c3)CN(C)C4=O)cc(=O)c2c1]

2-[1-[6-Methyl-2-(2-methyl-1-oxo-isoindolin-5-yl)-4-oxo-chromen-8-yl]ethylamino]benzoic acid was dissolved in 2.75 mL of MeOH and the vial rinsed with another 0.5 mL of MeOH. The combined 3.25 mL of solution was separated on a Chiralpak AD-H column (250×21 mm) eluted with 65% $CO_{2/35}$% EtOH with 0.5% DMEA at a flowrate of 70 mL/min. After lyophilization of the necessary fractions, obtained isomer 1 (10.2 mg) and isomer 2 (11 mg) respectively. MS ES+ m/z 469 $[M+H]^+$.

The following compounds in Table 46 were made in a similar way as described for Example 31 and Example 32.

TABLE 46

| Ex # | Chemical Name | Structure | MS ES+ m/z / Chiral Column |
|---|---|---|---|
| 33 | 2-[1-(6-Methyl-4-oxo-2-pyrazolo[1,5-a]pyrimidin-3-yl-chromen-8-yl)ethylamino]benzoic acid, Isomer 1 | 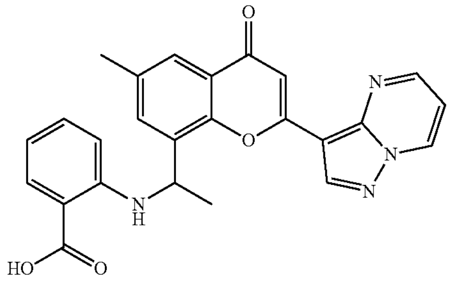 [SMILES: Cc1cc(C(C)Nc2ccccc2C(=O)O)c2oc(-c3cnn4cccnc34)cc(=O)c2c1] | 441 $[M + H]^+$ Chiralcel OD-H[a] |
| 34 | 2-[1-(6-Methyl-4-oxo-2-pyrazolo[1,5-a]pyrimidin-3-yl-chromen-8-yl)ethylamino]benzoic acid, Isomer 2 | 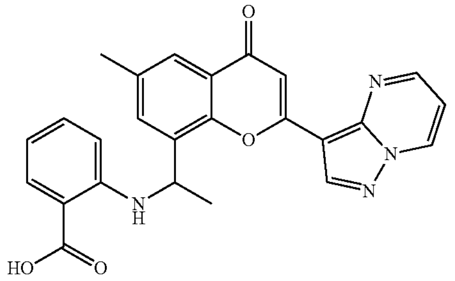 [SMILES: Cc1cc(C(C)Nc2ccccc2C(=O)O)c2oc(-c3cnn4cccnc34)cc(=O)c2c1] | 441 $[M + H]^+$ Chiralcel OD-H[a] |

TABLE 46-continued

| Ex # | Chemical Name | Structure | MS ES+ m/z / Chiral Column |
|---|---|---|---|
| 35 | 2-[1-(2-Imidazo[1,2-b]pyridazin-6-yl-6-methyl-4-oxo-chromen-8-yl)ethylamino]benzoic acid, Isomer 1 | 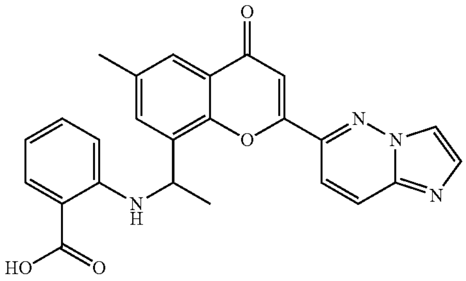 [SMILES: Cc1cc(C(C)Nc2ccccc2C(=O)O)c2oc(-c3ccc4nccn4n3)cc(=O)c2c1] | 441 [M + H]$^+$ Chiralcel OD-H[a] |
| 36 | 2-[1-(2-Imidazo[1,2-b]pyridazin-6-yl-6-methyl-4-oxo-chromen-8-yl)ethylamino]benzoic acid, Isomer 2 | 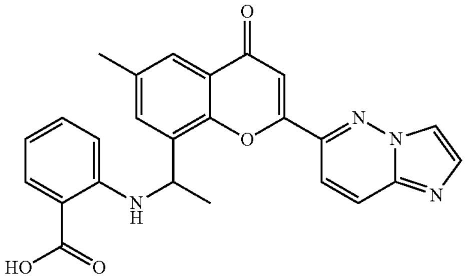 [SMILES: Cc1cc(C(C)Nc2ccccc2C(=O)O)c2oc(-c3ccc4nccn4n3)cc(=O)c2c1] | 441 [M + H]$^+$ Chiralcel OD-H[a] |
| 37 | 2-[1-[6-Methyl-2-(2-methylimidazo[1,2-a]pyridin-6-yl)-4-oxo-chromen-8-yl]ethylamino]benzoic acid, Isomer 1 | 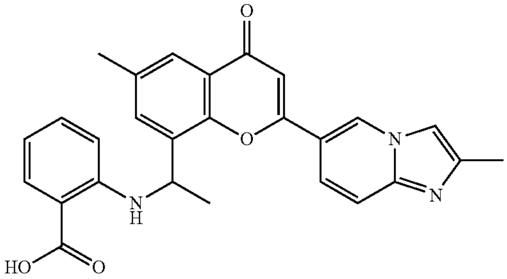 [SMILES: Cc1cc(C(C)Nc2ccccc2C(=O)O)c2oc(-c3ccc4nc(C)cn4c3)cc(=O)c2c1] | 454 [M + H]$^+$ Chiralcel OJ-H[b] |
| 38 | 2-[1-[6-Methyl-2-(2-methylimidazo[1,2-a]pyridin-6-yl)-4-oxo-chromen-8-yl]ethylamino]benzoic acid, Isomer 2 | 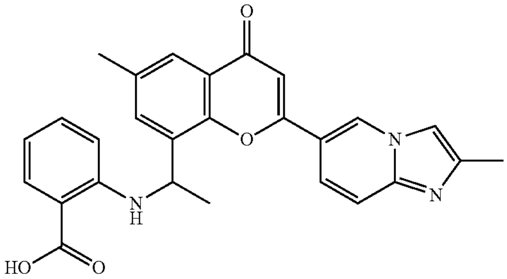 [SMILES: Cc1cc(C(C)Nc2ccccc2C(=O)O)c2oc(-c3ccc4nc(C)cn4c3)cc(=O)c2c1] | 454 [M + H]$^+$ Chiralcel OJ-H[b] |
| 39 | 2-[1-(2-Furo[2,3-c]pyridin-2-yl-6-methyl-4-oxo-chromen-8-yl)ethylamino]benzoic acid, Isomer 1 | 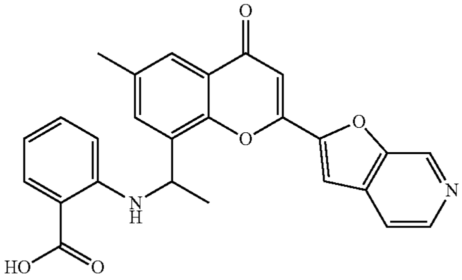 [SMILES: Cc1cc(C(C)Nc2ccccc2C(=O)O)c2oc(-c3cc4ccncc4o3)cc(=O)c2c1] | 441 [M + H]$^+$ Chiralpak IG[c] |

TABLE 46-continued

| Ex # | Chemical Name | Structure | MS ES+ m/z / Chiral Column |
|---|---|---|---|
| 40 | 2-[1-(2-Furo[2,3-c]pyridin-2-yl-6-methyl-4-oxo-chromen-8-yl)ethylamino]benzoic acid, Isomer 2 | 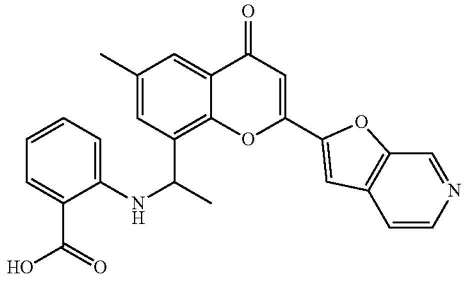 [SMILES: Cc1cc(C(C)Nc2ccccc2C(=O)O)c2oc(-c3cc4ccncc4o3)cc(=O)c2c1] | 441 [M + H]+ Chiralpak IG[c] |
| 41 | 2-[1-[6-Methyl-2-(2-methylpyrazolo[3,4-b]pyridin-5-yl)-4-oxo-chromen-8-yl]ethylamino]benzoic acid, Isomer 1 | 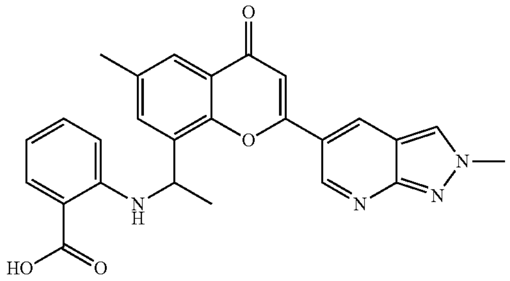 | 455 [M + H]+ Chiralpak IH[d] |
| 42 | 2-[1-[6-Methyl-2-(2-methylpyrazolo[3,4-b]pyridin-5-yl)-4-oxo-chromen-8-yl]ethylamino]benzoic acid, Isomer 2 | 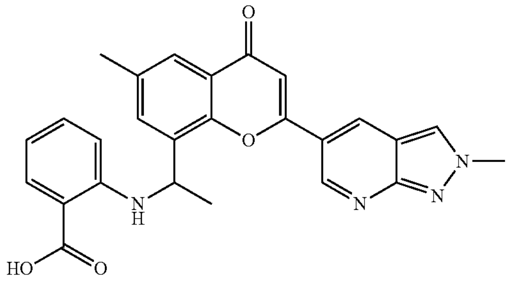 [SMILES: Cc1cc(C(C)Nc2ccccc2C(=O)O)c2oc(-c3cnc4cn(C)nc4c3)cc(=O)c2c1] | 455 [M + H]+ Chiralpak IH[d] |
| 43 | 2-[1-[6-Methyl-2-(2-methylpyrazolo[4,3-b]pyridin-6-yl)-4-oxo-chromen-8-yl]ethylamino]benzoic acid, Isomer 1 | 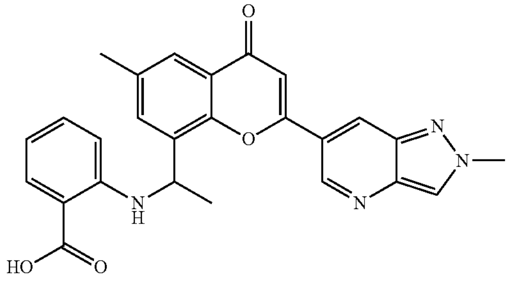 [SMILES: Cc1cc(C(C)Nc2ccccc2C(=O)O)c2oc(-c3cnc4cn(C)nc4c3)cc(=O)c2c1] | 455 [M + H]+ Chiralcel OJ[e] |
| 44 | 2-[1-[6-Methyl-2-(2-methylpyrazolo[4,3-b]pyridin-6-yl)-4-oxo-chromen-8-yl]ethylamino]benzoic acid, Isomer 2 | 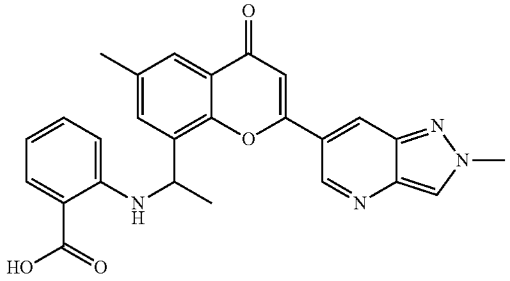 | 455 [M + H]+ Chiralcel OJ[e] |

TABLE 46-continued

| Ex # | Chemical Name | Structure | MS ES+ m/z / Chiral Column |
|---|---|---|---|
| 171 | 2-Fluoro-6-[1-[6-methyl-2-(2-methylindazol-5-yl)-4-oxo-chromen-8-yl]ethylamino]benzoic acid, Isomer 1 | 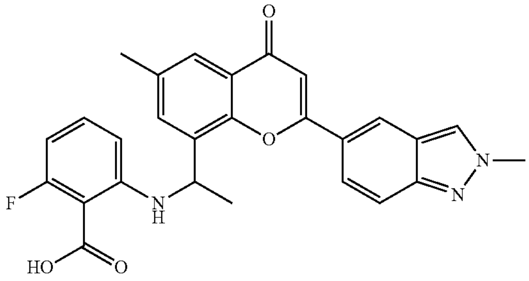 [SMILES: Cc1cc(C(C)Nc2cccc(F)c2C(=O)O)c2oc(-c3ccc4nn(C)cc4c3)cc(=O)c2c1] | 472 $[M + H]^+$ Chiralcel OJ[f] |
| 172 | 2-Fluoro-6-[1-[6-methyl-2-(2-methylindazol-5-yl)-4-oxo-chromen-8-yl]ethylamino]benzoic acid, Isomer 2 | 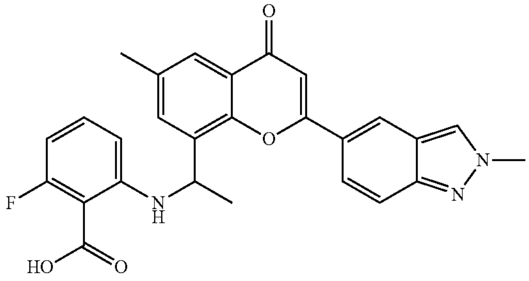 [SMILES: Cc1cc(C(C)Nc2cccc(F)c2C(=O)O)c2oc(-c3ccc4nn(C)cc4c3)cc(=O)c2c1] | 472 $[M + H]^+$ Chiralcel OJ[f] |
| 215 | 6-Chloro-3-[1-[6-methyl-4-oxo-2-(1H-pyrrolo[2,3-b]pyridin-6-yl)chromen-8-yl]ethylamino]pyridine-2-carboxylic acid, Isomer 1 | 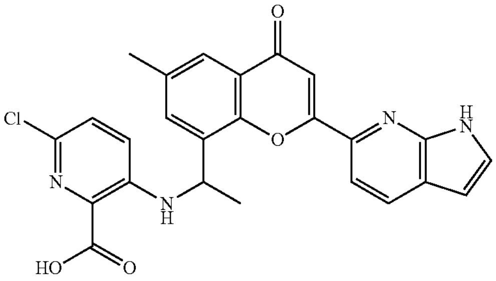 [SMILES: Cc1cc(C(C)Nc2ccc(Cl)nc2C(=O)O)c2oc(-c3ccc4cc[nH]c4n3)cc(=O)c2c1] | 475 $[M + H]^+$ Chiralcel OD[g] |
| 216 | 6-Chloro-3-[1-[6-methyl-4-oxo-2-(1H-pyrrolo[2,3-b]pyridin-6-yl)chromen-8-yl]ethylamino]pyridine-2-carboxylic acid, Isomer 2 | 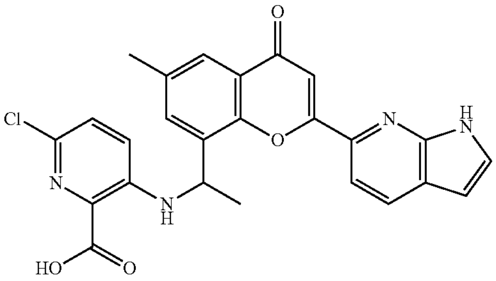 [SMILES: Cc1cc(C(C)Nc2ccc(Cl)nc2C(=O)O)c2oc(-c3ccc4cc[nH]c4n3)cc(=O)c2c1] | 475 $[M + H]^+$ Chiralcel OD[g] |
| 217 | 6-Chloro-3-[1-[6-methyl-2-(1-methylindazol-5-yl)-4-oxo-chromen-8-yl]ethylamino]pyridine-2-carboxylic acid, Isomer 1 | 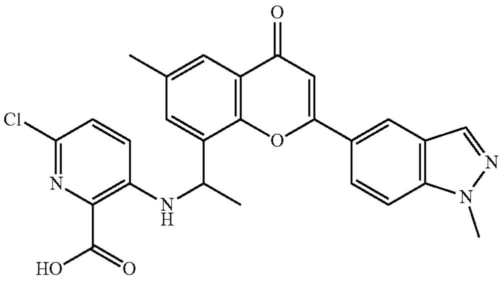 [SMILES: Cc1cc(C(C)Nc2ccc(Cl)nc2C(=O)O)c2oc(-c3ccc4c(cnn4C)c3)cc(=O)c2c1] | 489/491 $[M + H]^+$ Chiralcel OD[s] |

TABLE 46-continued

| Ex # | Chemical Name | Structure | MS ES+ m/z / Chiral Column |
|---|---|---|---|
| 218 | 6-Chloro-3-[1-[6-methyl-2-(1-methylindazol-5-yl)-4-oxo-chromen-8-yl]ethylamino]pyridine-2-carboxylic acid, Isomer 2 | 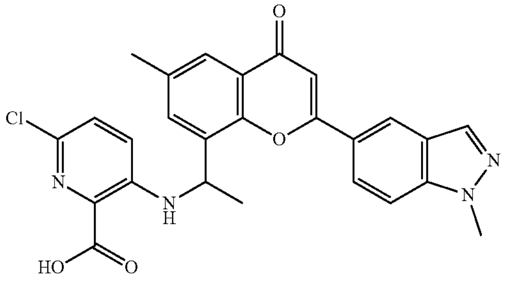 [SMILES: Cc1cc(C(C)Nc2ccc(Cl)nc2C(=O)O)c2oc(-c3ccc4c(cnn4C)c3)cc(=O)c2c1] | 489/491 [M + H]+ Chiralcel OD[g] |
| 219 | 6-Chloro-3-[1-[6-methyl-2-(1-methylindazol-6-yl)-4-oxo-chromen-8-yl]ethylamino]pyridine-2-carboxylic acid, Isomer 1 | 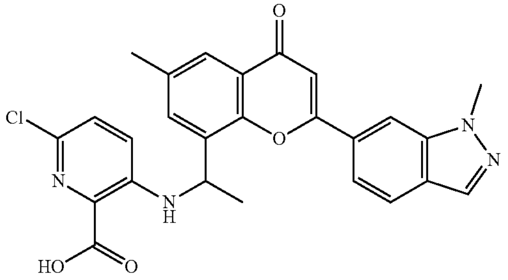 | 489/491 [M + H]+ Chiralcel OD[g] |
| 220 | 6-Chloro-3-[1-[6-methyl-2-(1-methylindazol-6-yl)-4-oxo-chromen-8-yl]ethylamino]pyridine-2-carboxylic acid, Isomer 2 | 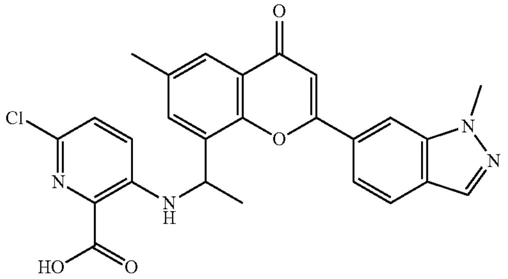 | 489/491 [M + H]+ Chiralcel OD[g] |
| 221 | 2-fluoro-6-[1-[6-methyl-2-(1-methylindazol-6-yl)-4-oxo-chromen-8-yl]ethylamino]benzoic acid, Isomer 1 | 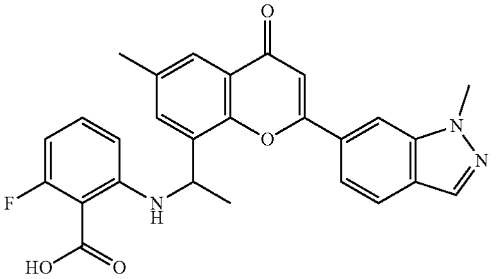 [SMILES: Cc1cc(C(C)Nc2cccc(F)c2C(=O)O)c2oc(-c3ccc4cnn(C)c4c3)cc(=O)c2c1] | 472 [M + H]+ Chiralcel OD[g] |
| 222 | 2-fluoro-6-[1-[6-methyl-2-(1-methylindazol-6-yl)-4-oxo-chromen-8-yl]ethylamino]benzoic acid, Isomer 2 | 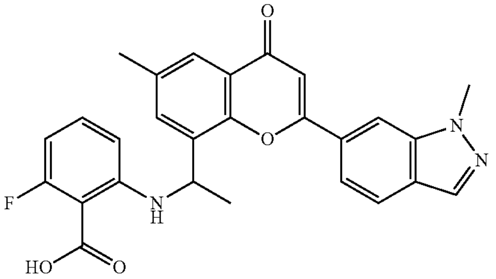 [SMILES: Cc1cc(C(C)Nc2cccc(F)c2C(=O)O)c2oc(-c3ccc4cnn(C)c4c3)cc(=O)c2c1] | 472 [M + H]+ Chiralcel OD[g] |

TABLE 46-continued

| Ex # | Chemical Name | Structure | MS ES+ m/z / Chiral Column |
|---|---|---|---|
| 223 | 6-Chloro-3-[1-[2-(1H-indol-2-yl)-6-methyl-4-oxo-chromen-8-yl]ethylamino]pyridine-2-carboxylic acid, Isomer 2 | 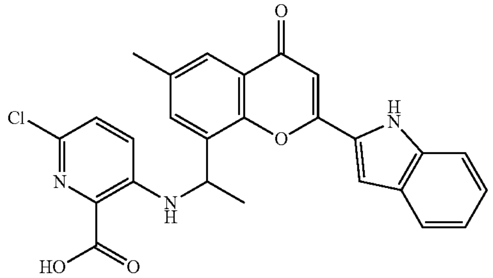 [SMILES: Cc1cc(C(C)Nc2ccc(Cl)nc2C(=O)O)c2oc(-c3cc4ccccc4[nH]3)cc(=O)c2c1] | 474/476 [M + H]+ Chiralpak AD[g] |
| 224 | 6-Chloro-3-[1-[2-(1,3-dimethylindazol-5-yl)-6-methyl-4-oxo-chromen-8-yl]ethylamino]pyridine-2-carboxylic acid, Isomer 2 | 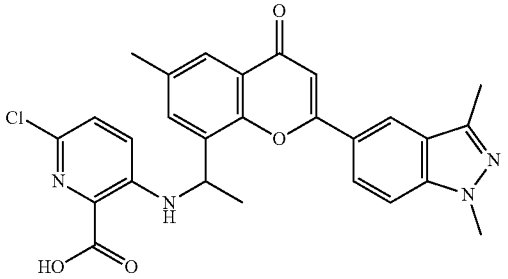 [SMILES: Cc1cc(C(C)Nc2ccc(Cl)nc2C(=O)O)c2oc(-c3ccc4c(c3)c(C)nn4C)cc(=O)c2c1] | 503/505 [M + H]+ Chiralcel OJ[h] |

[a]21 x 150 mm column eluted with 40% MeOH (w/ 0.5% DMEA) : 60% $CO_2$.
[b]21 x 150 mm column eluted with 30% MeOH (w/0.5% DMEA) : 70% $CO_2$.
[c]30 x 250 mm column eluted with 30% EtOH (w/0.5% DMEA) : 60% $CO_2$.
[d]20 x 250 mm column eluted with 40% MeOH (w/ 0.2% DMEA) : 60% $CO_2$.
[e]20 x 250 mm column eluted with 30% MeOH (w/0.2% DMEA) : 70% $CO_2$
[f]20 x 250 mm column eluted with 20% MeOH (w/0.5% DMEA) : 80% $CO_2$
[g]20 x 250 mm column eluted with 20% to 60% EtOH (0.05% TFA) in hexanes (0.05% TFA)
[h]20 x 150 mm column eluted with 30% to 60% EtOH (0.05% TFA) in hexanes (0.05% TFA)

Example 45: 2-[1-[2-(1,3-Benzodioxol-4-yl)-6-methyl-4-oxo-chromen-8-yl]ethylamino]benzoic acid, Isomer 2

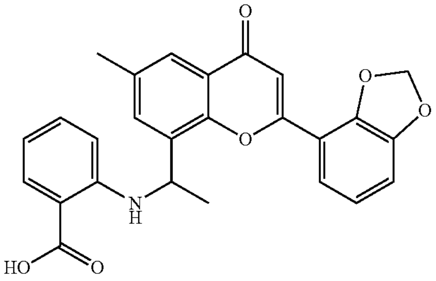

Methyl 2-[1-[2-(1,3-benzodioxol-4-yl)-6-methyl-4-oxo-chromen-8-yl]ethylamino]benzoate, Isomer 2 (60 mg, 0.131 mmol) was suspended in MeOH (2 mL) and treated with NaOH (10.5 mg, 0.262 mmol) in $H_2O$ (0.5 mL). The mixture was stirred at 45° C. for 6 h to give a yellow suspension. Filtered the reaction and concentrated the filtrate to a residue which was purified via prep HPLC (Boston Prime C18 150×30 mm column) eluted with 39% 79% acetonitrile in water with 0.05% ammonium hydroxide to give the product as a yellow solid (28.03 mg, 48.2%). MS ES+ m/z 444 $[M+H]^+$.

The following compounds in Table 47 were made in a similar way as described for Example 45.

TABLE 47

| Ex # | Chemical Name | Structure | MS ES+ mz |
|---|---|---|---|
| 46[a] | 2-[1-[2-(1,3-Benzodioxol-5-yl)-6-methyl-4-oxo-chromen-8-yl]ethylamino]benzoic acid, Isomer 2 | 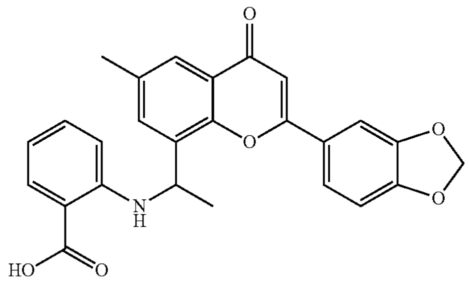 [SMILES: Cc1cc(C(C)Nc2ccccc2C(=O)O)c2oc(-c3ccc4c(c3)OCO4)cc(=O)c2c1] | 444 $[M + H]^+$ |
| 83 | 6-Chloro-3-[1-[6-methyl-2-(2-methylindazol-5-yl)-4-oxo-chromen-8-yl]ethylamino]pyridine-2-carboxylic acid, Isomer 2 | 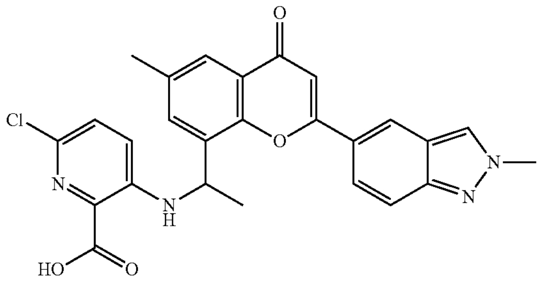 | 489 $[M + H]^+$ |
| 173[a] | 6-Chloro-3-[1-[2-(7-chloro-2-methyl-indazol-5-yl)-4-oxo-6-(trifluoromethyl)chromen-8-yl]ethylamino]pyridine-2-carboxylic acid; 2,2,2-trifluoroacetic acid | 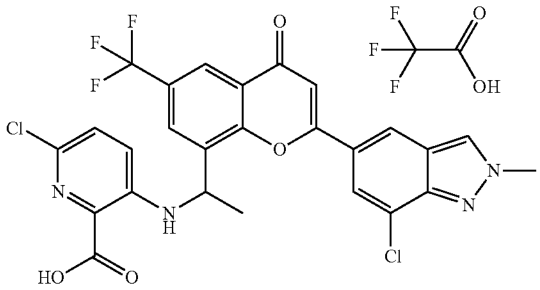 | 577 $[M + H]^+$ |
| 174[a] | 6-Chloro-3-[1-[2-(2,7-dimethylindazol-5-yl)-4-oxo-6-(trifluoromethyl)chromen-8-yl]ethylamino]pyridine-2-carboxylic acid; 2,2,2-trifluoroacetic acid | 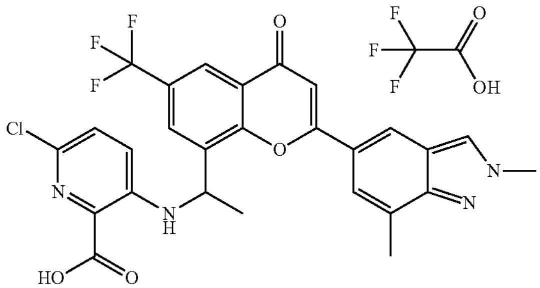 | 557 $[M + H]^+$ |
| 175 | 3-[1-[3,6-Dimethyl-2-(2-methylindazol-5-yl)-4-oxo-chromen-8-yl]ethylamino]-6-methyl-pyridine-2-carboxylic acid, Isomer 2 | 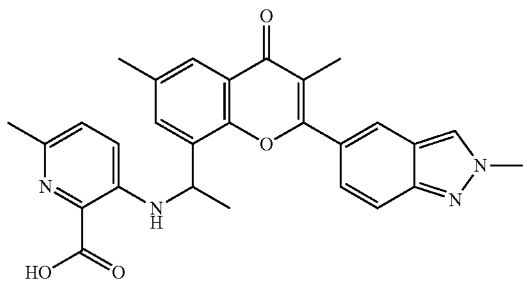 | 483 $[M + H]^+$ |

TABLE 47-continued

| Ex # | Chemical Name | Structure | MS ES+ mz |
|---|---|---|---|
| 176 | 6-Methyl-3-[1-[6-methyl-2-(1-methylindazol-3-yl)-4-oxo-chromen-8-yl]ethylamino]pyridine-2-carboxylic acid, Isomer 2 | 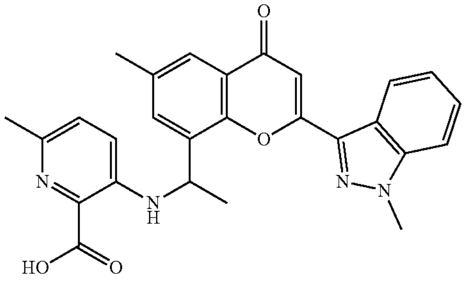 [SMILES: Cc1cc(C(C)Nc2ccc(C)nc2C(=O)O)c2oc(-c3nn(C)c4ccccc34)cc(=O)c2c1] | 469 [M + H]+ |
| 177 | 6-Chloro-3-[1-[6-methyl-2-(1-methylindazol-3-yl)-4-oxo-chromen-8-yl]ethylamino]pyridine-2-carboxylic acid, Isomer 2 | 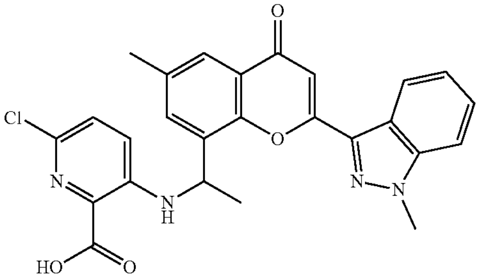 [SMILES: Cc1cc(C(C)Nc2ccc(Cl)nc2C(=O)O)c2oc(-c3nn(C)c4ccccc34)cc(=O)c2c1] | 489 [M + H]+ |
| 178 | 6-Chloro-3-[1-[3,6-dimethyl-2-(2-methylimidazo[1,2-a]pyridin-6-yl)-4-oxo-chromen-8-yl]ethylamino]pyridine-2-carboxylic acid, Isomer 2 | 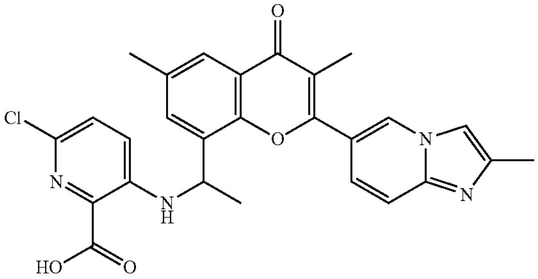 [SMILES: Cc1cc(C(C)Nc2ccc(Cl)nc2C(=O)O)c2oc(-c3ccc4nc(C)cn4c3)c(C)c(=O)c2c1] | 503 [M + H]+ |
| 179 | 6-Chloro-3-[1-[6-methyl-2-(2-methylimidazo[1,2-a]pyridin-6-yl)-4-oxo-chromen-8-yl]ethylamino]pyridine-2-carboxylic acid, Isomer 2 | 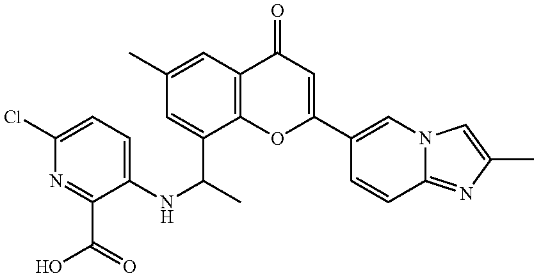 [SMILES: Cc1cc(C(C)Nc2ccc(Cl)nc2C(=O)O)c2oc(-c3ccc4nc(C)cn4c3)cc(=O)c2c1] | 489 [M + H]+ |
| 180 | 6-Methyl-3-[1-[6-methyl-2-(2-methylindazol-5-yl)-4-oxo-chromen-8-yl]ethylamino]pyridine-2-carboxylic acid, Isomer 2 | 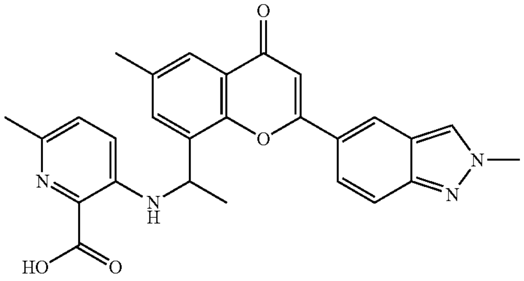 | 469 [M + H]+ |

TABLE 47-continued

| Ex # | Chemical Name | Structure | MS ES+ mz |
|---|---|---|---|
| 181 | 6-Chloro-3-[1-[3,6-dimethyl-2-(2-methylindazol-5-yl)-4-oxo-chromen-8-yl]ethylamino]pyridine-2-carboxylic acid, Isomer 2 | 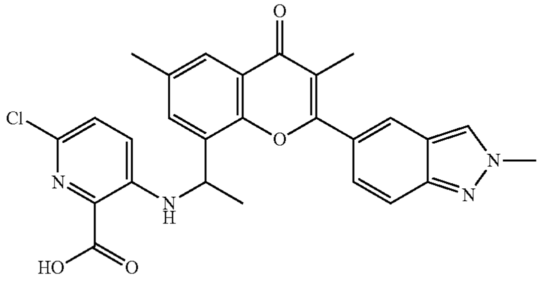 [SMILES: Cc1cc(C(C)Nc2ccc(Cl)nc2C(=O)O)c2oc(-c3ccc4nn(C)cc4c3)c(C)c(=O)c2c1] | 503 [M + H]+ |
| 189 | 2-Fluoro-6-[1-[6-methyl-2-(1-methylindazol-3-yl)-4-oxo-chromen-8-yl]ethylamino]benzoic acid, Isomer 2 | 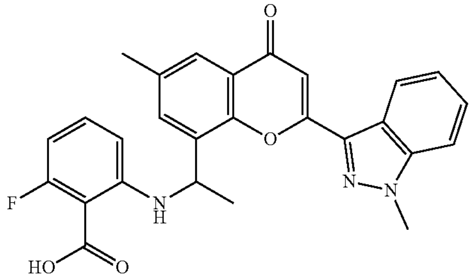 [SMILES: Cc1cc(C(C)Nc2cccc(F)c2C(=O)O)c2oc(-c3nn(C)c4ccccc34)cc(=O)c2c1] | 472 [M + H]+ |
| 190 | 2-[1-[2-(2,7-Dimethylindazol-5-yl)-6-methyl-4-oxo-chromen-8-yl]ethylamino]-6-fluoro-benzoic acid, Isomer 2 | 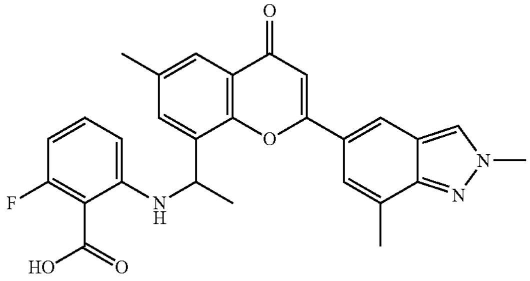 [SMILES: Cc1cc(C(C)Nc2cccc(F)c2C(=O)O)c2oc(-c3cc(C)c4nn(C)cc4c3)cc(=O)c2c1] | 486 [M + H]+ |
| 225[a] | 6-Methyl-3-[[(1R)-1-[6-methyl-2-(2-methylimidazo[1,2-a]pyridin-6-yl)-4-oxo-chromen-8-yl]ethyl]amino]pyridine-2-carboxylic acid | 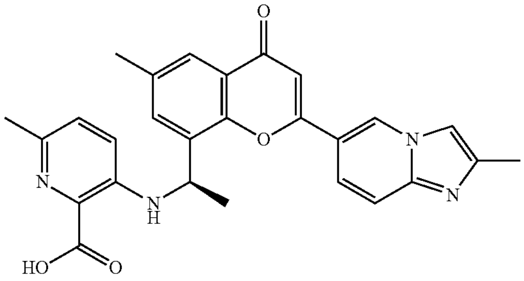 | 469 [M + H]+ |
| 226 | 3-[[(1R)-1-[6-Methyl-2-(2-methylindazol-5-yl)-4-oxo-chromen-8-yl]ethyl]amino]pyridine-2-carboxylic acid | 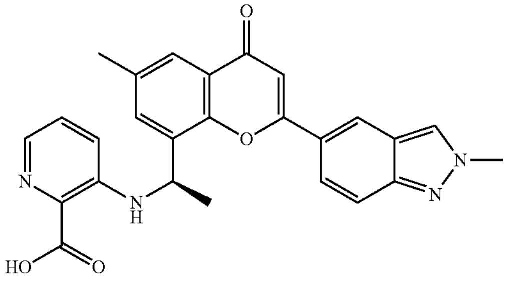 | 455 [M + H]+ |

TABLE 47-continued

| Ex # | Chemical Name | Structure | MS ES+ mz |
|---|---|---|---|
| 227[a] | 2-[[(1R)-1-[3,6-Dimethyl-2-(2-methylindazol-5-yl)-4-oxo-chromen-8-yl]ethyl]amino]-6-fluoro-benzoic acid | 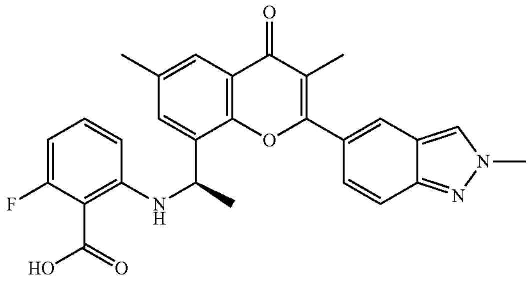 [SMILES: Cc1cc([C@@H](C)Nc2cccc(F)c2C(=O)O)c2oc(-c3ccc4nn(C)cc4c3)c(C)c(=O)c2c1] | 486 [M + H]+ |
| 228[a] | 2-Fluoro-6-[[(1R)-1-[6-methyl-2-(2-methylimidazo[1,2-a]pyridin-6-yl)-4-oxo-chromen-8-yl]ethyl]amino]benzoic acid | 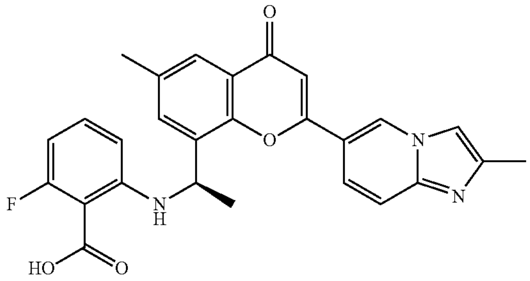 [SMILES: Cc1cc([C@@H](C)Nc2cccc(F)c2C(=O)O)c2oc(-c3ccc4nc(C)cn4c3)cc(=O)c2c1] | 472 [M + H]+ |
| 229[a] | 2-[[(1R)-1-[3,6-Dimethyl-2-(2-methylimidazo[1,2-a]pyridin-6-yl)-4-oxo-chromen-8-yl]ethyl]amino]-6-fluoro-benzoic acid | 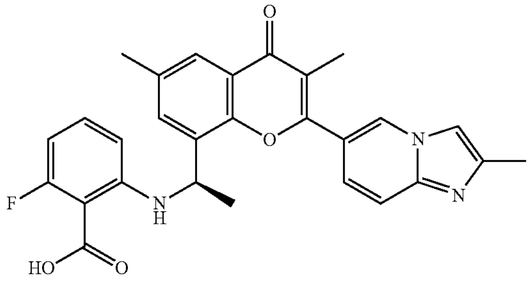 [SMILES: Cc1cc([C@@H](C)Nc2cccc(F)c2C(=O)O)c2oc(-c3ccc4nc(C)cn4c3)c(C)c(=O)c2c1] | 486 [M + H]+ |
| 230[a] | 2-[[(1R)-1-[3,6-Dimethyl-2-(1-methylindazol-3-yl)-4-oxo-chromen-8-yl]ethyl]amino]-6-fluoro-benzoic acid | 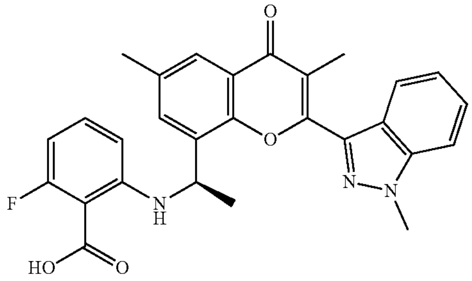 [SMILES: Cc1cc([C@@H](C)Nc2cccc(F)c2C(=O)O)c2oc(-c3nn(C)c4ccccc34)c(C)c(=O)c2c1] | 486 [M + H]+ |
| 231 | 3-[[(1R)-1-[2-(2,7-Dimethylindazol-5-yl)-6-methyl-4-oxo-chromen-8-yl]ethyl]amino]pyridine-2-carboxylic acid | 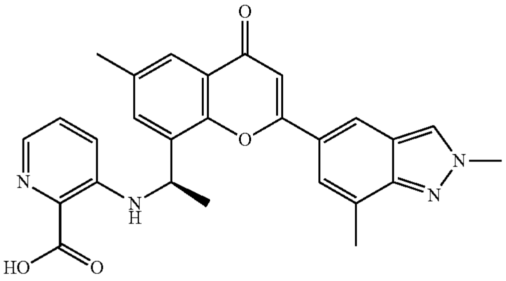 [SMILES: Cc1cc([C@@H](C)Nc2cccnc2C(=O)O)c2oc(-c3cc(C)c4nn(C)cc4c3)cc(=O)c2c1] | 469 [M + H]+ |

TABLE 47-continued

| Ex # | Chemical Name | Structure | MS ES+ mz |
|---|---|---|---|
| 232 | 3-[[(1R)-1-[6-Methyl-2-(1-methylindazol-3-yl)-4-oxo-chromen-8-yl]ethyl]amino]pyridine-2-carboxylic acid | 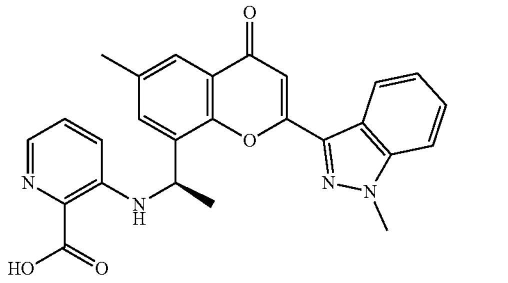 [SMILES: Cc1cc([C@@H](C)Nc2cccnc2C(=O)O)c2oc(-c3nn(C)c4ccccc34)cc(=O)c2c1] | 455 [M + H]+ |
| 233[a] | 3-[[(1R)-1-[3,6-Dimethyl-2-(2-methylthiazolo[5,4-b]pyridin-5-yl)-4-oxo-chromen-8-yl]ethyl]amino]-6-(trifluoromethyl)pyridine-2-carboxylic acid | 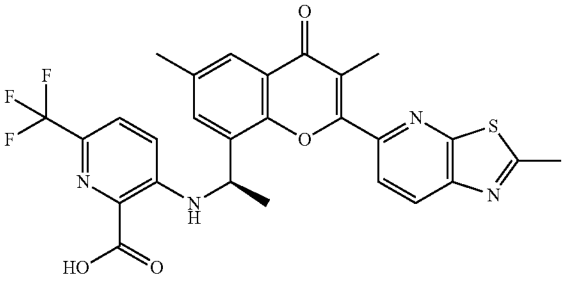 [SMILES: Cc1cc([C@@H](C)Nc2ccc(C(F)(F)F)nc2C(=O)O)c2oc(-c3ccc4nc(C)sc4n3)c(C)c(=O)c2c1] | 555 $[M + H]^+$ |
| 234[a] | 2-[[(1R)-1-[3,6-Dimethyl-2-(2-methylthiazolo[5,4-b]pyridin-5-yl)-4-oxo-chromen-8-yl]ethyl]amino]-5-(trifluoromethyl)benzoic acid | 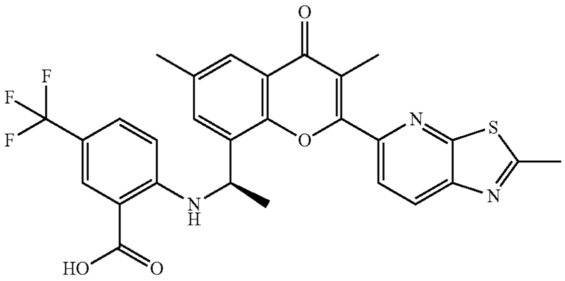 [SMILES: Cc1cc([C@@H](C)Nc2ccc(C(F)(F)F)cc2C(=O)O)c2oc(-c3ccc4nc(C)sc4n3)c(C)c(=O)c2c1] | 554 $[M + H]^+$ |
| 235[a] | 2-[[(1R)-1-[3,6-Dimethyl-2-(2-methylindazol-5-yl)-4-oxo-chromen-8-yl]ethyl]amino]-5-(trifluoromethyl)benzoic acid | 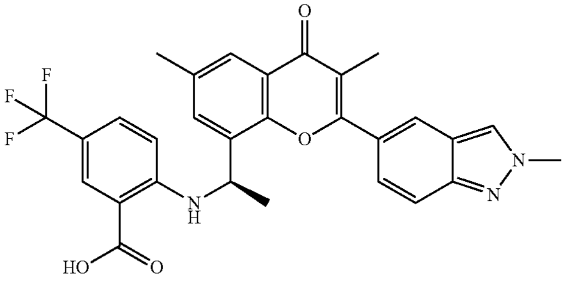 [SMILES: Cc1cc([C@@H](C)Nc2ccc(C(F)(F)F)cc2C(=O)O)c2oc(-c3ccc4nn(C)cc4c3)c(C)c(=O)c2c1] | 536 $[M + H]^+$ |
| 236[a] | 3-[[(1R)-1-[3,6-Dimethyl-2-(2-methylindazol-5-yl)-4-oxo-chromen-8-yl]ethyl]amino]-6-(trifluoromethyl)pyridine-2-carboxylic acid | 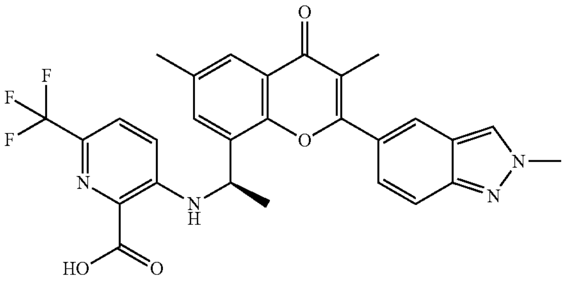 | 537 $[M + H]^+$ |

TABLE 47-continued

| Ex # | Chemical Name | Structure | MS ES+ mz |
|---|---|---|---|
| 237[a] | 5-Chloro-2-[[(1R)-1-[6-methyl-2-(1-methylindazol-6-yl)-4-oxo-chromen-8-yl]ethyl]amino]benzoic acid | 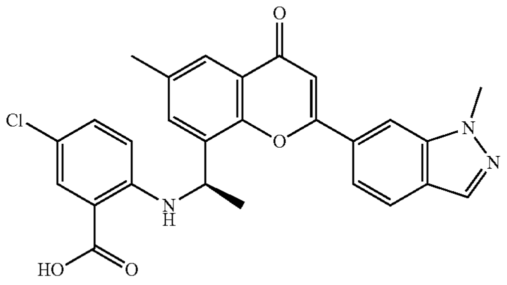 [SMILES: Cc1cc([C@@H](C)Nc2ccc(Cl)cc2C(=O)O)c2oc(-c3ccc4cnn(C)c4c3)cc(=O)c2c1] | 488 [M + H]+ |
| 238[a] | 5-Fluoro-2-[[(1R)-1-[6-methyl-2-(1-methylindazol-6-yl)-4-oxo-chromen-8-yl]ethyl]amino]benzoic acid | 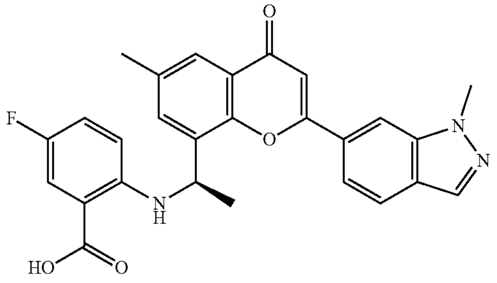 [SMILES: Cc1cc([C@@H](C)Nc2ccc(F)cc2C(=O)O)c2oc(-c3ccc4cnn(C)c4c3)cc(=O)c2c1] | 472 [M + H]+ |
| 239[a] | 3-[[(1R)-1-[6-Methyl-2-(2-methylthiazolo[5,4-b]pyridin-5-yl)-4-oxo-chromen-8-yl]ethyl]amino]pyridine-2-carboxylic acid | 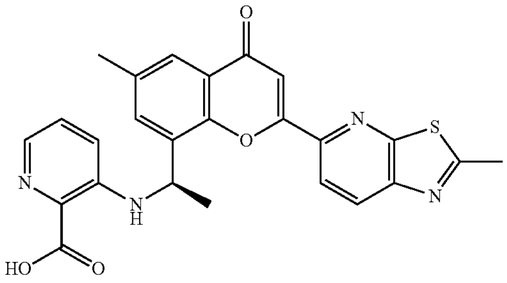 [SMILES: Cc1cc([C@@H](C)Nc2cccnc2C(=O)O)c2oc(-c3ccc4nc(C)sc4n3)cc(=O)c2c1] | 473 [M + H]+ |
| 240[a] | 3-[[(1R)-1-[3,6-Dimethyl-2-(2-methylindazol-5-yl)-4-oxo-chromen-8-yl]ethyl]amino]pyridine-2-carboxylic acid | 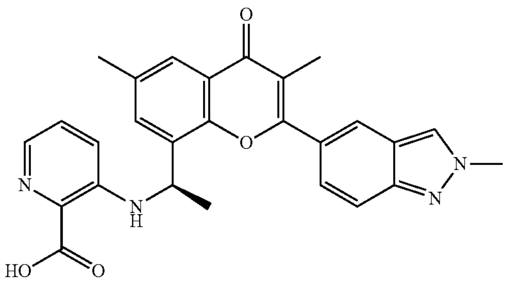 [SMILES: Cc1cc([C@@H](C)Nc2cccnc2C(=O)O)c2oc(-c3ccc4nn(C)cc4c3)c(C)c(=O)c2c1] | 469 [M + H]+ |
| 241[a] | 2-Fluoro-6-[[(1R)-1-[6-methyl-4-oxo-2-(1H-pyrrolo[2,3-b]pyridin-6-yl)chromen-8-yl]ethyl]amino]benzoic acid | 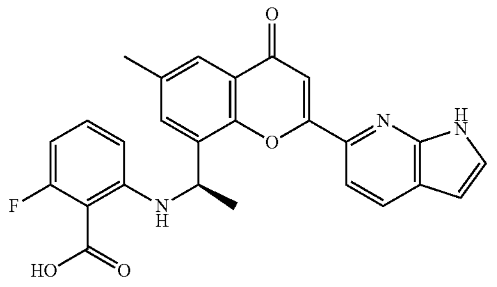 [SMILES: Cc1cc([C@@H](C)Nc2cccc(F)c2C(=O)O)c2oc(-c3ccc4cc[nH]c4n3)cc(=O)c2c1] | 458 [M + H]+ |

TABLE 47-continued

| Ex # | Chemical Name | Structure | MS ES+ mz |
|---|---|---|---|
| 242[a] | 6-Chloro-3-[[(1R)-1-[3,6-dimethyl-2-(2-methylthiazolo[5,4-b]pyridin-5-yl)-4-oxo-chromen-8-yl]ethyl]amino]pyridine-2-carboxylic acid | 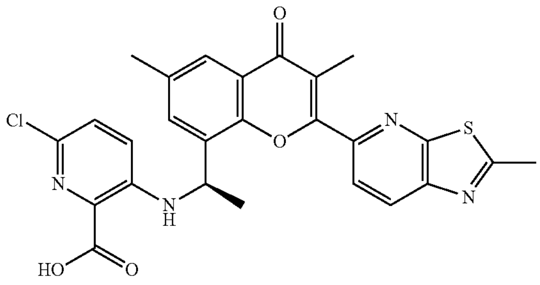 [SMILES: Cc1cc([C@@H](C)Nc2ccc(Cl)nc2C(=O)O)c2oc(-c3ccc4nc(C)sc4n3)c(C)c(=O)c2c1] | 521 $[M + H]^+$ |
| 243[a] | 3-[[(1R)-1-[3,6-Dimethyl-2-(2-methylthiazolo[5,4-b]pyridin-5-yl)-4-oxo-chromen-8-yl]ethyl]amino]pyridine-2-carboxylic acid | 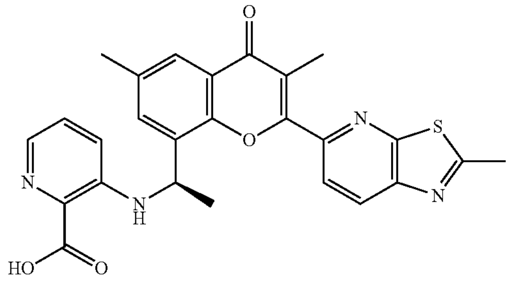 [SMILES: Cc1cc([C@@H](C)Nc2cccnc2C(=O)O)c2oc(-c3ccc4nc(C)sc4n3)c(C)c(=O)c2c1] | 487 $[M + H]^+$ |
| 244[a] | 6-Bromo-3-[[(1R)-1-[3,6-dimethyl-2-(2-methylindazol-5-yl)-4-oxo-chromen-8-yl]ethyl]amino]pyridine-2-carboxylic acid | 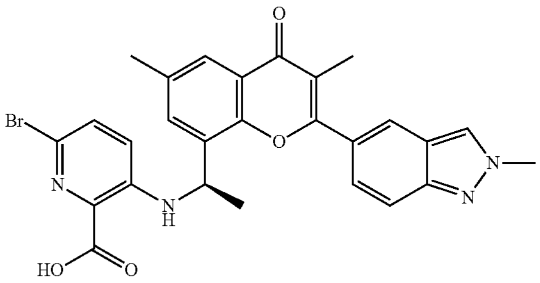 | 549 $[M + H]^+$ |
| 245[a] | 6-Bromo-3-[[(1R)-1-[3,6-dimethyl-2-(2-methylthiazolo[5,4-b]pyridin-5-yl)-4-oxo-chromen-8-yl]ethyl]amino]pyridine-2-carboxylic acid | 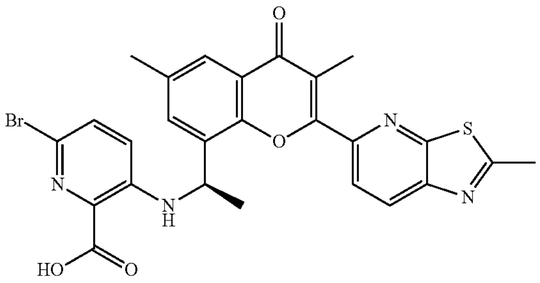 [SMILES: Cc1cc([C@@H](C)Nc2ccc(Br)nc2C(=O)O)c2oc(-c3ccc4nc(C)sc4n3)c(C)c(=O)c2c1] | 567 $[M + H]^+$ |
| 246[a] | 6-Chloro-3-[[(1R)-1-[3,6-dimethyl-2-(2-methyl-l,3-benzothiazol-6-yl)-4-oxo-chromen-8-yl]ethyl]amino]pyridine-2-carboxylic acid | 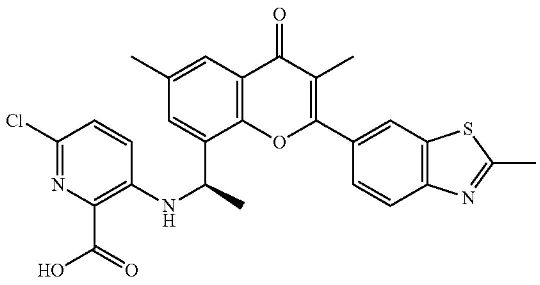 | 520 $[M + H]^+$ |

TABLE 47-continued

| Ex # | Chemical Name | Structure | MS ES+ mz |
|---|---|---|---|
| 247[a] | 6-Chloro-3-[[(1R)-1-[3,6-dimethyl-4-oxo-2-(1H-pyrrolo[2,3-b]pyridin-2-yl)chromen-8-yl]ethyl]amino]pyridine-2-carboxylic acid | 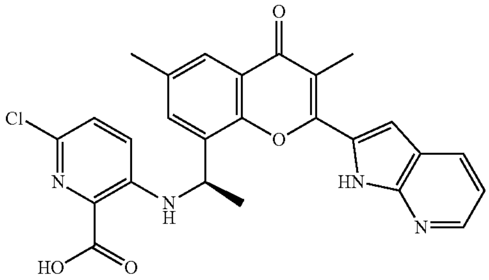 [SMILES: Cc1cc([C@@H](C)Nc2ccc(Cl)nc2C(=O)O)c2oc(-c3cc4cccnc4[nH]3)c(C)c(=O)c2c1] | 489 $[M + H]^+$ |
| 248[a] | 2-[[(1R)-1-[2-(2-Methoxy-8-methyl-6-quinolyl)-6-methyl-4-oxo-chromen-8-yl]ethyl]amino]benzoic acid | 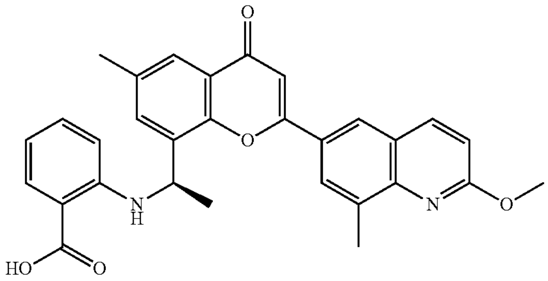 [SMILES: COc1ccc2cc(-c3cc(=O)c4cc(C)cc([C@@H](C)Nc5ccccc5C(=O)O)c4o3)cc(C)c2n1] | 495 $[M + H]^+$ |
| 249 | 2-[[(1R)-1-[2-(2-Methoxy-6-quinolyl)-6-methyl-4-oxo-chromen-8-yl]ethyl]amino]benzoic acid | 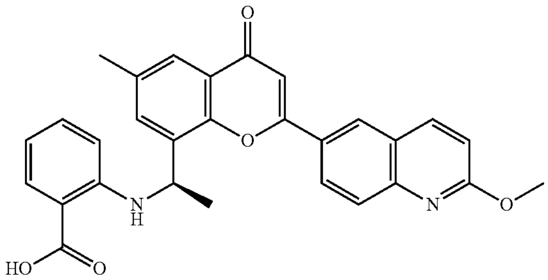 | 481 $[M + H]^+$ |
| 250[a] | 6-Methyl-3-[[(1R)-1-[6-methyl-2-(2-methylthiazolo[5,4-b]pyridin-5-yl)-4-oxo-chromen-8-yl]ethyl]amino]pyridine-2-carboxylic acid | 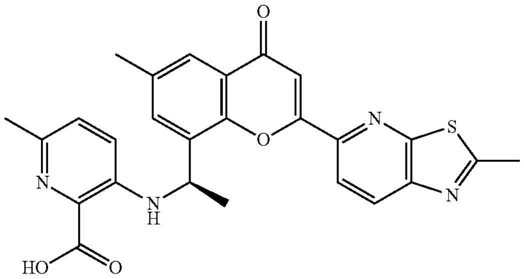 | 487 $[M + H]^+$ |
| 251[a] | 6-Chloro-3-[[(1R)-1-[6-methyl-2-(2-methylthiazolo[5,4-b]pyridin-5-yl)-4-oxo-chromen-8-yl]ethyl]amino]pyridine-2-carboxylic acid | 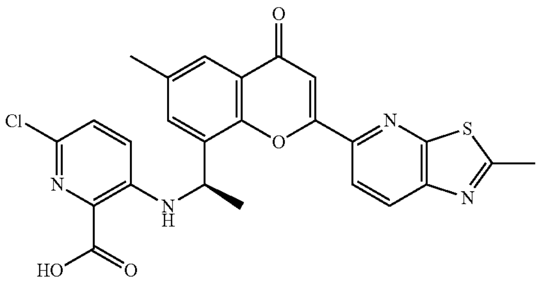 [SMILES: Cc1cc([C@@H](C)Nc2ccc(Cl)nc2C(=O)O)c2oc(-c3ccc4nc(C)sc4n3)cc(=O)c2c1] | 507 $[M + H]^+$ |

[a]The base used in this hydrolysis was $LiOH \cdot H_2O$.

Example 191 and Example 192: 6-Chloro-3-[1-[2-(2,7-dimethylindazol-5-yl)-4-oxo-6-(trifluoromethyl)chromen-8-yl]ethylamino]pyridine-2-carboxylic acid, Isomer 1 and Isomer 2

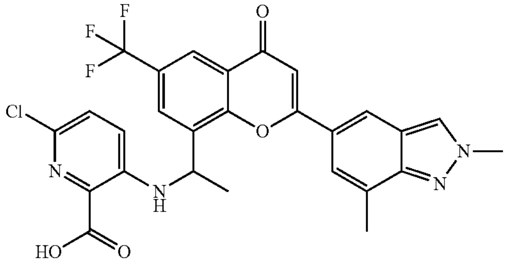 [SMILES: Cc1cc(-c2cc(=O)c3cc(C(F)(F)F)cc(C(C)Nc4ccc(Cl)nc4C(=O)O)c3o2)cc2cn(C)nc12]

6-Chloro-3-[1-[2-(2,7-dimethylindazol-5-yl)-4-oxo-6-(trifluoromethyl)chromen-8-yl]ethylamino]pyridine-2-carboxylic acid was separated by chiral HPLC using a Chiralcel OD column (20×150 mm; 5 um) eluted with a gradient of 20% to 60% EtOH (with 0.05% TFA) in hexane (with 0.05% TFA) to give Isomer 1 (4.2 mg, 97.7% purity with 2.3% other isomer) and Isomer 2 (1.2 mg; 94% purity with 6% other isomer). For both, MS ES+ m/z 557 $[M+H]^+$.

The following compounds in Table 48 were made in a similar way as described for Example 191 and Example 192.

Example 182 and Example 183: 3-Chloro-2-fluoro-6-[1-[6-methyl-2-(2-methylimidazo[1,2-a]pyridin-3-yl)-4-oxo-chromen-8-yl]ethylamino]benzoic acid, Isomer 2 and 3-chloro-2-fluoro-6-[1-[6-methyl-2-(2-methylimidazo[1,2-a]pyridin-6-yl)-4-oxo-chromen-8-yl]ethylamino]benzoic acid, Isomer 2

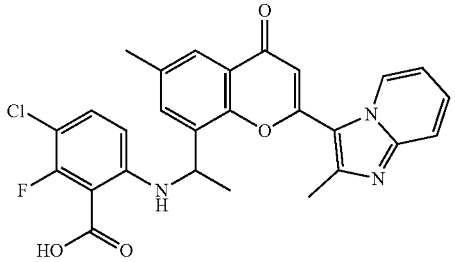

and

TABLE 48

| Ex # | Chemical Name | Structure | MS ES+ m/z |
|---|---|---|---|
| 193 | 6-Chloro-3-[1-[2-(7-chloro-2-methyl-indazol-5-yl)-4-oxo-6-(trifluoromethyl)chromen-8-yl]ethylamino]pyridine-2-carboxylic acid, Isomer 1 | 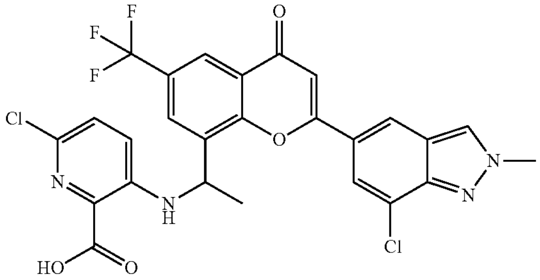 [SMILES: CC(Nc1ccc(Cl)nc1C(=O)O)c1cc(C(F)(F)F)cc2c(=O)cc(-c3cc(Cl)c4nn(C)cc4c3)oc12] | 577/579 $[M + H]^+$ |
| 194 | 6-Chloro-3-[1-[2-(7-chloro-2-methyl-indazol-5-yl)-4-oxo-6-(trifluoromethyl)chromen-8-yl]ethylamino]pyridine-2-carboxylic acid, Isomer 2 | 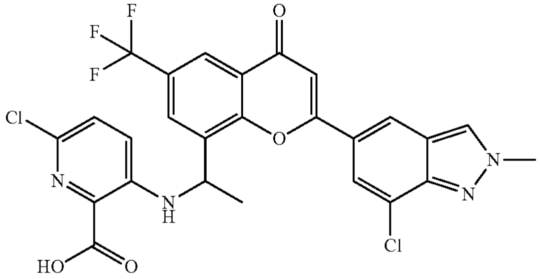 [SMILES: CC(Nc1ccc(Cl)nc1C(=O)O)c1cc(C(F)(F)F)cc2c(=O)cc(-c3cc(Cl)c4nn(C)cc4c3)oc12] | 577/579 $[M + H]^+$ |

-continued

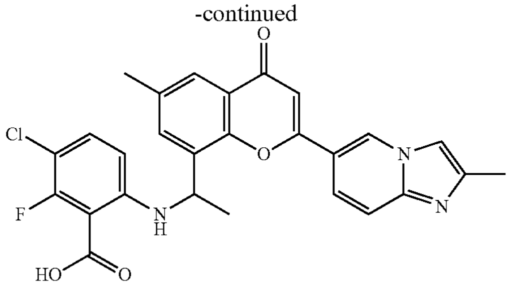

A mixture of methyl 3-chloro-2-fluoro-6-[1-[6-methyl-2-(2-methylimidazo[1,2-a]pyridin-6-yl)-4-oxo-chromen-8-yl]ethylamino]benzoate, Isomer 2 (0.03 g, 0.058 mmol) in tetrahydrofuran (0.6 mL) and methanol (0.2 mL) was treated with 1M aqueous sodium hydroxide (0.2 mL) and stirred at 45° for 1 h. This reaction was combined with a second reaction of the same amount, the pH adjusted to 4 with 2M aqueous hydrogen chloride, and concentrated. The residue was purified by prep HPLC using ammonium hydroxide as an additive giving the products Example 182 (3.21 mg, 11%) and Example 183 (3.16 mg, 9%) as light yellow solids. For both, MS ES+ m/z 506 $[M+H]^+$.

The following compound in Table 49 was made in a similar way as described for Example 182 and Example 183.

A mixture of $PBr_3$ (174.45 mg, 0.644 mmol) in DCM (0.5 mL) was added to a mixture of methyl 2-[1-(6-methyl-4-oxo-2-phthalazin-6-yl-chromen-8-yl)ethylamino]benzoate, Isomer 2 (100 mg, 0.214 mmol) in DCM (0.5 mL) and stirred at −78° C. for 40 h to give a brown/black suspension. Poured the reaction into water (10 mL) and extracted with DCM (3×10 mL). The combined organic layers were washed with brine (20 mL), dried over anhydrous $Na_2SO_4$, filtered, and concentrated to a residue. The residue was purified via preparative HPLC (Waters Xbridge BEH C18 100×25 mm column) eluted with 24%-44% acetonitrile in water with 0.225% formic acid giving the product as a light yellow solid (3.25 mg, 3.3%). MS ES+ m/z 452 $[M+H]^+$.

Example 252: 2-[1-[6-Methyl-2-(1,5-naphthyridin-2-yl)-4-oxo-chromen-8-yl]ethylamino]benzoic acid, Isomer 2

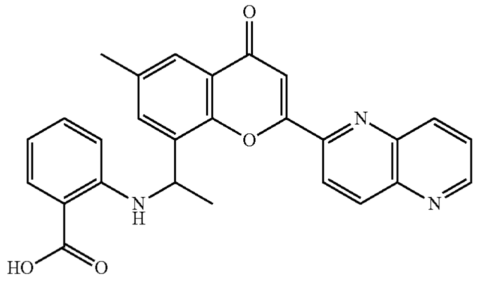

TABLE 49

| Ex # | Chemical Name | Structure | MS ES+ m/z |
|---|---|---|---|
| 184 | 3-Chloro-2-fluoro-6-[1-[6-methyl-2-(2-methylindazol-5-yl)-4-oxo-chromen-8-yl]ethylamino]benzoic acid, Isomer 2 | 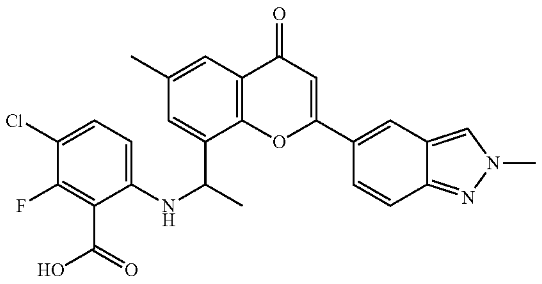 [SMILES: Cc1cc(C(C)Nc2ccc(Cl)c(F)c2C(=O)O)c2oc(-c3ccc4nn(C)cc4c3)cc(=O)c2c1] | 506 $[M + H]^+$ |

Example 47: 2-[1-(6-Methyl-4-oxo-2-phthalazin-6-yl-chromen-8-yl)ethylamino]benzoic acid, Isomer 2

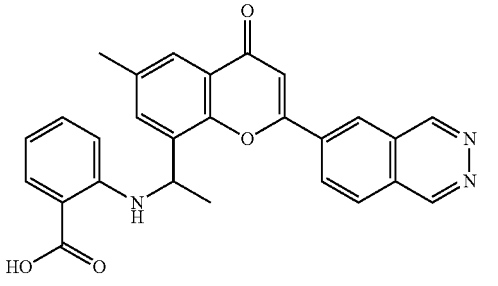 [SMILES: Cc1cc(C(C)Nc2ccccc2C(=O)O)c2oc(-c3ccc4cnncc4c3)cc(=O)c2c1]

A solution of methyl 2-[1-[6-methyl-2-(1,5-naphthyridin-2-yl)-4-oxo-chromen-8-yl]ethylamino]benzoate, isomer 2 (30 mg, 0.06 mmol) in 1 mL of dichloromethane was cooled to 0° C. and treated with boron tribromide (32.29 mg, 0.13 mmol). After stirring at 15° C. for 2 h, another aliquot of boron tribromide (16 mg) was added and the reaction stirred at 15° C. for another 12 h. The reaction was poured into 20 mL of water and extracted with EtOAc (3×50 mL). The combined organic layers were washed with brine (3×50 mL), dried over $Na_2SO_4$, filtered, and concentrated. The resulting residue was purified by prep-HPLC (Boston Green ODS 150×30 mm column [5 μm] eluted with 45% to 75% AcCN in water (with formic acid) to give the product (1.49 mg, 5%) as a white solid. MS ES+ m/z 452 $[M+H]^+$.

Example 48: 2-[1-(6-Methyl-4-oxo-2-pyrazolo[4,3-b]pyridin-1-yl-chromen-8-yl)ethylamino]benzoic acid, Isomer 2; 2,2,2-trifluoroacetic acid

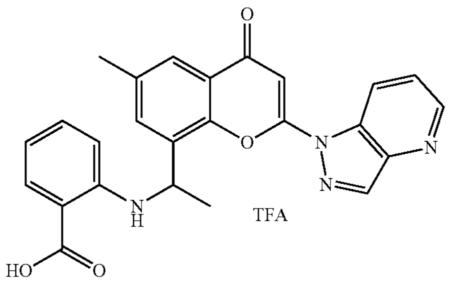 [SMILES: Cc1cc(C(C)Nc2ccccc2C(=O)O)c2oc(-n3ncc4ncccc43)cc(=O)c2c1]

1H-Pyrazolo[4,3-b]pyridine (38 mg, 0.32 mmol) was transferred to a 20 mL vial and dissolved in THE (1 mL) at 0° C. After cooling, the reaction was treated with sodium hydride (13 mg, 60% wt, 0.32 mmol) and allowed to stir at 0° for 15 min. Added 2-[1-(2-ethylsulfinyl-6-methyl-4-oxo-chromen-8-yl)ethylamino]benzoic acid, Isomer 2 (60 mg, 0.15 mmol) and allowed the reaction to stir for 20 min. Concentrated the reaction to a residue and purified via reverse phase C-18 chromatography eluted with 5%-95% acetonitrile in water with 0.1% TFA to give the product as a trifluoroacetate salt (18.6 mg, 22%). MS ES+ m/z 441 $[M+H]^+$.

The following compounds in Table 50 were made in a similar way as described for Example 48.

TABLE 50

| Ex # | Chemical Name | Structure | MS ES+ m/z |
|---|---|---|---|
| 84 | 2-[1-[2-(Benzimidazol-1-yl)-6-methyl-4-oxo-chromen-8-yl]ethylamino]benzoic acid, Isomer 2; 2,2,2-trifluoroacetic acid | 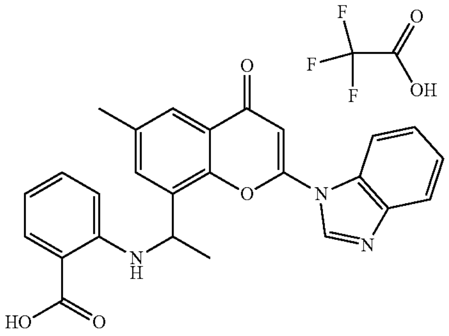 | 440 $[M + H]^+$ |
| 85 | 2-[1-[2-(Benzotriazol-1-yl)-6-methyl-4-oxo-chromen-8-yl]ethylamino]benzoic acid, Isomer 2; 2,2,2-trifluoroacetic acid | 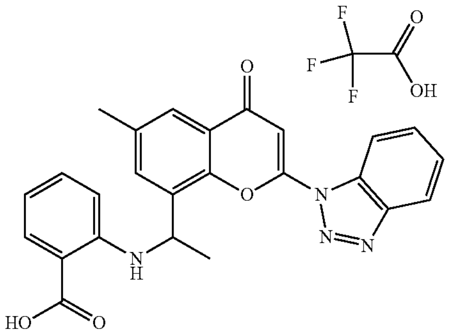 | 441 $[M + H]^+$ |

Example 185: 3-[1-[2-(1H-Indol-2-yl)-4-oxo-6-(trifluoromethyl)chromen-8-yl]ethylamino]pyridine-2-carboxylic acid; 2,2,2-trifluoroacetic acid

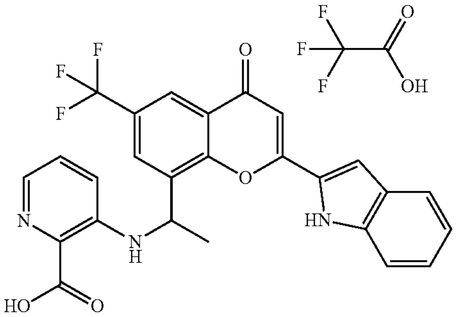

8-(1-Bromoethyl)-2-(1H-indol-2-yl)-6-(trifluoromethyl) chromen-4-one (0.28 g, 0.64 mmol) and tert-butyl 3-aminopyridine-2-carboxylate (0.19 g, 0.95 mmol) were dissolved in DMF (5 mL) and stirred at 80° C. overnight. The reaction was concentrated and the residue purified by preparative HPLC eluted with 10% to 70% AcCN (0.1% TFA) in water (0.1% TFA) giving the product (6.8 mg, 2.2%). MS ES+ m/z 494 $[M+H]^+$.

Example 49: 2-[1-(2-Indazol-1-yl-6-methyl-4-oxo-chromen-8-yl)ethylamino]benzoic acid, Isomer 2; 2,2,2-trifluoroacetic acid

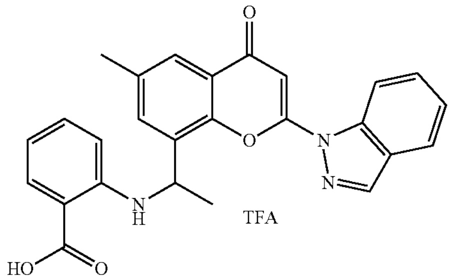 [SMILES: Cc1cc(C(C)Nc2ccccc2C(=O)O)c2oc(-n3ncc4ccccc43)cc(=O)c2c1]

2-[1-(2-Ethylsulfinyl-6-methyl-4-oxo-chromen-8-yl)ethylamino]benzoic acid, Isomer 2 (100.2 mg, 0.25 mmol), 2H-indazole HCl (90.7 mg, 0.58 mmol), and DIEA (227 mg, 0.31 mL, 1.76 mmol) were combined with acetonitrile (10 mL) in a 20 mL vial and stirred at 80° C. for 48 h. Concentrated the reaction to a residue and purified via reverse phase chromatography eluted with 5%-95% acetonitrile in water with 0.1% TFA to produce the product (14.8 mg, 13%). MS ES+ m/z 440 $[M+H]^+$.

The following compounds in Table 51 were made in a similar way as described for Example 49.

TABLE 51

| Ex # | Chemical Name | Structure | MS ES+ m/z |
|---|---|---|---|
| 50 | 2-[1-(2-Indazol-2-yl-6-methyl-4-oxo-chromen-8-yl)ethylamino]benzoic acid, Isomer 2; 2,2,2-trifluoroacetic acid | 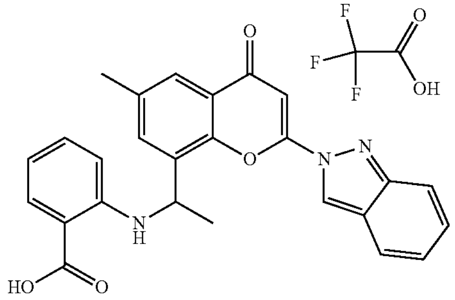 | 440 $[M + H]^+$ |
| 86[a] | 2-1-[2-(4-Fluoroindazol-1-yl)-6-methyl-4-oxo-chromen-8-yl]ethylamino]benzoic acid, Isomer 2; 2,2,2-trifluoroacetic acid | 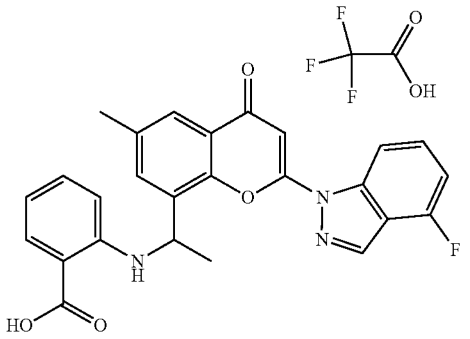 | 458 $[M + H]^+$ |

TABLE 51-continued

| Ex # | Chemical Name | Structure | MS ES+ m/z |
|---|---|---|---|
| 87[a] | 2-[1-[6-Methyl-2-(5-methylindazol-1-yl)-4-oxo-chromen-8-yl]ethylamino]benzoic acid, Isomer 2; 2,2,2-trifluoroacetic acid | 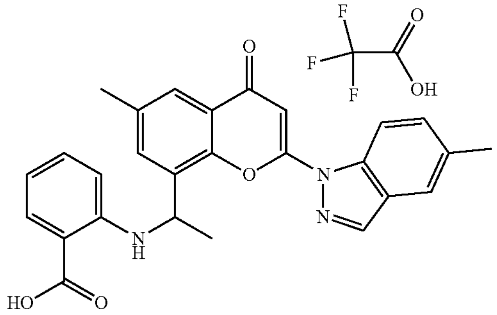 | 454 [M + H]$^+$ |
| 88[a] | 2-[1-[6-Methyl-2-(4-methylindazol-1-yl)-4-oxo-chromen-8-yl]ethylamino]benzoic acid, Isomer 2; 2,2,2-trifluoroacetic acid | 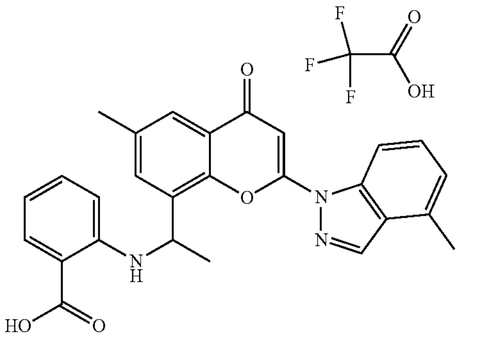 | 454 [M + H]$^+$ |
| 89[a] | 2-[1-[2-(5-Fluoroindazol-1-yl)-6-methyl-4-oxo-chromen-8-yl]ethylamino]benzoic acid, Isomer 2; 2,2,2-trifluoroacetic acid | 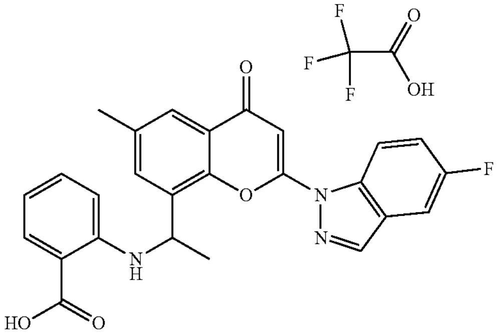 | 458 [M + H]$^+$ |

[a]1,8-Diazabicyclo[5.4.0]undec-7-ene (DBU) used as base.

Example 90: 2-[1-[2-(1H-Indol-6-yl)-3,6-dimethyl-4-oxo-chromen-8-yl]ethylamino]benzoic acid, Isomer 2

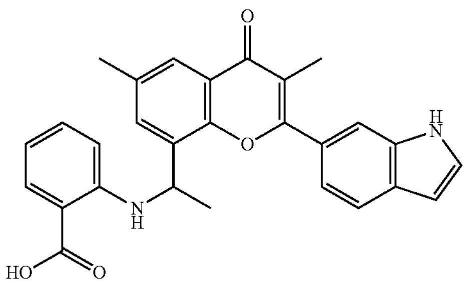

A mixture of 2-[1-(2-ethylsulfanyl-3,6-dimethyl-4-oxo-chromen-8-yl)ethylamino]benzoic acid, Isomer 2 (100 mg, 0.25 mmol), 1H-indol-6-ylboronic acid (121.5 mg, 0.75 mmol), copper(I) thiophene-2-carboxylate (143.9 mg, 0.75 mmol), sodium tert-butoxide (72.5 mg, 0.75 mmol) and BrettPhos Pd G3 (68.4 mg, 0.075 mmol) in 2-methyltetrahydrofuran (0.5 mL) was stirred under nitrogen at 85° C. for 40 h to give a suspension. Cooled the reaction and added 4 mL of aqueous 2,4,6-trimercapto-1,3,5-triazine and stirred for 2 h. Filtered, concentrated, diluted with 3 mL of DMSO and 0.5 mL of THF, and filtered again. The filtrate was purified by preparative HPLC (HCl used as an additive) to give the product as a light yellow solid (14.3 mg, 12.4%). MS ES+ m/z 453 [M+H]$^+$.

The following compounds in Table 52 were made in a similar way as described for Example 90.

TABLE 52

| Ex # | Chemical Name | Structure | MS ES+ m/z |
|---|---|---|---|
| 91 | 2-[1-[3,6-Dimethyl-2-(2-methylindazol-5-yl)-4-oxo-chromen-8-yl]ethylamino]benzoic acid, Isomer 2 | 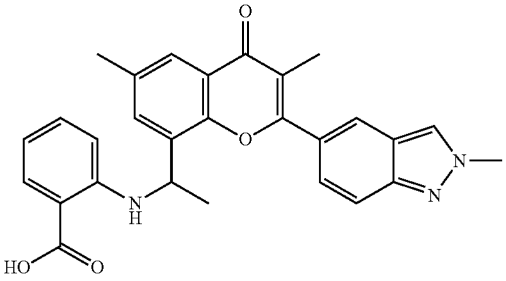 [SMILES: Cc1cc(C(C)Nc2ccccc2C(=O)O)c2oc(-c3ccc4nn(C)cc4c3)c(C)c(=O)c2c1] | 468 [M + H]+ |
| 92 | 2-[1-[2-(1,3-Benzodioxol-4-yl)-3,6-dimethyl-4-oxo-chromen-8-yl]ethylamino]benzoic acid, Isomer 2 | 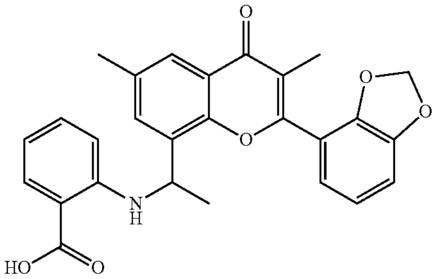 [SMILES: Cc1cc(C(C)Nc2ccccc2C(=O)O)c2oc(-c3cccc4c3OCO4)c(C)c(=O)c2c1] | 458 [M + H]+ |
| 93 | 2-[1-[2-(1,3-Benzodioxol-5-yl)-3,6-dimethyl-4-oxo-chromen-8-yl]ethylamino]benzoic acid, Isomer 2 | 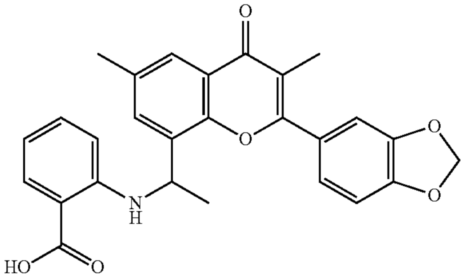 [SMILES: Cc1cc(C(C)Nc2ccccc2C(=O)O)c2oc(-c3ccc4c(c3)OCO4)c(C)c(=O)c2c1] | 458 [M + H]+ |
| 186 | 2-[1-[3,6-Dimethyl-4-oxo-2-[2-(trifluoromethyl)imidazo[1,2-a]pyridin-6-yl]chromen-8-yl]ethylamino]benzoic acid, Isomer 2 | 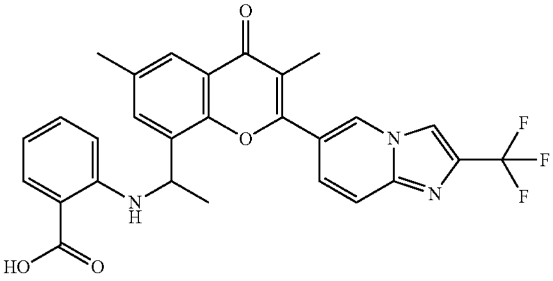 [SMILES: Cc1cc(C(C)Nc2ccccc2C(=O)O)c2oc(-c3ccc4nc(C(F)(F)F)cn4c3)c(C)c(=O)c2c1] | 522 [M + H]+ |
| 253 | 2-[[(1R)-1-[3,6-Dimethyl-2-(2-methylindazol-5-yl)-4-oxo-chromen-8-yl]ethyl]amino]-5-fluoro-benzoic acid | 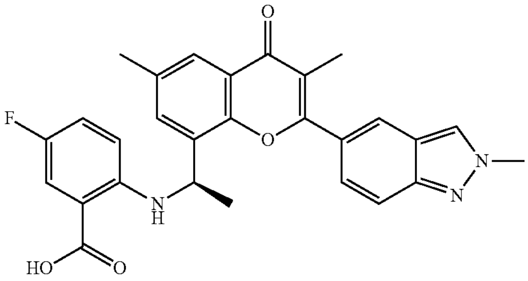 [SMILES: Cc1cc([C@@H](C)Nc2ccc(F)cc2C(=O)O)c2oc(-c3ccc4nn(C)cc4c3)c(C)c(=O)c2c1] | 486 [M + H]+ |

Example 254: 2-[[(1R)-1-[3,6-Dimethyl-2-(2-methylthiazolo[5,4-b]pyridin-5-yl)-4-oxo-chromen-8-yl]ethyl]amino]-5-fluoro-benzoic acid

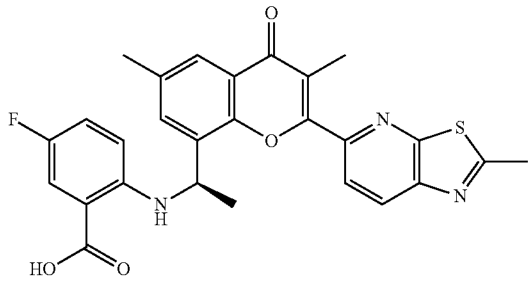 [SMILES: Cc1cc([C@@H](C)Nc2ccc(F)cc2C(=O)O)c2oc(-c3ccc4nc(C)sc4n3)c(C)c(=O)c2c1]

A mixture of 2-[[(1R)-1-(2-ethylsulfanyl-3,6-dimethyl-4-oxo-chromen-8-yl)ethyl]amino]-5-fluoro-benzoic acid (100 mg, 0.24 mmol) 5-chloro-2-methyl-thiazolo[5,4-b]pyridine (133.33 mg, 0.72 mmol), bis(pinacoloto)diboron (244.48 mg, 0.96 mmol), copper(I) thiophene-2-carboxylate (137.69 mg, 0.72 mmol), BrettPhos Pd G3 (21.82 mg, 0.02 mmol), [1,3-bis(diphenylphosphino)propane]dichloronickel(II) (13.05 mg, 0.02 mmol), sodium tert-butoxide (115.65 mg, 1.2 mmol) in 1,4-dioxane (4 mL) was stirred under $N_2$ for 16 h. Added a suspension of all starting materials except the chromene in the same amounts in 4 mL of 1,4-dioxane and stirred at 110° C. for 16 h. The black suspension was cooled, concentrated, and the resulting residue diluted with dichloromethane (20 mL) and water (20 mL). The pH was adjusted to 2 with 2 M aqueous HCl, the resulting suspension filtered, and solids washed with 30 mL of dichloromethane. The layers of the filtrate were separated and the aqueous layer extracted with dichloromethane (2×50 mL). The combined organic layers were dried over $Na_2SO_4$, filtered, and concentrated. The residue was purified by silica gel chromatography eluted with 10% to 40% EtOAc/dichloromethane (3:1) in petroleum ether followed by prep-HPLC using formic acid as an additive to obtain the title compound (13.68 mg, 11%) as a white solid. MS ES+ m/z 504 $[M+H]^+$.

The following compounds in Table 53 were made in a similar way as described for Example 254.

TABLE 53

| Ex # | Chemical Name | Structure | MS ES+ m/z |
|---|---|---|---|
| 255 | 2-[[(1R)-1-[2-(6-Methoxy-1,5-naphthyridin-2-yl)-6-methyl-4-oxo-chromen-8-yl]ethyl]amino]benzoic acid | 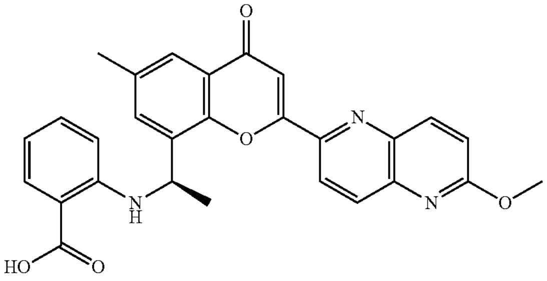 [SMILES: COc1ccc2nc(-c3cc(=O)c4cc(C)cc([C@@H](C)Nc5ccccc5C(=O)O)c4o3)ccc2n1] | 482 $[M + H]^+$ |
| 256 | 2-[[(1R)-1-[3,6-Dimethyl-2-(2-methyloxazolo[5,4-b]pyridin-5-yl)-4-oxo-chromen-8-yl]ethyl]amino]benzoic acid | 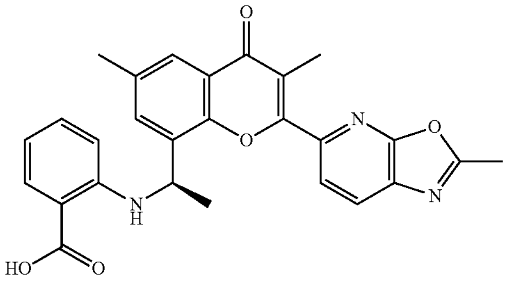 | 470 $[M + H]^+$ |
| 257 | 2-Fluoro-6-[[(1R)-1-[6-methyl-2-(2-methylthiazolo[5,4-b]pyridin-5-yl)-4-oxo-chromen-8-yl]ethyl]amino]benzoic acid | 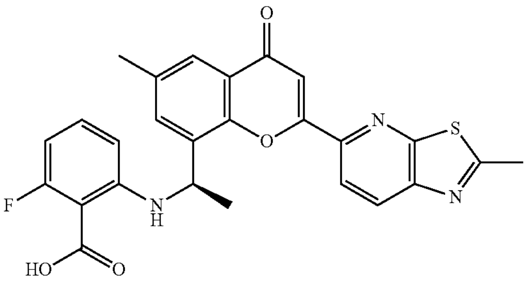 [SMILES: Cc1cc([C@@H](C)Nc2cccc(F)c2C(=O)O)c2oc(-c3ccc4nc(C)sc4n3)cc(=O)c2c1] | 490 $[M + H]^+$ |

Example 258: 5-Chloro-2-[[(1R)-1-[3,6-dimethyl-2-(2-methylindazol-5-yl)-4-oxo-chromen-8-yl]ethyl]amino]benzoic acid

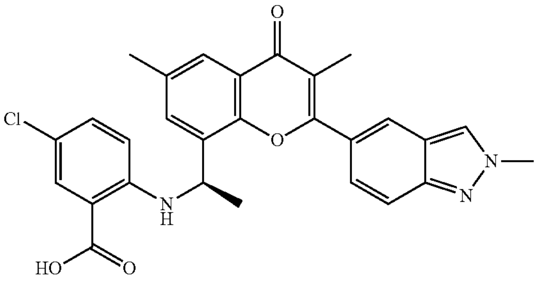 [SMILES: Cc1cc([C@@H](C)Nc2ccc(Cl)cc2C(=O)O)c2oc(-c3ccc4nn(C)cc4c3)c(C)c(=O)c2c1]

A mixture of 5-chloro-2-[[(1R)-1-(2-ethylsulfanyl-3,6-dimethyl-4-oxo-chromen-8-yl)ethyl]amino]benzoic acid (120 mg, 0.28 mmol), (2-methylindazol-5-yl)boronic acid (146.67 mg, 0.83 mmol), copper(I) thiophene-2-carboxylate (190.69 mg, 0.83 mmol), BrettPhos Pd G3 (27.78 mg, 0.03 mmol), [1,3-bis(diphenylphosphino)propane]dichloronickel (II) (15.06 mg, 0.03 mmol), and sodium tert-butoxide (133.50 mg, 1.39 mmol) in 1,4-dioxane (2 mL) was stirred at 100° C. for 12 h. The reaction was cooled to rt, the pH adjusted to 4 with 2M aqueous HCl, filtered, and concentrated. The residue was purified by silica gel chromatography eluted with 0% to 100% EtOAc in petroleum ether and then prep-HPLC (with formic acid as additive) to give the product (59.40 mg, 43%) as a white solid. MS ES+ m/z 502 $[M+H]^+$.

The following compounds in Table 54 were made in a similar way as described for Example 258.

TABLE 54

| Ex # | Chemical Name | Structure | MS ES+ m/z |
|---|---|---|---|
| 259 | 5-Chloro-2-[[(1R)-1-[3,6-dimethyl-2-(1-methylindazol-5-yl)-4-oxo-chromen-8-yl]ethyl]amino]benzoic acid | 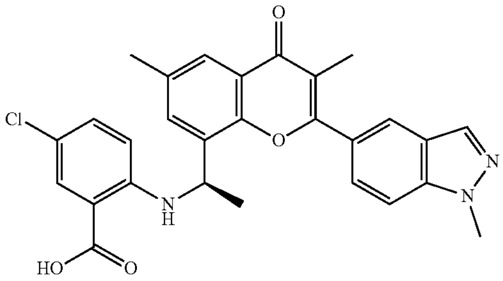 [SMILES: Cc1cc([C@@H](C)Nc2ccc(Cl)cc2C(=O)O)c2oc(-c3ccc4c(cnn4C)c3)c(C)c(=O)c2c1] | 502 $[M + H]^+$ |
| 260 | 2-[[(1R)-1-[3,6-Dimethyl-2-(1-methylindazol-5-yl)-4-oxo-chromen-8-yl]ethyl]amino]-5-fluoro-benzoic acid | 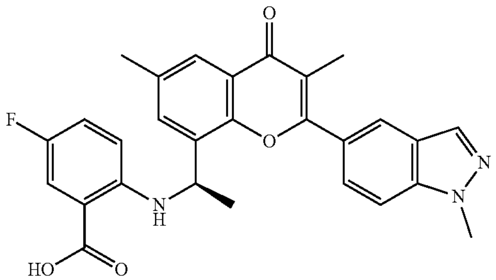 [SMILES: Cc1cc([C@@H](C)Nc2ccc(F)cc2C(=O)O)c2oc(-c3ccc4c(cnn4C)c3)c(C)c(=O)c2c1] | 486 $[M + H]^+$ |
| 261 | 2-[[(1R)-1-[3,6-Dimethyl-2-(2-methyl-1,3-benzoxazol-6-yl)-4-oxo-chromen-8-yl]ethyl]amino]benzoic acid | 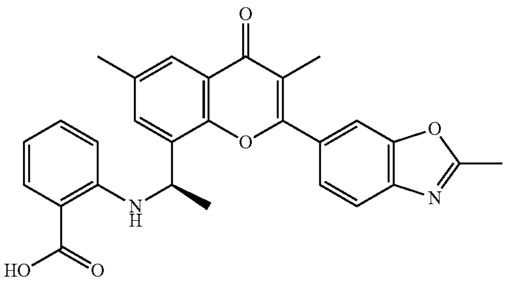 | 469 $[M + H]^+$ |

Example 262: 2-[[(1R)-1-[3,6-Dimethyl-2-(2-methyl-1,3-benzothiazol-6-yl)-4-oxo-chromen-8-yl]ethyl]amino]benzoic acid

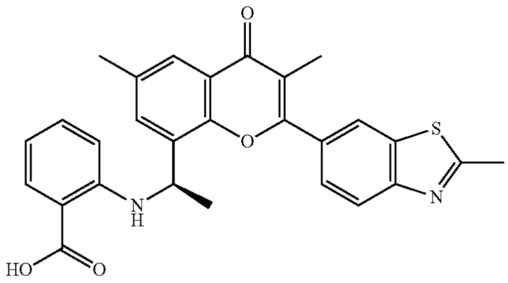 [SMILES: Cc1cc([C@@H](C)Nc2ccccc2C(=O)O)c2oc(-c3ccc4nc(C)oc4c3)c(C)c(=O)c2c1]

A mixture of 2-[[(1R)-1-(2-ethylsulfanyl-3,6-dimethyl-4-oxo-chromen-8-yl)ethyl]amino]benzoic acid (150 mg, 0.38 mmol), 6-bromo-2-methyl-1,3-benzothiazole (172.16 mg, 0.75 mmol), bis(pinacoloto)diboron (383.32 mg, 1.51 mmol), copper(I) thiophene-2-carboxylate (215.88 mg, 1.13 mmol), cesium carbonate (491.82 mg, 1.51 mmol), RuPhos Pd G3 (31.56 mg, 0.04 mmol), and XPhos Pd G3 (31.94 mg, 0.04 mmol) in 1,4-dioxane (10 mL) and water (0.2 mL) was stirred at 80° C. for 20 h under $N_2$. Treated the reaction with 6-bromo-2-methyl-1,3-benzothiazole (172.16 mg, 0.75 mmol), bis(pinacoloto)diboron (383.32 mg, 1.51 mmol), copper(I) thiophene-2-carboxylate (215.88 mg, 1.13 mmol), cesium carbonate (491.82 mg, 1.51 mmol), RuPhos Pd G3 (31.56 mg, 0.04 mmol), and XPhos Pd G3 (31.94 mg, 0.04 mmol) to the reaction and stirred at 80° C. for another 16 h. The reaction was concentrated and diluted with 30 mL each of dichloromethane and water. The pH was adjusted to pH 3 with 2M aqueous HCl, the organic layer removed and the remaining aqueous layer extracted with dichloromethane (3×30 mL). The combined organic layers were dried over $Na_2SO_4$, filtered, and concentrated. The resulting residue was purified by silica gel chromatography eluted with 0% to 100% (EtOAc/dichloromethane=3:1) in petroleum ether and then 0% to 6% MeOH in dichoromethane to give the product (22.86 mg, 13%) as an off-white solid. MS ES+ m/z 485 $[M+H]^+$.

Example 263: 3-[[(1R)-1-[2-(1,3-benzoxazol-2-yl)-3,6-dimethyl-4-oxo-chromen-8-yl]ethyl]amino]-6-chloro-pyridine-2-carboxylic acid; 2,2,2-trifluoro-acetic acid

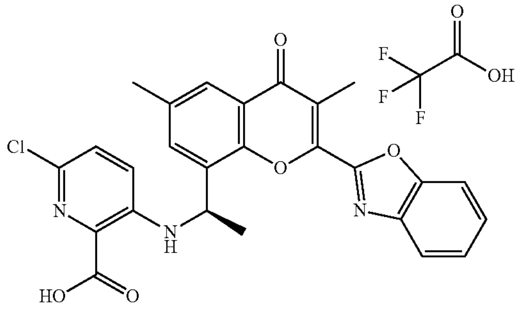

A vial was charged with 2-(4,4,5,5-tetramethyl-1,3,2-dioxaborolan-2-yl)-1,3-benzoxazole (200 mg, 0.82 mmol), tert-butyl 6-chloro-3-[[(1R)-1-(2-ethylsulfanyl-3,6-dimethyl-4-oxo-chromen-8-yl)ethyl]amino]pyridine-2-carboxylate (200 mg, 0.41 mmol), zinc(II) acetate (150 mg, 0.82 mmol), tri(2-furyl)phosphine (38 mg, 0.16 mmol), tris(dibenzylideneacetone)dipalladium(0) (37.5 mg, 0.04 mmol), and copper(I) thiophene-2-carboxylate (156 mg, 0.82 mmol). The tube was evacuated and refilled with argon twice, 1,4-dioxane added to the tube, and the tube evacuated and refilled with argon 2 more times. The tube was sealed and the reaction heated at 90° C. After 5 h, added 50% of the coupling reactants to the tube, resealed, and stirred overnight at 90° C. LCMS indicated a mixture of the ester and the acid. Concentrated the reaction and the resulting residue was treated with 2 mL of dichloromethane and 5 mL of trifluoroacetic acid and the reaction allowed to stir at rt overnight. Concentrated the reaction and purified the residue via reversed phase chromatography eluted with 10% to 100% 0.1 TFA in water in AcCN (0.1% TFA as an additive) to obtain the product (110 mg, 55%) as a light tan solid. MS ES+ m/z 490 $[M+H]^+$.

The following compounds in Table 55 were made in a similar way as described for Example 263.

TABLE 55

| Ex # | Chemical Name | Structure | MS ES+ m/z |
|---|---|---|---|
| 264 | 2-Fluoro-6-[[(1R)-1-(2-furo[3,2-c]pyridin-2-yl-3,6-dimethyl-4-oxo-chromen-8-yl)ethyl]amino]benzoic acid; 2,2,2-trifluoroacetic acid | 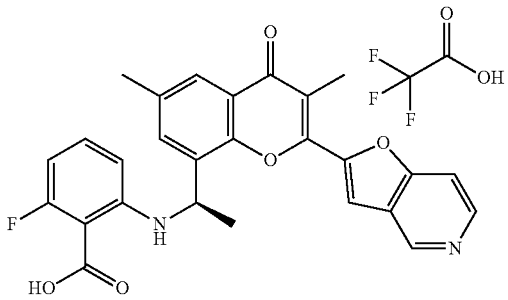 | 473 $[M + H]^+$ |

Example 265: 3-[[(1R)-1-[3,6-Dimethyl-2-(2-methylthiazolo[5,4-b]pyridin-5-yl)-4-oxo-chromen-8-yl]ethyl]amino]-6-methyl-pyridine-2-carboxylic acid

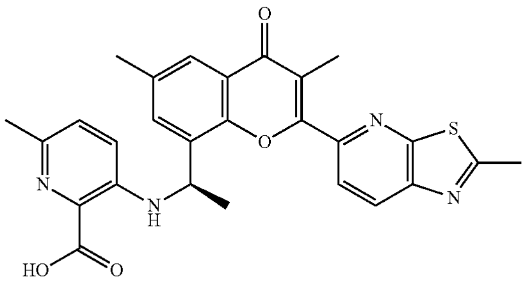

A mixture of methyl 6-chloro-3-[[(1R)-1-[3,6-dimethyl-2-(2-methylthiazolo[5,4-b]pyridin-5-yl)-4-oxo-chromen-8-yl]ethyl]amino]pyridine-2-carboxylate (200 mg, 0.37 mmol), [1,1'-bis(diphenylphosphino)ferrocene]dichloropalladium(II) (30.53 mg, 0.04 mmol), and dimethylzinc (0.56 mL, 1M in toluene, 0.56 mmol) in 3 mL of toluene was stirred at 120° C. for 12 h. The reaction was allowed to cool to rt, diluted with 5 mL of water, the pH adjusted to 3 with 2M aqueous HCl, and extracted with 2 mL of dichloromethane. The organic layer was collected, dried over $Na_2SO_4$, filtered, concentrated, and purified by silica gel chromatography eluted with 0% to 20% MeOH in dichloromethane and prep-HPLC (formic acid as an additive to give the product (7.43 mg, 4%) as a yellow solid. MS ES+ m/z 501 $[M+H]^+$.

Example 266: 2-[[(1R)-1-(3,6-Dimethyl-4-oxo-2-pyrazolo[1,5-a]pyridin-6-yl-chromen-8-yl)ethyl]amino]benzoic acid

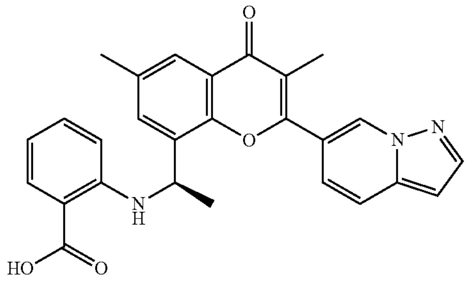 [SMILES: Cc1cc([C@@H](C)Nc2ccccc2C(=O)O)c2oc(-c3ccc4ccnn4c3)c(C)c(=O)c2c1]

A suspension of 8-[(1S)-1-chloroethyl]-3,6-dimethyl-2-pyrazolo[1,5-a]pyridin-6-yl-chromen-4-one (0.10 g, 0.283 mmol) and anthranilic acid (0.12 g, 0.845 mmol) in isopropanol (2 mL) was treated with triethylamine (0.11 g, 1.13 mmol) and heated at 90° C. for 4 h. The reaction was cooled to rt, diluted with 10 mL of water, and extracted with DCM (2×10 mL). The organic layers were combined, concentrated, and the residue purified using silica gel chromatography eluted with 91% THE in heptane to give the product (0.08 g, 62%, 61% ee) as a light yellow solid. MS ES+ m/z 454 $[M+H]^+$. This compound was also synthesized as the trifluoroacetic acid salt as Example 157 and can be found in Table 44.

TABLE 56

| Ex # | NMR Line Listing |
|---|---|
| 1 | $^1$H NMR (400 MHz, METHANOL-d4) δ ppm 1.78 (d, J = 6.7 Hz, 3H), 2.41 (s, 3H), 4.28 (s, 3H), 5.44 (q, J = 6.6 Hz, 1H), 6.48 (d, J = 8.1 Hz, 1H), 6.55 (t, J = 7.2 Hz, 1H), 7.04 (s, 1H), 7.18 (ddd, J = 8.5, 7.1, 1.6 Hz, 1H), 7.63 (d, J = 2.2 Hz, 1H), 7.71 (dd, J = 8.8, 1.5 Hz, 1H), 7.87 (d, J = 1.2 Hz, 1H), 7.92 (t, J = 7.8 Hz, 2H), 8.32 (s, 1H), 8.44 (s, 1H) |
| 2 | $^1$H NMR (400 MHz, DMSO-d6) δ ppm 1.62 (d, J = 6.60 Hz, 3H), 2.36 (s, 3H), 3.79 (s, 3H), 5.19-5.35 (m, 1H), 6.52-6.58 (m, 2H), 6.95 (s, 1H), 7.12-7.22 (m, 1H), 7.43 (br d, J = 8.07 Hz, 1H), 7.51 (d, J = 2.08 Hz, 1H), 7.79 (dd, J = 5.26, 1.47 Hz, 2H), 7.82 (d, J = 1.71 Hz, 1H), 8.39 (br d, J = 4.03 Hz, 1H), 8.46-8.58 (m, 1H), 8.66-8.77 (m, 1H), 12.81 (br s, 1H) |
| 3 | $^1$H NMR (400 MHz, METHANOL-d4) δ ppm 1.80 (d, J = 6.7 Hz, 3H), 2.43 (s, 3H), 2.62 (s, 3H), 5.38 (q, J = 6.4 Hz, 1H), 6.52 (d, J = 8.4 Hz, 1H), 6.56 (t, J = 7.5 Hz, 1H), 7.17-7.23 (m, 1H), 7.24 (s, 1H), 7.68-7.71 (m, 1H), 7.85-7.95 (m, 2H), 8.02 (d, J = 6.9 Hz, 1H), 8.10 (s, 1H), 8.50 (s, 1H), 8.85 (br d, J = 7.3 Hz, 1H) |
| 4 | $^1$H NMR (400 MHz, METHANOL-d4) δ ppm 1.79 (d, J = 6.7 Hz, 3H), 2.42 (s, 3H), 5.46 (q, J = 6.5 Hz, 1H), 6.51-6.6 (m, 3H), 7.20 (ddd, J = 8.5, 7.0, 1.7 Hz, 1H), 7.48 (s, 1H), 7.61 (d, J = 3.5 Hz, 1H), 7.64 (d, J = 2.2 Hz, 1H), 7.88 (d, J = 1.3 Hz, 1H), 7.93 (dd, J = 8.0, 1.5 Hz, 1H), 8.01 (d, J = 8.1 Hz, 1H), 8.15 (d, J = 8.3 Hz, 1H) |
| 5 | $^1$H NMR (400 MHz, DMSO-d6) δ ppm 1.66 (d, J = 6.60 Hz, 3H), 2.37 (s, 3H), 4.70 (s, 3H), 5.18-5.31 (m, 1H), 6.48-6.59 (m, 2H), 7.12-7.24 (m, 1H), 7.49 (dd, J = 8.68, 4.16 Hz, 1H), 7.55 (d, J = 2.20 Hz, 1H), 7.70 (s, 1H), 7.79-7.84 (m, 2H), 8.31 (dd, J = 8.68, 1.47 Hz, 1H), 8.42 (br d, J = 4.52 Hz, 1H), 8.77 (dd, J = 4.16, 1.34 Hz, 1H), 12.81 (br s, 1H) |
| 6 | $^1$H NMR (400 MHz, DMSO-d6) δ ppm 1.69 (br d, J = 5.1 Hz, 3H), 2.36 (br s, 3H), 5.47 (br s, 1H), 6.51-6.62 (m, 2H), 7.21-7.30 (m, 2H), 7.36 (br s, 1H), 7.54 (br s, 1H), 7.73 (br s, 1H), 7.81 (br d, J = 7.7 Hz, 1H), 8.46 (br s, 1H), 8.91 (br s, 1H), 8.99 (br s, 1H), 9.39 (br d, J = 6.3 Hz, 1H), 12.76 (br s, 1H) |
| 7 | $^1$H NMR (400 MHz, DMSO-d6) δ ppm 1.71 (br s, 3H), 2.31-2.46 (m, 3H), 5.39 (br s, 1H), 6.58 (br d, J = 6.85 Hz, 2H), 7.05 (br s, 1H), 7.25 (br s, 1H), 7.62 (br s, 1H), 7.78 (br s, 1H), 7.82 (br d, J = 7.09 Hz, 1H), 8.01 (br s, 1H), 8.11 (br s, 1H), 8.48 (br s, 1H), 8.61 (br s, 1H), 9.31 (br s, 1H), 12.77 (br s, 1H) |
| 8 | $^1$H NMR (400 MHz, DMSO-d6) δ ppm 1.70 (d, J = 6.60 Hz, 3H), 2.37 (s, 3H), 4.22 (s, 3H), 5.36-5.42 (m, 1H), 6.54-6.60 (m, 2H), 7.05 (s, 1H), 7.21-7.28 (m, 1H), 7.57 (d, J = 2.08 Hz, 1H), 7.71-7.77 (m, 2H), 7.82 (dd, J = 8.13, 1.65 Hz, 1H), 7.89-7.94 (m, 1H), 8.45 (br d, J = 5.87 Hz, 1H), 8.54-8.57 (m, 1H), 8.60-8.63 (m, 1H), 12.77 (br s, 1H) |
| 9 | $^1$H NMR (400 MHz, DMSO-d6) δ ppm 1.66-1.75 (m, 3H), 2.38 (br s, 3H), 4.27 (br s, 3H), 5.35-5.47 (m, 1H), 6.52-6.63 (m, 2H), 7.18-7.30 (m, 2H), 7.54-7.62 (m, 1H), |

TABLE 56-continued

| Ex # | NMR Line Listing |
|---|---|
| | 7.74-7.80 (m, 1H), 7.80-7.85 (m, 1H), 8.42-8.50 (m, 1H), 8.60-8.67 (m, 1H), 8.97-9.04 (m, 1H), 9.25-9.31 (m, 1H), 12.77 (br s, 1H) |
| 10 | $^1$H NMR (400 MHz, DMSO-d6) δ ppm 1.59-1.71 (m, 3H), 2.29 (br s, 3H), 5.25-5.34 (m, 1H), 6.43 (br d, J = 8.19 Hz, 1H), 6.50 (br t, J = 6.91 Hz, 1H), 6.85 (br s, 1H), 7.08-7.18 (m, 2H), 7.45 (br s, 1H), 7.51-7.61 (m, 1H), 7.69 (br s, 1H), 7.77 (br d, J = 7.95 Hz, 1H), 8.17 (br d, J = 8.56 Hz, 1H), 8.39 (br s, 1H), 8.81 (br s, 1H), 8.86 (br d, J = 5.75 Hz, 1H), 12.75 (br s, 1H) |
| 11 | $^1$H NMR (400 MHz, DMSO-d6) δ ppm 1.69-1.72 (m, 3H), 2.38 (br s, 3H), 5.36-5.45 (m, 1H), 6.50-6.61 (m, 2H), 7.06 (br s, 1H), 7.20-7.32 (m, 2H), 7.57 (br s, 1H), 7.65 (d, J = 7.83 Hz, 1H), 7.74-7.86 (m, 2H), 8.05 (d, J = 8.44 Hz, 1H), 8.46 (br s, 1H), 8.54 (s, 1H), 12.69 (s, 1H), 12.81 (br s, 1H) |
| 12 | $^1$H NMR (400 MHz, DMSO-d6) δ ppm 1.68-1.82 (m, 3H), 2.38 (br s, 3H), 4.24 (br s, 3H), 5.35-5.44 (m, 1H), 6.48 (br d, J = 8.19 Hz, 1H), 6.53-6.60 (m, 1H), 7.01 (br s, 1H), 7.17-7.25 (m, 1H), 7.38-7.44 (m, 1H), 7.57 (br s, 2H), 7.78-7.89 (m, 3H), 8.26 (br d, J = 7.83 Hz, 1H), 8.48 (br s, 1H), 12.82 (br s, 1H) |
| 13 | $^1$H NMR (400 MHz, DMSO-d6) δ ppm 1.62 (br s, 3H), 2.29 (br s, 3H), 4.14 (br s, 3H), 5.29 (br s, 1H), 6.49 (br s, 2H), 6.97 (br s, 1H), 7.16 (br s, 1H), 7.49 (br s, 1H), 7.63-7.70 (m, 2H), 7.74 (br d, J = 7.0 Hz, 1H), 7.83 (br d, J = 7.8 Hz, 1H), 8.37 (br s, 1H), 8.48 (br s, 1H), 8.53 (br s, 1H), 12.68 (br s, 1H) |
| 14 | $^1$H NMR (400 MHz, DMSO-d6) δ ppm 1.73 (br d, J = 4.0 Hz, 3H), 2.37 (s, 3H), 5.41 (br s, 1H), 6.56 (br d, J = 6.4 Hz, 2H), 6.60 (br s, 1H), 7.19-7.26 (m, 2H), 7.58 (br s, 1H), 7.74 (br s, 1H), 7.77 (br s, 1H), 7.82 (br d, J = 6.9 Hz, 1H), 8.00 (br d, J = 8.3 Hz, 1H), 8.19 (br d, J = 8.0 Hz, 1H), 8.47 (br s, 1H), 12.09 (br s, 1H), 12.78 (br s, 1H) |
| 15 | $^1$H NMR (400 MHz, DMSO-d6) δ ppm 1.71 (br d, J = 5.5 Hz, 3H), 2.38 (br s, 3H), 5.37 (br s, 1H), 6.57 (br d, J = 8.5 Hz, 2H), 7.20-7.26 (m, 2H), 7.61 (br s, 1H), 7.78 (br s, 1H), 7.82 (br s, 1H), 7.95-8.05 (m, 2H), 8.37 (br d, J = 9.1 Hz, 1H), 8.46 (br s, 1H), 8.52 (br s, 1H), 12.75 (br s, 1H) |
| 16 | $^1$H NMR (400 MHz, DMSO-d6) δ ppm 1.69 (br d, J = 5.75 Hz, 3H), 2.31 (s, 3H), 2.52 (s, 3H), 5.44 (br s, 1H), 6.51-6.60 (m, 2H), 7.13-7.21 (m, 1H), 7.25 (br s, 1H), 7.59 (br s, 1H), 7.77 (br s, 1H), 7.84 (br d, J = 7.95 Hz, 1H), 7.96 (br d, J = 9.41 Hz, 1H), 8.19 (br s, 1H), 8.36 (br d, J = 8.80 Hz, 1H), 8.46 (br s, 1H), 9.51 (br s, 1H), 12.81 (br s, 1H) |
| 17 | $^1$H NMR (400 MHz, DMSO-d6) δ ppm 1.69 (d, J = 6.60 Hz, 3H), 2.30-2.46 (br s, 3H), 2.52 (s, 3H), 5.45 (br t, J = 6.24 Hz, 1H), 6.53 (d, J = 8.56 Hz, 1H), 6.57 (t, J = 7.52 Hz, 1H), 7.21-7.27 (m, 2H), 7.60 (d, J = 1.96 Hz, 1H), 7.76-7.80 (m, 1H), 7.84 (dd, J = 7.95, 1.59 Hz, 1H), 8.01 (d, J = 9.66 Hz, 1H), 8.22 (s, 1H), 8.38-8.50 (m, 2H), 9.53 (s, 1H), 12.82 (br s, 1H) |
| 18 | $^1$H NMR (400 MHz, CHLOROFORM-d) δ ppm 1.83 (br d, J = 5.7 Hz, 3H), 2.48 (br s, 3H), 5.26 (br d, J = 5.9 Hz, 1H), 6.45-6.55 (m, 1H), 6.56-6.67 (m, 1H), 6.66-6.78 (m, 1H), 7.13 (br s, 1H), 7.33-7.39 (m, 2H), 7.54-7.61 (m, 2H), 7.64 (br s, 1H), 7.94-8.04 (m, 1H), 8.04-8.18 (m, 2H), 8.84-8.99 (m, 1H) |
| 20 | $^1$H NMR (400 MHz, DMSO-d6) δ ppm 1.72 (d, J = 6.6 Hz, 3H), 2.38 (s, 3H), 2.46-2.49 (m, 3H), 5.40 (br s, 1H), 6.31 (s, 1H), 6.52-6.60 (m, 2H), 7.20 (s, 1H), 7.24 (t, J = 7.3 Hz, 1H), 7.57 (d, J = 2.1 Hz, 1H), 7.77 (s, 1H), 7.82 (dd, J = 8.1, 1.7 Hz, 1H), 7.94 (d, J = 8.2 Hz, 1H), 8.01 (d, J = 8.3 Hz, 1H), 8.41-8.54 (m, 1H), 11.94 (s, 1H), 12.79 (br s, 1H) |
| 21 | $^1$H NMR (400 MHz, DMSO-d6) δ ppm 1.73 (d, J = 6.60 Hz, 3H), 2.32-2.42 (m, 3H), 5.39 (br t, J = 6.11 Hz, 1H), 6.48-6.63 (m, 3H), 7.03 (s, 1H), 7.17-7.30 (m, 1H), 7.55 (d, J = 1.96 Hz, 1H), 7.59 (t, J = 2.69 Hz, 1H), 7.69-7.79 (m, 3H), 7.84 (dd, J = 7.95, 1.47 Hz, 1H), 8.24 (s, 1H), 8.49 (br d, J = 5.62 Hz, 1H), 11.48 (br s, 1H), 12.82 (br s, 1H) |
| 22 | $^1$H NMR (400 MHz, DMSO-d6) δ ppm 1.71 (d, J = 6.72 Hz, 3H), 2.36-2.41 (m, 3H), 5.39 (br t, J = 6.30 Hz, 1H), 6.55-6.60 (m, 2H), 6.97 (s, 1H), 7.25 (t, J = 7.34 Hz, 1H), 7.61 (d, J = 2.08 Hz, 1H), 7.77 (d, J = 1.34 Hz, 1H), 7.82 (dd, J = 8.19, 1.71 Hz, 1H), 7.98 (br d, J = 5.87 Hz, 1H), 8.14 (s, 1H), 8.48 (br d, J = 6.60 Hz, 1H), 8.70 (d, J = 5.75 Hz, 1H), 9.21 (s, 1H), 12.67-12.89 (m, 1H) |
| 23 | $^1$H NMR (400 MHz, DMSO-d6) δ ppm 1.75 (d, J = 6.72 Hz, 3H), 2.38 (s, 3H), 4.24 (s, 3H), 5.36-5.44 (m, 1H), 6.48 (d, J = 8.44 Hz, 1H), 6.57 (t, J = 7.26 Hz, 1H), 7.01 (s, 1H), 7.18-7.24 (m, 1H), 7.41 (t, J = 7.52 Hz, 1H), 7.53-7.60 (m, 2H), 7.79-7.89 (m, 3H), 8.26 (d, J = 8.31 Hz, 1H), 8.47 (br d, J = 5.87 Hz, 1H), 12.82 (s, 1H) |
| 24 | $^1$H NMR (400 MHz, DMSO-d6) δ ppm 1.67 (d, J = 6.60 Hz, 3H), 2.36 (s, 3H) 5.26-5.4 (m, 1H), 6.46-6.59 (m, 2H), 7.08 (s, 1H), 7.18-7.26 (m, 1H), 7.48 (d, J = 8.44 Hz, 1H), 7.55 (d, J = 1.96 Hz, 1H), 7.74 (s, 1H), 7.79 (d, J = 1.71 Hz, 1H), 7.82 (dd, J = 7.95, 1.59 Hz, 1H), 7.91 (dd, J = 8.44, 1.83 Hz, 1H), 8.44 (br d, J = 5.99 Hz, 1H), 11.91 (s, 1H), 12.78 (br s, 1H) |
| 25 | $^1$H NMR (400 MHz, DMSO-d6) δ ppm 1.74 (d, J = 6.72 Hz, 3H), 2.39 (s, 3H), 4.16 (s, 3H), 5.38-5.46 (m, 1H), 6.54-6.61 (m, 2H), 7.22-7.25 (m, 1H), 7.27 (s, 1H), 7.60 (d, J = 2.08 Hz, 1H), 7.78 (s, 1H), 7.81-7.90 (m, 2H), 7.91-7.98 (m, 1H), 8.18 (s, 1H), 8.47 (s, 2H), 12.77 (br s, 1H) |
| 26 | $^1$H NMR (400 MHz, DMSO-d6) δ ppm 1.71 (d, J = 6.72 Hz, 3H), 2.38 (s, 3H), 4.12 (s, 3H), 5.37-5.45 (m, 1H), 6.56-6.61 (m, 2H), 7.12 (s, 1H), 7.26 (t, J = 7.70 Hz, 1H), 7.58 (d, J = 1.96 Hz, 1H), 7.77 (s, 1H), 7.83 (d, J = 8.44 Hz, 2H), 8.14 (dd, J = 8.93, 1.59 Hz, 1H), 8.24 (s, 1H), 8.46 (br d, J = 5.50 Hz, 1H), 8.61 (s, 1H), 12.77 (br s, 1H) |
| 27 | $^1$H NMR (400 MHz, DMSO-d6) δ ppm 0.83-1.73 (d, J = 6.60 Hz, 3H), 2.31-2.46 (m, 3H), 2.53-2.54 (m, 3H), 4.07 (s, 3H), 5.37-5.45 (m, 1H), 6.55-6.61 (m, 2H), 7.22-7.28 (m, 2H), 7.60 (d, J = 2.08 Hz, 1H), 7.78 (s, 1H), 7.81-7.86 (m, 2H), 7.87-7.92 (m, 1H), 8.38 (s, 1H), 8.46 (br d, J = 6.11 Hz, 1H), 12.77 (br s, 1H) |
| 28 | $^1$H NMR (400 MHz, DMSO-d6) δ ppm 1.72 (d, J = 6.60 Hz, 3H), 2.34-2.42 (m, 3H), 2.54-2.57 (m, 3H), 5.37 (br t, J = 6.36 Hz, 1H), 6.53-6.59 (m, 2H), 7.17 (s, 1H), 7.24 (t, J = 7.75 Hz, 1H), 7.57 (d, J = 1.96 Hz, 1H), 7.77 (s, 1H), 7.83 (t, J = 7.66 Hz, 2H), 7.88- |

TABLE 56-continued

| Ex # | NMR Line Listing |
|---|---|
| | 7.92 (m, 1H), 8.27 (s, 1H), 8.49 (br d, J = 6.24 Hz, 1H), 12.81 (br s, 1H), 12.96 (br s, 1H) |
| 30 | $^1$H NMR (400 MHz, DMSO-d6) δ ppm 1.69 (br d, J = 5.9 Hz, 3H), 2.38 (br s, 3H), 3.12 (br s, 3H), 4.57 (br s, 2H), 5.36 (br s, 1H), 6.53-6.60 (m, 2H), 7.15-7.19 (m, 1H), 7.25 (br t, J = 7.3 Hz, 1H), 7.60 (br s, 1H), 7.77 (br s, 1H), 7.79-7.85 (m, 2H), 8.23 (br d, J = 7.9 Hz, 1H), 8.34 (br s, 1H), 8.40-8.48 (m, 1H), 12.78 (br s, 1H) |
| 33 | $^1$H NMR (400 MHz, DMSO-d6) δ ppm 1.69 (br d, J = 5.1 Hz, 3H), 2.36 (br s, 3H), 5.47 (br s, 1H), 6.51-6.62 (m, 2H), 7.21-7.30 (m, 2H), 7.36 (br s, 1H), 7.54 (br s, 1H), 7.73 (br s, 1H), 7.81 (br d, J = 7.7 Hz, 1H), 8.46 (br s, 1H), 8.91 (br s, 1H), 8.99 (br s, 1H), 9.39 (br d, J = 6.3 Hz, 1H), 12.76 (br s, 1H) |
| 34 | $^1$H NMR (400 MHz, DMSO-d6) δ ppm 1.69 (br d, J = 5.1 Hz, 3H), 2.36 (br s, 3H), 5.47 (br s, 1H), 6.51-6.62 (m, 2H), 7.21-7.30 (m, 2H), 7.36 (br s, 1H), 7.54 (br s, 1H), 7.73 (br s, 1H), 7.81 (br d, J = 7.7 Hz, 1H), 8.46 (br s, 1H), 8.91 (br s, 1H), 8.99 (br s, 1H), 9.39 (br d, J = 6.3 Hz, 1H), 12.76 (br s, 1H) |
| 35 | $^1$H NMR (400 MHz, DMSO-d6) δ ppm 1.71 (br d, J = 5.5 Hz, 3H), 2.38 (br s, 3H), 5.37 (br s, 1H), 6.57 (br d, J = 8.5 Hz, 2H), 7.20-7.26 (m, 2H), 7.61 (br s, 1H), 7.78 (br s, 1H), 7.82 (br s, 1H), 7.95-8.05 (m, 2H), 8.37 (br d, J = 9.1 Hz, 1H), 8.46 (br s, 1H), 8.52 (br s, 1H), 12.75 (br s, 1H) |
| 36 | $^1$H NMR (400 MHz, DMSO-d6) δ ppm 1.71 (br d, J = 5.5 Hz, 3H), 2.38 (br s, 3H), 5.37 (br s, 1H), 6.57 (br d, J = 8.5 Hz, 2H), 7.20-7.26 (m, 2H), 7.61 (br s, 1H), 7.78 (br s, 1H), 7.82 (br s, 1H), 7.95-8.05 (m, 2H), 8.37 (br d, J = 9.1 Hz, 1H), 8.46 (br s, 1H), 8.52 (br s, 1H), 12.75 (br s, 1H) |
| 41 | $^1$H NMR (400 MHz, DMSO-d6) δ ppm 1.70-1.80 (m, 3H), 2.44 (br s, 3H), 4.31 (br s, 3H), 5.41-5.49 (m, 1H), 6.55-6.67 (m, 2H), 7.23-7.35 (m, 2H), 7.59-7.69 (m, 1H), 7.79-7.85 (m, 1H), 7.85-7.90 (m, 1H), 8.47-8.55 (m, 1H), 8.65-8.72 (m, 1H), 9.01-9.09 (m, 1H), 9.30-9.34 (m, 1H), 12.83 (br s, 1H) |
| 42 | $^1$H NMR (400 MHz, DMSO-d6) δ ppm 1.70-1.80 (m, 3H), 2.44 (br s, 3H), 4.31 (br s, 3H), 5.41-5.49 (m, 1H), 6.55-6.67 (m, 2H), 7.23-7.35 (m, 2H), 7.59-7.69 (m, 1H), 7.79-7.85 (m, 1H), 7.85-7.90 (m, 1H), 8.47-8.55 (m, 1H), 8.65-8.72 (m, 1H), 9.01-9.09 (m, 1H), 9.30-9.34 (m, 1H), 12.83 (br s, 1H) |
| 43 | $^1$H NMR (400 MHz, DMSO-d6) δ ppm 1.66 (d, J = 6.60 Hz, 3H), 2.37 (s, 3H), 4.70 (s, 3H), 5.18-5.31 (m, 1H), 6.48-6.59 (m, 2H), 7.12-7.24 (m, 1H), 7.49 (dd, J = 8.68, 4.16 Hz, 1H), 7.55 (d, J = 2.20 Hz, 1H), 7.70 (s, 1H), 7.79-7.84 (m, 2H), 8.31 (dd, J = 8.68, 1.47 Hz, 1H), 8.42 (br d, J = 4.52 Hz, 1H), 8.77 (dd, J = 4.16, 1.34 Hz, 1H), 12.81 (br s, 1H) |
| 44 | $^1$H NMR (400 MHz, DMSO-d6) δ ppm 1.66 (d, J = 6.60 Hz, 3H), 2.37 (s, 3H), 4.70 (s, 3H), 5.18-5.31 (m, 1H), 6.48-6.59 (m, 2H), 7.12-7.24 (m, 1H), 7.49 (dd, J = 8.68, 4.16 Hz, 1H), 7.55 (d, J = 2.20 Hz, 1H), 7.70 (s, 1H), 7.79-7.84 (m, 2H), 8.31 (dd, J = 8.68, 1.47 Hz, 1H), 8.42 (br d, J = 4.52 Hz, 1H), 8.77 (dd, J = 4.16, 1.34 Hz, 1H), 12.81 (br s, 1H) |
| 45 | $^1$H NMR (400 MHz, DMSO-d6) δ ppm 1.65 (d, J = 6.8 Hz, 3H), 2.35 (s, 3H), 5.29-5.32 (m, 1H), 6.25 (s, 2H), 6.49 (d, J = 8.4 Hz, 1H), 6.55 (t, J = 7.6 Hz, 1H), 6.97 (s, 1H), 7.04 (t, J = 8.0 Hz, 2H), 7.15-7.22 (m, 2H), 8.54-7.56 (m, 2H), 7.73 (s, 1H), 7.81 (d, J = 8.0 Hz, 1H), 8.43-8.44 (m, 1H) |
| 46 | $^1$H NMR (400 MHz, DMSO-d6) δ ppm 1.66 (d, J = 6.4 Hz, 3H), 2.35 (s, 3H), 5.31-5.34 (m, 1H), 6.17 (s, 2H), 6.49-6.56 (m, 2H), 7.00 (s, 1H), 7.11 (d, J = 8.4 Hz, 1H), 7.22 (t, J = 7.2 Hz, 1 H), 7.53 (d, J = 2.0 Hz, 1 H), 7.69-7.73 (m, 3 H), 7.82 (d, J = 6.4 Hz, 1 H), 8.45 (s, 1 H), 12.81 (s, 1 H). |
| 47 | $^1$H NMR (400 MHz, DMSO-d6) δ ppm 1.72 (d, J = 6.8 Hz, 3H), 2.38 (s, 3H), 5.46-5.49 (m, 1H), 6.55-6.60 (m, 2H), 7.22-7.26 (m, 1H), 7.35 (s, 1H), 7.60-7.61 (m, 1H), 7.78-7.83 (m, 2H), 8.34 (d, J = 8.4 Hz, 1H), 8.45 (d, J = 6.0 Hz, 1H), 8.71 (d, J = 8.8 Hz, 1H), 8.93 (s, 1H), 9.80 (s, 1H), 9.84 (s, 1H) |
| 48 | $^1$H NMR (400 MHz, DMSO-d6) δ ppm 1.76 (br d, J = 6.0 Hz, 3H), 2.35-2.40 (m, 3H), 5.33 (br s, 1H), 6.52 (br d, J = 8.2 Hz, 1H), 6.58 (br t, J = 7.4 Hz, 1H), 6.81 (s, 1H), 7.20 (br t, J = 7.2 Hz, 1H), 7.57 (br s, 1H), 7.69-7.76 (m, 1H), 7.82 (br s, 1H), 7.85 (br s, 1H), 8.45 (br s, 1H), 8.61 (br d, J = 8.8 Hz, 1H), 8.77 (br s, 1H), 8.93 (s, 1H), 12.84 (br s, 1H) |
| 49 | $^1$H NMR (400 MHz, DMSO-d6) δ ppm 1.77 (d, J = 6.60 Hz, 3H) 2.38 (s, 3H) 5.35 (br t, J = 6.11 Hz, 1H) 6.47-6.54 (m, 1H) 6.54-6.61 (m, 1H) 6.76 (s, 1H) 7.20 (ddd, J = 8.50, 7.09, 1.65 Hz, 1H) 7.43 (t, J = 7.52 Hz, 1H) 7.57 (d, J = 2.08 Hz, 1H) 7.70 (ddd, J = 8.44, 7.21, 0.98 Hz, 1H) 7.77-7.83 (m, 1H) 7.85 (dd, J = 7.95, 1.59 Hz, 1H) 8.00 (d, J = 7.95 Hz, 1H) 8.27 (d, J = 8.56 Hz, 1H) 8.47 (br d, J = 5.62 Hz, 1H) 8.70 (s, 1H) 12.85 (br s, 1H) |
| 50 | $^1$H NMR (400 MHz, DMSO-d6) δ ppm 1.73 (d, J = 6.60 Hz, 3H) 2.40 (s, 3H) 5.49 (br t, J = 6.48 Hz, 1H) 6.56-6.65 (m, 2H) 7.02 (s, 1H) 7.18-7.27 (m, 2H) 7.41-7.48 (m, 1H) 7.60 (d, J = 2.08 Hz, 1H) 7.75-7.79 (m, 1H) 7.80-7.82 (m, 1H) 7.86 (s, 2H) 8.48 (br d, J = 6.24 Hz, 1H) 9.29 (s, 1H) 12.51-13.14 (m, 1H) |
| 51 | $^1$H NMR (400 MHz, METHANOL-d4) δ ppm 1.80 (d, J = 6.7 Hz, 3H), 2.62 (s, 3H), 5.41 (q, J = 6.6 Hz, 1H), 6.56 (d, J = 8.5 Hz, 1H), 6.60 (t, J = 7.5 Hz, 1H), 7.14 (s, 1H), 7.23 (t, J = 7.8 Hz, 1H), 7.63 (dd, J = 8.7, 3.0 Hz, 1H), 7.73 (dd, J = 7.7, 3.1 Hz, 1H), 7.94 (d, J = 7.9 Hz, 1H), 8.01 (d, J = 9.5 Hz, 1H), 8.23 (s, 1H), 8.48 (d, J = 9.5 Hz, 1H), 9.50 (s, 1H) |
| 52 | $^1$H NMR (400 MHz, DMSO-d6) δ ppm 1.60 (d, J = 6.5 Hz, 3H), 2.33-2.39 (m, 6H), 5.66 (br t, J = 6.3 Hz, 1H), 6.52-6.58 (m, 2H), 7.13 (t, J = 7.5 Hz, 1H), 7.19-7.26 (m, 2H), 7.30 (t, J = 7.6 Hz, 1H), 7.49 (s, 1H), 7.63 (d, J = 8.1 Hz, 1H), 7.72 (d, J = 8.1 Hz, 1H), 7.78 (s, 1H), 7.83 (d, J = 7.8 Hz, 1H), 8.40 (br d, J = 6.2 Hz, 1H), 11.58 (s, 1H), 12.83 (br s, 1H) |
| 53 | $^1$H NMR (400 MHz, DMSO-d6) δ ppm 1.73 (d, J = 6.6 Hz, 3H), 2.38 (s, 3H), 4.17 (s, 3H), 5.44 (br t, J = 6.0 Hz, 1H), 6.54-6.60 (m, 2H), 7.24 (t, J = 7.8 Hz, 1H), 7.29 (s, 1H), |

TABLE 56-continued

| Ex # | NMR Line Listing |
|---|---|
| | 7.59 (s, 1H), 7.78 (s, 1H), 7.83 (d, J = 7.9 Hz, 1H), 8.30 (d, J = 8.9 Hz, 1H), 8.39 (d, J = 8.9 Hz, 1H), 8.46-8.52 (m, 2H), 12.81 (br s, 1H) |
| 54 | $^1$H NMR (400 MHz, DMSO-d6) δ ppm 1.73 (d, J = 6.6 Hz, 3H), 2.38 (s, 3H), 4.30 (s, 3H), 5.41 (br t, J = 6.2 Hz, 1H), 6.54-6.60 (m, 2H), 7.24 (br t, J = 7.6 Hz, 1H), 7.27 (s, 1H), 7.59 (s, 1H), 7.78 (s, 1H), 7.82 (d, J = 7.8 Hz, 1H), 8.14 (d, J = 9.2 Hz, 1H), 8.32 (d, J = 9.0 Hz, 1H), 8.48 (br d, J = 6.1 Hz, 1H), 8.92 (s, 1H), 12.81 (br s, 1H) |
| 55 | $^1$H NMR (400 MHz, DMSO-d6) δ ppm 1.73 (d, J = 6.6 Hz, 3H), 4.22 (s, 3H), 5.42 (br t, J = 6.4 Hz, 1H), 6.55 (d, J = 8.5 Hz, 1H), 6.59 (t, J = 7.5 Hz, 1H), 7.14 (s, 1H), 7.25 (t, J = 7.8 Hz, 1H), 7.55 (dd, J = 8.8, 2.8 Hz, 1H), 7.63 (dd, J = 7.9, 3.0 Hz, 1H), 7.74 (d, J = 9.1 Hz, 1H), 7.84 (d, J = 7.9 Hz, 1H), 7.94 (d, J = 9.1 Hz, 1H), 8.46 (br d, J = 5.9 Hz, 1H), 8.58 (s, 1H), 8.65 (s, 1H), 12.84 (br s, 1H) |
| 56 | $^1$H NMR (400 MHz, 1,4-DIOXANE-d8) δ ppm 1.56 (br d, J = 6.60 Hz, 3H), 2.09 (s, 3H), 2.44 (s, 3H), 4.95-5.04 (m, 1H), 6.33 (br d, J = 8.44 Hz, 1H), 6.49 (t, J = 7.46 Hz, 1H), 7.05-7.13 (m, 1H), 7.43-7.50 (m, 1H), 7.59 (s, 1H), 7.67-7.76 (m, 2H), 7.81 (br d, J = 7.82 Hz, 1H), 8.05 (br d, J = 9.17 Hz, 1H), 8.35 (br d, J = 4.77 Hz, 1H), 8.60 (s, 1H) |
| 57 | $^1$H NMR (400 MHz, DMSO-d6) δ ppm 1.63 (br d, J = 6.60 Hz, 3H), 2.15 (s, 3H), 4.24 (s, 3H), 5.12-5.21 (m, 1H), 6.48 (d, J = 8.44 Hz, 1H), 6.58 (t, J = 7.52 Hz, 1H), 7.22 (br t, J = 7.52 Hz, 1H), 7.48-7.55 (m, 1H), 7.62-7.69 (m, 2H), 7.78 (d, J = 9.05 Hz, 1H), 7.83 (br d, J = 7.70 Hz, 1H), 8.25 (s, 1H), 8.37 (br d, J = 6.11 Hz, 1H), 8.57 (s, 1H), 12.83 (br s, 1H) |
| 58 | $^1$H NMR (400 MHz, DMSO-d6) δ ppm 1.75 (d, J = 6.5 Hz, 3H), 2.37 (s, 3H), 5.36 (br t, J = 6.2 Hz, 1H), 6.48 (d, J = 8.4 Hz, 1H), 6.57 (t, J = 7.5 Hz, 1H), 7.13 (s, 1H), 7.21 (t, J = 7.7 Hz, 1H), 7.42 (t, J = 6.9 Hz, 1H), 7.55 (s, 1H), 7.77-7.86 (m, 3H), 8.34 (d, J = 9.0 Hz, 1H), 8.47 (br d, J = 5.9 Hz, 1H), 9.34 (d, J = 7.0 Hz, 1H), 12.85 (br s, 1H) |
| 59 | $^1$H NMR (400 MHz, DMSO-d6) δ ppm 1.73 (d, J = 6.60 Hz, 3H), 2.30-2.45 (m, 3H), 2.56 (s, 3H), 4.03 (s, 3H), 5.36-5.44 (m, 1H), 6.55-6.60 (m, 2H), 7.17 (s, 1H), 7.25 (t, J = 7.40 Hz, 1H), 7.57 (s, 1H), 7.73-7.78 (m, 2H), 7.83 (d, J = 7.95 Hz, 1H), 8.13 (d, J = 8.93 Hz, 1H), 8.48 (br d, J = 5.26 Hz, 1H), 8.58 (s, 1H), 12.79 (br s, 1H) |
| 60 | $^1$H NMR (400 MHz, DMSO-d6) δ ppm 1.71 (d, J = 6.60 Hz, 3H), 2.30-2.46 (m, 3H), 5.41 (br t, J = 6.24 Hz, 1H), 6.55-6.60 (m, 2H), 7.09 (s, 1H), 7.26 (t, J = 7.76 Hz, 1H), 7.58 (s, 1H), 7.71 (d, J = 8.93 Hz, 1H), 7.77 (s, 1H), 7.84 (d, J = 8.19 Hz, 1H), 8.09 (d, J = 9.05 Hz, 1H), 8.27 (s, 1H), 8.46 (br d, J = 6.11 Hz, 1H), 8.64 (s, 1H), 12.81 (br s, 1H), 13.42 (br s, 1H) |
| 61 | $^1$H NMR (400 MHz, DMSO-d6) δ ppm 1.72 (d, J = 6.60 Hz, 3H), 2.30-2.45 (m, 3H), 2.54-2.56 (m, 3H), 5.37 (br t, J = 6.48 Hz, 1H), 6.52-6.59 (m, 2H), 7.18 (s, 1H), 7.24 (t, J = 7.70 Hz, 1H), 7.57 (s, 1H), 7.77 (s, 1H), 7.83 (br t, J = 6.72 Hz, 2H), 7.88-7.93 (m, 1H), 8.27 (s, 1H), 8.50 (br d, J = 5.87 Hz, 1H), 12.84 (br s, 1H), 12.98 (br s, 1H) |
| 62 | $^1$H NMR (400 MHz, CHLOROFORM-d) δ ppm 1.71 (br d, J = 6.6 Hz, 3H), 2.36 (s, 3H), 3.22 (s, 3H), 3.60 (br s, 2H), 5.21 (q, J = 6.6 Hz, 1H), 6.37 (d, J = 8.3 Hz, 1H), 6.58 (t, J = 7.5 Hz, 1H), 6.90-6.98 (m, 2H), 7.21 (s, 2H), 7.52 (s, 1H), 7.77 (s, 1H), 7.85-7.91 (m, 2H), 7.95 (d, J = 8.1 Hz, 1H) |
| 63 | $^1$H NMR (400 MHz, DMSO-d6) δ ppm 1.73 (d, J = 6.60 Hz, 3H), 2.38 (s, 3H), 5.33-5.42 (m, 1H), 6.53-6.60 (m, 2H), 7.17 (s, 1H), 7.23 (t, J = 7.81 Hz, 1H), 7.58 (d, J = 1.71 Hz, 1H), 7.77 (s, 1H), 7.81-7.87 (m, 2H), 7.96 (d, J = 8.56 Hz, 1H), 8.22 (s, 1H), 8.36 (s, 1H), 8.49 (br d, J = 5.99 Hz, 1H), 12.79 (br s, 1H), 13.38 (br s, 1H) |
| 64 | $^1$H NMR (400 MHz, CHLOROFORM-d) δ ppm 1.81 (br d, J = 6.6 Hz, 3H), 2.44 (s, 3H), 5.28-5.34 (m, 1H), 6.43 (d, J = 8.5 Hz, 1H), 6.68 (t, J = 7.5 Hz, 1H), 7.03 (br s, 1H), 7.27-7.31 (m, 2H), 7.62 (s, 1H), 7.67 (s, 1H), 7.77 (br d, J = 8.4 Hz, 1H), 7.99 (br s, 1H), 8.08 (br d, J = 7.9 Hz, 1H), 8.29 (br s, 1H), 9.95 (br s, 1H) |
| 65 | $^1$H NMR (400 MHz, METHANOL-d4) δ ppm 1.78 (d, J = 6.6 Hz, 3H), 2.42 (s, 3H), 2.91 (s, 3H), 5.39 (q, J = 6.4 Hz, 1H), 6.49 (d, J = 8.5 Hz, 1H), 6.56 (t, J = 7.5 Hz, 1H), 7.08 (s, 1H), 7.18 (br t, J = 7.8 Hz, 1H), 7.66 (s, 1H), 7.88 (s, 1H), 7.92 (d, J = 8.2 Hz, 2H), 8.26 (d, J = 8.7 Hz, 1H), 8.46 (s, 1H) |
| 66 | $^1$H NMR (400 MHz, DMSO-d6) δ ppm 1.60 (d, J = 6.60 Hz, 3H), 2.32 (s, 3H) 5.09-5.19 (m, 1H), 6.44 (d, J = 8.44 Hz, 1H), 6.52-6.58 (m, 1H), 6.86 (s, 1H), 7.06-7.15 (m, 1H), 7.19-7.28 (m, 1H), 7.38-7.45 (m, 1H), 7.43-7.50 (m, 1H), 7.74-7.79 (m, 1H), 7.82 (dd, J = 7.95, 1.47 Hz, 1H), 8.19-8.24 (m, 1H), 8.36-8.45 (m, 1H), 8.66 (d, J = 6.72 Hz, 1H), 8.70 (s, 1H), 12.78 (br s, 1H) |
| 67 | $^1$H NMR (400 MHz, DMSO-d6) δ ppm 1.69 (d, J = 6.60 Hz, 3H), 2.36 (s, 3H), 5.46-5.52 (m, 1H), 6.52-6.63 (m, 2H), 6.77 (d, J = 2.08 Hz, 1H), 7.19 (s, 1H), 7.20-7.27 (m, 1H), 7.55 (d, J = 2.08 Hz, 1H), 7.76 (d, J = 1.22 Hz, 1H), 7.82 (dd, J = 8.01, 1.41 Hz, 1H), 7.85-7.88 (m, 2H), 8.19 (d, J = 2.20 Hz, 1H), 8.40-8.49 (m, 1H), 9.50 (s, 1H), 12.78 (br s, 1H) |
| 68 | $^1$H NMR (400 MHz, CHLOROFORM-d) δ ppm 1.75 (d, J = 6.7 Hz, 3H), 2.38 (s, 3H), 5.04 (d, J = 7.1 Hz, 1H), 6.53-6.60 (m, 2H), 6.79 (s, 1H), 7.09-7.15 (m, 3H), 7.23-7.29 (m, 2H), 7.47-7.50 (m, 2H), 7.61 (d, J = 8.3 Hz, 1H), 7.88-7.93 (m, 2H), 9.12 (br s, 1H) |
| 69 | $^1$H NMR (400 MHz, DMSO-d6) δ ppm 1.71 (d, J = 6.8 Hz, 3H), 2.38 (s, 3H), 2.46 (s, 3H), 5.34-5.37 (m, 1H), 6.54-6.58 (m, 2H), 7.19-7.22 (m, 2H), 7.60 (d, J = 2.0 Hz, 1H), 7.77 (s, 1H), 7.81 (d, J = 7.6 Hz, 1H), 7.94 (d, J = 9.6 Hz, 1H), 8.22 (d, J = 9.6 Hz, 1H), 8.28 (s, 1H), 8.45 (d, J = 6.0 Hz, 1H), 12.77 (s, 1H) |
| 70 | $^1$H NMR (400 MHz, DMSO-d6) δ ppm 1.68 (d, J = 6.60 Hz, 3H), 2.36 (s, 3H), 5.41-5.48 (m, 1H), 6.51 (d, J = 8.4 Hz, 1H), 6.56 (t, J = 7.5 Hz, 1H), 7.15-7.25 (m, 2H), 7.56 (d, J = 1.8 Hz, 1H), 7.75 (s, 1H), 7.80-7.87 (m, 2H), 8.11 (dd, J = 9.8, 1.6 Hz, 1H), 8.45 (br d, J = 6.0 Hz, 1H), 8.73 (s, 1H), 9.41 (s, 1H), 12.81 (br s, 1H) |

TABLE 56-continued

| Ex # | NMR Line Listing |
|---|---|
| 71 | $^1$H NMR (400 MHz, DMSO-d6) δ ppm 1.71 (d, J = 6.7 Hz, 3H), 2.37 (s, 3H), 5.40 (br t, J = 5.8 Hz, 1H), 6.52-6.58 (m, 2H), 6.81 (br s, 1H), 7.22 (br t, J = 7.0 Hz, 1H), 7.26 (s, 1H), 7.55-7.57 (m, 1H), 7.77 (s, 1H), 7.82 (d, J = 6.9 Hz, 1H), 8.12 (br s, 1H), 8.48 (br d, J = 5.1 Hz, 1H), 8.78 (s, 1H), 9.22 (br s, 1H), 12.23 (br s, 1H), 12.79 (br s, 1H) |
| 72 | $^1$H NMR (400 MHz, DMSO-d6) δ ppm 1.57 (d, J = 6.6 Hz, 3H), 2.39 (s, 3H), 2.65 (s, 3H), 5.09 (br s, 1H), 6.49 (d, J = 8.4 Hz, 1H), 6.54 (t, J = 7.4 Hz, 1H), 6.75 (s, 1H), 6.83 (s, 1H), 7.20 (br t, J = 7.7 Hz, 1H), 7.58-7.62 (m, 1H), 7.75-7.85 (m, 2H), 8.33 (br d, J = 4.4 Hz, 1H), 8.91 (br s, 1H), 9.18 (br s, 1H), 12.73 (br s, 1H) |
| 73 | $^1$H NMR (400 MHz, DMSO-d6) δ ppm 1.69 (d, J = 6.6 Hz, 3H), 2.38 (s, 3H), 5.46 (br t, J = 6.1 Hz, 1H), 6.53 (d, J = 8.6 Hz, 1H), 6.57 (t, J = 7.5 Hz, 1H), 7.21-7.27 (m, 2H), 7.59 (s, 1H), 7.78 (s, 1H), 7.84 (d, J = 8.2 Hz, 1H), 8.04 (d, J = 9.7 Hz, 1H), 8.15 (s, 1H), 8.38-8.49 (m, 3H), 9.57 (s, 1H), 12.82 (br s, 1H) |
| 74 | $^1$H NMR (400 MHz, DMSO-d6) δ ppm 1.68 (d, J = 6.60 Hz, 3H), 2.37 (s, 3H), 2.86 (s, 3H), 5.39-5.51 (m, 1H), 6.52-6.60 (m, 2H), 7.16 (s, 1H), 7.19-7.28 (m, 1H), 7.57 (d, J = 1.83 Hz, 1H), 7.74-7.77 (m, 1H), 7.82 (dd, J = 8.13, 1.53 Hz, 1H), 8.02-8.07 (m, 1H), 8.22 (dd, J = 8.68, 1.71 Hz, 1H), 8.42 (br d, J = 5.75 Hz, 1H), 8.85-8.90 (m, 1H), 12.76 (br s, 1H) |
| 75 | $^1$H NMR (400 MHz, DMSO-d6) δ ppm 1.70 (d, J = 6.4 Hz, 3H), 2.36 (s, 3H), 4.21 (s, 3H), 5.36-5.39 (m, 1H), 6.55-6.58 (m, 2H), 7.03 (s, 1H), 7.20-7.25 (m, 1H), 7.57 (s, 1H), 7.71-7.75 (m, 2H), 7.83 (d, J = 7.2 Hz, 1H), 7.87-7.89 (m, 1H), 8.45-8.46 (m, 1H), 8.54 (s, 1H), 8.59 (s, 1H), 12.77 (s, 1H) |
| 76 | $^1$H NMR (400 MHz, DMSO-d6) δ ppm 1.72 (d, J = 6.4 Hz, 3H), 2.38 (s, 3H), 5.26-5.28 (m, 1H), 6.50-6.58 (m, 2H), 7.17-7.21 (m, 2H), 7.26 (t, J = 6.8 Hz, 1H), 7.58-7.62 (m, 2H), 7.81-7.83 (m, 2H), 8.04 (d, J = 9.2 Hz, 1H), 8.42 (d, J = 4.4 Hz, 1H), 8.97 (d, J = 7.2 Hz, 1H), 12.84 (br s, 1H) |
| 77 | $^1$H NMR (400 MHz, DMSO-d6) δ ppm 1.70 (d, J = 6.8 Hz, 3H), 2.36 (s, 3H), 2.75 (s, 3H), 5.41-5.47 (m, 1H), 6.53-6.57 (m, 2H), 7.20 (t, J = 7.2 Hz, 1H), 7.22 (s, 1H), 7.56 (s, 1H), 7.64-7.66 (m, 1H), 7.75-7.77 (m, 1H), 7.81 (d, J = 6.8 Hz, 1H), 8.46 (d, J = 3.6 Hz, 1H), 8.52-8.54 (m, 2H), 12.76 (s, 1H) |
| 78 | $^1$H NMR (400 MHz, DMSO-d6) δ ppm 1.41-1.43 (m, 6H), 1.71 (d, J = 6.8 Hz, 3H), 2.37 (s, 3H), 3.68-3.76 (m, 1H), 5.36-5.38 (m, 1H), 6.55-6.59 (m, 2H), 7.23-7.25 (m, 1H), 7.29 (s, 1H), 7.58 (d, J = 2.0 Hz, 1H), 7.75-7.77 (m, 1H), 7.80-7.82 (m, 1H), 7.91-7.93 (m, 1H), 8.01-8.03 (m, 1H), 8.46-8.47 (m, 1H), 9.11 (s, 1H), 12.78 (s, 1H) |
| 79 | $^1$H NMR (400 MHz, DMSO-d6) δ ppm 1.68 (d, J = 6.4 Hz, 3H), 2.36 (s, 3H), 5.42-5.45 (m, 1H), 6.53-6.56 (m, 2H), 7.06 (s, 1H), 7.22-7.26 (m, 1H), 7.40 (d, J = 9.6 Hz, 1H), 7.50 (s, 1H), 7.57 (d, J = 2.0 Hz, 1H), 7.71-7.75 (m, 2H), 7.83 (d, J = 7.6 Hz, 1H), 8.44 (d, J = 6.0 Hz, 1H), 8.66 (s, 1H), 9.19 (s, 1H), 12.79 (s, 1H) |
| 80 | $^1$H NMR (400 MHz, DMSO-d6) δ ppm 1.70 (d, J = 6.8 Hz, 3H), 2.36 (s, 3H), 5.40-5.43 (m, 1H), 6.54-6.57 (m, 2H), 7.21-7.24 (m, 2H), 7.55 (d, J = 2.0 Hz, 1H), 7.59 (d, J = 7.2 Hz, 1H), 7.75 (s, 1H), 7.78 (s, 1H), 7.82 (d, J = 8.0 Hz, 1H), 8.13 (s, 1H), 8.41 (s, 1H), 8.46 (d, J = 6.4 Hz, 1H), 8.71 (d, J = 7.6 Hz, 1H) |
| 81 | $^1$H NMR (400 MHz, DMSO-d6) δ ppm 1.70 (d, J = 6.8 Hz, 3H), 2.38 (s, 3H), 2.91 (s, 3H), 5.41-5.44 (m, 1H), 6.54-6.59 (m, 2H), 7.22 (t, J = 7.2 Hz, 1H), 7.35 (s, 1H), 7.57 (d, J = 2.0 Hz, 1H), 7.78-7.83 (m, 2H), 8.46 (d, J = 6.0 Hz, 1H), 8.99 (d, J = 2.0 Hz, 1H), 9.30 (d, J = 2.0 Hz, 1H), 12.76 (s, 1H) |
| 82 | $^1$H NMR (400 MHz, DMSO-d6) δ ppm 1.74 (d, J = 6.4 Hz, 3H), 2.38 (s, 3H), 4.16 (s, 3H), 5.39-5.42 (m, 1H), 6.54-6.60 (m, 2H), 7.21-7.25 (m, 1H), 7.44 (s, 1H), 7.61 (s, 1H), 7.77-7.82 (m, 2H), 8.09 (d, J = 8.0 Hz, 1H), 8.30 (s, 1H), 8.48 (d, J = 8.4 Hz, 2H), 12.76 (s, 1H) |
| 83 | $^1$H NMR (400 MHz, DMSO-d6) δ ppm 1.71 (d, J = 6.8 Hz, 3H), 2.37 (s, 3H), 4.22 (s, 3H), 5.39-5.43 (m, 1H), 7.04 (s, 1H), 7.15 (d, J = 9.2 Hz, 1H), 7.34 (d, J = 8.8 Hz, 1H), 7.55 (d, J = 2.0 Hz, 1H), 7.72-7.76 (m, 2H), 7.90 (d, J = 9.6 Hz, 1H), 8.49 (s, 1H), 8.56 (s, 1H), 8.60 (s, 1H) |
| 84 | $^1$H NMR (400 MHz, DMSO-d6) δ ppm 1.68 (d, J = 6.6 Hz, 3H), 2.39 (s, 3H), 5.24-5.34 (m, 1H), 6.53 (d, J = 8.6 Hz, 1H), 6.57 (t, J = 7.5 Hz, 1H), 6.89 (s, 1H), 7.21 (t, J = 7.8 Hz, 1H), 7.44 (qd, J = 7.5, 6.2 Hz, 2H), 7.58 (d, J = 1.8 Hz, 1H), 7.79-7.87 (m, 3H), 8.07 (d, J = 7.3 Hz, 1H), 8.41 (br s, 1H), 8.96 (s, 1H), 12.81 (br s, 1H) |
| 85 | $^1$H NMR (400 MHz, DMSO-d6) δ ppm 1.74 (d, J = 6.7 Hz, 3H), 2.40 (s, 3H), 5.29 (br t, J = 6.0 Hz, 1H), 6.52 (d, J = 8.4 Hz, 1H), 6.58 (t, J = 7.5 Hz, 1H), 7.06 (s, 1H), 7.19 (t, J = 7.8 Hz, 1H), 7.59-7.66 (m, 2H), 7.81-7.87 (m, 3H), 8.26 (d, J = 8.4 Hz, 1H), 8.32 (d, J = 8.3 Hz, 1H), 8.44 (br d, J = 5.7 Hz, 1H), 12.81 (br s, 1H) |
| 86 | $^1$H NMR (400 MHz, DMSO-d6) δ ppm 1.76 (d, J = 6.7 Hz, 3H), 2.38 (s, 3H), 5.32 (br t, J = 6.1 Hz, 1H), 6.50 (d, J = 8.6 Hz, 1H), 6.58 (t, J = 7.5 Hz, 1H), 6.79 (s, 1H), 7.19 (t, J = 7.4 Hz, 1H), 7.27 (dd, J = 9.6, 8.1 Hz, 1H), 7.58 (d, J = 2.0 Hz, 1H), 7.73 (td, J = 8.2, 5.4 Hz, 1H), 7.81-7.86 (m, 2H), 8.09 (d, J = 8.6 Hz, 1H), 8.45 (br d, J = 5.5 Hz, 1H), 8.85 (s, 1H), 12.83 (br s, 1H) |
| 87 | $^1$H NMR (400 MHz, DMSO-d6) δ ppm 1.76 (d, J = 6.60 Hz, 3H) 2.38 (s, 3H) 2.46 (s, 3H) 5.30-5.38 (m, 1H) 6.49 (d, J = 8.44 Hz, 1H) 6.58 (t, J = 7.52 Hz, 1H) 6.73 (s, 1H) 7.16-7.24 (m, 1H) 7.52-7.56 (m, 1H) 7.56-7.58 (m, 1H) 7.73-7.79 (m, 1H) 7.79-7.82 (m, 1H) 7.85 (dd, J = 7.89, 1.41 Hz, 1H) 8.16 (d, J = 8.68 Hz, 1H) 8.37-8.56 (m, 1H) 8.61 (s, 1H) 12.85 (br s, 1H) |
| 88 | $^1$H NMR (400 MHz, DMSO-d6) δ ppm 1.76 (br d, J = 6.60 Hz, 3H) 2.38 (s, 3H) 2.65 (s, 3H) 5.29-5.38 (m, 1H) 6.46-6.54 (m, 1H) 6.54-6.62 (m, 1H) 6.75 (s, 1H) 7.14-7.27 (m, 2H) 7.50-7.64 (m, 2H) 7.80-7.82 (m, 1H) 7.85 (d, J = 7.58 Hz, 1H) 8.07 (d, J = 8.56 Hz, 1H) 8.37-8.55 (m, 1H) 8.78 (s, 1H) 12.85 (br s, 1H) |
| 89 | $^1$H NMR (400 MHz, DMSO-d6) δ ppm 1.76 (d, J = 6.6 Hz, 3H), 2.38 (s, 3H), 5.27-5.35 (m, 1H), 6.50 (d, J = 8.4 Hz, 1H), 6.58 (t, J = 7.5 Hz, 1H), 6.76 (s, 1H), 7.20 (t, J = 7.7 Hz, |

TABLE 56-continued

| Ex # | NMR Line Listing |
|---|---|
| | 1H), 7.57 (d, J = 2.0 Hz, 1H), 7.63 (td, J = 9.2, 2.4 Hz, 1H), 7.79-7.86 (m, 3H), 8.26 (dd, J = 9.2, 4.1 Hz, 1H), 8.45 (br d, J = 5.1 Hz, 1H), 8.68 (s, 1H), 12.84 (br s, 1H) |
| 90 | $^1$H NMR (400 MHz, DMSO-d6) δ ppm 1.60 (d, J = 6.4 Hz, 3H), 2.17 (s, 3H), 2.36 (s, 3H), 5.15-5.16 (m, 1H), 6.44 (d, J = 8.0 Hz, 1H), 6.54-6.56 (m, 2H), 7.20-7.22 (m, 1H), 7.43-7.45 (m, 1H), 7.50-7.51 (m, 1H), 7.54-7.56 (m, 1H), 7.73 (d, J = 8.0 Hz, 1H), 7.78-7.82 (m, 2H), 7.90 (s, 1H), 8.38-8.39 (m, 1H), 11.44 (s, 1H), 12.90 (s, 1H) |
| 91 | $^1$H NMR (400 MHz, DMSO-d6) δ ppm 1.59 (d, J = 6.8 Hz, 3H), 2.13 (s, 3H), 2.37 (s, 3H), 4.23 (s, 3H), 5.11-5.16 (m, 1H), 6.48 (d, J = 8.4 Hz, 1H), 6.55 (t, J = 7.6 Hz, 2H), 7.53 (d, J = 2.0 Hz, 1H), 7.62-7.63 (m, 1H), 7.74-7.82 (m, 3H), 8.21 (s, 1H), 8.42 (s, 1H), 8.55 (s, 1H), 12.82 (br s, 1H) |
| 92 | $^1$H NMR (400 MHz, DMSO-d6) δ ppm 1.57 (d, J = 6.8 Hz, 3H), 2.00 (s, 3H), 2.36 (s, 3H), 5.10-5.13 (m, 1H), 6.14 (s, 1H), 6.17 (s, 1H), 6.43 (d, J = 8.4 Hz, 1H), 6.53 (t, J = 7.2 Hz, 1H), 7.01-7.05 (m, 1H), 7.13-7.15 (m, 1H), 7.19-7.20 (m, 2H), 7.52 (d, J = 2.0 Hz, 1H), 7.77 (s, 1H), 7.80 (d, J = 8.0 Hz, 1H), 8.37 (s, 1H), 12.75 (br s, 1H) |
| 93 | $^1$H NMR (400 MHz, DMSO-d6) δ ppm 1.58 (d, J = 6.8 Hz, 3H), 2.08 (s, 3H), 2.35 (s, 3H), 5.10-5.13 (m, 1H), 6.15 (s, 2H), 6.45 (d, J = 8.0 Hz, 1H), 6.54-6.56 (m, 1H), 7.11 (d, J = 8.0 Hz, 1H), 7.19-7.21 (m, 1H), 7.30-7.32 (m, 1H), 7.38 (s, 1H), 7.50 (s, 1H), 7.75 (s, 1H), 7.79 (d, J = 6.8 Hz, 1H), 8.35-8.36 (m, 1H), 12.76 (s, 1H) |
| 94 | $^1$H NMR (400 MHz, DMSO-d6) δ ppm 1.68 (d, J = 6.72 Hz, 3H), 2.41 (s, 3H), 2.55 (s, 3H), 5.55-5.64 (m, 1H), 6.48 (td, J = 9.54, 3.42 Hz, 1H), 7.12-7.28 (m, 3H), 7.62 (d, J = 2.20 Hz, 1H), 7.75-7.79 (m, 1H), 7.87 (d, J = 9.66 Hz, 1H), 8.26-8.32 (m, 2H) 13.64 (br s, 1H) |
| 95 | $^1$H NMR (400 MHz, DMSO-d6) δ ppm 1.70 (d, J = 6.60 Hz, 3H), 2.37 (s, 3H), 4.26 (s, 3H), 5.31-5.46 (m, 1H), 6.52-6.61 (m, 2H), 7.13 (s, 1H), 7.25 (td, J = 7.79, 1.65 Hz, 1H), 7.57 (d, J = 2.08 Hz, 1H), 7.75 (d, J = 1.47 Hz, 1H), 7.82 (dd, J = 8.07, 1.59 Hz, 1H), 8.04 (d, J = 1.47 Hz, 1H), 8.44 (br d, J = 6.11 Hz, 1H), 8.59 (d, J = 1.47 Hz, 1H), 8.69 (s, 1H), 12.75 (br s, 1H) |
| 96 | $^1$H NMR (400 MHz, DMSO-d6) δ ppm 1.56 (d, J = 6.6 Hz, 3H), 2.41 (s, 3H), 4.01 (s, 3H), 5.11 (m, 1H), 6.43 (d, J = 8.0 Hz, 1H), 6.53 (m, 1H), 6.82 (s, 1H), 7.16 (m, 1H), 7.65 (s, 1H), 7.75 (m, 1H), 7.87 (m, 1H), 8.04 (d, J = 5.2 Hz, 1H), 8.44 (d, J = 5.5 Hz, 1H), 12.74 (br s, 1H) |
| 97 | $^1$H NMR (400 MHz, DMSO-d6) δ ppm 1.71 (d, J = 6.72 Hz, 3H), 2.38 (s, 3H), 4.26 (s, 3H), 5.39 (m, 1H), 6.58 (m, 2H), 7.12 (s, 1H), 7.25 (m, 1H), 7.58 (d. J = 2.08 Hz, 1H), 7.79 (m, 3H), 8.47 (m, 2H), 8.69 (d, J = 2.69, 1H), 12.76 (br s, 1H) |
| 99 | $^1$H NMR (400 MHz, DMSO-d6) δ ppm 1.71 (d, J = 6.6 Hz, 3H), 2.36 (s, 3H), 2.40 (s, 3H), 5.53 (br s, 1H), 7.03 (s, 1H), 7.12 (t, J = 7.4 Hz, 1H), 7.22 (d, J = 8.9 Hz, 1H), 7.28-7.33 (m, 2H), 7.45 (d, J = 1.3 Hz, 1H), 7.53 (d, J = 9.7 Hz, 1H), 7.55 (s, 1H), 7.69 (d, J = 8.1 Hz, 1H), 7.75 (d, J = 1.3 Hz, 1H), 8.53 (br s, 1H), 11.93 (s, 1H) |
| 100 | $^1$H NMR (500 MHz, DMSO-d6) δ ppm 1.76 (d, J = 6.7 Hz, 3H), 5.57-5.63 (m, 1H), 7.13-7.16 (m, 2H), 7.18-7.20 (m, 1H), 7.31-7.35 (m, 2H), 7.54-7.55 (m, 2H), 7.71-7.72 (m, 1H), 7.99 (d, J = 1.8 Hz, 1H), 8.21 (d, J = 1.7 Hz, 1H), 8.50-8.51 (m, 1H), 12.00 (d, J = 0.7 Hz, 1H), 13.33-13.39 (m, 1H) |
| 101 | $^1$H NMR (500 MHz, DMSO-d6) δ ppm 1.78 (d, J = 6.7 Hz, 3H), 3.76 (br, 3H), 5.42-5.48 (m, 1H), 6.58-6.61 (m, 2H), 7.21-7.25 (m, 1H), 7.39 (s, 1H), 7.83-7.84 (m, 1H), 8.03 (d, J = 1.9 Hz, 1H), 8.11-8.16 (m, 1H), 8.25 (d, J = 1.4 Hz, 1H), 8.37-8.42 (m, 2H), 8.52-8.54 (m, 1H), 13.12-13.18 (m, 1H) |
| 102 | $^1$H NMR (500 MHz, DMSO-d6) δ ppm 1.73-1.74 (m, 3H), 2.48 (br, 3H), 5.36-5.38 (m, 1H), 6.83-6.85 (m, 1H), 6.96-6.98 (m, 1H), 7.34-7.36 (m, 1H), 7.97-7.98 (m, 1H), 8.03-8.05 (m, 2H), 8.27-8.29 (m, 2H), 8.34-8.37 (m, 1H), 10.20-10.21 (m, 1H) |
| 103 | $^1$H NMR (400 MHz, DMSO-d6) δ ppm 1.61 (d, J = 6.8 Hz, 3H), 2.37 (s, 3H), 4.22 (s, 3H), 5.17-5.24 (m, 1H), 6.02-6.06 (m, 1H), 6.10-6.17 (m, 1H), 6.78 (br s, 1H), 7.04 (s, 1H), 7.60 (br s, 1H), 7.72 (br s, 1H), 7.75 (d, J = 9.2 Hz, 1H), 7.91 (dd, J = 8.8, 2.0 Hz, 1H), 8.60-8.69 (m, 3H) |
| 104 | $^1$H NMR (400 MHz, DMSO-d6) δ ppm 1.73 (d, J = 6.72 Hz, 3H), 2.39 (s, 3H), 4.32 (s, 3H), 5.42 (m, 1 H), 6.58 (m, 2H), 7.24 (m, 1H), 7.34 (s, 1H), 7.62 (d, J = 2.08 Hz, 1H), 7.79 (m, 1H), 7.83 (m, 1H), 8.12 (m, 2H), 8.46 (m, 1H), 8.77 (s, 1H), 12.77 (br s, 1H) |
| 105 | $^1$H NMR (400 MHz, DMSO-d6) δ ppm 1.7 (d, J = 6.6 Hz, 3H), 2.39 (s, 3H), 5.34 (m, 1H), 6.46 (d, J = 8.44 Hz, 1H), 6.57 (m, 1H), 7.11 (dd, J = 4.22, 2.51 Hz, 1H), 7.21 (m, 2H), 7.39 (d, J = 4.16 Hz, 1H), 7.62 (d, J = 2.2 Hz, 1H), 7.78 (d, J = 4.65 Hz, 1H), 7.83 (m, 2H), 8.01 (m, 1H), 8.45 (m, 1H), 8.57 (m, 1H), 12.86 (br s, 1H) |
| 106 | $^1$H NMR (400 MHz, DMSO-d6) δ ppm 1.66 (d, J = 6.60 Hz, 3H) 2.39 (s, 3H) 5.30 (br s, 1H) 6.49-6.59 (m, 2H) 7.01 (s, 1H) 7.06-7.14 (m, 2H) 7.23 (ddd, J = 8.47, 7.12, 1.65 Hz, 1H) 7.60 (d, J = 2.08 Hz, 1H) 7.79-7.85 (m, 2H) 8.02 (dd, J = 7.27, 0.67 Hz, 1H) 8.20 (d, J = 2.32 Hz, 1H) 8.41 (br s, 1H) 8.97 (d, J = 6.97 Hz, 1H) 12.48-13.13 (m, 1H) |
| 107 | $^1$H NMR (400 MHz, METHANOL-d4) δ ppm 1.79 (d, J = 6.7 Hz, 3H), 2.43 (s, 3H), 2.64 (br s, 3H), 5.38 (q, J = 6.7 Hz, 1H), 6.52-6.60 (m, 2H), 7.20 (t, J = 7.8 Hz, 1H), 7.37 (s, 1H), 7.70 (d, J = 2.2 Hz, 1H), 7.89 (dd, J = 2.1, 0.9 Hz, 1H), 7.91 (dd, J = 7.9, 1.5 Hz, 1H), 8.34 (d, J = 9.4 Hz, 1H), 8.39 (s, 1H), 8.40 (d, J = 8.5 Hz, 1H) |
| 108 | $^1$H NMR (500 MHz, DMSO-d6) δ ppm 1.81 (d, J = 6.7 Hz, 3H), 4.19 (s, 3H), 5.51-5.56 (m, 1H), 7.20 (d, J = 9.1 Hz, 1H), 7.33 (d, J = 8.9 Hz, 1H), 7.43 (s, 1H), 7.92 (dd, J = 1.3, 8.5 Hz, 1H), 7.98 (d, J = 8.6 Hz, 1H), 8.01 (d, J = 1.9 Hz, 1H), 8.20 (d, J = 0.6 Hz, 1H), 8.26 (d, J = 1.4 Hz, 1H), 8.45-8.50 (m, 1H), 8.51 (s, 1H), 13.27-13.31 (m, 1H) |
| 110 | $^1$H NMR (400 MHz, DMSO-d6) δ ppm 1.66 (d, J = 6.4 Hz, 3H), 2.31 (s, 3H), 5.25 (m, 1H), 6.48 (m, 2H), 7.15 (m, 2H), 7.52 (m, 3H), 7.74 (m, 2H), 7.87 (m, 1H), 7.94 (m, 1H), 8.42 (d, J = 6.4 Hz, 1H), 12.73 (br s, 1H) |
| 111 | $^1$H NMR (400 MHz, DMSO-d6) δ ppm 1.63 (d, J = 6.4 Hz, 3H), 2.32 (s, 3H), 4.17 (s, 3H), 5.28 (m, 1H), 6.48 (m, 2H), 6.93 (s, 1H), 7.16 (m, 1H), 7.38 (dd, J = 8.62, 7.15 Hz, |

TABLE 56-continued

| Ex # | NMR Line Listing |
|---|---|
| | 1H), 7.53 (d, J = 2.08 Hz, 1H), 7.74 (m, 2H), 7.84 (dd, J = 7.89, 5.69, 2H), 8.36 (d, J = 6.11 Hz, 1H), 8.82 (s, 1H), 12.75 (br s, 1H) |
| 112 | $^1$H NMR (400 MHz, DMSO-d6) δ ppm 1.71 (d, J = 6.4 Hz, 3H), 2.36 (s, 3H), 2.45 (s, 3H), 5.38-5.42 (m, 1H), 6.54-6.57 (m, 2H), 7.22-7.25 (m, 2H), 7.55 (d, J = 2.4 Hz, 1H), 7.59 (dd, J = 7.2, 2.0 Hz, 1H), 7.62-7.65 (m, 1H), 7.75-7.76 (m, 1H), 7.82 (dd, J = 8.4, 2.0 Hz, 1H), 8.08-8.11 (m, 1H), 8.42-8.48 (m, 3H), 8.70 (d, J = 4.8 Hz, 1H), 8.83-8.84 (m, 1H), 12.81 (s, 1H) |
| 113 | $^1$H NMR (400 MHz, DMSO-d6) δ ppm 1.69 (d, J = 6.4 Hz, 3H), 2.37 (s, 3H), 5.39-5.43 (m, 1H), 6.54-6.58 (m, 2H), 6.89 (d, J = 2.0 Hz, 1H), 7.21-7.25 (m, 2H), 7.54 (dd, J = 7.6, 2.0 Hz, 1H), 7.59 (d, J = 2.0 Hz, 1H), 7.76 (s, 1H), 7.82 (d, J = 8.0 Hz, 1H), 8.13 (d, J = 2.0 Hz, 1H), 8.50 (s, 1H), 8.54 (s, 1H), 8.83 (d, J = 7.2 Hz, 1H) |
| 114 | $^1$H NMR (400 MHz, DMSO-d6) δ ppm 1.54-1.73 (m, 3H), 2.33-2.41 (m, 3H), 5.16-5.26 (m, 1H), 6.09-6.16 (m, 1H), 6.51-7.42 (m, 4H), 7.60-8.06 (m, 5H), 7.34-8.69 (m, 2H), 10.99-11.64 (m, 1H), 12.42-13.29 (m, 1H) |
| 115 | $^1$H NMR (400 MHz, DMSO-d6) δ ppm 1.67 (d, J = 6.60 Hz, 3H), 2.08 (s, 2H), 2.35 (s, 3H), 5.21-5.37 (m, 1H), 6.46-6.50 (m, 1H), 6.53-6.60 (m, 1H), 7.00 (s, 1H), 7.19-7.25 (m, 1H), 7.38-7.43 (m, 1H), 7.49-7.51 (m, 1H), 7.52-7.54 (m, 1H), 7.71-7.76 (m, 2H), 7.82 (dd, J = 7.95, 1.71 Hz, 1H), 8.45 (br d, J = 6.11 Hz, 1H), 10.57 (s, 1H), 12.83 (br s, 1H) |
| 116 | $^1$H NMR (400 MHz, DMSO-d6) δ ppm 1.71 (d, J = 6.6 Hz, 3H), 2.38 (s, 3H), 4.31 (s, 3H), 5.41-5.49 (m, 1H), 6.54-6.59 (m, 2H), 7.22-7.30 (m, 2H), 7.57 (d, J = 2.2 Hz, 1H), 7.77 (dd, J = 2.1, 0.8 Hz, 1H), 7.83 (dd, J = 8.1, 1.6 Hz, 1H), 8.02-8.06 (m, 2H), 8.23 (dd, J = 7.2, 0.7 Hz, 1H), 8.47 (br d, J = 5.3 Hz, 1H), 8.64 (s, 1H), 12.81 (br s, 1H) |
| 117 | $^1$H NMR (400 MHz, DMSO-d6) δ ppm 1.70 (d, J = 6.6 Hz, 3H), 2.38 (s, 3H), 2.76 (s, 3H), 5.44 (quin, J = 6.4 Hz, 1H), 6.54-6.59 (m, 2H), 7.23 (td, J = 7.8, 1.7 Hz, 1H), 7.54-7.61 (m, 2H), 7.77 (dd, J = 2.1, 0.8 Hz, 1H), 7.82 (dd, J = 8.3, 1.7 Hz, 1H), 7.85 (s, 1H), 7.96 (dd, J = 8.1, 0.8 Hz, 1H), 8.15 (dd, J = 7.9, 0.8 Hz, 1H), 8.46 (br d, J = 6.2 Hz, 1H), 12.81 (br s, 1H) |
| 118 | $^1$H NMR (400 MHz, DMSO-d6) δ ppm 1.63 (bd, J = 6.5 Hz, 3H), 2.41 (bs, 3H), 5.23-5.26 (m, 1H), 6.52-6.59 (m, 2H), 7.19-7.23 (m, 1H), 7.69 (s, 1H), 7.81-7.85 (m, 2H), 8.05 (br d, J = 9.5, 1H), 8.22 (br d, J = 8.8 Hz, 1H), 8.30 (s, 1H), 8.40 (br d, J = 5.6 Hz, 1H), 9.57 (s, 1H), 12.77 (s, 1H) |
| 119 | $^1$H NMR (400 MHz, METHANOL-d4) δ ppm 1.60 (d, J = 6.6 Hz, 3H), 2.33 (s, 3H), 4.44 (s, 3H), 5.25 (q, J = 6.6 Hz, 1H), 6.36 (d, J = 8.4 Hz, 1H), 6.47 (t, J = 7.6 Hz, 1H), 6.79 (s, 1H), 7.07 (t, J = 7.8 Hz, 1H), 7.18-7.25 (m, 1H), 7.34 (t, J = 7.7 Hz, 1H), 7.59 (s, 1H), 7.66 (d, J = 8.7 Hz, 1H), 7.79-7.88 (m, 3H) |
| 120 | $^1$H NMR (400 MHz, DMSO-d6) δ ppm 1.60 (br d, J = 6.60 Hz, 3H), 2.08-2.16 (m, 3H), 2.30-2.45 (m, 3H), 5.13 (br s, 1H), 6.46 (d, J = 8.56 Hz, 1H), 6.55 (t, J = 7.52 Hz, 1H), 7.22 (t, J = 7.76 Hz, 1H), 7.51-7.56 (m, 2H), 7.79-7.83 (m, 2H), 7.97 (d, J = 8.31 Hz, 1H), 8.03 (s, 1H), 8.23 (s, 1H), 8.39 (br d, J = 4.77 Hz, 1H), 12.80 (br s, 1H), 13.41 (br s, 1H) |
| 121 | $^1$H NMR (500 MHz, DMSO-d6) δ ppm 1.73 (d, J = 6.7 Hz, 3H), 2.39 (s, 3H), 5.40-5.46 (m, 1H), 6.56-6.59 (m, 2H), 7.22-7.25 (m, 1H), 7.31 (s, 1H), 7.61 (d, J = 1.8 Hz, 1H), 7.80 (d, J = 1.0 Hz, 1H), 7.83 (dd, J = 1.3, 7.9 Hz, 1H), 8.10 (d, J = 8.3 Hz, 1H), 8.32 (s, 1H), 8.47-8.52 (m, 2H), 12.95-12.98 (m, 2H) |
| 122 | $^1$H NMR (500 MHz, DMSO-d6) δ ppm 1.13 (s, 6H), 1.71 (d, J = 6.7 Hz, 3H), 2.38 (s, 3H), 4.40 (s, 2H), 5.42-5.45 (m, 1H), 6.56-6.59 (m, 2H), 7.05 (s, 1H), 7.24-7.27 (m, 1H), 7.57 (d, J = 1.2 Hz, 1H), 7.76-7.77 (m, 2H), 7.83-7.84 (m, 1H), 7.91 (dd, J = 1.3, 9.2 Hz, 1H), 8.48-8.50 (m, 1H), 8.53 (s, 1H), 8.66 (s, 1H) |
| 123 | $^1$H NMR (500 MHz, DMSO-d6) δ ppm 1.15 (s, 6H), 1.71 (d, J = 6.6 Hz, 3H), 2.38 (s, 3H), 4.38 (s, 2H), 4.71 (s, 1H), 5.39-5.44 (m, 1H), 6.58 (t, J = 7.0 Hz, 2H), 7.10 (s, 1H), 7.23-7.27 (m, 1H), 7.58 (s, 1H), 7.77 (s, 1H), 7.82-7.85 (m, 1H), 7.88 (d, J = 8.9 Hz, 1H), 8.10 (d, J = 8.7 Hz, 1H), 8.25 (s, 1H), 8.52-8.54 (m, 1H), 8.59 (s, 1H), 12.99-13.04 (m, 1H) |
| 124 | $^1$H NMR (400 MHz, DMSO-d6) δ ppm 1.56 (br d, J = 6.48 Hz, 3H), 2.07 (s, 3H), 2.46 (s, 3H), 5.06-5.15 (m, 1H), 6.43 (d, J = 8.44 Hz, 1H), 6.49 (t, J = 7.52 Hz, 1H), 7.15 (br t, J = 7.76 Hz, 1H), 7.52 (br d, J = 8.80 Hz, 1H), 7.59-7.65 (m, 1H), 7.74 (d, J = 7.95 Hz, 1H), 7.96 (br d, J = 9.29 Hz, 1H), 8.03-8.17 (m, 2H), 8.30 (br d, J = 6.24 Hz, 1H), 9.25 (s, 1H), 12.74 (br s, 1H) |
| 125 | $^1$H NMR (400 MHz, DMSO-d6) δ ppm 1.65 (br d, J = 6.36 Hz, 3H), 2.29 (s, 3H), 5.25-5.33 (m, 1H), 6.42 (br d, J = 8.56 Hz, 1H), 6.50 (t, J = 7.46 Hz, 1H), 6.86 (s, 1H), 7.07-7.19 (m, 2H), 7.45 (s, 1H), 7.56 (br t, J = 7.83 Hz, 1H), 7.69 (s, 1H), 7.77 (br d, J = 7.95 Hz, 1H), 8.17 (br d, J = 8.93 Hz, 1H), 8.39 (br d, J = 5.38 Hz, 1H), 8.81 (s, 1H), 8.87 (d, J = 6.72 Hz, 1H), 12.77 (br s, 1H) |
| 126 | $^1$H NMR (400 MHz, DMSO-d6) δ ppm 1.70 (br d, J = 6.48 Hz, 3H), 2.37 (s, 3H), 2.57 (s, 3H), 4.22 (s, 3H), 5.33-5.44 (m, 1H), 6.52-6.62 (m, 2H), 7.04 (s, 1H), 7.22-7.29 (m, 1H), 7.53-7.60 (m, 1H), 7.66-7.72 (m, 1H), 7.73-7.78 (m, 1H), 7.79-7.86 (m, 1H), 8.41-8.47 (m, 2H), 8.50-8.54 (m, 1H), 12.78 (br s, 1H) |
| 127 | $^1$H NMR (400 MHz, DMSO-d6) δ ppm 1.68 (br d, J = 6.60 Hz, 3H) 2.38 (s, 3H) 5.38 (br d, J = 6.60 Hz, 1H) 6.53-6.59 (m, 2H) 7.20-7.29 (m, 2H) 7.59 (s, 1H) 7.76-7.84 (m, 2H) 7.84-7.93 (m, 1H) 8.16 (br s, 1H) 8.20-8.33 (m, 3H) 8.44 (br s, 1H) 8.89 (d, J = 6.72 Hz, 1H) |
| 128 | $^1$H NMR (400 MHz, DMSO-d6) δ ppm 1.71 (br d, J = 6.5 Hz, 3H), 5.53 (br s, 1H), 6.54 (d, J = 8.5 Hz, 1H), 6.59 (t, J = 7.5 Hz, 1H), 7.06-7.14 (m, 2H), 7.24 (br t, J = 7.8 Hz, 1H), 7.30 (t, J = 7.6 Hz, 1H), 7.47-7.55 (m, 3H), 7.61 (dd, J = 7.7, 2.8 Hz, 1H), 7.69 (d, J = 7.9 Hz, 1H), 7.84 (d, J = 7.9 Hz, 1H), 8.38-8.52 (m, 1H), 11.98 (s, 1H), 12.87 (br s, 1H) |

TABLE 56-continued

| Ex # | NMR Line Listing |
|---|---|
| 129 | $^1$H NMR (400 MHz, DMSO-d6) δ ppm 1.62 (br d, J = 6.5 Hz, 3H), 2.37 (s, 3H), 5.71 (br t, J = 6.3 Hz, 1H), 6.52 (d, J = 8.5 Hz, 1H), 6.58 (t, J = 7.5 Hz, 1H), 7.13 (t, J = 7.4 Hz, 1H), 7.21-7.33 (m, 3H), 7.45 (dd, J = 8.9, 2.8 Hz, 1H), 7.60-7.67 (m, 2H), 7.73 (d, J = 8.1 Hz, 1H), 7.84 (d, J = 7.9 Hz, 1H), 8.39 (br d, J = 5.9 Hz, 1H), 11.62 (s, 1H), 12.88 (br s, 1H) |
| 130 | $^1$H NMR (400 MHz, METHANOL-d4) δ ppm 1.57 (d, J = 6.6 Hz, 3H), 2.20 (s, 3H), 2.32 (s, 3H), 4.25 (s, 3H), 5.15 (q, J = 6.6 Hz, 1H), 6.38 (d, J = 8.4 Hz, 1H), 6.44 (t, J = 7.5 Hz, 1H), 7.03-7.12 (m, 1H), 7.48-7.57 (m, 1H), 7.73-7.83 (m, 3H), 8.13-8.20 (m, 1H), 8.51-8.57 (m, 1H) |
| 131 | $^1$H NMR (400 MHz, METHANOL-d4) δ ppm 1.57 (d, J = 6.72 Hz, 3H), 2.20 (s, 3H), 2.32 (s, 3H), 4.09 (s, 3H), 5.14 (q, J = 6.5 Hz, 1H), 6.33-6.50 (m, 2H), 7.01-7.12 (m, 1H), 7.45-7.58 (m, 1H), 7.74-7.82 (m, 2H), 7.85-7.95 (m, 1H), 8.10-8.20 (m, 1H), 8.20-8.27 (m, 1H) |
| 132 | $^1$H NMR (400 MHz, DMSO-d6) δ ppm 1.60 (br d, J = 6.60 Hz, 3H), 2.14 (s, 3H), 2.38 (s, 3H), 5.15 (br s, 1H), 6.48 (d, J = 8.56 Hz, 1H), 6.56 (t, J = 7.52 Hz, 1H), 7.22 (t, J = 7.70 Hz, 1H), 7.54 (s, 1H), 7.71-7.75 (m, 1H), 7.75-7.84 (m, 3H), 8.26 (s, 2H), 8.37 (br s, 1H), 12.79 (br s, 1H), 13.40 (br s, 1H) |
| 133 | $^1$H NMR (400 MHz, METHANOL-d4) δ ppm 1.81 (br d, J = 8.0 Hz, 3H), 2.42 (s, 3H), 2.83 (s, 3H), 5.41-5.48 (m, 1H), 6.49-6.54 (m, 1H), 6.54-6.60 (m, 1H), 7.10-7.25 (m, 2H), 7.41-7.50 (m, 1H), 7.60-7.68 (m, 1H), 7.74-7.83 (m, 1H), 7.84-7.90 (m, 1H), 7.91-7.97 (m, 1H), 8.04-8.18 (m, 1H), 8.39-8.43 (m, 1H), 9.67-9.77 (m, 1H) |
| 134 | $^1$H NMR (400 MHz, DMSO-d6) δ ppm 1.69 (br d, J = 6.60 Hz, 3H), 2.35 (s, 3H), 2.44 (s, 3H), 5.37-5.51 (m, 1H), 6.52-6.59 (m, 3H), 7.16 (s, 1H), 7.19-7.27 (m, 1H), 7.50-7.56 (m, 1H), 7.70-7.76 (m, 2H), 7.77-7.86 (m, 2H), 8.45 (br d, J = 5.87 Hz, 1H), 9.35-9.41 (m, 1H), 12.80 (br s, 1H) |
| 135 | $^1$H NMR (400 MHz, DMSO-d6) δ ppm 1.72 (br d, J = 6.60 Hz, 3H) 2.38 (s, 3H) 4.29 (s, 3H) 5.42 (br t, J = 6.24 Hz, 1H) 6.53-6.60 (m, 2H) 7.19-7.27 (m, 1H) 7.33 (s, 1H) 7.59 (s, 1H) 7.78-7.81 (m, 1H) 7.81-7.84 (m, 1H) 7.98 (d, J = 8.68 Hz, 1H) 8.44-8.53 (m, 2H) 8.59 (s, 1H) 12.81 (br s, 1H) |
| 136 | $^1$H NMR (400 MHz, DMSO-d6) δ ppm 1.66 (d, J = 6.60 Hz, 3H) 2.38 (s, 3H) 4.15 (s, 3H) 5.27-5.35 (m, 1H) 6.49 (d, J = 8.56 Hz, 1H) 6.56 (t, J = 7.52 Hz, 1H) 7.05 (s, 1H) 7.21 (t, J = 7.76 Hz, 1H) 7.57-7.63 (m, 2H) 7.79-7.85 (m, 2H) 7.88-7.92 (m, 1H) 7.97 (d, J = 8.31 Hz, 1H) 8.44 (br d, J = 5.14 Hz, 1H) 8.47-8.53 (m, 1H) 12.84 (br s, 1H) |
| 137 | $^1$H NMR (400 MHz, DMSO-d6) δ ppm 1.59 (br d, J = 6.5 Hz, 3H), 2.09 (s, 3H), 2.38 (s, 3H), 3.13 (s, 3H), 4.58 (s, 2H), 5.12 (br t, J = 5.9 Hz, 1H), 6.48 (d, J = 8.6 Hz, 1H), 6.55 (t, J = 7.5 Hz, 1H), 7.22 (t, J = 7.8 Hz, 1H), 7.56 (s, 1H), 7.78-7.91 (m, 4H), 8.00 (s, 1H), 8.35 (br d, J = 5.4 Hz, 1H), 12.77 (br s, 1H) |
| 138 | $^1$H NMR (500 MHz, DMSO-d6) δ ppm 1.69 (d, J = 6.7 Hz, 3H), 2.38 (s, 3H), 3.59-3.63 (m, 1H), 3.67-3.69 (m, 1H), 4.57-4.62 (m, 1H), 4.69-4.74 (m, 1H), 4.80-4.84 (m, 1H), 4.94-4.99 (m, 1H), 5.19-5.22 (m, 1H), 5.37-5.42 (m, 1H), 6.56 (t, J = 7.1 Hz, 2H), 7.21-7.24 (m, 2H), 7.61 (s, 1H), 7.77 (d, J = 1.0 Hz, 1H), 7.83 (d, J = 7.5 Hz, 1H), 8.11 (d, J = 9.2 Hz, 1H), 8.50-8.54 (m, 2H), 8.93 (s, 1H), 9.35 (s, 1H), 13.15-13.28 (m, 1H) |
| 139 | $^1$H NMR (400 MHz, DMSO-d6) δ ppm 1.72 (d, J = 6.48 Hz, 3H), 2.37 (s, 3H), 2.91 (s, 3H), 5.37-5.47 (m, 1H), 6.53-6.59 (m, 2H), 7.19-7.26 (m, 1H), 7.27 (s, 1H), 7.56-7.61 (m, 1H), 7.74-7.78 (m, 1H), 7.79-7.84 (m, 1H), 8.37-8.41(m, 1H), 8.45-8.54 (m, 2H), 12.80 (br s, 1H) |
| 140 | $^1$H NMR (400 MHz, DMSO-d6) δ ppm 1.61 (br d, J = 6.60 Hz, 3H), 2.24 (s, 3H), 2.37 (s, 3H), 3.95 (s, 3H), 5.22-5.31 (m, 1H), 6.39 (d, J = 8.68 Hz, 1H), 6.55 (t, J = 7.52 Hz, 1H), 7.19 (br t, J = 7.15 Hz, 2H), 7.31 (t, J = 7.58 Hz, 1H), 7.51 (s, 1H), 7.62 (d, J = 8.31 Hz, 1H), 7.77-7.84 (m, 2H), 8.00 (d, J = 8.19 Hz, 1H), 8.11 (s, 1H), 8.38-8.43 (m, 1H), 12.84 (br s, 1H) |
| 141 | $^1$H NMR (400 MHz, DMSO-d6) δ ppm 1.70 (br d, J = 6.60 Hz, 3H), 2.37 (s, 3H), 3.24 (s, 3H), 3.73 (s, 2H), 5.32-5.43 (m, 1H), 6.52-6.58 (m, 2H), 7.20-7.26 (m, 1H), 7.27-7.30 (m, 1H), 7.56-7.61 (m, 1H), 7.74-7.78 (m, 1H), 7.81 (d, J = 7.58 Hz, 2H), 7.91 (d, J = 7.58 Hz, 1H), 8.46 (br d, J = 4.28 Hz, 1H), 12.80 (br s, 1H) |
| 142 | $^1$H NMR (400 MHz, DMSO-d6) δ ppm 1.58-1.67 (m, 3H), 2.24 (s, 3H), 2.39 (s, 3H), 5.15-5.23 (m, 1H), 6.50-6.58 (m, 2H), 6.66-6.71 (m, 1H), 7.16-7.26 (m, 1H), 7.59 (s, 1H), 7.75-7.84 (m, 3H), 8.04-8.08 (m, 1H), 8.24-8.31 (m, 2H), 8.36-8.41 (m, 1H), 12.67-12.92 (m, 1H) |
| 143 | $^1$H NMR (400 MHz, DMSO-d6) δ ppm 1.70 (br d, J = 6.48 Hz, 3H), 2.36 (s, 3H), 3.94 (s, 3H), 5.39-5.46 (m, 1H), 6.49 (d, J = 8.56 Hz, 1H), 6.57 (t, J = 7.58 Hz, 1H), 6.76 (s, 1H), 7.21-7.38 (m, 3H), 7.51 (s, 1H), 7.65 (d, J = 8.19 Hz, 1H), 7.74 (s, 1H), 7.84 (d, J = 7.95 Hz, 1H), 8.09 (d, J = 7.70 Hz, 1H), 8.43-8.49 (m, 2H), 12.84 (br s, 1H) |
| 144 | $^1$H NMR (400 MHz, DMSO-d6) δ ppm 1.70 (d, J = 6.8 Hz, 3H), 2.37 (s, 3H), 2.57 (s, 3H), 4.22 (s, 3H), 5.36-5.40 (m, 1H), 6.55-6.58 (m, 2H), 7.03 (s, 1H), 7.25 (t, J = 7.6 Hz, 1H), 7.57 (d, J = 2.0 Hz, 1H), 7.69 (s, 1H), 7.75 (s, 1H), 7.82 (d, J = 8.0 Hz, 1H), 8.43 (s, 1H), 8.47 (s, 1H), 8.52 (s, 1H), 12.76 (s, 1H) |
| 145 | $^1$H NMR (400 MHz, DMSO-d6) δ ppm 1.69 (d, J = 6.4 Hz, 3H), 2.36 (s, 3H), 5.25-5.28 (m, 1H), 6.51 (d, J = 8.4 Hz, 1H), 6.56 (t, J = 7.6 Hz, 1H), 6.97 (s, 1H), 7.18-7.20 (m, 2H), 7.51-7.54 (m, 2H), 7.78-7.83 (m, 3H), 8.44 (s, 1H), 8.53 (s, 1H), 9.06 (d, J = 6.8 Hz, 1H) |
| 146 | $^1$H NMR (400 MHz, DMSO-d6) δ ppm 1.64 (br d, J = 6.48 Hz, 3H), 2.36 (s, 3H), 2.39 (s, 3H), 4.24 (s, 3H), 5.21-5.29 (m, 1H), 6.41 (d, J = 8.44 Hz, 1H), 6.55 (t, J = 7.58 Hz, 1H), 7.19 (t, J = 7.83 Hz, 1H), 7.30 (t, J = 7.46 Hz, 1H), 7.51-7.58 (m, 2H), 7.80-7.87 (m, 3H), 8.17 (d, J = 7.95 Hz, 1H), 8.40 (br d, J = 5.50 Hz, 1H), 12.84 (br s, 1H) |
| 147 | $^1$H NMR (400 MHz, DMSO-d6) δ ppm 1.68 (br d, J = 6.5 Hz, 3H), 2.37 (s, 3H), 5.57 (br t, J = 5.8 Hz, 1H), 6.52-6.59 (m, 2H), 7.23 (t, J = 7.8 Hz, 1H), 7.35 (s, 1H), 7.58 (s, 1H), |

TABLE 56-continued

| Ex # | NMR Line Listing |
|---|---|
| | 7.65-7.72 (m, 2H), 7.77 (s, 1H), 7.84 (d, J = 7.8 Hz, 1H), 8.42-8.52 (m, 2H), 8.73 (br d, J = 4.8 Hz, 1H), 12.85 (br s, 1H), 13.07 (br s, 1H) |
| 148 | $^{1}$H NMR (400 MHz, DMSO-d6) δ ppm 1.55 (br d, J = 6.60 Hz, 3H), 2.08 (s, 3H), 4.17 (s, 3H), 5.06-5.15 (m, 1H), 6.40 (d, J = 8.44 Hz, 1H), 6.51 (t, J = 7.52 Hz, 1H), 7.15 (t, J = 7.83 Hz, 1H), 7.43-7.50 (m, 1H), 7.54-7.63 (m, 2H), 7.70 (d, J = 8.93 Hz, 1H), 7.76 (d, J = 7.95 Hz, 1H), 8.18 (s, 1H), 8.30 (br d, J = 5.75 Hz, 1H), 8.50 (s, 1H), 12.77 (br s, 1H) |
| 149 | $^{1}$H NMR (400 MHz, DMSO-d6) δ ppm 1.60 (d, J = 6.60 Hz, 3H), 2.15 (s, 3H), 2.39 (s, 3H), 4.13 (s, 3H), 5.11-5.19 (m, 1H), 6.48 (d, J = 8.31 Hz, 1H), 6.54 (t, J = 7.52 Hz, 1H), 7.22 (t, J = 7.89 Hz, 1H), 7.53-7.57 (m, 2H), 7.78-7.83 (m, 2H), 7.96 (d, J = 8.31 Hz, 1H), 8.11 (s, 1H), 8.20 (s, 1H), 8.37 (br d, J = 5.26 Hz, 1H), 12.79 (br s, 1H) |
| 150 | $^{1}$H NMR (400 MHz, DMSO-d6) δ ppm 1.59 (d, J = 6.48 Hz, 3H), 2.13 (s, 3H), 2.38 (s, 3H), 4.13 (s, 3H), 5.15 (br t, J = 5.81 Hz, 1H), 6.49 (d, J = 8.44 Hz, 1H), 6.56 (t, J = 7.52 Hz, 1H), 7.22 (t, J = 7.83 Hz, 1H), 7.54 (s, 1H), 7.78-7.86 (m, 4H), 8.25 (d, J = 7.46 Hz, 2H), 8.38 (br d, J = 5.26 Hz, 1H), 12.79 (br s, 1H) |
| 151 | $^{1}$H NMR (400 MHz, DMSO-d6) δ ppm 1.70 (br d, J = 5.62 Hz, 3H), 2.39 (br s, 3H), 2.44-2.48 (m, 3H), 5.34 (br s, 1H), 6.55 (br d, J = 7.82 Hz, 2H), 7.24 (br s, 1H), 7.61 (br s, 1H), 7.80 (br s, 1H), 7.83 (br s, 1H), 7.98 (br s, 2H), 8.47 (br s, 1H), 8.60 (br s, 1H), 9.32 (br s, 1H), 12.42-13.01 (m, 1H) |
| 152 | $^{1}$H NMR (400 MHz, DMSO-d6) δ ppm 1.70 (d, J = 6.60 Hz, 3H), 2.36-2.41 (m, 3H), 5.39 (br t, J = 6.24 Hz, 1H), 6.55-6.59 (m, 2H), 7.05 (s, 1H), 7.24 (t, J = 7.38 Hz, 1H), 7.62 (d, J = 2.08 Hz, 1H), 7.78 (d, J = 1.34 Hz, 1H), 7.82 (dd, J = 8.19, 1.71 Hz, 1H), 7.97 (d, J = 5.14 Hz, 1H), 8.10 (s, 1H), 8.48 (br d, J = 6.11 Hz, 1H), 8.59 (br s, 1H), 9.27 (br s, 1H), 12.54-13.03 (m, 1H) |
| 153 | $^{1}$H NMR (400 MHz, DMSO-d6) δ ppm 1.70 (d, J = 6.60 Hz, 3H), 2.39 (s, 3H), 2.42-2.46 (m, 3H),, 5.33 (br t, J = 6.24 Hz, 1H), 6.53-6.59 (m, 2H), 7.24 (t, J = 7.70 Hz, 1H), 7.60 (s, 1H), 7.78-7.83 (m, 2H), 8.05 (s, 1H), 8.12 (br d, J = 5.26 Hz, 1H), 8.47 (br d, J = 5.75 Hz, 1H), 8.75 (br d, J = 5.38 Hz, 1H), 9.28 (br s, 1H), 12.41-13.32 (m, 1H) |
| 154 | $^{1}$H NMR (400 MHz, DMSO-d6) δ ppm 1.61 (d, J = 6.5 Hz, 3H), 2.23 (s, 3H), 2.36 (s, 3H), 5.15-5.40 (m, 1H), 6.38 (d, J = 8.4 Hz, 1H), 6.54 (t, J = 7.5 Hz, 1H), 7.10-7.26 (m, 3H), 7.50 (s, 1H), 7.55 (d, J = 8.1 Hz, 1H), 7.78 (s, 1H), 7.81 (d, J = 7.9 Hz, 1H), 7.98 (d, J = 7.9 Hz, 1H), 8.07 (d, J = 2.7 Hz, 1H), 8.40 (br s, 1H), 12.06 (br s, 1H), 12.83 (br s, 1H) |
| 155 | $^{1}$H NMR (400 MHz, DMSO-d6) δ ppm 1.70 (br d, J = 6.5 Hz, 3H), 2.35 (s, 3H), 5.42 (br s, 1H), 6.48 (d, J = 8.6 Hz, 1H), 6.56 (t, J = 7.5 Hz, 1H), 6.82 (s, 1H), 7.19-7.24 (m, 1H), 7.24-7.29 (m, 2H), 7.50 (s, 1H), 7.57 (d, J = 6.7 Hz, 1H), 7.74 (s, 1H), 7.83 (d, J = 7.9 Hz, 1H), 8.08 (br d, J = 8.3 Hz, 1H), 8.42 (d, J = 2.8 Hz, 1H), 8.44-8.48 (m, 1H), 12.18 (br s, 1H), 12.83 (br s, 1H) |
| 156 | $^{1}$H NMR (400 MHz, DMSO-d6) δ ppm 1.73 (d, J = 6.6 Hz, 3H), 4.22 (s, 3H), 5.42 (br t, J = 6.4 Hz, 1H), 6.55 (d, J = 8.6 Hz, 1H), 6.59 (t, J = 7.5 Hz, 1H), 7.13 (s, 1H), 7.25 (t, J = 7.7 Hz, 1H), 7.55 (dd, J = 8.9, 2.9 Hz, 1H), 7.63 (dd, J = 7.9, 3.0 Hz, 1H), 7.74 (d, J = 9.2 Hz, 1H), 7.84 (d, J = 7.9 Hz, 1H), 7.94 (d, J = 9.2 Hz, 1H), 8.46 (br d, J = 6.1 Hz, 1H), 8.58 (s, 1H), 8.65 (s, 1H), 12.84 (br s, 1H) |
| 157 | $^{1}$H NMR (400 MHz, DMSO-d6) δ ppm 1.60 (d, J = 6.48 Hz, 3H), 2.15 (s, 3H), 2.36 (s, 3H), 5.12-5.23 (m, 1H), 6.46-6.56 (m, 2H), 6.76-6.79 (m, 1H), 7.15-7.23 (m, 1H), 7.50-7.54 (m, 1H), 7.56-7.62 (m, 1H), 7.77-7.83 (m, 2H), 7.85-7.91 (m, 1H), 8.19 (d, J = 1.96 Hz, 1H), 8.36 (br d, J = 4.20 Hz, 1H), 9.26-9.29 (m, 1H), 12.78 (br s, 1H) |
| 158 | $^{1}$H NMR (400 MHz, DMSO-d6) δ ppm 1.73 (d, J = 6.4 Hz, 3H), 2.37 (s, 3H), 3.90 (s, 3H), 5.37-5.41 (m, 1H), 6.54-6.58 (m, 3H), 7.15 (s, 1H), 7.22-7.26 (m, 1H), 7.55-7.56 (m, 2H), 7.70-7.72 (m, 1H), 7.76-7.83 (m, 3H), 8.27 (s, 1H), 8.47 (d, J = 6.0 Hz, 1H), 12.75 (s, 1H) |
| 159 | $^{1}$H NMR (400 MHz, DMSO-d6) δ ppm 1.75 (d, J = 6.8 Hz, 3H), 2.39 (s, 3H), 3.94 (s, 3H), 5.39-5.43 (m, 1H), 6.56-6.60 (m, 2H), 6.62 (d, J = 3.2 Hz, 1H), 7.21-7.25 (m, 1H), 7.38 (s, 1H), 7.59 (d, J = 2.0 Hz, 1H), 7.78-7.79 (m, 2H), 7.82 (d, J = 8.0 Hz, 1H), 8.01 (d, J = 8.4 Hz, 1H), 8.19 (d, J = 8.4 Hz, 1H), 8.52 (s, 1H) |
| 160 | $^{1}$H NMR (400 MHz, DMSO-d6) δ ppm 1.71 (d, J = 6.4 Hz, 3H), 2.37 (s, 3H), 4.30 (s, 3H), 5.41-5.42 (m, 1H), 6.54-6.60 (m, 2H), 7.23-7.25 (m, 2H), 7.58 (s, 1H), 7.75 (s, 1H), 7.82 (d, J = 8.0 Hz, 1H), 8.55-8.64 (m, 3H), 9.27 (s, 1 H) |
| 161 | $^{1}$H NMR (400 MHz, DMSO-d6) δ ppm 1.68 (d, J = 6.8 Hz, 3H), 2.37 (s, 3H), 5.44-5.47 (m, 1H), 6.55 (d, J = 7.6 Hz, 2H), 7.22 (t, J = 7.2 Hz, 1H), 7.32 (s, 1H), 7.56-7.57 (m, 1H), 7.64-7.66 (m, 1H), 7.77 (s, 1H), 7.80-7.83 (m, 1H), 8.43 (d, J = 2 Hz, 1H), 8.62 (s, 1H), 8.71 (d, J = 7.6 Hz, 1H), 9.39 (s, 1H), 12.75 (s, 1H) |
| 162 | $^{1}$H NMR (400 MHz, DMSO-d6) δ ppm 1.71 (d, J = 6.8 Hz, 3H), 2.37 (s, 3H), 5.28-5.32 (m, 1H), 6.54-6.58 (m, 2H), 7.21-7.25 (m, 1H), 7.36 (s, 1H), 7.60 (d, J = 2.0 Hz, 1H), 7.77 (s, 1H), 7.80 (d, J = 8.4 Hz, 1H), 8.22-8.25 (m, 1H), 8.28-8.31 (m, 1H), 8.49 (d, J = 6.0 Hz, 1H), 9.14 (s, 1H), 12.72 (br s, 1H) |
| 163 | $^{1}$H NMR (400 MHz, CHLOROFORM-d) δ ppm 1.77 (d, J = 6.8 Hz, 3H), 2.39 (s, 3H), 4.34-4.36 (m, 2H), 4.55-4.57 (m, 2H), 5.19-5.24 (m, 1H), 6.35 (d, J = 8.4 Hz, 2H), 6.62 (t, J = 7.6 Hz, 1H), 6.82 (s, 1H), 7.19-7.24 (m, 1H), 7.54 (s, 1H), 7.67 (s, 1H), 7.92 (s, 1H), 8.01 (d, J = 8.0 Hz, 1H), 8.53 (s, 1H) |
| 164 | $^{1}$H NMR (400 MHz, DMSO-d6) δ ppm 1.72 (d, J = 6.4 Hz, 3H), 2.38 (s, 3H), 4.16 (s, 3H), 5.41-5.44 (m, 1H), 6.54-6.59 (m, 2H), 7.22 (t, J = 6.8 Hz, 1H), 7.29 (s, 1H), 7.59 (s, 1H), 7.78 (s, 1H), 7.82 (d, J = 8.0 Hz, 1H), 8.28-8.30 (m, 1H), 8.37-8.39 (m, 1H), 8.50 (s, 1H), 8.53 (s, 1H) |
| 165 | $^{1}$H NMR (400 MHz, DMSO-d6) δ ppm 1.72 (d, J = 6.8 Hz, 3H), 2.37 (s, 3H), 2.55 (s, 3H), 4.01 (s, 3H), 5.38-5.39 (m, 1H), 6.53-6.58 (m, 2H), 7.15 (s, 1H), 7.21-7.23 (m, 1H), 7.57 (s, 1H), 7.73 (d, J = 8.8 Hz, 1H), 7.75-7.76 (m, 1H), 7.82 (d, J = 8.0 Hz, 1H), 8.11 (d, J = 8.8 Hz, 1H), 8.55-8.56 (m, 2H), 12.70 (br s, 1H) |

TABLE 56-continued

| Ex # | NMR Line Listing |
|---|---|
| 166 | $^1$H NMR (400 MHz, DMSO-d6) δ ppm 1.71 (d, J = 6.8 Hz, 3H), 2.36 (s, 3H), 3.90 (s, 3H), 5.37-5.40 (m, 1H), 6.52-6.57 (m, 2H), 7.12 (s, 1H), 7.20-7.21 (m, 1H), 7.54 (d, J = 2.0 Hz, 1H), 7.75-7.78 (m, 2H), 7.82 (dd, J = 8.0, 2.0 Hz, 1H), 8.07 (d, J = 8.8 Hz, 1H), 8.35 (s, 1H), 8.45 (s, 1H), 8.50 (s, 1H) |
| 167 | $^1$H NMR (400 MHz, DMSO-d6) δ ppm 1.70-1.79 (m, 3H), 2.87 (s, 3H), 5.51-5.63 (m, 1H), 7.15-7.19 (m, 1H), 7.30-7.36 (m, 2H), 7.98 (d, J = 2.20 Hz, 1H), 8.08 (d, J = 8.68 Hz, 1H), 8.23 (d, J = 1.71 Hz, 1H), 8.27 (dd, J = 8.68, 1.83 Hz, 1H), 8.41 (d, J = 6.24 Hz, 1H), 8.94 (d, J = 1.71 Hz, 1H), 13.20 (br s, 1H) |
| 168 | $^1$H NMR (500 MHz, DMSO-d6) δ ppm 1.70-1.79 (m, 3H), 4.12 (s, 3H), 5.48-5.52 (m, 1H), 7.06 (m, 2H), 7.27 (s, 1H), 7.84-7.94 (m, 2H), 8.17-8.28 (m, 3H), 8.69 (s, 1H), 10.13-10.16 (m, 1H) |
| 169 | $^1$H NMR (500 MHz, DMSO-d6) δ ppm 1.78 (d, J = 6.7 Hz, 3H), 4.24 (s, 3H), 5.49-5.53 (m, 1H), 7.15-7.21 (m, 1H), 7.22 (s, 1H), 7.29-7.32 (m, 1H), 7.76 (d, J = 9.1 Hz, 1H), 7.94-7.99 (m, 2H), 8.23 (s, 1H), 8.61 (m, 2H), 8.69 (s, 1H), 13.41-13.44 (m, 1H) |
| 170 | $^1$H NMR (400 MHz, DMSO-d6) δ ppm 1.64 (d, J = 6.8 Hz, 3H), 2.33 (s, 3H), 2.38 (s, 3H), 4.22 (s, 3H), 5.14-5.23 (m, 1H), 6.95-6.97 (m, 1H), 7.21-7.31 (m, 2H), 7.51-7.55 (m, 2H), 7.81-7.84 (m, 2H), 8.12 (d, J = 8.4 Hz, 1H), 8.43 (s, 1H) |
| 171 | $^1$H NMR (400 MHz, DMSO-d6) δ ppm 1.61 (d, J = 6.8 Hz, 3H), 2.37 (s, 3H), 4.22 (s, 3H), 5.17-5.24 (m, 1H), 6.02-6.06 (m, 1H), 6.10-6.17 (m, 1H), 6.78 (br s, 1H), 7.04 (s, 1H), 7.60 (br s, 1H), 7.72 (br s, 1H), 7.75 (d, J = 9.2 Hz, 1H), 7.91 (dd, J = 8.8, 2.0 Hz, 1H), 8.60-8.69 (m, 3H) |
| 172 | $^1$H NMR (400 MHz, DMSO-d6) δ ppm 1.61 (d, J = 6.8 Hz, 3H), 2.37 (s, 3H), 4.22 (s, 3H), 5.17-5.24 (m, 1H), 6.02-6.06 (m, 1H), 6.10-6.17 (m, 1H), 6.78 (br s, 1H), 7.04 (s, 1H), 7.60 (br s, 1H), 7.72 (br s, 1H), 7.75 (d, J = 9.2 Hz, 1H), 7.91 (dd, J = 8.8, 2.0 Hz, 1H), 8.60-8.69 (m, 3H) |
| 173 | $^1$H NMR (400 MHz, DMSO-d6) δ ppm 1.77 (d, J = 6.72 Hz, 3H), 4.27 (s, 3H), 5.46-5.56 (m, 1H), 7.21 (d, J = 9.05 Hz, 1H), 7.30 (s, 1H), 7.34 (d, J = 8.93 Hz, 1H), 7.99 (d, J = 2.20 Hz, 1H), 8.08 (d, J = 1.47 Hz, 1H), 8.23 (d, J = 1.83 Hz, 1H), 8.42 (br d, J = 6.50 Hz, 1H), 8.65 (d, J = 1.35 Hz, 1H), 8.72 (s, 1H), 13.18 (br s, 1H) |
| 174 | $^1$H NMR (400 MHz, DMSO-d6) δ ppm 1.78 (d, J = 6.60 Hz, 3H), 2.58 (s, 3H), 4.23 (s, 3H), 5.46-5.56 (m, 1H), 7.19 (s, 1H), 7.21 (d, J = 9.17 Hz, 1H), 7.35 (d, J = 8.93 Hz, 1H), 7.71-7.74 (m, 1H), 7.99 (d, J = 2.20 Hz, 1H), 8.22 (d, J = 1.71 Hz, 1H), 8.43 (d, J = 6.36 Hz, 1H), 8.49 (d, J = 0.86 Hz, 1H), 8.55 (s, 1H), 13.19 (br s, 1H) |
| 175 | $^1$H NMR (400 MHz, DMSO-d6) δ ppm 1.59-1.60 (m, 3H), 2.12 (s, 3H), 2.36-2.38 (m, 6H), 4.23 (s, 3H), 5.1-5.16 (m, 1H), 7.04 (d, J = 9.2 Hz, 1H), 7.18 (d, J = 6.8 Hz, 1H), 7.52 (s, 1H), 7.61 (d, J = 8.0 Hz, 1H), 7.73 (d, J = 8.0 Hz, 1H), 7.78 (s, 1H), 8.20 (s, 1H), 8.43 (s, 1H), 8.53 (s, 1H) |
| 176 | $^1$H NMR (400 MHz, DMSO-d6) δ ppm 1.75 (d, J = 6.8 Hz, 3H), 2.35 (s, 3H), 2.37 (s, 3H), 4.24 (s, 3H), 5.36-5.40 (m, 1H), 7.01-7.03 (m, 2H), 7.17 (d, J = 8.8 Hz, 1H), 7.41 (t, J = 7.6 Hz, 1H), 7.55-7.58 (m, 2H), 7.80 (s, 1H), 7.86 (d, J = 8.4 Hz, 1H), 8.24 (d, J = 8.4 Hz, 1H), 8.60 (s, 1H), 12.18 (br s, 1H) |
| 177 | $^1$H NMR (400 MHz, DMSO-d6) δ ppm 1.75 (d, J = 6.4 Hz, 3H), 2.37 (s, 3H), 4.23 (s, 3H), 5.35-5.38 (m, 1H), 7.00 (s, 1H), 7.03 (d, J = 9.2 Hz, 1H), 7.25 (d, J = 8.8 Hz, 1H), 7.41-7.43 (m, 1H), 7.54-7.58 (m, 2H), 7.80 (s, 1H), 7.85 (d, J = 8.4 Hz, 1H), 8.23 (d, J = 8.4 Hz, 1H), 8.63 (s, 1H) |
| 178 | $^1$H NMR (400 MHz, DMSO-d6) δ ppm 1.61 (d, J = 6.8 Hz, 3H), 2.12 (s, 3H), 2.38 (s, 3H), 2.40 (s, 3H), 5.17-5.23 (m, 1H), 7.12 (d, J = 9.2 Hz, 1H), 7.29 (d, J = 9.2 Hz, 1H), 7.57 (d, J = 2.0 Hz, 1H), 7.60-7.62 (m, 2H), 7.79 (s, 1H), 7.86 (s, 1H), 8.31 (d, J = 6.8 Hz, 1H), 9.02 (s, 1H) |
| 179 | $^1$H NMR (400 MHz, DMSO-d6) δ ppm 1.72-1.74 (m, 3H), 2.37 (s, 3H), 2.39 (s, 3H), 5.49-5.52 (m, 1H), 7.07 (s, 1H), 7.36-7.39 (m, 1H), 7.57-7.59 (m, 3H), 7.77 (s, 1H), 7.83 (d, J = 9.2 Hz, 1H), 7.88 (s, 1H), 9.21 (s, 1H), 9.28 (s, 1H) |
| 180 | $^1$H NMR (400 MHz, DMSO-d6) δ ppm 1.66-1.71 (m, 3H), 2.18-2.35 (m, 6H), 4.16-4.22 (m, 3H), 5.33-5.40 (m, 1H), 6.89-7.24 (m, 3H), 7.487.54 (m, 1H), 7.72-7.74 (m, 2H), 7.89-7.91 (m, 1H), 8.51-8.60 (m, 2H), 9.80 (s, 1H) |
| 181 | $^1$H NMR (400 MHz, DMSO-d6) δ ppm 1.61 (d, J = 6.8 Hz, 3H), 2.12 (s, 3H), 2.38 (s, 3H), 4.23 (s, 3H), 5.15-5.18 (m, 1H), 7.09 (d, J = 9.2 Hz, 1H), 7.29 (d, J = 8.8 Hz, 1H), 7.54 (s, 1H), 7.61 (d, J = 9.2, 1H), 7.73 (d, J = 9.2 Hz, 1H), 7.80 (s, 1H), 8.19 (s, 1H), 8.30 (d, J = 6.4 Hz, 1H), 8.53 (s, 1H), 13.06 (s, 1H) |
| 182 | $^1$H NMR (400 MHz, DMSO-d6) δ ppm 1.56 (d, J = 6.4 Hz, 3H), 2.37 (s, 3H), 2.61 (s, 3H), 5.06-5.07 (m, 1H), 6.19 (d, J = 8.8 Hz, 1H), 6.64 (s, 1H), 7.04 (t, J = 6.8 Hz, 1H), 7.12 (t, J = 8.4 Hz, 1H), 7.44 (t, J = 8.0 Hz, 1H), 7.54 (s, 1H), 7.66 (d, J = 8.8 Hz, 1H), 7.78 (s, 1H), 8.16 (s, 1H), 8.89 (d, J = 6.8 Hz, 1H) |
| 183 | $^1$H NMR (400 MHz, DMSO-d6) δ ppm 1.64 (d, J = 6.4 Hz, 3H), 2.37-2.38 (m, 6H), 5.36-5.38 (m, 1H), 6.33 (d, J = 9.2 Hz, 1H), 7.06 (s, 1H), 7.27 (t, J = 8.4 Hz, 1H), 7.55-7.59 (m, 2H), 7.74 (s, 1H), 7.82 (dd, J = 9.6, 2.0 Hz, 1H), 7.91 (s, 1H), 8.22 (s, 1H), 9.29 (s, 1H) |
| 184 | $^1$H NMR (400 MHz, DMSO-d6) δ ppm 1.68 (d, J = 6.4 Hz, 3H), 2.37 (s, 3H), 4.22 (s, 3H), 5.35-5.37 (m, 1H), 6.39 (d, J = 9.2 Hz, 1H), 7.04 (s, 1H), 7.33 (t, J = 8.8 Hz, 1H), 7.54 (d, J = 2.0 Hz, 1H), 7.72-7.76 (m, 2H), 7.89 (d, J = 9.2 Hz, 1H), 8.17 (d, J = 5.6 Hz, 1H), 8.55 (s, 1H), 8.59 (s, 1H) |
| 185 | $^1$H NMR (400 MHz, DMSO-d6) δ ppm 1.85 (d, J = 6.7, 3H), 4.20 (s, 1H), 6.82 (q, J = 6.6 Hz, 2H), 7.12-7.16 (m, 2H), 7.27-7.36 (m, 3H), 7.51-7.54 (m, 2H), 7.75 (d, J = 8.1 Hz, 1H), 7.92 (dd, J = 4.1, J = 1.4, 1H), 8.23 (m, 1H), 8.28 (m, 1H), 12.02 (s, 1H) |
| 186 | $^1$H NMR (400 MHz, DMSO-d6) δ ppm 1.60 (d, J = 6.8 Hz, 3H), 2.14 (s, 3H), 2.38 (s, 3H), 5.15-5.17 (m, 1H), 6.48-6.54 (m, 2H), 7.19-7.21 (m, 1H), 7.56 (s, 1H), 7.79-7.88 (m, 4H), 8.43 (s, 1H), 8.70 (s, 1H), 9.15 (s, 1H) |

TABLE 56-continued

| Ex # | NMR Line Listing |
|---|---|
| 187 | $^1$H NMR (400 MHz, DMSO-d6) δ ppm 1.74 (d, J = 6.4 Hz, 3H), 2.39 (s, 3H), 5.50-5.52 (m, 1H), 6.53-6.59 (m, 2H), 7.23 (t, J = 7.6 Hz, 1H), 7.39 (s, 1H), 7.62 (s, 1H), 7.79 (s, 1H), 7.83 (d, J = 8.0 Hz, 1H), 7.91 (dd, J = 8.4, 4.4 Hz, 1H), 8.62 (s, 1H), 8.75 (d, J = 8.0 Hz, 1H), 8.81 (s, 1H), 9.17 (d, J = 2.8 Hz, 1H), 9.55 (s, 1H) |
| 188 | $^1$H NMR (400 MHz, DMSO-d6) δ ppm 1.67 (d, J = 6.4 Hz, 3H), 2.35 (s, 3H), 2.57 (s, 3H), 4.22 (s, 3H), 5.30-5.33 (m, 1H), 6.85-7.07 (m, 3H), 7.50 (s, 1H), 7.68 (s, 1H), 7.74 (s, 1H), 8.44 (s, 1H), 8.53 (s, 1H), 9.69 (s, 1H) |
| 189 | $^1$H NMR (400 MHz, DMSO-d6) δ ppm 1.69 (d, J = 6.0 Hz, 3H), 2.37 (s, 3H), 4.23 (s, 3H), 5.31-5.32 (m, 1H), 6.18-6.19 (m, 1H), 6.29-6.30 (m, 1H), 6.99-7.00 (m, 2H), 7.42 (t, J = 7.6 Hz, 1H), 7.53-7.58 (m, 2H), 7.78 (s, 1H), 7.85 (d, J = 8.8 Hz, 1H), 8.24 (d, J = 8.4 Hz, 1H), 8.35 (s, 1H) |
| 190 | $^1$H NMR (400 MHz, DMSO-d6) δ ppm 1.69 (d, J = 6.4 Hz, 3H), 2.38 (s, 3H), 2.57 (s, 3H), 4.22 (s, 3H), 5.36-5.39 (m, 1H), 6.36-6.41 (m, 2H), 7.03 (s, 1H), 7.18-7.24 (m, 1H), 7.57 (d, J = 2.0 Hz, 1H), 7.68 (s, 1H), 7.76 (s, 1H), 8.20 (d, J = 6.0 Hz, 1H), 8.42 (s, 1H), 8.52 (s, 1H) |
| 191 | $^1$H NMR (400 MHz, DMSO-d6) δ ppm 1.85 (d, J = 6.50 Hz, 3H), 2.61 (s, 3H), 4.30 (s, 3H), 5.38-5.45 (m, 1H), 7.05 (s, 1H), 7.27-7.34 (m, 1H), 7.38-7.44 (m, 1H), 7.79-7.84 (m, 1H), 8.06 (d, J = 2.10 Hz, 1H), 8.28 (d, J = 1.91 Hz, 1H), 8.49 (d, J = 6.17 Hz, 1H), 8.55 (m, 1H), 8.60 (s, 1H), 13.26 (br s, 1H) |
| 192 | $^1$H NMR (400 MHz, DMSO-d6) δ ppm 1.84 (d, J = 6.50 Hz, 3H), 2.61 (s, 3H), 4.31 (s, 3H), 5.38-5.45 (m, 1H), 7.05 (s, 1H), 7.28-7.35 (m, 1H), 7.38-7.45 (m, 1H), 7.77-7.83 (m, 1H), 8.06 (d, J = 2.20 Hz, 1H), 8.30 (d, J = 1.87 Hz, 1H), 8.47 (d, J = 6.20 Hz, 1H), 8.57 (m, 1H), 8.60 (s, 1H), 13.26 (br s, 1H) |
| 193 | $^1$H NMR (400 MHz, DMSO-d6) δ ppm 1.78 (d, J = 6.70 Hz, 3H), 4.26 (s, 3H), 5.49-5.59 (m, 1H), 7.25 (m, 1H), 7.37 (s, 1H), 7.49 (m, 1H), 8.02 (d, J = 2.10 Hz, 1H), 8.18 (d, J = 1.51 Hz, 1H), 8.28 (d, J = 1.80 Hz, 1H), 8.41 (br d, J = 6.42 Hz, 1H), 8.69 (d, J = 1.33 Hz, 1H), 8.79 (s, 1H), 13.25 (br s, 1H) |
| 194 | $^1$H NMR (400 MHz, DMSO-d6) δ ppm 1.78 (d, J = 6.70 Hz, 3H), 4.26 (s, 3H), 5.49-5.59 (m, 1H), 7.25 (m, 1H), 7.37 (s, 1H), 7.49 (m, 1H), 8.02 (d, J = 2.10 Hz, 1H), 8.18 (d, J = 1.51 Hz, 1H), 8.28 (d, J = 1.80 Hz, 1H), 8.41 (br d, J = 6.42 Hz, 1H), 8.69 (d, J = 1.33 Hz, 1H), 8.79 (s, 1H), 13.25 (br s, 1H) |
| 195 | $^1$H NMR (400 MHz, CHLOROFORM-d) δ ppm 1.82 (d, J = 6.7 Hz, 3H), 2.44 (s, 3H), 5.37 (br d, J = 5.6 Hz, 1H), 6.45 (br s, 1H), 6.70 (d, J = 3.4 Hz, 1H), 6.93 (d, J = 8.9 Hz, 1H), 7.18 (d, J = 8.9 Hz, 1H), 7.42 (s, 1H), 7.52 (d, J = 2.0 Hz, 1H), 7.62 (d, J = 3.5 Hz, 1H), 7.86 (d, J = 8.2 Hz, 1H), 8.00 (s, 1H), 8.26 (d, J = 8.2 Hz, 1H), 8.34 (br s, 1H), 11.07 (br s, 1H) |
| 196 | $^1$H NMR (400 MHz, CHLOROFORM-d) δ ppm 1.75 (d, J = 6.8 Hz, 3H), 2.37 (s, 3H), 2.38 (s, 3H), 4.89 (br s, 1H), 6.97 (d, J = 8.9 Hz, 1H), 7.06 (s, 1H), 7.12-7.18 (m, 2H), 7.30 (t, J = 7.6 Hz, 1H), 7.38 (d, J = 2.0 Hz, 1H), 7.66 (dd, J = 7.9, 3.3 Hz, 2H), 7.92-7.94 (m, 1H), 8.41 (br s, 1H), 9.35 (br s, 1H) |
| 197 | $^1$H NMR (400 MHz, DMSO-d6) δ ppm 1.70 (d, J = 6.60 Hz, 3H), 2.39 (s, 3H), 4.11 (s, 3H), 5.39 (br t, J = 5.99 Hz, 1H), 6.34-6.42 (m, 2H), 7.11 (s, 1H), 7.21 (td, J = 8.28, 6.30 Hz, 1H), 7.57 (d, J = 2.08 Hz, 1H), 7.77 (d, J = 1.34 Hz, 1H), 7.83 (d, J = 9.05 Hz, 1H), 8.11-8.27 (m, 3H), 8.60 (s, 1H), 13.20 (br s, 1H) |
| 198 | $^1$H NMR (400 MHz, DMSO-d6) δ ppm 1.72 (d, J = 6.4 Hz, 3H), 2.38 (m, 3H), 4.30 (s, 3H), 5.38 (m, 1H), 6.54 (m, 2H), 7.24 (m, 2H), 7.59 (m, 1H), 7.77 (m, 2H), 8.29 (s, 1H), 8.47 (m, 1H), 8.80 (m, 1H), 8.93 (s, 1H), 12.76 (br s, 1H) |
| 200 | $^1$H NMR (400 MHz, DMSO-d6) δ ppm 1.63 (d, J = 6.6 Hz, 3H), 2.13 (m, 3H), 2.38 (m, 3H), 2.40 (s, 3H), 4.24 (s, 3H), 5.22 (m, 1H), 7.22 (m, 2H), 7.55 (d, J = 2.0 Hz, 1H), 7.62 (m, 1H), 7.73 (m, 1H), 7.80 (m, 1H), 8.20 (s, 1H), 8.39 (m, 1H), 8.54 (s, 1H) |
| 203 | $^1$H NMR (400 MHz, DMSO-d6) δ ppm 1.70 (d, J = 6.60 Hz, 3H), 2.38 (s, 3H), 2.42 (s, 3H), 5.24-5.32 (m, 1H), 6.49 (d, J = 8.31 Hz, 1H), 6.57 (t, J = 7.52 Hz, 1H), 7.22 (t, J = 7.71 Hz, 1H), 7.57 (d, J = 2.08 Hz, 1H), 7.82 (td, J = 8.25, 1.47 Hz, 2H), 8.49 (s, 1H), 8.50 (d, J = 6.43 Hz, 2H), 8.66 (d, J = 5.99 Hz, 1H), 9.48 (s, 1H), 12.81 (br s, 1H) |
| 204 | $^1$H NMR (400 MHz, ACETONE-d6) δ ppm 1.65 (d, J = 6.8 Hz, 3H), 2.17 (s, 3H), 2.39 (s, 3H), 4.28 (s, 3H), 5.19-5.22 (m, 1H), 6.31-6.34 (m, 1H), 7.13-7.18 (m, 1H), 7.57 (d, J = 2.0 Hz, 1H), 7.66 (d, J = 9.2 Hz, 1H), 7.77 (d, J = 9.2 Hz, 1H), 7.85 (s, 1H), 8.21 (s, 1H), 8.43 (s, 1H) |
| 205 | $^1$H NMR (400 MHz, DMSO-d6) δ ppm 1.65 (d, J = 6.8 Hz, 3H), 2.34 (s, 3H), 2.37 (s, 3H), 4.22 (s, 3H), 5.23-5.26 (m, 1H), 7.01 (d, J = 8.8 Hz, 1H), 7.26-7.31 (m, 2H), 7.51-7.55 (m, 1H), 7.56 (s, 1H), 7.82-7.84 (m, 3H), 8.14 (d, J = 8.4 Hz, 1H), 8.67 (d, J = 5.6 Hz, 1H) |
| 206 | $^1$H NMR (400 MHz, METHANOL-d4) δ ppm 1.81 (d, J = 6.7 Hz, 3H), 2.42 (s, 3H), 4.26 (s, 3H), 5.40 (q, J = 6.6 Hz, 1H), 6.93 (s, 1H), 7.13 (d, J = 9.0 Hz, 1H), 7.27 (d, J = 8.9 Hz, 1H), 7.62 (d, J = 2.1 Hz, 1H), 7.74 (d, J = 9.2 Hz, 1H), 7.84-7.89 (m, 2H), 8.43 (s, 1H), 8.54 (s, 1H) |
| 207 | $^1$H NMR (400 MHz, DMSO-d6) δ ppm 1.72 (d, J = 6.8 Hz, 3H), 2.38 (s, 3H), 5.44-5.45 (m, 1H), 6.54-6.58 (m, 2H), 7.22 (t, J = 7.2 Hz, 1H), 7.34 (s, 1H), 7.61 (s, 1H), 7.78 (s, 1H), 7.83 (d, J = 7.6 Hz, 1H), 8.14 (d, J = 8.4 Hz, 1H), 8.28 (d, J = 9.2 Hz, 1H), 8.59 (d, J = 8.8 Hz, 2H), 8.89 (d, J = 8.4 Hz, 1H), 8.93 (s, 1H) |
| 208 | $^1$H NMR (400 MHz, METHANOL-d4) δ ppm 1.51 (d., J = 7.0 Hz, 3H), 2.32 (m, 3H), 4.18 (s, 3H), 5.02 (m, 1H), 6.34 (d, J = 8 Hz, 1H), 6.44 (t, J = 8 Hz, J = 12 Hz, 1H), 7.08 (t, J = 8 Hz, J = 12 Hz, 1H), 7.48 (m, 1H), 7.56 (m, 1H), 7.64 (m, 1H), 7.79 (m, 2H), 8.05 (s, 1H), 8.33 (s, 1H) |
| 209 | $^1$H NMR (400 MHz, DMSO-d6) δ ppm 1.65 (d, J = 6.72 Hz, 3H), 2.40 (s, 3H), 5.20 (m, 1H), 6.56 (m, 2H), 7.21 (m, 1H), 7.65 (m, 1H), 7.81 (m, 2H), 8.04 (m, 1H), 8.10 (s, 1H), 8.40 (m, 1H), 8.73 (d, J = 5.99 Hz, 1H), 9.28 (s, 1H), 12.68 (br s, 1H) |

TABLE 56-continued

| Ex # | NMR Line Listing |
|---|---|
| 210 | $^1$H NMR (400 MHz, CHLOROFORM-d) δ ppm 1.68 (d, J = 6.6 Hz, 3H), 2.27 (s, 3H), 2.43 (s, 3H), 5.15-5.25 (m, 1H), 5.70 (s, 2H), 6.38-6.45 (m, 1H), 6.58-6.65 (m, 1H), 7.17-7.26 (m, 1H), 7.34-7.47 (m, 5H), 7.52-7.55 (m, 1H), 7.61-7.68 (m, 1H), 7.88-8.12 (m, 5H) |
| 211 | $^1$H NMR (400 MHz, METHANOL-d4) δ ppm 1.66 (d, J = 6.02 Hz, 3H), 2.22 (s, 3H), 2.43 (s, 3H), 5.22 (m, 1H), 5.73 (s, 2H), 6.47 (d, J = 8.5 Hz, 1H), 6.54 (m, 1H), 7.15 (m, 1H), 7.28 (m, 5H), 7.60 (m, 1H), 7.73 (m, 2H), 7.91 (m, 2H), 8.23 (s, 1H), 8.25 (s, 1H) |
| 214 | $^1$H NMR (400 MHz, DMSO-d6) δ ppm 1.73 (d, J = 6.72 Hz, 3H), 2.39 (s, 3H), 2.43 (s, 3H), 5.36 (t, J = 6.66 Hz, 1H), 7.17 (d, J = 9.05 Hz, 1H), 7.35 (d, J = 8.93 Hz, 1H), 7.62 (d, J = 2.08 Hz, 1H), 7.80 (s, 1H), 8.03-8.09 (m, 2H), 8.44 (d, J = 6.72 Hz, 1H), 8.73 (br s, 1H), 9.27 (br s, 1H), 12.74-13.30 (m, 1H) |
| 215 | $^1$H NMR (400 MHz, CHLOROFORM-d) δ ppm 1.82 (d, J = 6.7 Hz, 3H), 2.44 (s, 3H), 5.37 (br d, J = 5.6 Hz, 1H), 6.45 (br s, 1H), 6.70 (d, J = 3.4 Hz, 1H), 6.93 (d, J = 8.9 Hz, 1H), 7.18 (d, J = 8.9 Hz, 1H), 7.42 (s, 1H), 7.52 (d, J = 2.0 Hz, 1H), 7.62 (d, J = 3.5 Hz, 1H), 7.86 (d, J = 8.2 Hz, 1H), 8.00 (s, 1 H), 8.26 (d, J = 8.2 Hz, 1H), 8.34 (br s, 1H), 11.07 (br s, 1H) |
| 216 | $^1$H NMR (400 MHz, CHLOROFORM-d) δ ppm 1.82 (d, J = 6.7 Hz, 3H), 2.44 (s, 3H), 5.37 (br d, J = 5.6 Hz, 1H), 6.45 (br s, 1H), 6.70 (d, J = 3.4 Hz, 1H), 6.93 (d, J = 8.9 Hz, 1H), 7.18 (d, J = 8.9 Hz, 1H), 7.42 (s, 1H), 7.52 (d, J = 2.0 Hz, 1H), 7.62 (d, J = 3.5 Hz, 1H), 7.86 (d, J = 8.2 Hz, 1H), 8.00 (s, 1H), 8.26 (d, J = 8.2 Hz, 1H), 8.34 (br s, 1H), 11.07 (br s, 1H) |
| 217 | $^1$H NMR (400 MHz, DMSO-d6) δ ppm 1.73 (d, J = 6.60 Hz, 3H), 2.30-2.46 (s, 3H), 4.12 (s, 3H), 5.45 (br t, J = 6.48 Hz, 1H), 7.11 (s, 1H), 7.19 (d, J = 9.17 Hz, 1H), 7.37 (d, J = 9.05 Hz, 1H), 7.57 (d, J = 2.08 Hz, 1H), 7.78 (d, J = 1.34 Hz, 1H), 7.83 (d, J = 9.05 Hz, 1H), 8.13 (dd, J = 9.05, 1.59 Hz, 1H), 8.24 (d, J = 0.86 Hz, 1H), 8.42 (d, J = 6.36 Hz, 1H), 8.60 (s, 1H), 12.71-13.44 (m, 1H) |
| 218 | $^1$H NMR (400 MHz, DMSO-d6) δ ppm 1.73 (d, J = 6.60 Hz, 3H), 2.30-2.46 (s, 3H), 4.12 (s, 3H), 5.45 (br t, J = 6.48 Hz, 1H), 7.11 (s, 1H), 7.19 (d, J = 9.17 Hz, 1H), 7.37 (d, J = 9.05 Hz, 1H), 7.57 (d, J = 2.08 Hz, 1H), 7.78 (d, J = 1.34 Hz, 1H), 7.83 (d, J = 9.05 Hz, 1H), 8.13 (dd, J = 9.05, 1.59 Hz, 1H), 8.24 (d, J = 0.86 Hz, 1H), 8.42 (d, J = 6.36 Hz, 1H), 8.60 (s, 1H), 12.71-13.44 (m, 1H) |
| 223 | $^1$H NMR (400 MHz, METHANOL-d4) δ ppm 1.80 (d, J = 6.7 Hz, 3H), 2.40 (s, 3H), 5.52 (q, J = 6.6 Hz, 1H), 6.91 (s, 1H), 7.08-7.15 (m, 2H), 7.23-7.32 (m, 2H), 7.39 (s, 1H), 7.50 (d, J = 7.8 Hz, 1H), 7.59 (d, J = 2.1 Hz, 1H), 7.68 (d, J = 8.1 Hz, 1H), 7.86 (s, 1H) |
| 224 | $^1$H NMR (400 MHz, DMSO-d6) δ ppm 1.74 (d, J = 6.6 Hz, 3H), 2.37 (s, 3H), 2.55 (s, 3H), 4.02 (s, 3H), 5.39-5.47 (m, 1H), 7.14 (s, 1H), 7.18 (d, J = 9.0 Hz, 1H), 7.35 (d, J = 8.9 Hz, 1H), 7.55 (d, J = 2.1 Hz, 1H), 7.73 (d, J = 8.8 Hz, 1H), 7.77 (d, J = 1.3 Hz, 1H), 8.10 (dd, J = 8.9, 1.6 Hz, 1H), 8.30-8.46 (m, 1H), 8.54 (s, 1H), 13.04 (br s, 1H) |
| 225 | $^1$H NMR (400 MHz, DMSO-d6) δ ppm 1.68 (d, J = 6.4 Hz, 3H), 2.34-2.35 (m, 6H), 2.38 (s, 3H), 5.42-5.44 (m, 1H), 7.06 (s, 1H), 7.09 (d, J = 8.8 Hz, 1H), 7.22 (d, J = 8.8 Hz, 1H), 7.55 (s, 1H), 7.58 (d, J = 9.2 Hz, 1H), 7.74 (s, 1H), 7.83 (d, J = 9.6 Hz, 1H), 7.91 (s, 1H), 8.62 (br s, 1H), 9.30 (s, 1H) |
| 226 | $^1$H NMR (400 MHz, DMSO-d6) δ ppm 1.73 (d, J = 6.8 Hz, 3H), 2.38 (s, 3H), 4.23 (s, 3H), 5.41-5.43 (m, 1H), 7.05 (s, 1H), 7.15 (d, J = 9.2 Hz, 1H), 7.34 (d, J = 4.0 Hz, 1H), 7.58 (s, 1H), 7.73-7.77 (m, 2H), 7.85 (d, J = 4.0 Hz, 1 H), 7.90-7.93 (m, 1H), 8.57 (s, 1H), 8.63 (s, 1H), 8.82-8.83 (s, 1H) |
| 227 | $^1$H NMR (400 MHz, DMSO-d6) δ ppm 1.57 (d, J = 6.8 Hz, 3H), 2.13 (s, 3H), 2.37 (s, 3H), 4.23 (s, 3H), 5.09-5.11 (m, 1H), 6.24 (d, J = 8.8 Hz, 1H), 6.31 (t, J = 7.6 Hz, 1H), 7.10-7.11 (m, 1H), 7.53 (d, J = 2.4 Hz, 1H), 7.60-7.63 (m, 1H), 7.74 (s, 1H), 7.77 (d, J = 6.4 Hz, 1H), 8.06-8.13 (m, 1H), 8.21 (s, 1H), 8.54 (s, 1H) |
| 228 | $^1$H NMR (400 MHz, DMSO-d6) δ ppm 1.65 (d, J = 6.4 Hz, 3H), 2.36-2.38 (m, 6H), 5.36-5.38 (m, 1H), 6.29-6.35 (m, 2H), 7.06 (s, 1H), 7.12-7.13 (m, 1H), 7.57-7.59 (m, 2H), 7.74 (s, 1H), 7.82 (dd, J = 9.6, 2.0 Hz, 1H), 7.92 (s, 1H), 8.26 (br s, 1H), 9.30 (s, 1H) |
| 229 | $^1$H NMR (400 MHz, DMSO-d6) δ ppm 1.59 (d, J = 6.4 Hz, 3H), 2.14 (s, 3H), 2.38-2.40 (m, 6H), 5.13-5.15 (m, 1H), 6.30-6.36 (m, 2H), 7.13-7.17 (m, 1H), 7.55-7.56 (m, 2H), 7.57-7.62 (m, 1H), 7.79 (s, 1H), 7.85 (s, 1H), 8.10-8.12 (m, 1H), 9.02 (s, 1H), 13.17 (br s, 1H) |
| 230 | $^1$H NMR (400 MHz, ACETONE-d6) δ ppm 1.70 (d, J = 6.8 Hz, 3H), 2.41-2.43 (m, 6H), 4.29 (s, 3H), 5.36-5.41 (m, 1H), 6.29-6.34 (m, 2H), 7.09-7.10 (m, 1H), 7.34 (t, J = 7.6 Hz, 1H), 7.54 (t, J = 7.2 Hz, 1H), 7.65 (d, J = 2.0 Hz, 1H), 7.77 (d, J = 8.8 Hz, 1H), 7.89 (s, 1H), 8.28 (d, J = 8.4 Hz, 1H) |
| 231 | $^1$H NMR (400 MHz, DMSO-d6) δ ppm 1.72 (d, J = 6.8 Hz, 3H), 2.37 (s, 3H), 2.57 (s, 3H), 4.22 (s, 3H), 5.40-5.44 (m, 1H), 7.02 (s, 1H), 7.18 (d, J = 8.8 Hz, 1H), 7.36-7.39 (m, 1H), 7.57 (d, J = 2.0 Hz, 1H), 7.68 (s, 1H), 7.76 (s, 1H), 7.85 (d, J = 4.4 Hz, 1H), 8.43 (s, 1H), 8.52 (s, 1H), 8.76 (d, J = 6.0 Hz, 1H). |
| 232 | $^1$H NMR (400 MHz, DMSO-d6) δ ppm 1.77 (d, J = 6.4 Hz, 3H), 2.37 (s, 3H), 4.23 (s, 3H), 5.38-5.41 (m, 1H), 7.00 (s, 1H), 7.09 (d, J = 8.8 Hz, 1H), 7.31-7.32 (m, 1H), 7.40 (t, J = 7.6 Hz, 1H), 7.53-7.57 (m, 2H), 7.80 (s, 1H), 7.85 (d, J = 8.0 Hz, 2H), 8.24 (d, J = 8.0 Hz, 1H), 8.76 (d, J = 4.8 Hz, 1H) |
| 233 | $^1$H NMR (400 MHz, METHANOL-d4) δ ppm 1.76 (d, J = 6.8 Hz, 3H), 2.31 (s, 3H), 2.43 (s, 3H), 2.93 (s, 3H), 5.32-5.35 (m, 1H), 7.18 (d, J = 8.8 Hz, 1H), 7.55 (d, J = 8.8 Hz, 1H), 7.64 (s, 1H), 7.92 (s, 1H), 8.11 (d, J = 8.4 Hz, 1H), 8.41 (d, J = 8.4 Hz, 1H) |
| 234 | $^1$H NMR (400 MHz, DMSO-d6) δ ppm 1.67 (d, J = 6.4 Hz, 3H), 2.28 (s, 3H), 2.39 (s, 3H), 2.90 (s, 3H), 5.31-5.32 (m, 1 H), 6.72 (d, J = 8.8 Hz, 1H), 7.50 (d, J = 8.0 Hz, 1H), |

TABLE 56-continued

| Ex # | NMR Line Listing |
|---|---|
| | 7.60 (s, 1H), 7.81 (s, 1H), 8.03 (s, 1H), 8.18 (d, J = 8.8 Hz, 1H), 8.49 (d, J = 8.4 Hz, 1H), 8.78 (d, J = 6.0 Hz, 1H), 13.30 (br s, 1H) |
| 235 | $^1$H NMR (400 MHz, DMSO-d6) δ ppm 1.63 (d, J = 6.4 Hz, 3H), 2.13 (s, 3H), 2.38 (s, 3H), 4.22 (s, 3H), 5.19-5.24 (m, 1H), 6.67 (d, J = 8.8 Hz, 1H), 7.51 (dd, J = 8.8, 2.0 Hz, 1H), 7.56 (d, J = 2.0 Hz, 1H), 7.59 (d, J = 8.8 Hz, 1H), 7.73 (d, J = 9.2 Hz, 1H), 7.80 (s, 1H), 8.05 (d, J = 2.0 Hz, 1H), 8.20 (s, 1H), 8.53 (s, 1H), 8.78 (d, J = 6.4 Hz, 1H), 13.35 (br s, 1H) |
| 236 | $^1$H NMR (400 MHz, DMSO-d6) δ ppm 1.63 (d, J = 6.8 Hz, 3 H), 2.12 (s, 3H), 2.38 (s, 3H), 4.22 (s, 3H), 5.18-5.24 (m, 1H), 7.09 (d, J = 8.8 Hz, 1H), 7.57-7.60 (m, 3H), 7.72 (d, J = 8.8 Hz, 1H), 7.80 (s, 1H), 8.20 (s, 1H), 8.52 (s, 1H), 8.82 (br s, 1H) |
| 237 | $^1$H NMR (500.11 MHz, DMSO-d6) δ ppm 1.73 (d, J = 6.7 Hz, 3H), 2.39 (s, 3H), 4.16 (s, 3H), 5.38-5.44 (m, 1H), 6.58-6.61 (m, 1H), 7.27-7.29 (m, 2H), 7.57 (d, J = 1.5 Hz, 1H), 7.76-7.78 (m, 2H), 7.86-7.89 (m, 1H), 7.95 (d, J = 8.6 Hz, 1H), 8.18 (s, 1H), 8.48-8.50 (m, 2H) |
| 238 | $^1$H NMR (500.11 MHz, DMSO-d6) δ ppm 1.73 (d, J = 6.7 Hz, 3H), 2.39 (s, 3H), 4.17 (s, 3H), 5.38-5.39 (m, 1H), 6.58 (dd, J = 4.5, 9.4 Hz, 1H), 7.16 (td, J = 8.6, 3.1 Hz, 1H), 7.26 (s, 1H), 7.53-7.56 (m, 1H), 7.57 (d, J = 1.8 Hz, 1H), 7.78 (s, 1H), 7.87 (d, J = 8.6 Hz, 1H), 7.95 (d, J = 8.6 Hz, 1H), 8.18 (s, 1H), 8.32-8.34 (m, 1H), 8.47 (s, 1H) |
| 239 | $^1$H NMR (400 MHz, DMSO-d6) δ ppm 1.73-1.75 (m, 3H), 2.36 (s, 3H), 2.90 (s, 3H), 5.45-5.47 (m, 1H), 7.18-7.34 (m, 3H), 7.59 (s, 1H), 7.76 (s, 1H), 7.85 (s, 1H), 8.38-8.53 (m, 2H), 8.82 (br s, 1H) |
| 240 | $^1$H NMR (500 MHz, DMSO-d6) δ ppm 1.62 (d, J = 3.2 Hz, 3H), 2.13 (s, 3H), 2.41 (s, 3H), 4.23 (s, 3H), 5.12-5.19 (s, 1H), 7.11 (d, J = 5.6 Hz, 1H), 7.33 (s, 1H), 7.55 (s, 1H), 7.62 (d, J = 6.8 Hz, 1H), 7.74 (d, J = 6.4 Hz, 1H), 7.81 (d, J = 14.0 Hz, 2H), 8.21 (s, 1H), 8.53 (s, 1H), 8.66 (s, 1H) |
| 241 | $^1$H NMR (400 MHz, DMSO-d6) δ ppm 1.71 (d, J = 6.8 Hz, 3H), 2.38 (s, 3H), 5.37-5.39 (m, 1H), 6.34-6.37 (m, 2H), 6.60 (s, 1H), 7.16-7.18 (m, 1H), 7.24 (s, 1H), 7.57 (s, 1H), 7.73 (t, J = 2.8 Hz, 1H), 7.77 (s, 1H), 7.98 (d, J = 8.4 Hz, 1H), 8.18-8.21 (m, 1H), 12.08 (s, 1H), 13.24 (br s, 1H) |
| 242 | $^1$H NMR (400 MHz, DMSO-d6) δ ppm 1.66 (d, J = 6.4 Hz, 3H), 2.27 (s, 3H), 2.38 (s, 3H), 2.90 (s, 3H), 5.23-5.27 (m, 1H), 7.13 (d, J = 8.8 Hz, 1H), 7.29 (d, J = 9.2 Hz, 1H), 7.57 (s, 1H), 7.80 (s, 1H), 8.19 (d, J = 8.4 Hz, 1H), 8.34 (d, J = 6.4 Hz, 1H), 8.50 (d, J = 8.4 Hz, 1H), 13.02 (br s, 1H) |
| 243 | $^1$H NMR (400 MHz, DMSO-d6) δ ppm 1.66 (d, J = 6.4 Hz, 3H), 2.27 (s, 3H), 2.38 (s, 3H), 2.91 (s, 3H), 5.24-5.28 (m, 1H), 7.16 (d, J = 8.8 Hz, 1H), 7.31-7.34 (m, 1H), 7.59 (s, 1H), 7.80-7.83 (m, 2H), 8.21 (d, J = 8.4 Hz, 1H), 8.50 (d, J = 8.4 Hz, 1H), 8.67 (d, J = 6.4 Hz, 1H) |
| 244 | $^1$H NMR (400 MHz, DMSO-d6) δ ppm 1.61 (d, J = 6.8 Hz, 3H), 2.12 (s, 3H), 2.38 (s, 3H), 4.23 (s, 3H), 5.13-5.19 (m, 1H), 6.99 (d, J = 9.2 Hz, 1H), 7.38 (d, J = 8.8 Hz, 1H), 7.53 (d, J = 2.0 Hz, 1H), 7.58-7.60 (m, 1 H), 7.73 (d, J = 9.2 Hz, 1H), 7.80 (s, 1H), 8.18 (s, 1H), 8.30 (d, J = 6.8 Hz, 1H), 8.52 (s, 1H), 13.12 (br s, 1H) |
| 245 | $^1$H NMR (400 MHz, DMSO-d6) δ ppm 1.65 (d, J = 6.4 Hz, 3H), 2.27 (s, 3H), 2.38 (s, 3H), 2.91 (s, 3H), 5.22-5.25 (m, 1H), 7.03 (d, J = 9.2 Hz, 1H), 7.37 (d, J = 8.8 Hz, 1H), 7.57 (s, 1H), 7.80 (s, 1H), 8.18 (d, J = 8.4 Hz, 1H), 8.31-8.34 (m, 1H), 8.50 (d, J = 8.4 Hz, 1H) |
| 246 | $^1$H NMR (400 MHz, DMSO-d6) δ ppm 1.61 (d, J = 6.4 Hz, 3H), 2.11 (s, 3H), 2.38 (s, 3H), 2.87 (s, 3H), 5.19-5.23 (m, 1H), 7.10 (d, J = 9.2 Hz, 1H), 7.29 (d, J = 9.2 Hz, 1H), 7.55 (s, 1H), 7.81 (s, 1H), 7.87 (d, J = 8.4 Hz, 1H), 8.07 (d, J = 8.4 Hz, 1H), 8.29 (d, J = 6.4 Hz, 1H), 8.51 (s, 1H), 13.06 (br s, 1H) |
| 247 | $^1$H NMR (400 MHz, DMSO-d6) δ ppm 1.59 (d, J = 6.8 Hz, 3H), 2.34 (s, 3H), 2.36 (s, 3H), 5.77-5.80 (m, 1H), 7.12 (d, J = 9.2 Hz, 1H), 7.20-7.23 (m, 2H), 7.32 (d, J = 8.8 Hz, 1H), 7.48 (d, J = 2.0 Hz, 1H), 7.79 (s, 1H), 8.17 (m, 1H), 8.43-8.44 (m, 2H), 12.56 (s, 1H) |
| 248 | $^1$H NMR (400 MHz, DMSO-d6) δ ppm 1.72 (d, J = 6.8 Hz, 3H), 2.37 (s, 3H), 2.69 (s, 3H), 4.03 (s, 3H), 5.43-5.44 (m, 1H), 6.54-6.60 (m, 2H), 7.09 (d, J = 8.8 Hz, 1H), 7.14 (s, 1H), 7.22-7.26 (m, 1H), 7.58 (s, 1H), 7.75 (s, 1H), 7.83 (d, J = 8.0 Hz, 1H), 8.21 (s, 1H), 8.37 (d, J = 8.8 Hz, 1H), 8.50-8.51 (m, 2 H) |
| 249 | $^1$H NMR (400 MHz, DMSO-d6) δ ppm 1.71 (d, J = 6.4 Hz, 3H), 2.38 (s, 3H), 4.02 (s, 3H), 5.42-5.44 (m, 1H), 6.55-6.59 (m, 2H), 7.13 (d, J = 9.2 Hz, 1H), 7.18 (s, 1H), 7.24 (t, J = 6.8 Hz, 1H), 7.58 (s, 1H), 7.77 (s, 1H), 7.82 (d, J = 8.0 Hz, 1H), 7.90 (d, J = 9.2 Hz, 1H), 8.34 (d, J = 8.4 Hz, 1H), 8.40-8.46 (m, 2H), 8.70 (s, 1H), 12.79 (br s, 1H) |
| 250 | $^1$H NMR (400 MHz, CHLOROFORM-d) δ ppm 1.84 (d, J = 6.8 Hz, 3H), 2.41 (s, 3H), 2.46 (s, 3H), 2.94 (s, 3H), 5.30-5.32 (m, 1H), 6.85 (d, J = 8.8 Hz, 1H), 7.08-7.10 (m, 1H), 7.51-7.53 (m, 2H), 7.97 (s, 1H), 8.14-8.26 (m, 1H), 8.29 (s, 1H), 8.34-8.36 (m, 1H) |
| 251 | $^1$H NMR (400 MHz, CHLOROFORM-d) δ ppm 1.84 (d, J = 6.8 Hz, 3H), 2.41 (s, 3H), 2.93 (s, 3H), 5.27-5.30 (s, 1H), 6.87 (d, J = 9.2 Hz, 1H), 7.17 (d, J = 8.8 Hz, 1H), 7.47-7.49 (m, 2H), 7.97 (s, 1H), 8.12 (d, J = 8.8 Hz, 1H), 8.32-8.35 (m, 2H), 10.74 (br s, 1H) |
| 252 | $^1$H NMR (400 MHz, DMSO-d6) δ ppm 1.75 (d, J = 6.8 Hz, 3H), 2.39 (s, 3H), 5.39-5.54 (s, 1H), 6.53-6.61 (m, 2H), 7.22 (t, J = 6.8 Hz, 1H), 7.46 (s, 1H), 7.62 (d, J = 2.0 Hz, 1H), 7.79-7.83 (m, 2H), 7.92 (dd, J = 8.8, 4.0 Hz, 1H), 8.58-8.62 (m, 3H), 8.68 (d, J = 4.4 Hz, 1H), 9.12 (d, J = 4.0 Hz, 1H) |
| 253 | $^1$H NMR (400 MHz, ACETONE-d6) δ ppm 1.65 (d, J = 6.4 Hz, 3H), 2.17 (s, 3H), 2.38 (s, 3H), 4.28 (s, 3H), 5.21-5.25 (m, 1H), 6.56 (dd, J = 9.2, 4.0 Hz, 1H), 7.00-7.04 (m, 1H), 7.58-7.68 (m, 3H), 7.77 (d, J = 8.8 Hz, 1H), 7.84 (s, 1H), 8.22 (s, 1H), 8.43 (s, 1H) |
| 254 | $^1$H NMR (400 MHz, DMSO-d6) δ ppm 1.63 (d, J = 6.8 Hz, 3H), 2.29 (s, 3H), 2.38 (s, 3H), 2.90 (s, 3H), 5.20-5.21 (m, 1H), 6.53 (dd, J = 9.2, 4.4 Hz, 1H), 7.10-7.12 (m, 1H), |

TABLE 56-continued

| Ex # | NMR Line Listing |
|---|---|
| | 7.50 (dd, J = 9.6, 3.2 Hz, 1H), 7.55 (d, J = 2.0 Hz, 1H), 7.79 (s, 1 H), 8.19 (d, J = 8.8 Hz, 2H), 8.51 (d, J = 8.4 Hz, 1H), 13.08 (br s, 1H) |
| 255 | $^1$H NMR (400 MHz, DMSO-d6) δ ppm 1.73 (d, J = 6.8 Hz, 3H), 2.38 (s, 3H), 4.05 (s, 3H), 5.42-5.43 (m, 1H), 6.56-6.60 (m, 2H), 7.22 (t, J = 7.6 Hz, 1H), 7.36 (s, 1H), 7.39 (d, J = 9.2 Hz, 1H), 7.61 (s, 1H), 7.77 (s, 1H), 7.82 (d, J = 7.2 Hz, 1H), 8.37-8.41 (m, 2 H), 8.48 (d, J = 8.4 Hz, 1H), 8.56 (s, 1 H), 12.80 (s, 1H) |
| 256 | $^1$H NMR (400 MHz, DMSO-d6) δ ppm 1.64 (d, J = 6.8 Hz, 3H), 2.29 (s, 3H), 2.38 (s, 3H), 2.72 (s, 3H), 5.20-5.25 (m, 1H), 6.50-6.56 (m, 2H), 7.18-7.22 (m, 1H), 7.57 (d, J = 2.0 Hz, 1H), 7.78-7.80 (m, 2H), 8.12 (d, J = 8.0 Hz, 1H), 8.34 (d, J = 8.4 Hz, 1H), 8.39 (d, J = 5.2 Hz, 1H), 12.71 (br s, 1H) |
| 257 | $^1$H NMR (400 MHz, CHLOROFORM-d) δ ppm 1.80 (d, J = 6.8 Hz, 3H), 2.42 (s, 3H), 2.92 (s, 3H), 5.28-5.32 (m, 1H), 6.24 (d, J = 8.8 Hz, 1H), 6.33-6.38 (m, 1H), 7.13-7.17 (m, 1H), 7.51-7.52 (m, 2H), 7.96 (s, 1H), 8.15 (d, J = 8.4 Hz, 1H), 8.33 (d, J = 8.8 Hz, 1H), 8.54-8.58 (m, 1H) |
| 258 | $^1$H NMR (400 MHz, DMSO-d6) δ ppm 1.59 (d, J = 6.4 Hz, 3H), 2.13 (s, 3H), 2.37 (s, 3H), 4.23 (s, 3H), 5.10-5.14 (m, 1H), 6.51 (d, J = 8.8 Hz, 1H), 7.21-7.23 (m, 1H), 7.51 (s, 1H), 7.61-7.62 (m, 1H), 7.73-7.75 (m, 2H), 7.79 (s, 1H), 8.20 (s, 1H), 8.40-8.41 (m, 1H), 8.54 (s, 1H) |
| 259 | $^1$H NMR (400 MHz, CHLOROFORM-d) δ ppm 1.68 (d, J = 6.4 Hz, 3H), 2.26 (s, 3H), 2.42 (s, 3H), 4.16 (s, 3H), 5.14-5.15 (m, 1H), 6.35 (d, J = 9.2 Hz, 1H), 7.13-7.14 (m, 1H), 7.47 (s, 1H), 7.55 (d, J = 8.8 Hz, 1H), 7.69 (d, J = 8.4 Hz, 1H), 7.97-7.99 (m, 3H), 8.06 (s, 1H), 8.14 (s, 1H) |
| 260 | $^1$H NMR (400 MHz, DMSO-d6) δ ppm 1.58 (d, J = 6.4 Hz, 3H), 2.12 (s, 3H), 2.37 (s, 3H), 4.12 (s, 3H), 5.11-5.12 (m, 1H), 6.48 (dd, J = 9.2, 4.4 Hz, 1H), 7.10-7.15 (m, 1H), 7.50-7.53 (m, 2H), 7.79-7.82 (m, 3H), 8.18 (s, 1H), 8.22-8.23 (m, 2 H), 13.10 (br s, 1H) |
| 261 | $^1$H NMR (400 MHz, DMSO-d6) δ ppm 1.59 (d, J = 6.8 Hz, 3H), 2.11 (s, 3H), 2.38 (s, 3H), 2.69 (s, 3H), 5.13-5.15 (m, 1 H), 6.48 (d, J = 8.4 Hz, 1H), 6.54 (t, J = 7.6 Hz, 1H), 7.19-7.21 (m, 1H), 7.53 (d, J = 2.0 Hz, 1H), 7.78-7.86 (m, 4H), 8.15-8.16 (m, 1H), 8.36-8.37 (m, 1 H), 12.75 (br s, 1H) |
| 262 | $^1$H NMR (400 MHz, DMSO-d6) δ ppm 1.58 (d, J = 6.4 Hz, 3H), 2.12 (s, 3H), 2.37 (s, 3H), 2.86 (s, 3H), 5.15-5.18 (m, 1H), 6.48 (d, J = 8.4 Hz, 1H), 6.54 (t, J = 7.2 Hz, 1H), 7.18-7.22 (m, 1H), 7.53 (d, J = 2.0 Hz, 1H), 7.79-7.81 (m, 2H), 7.88 (d, J = 8.4 Hz, 1H), 8.08 (d, J = 8.8 Hz, 1H), 8.34 (d, J = 6.0 Hz, 1H), 8.53 (s, 1H), 12.74 (br s, 1H) |
| 263 | $^1$H NMR (400 MHz, DMSO-d6) δ ppm 1.78 (d, J = 6.72 Hz, 3H), 2.41 (s, 3H), 2.55-2.57 (m, 3H), 5.30 (quin, J = 6.69 Hz, 1H), 7.23 (d, J = 9.05 Hz, 1H), 7.34 (d, J = 8.93 Hz, 1H), 7.52-7.57 (m, 1H), 7.61 (t, J = 7.38 Hz, 1H), 7.68 (d, J = 2.08 Hz, 1H), 7.81-7.83 (m, 1H), 7.94 (d, J = 7.95 Hz, 1H), 8.01 (d, J = 7.46 Hz, 1H), 8.47 (d, J = 6.97 Hz, 1H), 12.98 (br s, 1H) |
| 264 | $^1$H NMR (400 MHz, DMSO-d6) δ ppm 1.69 (d, J = 6.60 Hz, 3H), 2.39 (s, 3H), 2.43 (s, 3H), 5.31 (br t, J = 6.36 Hz, 1H), 6.34-6.40 (m, 2H), 7.19 (td, J = 8.25, 6.36 Hz, 1H), 7.60 (d, J = 2.08 Hz, 1H), 7.78-7.82 (m, 1H), 8.03 (s, 1H), 8.09 (d, J = 5.87 Hz, 1H), 8.18 (br d, J = 6.36 Hz, 1H), 8.74 (br d, J = 5.50 Hz, 1H), 9.27 (br s, 1H), 12.77-13.54 (m, 1H) |
| 265 | $^1$H NMR (400 MHz, DMSO-d6) δ ppm 1.64 (d, J = 5.2 Hz, 3H), 2.28 (s, 3H), 2.34 (s, 3H), 2.37 (s, 3H), 2.92 (s, 3H), 5.23-5.25 (m, 1H), 7.10-7.18 (m, 2H), 7.55 (s, 1H), 7.80 (s, 1H), 8.22 (s, 1H), 8.50-8.52 (m, 2H) |

PI3K-Alpha Kinase (PIK3CA) Activity, Wild-Type and H1047R Mutant and Determining IC50 Values for Inhibitors Recombinant, catalytically active human full length PIK3KA Wild-type and H1047R mutant were purchased as 1:1 complex of N-terminal 6×his tagged p110α (catalytic) and untagged p85α (regulatory subunit) from EMD Millipore Sigma (cat. no. 14-602M and 14-792M, respectively). PIP2diC8 (Avanti Polar Lipids Inc., cat. no. 850185) or Soy PI (Avanti Polar Lipids Inc., cat. No. 840044P) was used as lipid substrate. PIP2diC8 or PI lyophilized powder was dissolved in milliQ water to a concentration of 1 mM just before use. 10 mM stock compounds in DMSO were serially diluted 1:3 to generate a 10-point curve and plated using an acoustic liquid handler system (Echo 550 series instrument, Labcyte). A 10× intermediate compound plate (200 uM starting compound concentration and 10% DMSO) was prepared before starting the reaction. A typical reaction mixture (50 uL) comprised 40 mM HEPES buffer, pH 7.4, 25 mM $MgCl_2$, 0.01% v/v triton-X-100, 1% v/v DMSO, 20 mM NaCl, 1-5 nM WT or H1047R PI3K protein, 20 uM ATP, and 50 uM PIP2diC8 or Soy PI. 1% DMSO buffer alone without test compound was employed as MAX control (full activity in the absence of any inhibitor), and no enzyme control was used to determine the level of background Adenosine 5'-diphosphate (ADP) (MIN control). First, Wild-type (WT) and H1047R mutant protein in kinase buffer with all components except ATP were incubated with or without compound at 27° C. for 1 h. After the pre-incubation, the reaction was initiated by the addition of 20 uL of 50 uM ATP (20 uM final concentration). The reaction was allowed to proceed until about 10% conversion of ATP (2 uM ADP) at 27° C. After that time, 5 uL of reaction was mixed with 5 uL of ADP-Kinase Glo Reagent (ADP-Glo Kinase assay kit, Promega cat. no. V9102) supplemented with $MgCl_2$ 10 mM to stop the reaction and deplete the remaining ATP for 40 min at room temperature. Then, 10 uL of Kinase Detection Reagent (ADP-Glo Kinase assay kit, Promega cat. no. V9102) was added to simultaneously convert ADP to ATP and allow the newly synthesized ATP to be measured using a luciferase/luciferin reaction. After 30 min at room temperature the light generated was measured using a luminometer (EnVision plate reader, Perkin Elmer). Process data through Genedata-Screener tool. Relative $IC_{50}$ values are determined using luminescence units by calculating percent inhibition with respect to on-plate "MIN" and "MAX" controls. Data was analyzed using a 4-parameter nonlinear logistic equation (four-parameter logistic concentration-response curve):

$$Y=\text{bot}+[(\text{top}-\text{bot})/1+(x/\text{IC50})\text{slope}]$$

where Y=% inhibition, X=concentration yielding y % inhibition, Bottom=minimum value of y attained by curve, Top=maximum value of y attained by curve and Slope=steepness of curve at IC50.

$$\%\ \text{Inh}=[(\text{median Max}-x/\text{median Max}-\text{median Min})]\cdot 100$$

IC50: concentration of compound that reduces a given response (ligand binding, enzyme response) by 50%. IC50 relative: concentration giving half the compound's maximum response.

For $IC_{50}$ values shown in Table A, "A" means $IC_{50}$<0.5 μM; "B" means $IC_{50}$ ranging between 0.5 μM and 1.0 μM; "C" means $IC_{50}$ ranging between 1 μM and 5 μM; "D" means $IC_{50}$ ranging between 5 μM and 10 μM; "E" means $IC_{50}$>10 μM.

TABLE A

PI3K-α (PIK3CA) Biochemical $IC_{50}$ of PI3K wild-type (WT) and H1047R mutant, using Soy PI lipid substrate

| Example # | $IC_{50}$ H1047R | $IC_{50}$ WT |
|---|---|---|
| 1 | A | C |
| 2 | B | C |
| 3 | A | C |
| 4 | A | B |
| 5 | C | D |
| 6 | A | C |
| 7[1] | A | A |
| 8 | A | B |
| 9[1] | A | B |
| 10 | A | C |
| 11[1] | B | B |
| 12 | A | D |
| 13 | A | A |
| 14 | A | C |
| 15 | A | C |
| 16 | A | C |
| 17 | A | C |
| 18 | A | C |
| 19 | A | C |
| 20 | A | C |
| 21 | A | B |
| 22 | A | B |
| 23 | A | B |
| 24 | A | C |
| 25 | A | A |
| 26 | A | A |
| 27 | A | B |
| 28 | A | C |
| 29 | A | D |
| 30 | A | C |
| 31 | A | C |
| 32 | E | D |
| 33 | E | E |
| 34 | A | C |
| 35 | D | D |
| 36 | A | C |
| 37 | E | C |
| 38 | A | C |
| 39 | A | C |
| 40 | C | D |
| 41 | C | D |
| 42 | A | C |
| 43 | E | E |
| 44 | C | D |
| 45 | A | A |
| 46[1] | A | A |
| 47 | A | C |

TABLE A-continued

PI3K-α (PIK3CA) Biochemical $IC_{50}$ of PI3K wild-type (WT) and H1047R mutant, using Soy PI lipid substrate

| Example # | $IC_{50}$ H1047R | $IC_{50}$ WT |
|---|---|---|
| 48 | A | A |
| 49 | A | B |
| 50 | A | C |
| 51 | A | C |
| 52 | A | B |
| 53 | A | C |
| 54 | A | C |
| 55 | A | C |
| 56 | E | E |
| 57 | C | C |
| 58 | A | C |
| 59 | A | A |
| 60 | A | B |
| 61 | A | B |
| 62 | A | C |
| 63 | A | B |
| 64 | A | C |
| 65 | A | C |
| 66 | C | D |
| 67 | A | C |
| 68 | A | B |
| 69 | A | C |
| 70 | A | C |
| 71 | A | C |
| 72 | A | B |
| 73 | A | C |
| 74 | A | B |
| 75 | A | B |
| 76 | A | E |
| 77 | A | D |
| 78 | C | E |
| 79 | A | C |
| 80 | A | C |
| 81 | A | C |
| 82 | A | B |
| 83 | A | B |
| 84 | A | D |
| 85 | A | C |
| 86 | A | B |
| 87 | A | C |
| 88 | A | B |
| 89 | A | C |
| 90 | A | C |
| 91 | A | B |
| 92 | A | C |
| 93 | A | B |
| 94 | C | E |
| 95 | A | B |
| 96 | C | D |
| 97 | A | C |
| 98 | D | D |
| 99 | C | C |
| 100 | A | E |
| 101 | A | C |
| 102 | A | C |
| 103 | A | C |
| 104 | A | C |
| 105 | A | D |
| 106 | A | A |
| 107 | B | C |
| 108 | A | B |
| 109 | A | C |
| 110 | A | D |
| 111 | A | B |
| 112 | B | C |
| 113 | A | B |
| 114 | E | E |
| 115 | A | C |
| 116 | A | E |
| 117 | B | C |
| 118 | A | C |
| 119 | C | C |
| 120 | A | B |
| 121 | A | C |

TABLE A-continued

| PI3K-α (PIK3CA) Biochemical $IC_{50}$ of PI3K wild-type (WT) and H1047R mutant, using Soy PI lipid substrate | | |
|---|---|---|
| Example # | $IC_{50}$ H1047R | $IC_{50}$ WT |
| 122 | B | E |
| 123 | A | C |
| 124 | A | B |
| 125 | A | C |
| 126 | A | C |
| 127 | B | D |
| 128 | A | B |
| 129 | A | B |
| 130 | A | B |
| 131 | A | C |
| 132 | A | B |
| 133 | E | E |
| 134 | A | C |
| 135 | A | D |
| 136 | A | C |
| 137 | A | C |
| 138 | B | E |
| 139 | A | C |
| 140 | A | C |
| 141 | A | C |
| 142 | A | C |
| 143 | A | B |
| 144 | A | C |
| 145 | A | C |
| 146 | A | B |
| 147 | A | C |
| 148 | A | B |
| 149 | A | A |
| 150 | A | A |
| 151 | A | B |
| 152 | A | C |
| 153 | A | A |
| 154 | A | C |
| 155 | A | C |
| 156 | C | C |
| 157 | A | C |
| 158 | A | C |
| 159 | A | C |
| 160 | A | C |
| 161 | B | E |
| 162 | B | E |
| 163 | A | D |
| 164 | A | C |
| 165 | A | A |
| 166 | A | D |
| 167 | A | C |
| 168 | A | A |
| 169 | A | B |
| 170 | A | A |
| 171 | C | C |
| 172 | A | A |
| 173 | A | E |
| 174 | A | E |
| 175 | A | B |
| 176 | A | E |
| 177 | A | A |
| 178 | A | B |
| 179 | B | D |
| 180 | A | C |
| 181 | A | A |
| 182 | A | C |
| 183 | A | B |
| 184 | A | B |
| 185 | E | E |
| 186 | A | C |
| 187 | A | C |
| 188 | A | B |
| 189 | A | B |
| 190 | A | B |
| 191 | A | B |
| 192 | B | B |
| 193 | A | B |
| 194 | B | B |
| 195 | A | B |

TABLE A-continued

| PI3K-α (PIK3CA) Biochemical $IC_{50}$ of PI3K wild-type (WT) and H1047R mutant, using Soy PI lipid substrate | | |
|---|---|---|
| Example # | $IC_{50}$ H1047R | $IC_{50}$ WT |
| 196 | A | C |
| 197 | A | B |
| 198 | A | A |
| 200 | A | B |
| 203 | A | A |
| 204 | A | B |
| 205 | C | E |
| 206 | A | A |
| 207 | A | B |
| 208 | A | A |
| 209 | A | B |
| 210 | A | B |
| 211 | A | B |
| 214 | A | A |
| 215 | A | B |
| 216 | C | E |
| 217 | C | C |
| 218 | A | A |
| 219 | C | C |
| 220 | A | A |
| 221 | C | B |
| 222 | A | B |
| 223 | A | B |
| 224 | A | A |
| 225 | A | C |
| 226 | B | C |
| 227 | A | B |
| 228 | A | B |
| 229 | A | A |
| 230 | A | A |
| 231 | C | E |
| 232 | B | E |
| 233 | A | C |
| 234 | C | C |
| 235 | A | C |
| 236 | A | B |
| 237 | A | B |
| 238 | A | A |
| 239 | C | E |
| 240 | B | C |
| 241 | A | B |
| 242 | A | B |
| 243 | C | C |
| 244 | A | A |
| 245 | A | A |
| 246 | A | B |
| 247 | A | A |
| 248 | B | C |
| 249 | A | C |
| 250 | C | D |
| 251 | A | C |
| 252 | B | C |
| 253 | A | A |
| 254 | A | B |
| 255 | B | C |
| 256 | A | B |
| 257 | A | C |
| 258 | A | B |
| 259 | A | A |
| 260 | A | A |
| 261 | A | B |
| 262 | A | B |
| 263 | A | C |
| 264 | A | A |
| 265 | A | C |

[1]PIP2diC8 lipid substrate
*For Example 34, $IC_{50}$ WT/$IC_{50}$ H1047R = 10.7

PI3K-Alpha Kinase (PIK3CA) Activity In Vitro Cell Based Assay and Determining IC50 Values for Inhibitors The MDA-MB-453 (ATCC-HTB-131) cell line was obtained from the American Type Culture Collection (Manassas, VA). Cells were maintained in Dulbecco's Modified Eagle Media (DMEM, Gibco 11965-092) supplemented with 10% Fetal Bovine Serum, heat inactivated (FBS HI, Gibco 10082-147), 1× non-essential amino acids (NEAA, Gibco 11140-050), and 1 mM sodium pyruvate (Gibco 11360-070). Cultures were maintained in a humidified incubator at 37° C. under 5% $CO_2$/95% air.

For compound testing in 0% FBS, MDA-MB-453 cells were seeded at a density of $1.5\times10^4$ cells per well in white 384-well plates in 20 μl of Minimum Essential Media (MEM) assay media with 1×NEAA, 1 mM sodium pyruvate, and 1 μg/mL human insulin (Sigma I9278). Compounds dissolved in 10 mM stock solutions in DMSO were serially diluted 1:3 in DMSO to generate a 10-point dilution series and plated using an acoustic liquid handler system (Echo 550 Series Liquid Handler, Labcyte). A 5× intermediate compound dilution plate in MEM with 1×NEAA and 1 mM sodium pyruvate (150 μM starting compound concentration in 1.5% DMSO) was then prepared. Five μl of the intermediate serially diluted compounds were added to the cell plate to final concentrations ranging from 30 mM to 0.0015 mM in 0.3% DMSO. 0.3% DMSO alone was used to establish the maximum (MAX) signal and GDC-0032 at a final concentration of 1 μM was used as a reference compound for the minimum (MIN) signal. After 3 hours treatment, the medium was removed, and the cells lysed in 10 μL of 1× SureFire Lysis buffer with shaking for 10 minutes at room temperature. The Acceptor Mix (Reaction Buffer 1+Reaction Buffer 2+Activation Buffer+SureFire Ultra Acceptor Beads) was prepared by diluting Activation buffer 25-fold in combined Reaction Buffer 1 and Reaction Buffer 2. The Acceptor beads were diluted 50-fold in the combined Reaction Buffers. Five μL of Acceptor Mix was added to each well, the plate was sealed and covered with foil and incubated for 1 hour at room temperature. The Donor Mix (dilution buffer+SureFire Ultra Donor Beads) was prepared by diluting Donor Beads 50-fold in dilution buffer. Five μL of the Donor Mix was added to each well and the plate sealed and covered with foil and incubated for 1 hour at room temperature in the dark. The plates were read on a Neo2 plate reader instrument from Biotek using standard AlphaLisa settings. Compounds were tested in duplicate and the average % inhibition at each compound concentration was used to generate a single dose response curve. The data were processed using the Genedata-Screener tool. Relative IC50 values were determined using luminescence units by calculating percent inhibition with respect to the in-plate "MIN" (GDC-0032 reference control) and "MAX" (DMSO) controls. The data was analyzed using a 4-parameter non-linear logistic equation (four-parameter logistic concentration-response curve):

$$Y=\text{bottom}+[(\text{top}-\text{bottom})/1+(X/\text{IC50})\text{slope}]$$

where Y=% inhibition, X=concentration of inhibitor, bottom=minimum value of y attained by curve-fit, top=maximum value of y attained by curve-fit and slope=steepness of curve at the $IC_{50}$.

$$\%\ \text{Inhibition}=[(\text{signal at } X-\text{median Min})/(\text{median Max}-\text{median Min})]\times100$$

$IC_{50}$: concentration of compound that reduces a given response (ligand binding, enzyme response) by 50%. Relative $IC_{50}$: concentration giving half the compound's maximum response.

For $IC_{50}$ values shown in Table B, "A" means $IC_{50}$<50 nM; "B" means $IC_{50}$ ranging between 50 nM and 100 nM; "C" means $IC_{50}$ ranging between 100 nM and 500 nM; "D" means $IC_{50}$>500 nM.

TABLE B

PI3K-α (PIK3CA) in vitro cell based assay $IC_{50}$

| Example # | $IC_{50}$ |
|---|---|
| 1 | B |
| 3 | B |
| 4 | A |
| 7 | B |
| 8 | A |
| 9 | D |
| 18 | C |
| 19 | D |
| 22 | A |
| 24 | B |
| 25 | B |
| 26 | A |
| 27 | A |
| 32 | D |
| 33 | D |
| 34 | B |
| 35 | D |
| 37 | D |
| 40 | C |
| 49 | A |
| 51 | A |
| 52 | A |
| 54 | A |
| 55 | A |
| 58 | C |
| 59 | A |
| 60 | A |
| 61 | B |
| 63 | A |
| 64 | A |
| 65 | C |
| 68 | A |
| 70 | B |
| 71 | C |
| 74 | A |
| 75 | A |
| 82 | C |
| 86 | B |
| 88 | C |
| 90 | A |
| 91 | A |
| 93 | A |
| 95 | A |
| 97 | A |
| 108 | A |
| 109 | A |
| 110 | A |
| 111 | C |
| 113 | A |
| 115 | C |
| 116 | C |
| 117 | D |
| 120 | A |
| 125 | A |
| 126 | A |
| 128 | A |
| 132 | A |
| 139 | A |
| 144 | A |
| 145 | C |
| 149 | A |
| 150 | A |
| 151 | A |
| 153 | A |
| 156 | D |
| 158 | A |
| 160 | B |
| 163 | B |
| 168 | B |
| 169 | B |
| 170 | A |

TABLE B-continued

| PI3K-α (PIK3CA) in vitro cell based assay $IC_{50}$ | |
|---|---|
| Example # | $IC_{50}$ |
| 171 | D |
| 178 | B |
| 187 | A |
| 188 | A |
| 189 | B |
| 190 | B |
| 191 | C |
| 192 | D |
| 193 | A |
| 195 | A |
| 196 | A |
| 197 | A |
| 198 | B |
| 203 | A |
| 204 | B |
| 205 | B |
| 207 | B |
| 209 | A |
| 210 | A |
| 211 | B |
| 214 | A |
| 215 | A |
| 216 | D |
| 217 | D |
| 218 | A |
| 219 | D |
| 220 | A |
| 221 | D |
| 222 | C |
| 223 | A |
| 224 | A |
| 225 | C |
| 226 | C |
| 227 | A |
| 228 | C |
| 229 | C |
| 230 | B |
| 231 | C |
| 232 | C |
| 233 | C |
| 234 | C |
| 235 | B |
| 236 | A |
| 237 | B |
| 238 | A |
| 239 | C |
| 240 | B |
| 241 | B |
| 242 | A |
| 243 | C |
| 244 | A |
| 245 | A |
| 246 | A |
| 247 | A |
| 248 | C |
| 249 | B |
| 250 | C |
| 251 | B |
| 252 | A |
| 253 | A |
| 254 | A |
| 255 | B |
| 256 | A |
| 257 | A |
| 258 | A |
| 259 | B |
| 260 | A |
| 261 | A |
| 262 | A |
| 263 | A |
| 264 | A |
| 265 | B |

The invention claimed is:

1. A compound of the Formula:

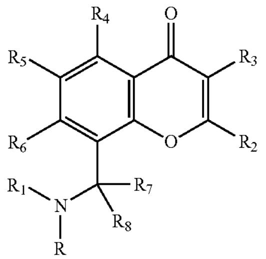

or pharmaceutically acceptable salt thereof, wherein:

R is —H or $C_1$-$C_3$ alkyl;

$R_1$ is a group of the formula:

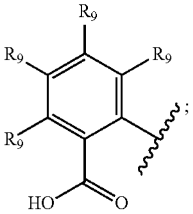
;
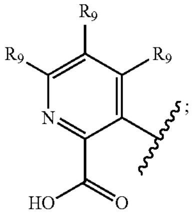
;
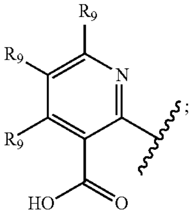
;
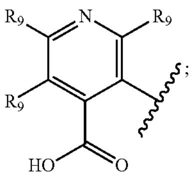
;
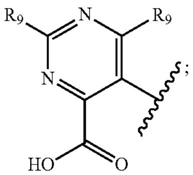
;
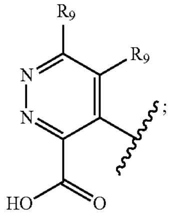
; or
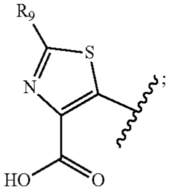
;

$R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine, or an optionally substituted bicyclic heteroaryl of 8 to 10 ring atoms containing 1, 2, 3, 4, or 5 ring heteroatoms independently selected from N, O, or S; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$CONR_{10}R_{10}$, —$NR_{10}R_{10}$, —$NR_{10}CO_2R_{10}$, an optionally substituted $C_1$-$C_6$ alkyl, an optionally substituted $C_2$-$C_6$ alkenyl, an optionally substituted $C_2$-$C_6$ alkynyl, an optionally substituted $C_3$-$C_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyridine, pyrimidine, pyridazine, pyrazine, pyrazole, isoxazole, isothiazole, imidazole, oxazole, or thiazole; wherein the optionally substituted $C_1$-$C_6$ alkyl, $C_2$-$C_6$ alkenyl, or $C_2$-$C_6$ alkynyl is each optionally substituted with a —CN, —OH, oxetanyl, or $C_1$-$C_3$ alkoxy; the optionally substituted $C_3$-$C_5$ cycloalkyl, phenyl, 1,3-benzodioxole, 2,3-dihydro-1,4-benzodioxine, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$SO_2R_{10}$, —$NR_{10}R_{10}$, —OH or —CN;

$R_3$ is —H, halogen, —CN, $C_1$-$C_6$ alkyl $C_1$-$C_6$ haloalkyl, $C_3$-$C_5$ cycloalkyl, a heterocycle of 3 to 5 ring atoms containing 1, 2, or 3 ring heteroatoms independently selected from N, O, or S, or a heteroaryl of 5 ring atoms containing 1, 2, or 3 ring heteroatoms independently selected from N, O, or S;

each of $R_4$, $R_5$ and $R_6$ is independently —H, halogen, $C_1$-$C_6$ alkyl or $C_1$-$C_6$ haloalkyl;

$R_7$ is —CN, $C_1$-$C_6$ alkyl or $C_1$-$C_6$ haloalkyl;

$R_8$ is —H or $C_1$-$C_6$ alkyl;

each $R_9$ is independently —H, halogen, $C_1$-$C_6$ alkyl, $C_1$-$C_6$ haloalkyl, $C_1$-$C_6$ alkoxy, or $C_3$-$C_5$ cycloalkyl; and each $R_{10}$ is independently —H or $C_1$-$C_3$ alkyl.

2. The compound of claim 1, or pharmaceutically acceptable salt thereof, having the Formula:

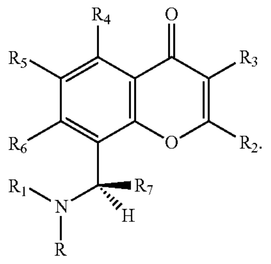

3. The compound of claim 1, or pharmaceutically acceptable salt thereof, having the Formula:

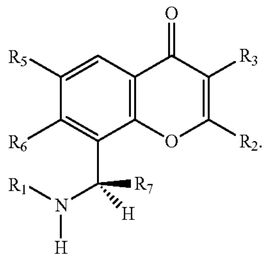

4. The compound of claim 1, or pharmaceutically acceptable salt thereof, wherein R is —H.

5. The compound of claim 1, or pharmaceutically acceptable salt thereof, wherein $R_1$ is a group of the formula:

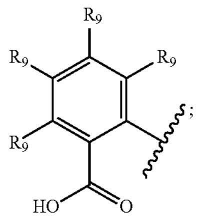
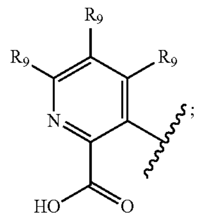
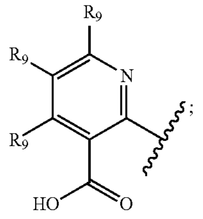
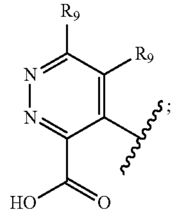
or
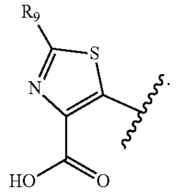

6. The compound of claim 1, or pharmaceutically acceptable salt thereof, wherein $R_1$ is a group of the formula

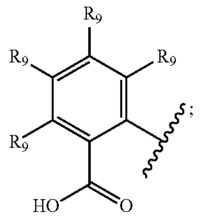
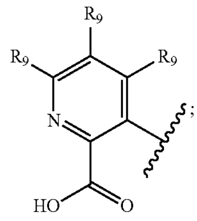
or
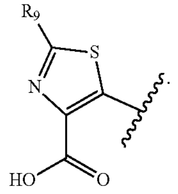

7. The compound of claim 1, or pharmaceutically acceptable salt thereof, wherein $R_1$ is a group of the formula

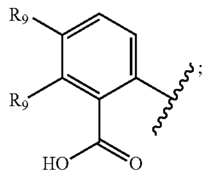
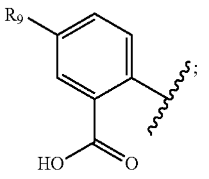

-continued

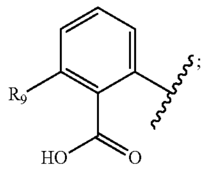
;
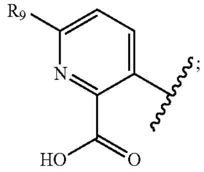
;
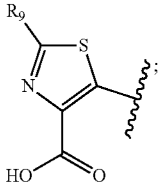
; or
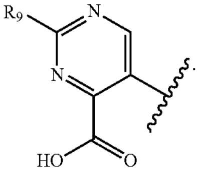
.

8. The compound of claim 1, or pharmaceutically acceptable salt thereof, wherein each $R_9$ is independently —H, halogen, $C_1$-$C_3$ alkyl, $C_1$-$C_3$haloalkyl, $C_1$-$C_3$ alkoxy, or $C_3$-$C_5$ cycloalkyl.

9. The compound of claim 1, or pharmaceutically acceptable salt thereof, wherein each $R_9$ is independently —H, halogen, $C_1$-$C_3$ alkyl, $C_1$-$C_3$haloalkyl, or $C_3$-$C_5$ cycloalkyl.

10. The compound of claim 1, or pharmaceutically acceptable salt thereof, wherein each $R_9$ is independently —H, halogen, $C_1$-$C_3$ alkyl or $C_1$-$C_3$haloalkyl.

11. The compound of claim 1, or pharmaceutically acceptable salt thereof, wherein $R_1$ is a group of the formula

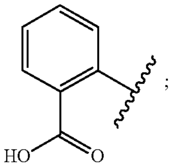
;
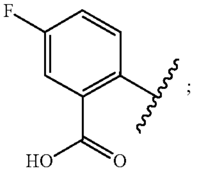
;
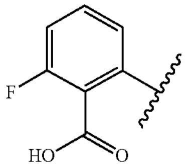
;
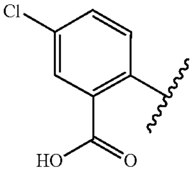
;
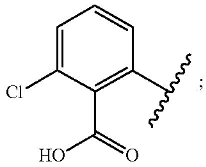
;
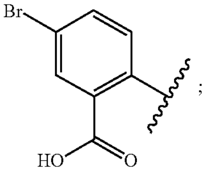
;
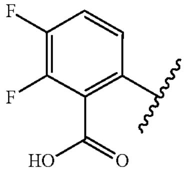
;
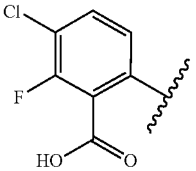
;
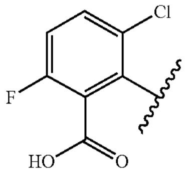
;
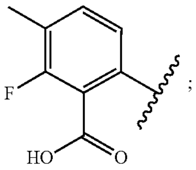
;

-continued

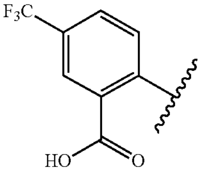
;
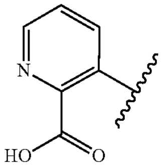
;
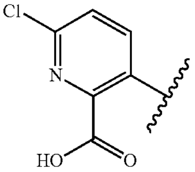
;
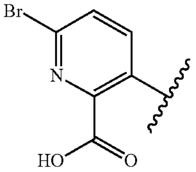
;
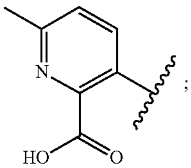
;
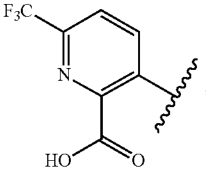
;
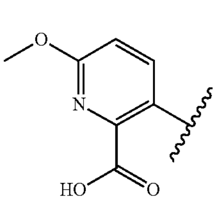
;
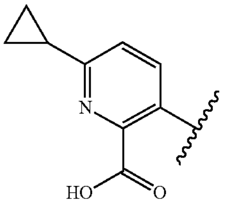
;
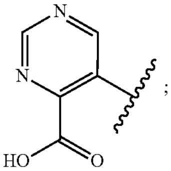
; or
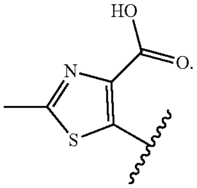
.

12. The compound of claim 1, or pharmaceutically acceptable salt thereof, wherein $R_1$ is a group of the formula

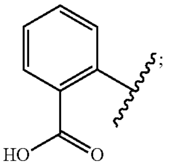
;
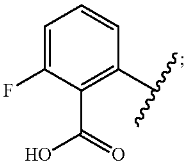
;
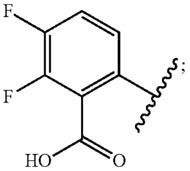
;
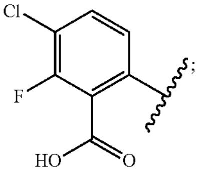
;
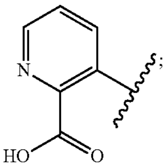
;
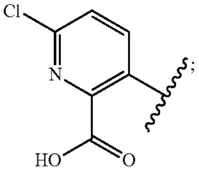
; or -continued

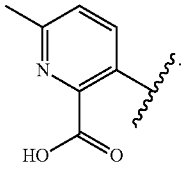

13. The compound of claim 1, or pharmaceutically acceptable salt thereof, wherein $R_2$ is an optionally substituted bicyclic ring selected from 1,3-benzodioxole, 2,3-dihydro-1,4-benzodioxine, isoindolin-1-one, indolin-2-one, or benzo[d]oxazol-2(3H)-one, or an optionally substituted bicyclic heteroaryl of 8 to 10 ring atoms containing 1, 2, 3, 4, or 5 ring heteroatoms independently selected from N, O, or S; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$CONR_{10}R_{10}$, —$NR_{10}R_{10}$, —$NR_{10}CO_2R_{10}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

14. The compound of claim 1, or pharmaceutically acceptable salt thereof, wherein $R_2$ is an optionally substituted bicyclic heteroaryl and the optionally substituted bicyclic heteroaryl is a phenyl, pyridine, pyrazine, pyrimidine, or pyridazine ring fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$CONR_{10}R_{10}$, —$NR_{10}R_{10}$, —$NR_{10}CO_2R_{10}$, an optionally substituted $C_1$-$C_6$ alkyl, an optionally substituted $C_2$-$C_6$ alkenyl, an optionally substituted $C_2$-$C_6$ alkynyl, an optionally substituted $C_3$-$C_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyridine, pyrimidine, pyridazine, pyrazine, pyrazole, isoxazole, isothiazole, imidazole, oxazole, or thiazole; wherein the optionally substituted $C_1$-$C_6$ alkyl, $C_2$-$C_6$ alkenyl, or $C_2$-$C_6$ alkynyl is each optionally substituted with a —CN, —OH, oxetanyl, or $C_1$-$C_3$ alkoxy; the optionally substituted $C_3$-$C_5$ cycloalkyl, phenyl, 1,3-benzodioxole, 2,3-dihydro-1,4-benzodioxine, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$SO_2R_{10}$, —$NR_{10}R_{10}$, —OH or —CN.

15. The compound of claim 1, or pharmaceutically acceptable salt thereof, wherein $R_2$ is an optionally substituted bicyclic ring selected from 1,3-benzodioxole, 2,3-dihydro-1,4-benzodioxine, isoindolin-1-one, indolin-2-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

16. The compound of claim 1, or pharmaceutically acceptable salt thereof, wherein $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

17. The compound of claim 1, or pharmaceutically acceptable salt thereof, wherein $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine, or an optionally substituted bicyclic heteroaryl selected from indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, quinazoline, or naphthyridine; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, —$SO_2R_{10}$, —$CONR_{10}R_{10}$, —$NR_{10}R_{10}$, —$NR_{10}CO_2R_{10}$, an optionally substituted $C_1$-$C_6$ alkyl, an optionally substituted $C_2$-$C_6$ alkenyl, an optionally substituted $C_2$-$C_6$ alkynyl, an optionally substituted $C_3$-$C_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyridine, pyrimidine, pyridazine, pyrazine, pyrazole, isoxazole, isothiazole, imidazole, oxazole, or thiazole; wherein the optionally substituted $C_1$-$C_6$ alkyl, $C_2$-$C_6$ alkenyl, or $C_2$-$C_6$ alkynyl is each optionally substituted with a —CN, —OH, oxetanyl, or $C_1$-$C_3$ alkoxy; the optionally substituted $C_3$-$C_5$ cycloalkyl, phenyl, 1,3-benzodioxole, 2,3-dihydro-1,4-benzodioxine, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$SO_2R_{10}$, —$NR_{10}R_{10}$, —OH or —CN.

18. The compound of claim 1, or pharmaceutically acceptable salt thereof, wherein $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine, or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, or quinazoline; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

19. The compound of claim 1, or pharmaceutically acceptable salt thereof, wherein $R_2$ is an optionally substituted bicyclic ring selected from 1,3-benzodioxole, 2,3-dihydro-1,4-benzodioxine, isoindolin-1-one, indolin-2-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, or benzoxazole; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

20. The compound of claim 1, or pharmaceutically acceptable salt thereof, wherein $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl selected from indole, indazole, pyrrolopyridine, furopyridine, pyrazolopyridine, imidazopyridine, pyrazolopyrimidine, imidazopyridazine, or phthalazine; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, —$NR_{10}R_{10}$, —OH or —CN.

21. The compound of claim 1, or pharmaceutically acceptable salt thereof, wherein $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine, or an optionally substituted bicyclic heteroaryl selected from indole, indazole, pyrrolopyridine, furopyridine, pyrazolopyridine, imidazopyridine, pyrazolopyrimidine, imidazopyridazine, phthalazine, triazolopyridine, benzimidazole, pyrrolopyrimidine, thiazolopyridine, benzotriazole, benzoxazole, benzothiazole, pyrrolopyrazine, quinazoline, or naphthyridine; wherein the optionally substituted bicyclic ring is optionally substituted with one to three substituents each independently selected from halogen and $C_1$-$C_6$ alkyl; and the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ alkyl optionally substituted with —OH or oxetanyl, or a heteroaryl selected from a pyridine or oxazole.

22. The compound of claim 1, or pharmaceutically acceptable salt thereof, wherein $R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine, or an optionally substituted bicyclic heteroaryl selected from indole, indazole, pyrrolo[2,3-b]pyridine, pyrrolo[3,2-b]pyridine, furo[2,3-c]pyridine, furo[3,2-c]pyridine, pyrazolo[1,5-a]pyridine, pyrazolo[3,4-b]pyridine, pyrazolo[3,4-c]pyridine, pyrazolo[4,3-b]pyridine, imidazo[1,2-a]pyridine, imidazo[1,5-a]pyridine, pyrazolo[1,5-a]pyrimidine, imidazo[1,2-b]pyridazine, phthalazine, [1,2,4]triazolo[4,3-a]pyridine, triazolo[1,5-a]pyridine, benzimidazole, pyrrolo[2,3-d]pyrimidine, thiazolo[5,4-b]pyridine, benzotriazole, 1,3-benzoxazole, 1,3-benzothiazole, pyrrolo[1,2-a]pyrazine, quinazoline, or 1,7-naphthyridine; wherein the optionally substituted bicyclic ring is optionally substituted with one to three substituents each independently selected from halogen and $C_1$-$C_6$ alkyl; and the optionally substituted bicyclic heteroaryl is optionally substituted with one to three substituents each independently selected from —CN, halogen, $C_1$-$C_6$ haloalkyl, $C_1$-$C_6$ alkoxy, $C_1$-$C_6$ alkyl optionally substituted with —OH or oxetanyl, or a heteroaryl selected from a pyridine or oxazole.

23. The compound of claim 1, or pharmaceutically acceptable salt thereof, wherein $R_2$ is a group of the formula:

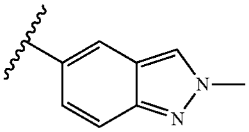 ;

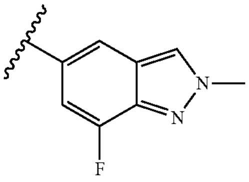 ;

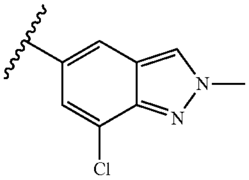 ;

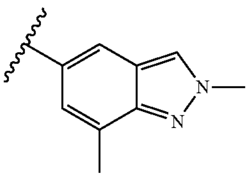 ;

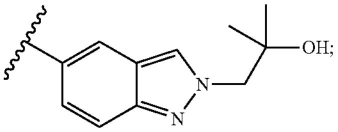

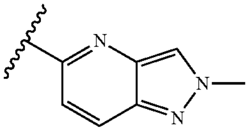 ;

-continued

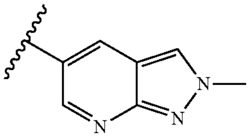 ;

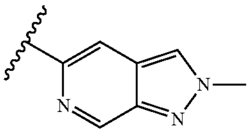 ;

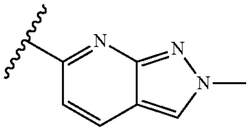 ;

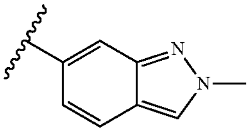 ;

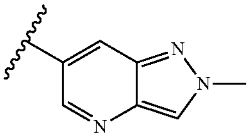 ;

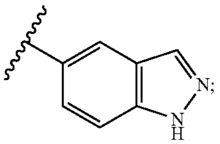 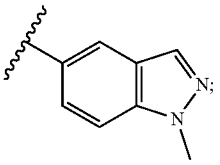

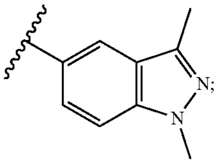 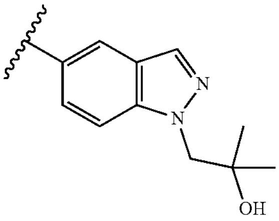 ;

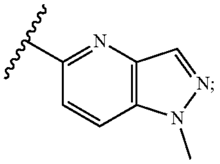 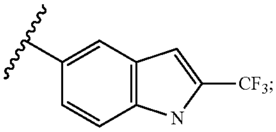

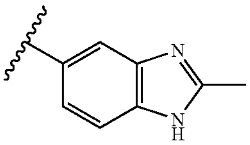 ; 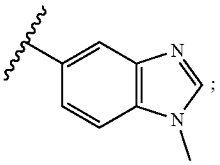

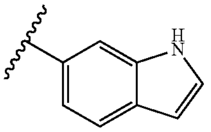 ; 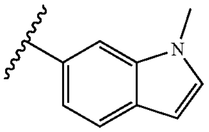 ;

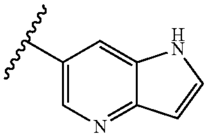 ; 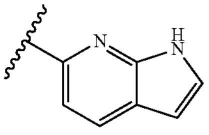 ;

-continued
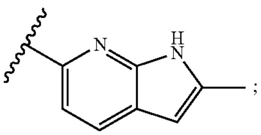
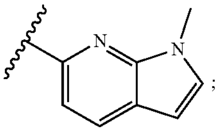
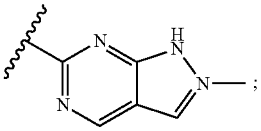
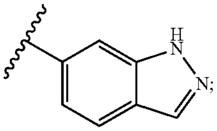
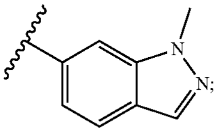
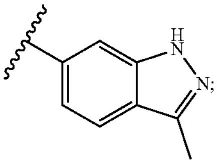
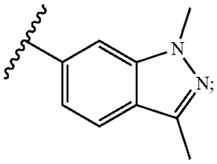
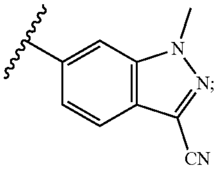
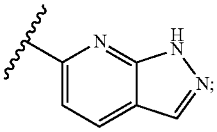
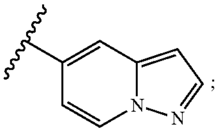
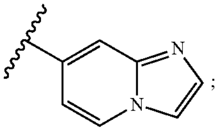
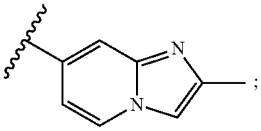
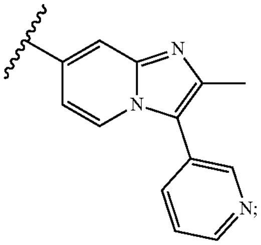
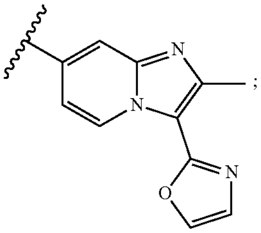
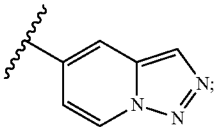
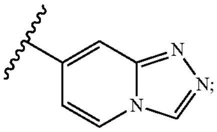
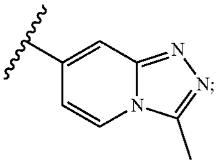
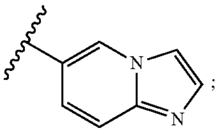
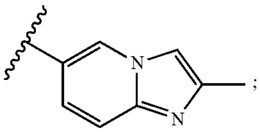
-continued
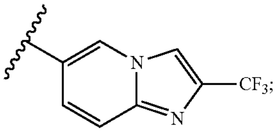
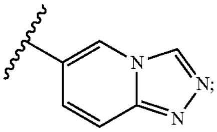
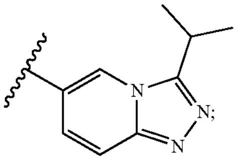
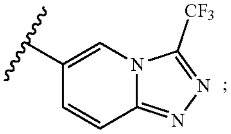
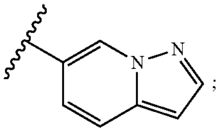
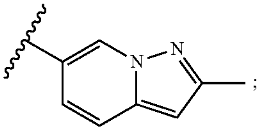
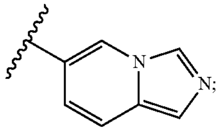
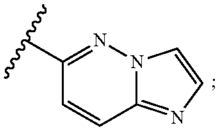
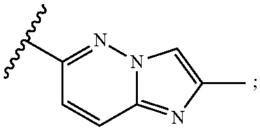
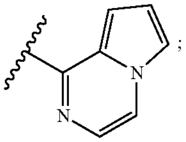
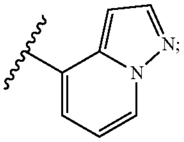
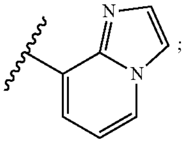
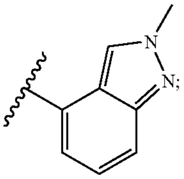
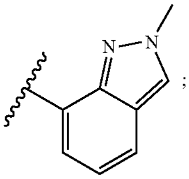
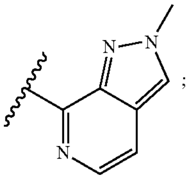
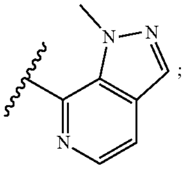
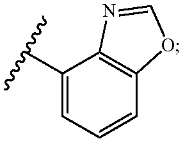
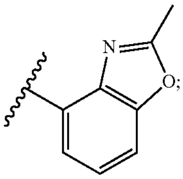
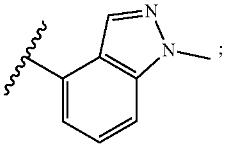

-continued
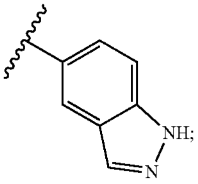
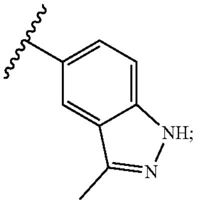
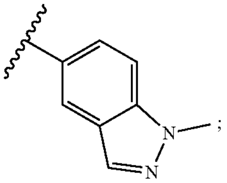
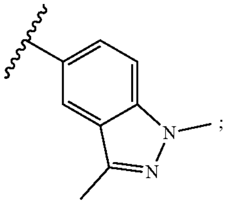
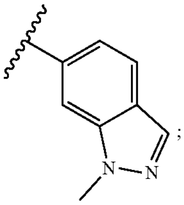
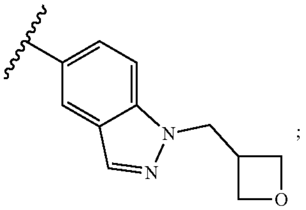
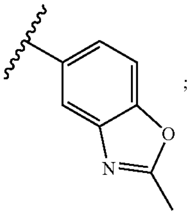
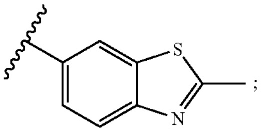
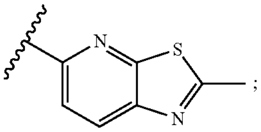
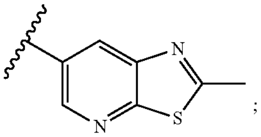
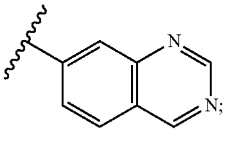
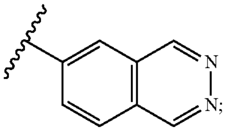
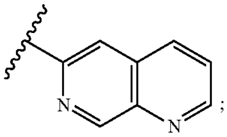
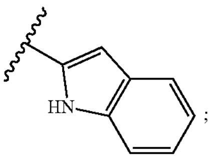
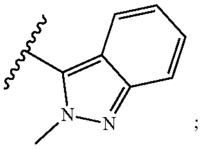
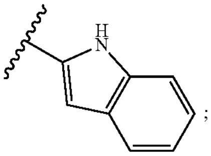
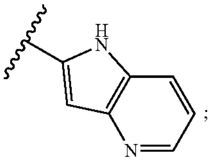
-continued
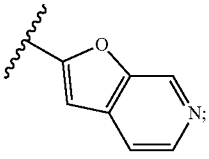
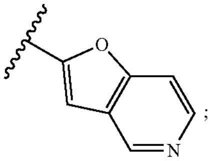
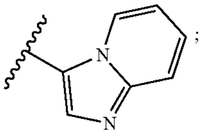
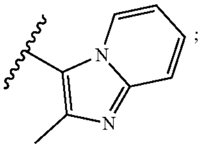
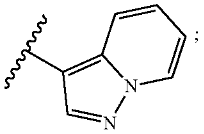
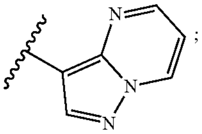
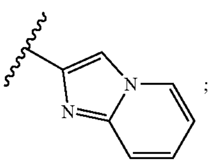
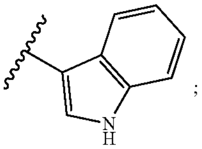
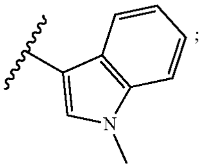
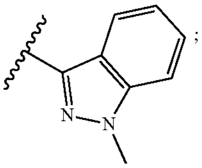
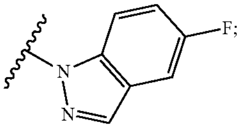
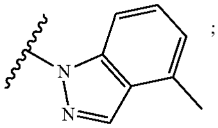
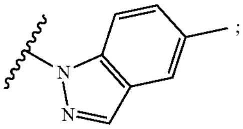
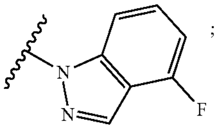
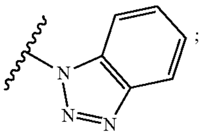
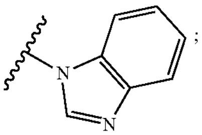
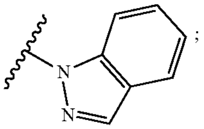
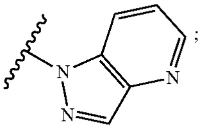
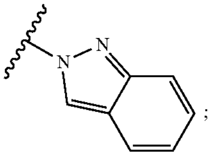
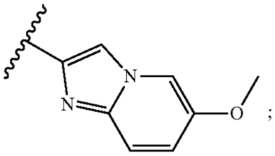
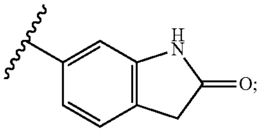
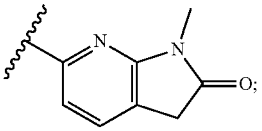

-continued
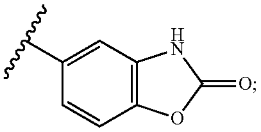
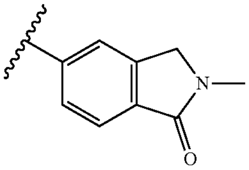
;
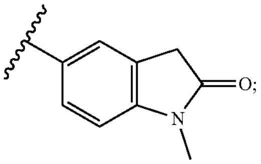
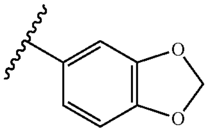
;
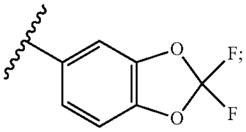
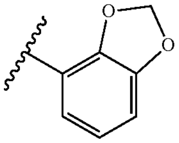
;
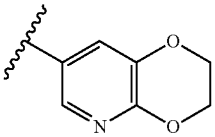
;
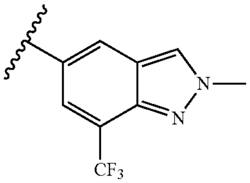
;
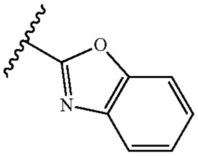
;
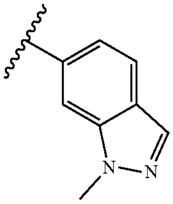
;
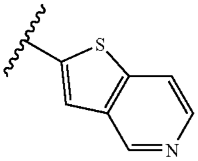
;
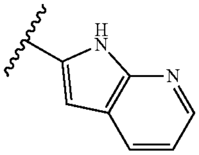
;
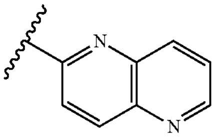
;
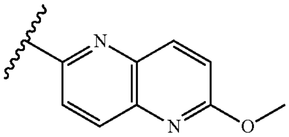
;
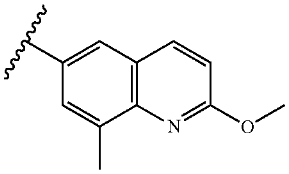
;
-continued
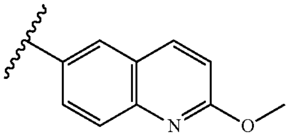
;
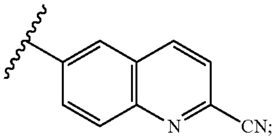
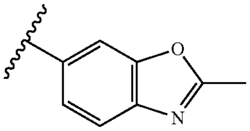
; or
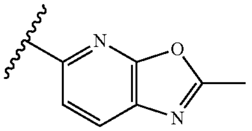
.
24. The compound of claim 1, or pharmaceutically acceptable salt thereof, wherein $R_2$ is a group of the formula:
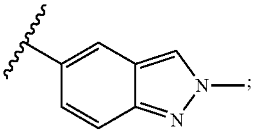
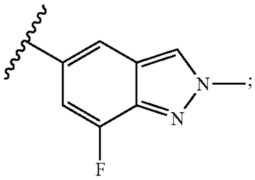
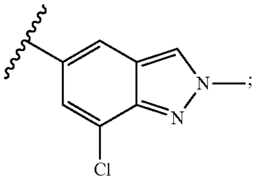
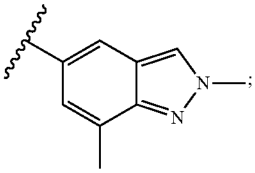
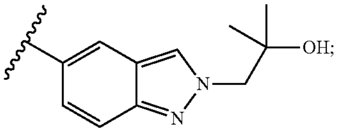
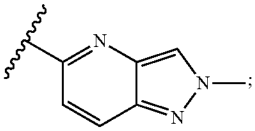

-continued
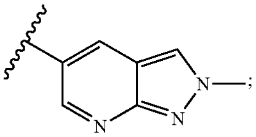
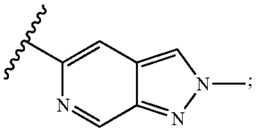
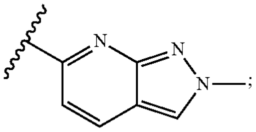
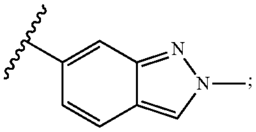
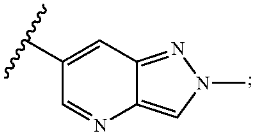
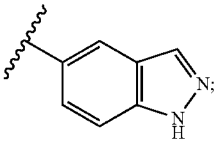
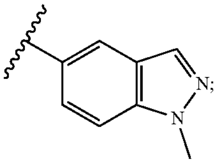
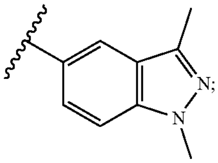
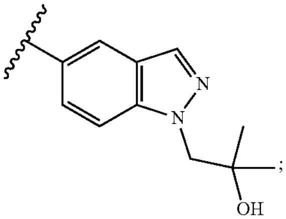
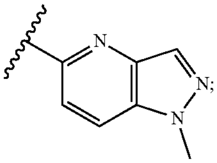
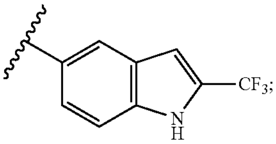
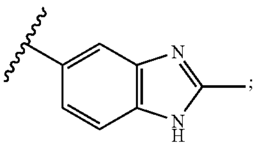
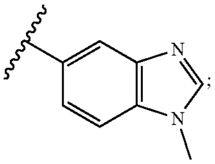
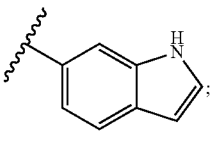
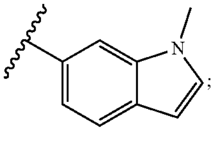
-continued
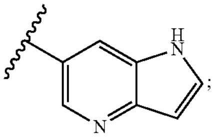
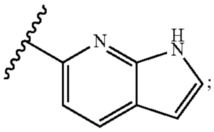
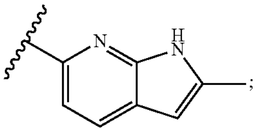
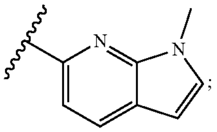
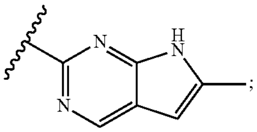
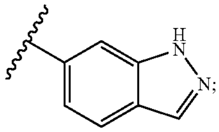
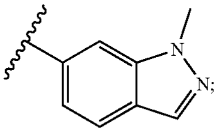
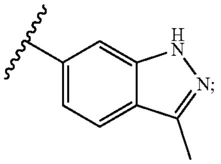
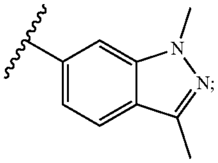
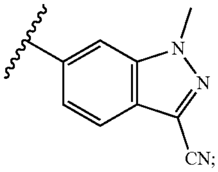
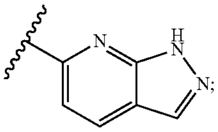
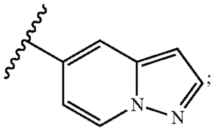
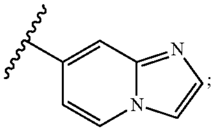
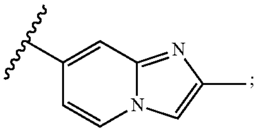
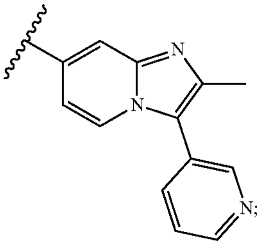
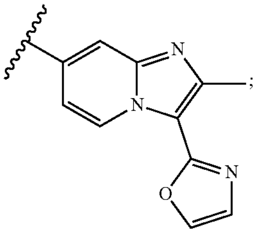
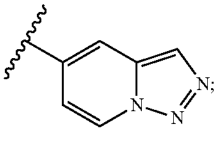
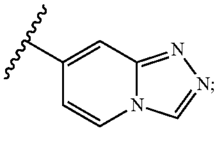

-continued
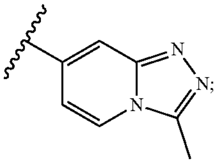
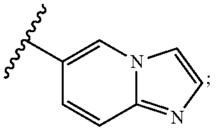
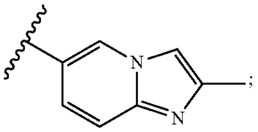
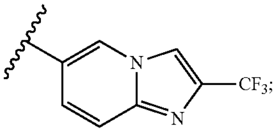
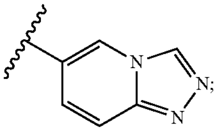
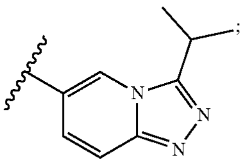
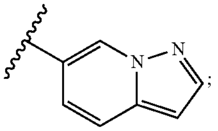
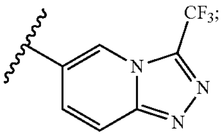
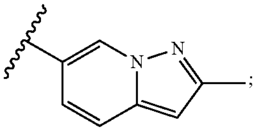
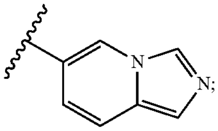
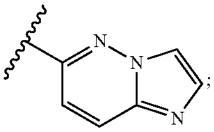
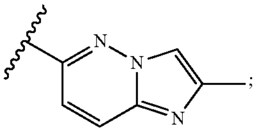
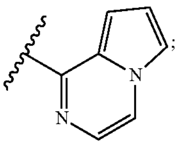
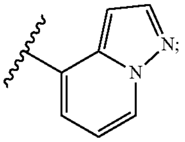
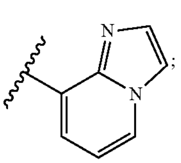
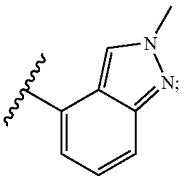
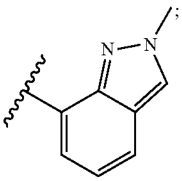
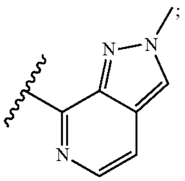
-continued
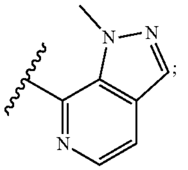
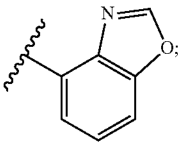
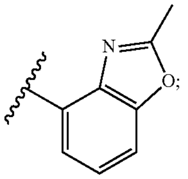
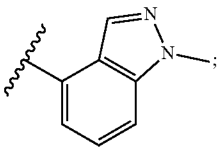
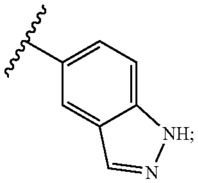
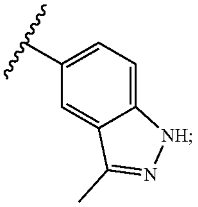
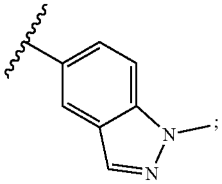
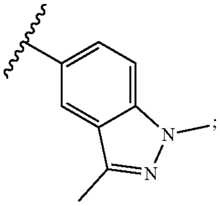
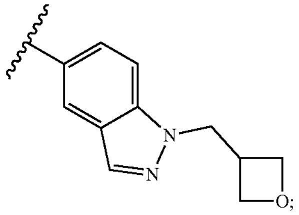
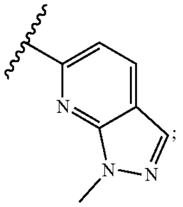
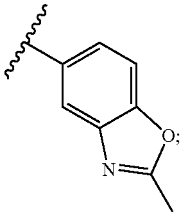
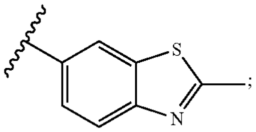
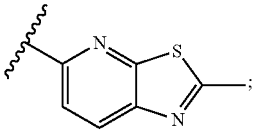
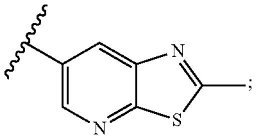
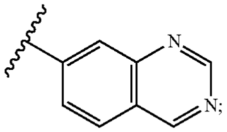
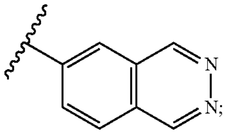
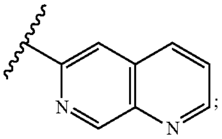

-continued
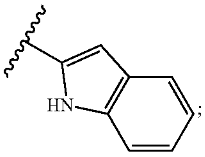;
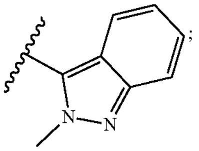;
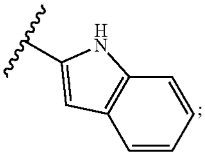;
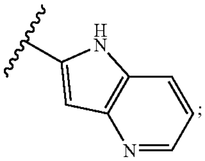;
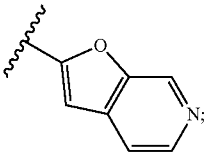;
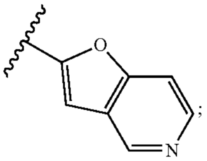;
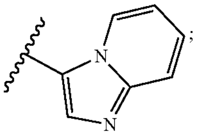;
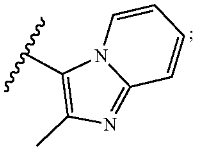;
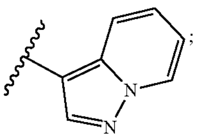;
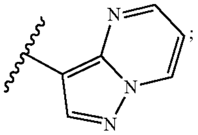;
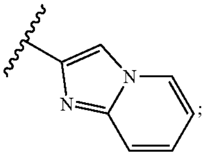;
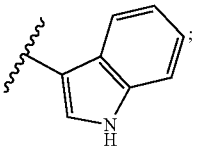;
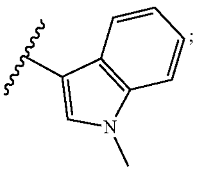;
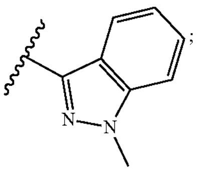;
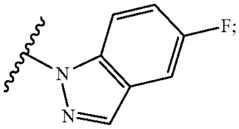;
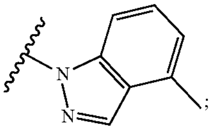;
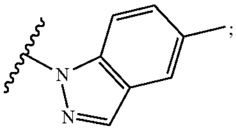;
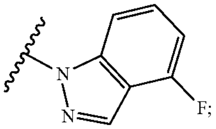;
-continued
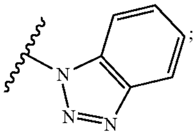;
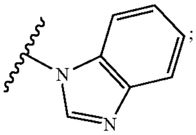;
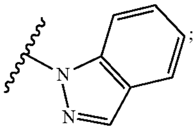;
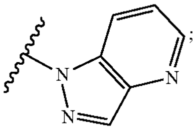;
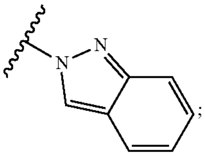;
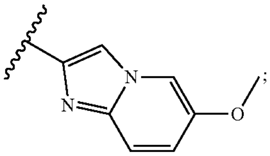;
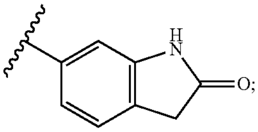;
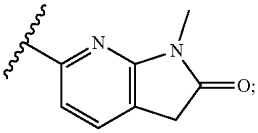;
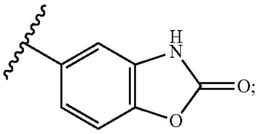;
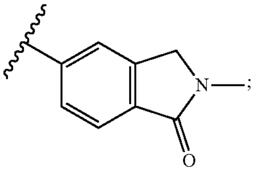;
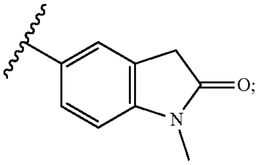;
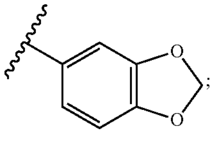;
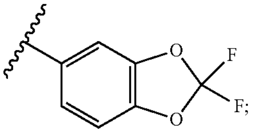;
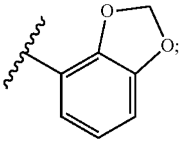; or
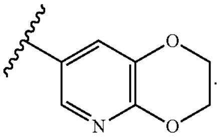.
25. The compound of claim 1, or pharmaceutically acceptable salt thereof, wherein $R_3$ is —H, —CN, $C_1$-$C_6$ alkyl, or $C_1$-$C_6$ haloalkyl.
26. The compound of claim 1, or pharmaceutically acceptable salt thereof, wherein $R_3$ is —H, —CN, $C_1$-$C_3$ alkyl, or $C_1$-$C_3$ haloalkyl.

27. The compound of claim 1, or pharmaceutically acceptable salt thereof, wherein $R_3$ is —H, —CN or $C_1$-$C_3$ alkyl.

28. The compound of claim 1, or pharmaceutically acceptable salt thereof, wherein $R_3$ is —H, methyl, or trifluoromethyl.

29. The compound of claim 1, or pharmaceutically acceptable salt thereof, wherein $R_3$ is —H or methyl.

30. The compound of claim 1, or pharmaceutically acceptable salt thereof, wherein $R_4$ is —H or halogen.

31. The compound of claim 1, or pharmaceutically acceptable salt thereof, wherein $R_4$ is —H.

32. The compound of claim 1, or pharmaceutically acceptable salt thereof, wherein $R_5$ is —H, halogen, $C_1$-$C_3$ alkyl or $C_1$-$C_3$ haloalkyl.

33. The compound of claim 1, or pharmaceutically acceptable salt thereof, wherein $R_6$ is —H or halogen.

34. The compound of claim 1, or pharmaceutically acceptable salt thereof, wherein $R_7$ is —CN, $C_1$-$C_3$ alkyl or $C_1$-$C_3$ haloalkyl.

35. The compound of claim 1, or pharmaceutically acceptable salt thereof, wherein $R_7$ is —CN, methyl or trifluoromethyl.

36. The compound of claim 1, or pharmaceutically acceptable salt thereof, wherein $R_7$ is methyl.

37. The compound of claim 1, or pharmaceutically acceptable salt thereof, wherein $R_8$ is —H.

38. The compound of claim 1, selected from the group consisting of:

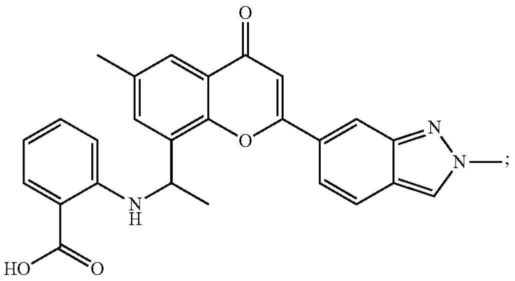

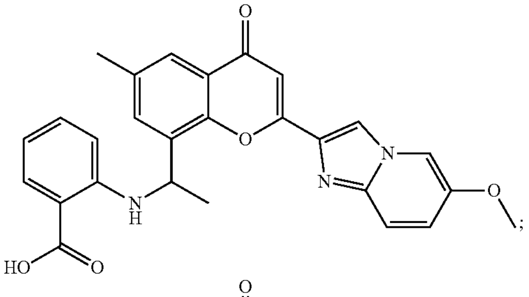

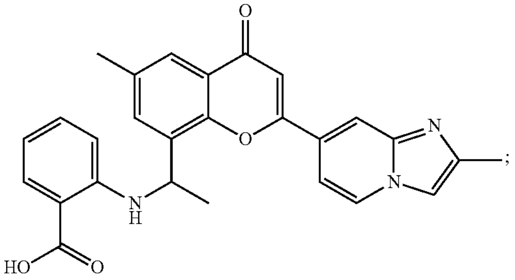

-continued

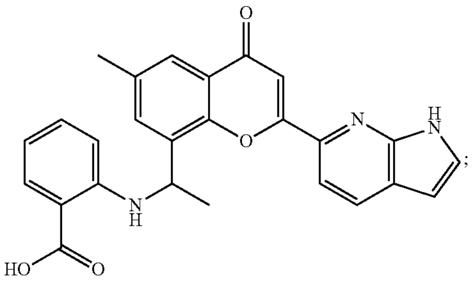

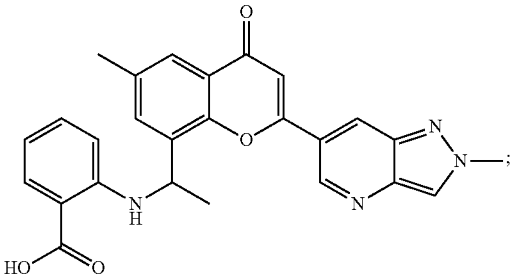

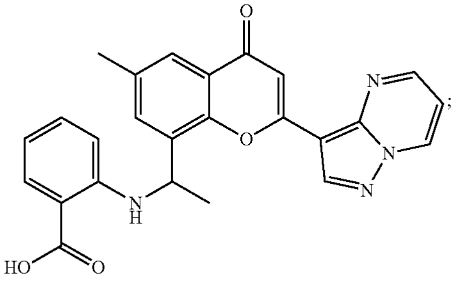

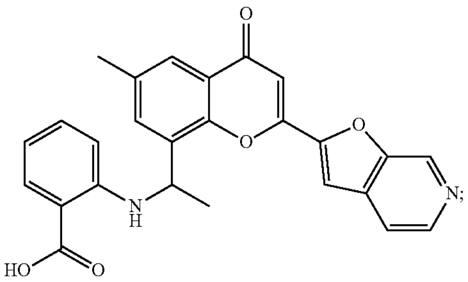

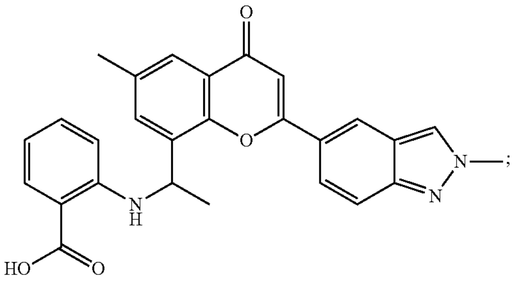

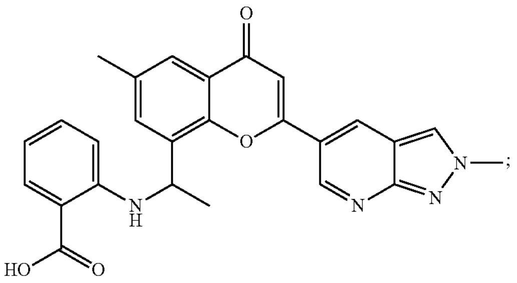

-continued
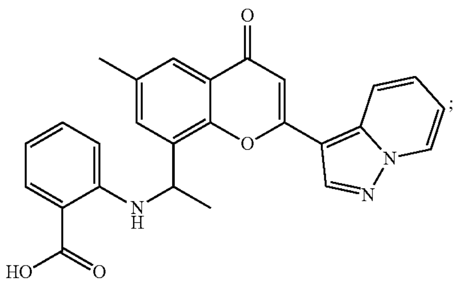
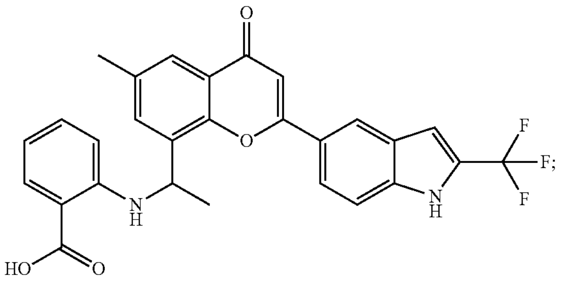
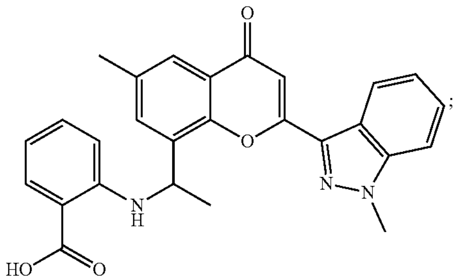
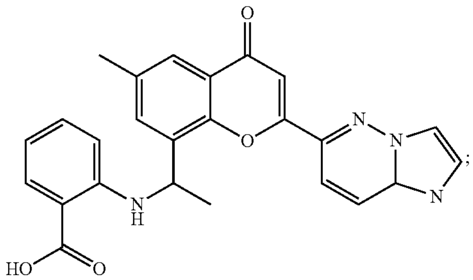
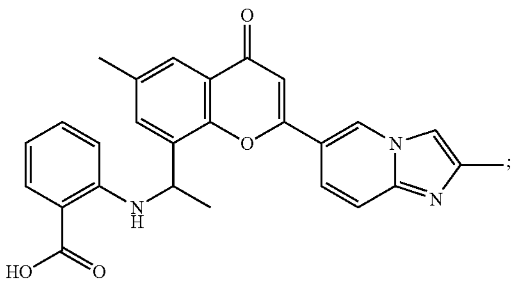
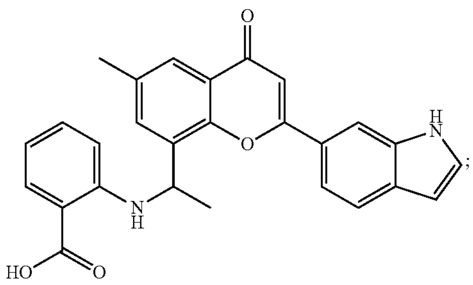
-continued
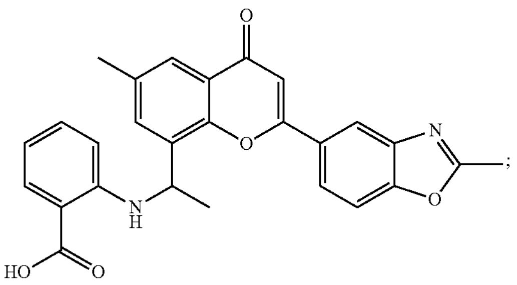
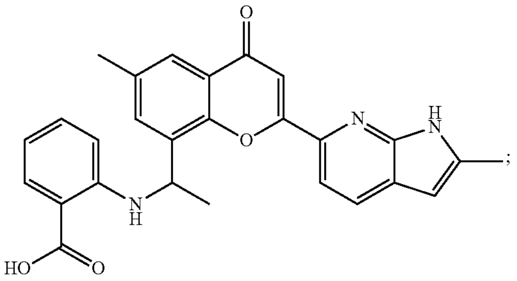
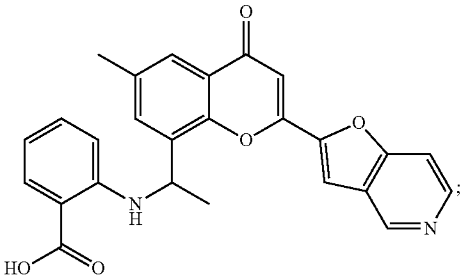
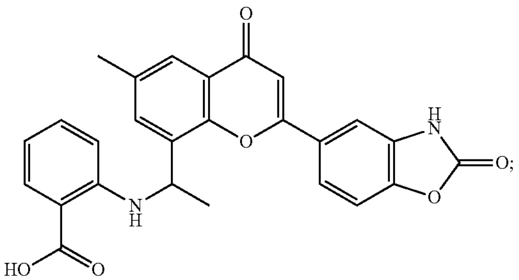
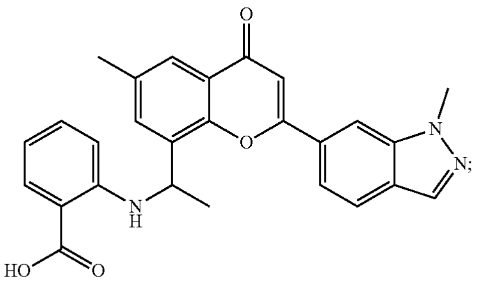
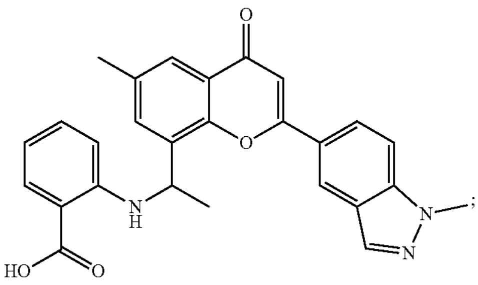

-continued
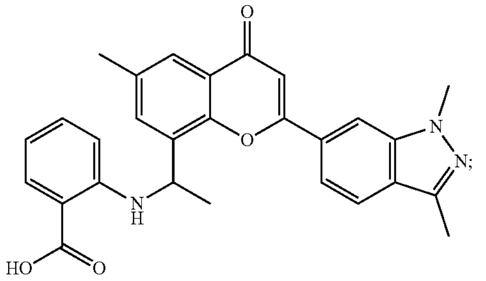
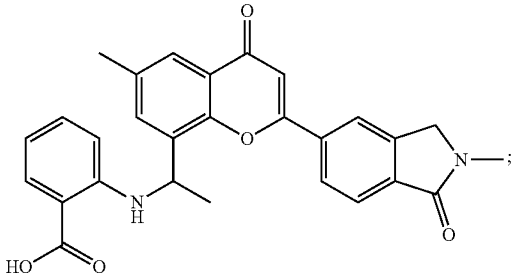
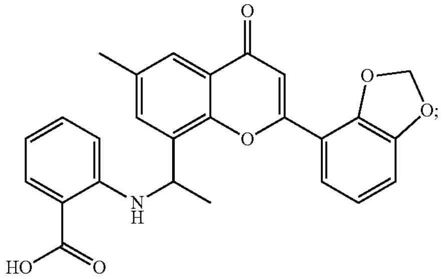
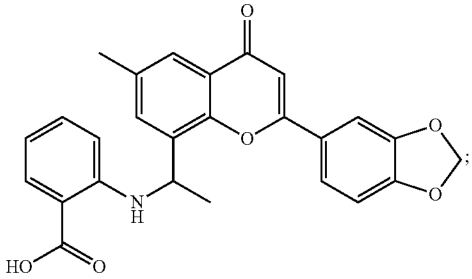
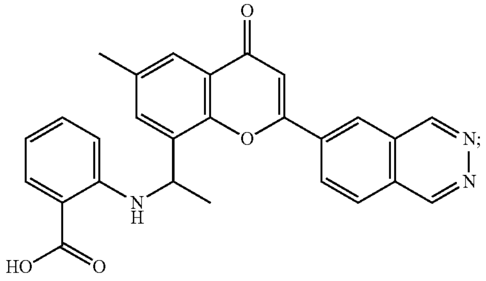
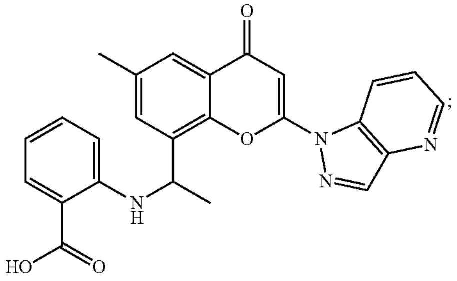
-continued
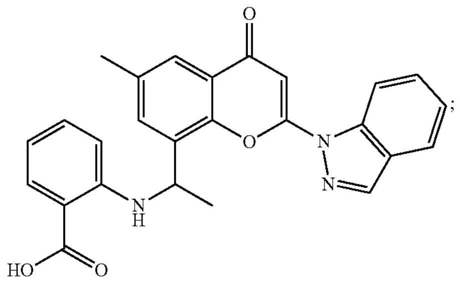
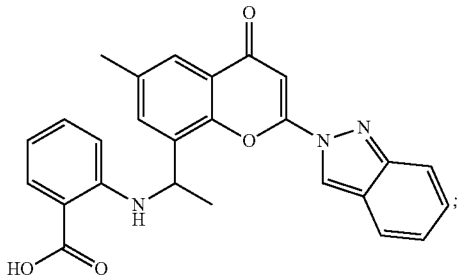
and
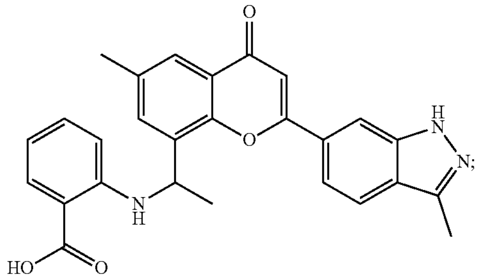
or a pharmaceutically acceptable salt thereof.
39. The compound of claim 1, selected from the group consisting of:
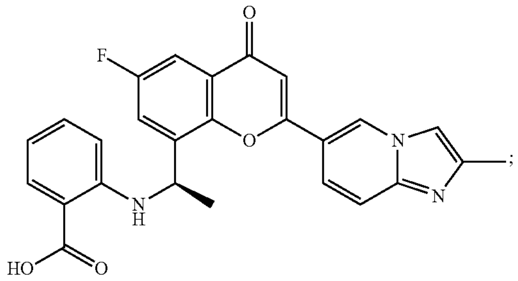
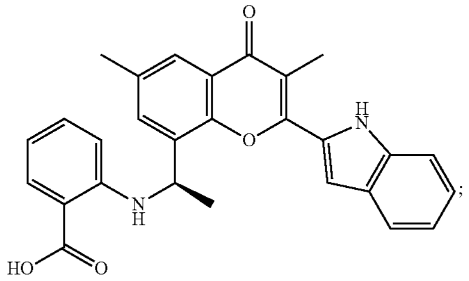

-continued
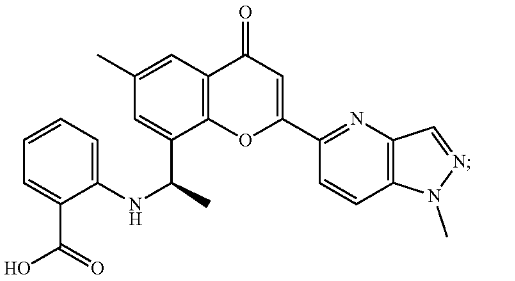
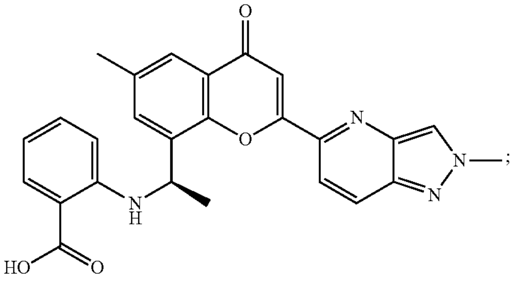
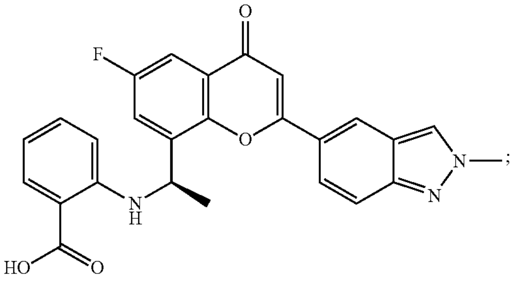
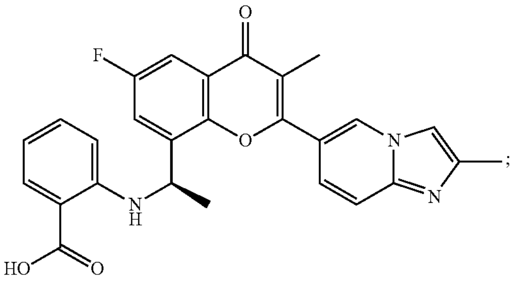
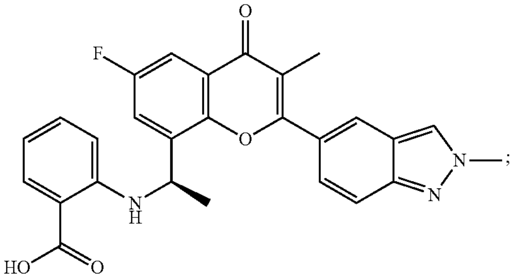
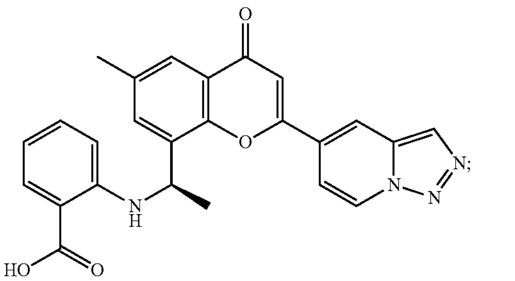
-continued
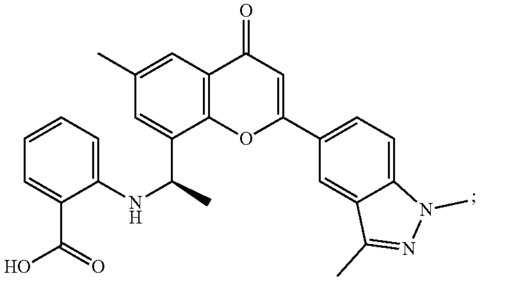
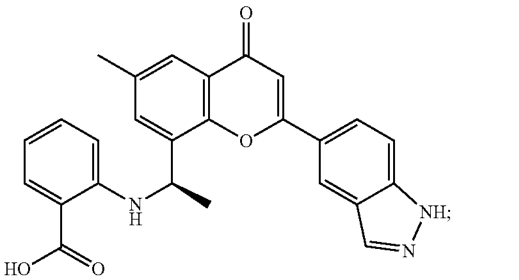
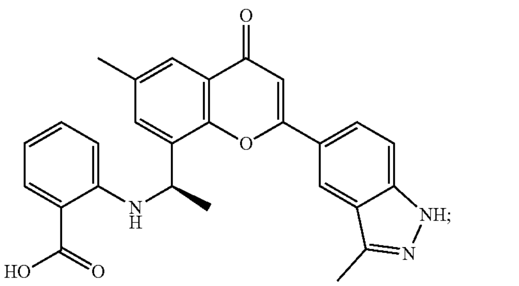
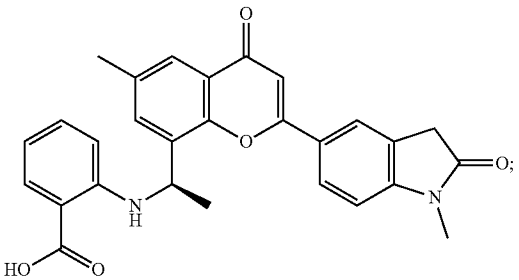
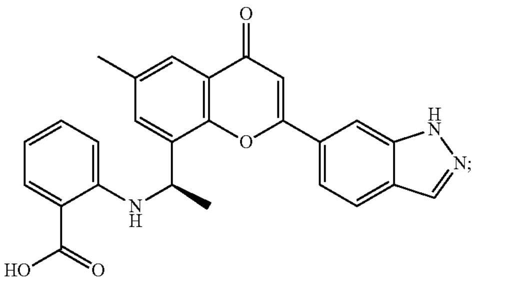
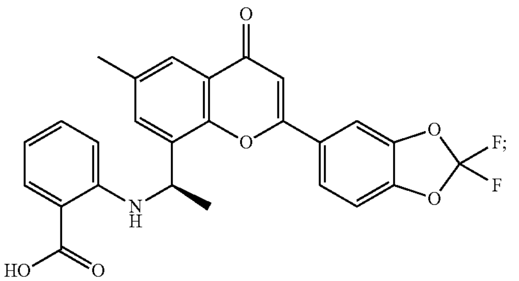

-continued
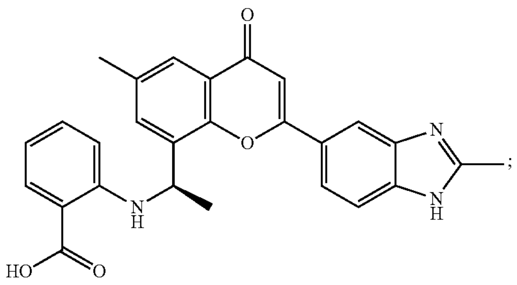
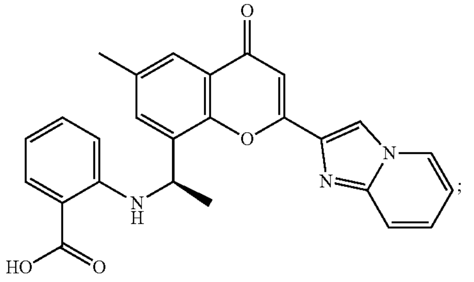
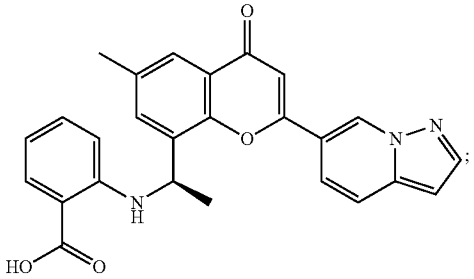
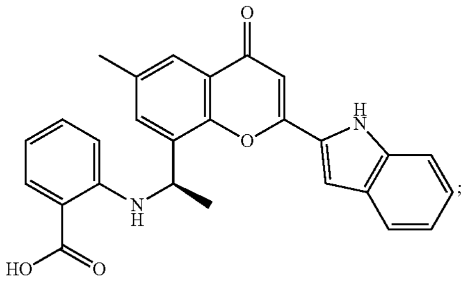
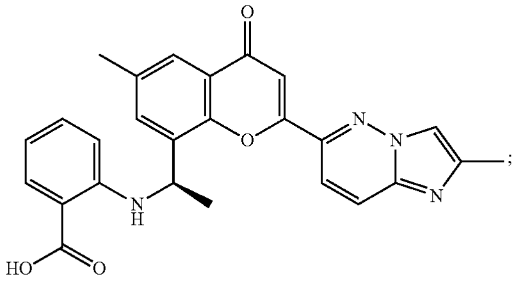
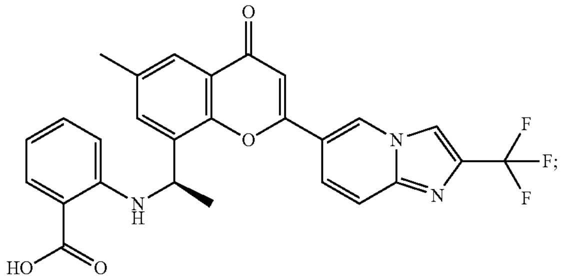
-continued
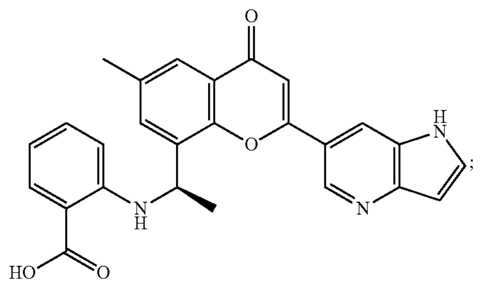
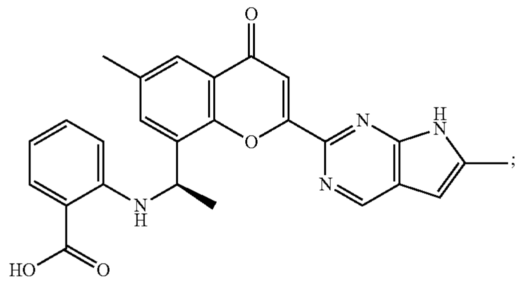
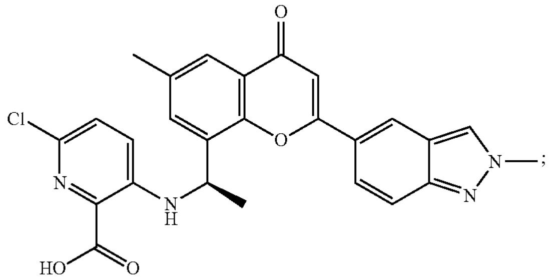
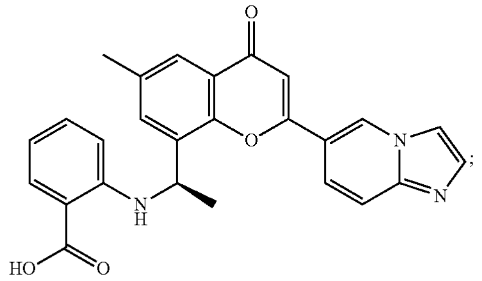
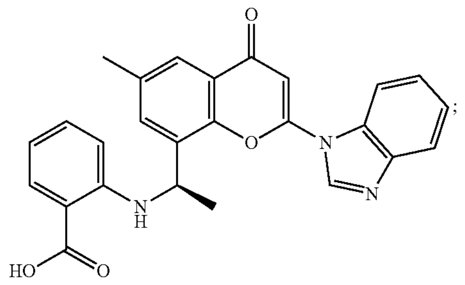
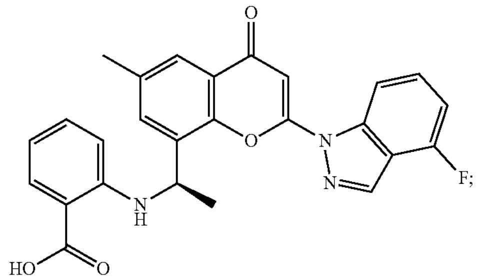

-continued
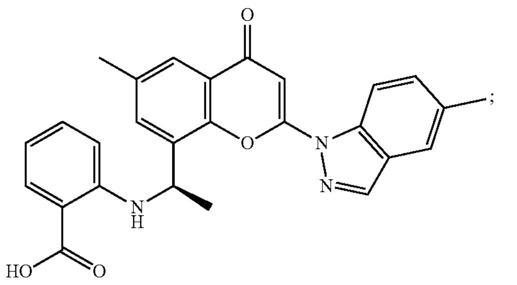
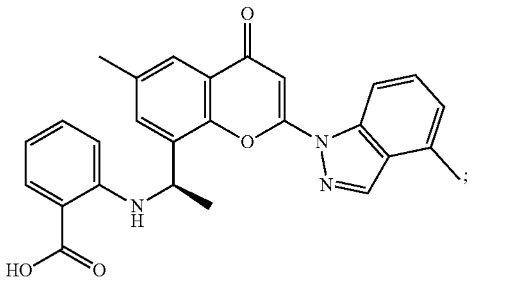
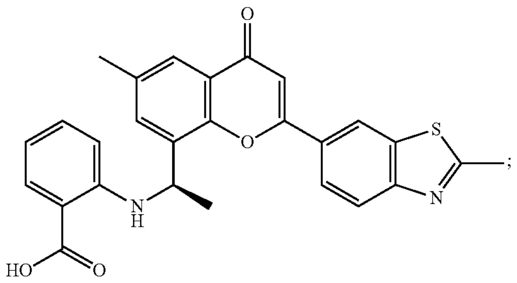
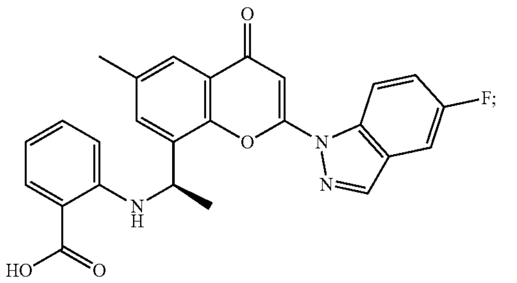
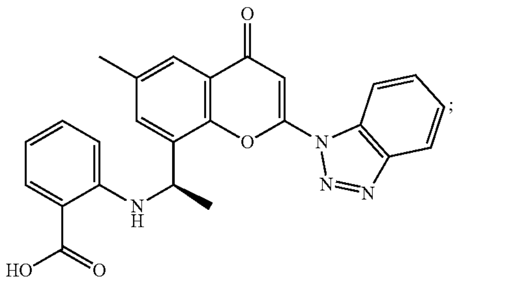
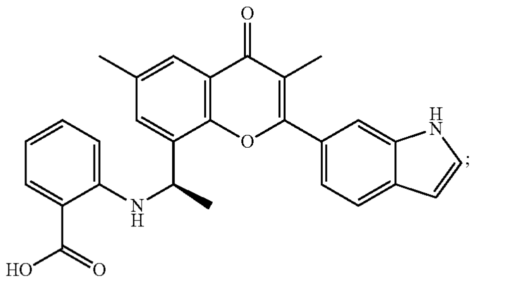
-continued
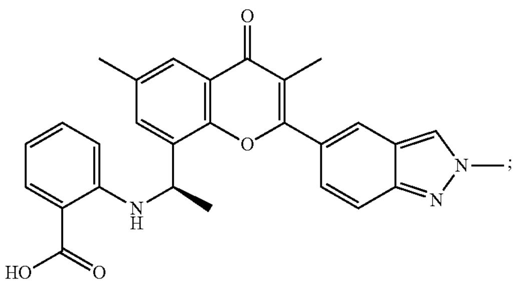
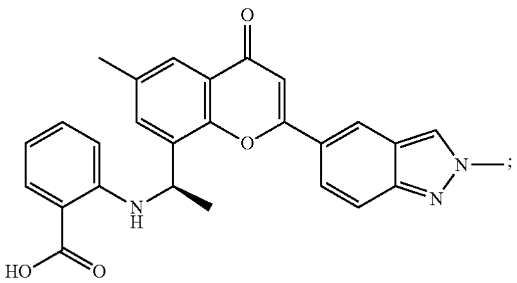
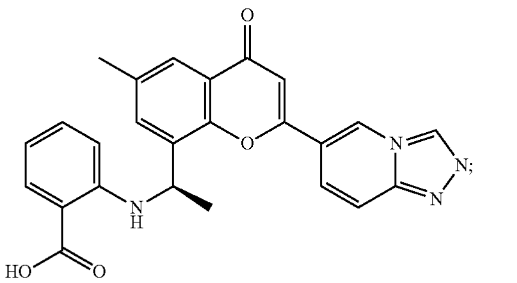
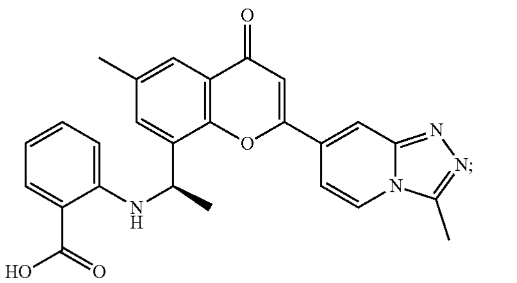
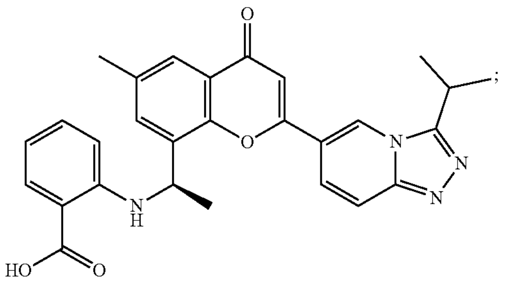
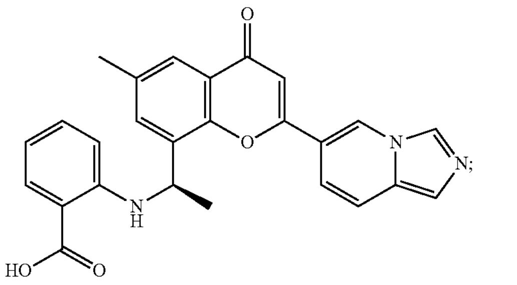

-continued
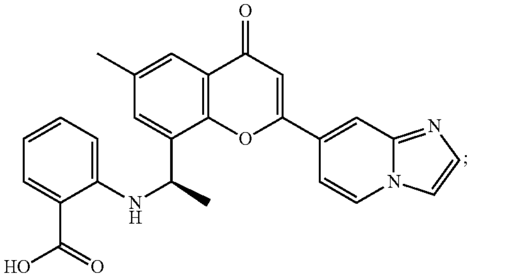
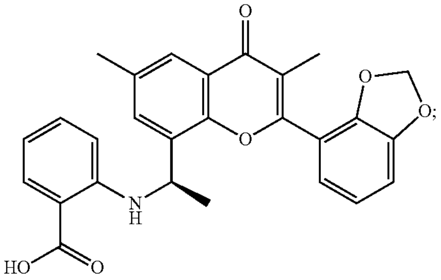
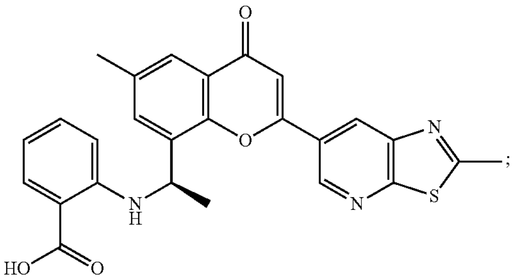
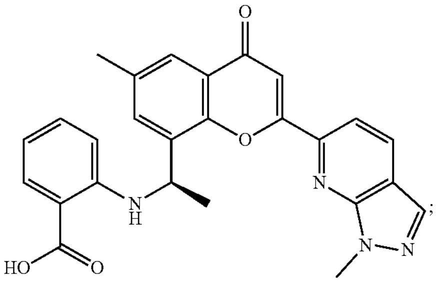
and
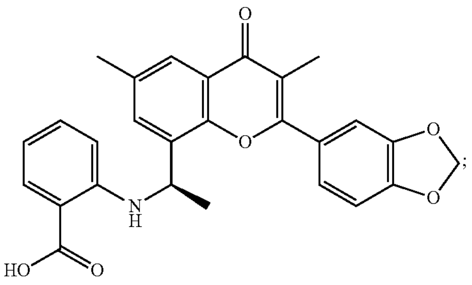 [SMILES: Cc1cc([C@@H](C)Nc2ccccc2C(=O)O)c2oc(-c3ccc4c(c3)OCO4)c(C)c(=O)c2c1]
or a pharmaceutically acceptable salt thereof.
40. The compound of claim 1, selected from the group consisting of:
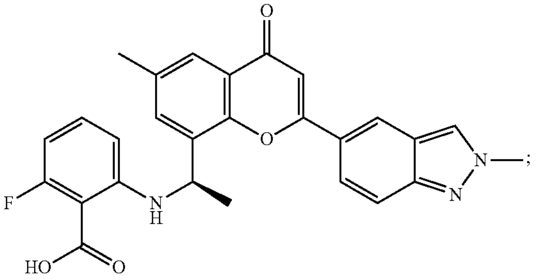
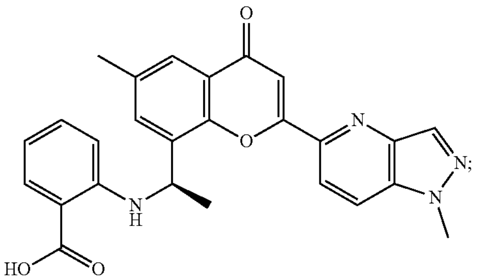
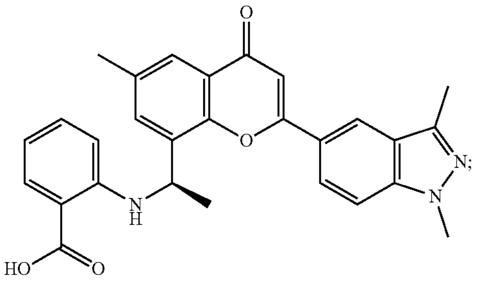
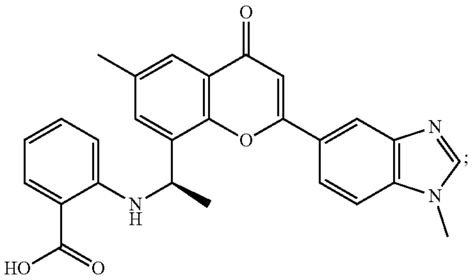
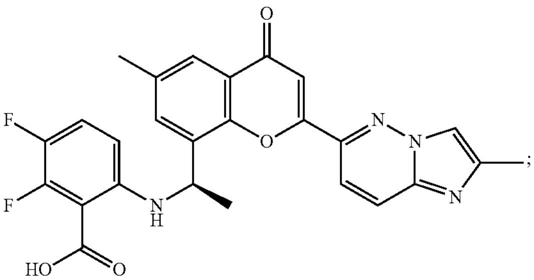
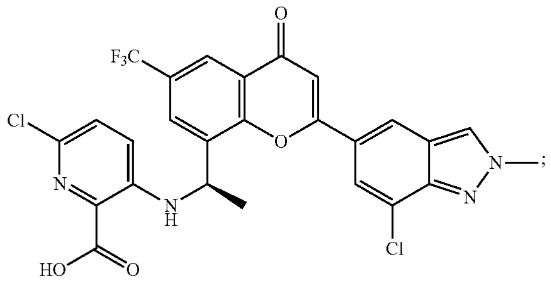

-continued
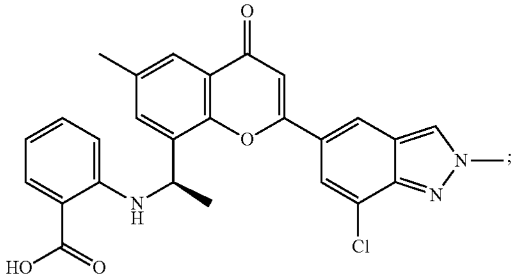
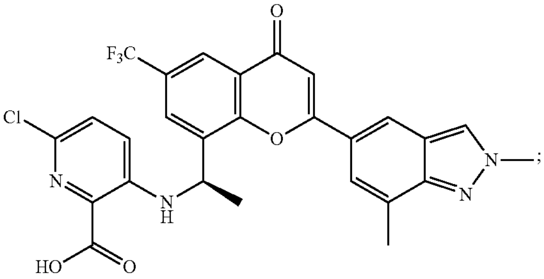
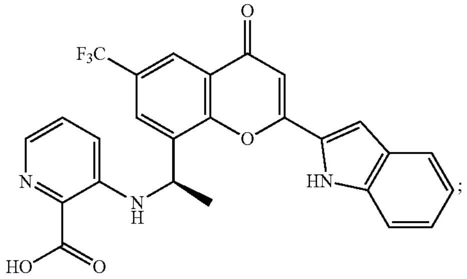
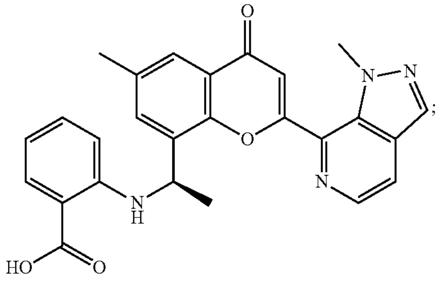
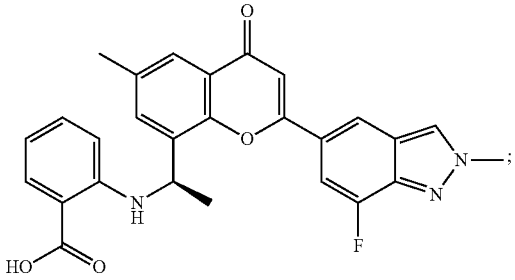
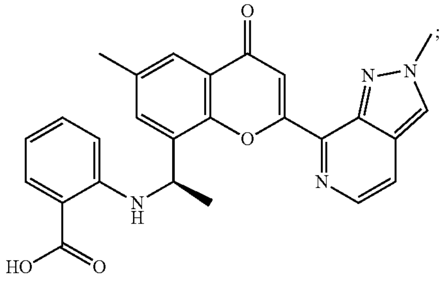
-continued
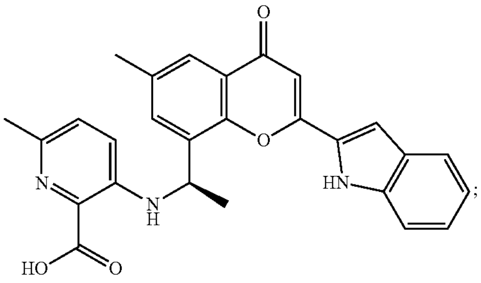
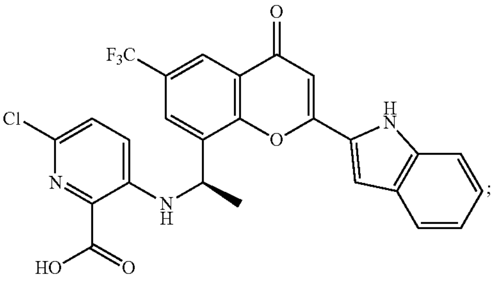
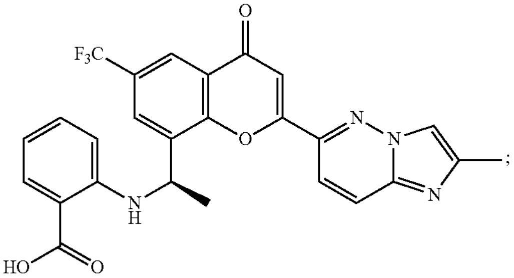
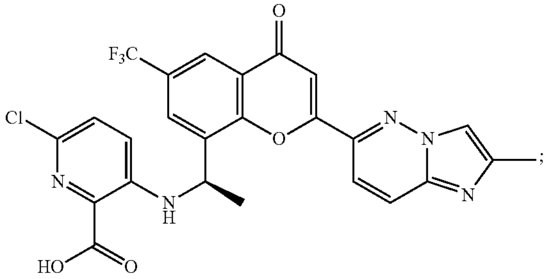
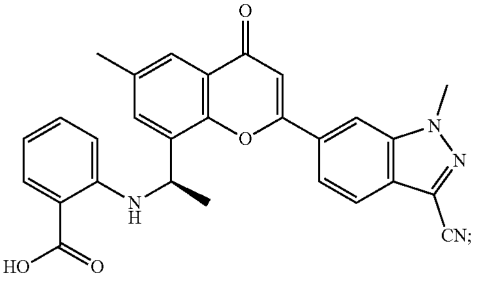
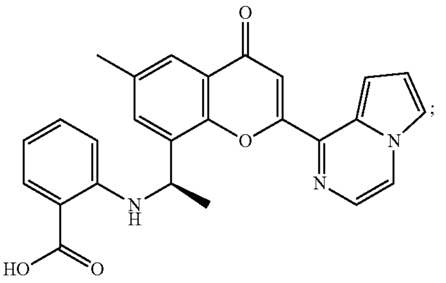

-continued
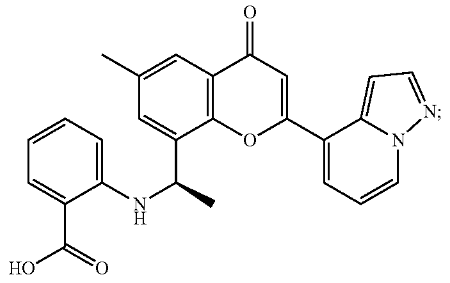
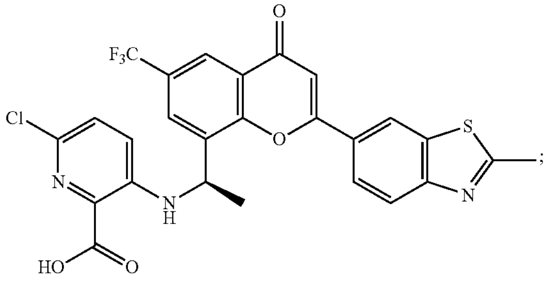
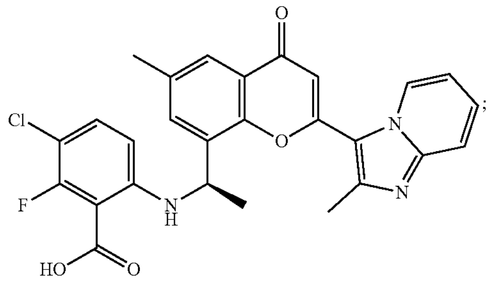
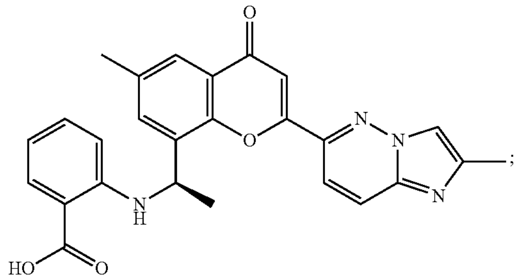
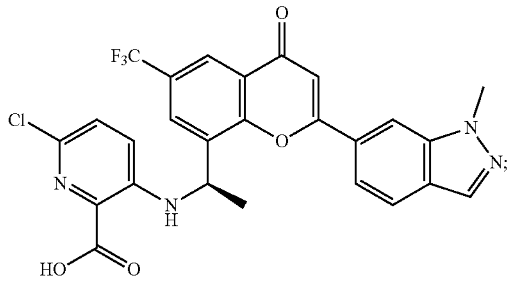
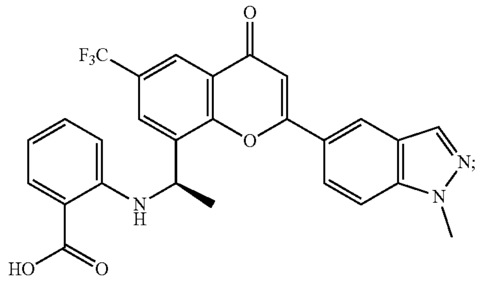
-continued
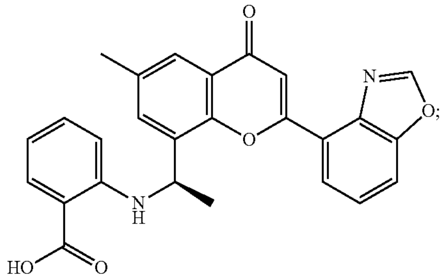
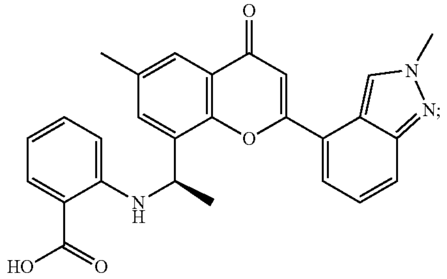
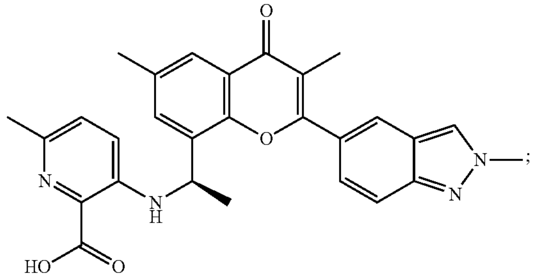
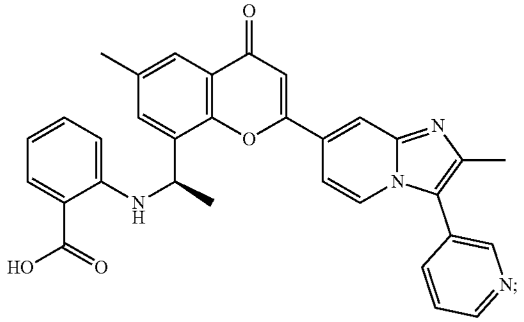
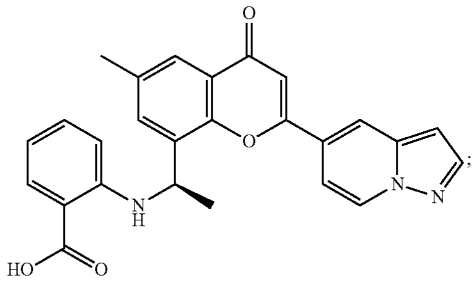
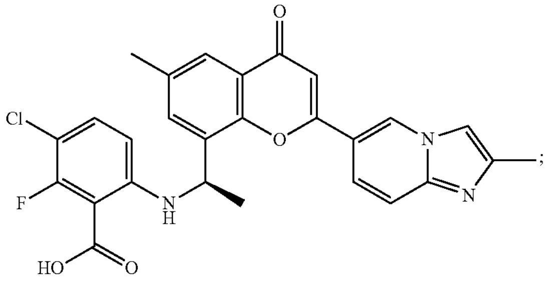

-continued
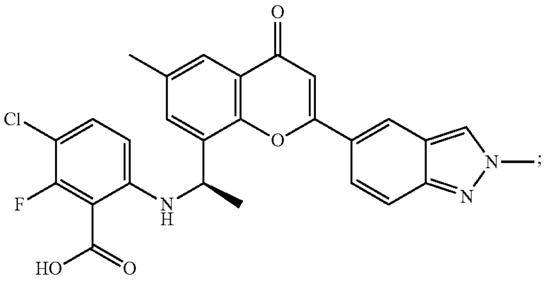
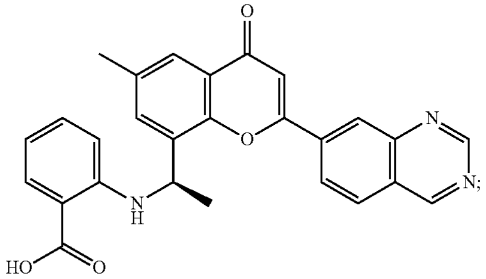
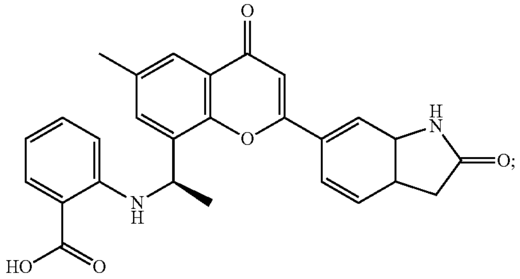
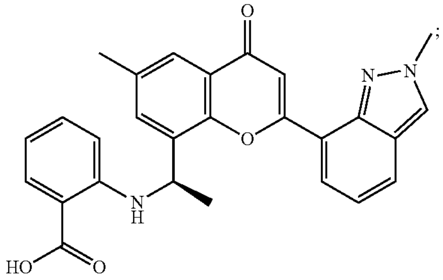
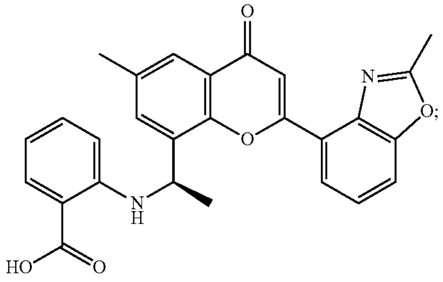
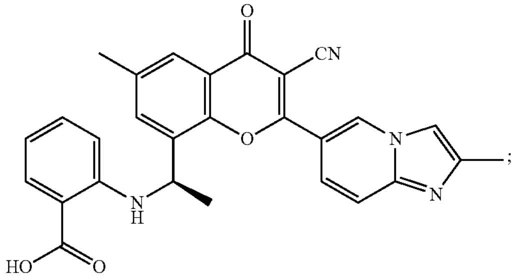
-continued
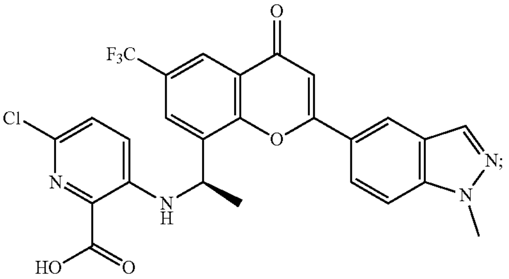
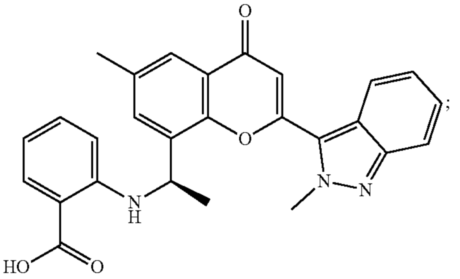
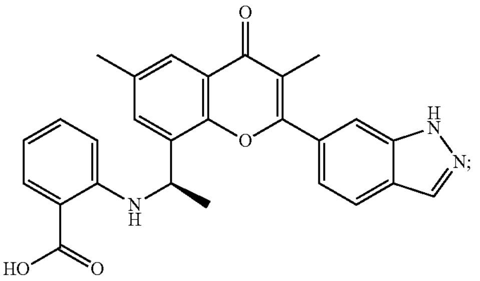
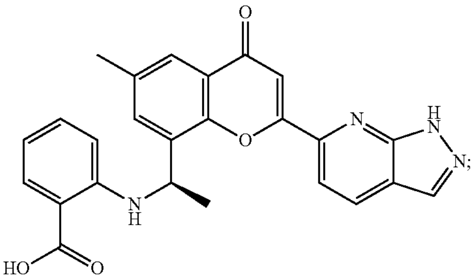
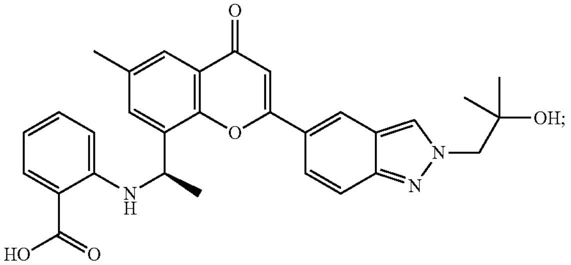
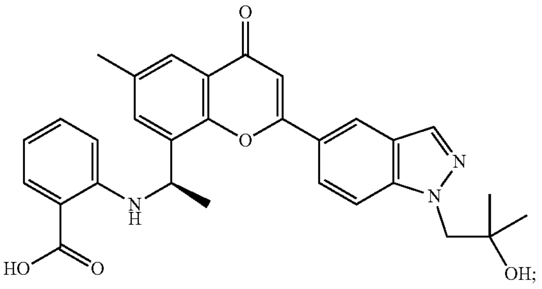

-continued
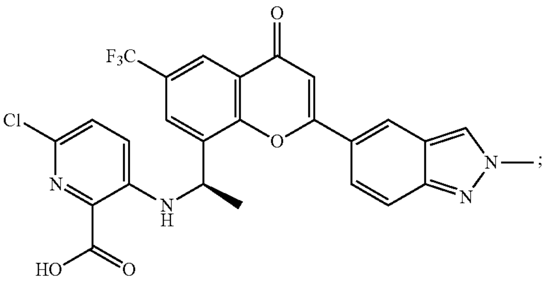
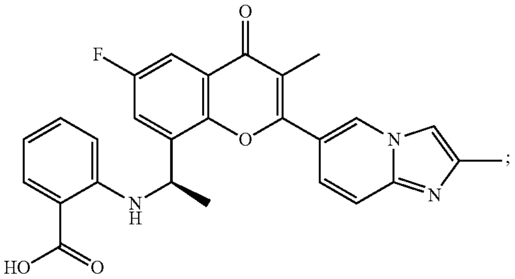
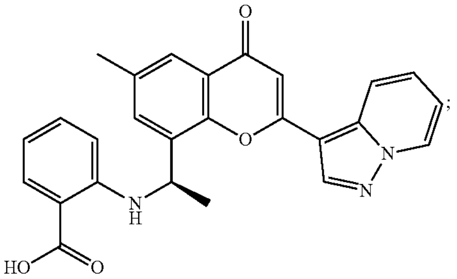
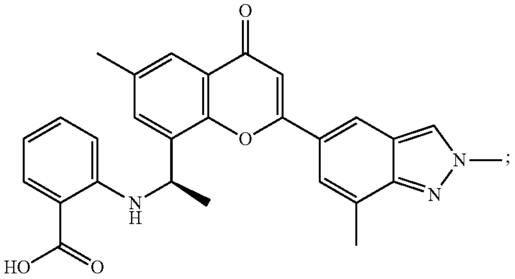
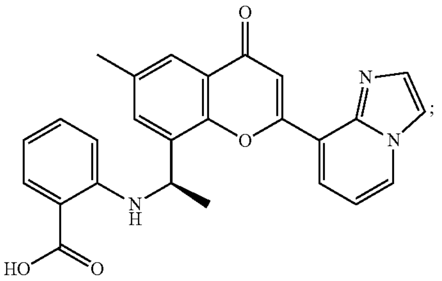
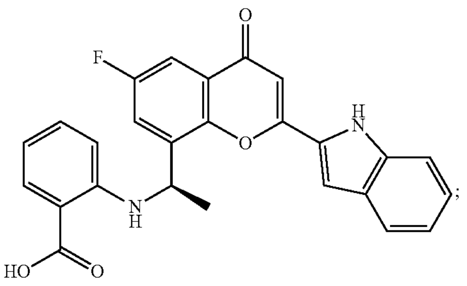
-continued
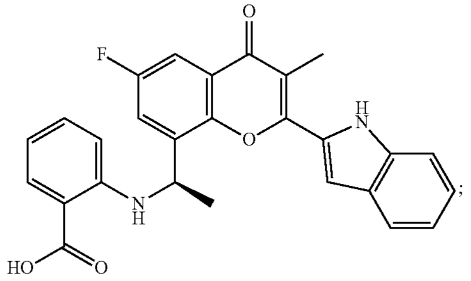
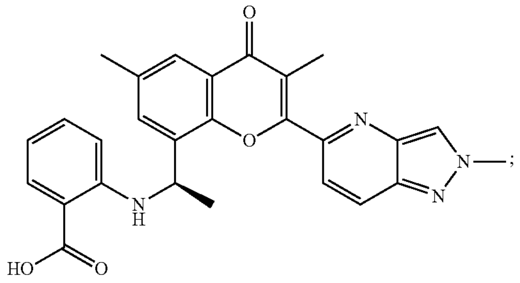
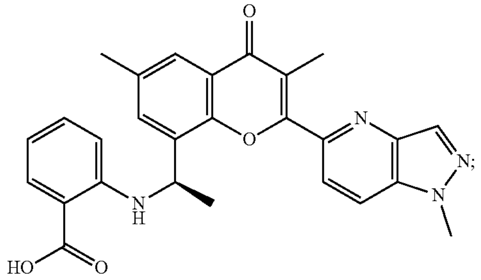
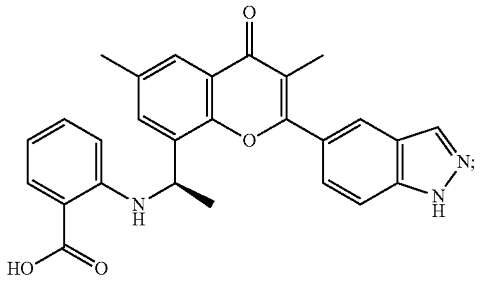
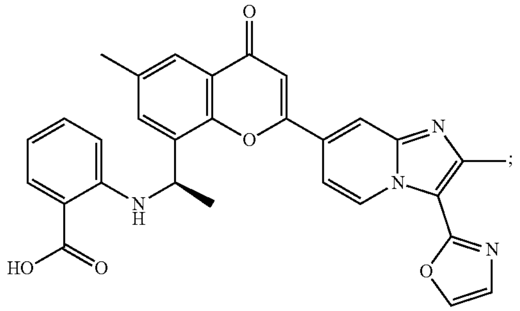
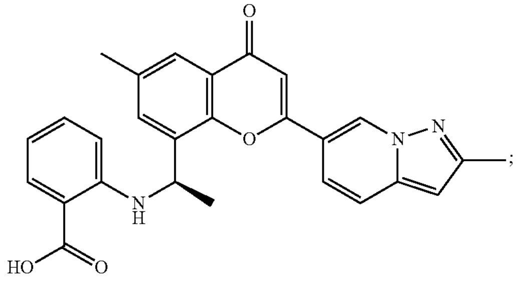

-continued
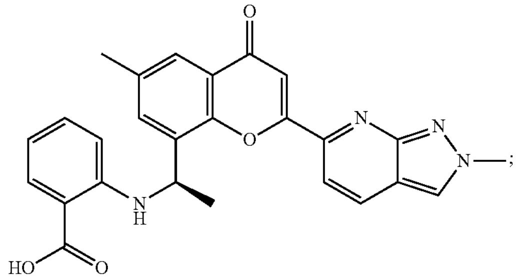
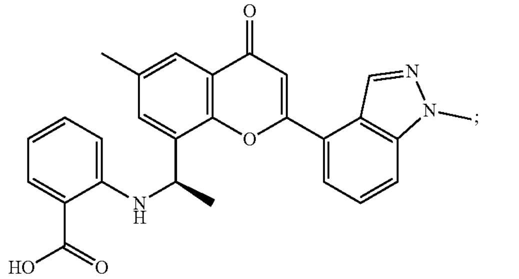
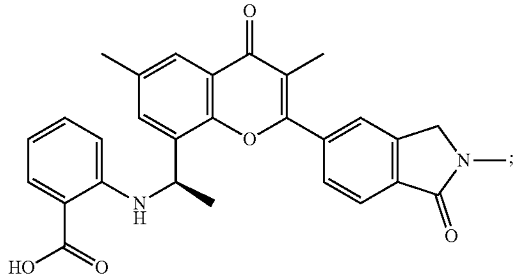
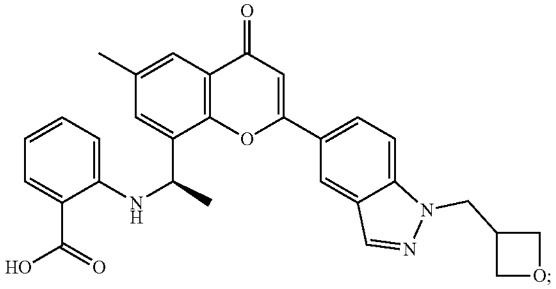
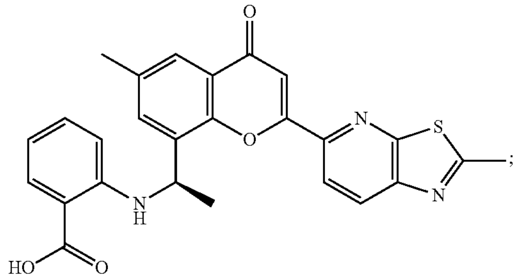
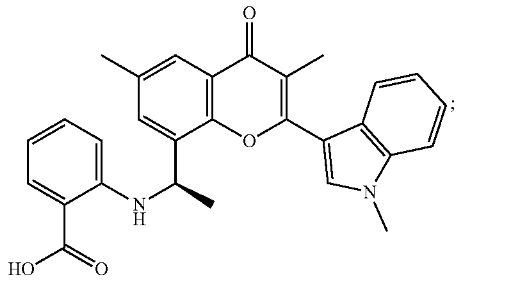
-continued
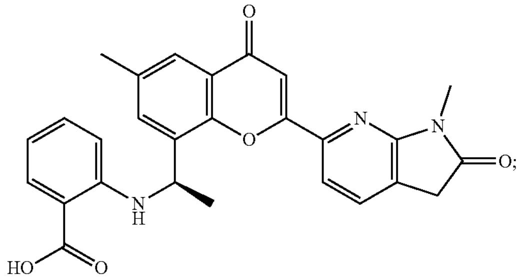
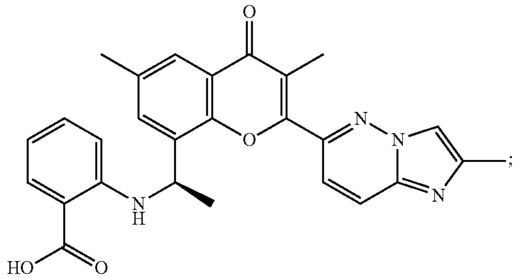
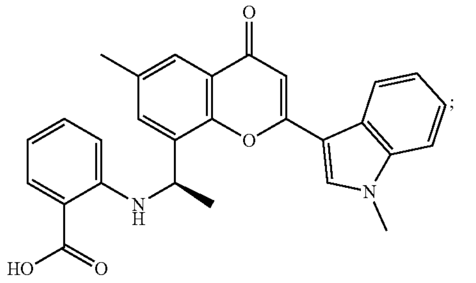
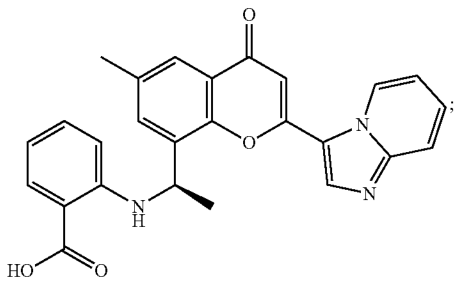
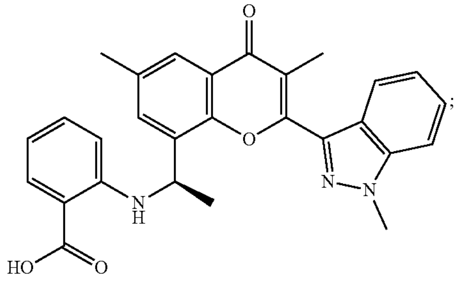
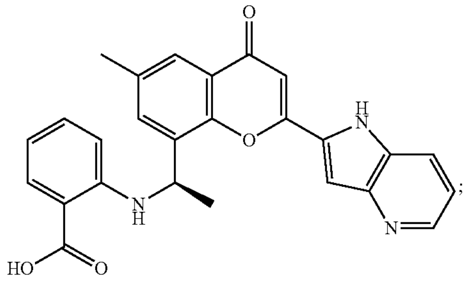

-continued
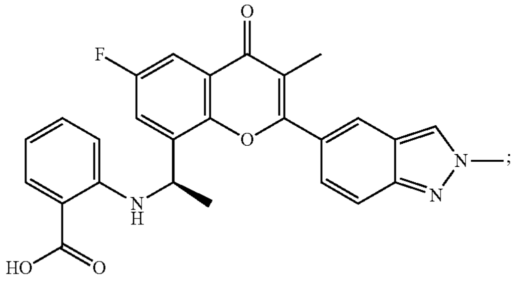
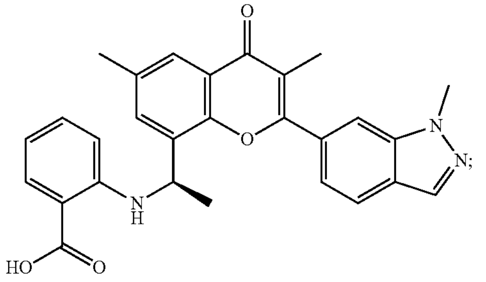
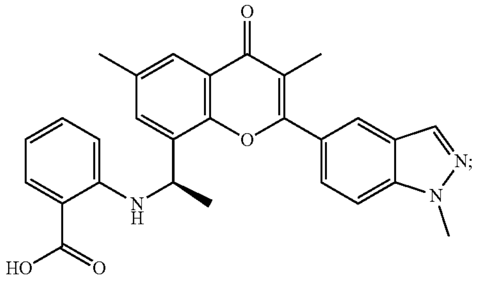
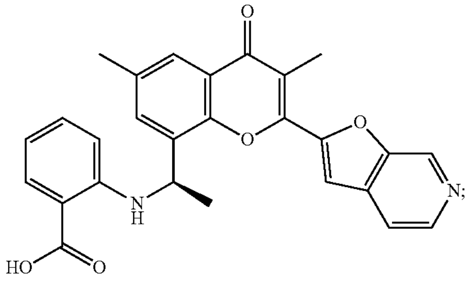
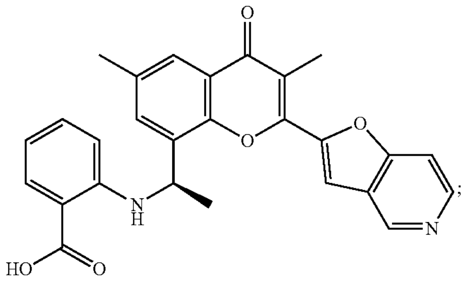
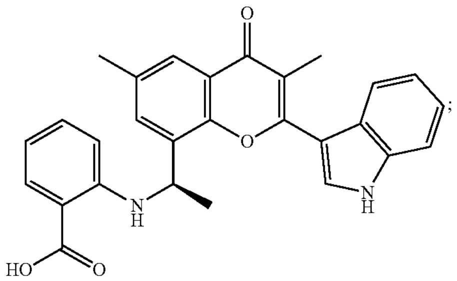
-continued
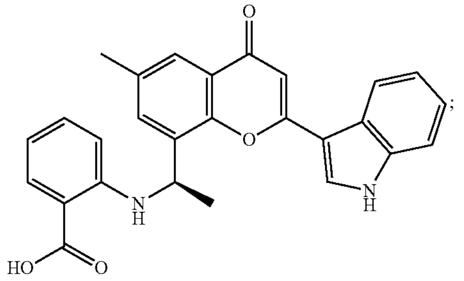
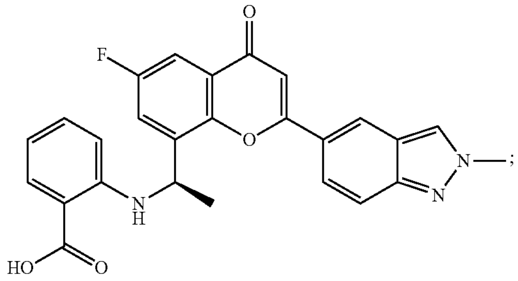
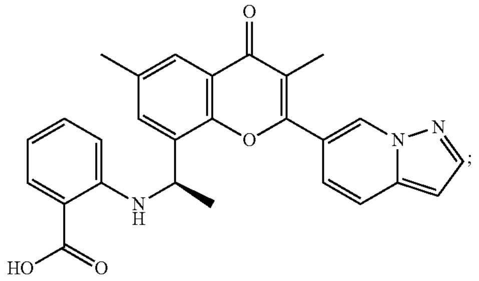
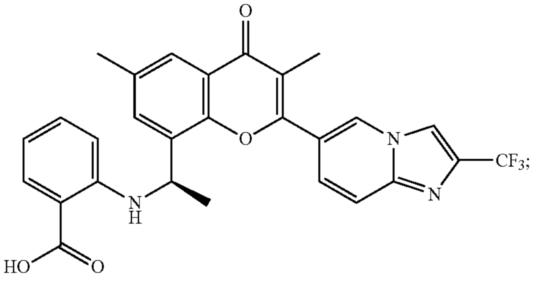
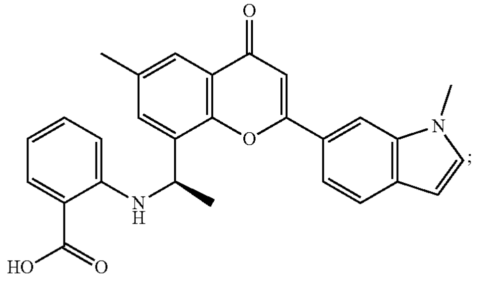
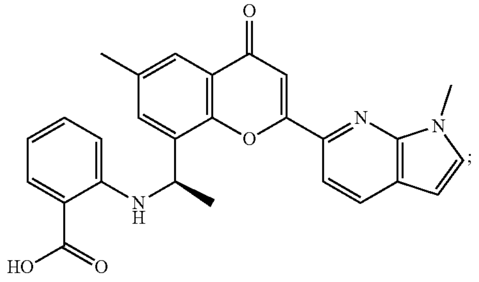

-continued
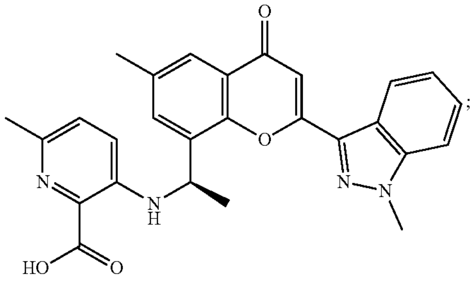
;
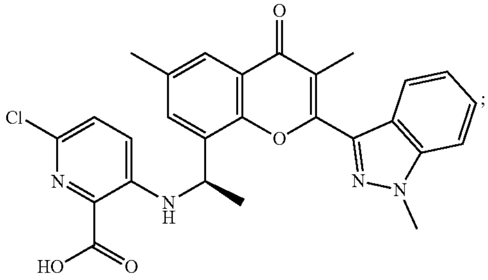
;
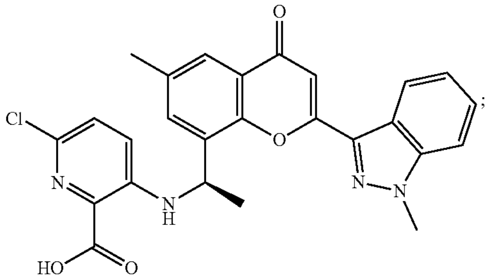
;
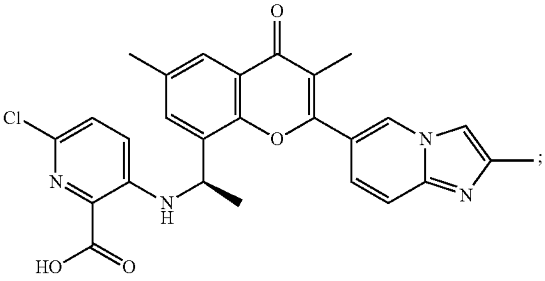
;
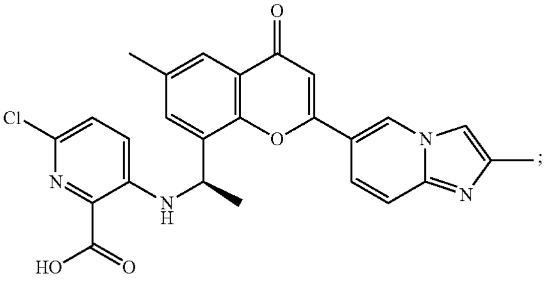
;
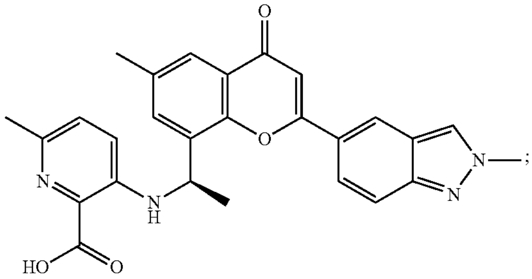
;
-continued
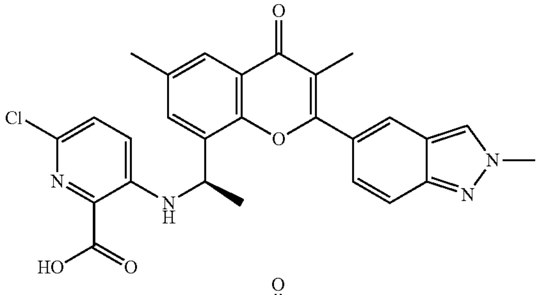
;
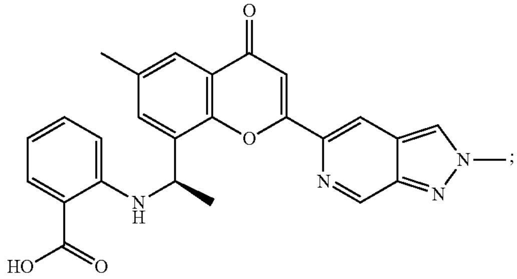
;
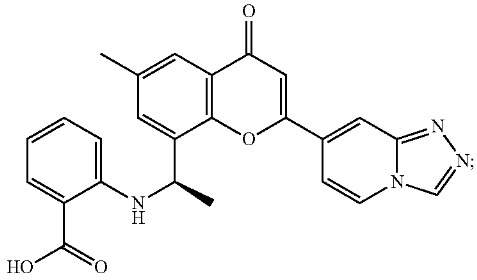
;
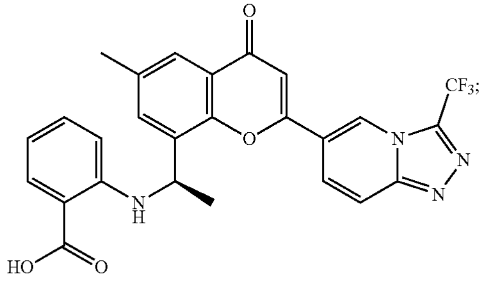
; and
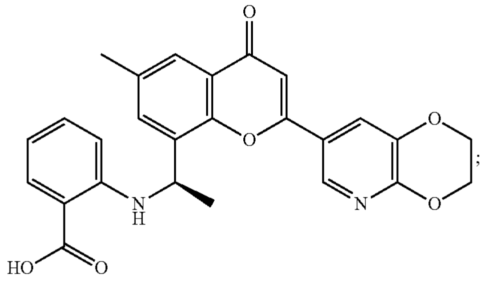
;
or a pharmaceutically acceptable sat thereof.
41. The compound of claim 1, selected from the group consisting of:

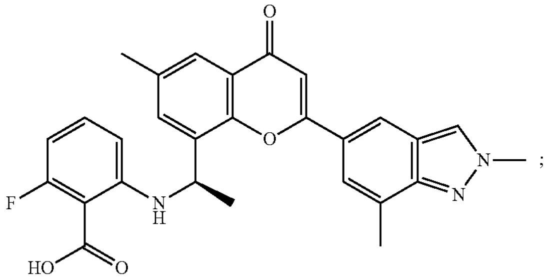
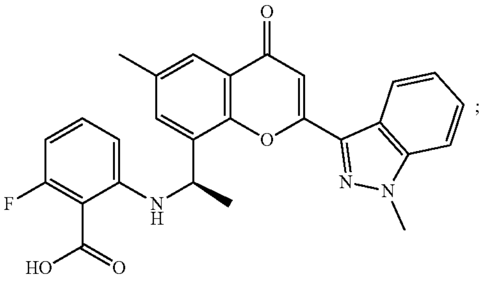
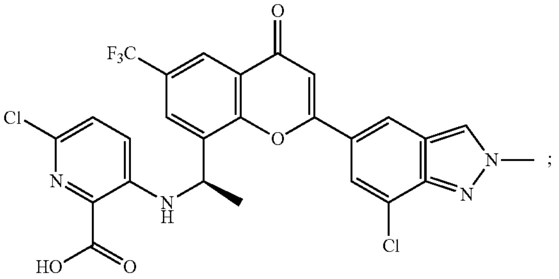
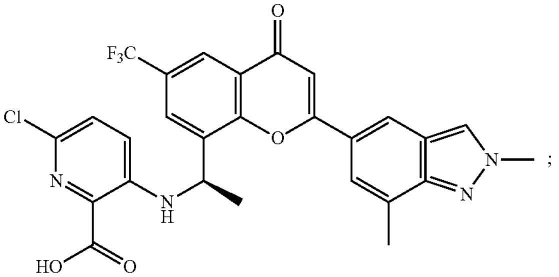
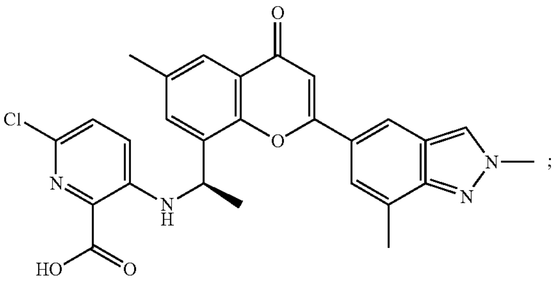
-continued
and
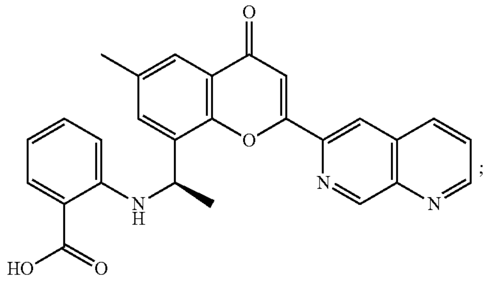
or a pharmaceutically acceptable salt thereof.
42. The compound of claim 1, selected from the group consisting of:
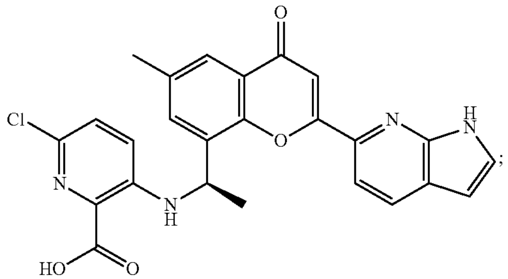
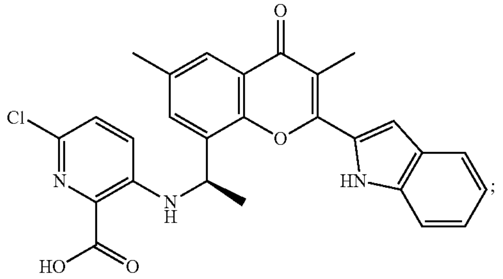
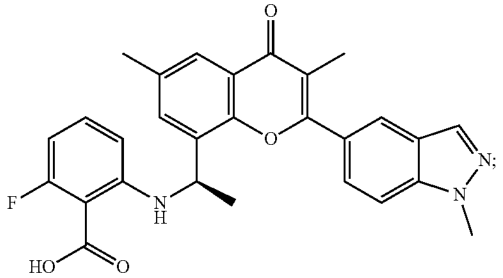
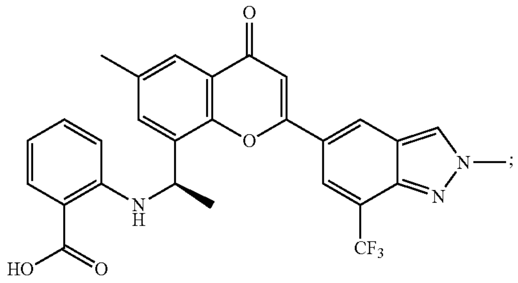

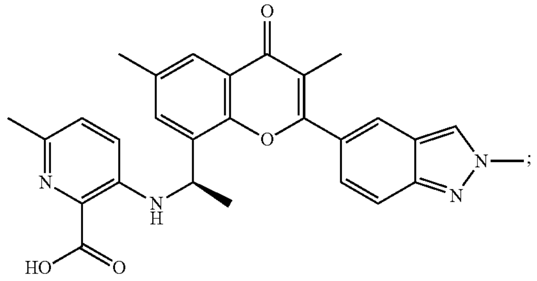
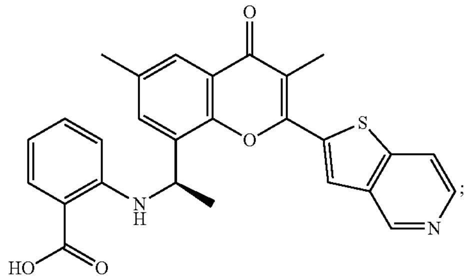
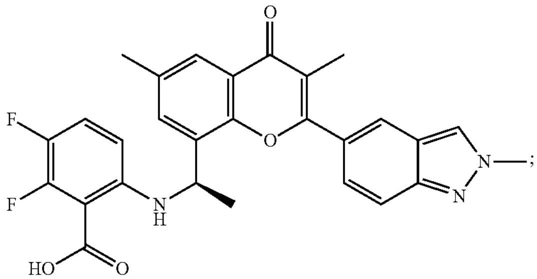
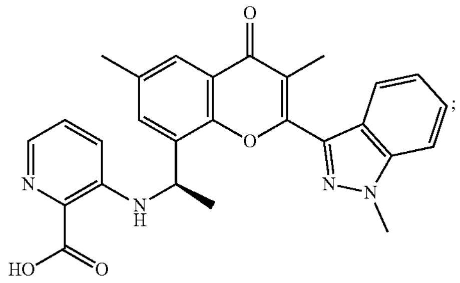
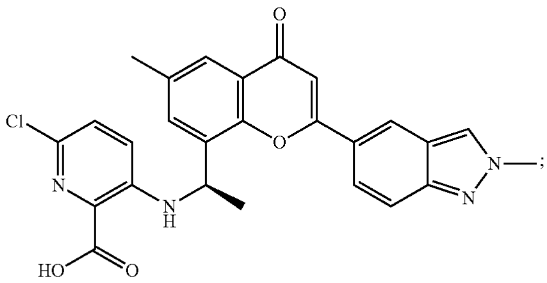
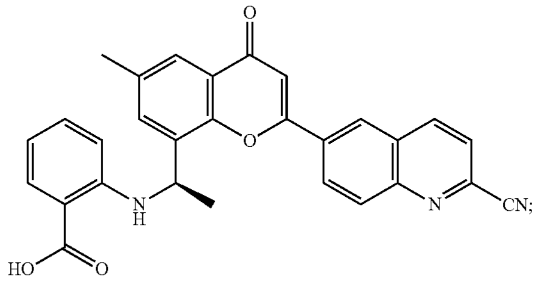
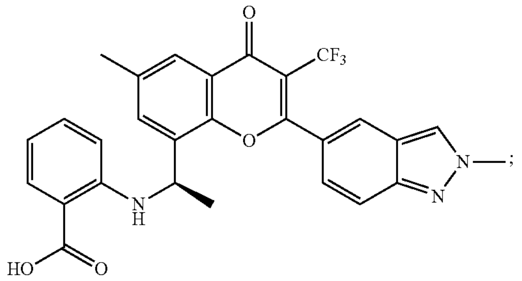
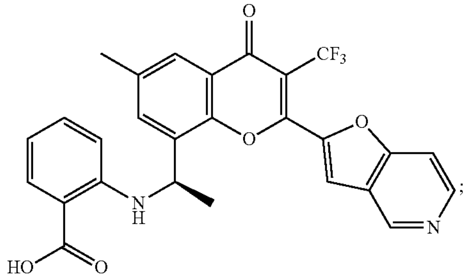
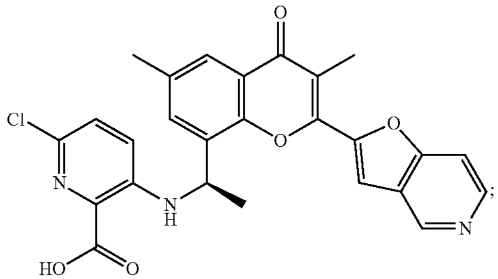
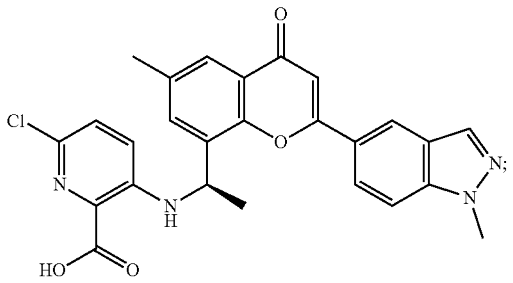
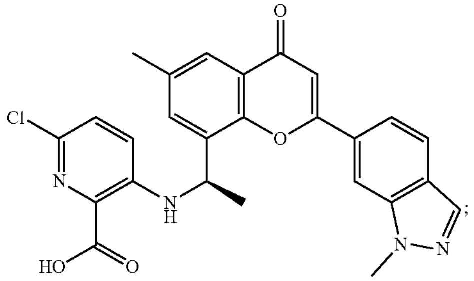
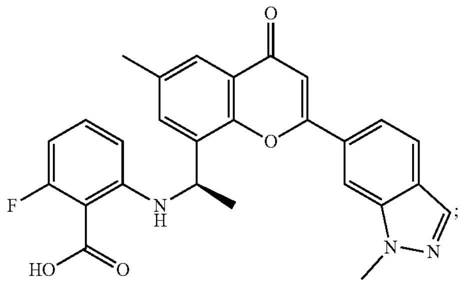

-continued
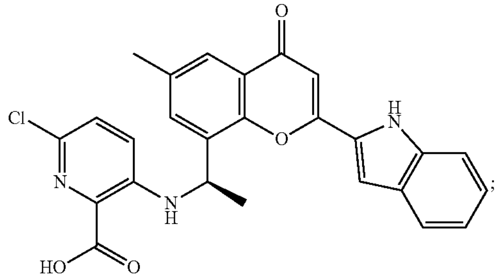
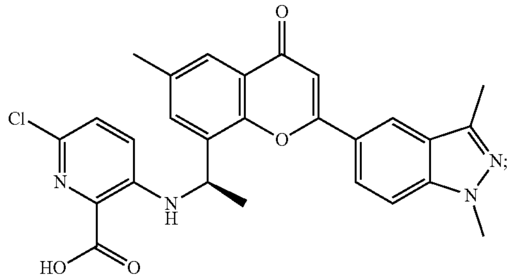
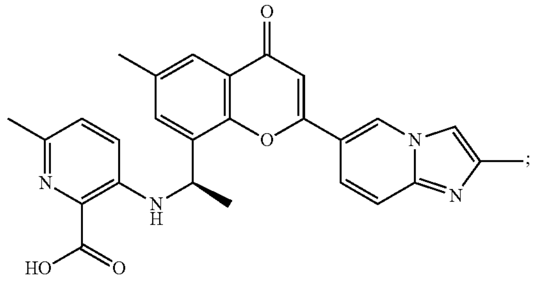
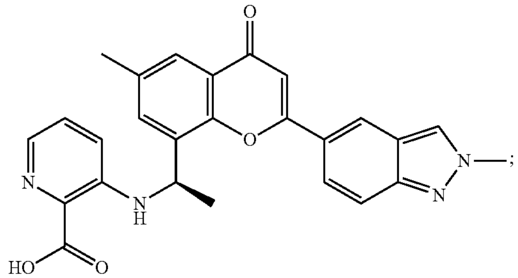
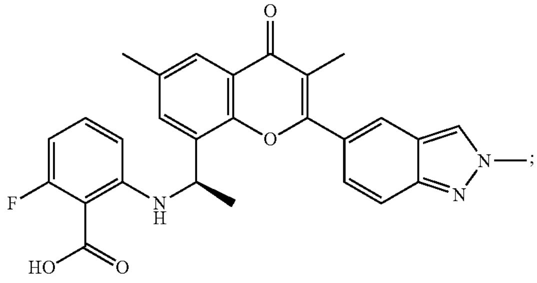
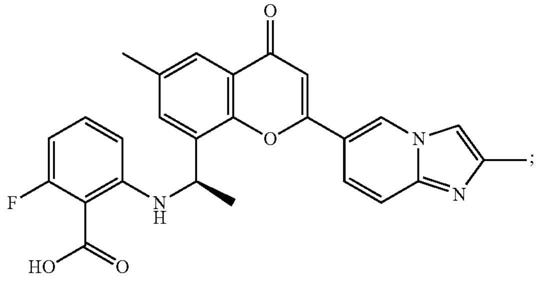
-continued
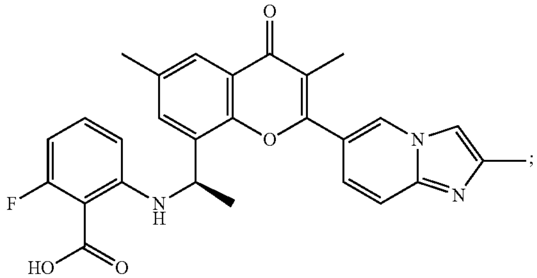
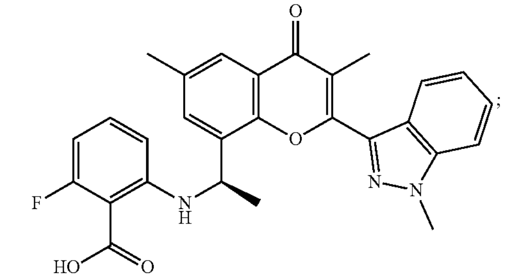
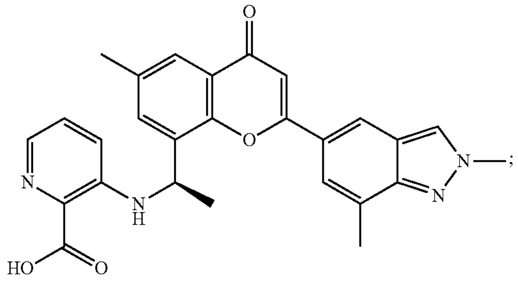
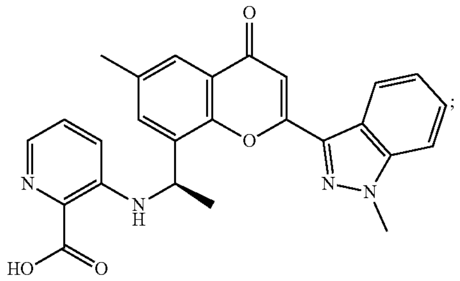
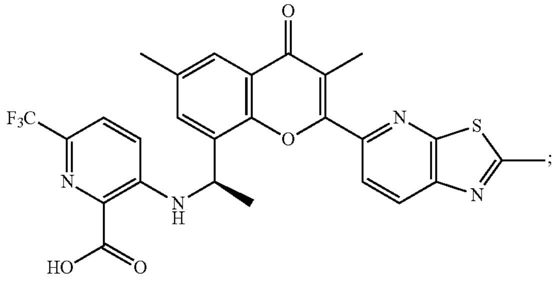
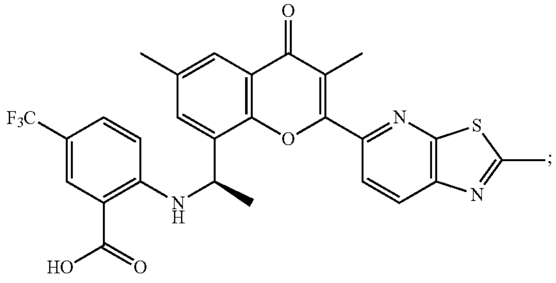

-continued
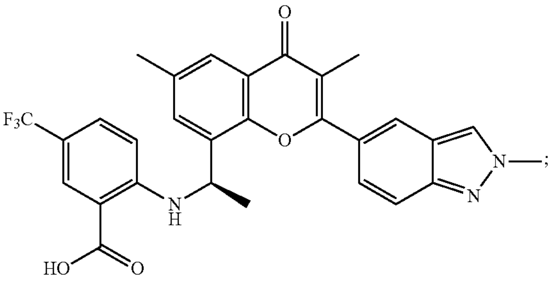
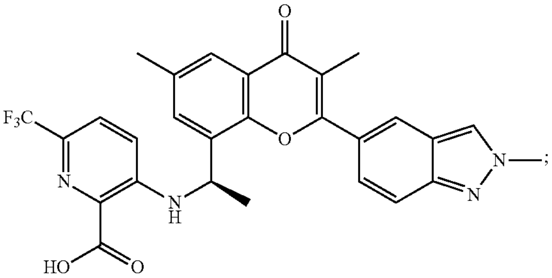
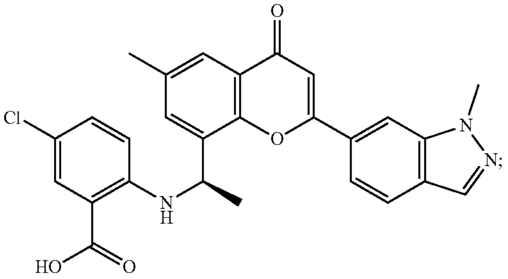
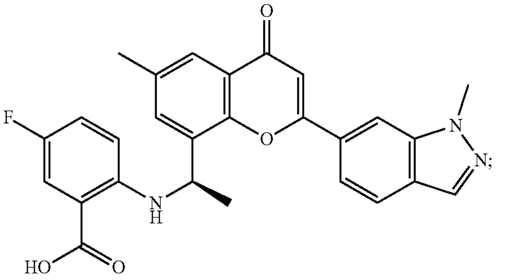
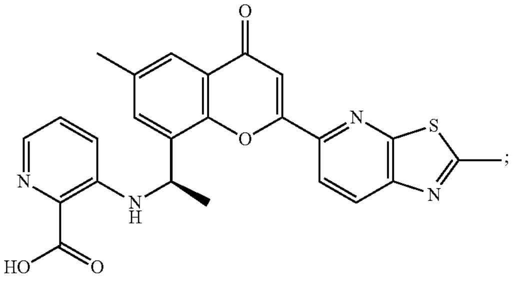
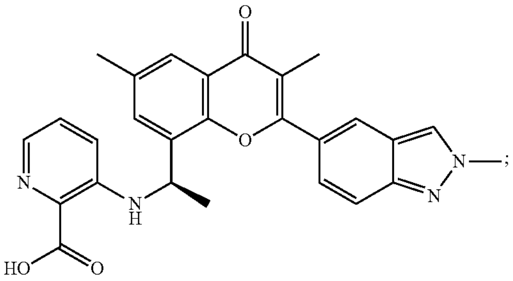
-continued
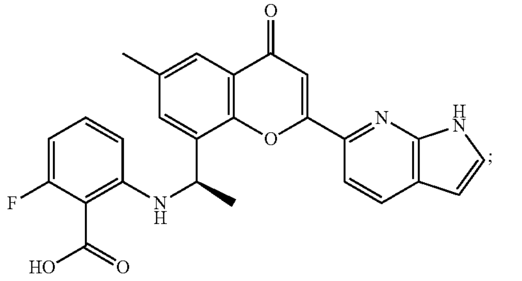
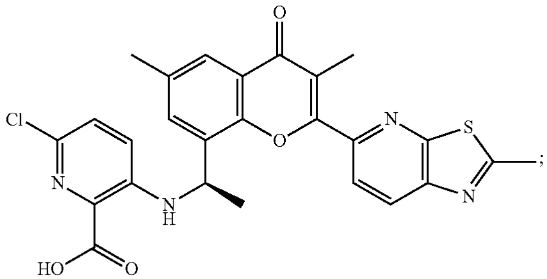
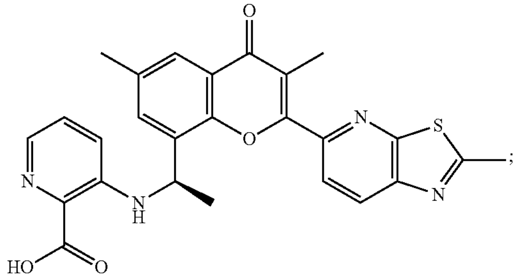
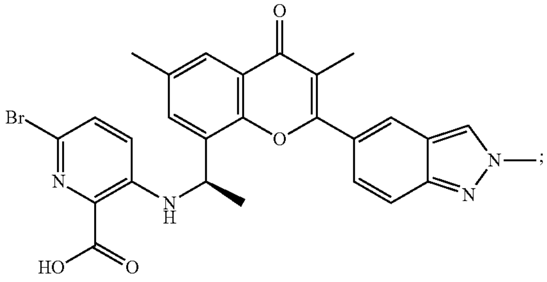
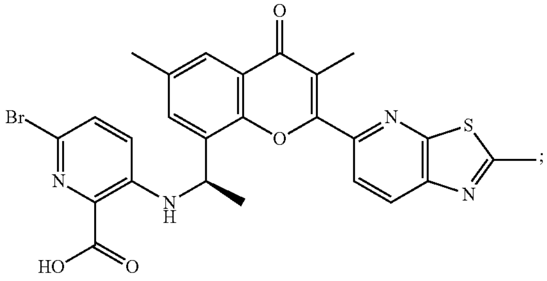
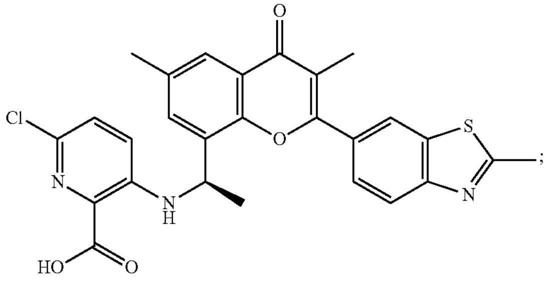

-continued
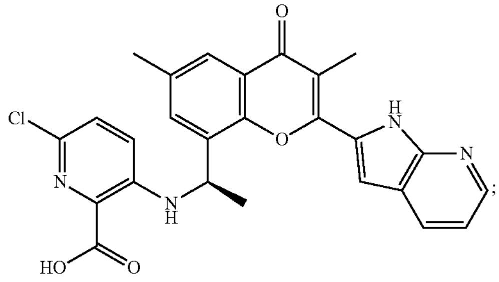
;
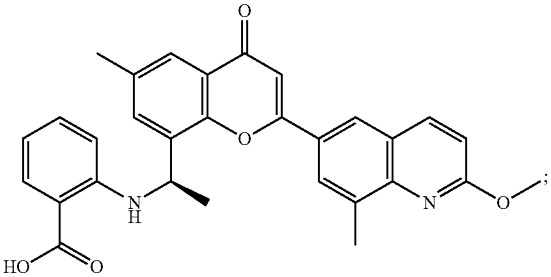
;
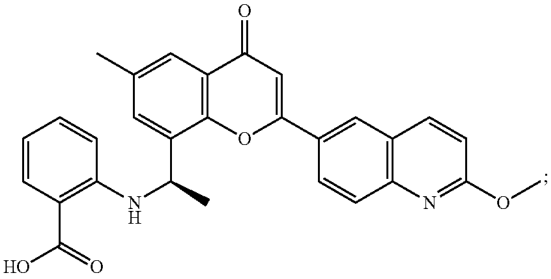
;
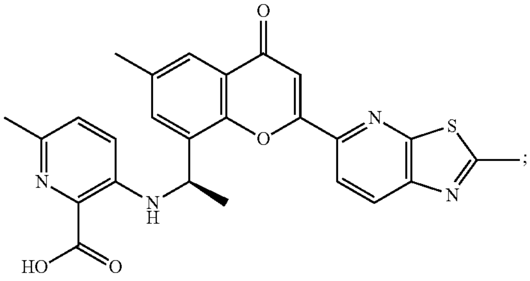
;
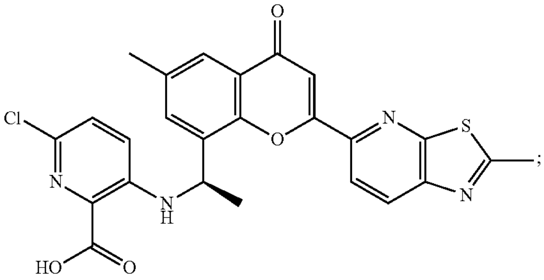
;
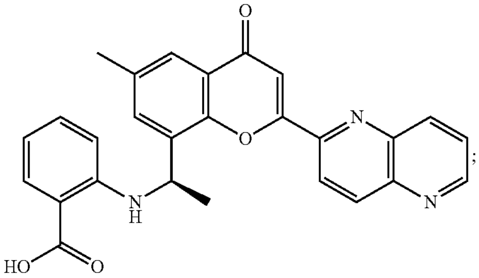
;
-continued
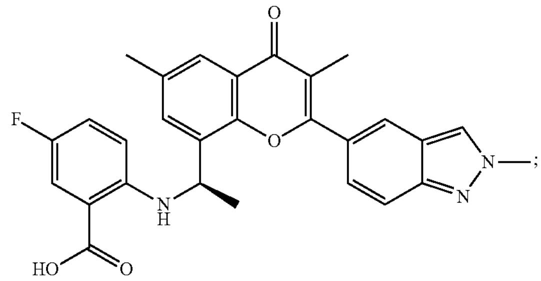
;
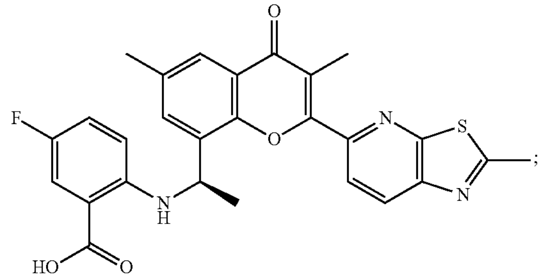
;
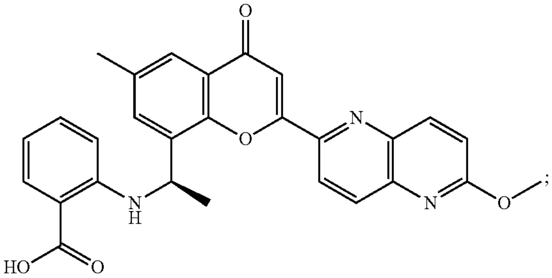
;
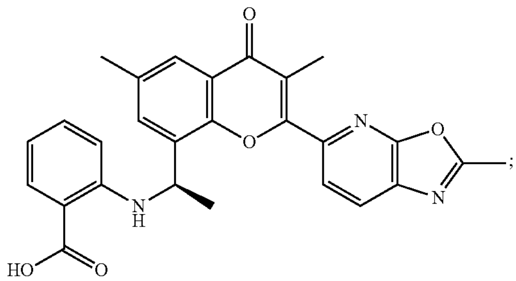
;
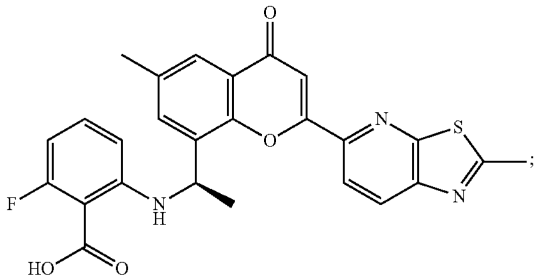
;
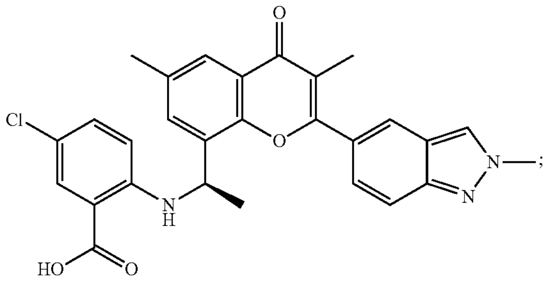
;

-continued

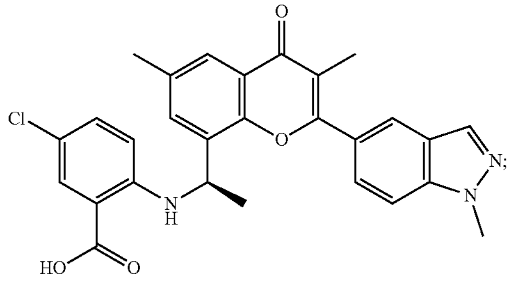

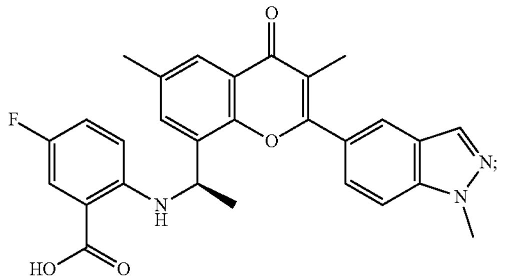

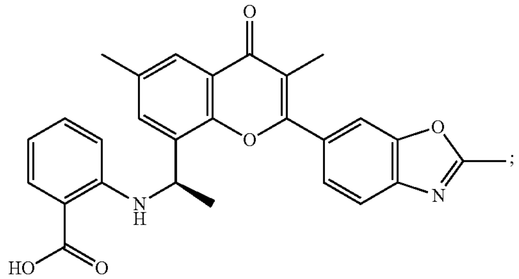

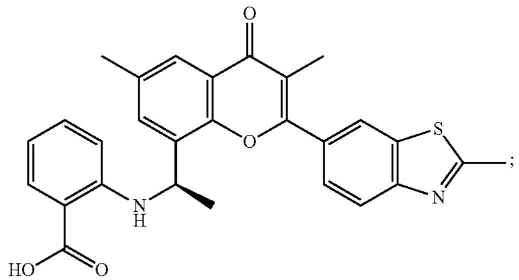

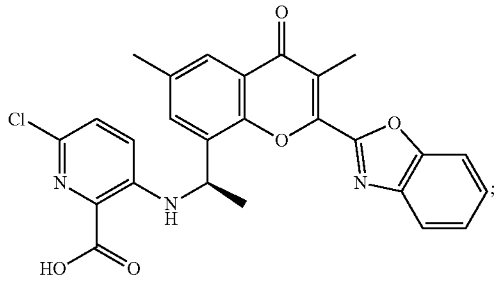

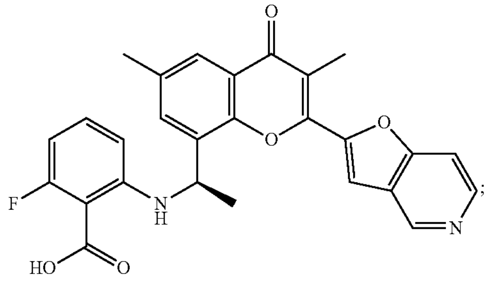

and

-continued

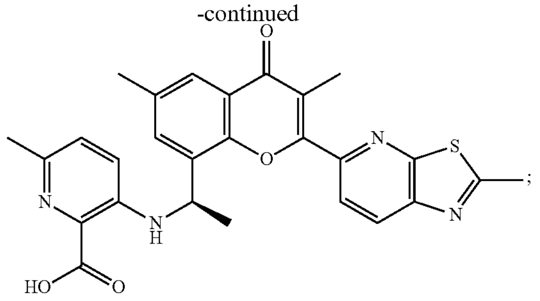

or a pharmaceutically acceptable salt thereof.

43. A pharmaceutical composition comprising a compound of claim 1, or a pharmaceutically acceptable salt thereof, and a pharmaceutically acceptable carrier.

44. A method of treating a disease or disorder associated with modulation of phosphoinositide 3-kinase (PI3K), comprising administering to a patient in need thereof a therapeutically effective amount of a compound of claim 1, or a pharmaceutically acceptable salt thereof.

45. The method of claim 44, wherein the PI31K is PI3Kα.

46. The method of claim 45, wherein the PI31K associated with the disease or disorder has a H1047R mutation.

47. The method of claim 44, wherein the disease or disorder is a cancer.

48. The method of claim 47, wherein the cancer is endometrial cancer, gastric cancer, leukemia, lymphoma, sarcoma, colorectal cancer, lung cancer, ovarian cancer, skin cancer, head and neck cancer, breast cancer, brain cancer, or prostate cancer.

49. The method of claim 47, wherein the cancer is breast cancer.

50. The method of claim 47, wherein the cancer is hormone receptor-positive (HR+), human epidermal growth factor receptor 2-negative (HER2−) advanced or metastatic breast cancer.

51. The method of claim 44, wherein the disease or disorder is CLOVES syndrome (congenital lipomatous overgrowth, vascular malformations, epidermal naevi, scoliosis/skeletal and spinal syndrome), or PIK3CA-related overgrowth syndrome (PROS).

52. A method of inhibiting phosphoinositide 3-kinase (PI3K), comprising administering to a patient in need thereof a therapeutically effective amount of a compound of claim 1, or a pharmaceutically acceptable salt thereof.

53. A method of treating cancer or a disorder, the method comprising administering to a patient in need thereof a therapeutically effective amount of a compound of claim 1, or a pharmaceutically acceptable salt thereof.

54. The method of claim 53, wherein the cancer is endometrial cancer, gastric cancer, leukemia, lymphoma, sarcoma, colorectal cancer, lung cancer, ovarian cancer, skin cancer, head and neck cancer, breast cancer, brain cancer, or prostate cancer.

55. The method of claim 53, wherein the cancer is breast cancer.

56. The method of claim 53, wherein the cancer is hormone receptor-positive (HR+), human epidermal growth factor receptor 2-negative (HER2−) advanced or metastatic breast cancer.

57. The method of claim 53, wherein the disorder is CLOVES syndrome (congenital lipomatous overgrowth, vascular malformations, epidermal naevi, scoliosis/skeletal and spinal syndrome) or PIK3CA-related overgrowth syndrome (PROS).

58. The compound of claim 1, or pharmaceutically acceptable salt thereof, wherein R is —H or $C_1$-$C_3$ alkyl;

$R_1$ is a group of the formula:

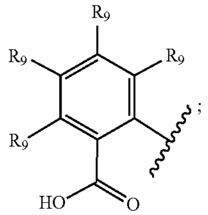
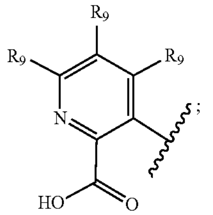
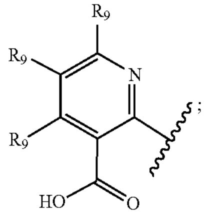
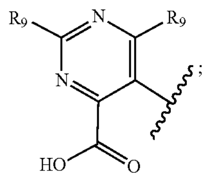
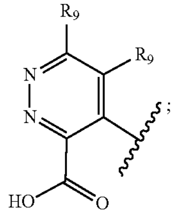
or
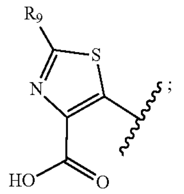

$R_2$ is an optionally substituted bicyclic ring selected from 1,3-benzodioxole, 2,3-dihydro-1,4-benzodioxine, isoindolin-1-one, indolin-2-one, or benzo[d]oxazol-2(3H)-one, or an optionally substituted bicyclic heteroaryl of 8 to 10 ring atoms containing 1, 2, 3, 4, or 5 ring heteroatoms independently selected from N, O, or S; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from -CN, halogen, C1-C6 haloalkyl, $C_1$-$C_6$ alkoxy, $C_1$-$C_6$ haloalkoxy, $—SO_2R_{10}$, $—CONR_{10}R_{10}$, $—NR_{10}R_{10}$, $—NR_{10}CO_2R_{10}$, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted C1-C6alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, $—NR_{10}R_{10}$, —OH or —CN;

$R_3$ is —H, —CN, $C_1$-$C_6$ alkyl or $C_1$-$C_6$ haloalkyl;

each of $R_4$, $R_5$ and $R_6$ is independently —H, halogen, $C_1$-$C_6$ alkyl or $C_1$-$C_6$ haloalkyl;

$R_7$ is —CN, $C_1$-$C_6$ alkyl or $C_1$-$C_6$ haloalkyl;

$R_8$ is —H or $C_1$-$C_6$ alkyl;

each $R_9$ is independently —H, halogen, $C_1$-$C_6$ alkyl, $C_1$-$C_6$ haloalkyl, $C_1$-$C_6$ alkoxy, or $C_3$-$C_5$ cycloalkyl; and each $R_{10}$ is independently —H or $C_1$-$C_3$ alkyl.

59. The compound of claim 58, or pharmaceutically acceptable salt thereof, having the Formula:

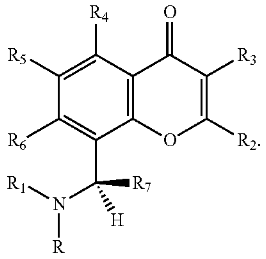

60. The compound of claim 59, or pharmaceutically acceptable salt thereof, wherein $R_1$ is a group of the formula:

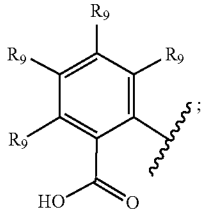
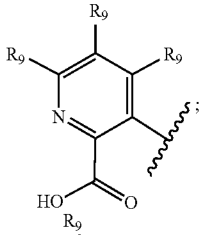
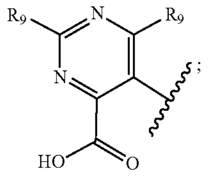
or
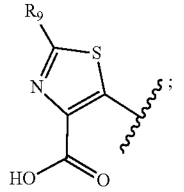

$R_2$ is an optionally substituted bicyclic ring selected from 1,3-benzodioxole, 2,3-dihydro-1,4-benzodioxine, isoindolin-1-one, indoline-2-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from -CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ cycloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a —CN, —OH, or $C_1$-$C_3$ alkoxy; the optionally substituted $C_3$-$C_5$ cycloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, $—NR_{10}R_{10}$, —OH or —CN;

$R_3$ is —H, —CN, $C_1$-$C_3$ alkyl, or $C_1$-$C_3$ haloalkyl;

$R_4$ is —H, or halogen;

$R_5$ is —H, halogen, C1-$C_3$ alkyl or $C_1$-$C_3$ haloalkyl;

$R_6$ is —H, or halogen;

$R_7$ is —CN, methyl or trifluoromethyl;

R is —H;

each $R_9$ is independently —H, halogen, methyl, C1-C3 haloalkyl, or cyclopropyl; and each $R_{10}$ is independently —H or $C_1$-$C_3$ alkyl.

61. The compound of claim 1, or pharmaceutically acceptable salt thereof, wherein R is —H or C1-C3alkyl;

Rlis a group of the formula:

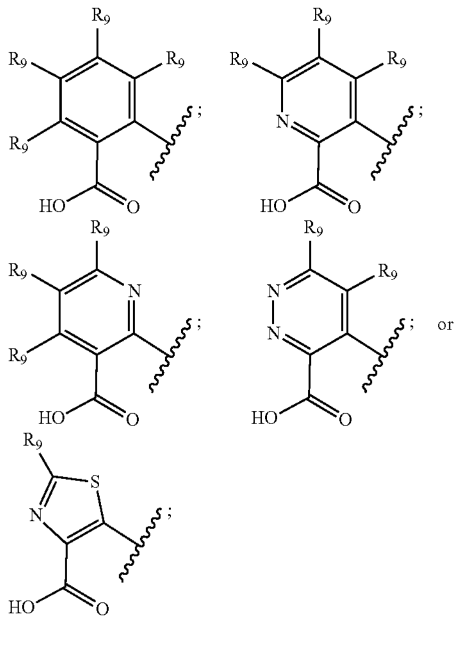

or

R2 is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from C1-C6 alkyl; the optionally substituted bicyclic heteroaryl is optionally substituted with one to three substituents each independently selected from 13 CN, halogen, C1-C6 haloalkyl, C1-C6 alkoxy, C1-C6 haloalkoxy, 13 S021110, 13 CONRio-Rio, 13 NRioRio, 13 NRI0CO2R10, an optionally substituted C1-C6 alkyl, an optionally substituted C3_05 $c_y$cloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted C1_C6 $a_l$kyl is optionally substituted with a 13 CN, 13 OH, or C1-C3alkoxy; the optionally substituted C3-$_0$5 $cy_c$loalkyl, phenyl, heterocycle or heteroaryl is each optionally substituted with one to three substituents each independently selected from halogen, C1-C3 alkyl, C1-C3haloalkyl, C1-C3 $_a$lkoxy, C1-C3 haloalkoxy, 13 NRioRio, 13 OH or 13 CN;

R3 is 13 H, 13 CN, C1-C6 alkyl or C1-C6 haloalkyl;

each of $R_4$, $R_5$ and $R_6$ is independently 13 H, halogen, $C_1$-$C_6$ alkyl or $C_1$-$C_6$ haloalkyl;

$R_7$ is 13 CN, $C_1$-$C_6$ alkyl or $C_1$-$C_6$ haloalkyl;

$R_8$ is 13 H or $C_1$-$C_6$ alkyl;

each $R_9$ is independently 13 H, halogen, $C_1$-$C_6$ alkyl, $C_1$-$C_6$ haloalkyl, $C_1$-$C_6$ alkoxy, or $C_3$-$C_5$ cycloalkyl; and each $R_{10}$ is independently 13 H or $C_1$-$C_3$ alkyl.

62. The compound of claim 61, or pharmaceutically acceptable salt thereof, having the Formula:

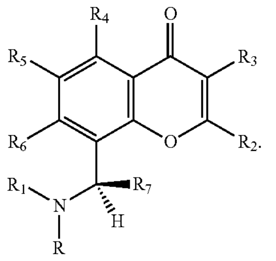

63. The compound of claim 62, or pharmaceutically acceptable salt thereof, wherein $R_1$ is a group of the formula:

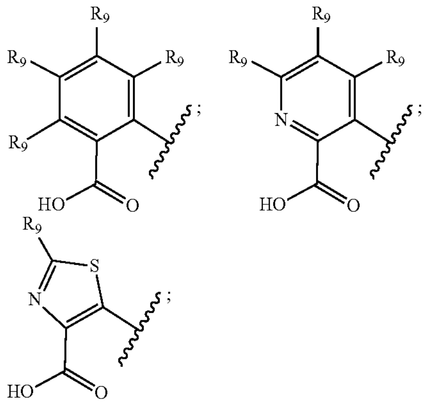

or $R_2$ is an optionally substituted bicyclic ring selected from 1,3-benzodioxole, 2,3-dihydro-1,4-benzodioxine, isoindolin-1-one, or benzo[d]oxazol-2(3H)-one, or an optionally substituted bicyclic heteroaryl wherein a phenyl, pyridine, pyrazine, pyrimidine, or pyridazine ring is fused to a pyrrole, furan, thiophene, pyrazole, isoxazole, imidazole, oxazole, thiazole, triazole, pyridine, pyrazine, pyrimidine, or pyridazine ring; wherein the optionally substituted bicyclic ring is optionally substituted with one to three substituents each independently selected from $C_1$-$C_6$ alkyl; the optionally substituted bicyclic heteroaryl is optionally substituted with one to three substituents each independently selected from 13 CN, halogen, $C_1$-$C_6$ haloalkyl, $C_1$-$C_6$ alkoxy, $C_1$-$C_6$ haloalkoxy, an optionally substituted $C_1$-$C_6$ alkyl, an optionally substituted $C_3$-$C_5$ $c_y$cloalkyl, an optionally substituted heterocycle selected from pyrrolidine, pyrrolidinone, piperidine or morpholine, an optionally substituted phenyl, or an optionally substituted heteroaryl selected from pyrazole, isoxazole, isothiazole, imidazole, oxazole, or thiazole; wherein the optionally substituted $C_1$-$C_6$ alkyl is optionally substituted with a 13 CN, 13 OH, or $C_1$-$C_3$alkoxy; the optionally substituted $C_3$-$C_5$ cloalkyl, phenyl, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, -$NR_{10}R_{10}$, 13 OH or 13 CN;

$R_3$ is -13 H, 13 CN, or $C_1$-$C_3$ alkyl;

$R_4$, and R are each -H;

$R_5$ is 13 H, halogen, $C_1$-$C_3$ alkyl or $C_1$-$C_3$ haloalkyl;

$R_6$ is 13 H or halogen;

$R_7$ is 13 CN, methyl or trifluoromethyl, each $R_9$, is independently 13 H, halogen, methyl, or $C_1$-$C_3$ haloalkyl; and each $R_{10}$ is independently 13 H or $C_1$-$C_3$ alkyl.

64. A compound of the Formula:

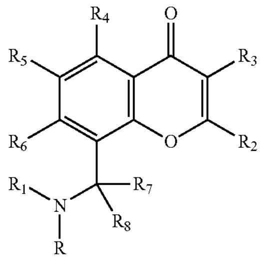

or pharmaceutically acceptable salt thereof, wherein:

R is -H or $C_1$-$C_3$ alkyl;

$R_1$ is a group of the formula:

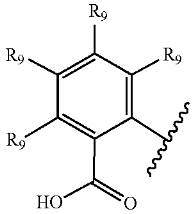
;
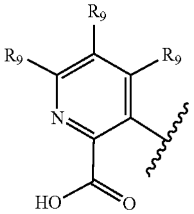
;
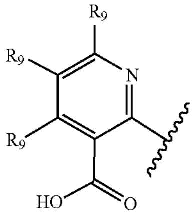
;
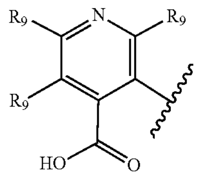
;
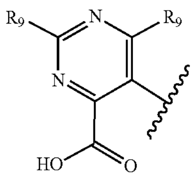
;
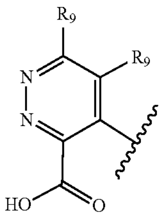
; or -continued

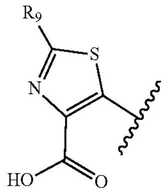
;

$R_2$ is an optionally substituted bicyclic ring selected from 1,3-benzodioxole, 2,3-dihydro-1,4-benzodioxine, isoindolin-1-one, indolin-2-one, benzo[d]oxazol-2(3H)-one, 1,3-dihydro-2H-pyrrolo[2,3-b]pyridin-2-one, or 2,3-dihydro-[1,4]dioxino[2,3-b]pyridine, or an optionally substituted bicyclic heteroaryl of 8 to 10 ring atoms containing 1, 2, 3, 4, or 5 ring heteroatoms independently selected from N, O, or S; wherein the optionally substituted bicyclic ring is optionally substituted with one to three substituents each independently selected from halogen and $C_1$-$C_6$ alkyl; the optionally substituted bicyclic heteroaryl is optionally substituted with one to three substituents each independently selected from -CN, halogen, $C_1$-$C_6$ haloalkyl, $C_1$-$C_6$ alkoxy, $C_1$-$C_6$ haloalkoxy, 13 $SO_2R_{10}$, 13 C(O)$OC_1$-$C_3$ alkyl, 13 $CONR_{10}R_{10}$, 13 $NR_{10}R_{10}$, 13 $NR_{10}CO_2R_{10}$, 13 OH, an optionally substituted $C_1$-$C_6$ alkyl, an optionally substituted $C_2$-$C_6$ alkenyl, an optionally substituted $C_2$-$C_6$ alkynyl, an optionally substituted $C_3$-$C_5$ cycloalkyl, an optionally substituted heterocycle selected from pyrrolidine, pyrrolidinone, piperidine or morpholine, an optionally substituted phenyl, an optionally substituted 1,3-benzodioxole, an optionally substituted 2,3-dihydro-1,4-benzodioxine, or an optionally substituted heteroaryl selected from pyridine, pyrimidine, pyridazine, pyrazine, pyrazole, isoxazole, isothiazole, imidazole, oxazole, or thiazole; wherein the optionally substituted $C_1$-$C_6$ alkyl, $C_2$-$C_6$ alkenyl, or $C_2$-$C_6$ alkynyl is each optionally substituted with a 13 CN, 13 OH, oxetanyl, $C_1$-$C_3$ alkoxy, 13 $CONR_{10}R_{10}$, or phenyl; the optionally substituted $C_3$-$C_5$ cycloalkyl, phenyl, 1,3-benzodioxole, 2,3-dihydro-1,4-benzodioxine, heterocycle or heteroaryl is each optionally substituted with one to three substituents each independently selected from halogen, $C_1$-$C_3$ alkyl, $C_1$-$C_3$ haloalkyl, $C_1$-$C_3$ alkoxy, $C_1$-$C_3$ haloalkoxy, 13 $SO_2R_{10}$, 13 $NR_{10}R_{10}$, 13 OH or 13 CN;

$R_3$ is halogen, 13 N(H)($C_1$-$C_3$ alkyl), 13 N($C_1$-$C_3$ alkyl)$_2$, 13 N(H)($CH_2CH_2CO_2H$), 13 C(O)$C_1$-$C_3$ alkyl, $C_1$-$C_6$ alkyl $C_1$-$C_6$ haloalkyl, $C_1$-$C_6$ hydroxyalkyl, $C_3$-$C_5$ cycloalkyl, an optionally substituted heterocycle of 3 to 5 ring atoms containing 1, 2, or 3 ring heteroatoms independently selected from N, O, or S, or an optionally substituted heteroaryl of 5 or 6 ring atoms containing 1, 2, or 3 ring heteroatoms independently selected from N, O, or S; wherein the optionally substituted heterocycle or heteroaryl is each optionally substituted with one to three substituents each independently selected from halogen, $C_1$-$C_3$ alkyl, or $C_1$-$C_3$ haloalkyl;

each of $R_4$, $R_5$ and $R_6$ is independently 13 H, halogen, $C_1$-$C_6$ alkyl or $C_1$-$C_6$ haloalkyl;

$R_7$ is 13 CN, $C_1$-$C_6$ alkyl or $C_1$-$C_6$ haloalkyl;

$R_8$ is 13 H or $C_1$-$C_6$ alkyl;

each $R_9$ is independently 13 H, halogen, -CN, $C_1$-$C_6$ alkyl, $C_1$-$C_6$ haloalkyl, $C_1$-$C_6$ alkoxy, or $C_3$-$C_5$ cycloalkyl; and each $R_{10}$ is independently 13 H or $C_1$-$C_3$ alkyl.

65. The compound of claim 64, selected from the group consisting of:
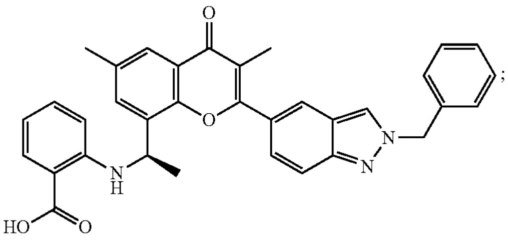
; and
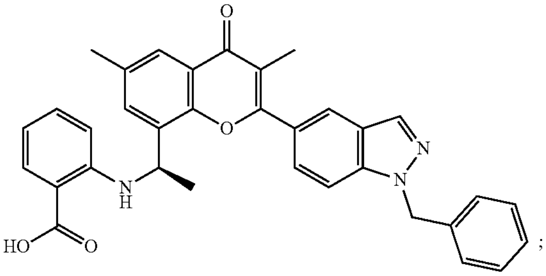
;
or a pharmaceutically acceptable salt thereof.
* * * * *